United States Patent
Binggeli et al.

[11] Patent Number: 6,150,526
[45] Date of Patent: *Nov. 21, 2000

[54] PIPERIDINE DERIVATIVE HAVING RENIN INHIBITING ACTIVITY

[75] Inventors: Alfred Binggeli, Flüh, Switzerland; Volker Breu, Schliengen, Germany; Daniel Bur, Basel, Switzerland; Walter Fischli, Allschwil, Switzerland; Rolf Güller, Rheinfelden, Switzerland; Georges Hirth, Huningue, France; Hans-Peter Märki, Basel, Switzerland; Marcel Müller, Frenkendorf, Switzerland; Christian Oefner, Freiburg, Germany; Heinz Stadler, Rheinfelden, Switzerland; Eric Vieira, Basel, Switzerland; Maurice Wilhelm, Morschwiller le Bas, France; Wolfgang Wostl, Grenzach-Wyhlen, Germany

[73] Assignee: Hoffmann-La Roche Inc., Nutley, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/456,283

[22] Filed: Dec. 7, 1999

Related U.S. Application Data

[60] Continuation of application No. 09/255,185, Feb. 22, 1999, which is a division of application No. 08/711,339, Sep. 6, 1996, abandoned.

[30] Foreign Application Priority Data

Sep. 7, 1995 [CH] Switzerland .............................. 2548/95
Jul. 26, 1996 [CH] Switzerland .............................. 1876/96

[51] Int. Cl.$^7$ .................................................. C07D 401/02
[52] U.S. Cl. ........................ 546/139; 546/153; 546/157; 546/166; 546/176; 514/307
[58] Field of Search ..................... 546/139, 157, 546/166, 176

[56] References Cited

U.S. PATENT DOCUMENTS

| | | |
|---|---|---|
| 4,007,196 | 2/1977 | Christenson et al. . |
| 4,320,137 | 3/1982 | Paioni . |
| 5,378,712 | 8/1996 | Alig et al. . |
| 5,545,658 | 8/1996 | Alig et al. . |
| 5,599,819 | 2/1997 | Chandraratna ........................ 546/166 |

FOREIGN PATENT DOCUMENTS

| | | |
|---|---|---|
| 34759 | 4/1985 | Chile . |
| 929-94 | 10/1986 | Chile . |
| 374674 | 6/1990 | European Pat. Off. . |
| 25213 | 2/1966 | Israel . |
| 84021/2 | 9/1987 | Israel . |
| 89903/2 | 4/1989 | Israel . |

OTHER PUBLICATIONS

Fischli et al., Hypertension 18(1):22–31 (1991).
Pals et al., Hypertension 8:1105–1112 (1986).
Clozel et al., Hypertension 22(1):9–17 (1993).
Dellaria et al., J. Med. Chem. 30:2137–2144 (1987).
Kokubu et al., Biochem. Biophys. Res. Commun. 118:929–933 (1984).
Willcocks et al., J. of Labelled Cmpds and Radiopharma., vol. 33, No. 8 783–794 (1993).
Beckett et al., Journal of Medicinal and Pharma. Chem. vol. 1(1), 37–58 (1959).
Jaeger et al., J. Org. Chem. 30(3):740–744 (1965).
Boger et al., J. Med. Chem., 28:1779–1790 (1985).
Ferles et al., Coll. Czechoslov. Chem. Commun. 35:2802–2809 (1970).
Lounasmaa et al., Tetrahedron Letters, 29:2509 (1974).
Kovacs et al., Helv. Chem. Acta vol. XXXCII, 802 (1954).
Ito et al., Chem. Pharm. Bull. 22(9):2131 (1974).
Arslan et al., J. Org. Chem. 58:2260 (1993).
Gribble et al., Synth. Commun. 17:377 (1987).
Mancuso et al., J. Org. Chem. 43:2480 (1978).
Cardwell et al., J. Am. Chem. Soc. 110:2242 (1988).
Moser et al., Helv. Chim. Acta 69:1224 (1986).

*Primary Examiner*—Robert W. Ramsuer
*Attorney, Agent, or Firm*—George W. Johnston; William H. Epstein; John P. Parise

[57] ABSTRACT

Piperidine derivatives, their manufacture and use as medicaments, are disclosed. The invention is concerned with the piperidine derivatives of general formula I

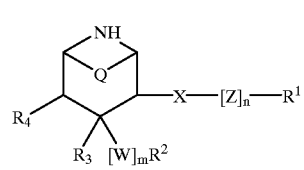

wherein $R^1$, $R^2$, $R^3$, $R^4$, Q, X, Z, m and n are as described herein.

5 Claims, No Drawings

PIPERIDINE DERIVATIVE HAVING RENIN INHIBITING ACTIVITY

This is a continuation of copending application Ser. No. 09/255,185, filed Feb. 22, 1999, which is a divisional of application Ser. No. 08/711,339, filed Sep. 6, 1996 now abandoned.

The present invention is concerned with novel piperidine derivatives, their manufacture and use as medicaments. In particular, the invention is concerned with the novel piperidine derivatives of general formula I:

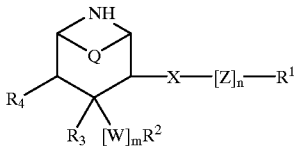

wherein $R^1$ is aryl or heterocyclyl;

$R^2$ is phenyl, naphthyl, acenaphthyl, cyclohexyl, pyridyl, pyrimidinyl, pyrazinyl, oxo-pyridyl, diazinyl, triazolyl, thienyl, oxazolyl, oxadiazolyl, thiazolyl, pyrrolyl or furyl, which groups can be substituted by 1–3 halogen, hydroxy, cyano, trifluoromethyl, lower-alkyl, halo-lower-alkyl, hydroxy-lower-alkyl, lower-alkoxy-lower-alkyl, cyano-lower-alkyl, carboxy-lower-alkyl, lower-alkanoyloxy-lower-alkyl, lower-alkoxycarbonyloxy-lower-alkyl, lower-alkoxycarbonyl, or lower-alkoxy groups, or by lower-alkylenedioxy, and/or by a group $L^1-T^1-L^2-T^2-L^3-T^3-L^4-T^4-L^5-U$;

$L^1, L^2, L^3, L^4$ and $L^5$ independently of one another are a bond, $C_{1-8}$-alkylene, $C_{2-8}$-alkenylene or $C_{2-8}$-alkynylene or are absent;

$T^1, T^2, T^3$ and $T^4$ independently of one another are
  (a) a bond or are absent or are one of the groups
  (b) —CH(OH)—
  (c) —CH(OR$^6$)—
  (d) —CH(NR$^5$R$^6$)—
  (e) —CO—
  (f) —CR$^7$R$^8$—
  (g) —O— or —NR$^6$—
  (h) —S(O)$_{0-2}$—
  (i) —SO$_2$NR$^6$—
  (j) —NR$^6$SO$_2$—
  (k) —CONR$^6$—
  (l) —NR$^6$CO—
  (m) —O—CO—
  (n) —CO—O—
  (o) —O—CO—O—
  (p) —O—CO—NR$^6$—
  (q) —NR$^6$—CO—NR$^6$—
  (r) —NR$^6$—CO—O— and the bonds emanating from (b), (d), (e) and (g)–(r) join to a C atom of the adjacent group and this C atom is saturated when the bond emanates from a hetero atom, and not more than two groups (b)–(f), three groups (g)–(h) and one group (i)–(R) are present;

$R^3$ is hydrogen, hydroxy, lower-alkoxy or lower-alkenyloxy; and $R^4$ is hydrogen, lower-alkyl, lower-alkenyl, lower-alkoxy, hydroxy-lower-alkyl, lower-alkoxy-lower-alkyl, benzyl, oxo or a group $R^{4a}$—$Z^1$—$X^1$— in which $R^{4a}$ is
  (a) H—
  (b) lower-alkyl—
  (c) lower-alkenyl—
  (d) hydroxy-lower-alkyl—
  (e) polyhydroxy-lower-alkyl—
  (f) lower-alkyl-O-lower-alkyl—
  (g) aryl—
  (h) heterocyclyl—
  (i) arylalkyl—
  (j) heterocyclylalkyl—
  (k) aryloxyalkyl—
  (l) heterocyclyloxylalkyl—
  (m) (R$^5$R$^6$)—N—(CH$_2$)$_{1-3}$—
  (n) (R$^5$R$^6$)—N—
  (o) lower-alkyl-S(O)$_{0-2}$—
  (p) aryl-S(O)$_{0-2}$—
  (q) heterocyclyl-S(O)$_{0-2}$—
  (r) HO—SO$_3$— or salt thereof
  (s) H$_2$N—C(NH)—NH—
  (t) NC—, and the bonds emanating from (n)–(t) join to a C atom of the adjacent group and this C atom is saturated when the bond emanates from a hetero atom;

$Z^1$ is
  (a) a bond, is absent or is one of the groups
  (b) lower-alkylene—
  (c) lower-alkenylene—
  (d) —O—,—N(R$^{11}$)—,—S(O)$_{0-2}$—
  (e) —CO—
  (f) —O—CO—
  (g) —O—CO—O—
  (h) —O—CO—N(R$^{11}$)—,
  (i) —N(R$^{11}$)—CO—O—
  (j) —CO—N(R$^{11}$)—
  (k) —N(R$^{11}$)—CO—
  (l) —N(R$^{11}$)—CO—N(R$^{11}$)—
  (m) —CH(OR$^9$)—, and the bonds emanating from (d) and (f)–(m) join to a C atom of the adjacent group and this C atom is saturated when the bond emanates from a hetero atom;

$X^1$ is
  (a) a bond, is absent or is one of the groups
  (b) —O—
  (c) —N(R$^{11}$)—,
  (d) —S(O))$_{0-2}$—
  (e) —(CH$_2$)$_{1-3}$— or $R^3$ and $R^4$ together are a bond;

$R^5$ and $R^6$ are hydrogen, lower-alkyl, lower-alkenyl, aryl-lower-alkyl or acyl or together with the N atom to which they are attached are a 5- or 6-membered heterocyclic ring which can contain an additional N atom or an O or S atom or a SO or SO$_2$ group and the additional N atom can be optionally substituted by lower-alkyl;

$R^7$ and $R^8$ together with the C atom to which they are attached are a 3–7 membered ring which can contain one or two O or S atoms or SO or SO$_2$ groups;

$R^9$ is hydrogen, lower-alkyl, acyl or arylalkyl;

$R^{10}$ is carboxyalkyl, alkoxycarbonylalkyl, alkyl or hydrogen;

$R^{11}$ is hydrogen or lower-alkyl;

U is hydrogen, lower-alkyl, cycloalkyl, cyano, optionally substituted cycloalkyl, aryl or heterocyclyl;

Q is ethylene or is absent;

X is a bond, oxygen, sulphur or a group —CH—$R^{11}$—, —$CHOR^9$—, —O—CO, —CO— or C=$NOR^{10}$— with the bond emanating from an oxygen or sulphur atom joining to a saturated C atom of group Z or to $R^1$;

W is oxygen or sulphur;

Z is lower-alkylene, lower-alkenylene, hydroxy-lower-alkylidene, —O—, —S—, —O-Alk-, —S-Alk-, -Alk-O— or -Alk-S—, in which Alk is lower alkylene; provided that a) X is —CH—$R^{11}$— and either $R^2$ contains a substituent $L^1$-$T^1$-$L^2$-$T^2$-$L^3$-$T^3$-$L^4$-$T^4$-$L^5$-U or $R^4$ is a substituent defined above other than hydrogen when Z is —O— or —S—;

b) X is —CH—$R^{11}$— when Z is —O-Alk- or —S-Alk-; and c) Z is lower-alkenylene, -Alk-O— or -Alk-S— when X is a bond;

n is 1 or, when X is —O—CO—, 0 or 1; and m is 0 or 1;

and pharmaceutically usable salts thereof;

with the exception of the compound 4-(4-fluorophenyl)-3-(3,4-methylenedioxybenzyloxy)piperidine and its hydrochloride.

The term "lower" used here denotes groups with 1–6, preferably 1–4, C atoms. Examples of lower alkyl and alkoxy groups are methyl, ethyl, n-propyl, isopropyl, n-butyl, isobutyl, sec.-butyl, tert-butyl, pentyl, hexyl and, respectively, methoxy, ethoxy, propoxy, isopropoxy, butoxy, isobutoxy, sec.-butoxy and tert-butoxy. Lower-alkylenedioxy groups are preferably methylenedioxy, ethylenedioxy and propylenedioxy. Acetyl, propionyl and butyryl are examples of lower-alkanoyl groups.

Cycloalkyl signifies a saturated, cyclic hydrocarbon group with 3–6 carbon atoms, i.e. cyclopropyl, cyclobutyl, cyclopentyl and cyclohexyl. $C_{1-8}$-Alkylene groups are, e.g., methylene, ethylene, propylene, 2-methyl-propylene, tetra-, penta- and hexamethylene; $C_{2-8}$-alkenylene groups are, e.g., vinylene and propenylene; $C_{2-8}$-alkynylene groups are, e.g., ethynylene. Acyl groups are alkanoyl groups, preferably lower-alkanoyl groups, or aroyl groups such as benzoyl. Aryl denotes mono-nuclear or poly-nuclear aromatic groups which can carry one or more substituents, such as, for example, phenyl, substituted phenyl, naphthyl, substituted naphthyl, tetrahydronaphthyl or substituted tetrahydronaphthyl. Examples of substitutents on such aryl groups are lower-alkyl, trifluoromethyl, nitro, amino, lower-alkenyl, lower-alkoxy, lower-alkylcarbonyloxy, hydroxy, halogen, cyano, carbamoyl and lower-alkylenedioxy, as well as optionally halo-, lower-alkyl-, lower-alkoxy- or dihydroxy-lower-alkylaminocarbonyl-substituted phenyl, phenoxy, phenylthio, phenyl-lower-alkyl or phenyl-lower-alkoxy. Further examples of substituents on aryl groups are lower-alkoxycarbonylphenyl, hydroxy-lower-alkylphenyl, benzyloxy, pyridylcarbonylamino-lower-alkyl, lower-alkenyloxy, lower-alkoxy-lower-alkoxy, methoxybenzyloxy, hydroxybenzyloxy, phenethyloxy, methylenedioxybenzyloxy, dioxolanyl-lower-alkoxy, cyclopropyl-lower-alkoxy, hydroxy-lower-alkoxy, carbamoyloxy-lower-alkoxy, pyridyl-carbamoyloxy-lower-alkoxy, benzoyloxy-lower-alkoxy; as well as optionally halo-, lower-alkyl-, lower-alkoxy- or dihydroxy-lower-alkylaminocarbonyl-substituted pyridyl, pyridyloxy, pyridylthio, pyridylamino, pyridyl-lower-alkyl, pyridyl-lower-alkoxy, pyrimidinyl, pyrimidinyloxy, pyrimidinylthio, pyrimidinylamino, pyrimidinyl-lower-alkyl, pyrimidinyl-lower-alkoxy, thienyl, thienyl-lower-alkyl, thienyl-lower-alkoxy, furyl, furyl-lower-alkyl and furyl-lower-alkoxy.

The term heterocyclyl denotes monocyclic or bicyclic, saturated and unsaturated heterocyclic groups with 1 to 4 nitrogen atoms and/or 1 or 2 sulphur or oxygen atoms, which can be mono- or multiply-substituted, especially by (in the case of unsaturated heterocyclyl groups) alkyl, hydroxy, alkoxy, nitro or halogen or by substituents as defined above for aryl groups or (in the case of saturated heterocyclyl groups) by alkyl or alkoxy. Examples of heterocyclyl groups are pyridyl, thienyl, pyrazinyl, triazolyl, imidazolyl, benzthiazolyl, furyl, pyrimidinyl, morpholinyl, quinazolinyl, quinolyl, quinoxalinyl, isoquinolyl, benzo[b] thienyl, isobenzofuranyl, benzimidazolyl, 2-oxo-benzimidazolyl or thiazolyl. Examples of substituted heterocyclyl groups are nitrobenzthiazolyl, phenyl-tetrazolyl, phenyl-oxadiazolyl, phenyl-oxadiazolyl, thienyl-oxadiazolyl, furanyl-oxadiazolyl, benzyl-oxadiazolyl and phenyl-oxazolyl. Examples of saturated heterocyclyl groups are dioxolanyl, dioxanyl, dithiolanyl, dithianyl, pyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxo-imidazolidinyl, 2-oxo-oxazolidinyl, 2-oxo-pyrrolidinyl, 2-oxo-[1,3]oxazinyl, 2-oxo-tetrahydro-pyrimidinyl and the like.

In the case of $R^1$, $R^{4a}$ and $R^9$ the aryl, aroyl and heterocyclyl groups can be additionally substituted by heterocyclylalkyl, heterocyclylalkoxy or heterocyclylalkoxyalkyl, such as, for example, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl or N-methylpiperazinoalkyl, N-methylpiperazinoalkoxy, N-methyl-piperazinoalkoxyalkyl, as well as alkylaminoalkyl, alkylamino-alkoxy, alkylamino-alkoxyalkyl, mono- and polyhydroxy-alkyl, -alkoxy, -alkoxyalkyl and -alkoxyalkoxy, carbamoylalkyloxy, lower-alkoxy, amino-lower-alkoxy, hydroxy-lower-alkoxy or by the —O—$CH_2CH(OH)CH_2NR^x$ group, in which $NR^x$ is a mono- or di-lower-alkyl-amino, piperidino, morpholino, piperazino or N-methylpiperazino group. Examples of 5- and 6-membered heterocyclic rings denoted by $NR^5R^6$ are pyrrolidinyl, piperidinyl, piperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxo-imidazolidinyl, 2-oxo-oxazolidinyl, 2-oxo-pyrrolidinyl, 2-oxo-[1,3]oxazinyl, 2-oxo-tetrahydro-pyrimidinyl and the like. Cyclopentyl, cyclohexyl, cycloheptyl, 1,3-dioxolanyl, 1,3-dioxanyl, 1,3-dithiolanyl and 1,3-dithianyl are examples of 3–7 membered rings denoted by $CR^7R^8$. The term polyhydroxy-alkyl denotes $C_1$–$C_7$-alkyl groups which can be substituted by 2–6 hydroxy groups, such as, e.g., glyceryl, arabityl, sorbityl etc.

The compounds of formula I have at least two asymmetric carbon atoms and can accordingly exist in the form of optically pure diastereomers, diastereomer mixtures, diastereomeric racemates or mixtures of diastereomeric racemates or as meso forms. The invention embraces all of these forms. Diastereomeric mixtures, diastereomeric racemates or mixtures of diastereomeric racemates can be separated according to usual methods, e.g., by column chromatography, thin-layer chromatography, HPLC and the like.

Preferred compounds in accordance with the invention are those of the general formula:

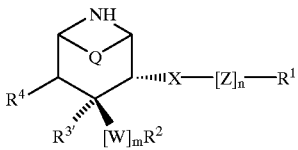

IA wherein $R^1$–$R^4$, Q, W, X, Z, n and m have the significance given above.

A further preferred group of compounds of formula I comprises compounds of the formula:

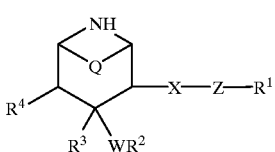

I-1 wherein
$R^1$ is aryl or heterocyclyl;
$R^2$ is phenyl, cyclohexyl, phenyl or cyclohexyl substituted by halogen, hydroxy, cyano, trifluoromethyl, lower-alkyl, halo-lower-alkyl, hydroxy-lower-alkyl, lower-alkoxy-lower-alkyl, cyano-lower-alkyl, carboxy-lower-alkyl, lower-alkanoyloxy-lower-alkyl, lower-alkoxycarbonyloxy-lower-alkyl, lower-alkoxycarbonyl, lower-alkoxy or lower-alkylenedioxy or by a group $L^1$-$T^1$-$L^2$-$T^2$-$L^3$-$T^3$-$L^4$-$T^4$-$L^5$-U; or naphthyl or acenaphthyl;
$L^1$, $L^2$, $L^3$, $L^4$ and $L^5$ independently of one another are a bond, $C_{1-8}$-alkylene, $C_{2-8}$-alkenylene or $C_{2-8}$-alkynylene or are absent;
$T^1$, $T^2$, $T^3$ and $T^4$ independently of one another are
a) a bond or are absent or are one of the groups
(b) —CH(OH)—
(c) —CH(OR$^6$)—
(d) —CH(NR$^5$R$^6$)—
(e) —CO—
(f) —CR$^7$R$^8$—
(g) —O— or —NR$^6$—,
(h) —S(O)$_{0-2}$—
(i) —SO$_2$NR$^6$—
(j) —NR$^6$SO$_2$—
(k) —CONR$^6$—
(l) —NR$^6$CO—
(m) —O—CO—
(n) —CO—O—
(o) —O—CO—O—
(p) —O—CO—NR$^6$—,
with the bonds emanating from (b), (d), (e) and (g)–(p) joining to a C atom of the adjacent group and this C atom being saturated when the bond emanates from a hetero atom, and not more than two groups (b)–(f), three groups (g)–(h) and one group (i)–(p) being present;
$R^3$ is hydrogen, hydroxy, lower-alkoxy or lower-alkenyloxy;
$R^4$ is hydrogen, lower-alkyl, lower-alkenyl, lower-alkoxy, hydroxy-lower-alkyl, lower-alkoxy-lower-alkyl or benzyl;

$R^5$ and $R^6$ are hydrogen, lower-alkyl or acyl or together with the N atom to which they are attached are a 5- or 6-membered heterocyclic ring which can contain an additional N atom or an O or S atom;
$R^7$ and $R^8$ together with the C atom to which they are attached are a 3–7 membered ring which can contain one or two oxygen or sulphur atoms;
U is hydrogen, lower-alkyl, cycloalkyl, cyano, aryl or heterocyclyl;
Q is ethylene or is absent;
X is oxygen, sulphur or a group —CH$_2$—, —CHOR$^9$— or —OCO— and $R^9$ is hydrogen, lower-alkyl, acyl or arylalkyl;
W is absent; or can are oxygen or sulphur when $R^3$ is hydrogen; and
Z is lower-alkylene or is absent;
and pharmaceutically usable salts thereof;
with the exception of the compound 4-(4-fluorophenyl)-3-(3,4-methylenedioxybenzyloxy)piperidine and its hydrochloride.

Furthermore, compounds of formulae I and IA in which W is absent, i.e, where m=0, and those in which Q is absent are preferred. X is preferably oxygen, sulphur or —CO—; Z is preferably methylene.

Preferred groups $R^1$ are phenyl and phenyl substituted by lower-alkyl, lower-alkenyl, lower-alkoxy, lower-alkylthio, halogen, hydroxy, hydroxy-lower-alkoxy, lower-alkoxy-lower-alkoxy, lower-alkylsulphinyl, lower-alkylsulphonyl, cyano, trifluoromethyl, trifluoromethoxy, carboxy, cyclobutylmethoxy-lower-alkyl, lower-alkylenedioxy, phenyl, phenoxy, lower-alkoxycarbonylphenyl, hydroxy-lower-alkylphenyl, 2,3-dihydroxypropylaminocarbonylphenyl, benzyloxy, benzoyl, pyridyl-lower-alkoxy-lower-alkyl or nicotinoylamino-lower-alkyl.

Other preferred groups $R^1$ are naphthyl, naphthyl substituted by hydroxy, oxo, lower-alkoxy, lower-alkenyloxy, lower-alkoxy-lower-alkoxy, di-lower-alkylamino, 2,3-dihydroxypropoxy, 2,3-dihydroxypropoxy-lower-alkoxy, 2,3-dimethoxypropoxy, lower-alkoxycarbonyl-lower-alkoxy, carbamoyl-lower-alkoxy, methoxybenzyloxy, hydroxybenzyloxy, phenethyloxy, methylenedioxybenzyloxy, dioxolanyl-lower-alkoxy, cyclopropyl-lower-alkoxy, hydroxy-lower-alkoxy, carbamoyloxy-lower-alkoxy, pyridyl-carbamoyloxy-lower-alkoxy, morpholino-lower-alkoxy, 3-morpholino-2-hydroxypropoxy, N-methylpiperazino-N-lower-alkoxy, benzoyloxy-lower-alkoxy or picolyloxy; tetrahydronaphthyl or methyl-substituted tetrahydronaphthyl, or indanyl.

Likewise preferred groups $R^1$ are pyridyl, benzimidazolyl, di-lower-alkoxypyrimidinyl or 2- and 5-benzo[b]thienyl, 6- and 7-quinolyl, 6- and 7-isoquinolyl, 6- and 7-tetrahydroquinolyl, 6- and 7-tetrahydroisoquinolinyl, 6-quinoxalinyl, 6- and 7-quinazolinyl, as well as 6- and 7-quinolyl, 6- and 7-isoquinolyl, 6- and 7-tetrahydroquinolyl, 6- and 7-tetrahydroisoquinolyl, 6-quinoxalinyl or 6- and 7-quinazolinyl substituted by hydroxy, oxo, lower-alkoxy, lower-alkenyloxy, lower-alkoxy-lower-alkoxy, di-lower-alkylamino, 2,3-dihydroxypropoxy, 2,3-dihydroxypropoxy-lower-alkoxy, 2,3-dimethoxypropoxy, lower-alkoxycarbonyl-lower-alkoxy, carbamoyl-lower-alkoxy, methoxybenzyloxy, hydroxybenzyloxy, phenethyloxy, methylenedioxybenzyloxy, dioxolanyl-lower-alkoxy, cyclopropyl-lower-alkoxy, hydroxy-lower-alkoxy, carbamoyloxy-lower-alkoxy, pyridyl-carbamoyloxy-loweralkoxy, morpholino-lower-alkoxy, 3-morpholino-2-hydroxypropoxy, N-methylpiperazino-N-lower-alkoxy, benzoyloxy-lower-alkoxy or picolyloxy.

Preferred groups $R^2$ are phenyl and phenyl substituted by halogen, hydroxy, cyano, trifluoromethyl, lower-alkyl, halo-lower-alkyl, hydroxy-lower-alkyl, lower-alkoxy-lower-alkyl, cyano-lower-alkyl, carboxy-lower-alkyl, lower-alkanoyloxy-lower-alkyl, lower-alkoxycarbonyloxy-lower-alkyl, lower-alkoxycarbonyl, lower-alkoxy or lower-alkylenedioxy.

Likewise preferred groups $R^2$ are phenyl substituted by a group $L^1$-$T^1$-$L^2$-$T^2$-$L^3$-$T^3$-$L^4$-$T^4$-$L^5$-U in which $L^1$ and $L^2$ are preferably absent or are $C_{1-8}$-alkylene and $L^3$ is absent and U is hydrogen, lower-alkyl, cyclo-lower-alkyl, phenyl, phenyl substituted by lower-alkyl, lower-alkoxy, lower-alkylthio, lower-alkylsulphinyl, lower-alkylenedioxy, halogen, benzoyl-lower-alkyl, halo-lower-alkyl, lower-alkanoyloxy or hydroxy; or naphthyl; or pyridyl, thienyl, pyrazinyl, triazolyl, imidazolyl, phenyl-oxadiazolyl, thienyl-oxadiazolyl, furyl-oxadiazolyl, phenyl-oxazolyl, benzthiazolyl, furyl, pyrimidinyl, nitrobenzthiazolyl, phenyltetrazolyl or morpholinyl.

In groups $T^1$–$T^4$ the meanings (a)–(c), (e)–(h), (m) and (n) are preferred.

Examples of especially preferred groups $R^2$ are phenyl or phenyl substituted by
2-benzothiazolyl-thio-lower-alkyl,
2-benzyloxy-3-methoxypropoxy,
2-benzoyloxy-3-methoxypropoxy,
2,3-dihydroxypropoxy,
2-hydroxy-3-benzylamino-propoxy,
2-hydroxy-3-phenoxypropoxy,
2-hydroxy-3-phenylthiopropoxy,
2-methoxy-3-phenoxypropoxy,
2-methoxy-3-benzyloxypropoxy,
2-methyl-3-fluoro-phenylbutyryloxy-lower-alkoxy,
2-lower-alkenyloxy-4-phenylbutyl,
3,4,5-trimethoxyphenyl-oxadiazolyl-lower-alkoxy,
6-nitro-2-benzothiazolyl-thio-lower-alkyl,
benzamido-lower-alkoxy,
benzamido-lower-alkyl,
benzoyl-lower-alkoxy and ketals thereof,
benzoyl-lower-alkyl and ketals thereof,
benzoyl-lower-alkyl-aminocarbonyl-lower-alkyl,
benzoyl-lower-alkoxycarbonyl-lower-alkyl,
benzoyl-lower-alkylaminocarbonyl,
benzoyloxy,
benzoyloxy-lower-alkyl-benzoyloxy-lower-alkoxy,
benzoyloxy-lower-alkoxy,
benzoyloxy-lower-alkyl,
benzthiazolylthio-lower-alkoxy,
benzthiazolylthio-lower-alkyl,
benzylcarbamoyl-lower-alkoxy,
benzyloxy-lower alkylcarbonyloxy-lower-alkyl,
benzyloxy-lower-alkoxy,
benzylthio-lower-alkoxy,
carbamoyloxy-lower-alkoxy,
carbamoyloxy-lower-alkyl,
carboxy-lower-alkoxy,
carboxy-lower-alkyl,
cyano,
cyano-lower-alkoxy,
cyano-lower-alkyl,
cyanophenyl-lower-alkoxy,
cyclohexylcarbonyloxy-lower-alkyl,
cyclopropylcarbonyloxy-lower-alkyl,
cyclopropyloxy-benzyloxy-lower-alkoxy,
dioxolanyl-lower-alkoxy,
furyl-oxadiazolyl-lower-alkoxy,
furoyloxy-lower-alkoxy,
halo-phenoxy-lower-alkyl,
halobenzoyl-lower-alkoxy,
halobenzoyloxy-lower-alkyl,
halobenzoyloxy-lower-alkoxy,
halobenzyloxy-lower-alkoxy,
halogen,
halogen-lower-alkyl,
halophenoxy,
halophenyl-oxadiazolyl-lower-alkoxy,
hydroxy,
hydroxy-benzoyloxy-lower-alkyl,
hydroxy-benzyloxy-lower-alkoxy,
hydroxy-lower-alkoxy,
hydroxy-lower-alkyl,
imidazolylcarbonyloxy-lower-alkyl,
methoxybenzoyl-lower-alkyl,
methoxybenzyloxy-lower-alkoxy,
methylenedioxybenzoyl-lower-alkoxy,
morpholino-lower-alkoxy,
morpholinocarbonyloxy-lower-alkoxy,
morpholinocarbonyloxy-lower-alkyl,
N-methylaminophenyl-carbonyloxy-lower-alkyl,
N-methyl-benzylamino-lower-alkoxy,
N-methylpyrrolylcarbonyloxy-lower-alkoxy,
N-lower-alkylbenzamido-lower-alkyl,
naphthyl-lower-alkoxy,
nicotinoyloxy-lower-alkoxy,
nicotinoyloxy-lower-alkyl,
lower-alkanoylbenzoyloxy-lower-alkyl,
lower-alkanoyloxy-lower-alkoxy
lower-alkanoyloxy-lower-alkyl,
lower-alkenyl-benzyloxy-lower-alkoxy,
lower-alkenyloxy,
lower-alkenyloxy-benzyloxy-lower-alkoxy,
lower-alkoxy,
lower-alkoxy-benzoyloxy-lower-alkyl,
lower-alkoxy-carbonyl,
lower-alkoxy-lower-alkyl,
lower-alkoxybenzoylamino-lower-alkyl,
lower-alkoxybenzylcarbonyloxy-lower-alkyl,
lower-alkoxy-benzyloxy-lower-alkoxy,
lower-alkoxy-benzylthio-lower-alkoxy,
lower-alkoxycarbonyl,
lower-alkoxycarbonyl-lower-alkoxy,
lower-alkoxycarbonyl-lower-alkyl,
lower-alkoxyphenyl-oxadiazolyl-lower-alkoxy,
lower-alkyl,
lower-alkylbenzyloxy-lower-alkoxy,
lower-alkylenedioxy,
lower-alkylenedioxybenzyloxy-lower-alkoxy,
lower-alkylsulphonylbenzoyl-lower-alkoxy,
lower-alkylthiobenzoyloxy-lower-alkoxy,
lower-alkylthio-benzyloxy-lower-alkoxy,
benzoyloxybenzyl-lower-alkoxy,
hydroxybenzyl-lower-alkoxy,
lower-alkoxybenzyl-lower-alkoxy,
lower-alkoxybenzylcarbonyloxy-alkoxy,
phenoxy-benzyloxy-lower-alkoxy,
phenoxycarbonyl-lower-alkyl,
phenoxy-lower-alkenyloxy,
phenoxy-lower-alkynyloxy,
phenyl-lower-alkanoylamino-lower-alkyl,
phenyl-lower-alkenyloxy, phenyl-lower-alkoxy,
phenoxy-lower-alkyl,
phenyl-lower-alkylaminocarbonyl,
phenoxy-lower-alkylcarbonyl-lower-alkoxy,
phenyl-lower-alkylaminocarbonyl-lower-alkyl,
phenylaminocarbonyloxy-lower-alkoxy,
phenylaminocarbonyloxy-lower-alkyl,
phenyl-hydroxy-lower-alkyl,
phenyl-oxadiazolyl-lower-alkoxy
phenyl-oxadiazolyl-lower-alkoxy,
phenyl-oxadiazolyl-lower-alkyl,
phenyl-oxazolyl-lower-alkoxy,
phenyloxy-lower-alkoxy,
phenylsulphamoyl-lower-alkyl,
phenylsulphinyl-lower-alkyl,
phenylsulphonyl-lower-alkoxy,
phenylsulphonyl-lower-alkyl,
phenyltetrazolyl-thio-lower-alkyl,
phenylthio-lower-alkoxy,
phenylthio-lower-alkyl,
pyrazinylcarbonyloxy-lower-alkyl,
pyridylaminocarbonyloxy-lower-alkoxy
pyridylaminocarbonyloxy-lower-alkyl,
pyridylcarbamoyloxy,
pyridyl-lower-alkoxy-lower-alkoxy,
pyridyl-lower-alkoxy-lower-alkyl,
pyridyl-oxadiazolyl-lower-alkoxy,
pyridylthio-lower-alkyl,
pyrimidinyloxy-lower-alkoxy,
pyrimidinylthio-lower-alkyl,
thenoyloxy-lower-alkoxy,
thenoyloxy-lower-alkyl,
thienyl-oxadiazolyl-lower-alkoxy,
triazolyl-lower-alkoxy,
trifluoromethylbenzyloxy-lower-alkoxy or
trifluoromethyl.

Preferred groups $R^4$ are
2-oxo-imidazolidin-1-yl-lower-alkyl,
4-hydroxy-piperidin-1-yl-lower-alkoxy,
4-hydroxy-piperidin-1-yl-lower-alkoxy-lower-alkyl,
4-methyl-piperazin-1-yl-lower-alkoxy,
4-methyl-piperazin-1-yl-lower-alkoxy-lower-alkyl,
4-methyl-piperazin-1-yl-lower-alkyl-carbamoyloxy-lower-alkyl,
1,2,4-triazolyl-lower-alkyl,
amino,
amino-lower-alkyl,
amino-lower-alkyl-amino
amino-lower-alkyl-amino-lower-alkyl,
amino-lower-alkoxy,
amino-lower-alkoxy-lower-alkyl,
aminocarbonyloxy-lower-alkyl,
benzyloxy or benzyloxy substituted by lower-alkyl, lower-alkenyl, lower-alkoxy,
trifluoromethoxy, lower-alkylthio, hydroxy or halogen,
benzyloxy-lower-alkyl or benzyloxy-lower-alkyl substituted by lower-alkyl, lower-alkenyl, lower-alkoxy or halogen,
carbamoyloxy-lower-alkyl,
cyano-lower-alkyl,
di-lower-alkyl-amino,
di-lower-alkyl-amino-lower-alkyl,
di-lower-alkyl-amino-lower-alkyl-(N-lower-alkyl)-amino-lower-alkyl,
di-lower-alkyl-amino-lower-alkyl-amino
di-lower-alkyl-amino-lower-alkyl-amino-lower-alkyl,
di-lower-alkyl-amino-lower-alkoxy
di-lower-alkyl-amino-lower-alkoxy-lower-alkyl,
dihydroxy-lower-alkoxy,
dihydroxy-lower-alkoxy-lower-alkyl
dihydroxy-lower-alkyl-amino,
dihydroxy-lower-alkyl-amino-lower-alkyl
guanidinyl-lower-alkoxy-lower-alkyl,
guanidinyl-lower-alkyl,
hydroxy,
hydroxy-lower-alkyl,
sulphooxy-lower-alkyl,
hydroxy-lower-alkoxy,
hydroxy-lower-alkoxy-lower-alkyl,
morpholin-4-yl-lower-alkoxy,
morpholin-4-yl-lower-alkoxy-lower-alkyl,
morpholin-4-yl-lower-alkyl-carbamoyloxy-lower-alkyl,
naphthyl-alkoxy or naphthyl-alkoxy substituted by lower-alkoxy,
lower-alkoxy,
lower-alkoxy-lower-alkoxy
lower-alkoxy-lower-alkoxy-lower-alkyl,
lower-alkoxy-lower-alkyl,
lower-alkyl,
lower-alkylsulphonylamino-lower-alkyl,
phenoxy-lower-alkyl or phenoxy-lower-alkyl substiuted by lower-alkyl, lower-alkoxy,
phenyl-thio-lower-alkyl or phenyl-thio-lower-alkyl substituted by lower-alkyl,
lower-alkoxy,
piperazin-4-yl-lower-alkoxy,
piperazin-4-yl-lower-alkoxy-lower-alkyl,
piperidin-1-yl-lower-alkyl-carbamoyloxy-lower-alkyl,
piperidin-4-yl-lower-alkoxy,
piperidin-4-yl-lower-alkoxy-lower-alkyl,
pyridyl-lower-alkoxy,
pyridyl-lower-alkoxy-alkyl,
pyridylthio-lower-alkyl,
pyrimidinyloxy-lower-alkyl or pyrimidinyloxy-lower-alkyl substituted by lower-alkoxy,
tetrazolyl-lower-alkyl,
trifluoromethylsulphonylamino-lower-alkyl or
hydrogen.

Other preferred groups of compounds of formula I are those in which $R^2$ is cyclohexyl or benzoyloxymethylcyclohexyl; those in which $R^2$ is naphthyl, tetrahydronaphthyl or acenaphthyl; those in which $R^2$ is pyridyl or oxopyridyl or pyridyl or oxopyridyl substituted by 3H-2-thioxo-benzthiazolyl, lower-alkoxyphenyl-lower-alkoxy-lower-alkoxy, phenyl-lower-alkoxy-lower-alkoxy, phenyl-lower-alkyl, cyclohexyl-lower-alkoxy, phenoxy-lower-alkyl or phenyl-lower-alkoxy-lower-alkyl; those in which $R^2$ is pyrimidinyl or pyrimidinyl substituted by benzodioxanyl-lower-alkoxy, biphenylyloxy, biphenylyl-lower-alkoxy, cyclohexyl-lower-alkoxy, cyclohexyloxy-lower-alkoxy, halophenyl-lower-alkoxy, halophenyl-oxadiazolyl-lower-alkoxy, indanyl-lower-alkoxy, naphthyl-lower-alkoxy, phenyl-lower-alkyl, N-lower-alkyl-phenyl-lower-alkoxy-lower-alkylamino, N-lower-alkyl-phenyl-lower-alkylamino, lower-alkythio, lower-alkoxy, lower-alkoxyphenyl-lower-alkoxy-lower-alkoxy, lower-alkoxyphenyl-lower-alkylamino, halophenyl-lower-alkylamino, halophenoxy-lower-alkoxy, lower-alkylpyridyl-lower-alkoxy, phenyl-lower-alkoxy-lower-alkoxy, phenyl-lower-alkoxy-lower-alkylthio, phenyl-lower-alkoxy-lower-alkylamino, phenyl-lower-alkenoxy, phenoxy-phenyl-lower-alkoxy, phenoxy-phenoxy, phenyl-lower-alkynyloxy, lower-alkoxy-phenyl-lower-alkoxy-lower-alkoxy, phenylthio-lower-alkoxy, phenyl-oxazolyl-lower-alkoxy, phenyl-lower-alkynyloxy, phenyl-lower-alkenyloxy, phenyl-lower-alkylamino, phenyl-pyridyl-lower-alkoxy or phenyl-pyridyl-lower-alkylamino; and finally those in which R² is halobenzoyloxy-lower-alkyl-triazolyl, phenyl-lower-alkoxy-lower-alkyl-triazolyl or phenyl-lower-alkoxy-lower-alkyl-triazolyl.

The most preferred R² groups are groups of the formulas:

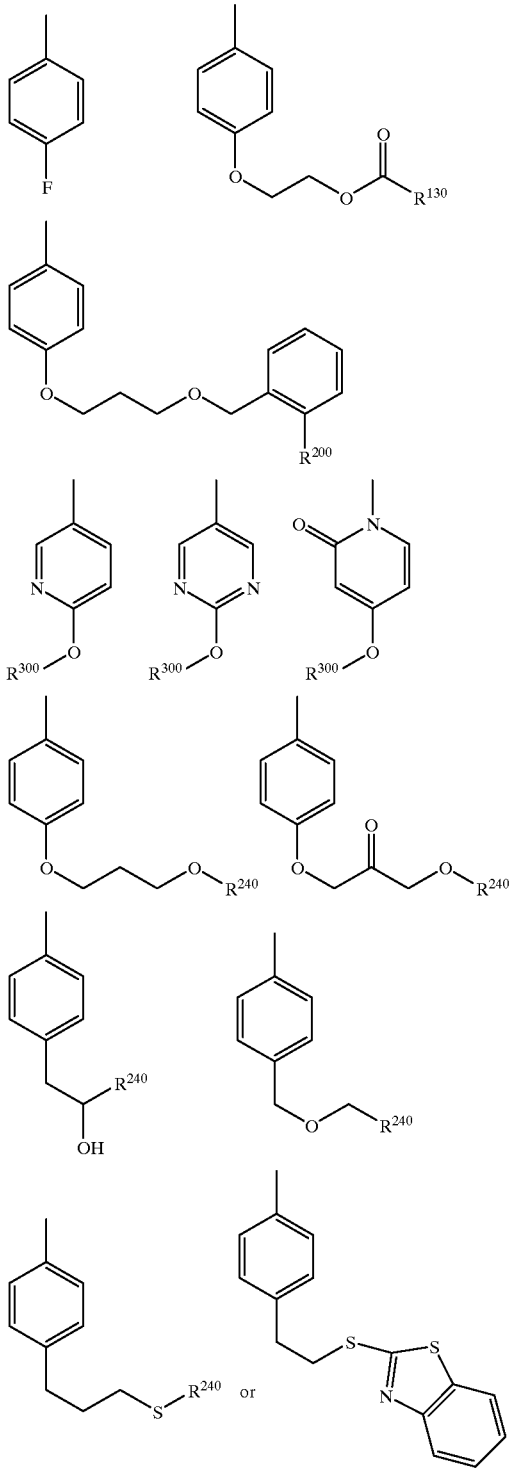

wherein R¹³⁰ is unsubstituted or substituted phenyl or unsubstituted or substituted thienyl, R²⁰⁰ is hydrogen or lower alkoxy, R²⁴⁰ is phenyl which may be substituted or unsubstituted, and R³⁰⁰ is lower alkoxy-benzyloxy in which the benzene is substituted by lower alkoxy or is unsubstituted, or lower alkyl-cycloalkyl. The most preferred R² group is a group of the formula:

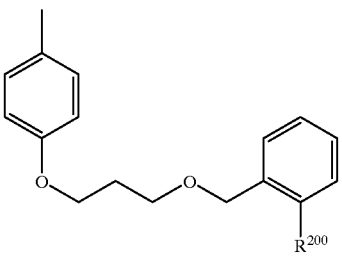

One embodiment of the invention (Embodiment A) comprises the compound of forumla I wherein R³ is hydrogen, m is 0, R² is phenyl, pyridyl, pyrimidinyl, pyrazinyl or triazolyl which are unsubstituted or para-substituted, Q is absent, X is oxygen, —CO— or —CHOR⁹— wherein R⁹ is acetyl, n is 1 and Z is lower alkylene. In Embodiment A it is particularly preferred (Embodiment A1) that X is oxygen, Z is methylene, and R¹ is naphthyl which is unsubstituted or substituted.

In Embodiment A1 it is especially preferred that the naphthyl group, R¹, is unsubstituted or substituted by lower alkoxy, hydroxy, benzyloxy wherein said benzene ring is substituted by methoxy or is unsubstituted, morpholino-lower-alkoxy, piperazino-lower alkoxy wherein the second nitrogen atom is substituted by methyl or is unsubstituted, dihyroxypropoxy, ethoxy dihydroxypropoxy, dihydroxypropoxy-lower alkyl, hydroxypropoxy-lower alkyl, hydroxyethoxy-lower alkyl, or lower alkyl di-lower alkyl amino.

An example of this especially preferred Embodiment A1 is a compound of the formula:

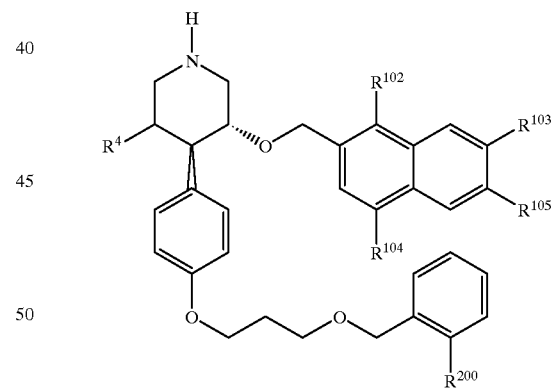

wherein R¹⁰², R¹⁰³, R¹⁰⁴ and R¹⁰⁵ are independently hydrogen, hydroxy, lower alkoxy, hydroxy lower alkoxy, methyl N,N-dimethyl amine, 2,3-dihyroxypropoxy, 2,3-dihyroxypropoxy-lower alkyl, 2,3-dihyroxypropoxy-lower alkoxy, N-methyl piperazino-N-lower alkoxy, morpholino-lower-alkoxy, benzyloxy, or methoxy-benzyloxy. R⁴ and R²⁰⁰ are as described previously, above. R¹⁰² and R¹⁰⁴ are preferably hydrogen, hydroxy, methoxy, benzyloxy or methoxybenzyloxy. It is also preferred that two, or more preferably three, of R¹⁰², R¹⁰³, R¹⁰⁴ and R¹⁰⁵ are hydrogen.

In the formula immediately above R⁴ is preferably hydrogen, hydroxy, lower alkyl hydroxy, lower alkyl-lower alkoxy, 2-oxo-lower-imidazolidin-1-yl-lower-alkyl, aminolower-alkyl-amino-lower-alkyl, 4-methyl-piperazin-1-yl-lower-alkoxy, 4-methyl-piperazin-1-yl-lower-alkyl-carbamoyloxy-lower-alkyl, hydroxy-lower-alkyl-oxy, morpholin-4-yl-lower-alkoxy, di-lower-alkyl-amino-lower-alkyl-amino-lower-alkyl, di-lower-alkyl-amino-lower-alkyl, pyridylthio-lower-alkyl, 1,2,4-triazolyl-lower-alkyl or tetrazolyl-lower-alkyl. Hydrogen is especially preferred.

Another example of Embodiment A1 is a compound of the formula:

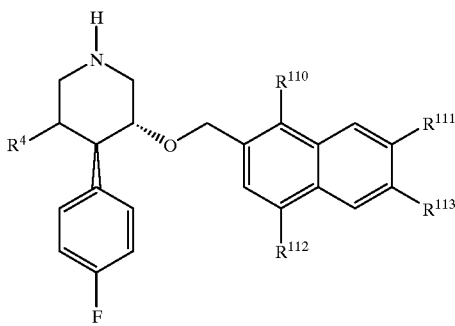

wherein $R^{110}$, $R^{111}$, $R^{112}$ and $R^{113}$ are independently hydrogen, lower alkoxy, hydroxy lower alkoxy, lower alkyl di-lower alkyl amino, 2,3-dihyroxypropoxy, 2,3-dihyroxypropoxy-lower alkyl, 2,3-dihyroxypropoxy-lower alkoxy, N-methyl piperazino-N-lower alkoxy, morpholino-lower-alkoxy, benzyloxy, and methoxy-benzyloxy. $R^4$ is as described previously, above. Preferably, $R^{112}$ is benzyloxy and $R^{110}$, $R^{111}$, $R^{113}$ are all hydrogen. In this example of the especially preferred embodiment of the invention, $R^4$ is preferably hydrogen or lower alkyl.

$R^1$ of Embodiment A may also be phenyl, which is unsubstituted or substituted (Embodiment A2). The preferred substituent is from 1–3 methoxy groups, or is ethylene dioxy. In Embodiment A2, $R^4$ is preferably hydrogen, hydroxy, or benzyloxy wherein the ring of said benzyloxy is unsubstituted or is substituted with from one to three methoxy groups.

In another variation of Embodiment A, Z is methylene and the group X is —CO— or —CHOR$^9$— where $R^9$ is acetyl (Embodiment A3). $R^9$, when present, is preferably benzoyl. In Embodiment A3, $R^2$ is preferably p-fluoro-phenyl or a group of the formula:

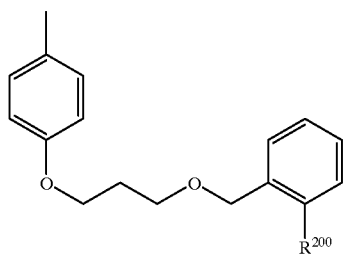

wherein $R^{200}$ is as described above.

Another embodiment of the invention (Embodiment B) comprises the compound of forumla I wherein $R^3$ is hydrogen, m is 0, $R^2$ is phenyl, pyridyl, pyrimidinyl, pyrazinyl or triazolyl which are unsubstituted or para-substituted, Q is ethylene, X is oxygen, —CO— or —CHOR$^9$— wherein $R^9$ is acetyl, n is 1 and Z is lower alkylene. In Embodiment B it is preferred (Embodiment B1) that X is oxygen, Z is methylene, and $R^1$ is naphthyl, phenyl or biphenyl which which unsubstituted or substituted. In Embodiment B1, it is especially preferred that $R^4$ is hydrogen and $R^1$ is naphthyl which is unsubstituted or substituted.

Especially preferred are the following compounds:
4-[2-[7-[(3R,4R)-4-[4-(3-benzyloxy-propoxy)-phenyl]-piperidin-3-yloxymethyl]-naphthalen-2-yloxy]-ethyl]-morpholine
(R)-3-[7-[(3R,4R)-4-[4-(3-benzyloxy-propoxy)-phenyl]-piperidin-3-yloxymethyl]-naphthalen-2-yloxy]-propane-1,2-diol
(S)-3-[7-[(3R,4R)-4-[4-(3-benzyloxy-propoxy)-phenyl]-piperidin-3-yloxymethyl]-naphthalen-2-yloxy]-propane-1,2-diol
(R)-3-[2-[7-[(3R,4R)-4-[4-(3-benzyloxy-propoxy)-phenyl]-piperidin-3-yloxymethyl]-naphthalen-2-yloxy]-ethoxy]-propane-1,2-diol
(S)-3-[2-[7-[(3R,4R)-4-[4-(3-benzyloxy-propoxy)-phenyl]-piperidin-3-yloxymethyl]-naphthalen-2-yloxy]-ethoxy]-propane-1,2-diol
1-[2-[7-[(3R,4R)-4-[4-(3-benzyloxy-propoxy)-phenyl]-piperidin-3-yloxymethyl]-naphthalen-2-yloxy]-ethyl]-4-methyl-piperazine
1-[(3R,4S-4-[4-(3-benzyloxy-propoxy)-phenyl]-piperidin-3-yl-2-naphthalen-2-yl-ethanone
(3R,4S,5S)-4-[4-(3-benzyloxy-propoxy)-phenyl]-3-(1,4-dimethoxy-naphthalen-2-ylmethoxy)-piperidin-5-ol
3R,4R)-4-[4-(3-benzyloxy-propoxy)-phenyl]-3-[7-[(R)-2,3-dihydroxy-propoxymethyl]-naphthalen-2-ylmethoxy]-piperidine
(3R,4R)-4-[4-(3-benzyloxy-propoxy)-phenyl]-3-[7-[(S)-2,3-dihydroxy-propoxymethyl]-naphthalen-2-ylmethoxy]-piperidine
(3R,4R)-4-[4-(3-benzyloxy-propoxy)-phenyl]-3-[6-[(R)-2,3-dihydroxy-propoxymethyl]-naphthalen-2-ylmethoxy]-piperidine
(3R,4R)-4-[4-(3-benzyloxy-propoxy)-phenyl]-3-[6-[(S)-2,3-dihydroxy-propoxymethyl]-naphthalen-2-ylmethoxy]-piperidine
4-[(3R,4S,5S)-4-[4-(3-benzyloxy-propoxy)-phenyl]-3-(naphthalen-2-ylmethoxy)-piperidin-5-yloxy]-butan-1-ol
3-[(3R,4S,5S)-4-[4-(3-benzyloxy-propoxy)-phenyl]-3-(naphthalen-2-ylmethoxy)-piperidin-5-yloxy]-propan-1-ol
1-{2-[(3R,4R,5S)-4-[4-(3-benzyloxy-propoxy)-phenyl]-3-(naphthalen-2-ylmethoxy)-piperidin-5-yloxy]-ethyl}-4-methyl-piperazine
(3R,4R,5S)-[4-[4(3-benzyloxy-propoxy)-phenyl]-3-(naphthalen-2-ylmethoxy)-piperidin-5-ylmethoxy]-ethyl]-morpholine
(3R,4S,5S)-4-[4-(3-benzyloxy-propoxy)-phenyl]-3-(4-methoxy-benzyloxy)-piperidin-5-ol
(3R,4s,5S)-4-[4-(3-benzyloxy-propoxy)-phenyl]-3,5-bis-(4-methoxy-benzyloxy)-piperidine
(3S,4R,5R)-4-[2-[4-[4-(3-benzyloxy-propoxy)-phenyl]-5-(naphthalen-2-ylmethoxy)-piperidin-3-ylmethoxy]-ethyl]-morpholine
(3S,4R,5R)-4-[4-(3-benzyloxy-propoxy)-phenyl]-3-methoxymethyl-5-(naphthalen-2-ylmethoxy)-piperidine
(3S,4R,5R)-4-[4-(3-benzyloxy-propoxy)-phenyl]-5-(naphthalen-2-ylmethoxy)-piperidin-3-ylmethyl [3-(4-methyl-piperazin-1-yl)-propyl]-carbamate
(3S,4R,5R)-4-[4-[4-(3-benzyloxy-propoxy)-phenyl]-5-(naphthalen-2-ylmethoxy)-piperidin-3-ylmethylsulphanyl]-pyridine
2-(4-cyclohexyl-butoxy)-5-[(3R,4R)-3-(1,4-dimethoxy-naphthalen-2-ylmethoxy)-piperidin-4-yl]-pyrimidine
(3'R,4'R)-6-(3-cyclohexyl-propoxy)-3'-(1,4-dimethoxy-naphthalen-2-ylmethoxy)-1',2',3',4',5',6'-hexahydro-[3,4']bipyridine (3S,4R,5R)-[4-[4-(3-benzyloxy-propoxy)-phenyl]-5-(naphthalen-2-ylmethoxy)-piperidin-3-yl]-methanol (3S,4R,5R)-N-[4-[4-(3-benzyloxy-propoxy)-phenyl]-5-(naphthalen-2-ylmethoxy)-piperidin-3-ylmethyl]-N,N',N'-trimethyl-ethane-1,2-diamine (3S,4R,5R)-[4-[4-(3-benzyloxy-propoxy)-phenyl]-5-(naphthalen-2-ylmethoxy)-piperidin-3-ylmethyl]-diethyl-amine 1-[(3R,4S,5S)-4-[4-(3-benzyloxy-propoxy)-phenyl]-5-(2-morpholin-4-yl-ethoxymethyl)-piperidin-3-yl]-2-naphthalen-2-yl-ethanone (3R,4R)-3-(1,4-dimethoxy-naphthalen-2-ylmethoxy)-4-[4-[3-(2-methoxy-phenoxy)-propoxy]-phenyl]-piperidine (3R,4s,5S)-4-[4-(3-benzyloxy-propoxy)-phenyl]-3,5-bis-(3,4,5-trimethoxy-benzyloxy)-piperidine (3R,4R,5S)-4-[4-(3-benzyloxy-propoxy)-phenyl]-3-(naphthalen-2-ylmethoxy)-5-[1,2,4]triazol-1-ylmethyl-piperidine (3R,4R)-4-[4-[3-(2-methoxy-benzyloxy)-propoxy]-phenyl]-3-(quinolin-7-ylmethoxy)-piperidine 2-(7-{(3R,4R)-4-[4-(3-benzyloxy-propoxy)-phenyl]-piperidin-3-yloxymethyl}-naphthalen-2-ylmethoxy)-ethanol 7-{(3R,4R)-4-[4-(3-benzyloxy-propoxy)-phenyl]-piperidin-3-yloxymethyl}-naphthalen-2-ylmethyl)-dimethyl-amine (3R,4R)-3-(4-benzyloxy-naphthalen-2-ylmethoxy)-4-(4-fluoro-phenyl)-piperidine (3'R,4'R)-3'-(1,4-dimethoxy-naphthalen-2-ylmethoxy)-6-[3-(2-methoxybenzyloxy)-propoxy]-1',2',3',4',5',6'-hexahydro-[3,4']bipyridine (3R,4R)-3-(1,4-dimethoxy-naphthalen-2-ylmethoxy)-4-[4-[3-(2-methoxy-benzyloxy)-propoxy]-phenyl]-piperidine (3S,4R,5R)-1-[4-[4-(3-benzyloxy-propoxy)-phenyl]-5-(naphthalen-2-ylmethoxy)-piperidin-3-ylmethyl]-imidazolidin-2-one (3R,4R)-4-[4-[3-(2-methoxy-benzyloxy)-propoxy]-phenyl]-3-(2-oxo-1,2-dihydro-quinolin-7-ylmethoxy)-piperidine (3R,4R)-3-(isoquinolin-7-ylmethoxy)-4-[4-[3-(2-methoxy-benzyloxy)-propoxy]-phenyl]-piperidine (3R,4R)-4-[4-[3-(2-methoxy-benzyloxy)-propoxy]-phenyl]-3-(1,2,3,4-tetrahydro-quinolin-7-ylmethoxy)-piperidine 1-[2-[7-[(3R,4R)-4-[4-[3-(2-methoxy-benzyloxy)-propoxy]-piperidin-3-yloxymethyl]-naphthalen-2-yloxy]-ethyl]-4-methyl-piperazine 1-[2-[7-[(3R,4S,5S)-5-hydroxy-4-[4-[-3-(2-methoxy-benzyloxy)-propoxy]-piperdin-3-yloxymethyl]-naphthalen-2-yloxy]-ethyl]-4-methyl-piperazine (3R,4S,5S)-3-(1,4-dimethoxy-naphthalen-2-ylmethoxy)-4-[4-[3-(2-methoxy-benzyloxy)-propoxy]-phenyl]-piperidin-5-ol (3R,4R,5S)-3-(1,4-dimethoxy-naphthalen-2-ylmethoxy)-4-{4-[3-(2-methoxy-benzyloxy)-propoxy]-phenyl}-5-(1H-tetrazol-5-ylmethyl)-piperidine (3'S,4'S)-3'-(1,4-dimethoxy-naphthalen-2-ylmethyoxy)-4-[S-(2-methoxy-benzyloxy)-propoxy]-1',2',3',4',5',6'-hexahydro-[1,4']bipyridin-2-one The term "pharmaceutically usable salts" embraces salts with inorganic or organic acid such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like.

The compounds of formula I can be manufactured in accordance with the invention by cleaving off the protecting group(s) from a compound of formula II

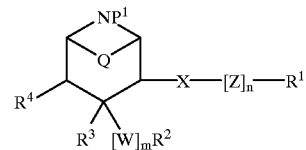

II in which $P^1$ is a protecting group and the remaining symbols have the significance given in claim 1 and hydroxy groups which may be contained in $R^1$, $R^2$ and $R^4$ may be present in protected form, if desired, functionally modifying reactive groups in the thus-obtained compound of formula I and/or converting the compound of formula I into a pharmaceutically usable salt, with the manufacture of 4-(4-fluorophenyl)-3-(3,4-methylenedioxy-benzyloxy)piperidine and its hydrochloride being excluded.

The cleavage of a protecting group $P^1$ and hydroxy protecting groups which may be present can be carried out in a manner known per se. Examples of protecting groups $P^1$ are usual amino protecting groups such as tert-butoxycarbonyl, benzyloxycarbonyl, vinyloxycarbonyl, alkylsilylalkyloxycarbonyl such as 2-(trimethylsilyl) ethoxycarbonyl, and trichloroethoxycarbonyl. Examples of hydroxy protecting groups are ether protecting groups such as tetrahydropyranyl, allyl, 2-(trimethylsilyl)ethoxymethyl, trityl, tert-butyldimethylsilyl or ester protecting groups such as acetyl.

The cleavage of these protecting groups is effected by acidic or basic hydrolysis, by hydrogenolysis, by reductive methods or by means of Lewis acids. A solution of a mineral acid such as hydrochloric acid, hydrobromic acid, sulphuric acid, phosphoric acid and the like in an inert solvent or solvent mixture is advantageously used for the acidic hydrolysis. Suitable solvents are alcohols such as methanol or ethanol, ethers such as tetrahydrofuran or dioxan, chlorinated hydrocarbons such as methylene chloride, and the like. Alkali metal hydroxides and alkali metal carbonates such as potassium hydroxide or sodium hydroxide or potassium carbonate or sodium carbonate, organic amines such as piperidine, and the like can be used for the basic hydrolysis. Inert organic solvents as referred to above for the acidic hydrolysis can be used as solubilizers. The reaction temperature for the acidic and basic hydrolysis can be varied in a range from 0° C. to the reflux temperature, with the reaction preferably being carried out at between about 0° C. and room temperature. The tert-butoxycarbonyl group is conveniently cleaved off with hydrochloric acid, hydrogen chloride, trifluoroacetic acid or formic acid in the presence or absence of an inert solvent. Furthermore, the tert-butoxycarbonyl group can be cleaved off by means of anhydrous zinc bromide in the presence of an inert solvent, preferably methylene chloride. The cleavage of the trichloroethoxycarbonyl group can be advantageously effected reductively with zinc in glacial acetic acid. The reaction temperature can lie in a range of 0° C. to 40° C., with the reaction preferably being carried out at room temperature. The cleavage of the 2-(trimethylsilyl)ethoxycarbonyl group can be effected by means of fluoride ions in the presence of an inert solvent such as acetonitrile, dimethyl sulphoxide, dimethylformamide or tetrahydrofuran, preferably by means of tetrabutyl-ammonium fluoride in tetrahydrofuran, at temperatures from about 0° C. to about room temperature.

The compounds of formula II are novel and are also an object of the invention. Their preparation is described in more detail hereinafter in Schemes 1–15 and in the Examples.

Scheme 1

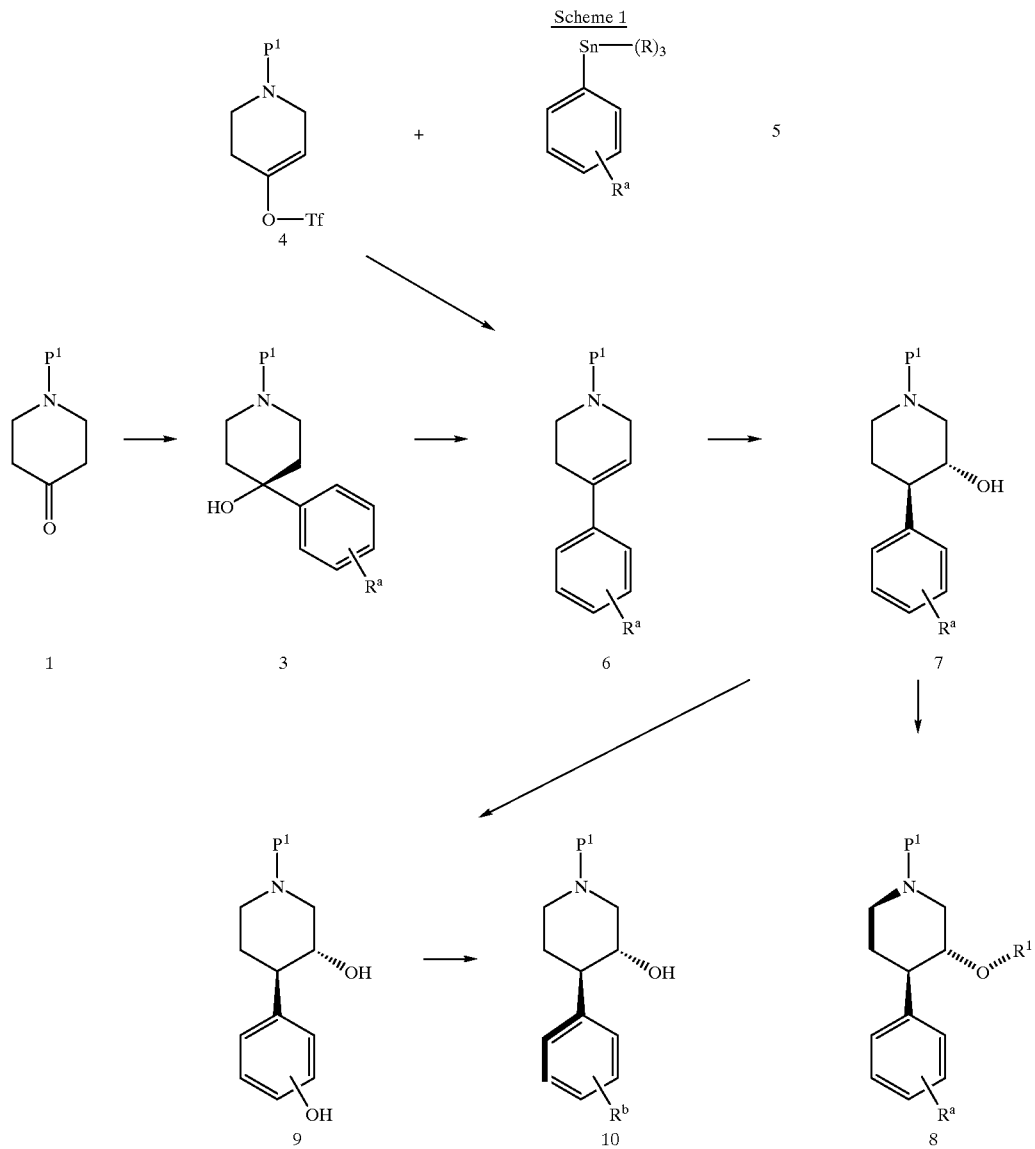

In accordance with Scheme 1 compounds of general formula 3 can be obtained by reacting compounds of general formula 1 in a manner known per se with metal-organic derivatives, preferably lithium or magnesium derivatives, prepared from compounds of general formula 2

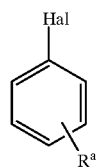

2 wherein $R^a$ is hydrogen or a substituent which is inert under the reaction conditions or in which reactive groups are present in protected form. Preferably, compounds 2 in which $R^a$ is halogen, lower-alkoxy or benzyloxy are used and these substituents are utilized for the synthesis of another desired substituent at an appropriate later stage of the reaction sequence.

The reaction with such a metal-organic compound is effected according to methods known per se, for example in a solvent which is inert under the reaction conditions, such as an ether, at a temperature between about −78° C. and 75° C. The compounds of general formula 6 can be obtained therefrom in the presence of an acid or another water-cleaving reagent, optionally in the presence of a base, in an organic solvent. As acids there come into consideration, e.g., hydrochloric acid, trifluoroacetic acid or p-toluenesulphonic acid, and as the water-cleaving reagent there can be used, e.g., phosphorus oxytrichloride in pyridine. The reaction temperature lies between 0–120° C.; as solvents there can be used, e.g., toluene, dimethylformamide or alcohols.

Compounds of general formula 6 can also be obtained directly starting from a compound of general formula 4 in which Tf is an activating group such as trifluoromethylsulphonyl (triflate) by reaction with a metal-organic compound, especially a tin derivative of general formula 5 in which R is lower-alkyl, e.g., butyl, or a corresponding arylboric acid derivative using a suitable catalyst such as, e.g., tetrakistriphenylphosphinepalladium in an inert solvent such as dioxan, dimethoxyethane or dimethylformamide at temperatures between room temperature and 150° C.

Compounds of general formula 7 can be obtained from compounds of general formula 6 by hydroboration and subsequent basic oxidative working-up. The hydroboration can be effected according to methods known per se, for example in a solvent which is inert under the reaction conditions, such as an ether, e.g., 1,2-dimethoxyethane, at a temperature between about 0° C. and 70° C., and with a diborane-containing or diborane-liberating reagent such as, e.g., borane in tetrahydrofuran or a mixture of sodium borohydride and boron trifluoride etherate. The carboboranes which are formed as intermediates can be converted into the secondary alcohols of general formula 7 by reaction with bases, e.g., potassium hydroxide, and an oxidizing agent, e.g., hydrogen peroxide, at a temperature between about room temperature and 120° C.

Compounds of general formula 8 in which $R^a$ is halogen, cyano, trifluoromethyl, lower-alkyl, lower-alkoxy-lower-alkyl, lower-alkoxy or lower-alkylenedioxy can be obtained from 7 by alkylation with a compound which yields the group $R^1$. The alkylation of the secondary alcohol is effected according to methods known per se, for example in a solvent which is inert under the reaction conditions, such as an ether, e.g., tetrahydrofuran or 1,2-dimethoxyethane, or dimethylformamide, with the aid of an alcoholate-forming base, e.g., sodium hydride, at a temperature between about 0° C. and 40° C. and using a halide, preferably chloride or bromide, or a sulphonic acid ester, e.g., a mesylate or tosylate, as the compound which yields $R^1$. Compounds of formula 7 in which $R^a$ is lower-alkoxy can be converted into compounds of general formula 9 by an alkyl-aryl ether cleavage. The ether cleavage is effected according to methods known per se by, preferably starting from compounds in which $R^a$ has the meaning methoxy, reacting the alkyl-aryl ether with mineral acids such as hydrobromic acid or hydroiodic acid or preferably with Lewis acids such as boron trichloride or boron tribromide in a solvent which is inert under the reaction conditions, such as, e.g., a halogenated hydrocarbon, at a temperature between about −10° C. and room temperature.

Compounds of general formula 9 can be used as starting materials for the preparation of compounds of general formula 10 in which $R^b$ is a group $-T^1-L^2-T^2-L^3-T^3-L^4-T^4-U$, $T^1$ is oxygen, (m), (o) or (p) and the remaining symbols $L^{2,3,4}$, $T^{2,3,4}$ and U can have the meanings referred to earlier. The linkage of the group $-L^2-T^2-L^3-T^3-L^4-T^4-U$ can be effected selectively by reaction with a derivative of the group to be introduced which carries a suitable leaving group, although the desired group can also be built up stepwise. The selective linkage with the phenolic alcohol is effected according to alkylation or acylation methods which are known per se in the presence of a base such as potassium carbonate. Chlorides, bromides, iodides, tosylates or mesylates come into consideration as alkylating agents. The reaction is effected in a solvent which is inert under the reaction conditions, such as, e.g., an ether such as tetrahydrofuran or an aromatic hydrocarbon such as, e.g., toluene, pyridine, acetone or methyl ethyl ketone, at a temperature between about 0° C. and 100° C. Suitable acylating agents are activated derivatives such as optionally activated esters, acid halides, acid anhydrides or mixed acid anhydrides. The reaction is effected in a solvent which is inert under the reaction conditions, such as, e.g., an ether such as tetrahydrofuran, an aromatic hydrocarbon such as, e.g., toluene, a chlorinated hydrocarbon such as methylene chloride or chloroform, and the like at a temperature between about 0° C. and 50° C.

Reactive groups such as keto or hydroxy groups contained in addition to the leaving group in the group to be introduced are preferably present in a form which is protected in a suitable manner, e.g., in the form of acetals, esters, carbamates, silyl derivatives and the like. After cleavage of these protecting groups a stepwise synthesis of the group $-T^1-L^2-T^2-L^3-T^3-L^4-T^4-U$ can be continued. The thus-obtained compounds containing a hydroxy group in the piperidine ring can be alkylated as described above for the conversion of 7 into 8.

Scheme 2

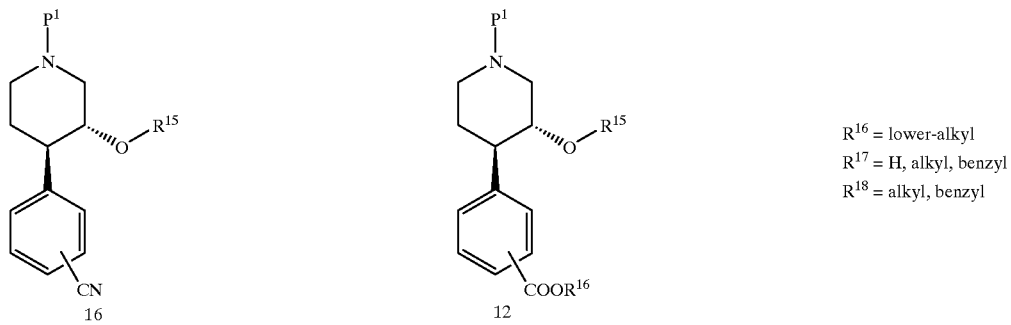

$R^{16}$ = lower-alkyl
$R^{17}$ = H, alkyl, benzyl
$R^{18}$ = alkyl, benzyl

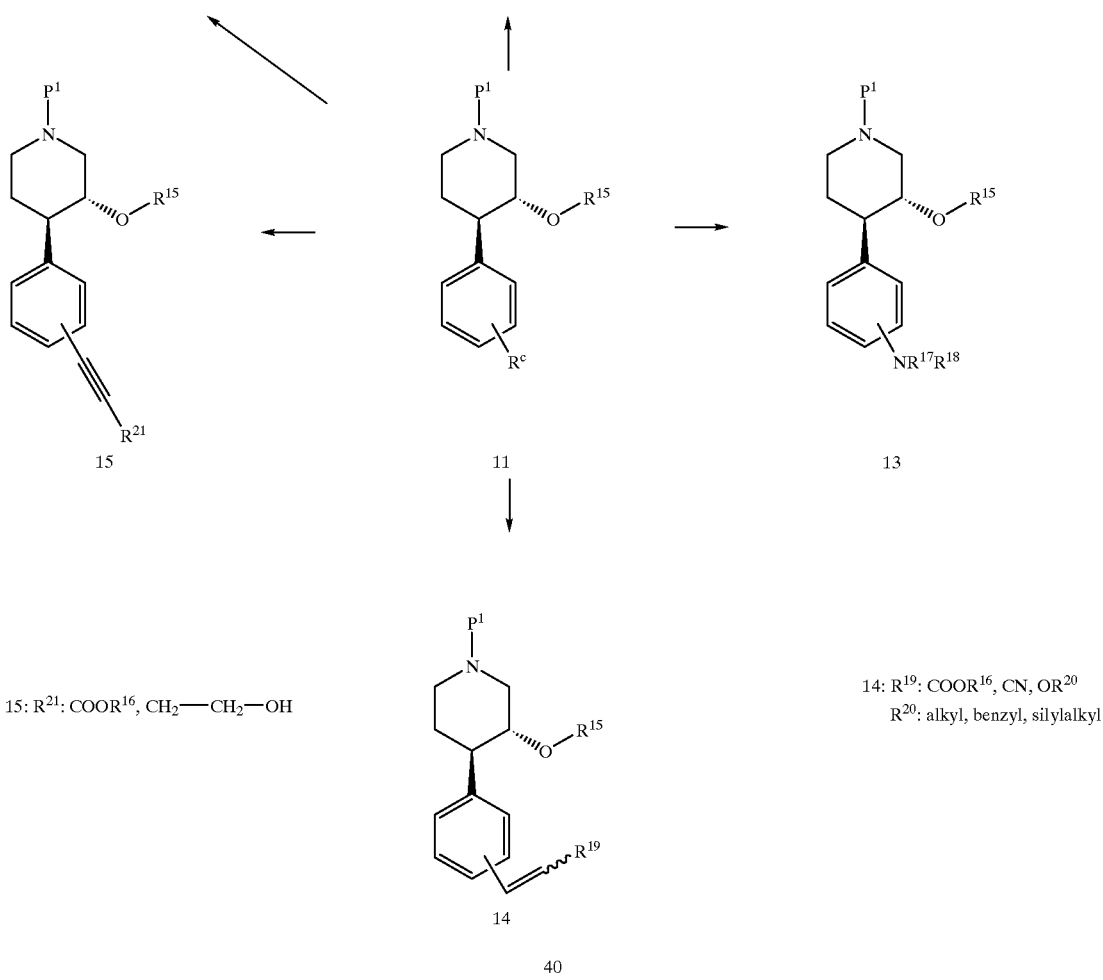

15: $R^{21}$: $COOR^{16}$, $CH_2$—$CH_2$—OH

14: $R^{19}$: $COOR^{16}$, CN, $OR^{20}$
$R^{20}$: alkyl, benzyl, silylalkyl

Compounds of formulae 12–16 can be prepared in accordance with Scheme 2 starting from compounds of general formula 11 in which $R^c$ is chlorine, bromine, iodine as well as hydroxy in the form of an activated derivative such as, e.g., the triflate and $R^{15}$ is hydrogen or a group which is inert under the reaction conditions by carrying out palladium-catalyzed couplings in a manner known per se with carbon monoxide, cyanides, amines or compounds of the general formulae

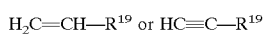

$H_2C$=CH—$R^{19}$ or HC≡C—$R^{19}$ wherein $R^{19}$ is —$COOR^{16}$, —CN or —$OR^{20}$.
As palladium catalysts there can be used complexes, prepared in situ, of, e.g., $PdCl_2(CH_3CN)_2$ or $Pd(OAc)_2$ with 1,1'-bis(diphenylphosphino)ferrocene, 1,3-bis(diphenylphosphino)propane or tri(o-tolyl)phosphine. The group —HC=CH—$R^{19}$ or —C≡C—$R^{19}$ in the thus-obtained compounds can be derivatized for a further stepwise synthesis of a substituent $L^1$-$T^1$-$L^2$-$T^2$-$L^3$-$T^3$-$L^4$-$T^4$-U. A C≡C triple bond can be converted into a double bond and the latter can be converted into a single bond. A cyano group can be converted into an amide, an aldehyde, an acid, an ester or an amine. Compounds of formula 13 with $R^{17,18}$= benzyl can be debenzylated and the thus-formed sec. or prim. amino group can also be utilized for a further derivatization. All of these transformations or derivatizations, which are presented in a non-limiting manner in Schemes 3–9, can be undertaken according to methods known per se.

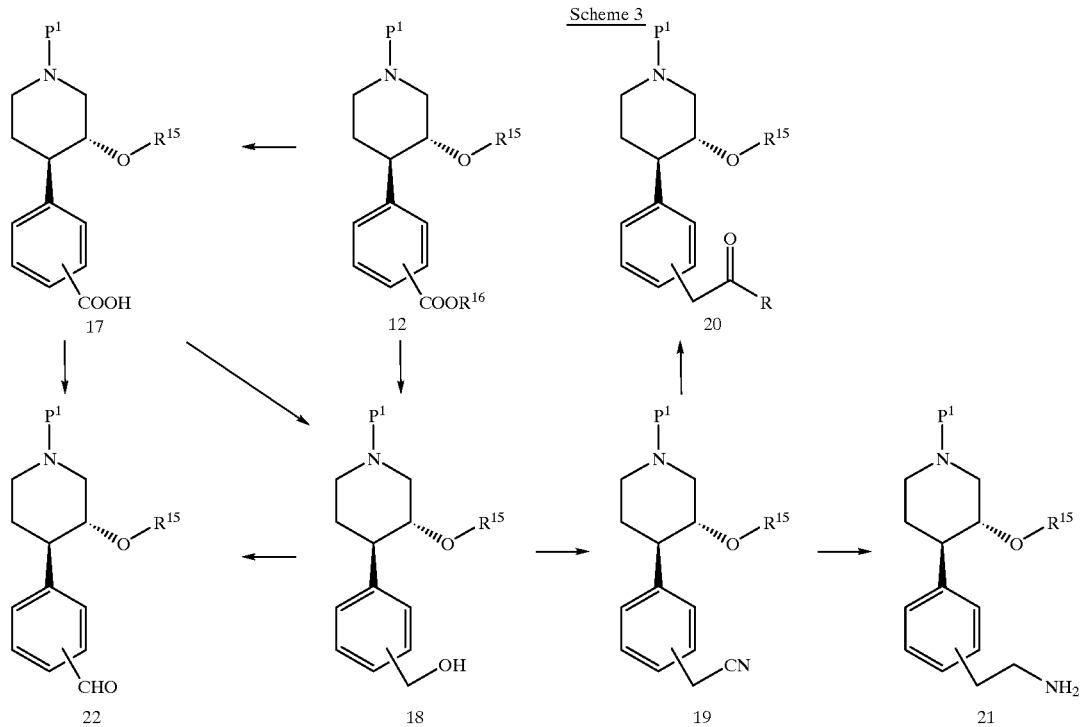
Scheme 3
Compounds of general formulae 17–22 can be obtained in accordance with Scheme 3 from compounds of general formula 12, obtained by reaction of compounds of general formula 11 with carbon monoxide by means of palladium catalysis.
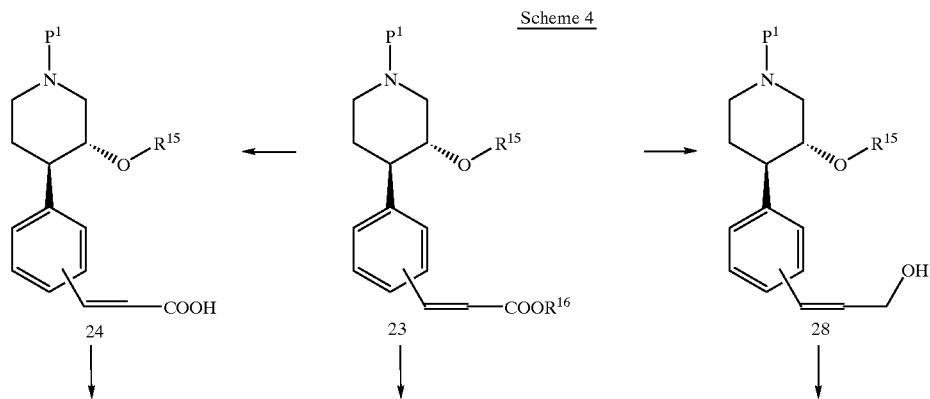
Scheme 4

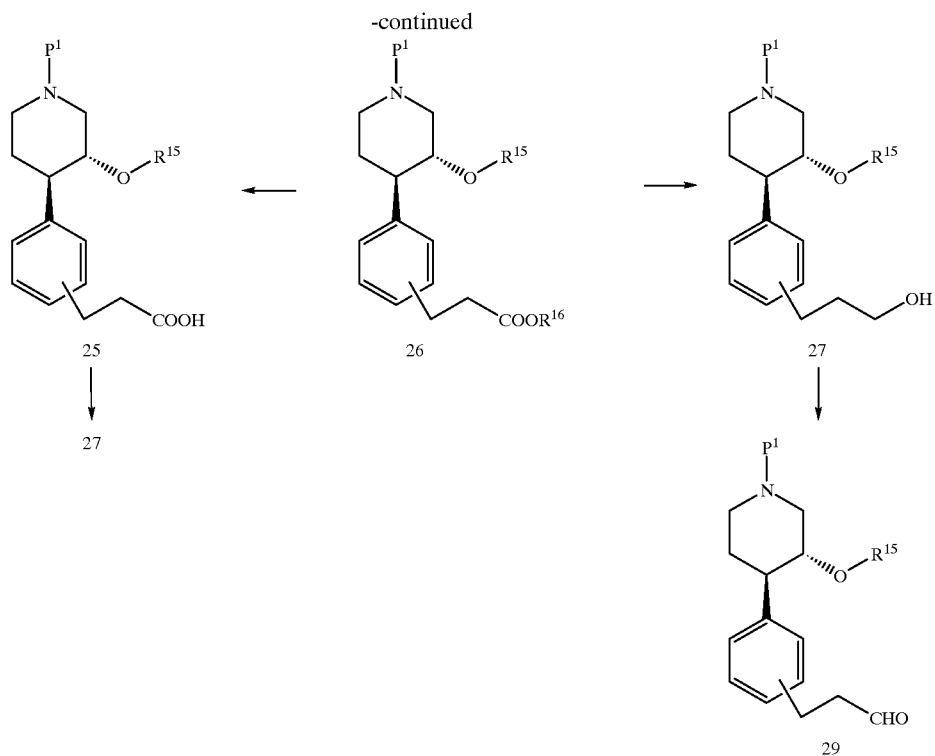
Compounds of general formulae 24–29 can be obtained in accordance with Scheme 4 from compounds of general formula 23, obtained by reaction of compounds of general formula 11 with acrylic acid esters by means of palladium catalysis.
Scheme 5
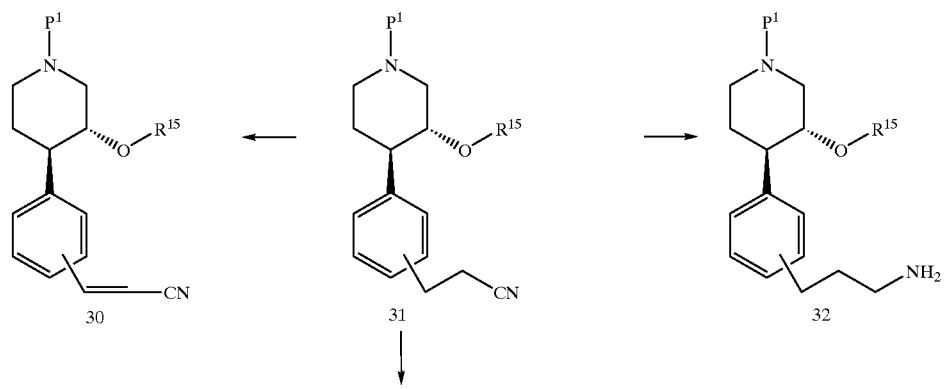

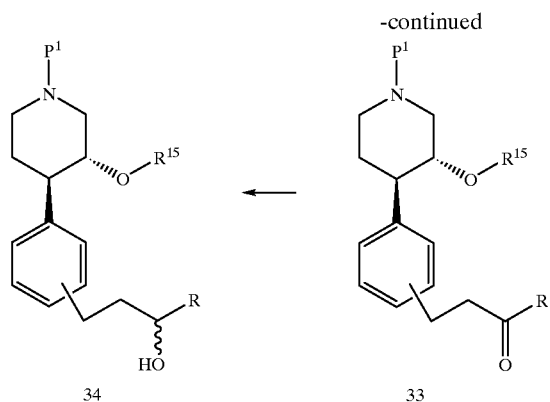
Compounds of general formulae 31–34 can be obtained in accordance with Scheme 5 from compounds of general formula 30, obtained by reaction of compounds of general formula 11 with acrylonitrile by means of palladium catalysis.
Scheme 6
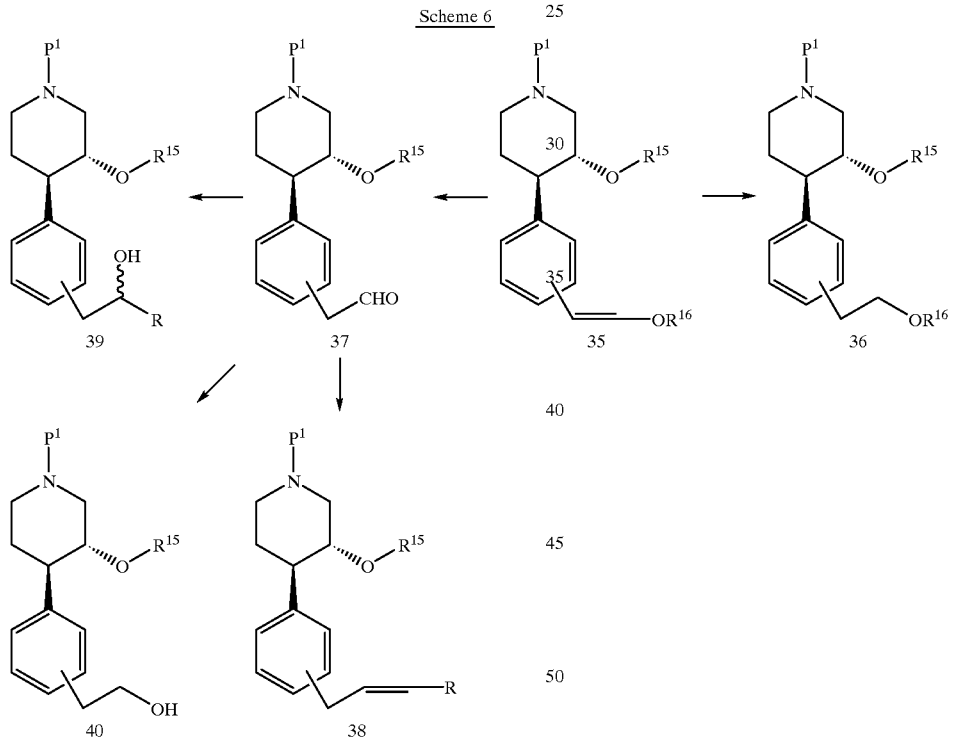

Compounds of general formulae 36–40 can be obtained in accordance with Scheme 6 from compounds of general formula 35, obtained by reaction of compounds of general formula 11 with vinyl ethers by means of palladium catalysis.

The piperidones of general formula 41 can be used as starting materials for the synthesis of the piperidine derivatives I analogously as described for the piperidone 1. They can be obtained analogously to the process of A. H. Beckett et al described in the Journal of Medicinal and Pharmaceutical Chemistry Vol 1(1), 37–58 (1959). The piperidones of general formula 41 can be obtained by intramolecular ring-closure of a propionic acid derivative of general formula 42,

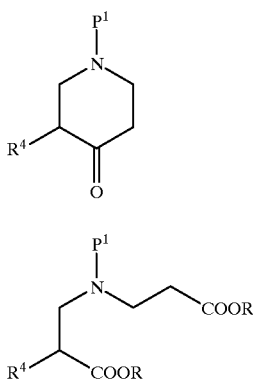

in which $R^4$ is as defined earlier or is a substituent, which is inert under the reaction conditions or wherein reactive groups are present in an appropriately protected form. Preferably, $R^4$ is choosen in a manner to make it possible to optionally construe another desired substituent at an appropriate later stage of the reaction sequence. $P^1$ has the meaning of methyl or benzyl. The ring closure is carried out in the presence of a base such as, e.g., sodium alcoholate, sodium hydride or sodium dispersion in xylene. The subsequent decarbalkoxylation of a thus-obtained compound of general formula 43 or 44

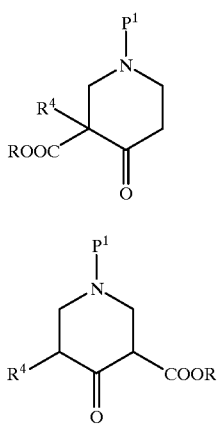

by means of hydrochloric acid leads to compounds of general formula 41.

Derivatives of general formula 43 in which $R^4$ signifies allyl or benzyl can also be prepared in a direct manner by C-alkylation of the sodium salt of a compound of general formula 45

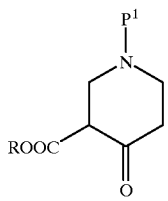

by means of allyidimethylanilinium bromide or benzyldimethylanilinium bromide analogously to the process described by A. H.Beckett et al. (see above).

Derivatives of general formula 41 in which $R^4$ signifies hydroxymethyl which is suitably protected at the hydroxy function can also be obtained from the compound of general formula 45 by reduction to the diol analogously to the process described by E.Jaeger und J. H.Biel in J.Org.Chem. 30(3), 740–744 (1965), introduction of a suitable protecting group for the primary alcohol, e.g., trityl, and oxidation of the secondary alcohol obtained.

Furthermore, derivatives of general formula 46 can be prepared by hydroxymethylating compounds of general formula 6 analogously to the process of K. Willcocks et al. described in the Journal of Labelled Compounds and Radiopharmaceuticals Vol. XXXIII, No.8, 783–794 (1993).

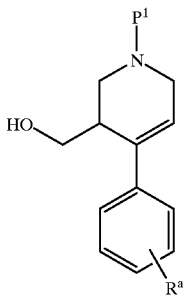

Compounds of general formula II in which $R^3$ has the meaning hydrogen and W has the meaning oxygen or sulphur can be obtained starting from compounds of general formula 47

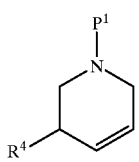

by epoxidation. Compounds of general formula 47 can be prepared according to the process described by M.Ferles and M.Jankovsky in Coll.Czechoslov.Chem.Commun. Vol, 35, 2802–2809 (1970). The epoxides can then be opened by reaction with suitable thiophenolates and phenolates as described by R. Paioni in German Offenlegungsschrift 2738477. The further synthesis to compounds of formula II can be effected as described previously.

Scheme 7

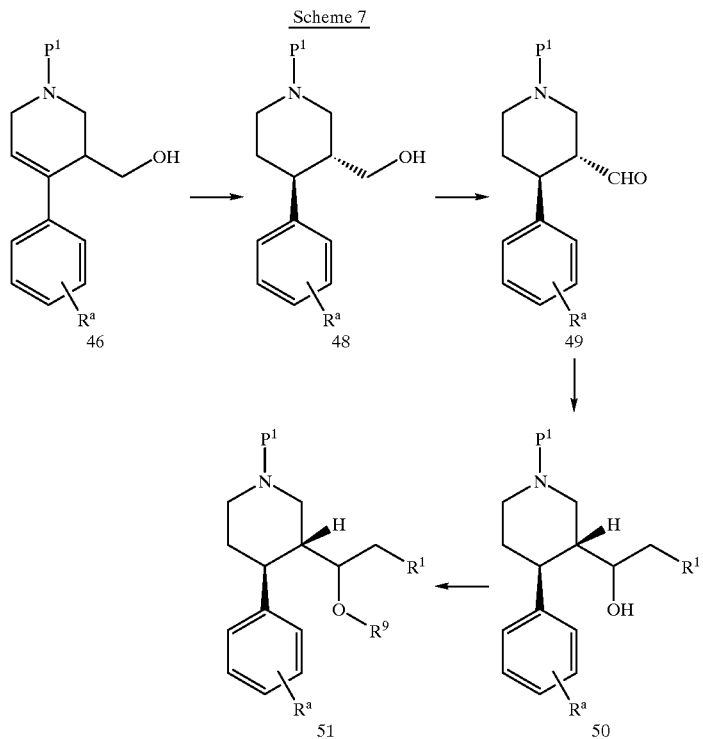

In accordance with Scheme 7 compounds of general formula 51 can be obtained from compounds of general formula 46 by firstly reducing the double bond using complex hydrides such as lithium aluminium hydride as described by J. M. Lundbeck et al. in European Patent Application E.P. 0 374 674 or sodium dihydrido-bis-(2-methoxyethoxy)aluminate in a solvent which is inert under the reaction conditions, such as tetrahydrofuran, dioxan or toluene, at temperatures between room temperature and 110° C. or hydrogenating the double bond with hydrogen using a catalyst, with compounds of general formula 48 being obtained. Compounds of general formula 48 can be converted into the corresponding aldehydes of general formula 49 by a usual oxidation process, e.g., using oxalyl chloride and dimethyl sulphoxide as described by A. J. Mancuso and D. Swern in Synthesis 1981, 165.

The condensation of aldehydes of general formula 49 with Grignard or lithium compounds in a solvent which is inert under the reaction conditions, such as ether, tetrahydrofuran or dioxan, at temperatures between −80° C. and room temperature leads to compounds of general formula 50 which can be converted according to known processes into the corresponding ester or ether compounds of general formula 51.

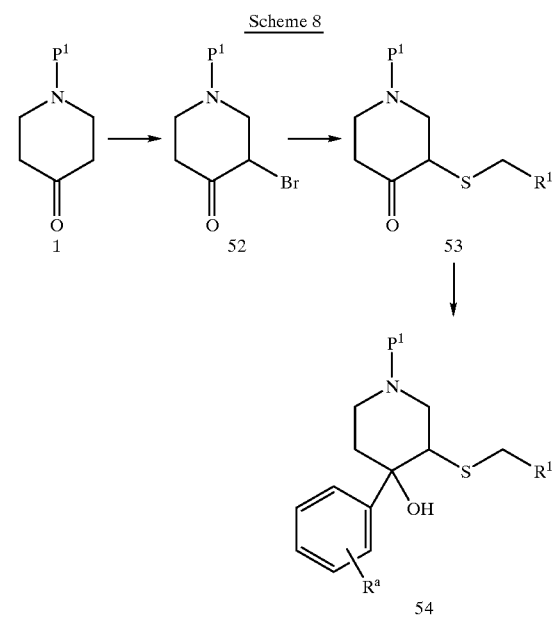

Scheme 8

In accordance with Scheme 8 compounds of general formula 54 are obtained by brominating compounds of general formula 1 in a solvent which is inert under the reaction conditions, such as chloroform or methylene chloride, and using a buffer salt such as disodium hydrogen phosphate at temperatures between 0° C. and 50° C. to firstly form compounds of general formula 52, reaction of which with an alkali metal salt of a thiol in a solvent such as acetone, acetonitrile or dimethylformamide at temperatures between room temperature and 100° C. gives compounds of general formula 53. Condensation of these with Grignard or lithium compounds in inert solvents such as ether, tetrahydrofuran or dioxan at temperatures between −80° C. and room temperature then yields compounds of general formula 54.

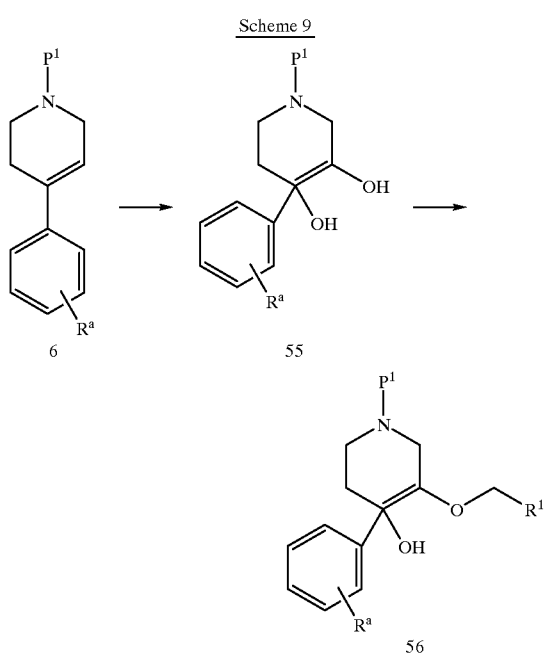

In accordance with Scheme 9 compounds of general formula 56 can be obtained by dihydroxylating compounds of general formula 6 to compounds of general formula 55. Alkylation of these yields, according to previously described processes, compounds of general formula 56. The dihydroxylation can be effected according to processes known per se, for example in a solvent which is inert under the reaction conditions, such as acetone or tert-butanol, at a temperature between 0° C. and 50° C., preferably at room temperature, with a hydroxylating reagent such as, e.g., a mixture of osmium tetroxide and hydrogen peroxide.

The compounds prepared in Schemes 2–9 can, moreover, be used as described above as starting materials for a further synthesis of a substituent

-L$^1$-T$^1$-L$^2$-T$^2$-L$^3$-T$^3$-L$^4$-T$^4$-U optionally present in R$^2$.

Furthermore, compounds of general formula II in which an ethylene bridge Q is present can be prepared in accordance with the processes described in Schemes 1–9 as well as the processes described hereinbefore and in more detail in the Examples.

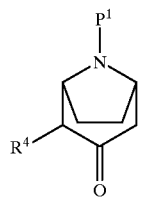

The tropinones of general formula 57 usable as starting materials can be prepared, inter alia, according to the processes described by M.Lounasmaa and C. J.Johansson in Tetrahedron Letters, No.29, 2509 (1974) or Ö.Kovács et al. in Helv.Chim.Acta Vol. XXXVII, 802 (1954).

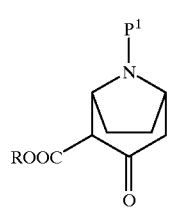

Derivatives of general formula 57 can be obtained from the compound of general formula 58 according to the process described by Ö.Kovács et al. in Helv.Chim.Acta Vol. XXXVII, 802 (1954) by reduction to the diol, introduction of a suitable protecting group for the primary alcohol, e.g., trityl, and oxidation of the secondary alcohol obtained. Herein, R$^4$ is as defined earlier or is a substituent which is inert under the raction conditions or wherein any reactive groups are present in protected form and are preferably choosen in a manner to make the construction of another desired substituent at an appropriate, later stage of the raction sequence possible.

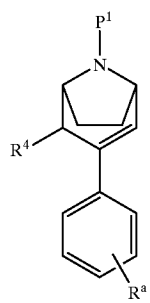

Furthermore, derivatives of general formula 59 in which R$^4$ signifies hydroxymethyl can be prepared by hydroxymethylating compounds of general formula 60 analogously to the process of K.Willcocks et al. described in Journal of Labelled Compounds and Radiopharmaceuticals Vol. XXXIII, No.8, 783–794 (1993).

Furthermore, there exists the possibility of preparing derivatives of general formula 57 starting from correspondingly substituted acetonedicarboxylic acid derivatives by a reaction with succindialdehyde and an amine analogously to procedures known in the literature, with the corresponding tropinone derivative being synthesized. The substituted acetonedicarboxylic acid derivatives used as starting materials can be prepared according to the procedures described by I.Ito and S. I.Nagai in Chem.Pharm.Bull. 22(9) 2131 (1974) or T.Arslan and S. A.Benner in J.Org.Chem. 58, 2260 (1993).

general formula LXI can be formed from olefins 6, for example, via a bromohydrin which is formed as an intermediate and which can be obtained by the addition of bromine in aqueous dioxan. Subsequently, the bromohydrin can be ring-closed to the epoxide 61 by the addition of aqueous sodium hydroxide solution. Treatment of such an oxirane with methyllithium, butyllithium or a lithium amide in aprotic solvents such as ether or tetrahydrofuran at temperatures between −80° C. and +60° C. leads to allyl alcohols 62 which, with a free OH or after the introduction of an ether function $R^{20}$, can be further processed. Hydroboration of these allyl alcohol derivatives 62, as described earlier for the preparation of compounds of general formula 7, yields the free or monofunctionalized dihydroxy derivatives 63. For the structural variation of the group $R^{20}$

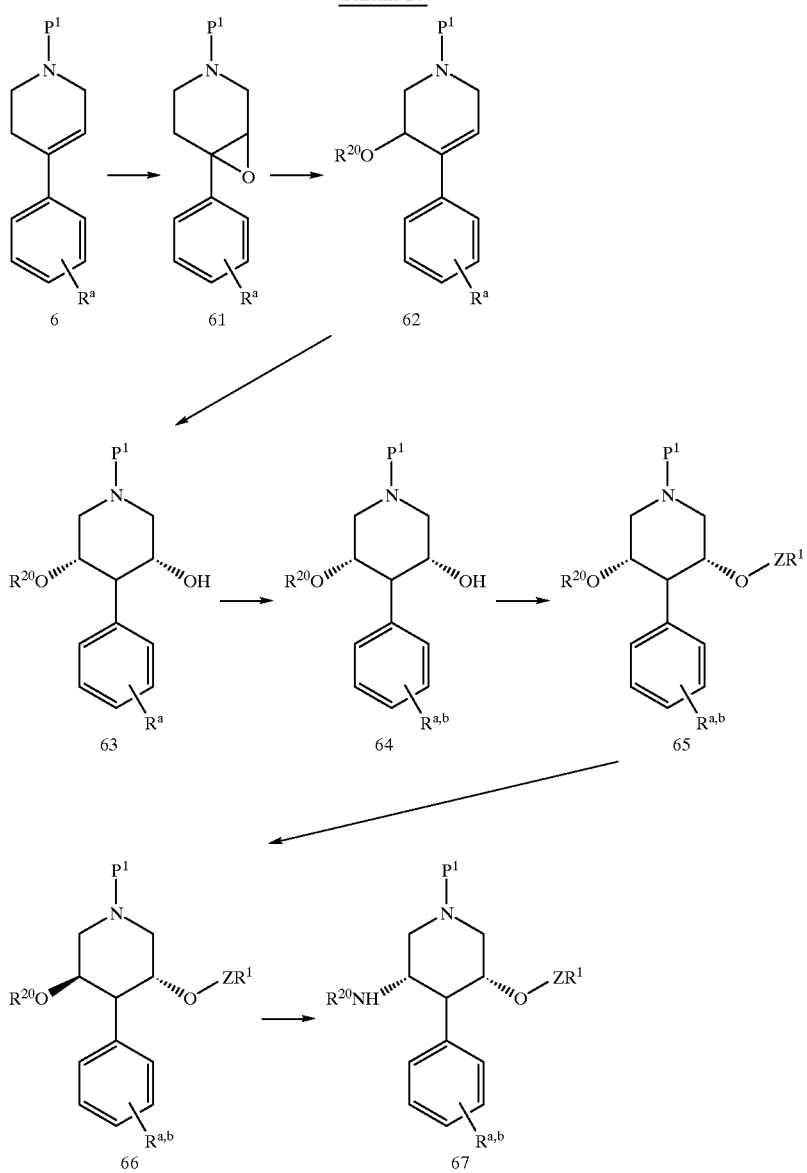

Scheme 10

One possible synthetic route to 4-aryl-piperidines which are substituted in each of positions 3 and 5 with O or N atoms is shown in Scheme 10. Oxirane compounds of ($R^{4a}Z^{1}$— or H), —$ZR^{1}$ and $R^{a}$, depending on the target molecule being prepared, groups $R^{20}$ and —$ZR^{1}$ can be introduced in a different sequence and group $R^{a}$ can be modified to $R^b$, a group of the general formula -$T^1$-$L^2$-$T^2$-$L^3$-$T^3$-$L^4$-$T^4$-U. It can be advisable to provide one of the two OH functions intermediately with a protecting group and to cleave this off at a later stage of the synthesis or to choose the groups —$ZR^1$ and $R^{20}$ such that, if desired, it is possible to synthesize another desired substituent at a suitable later stage of the reaction sequence. Starting from monoether-protected derivatives 65 the free OH function can, for example, be stereochemically inverted by reaction with formic acid, triphenylphosphine and an azodicarboxylic acid ester in an inert solvent such as tetrahydrofuran according to Mitsunobu [Synthesis 1981, 1], with compounds of general formula 66 being obtained. The use of diphenylphosphoryl azide in place of formic acid under similar conditions provides a possibility of introducing, starting from compounds 66 by a renewed inversion at the same centre, an azido function which can be converted into a primary amino function, for example, by reduction with triphenylphosphine/water in tetrahydrofuran at temperatures between room temperature and 80° C. [Synth. Commun. 17, 377 (1987)]. There are thus obtained compounds of general formula 67, which can be subsequently alkylated or acylated.

Scheme 11

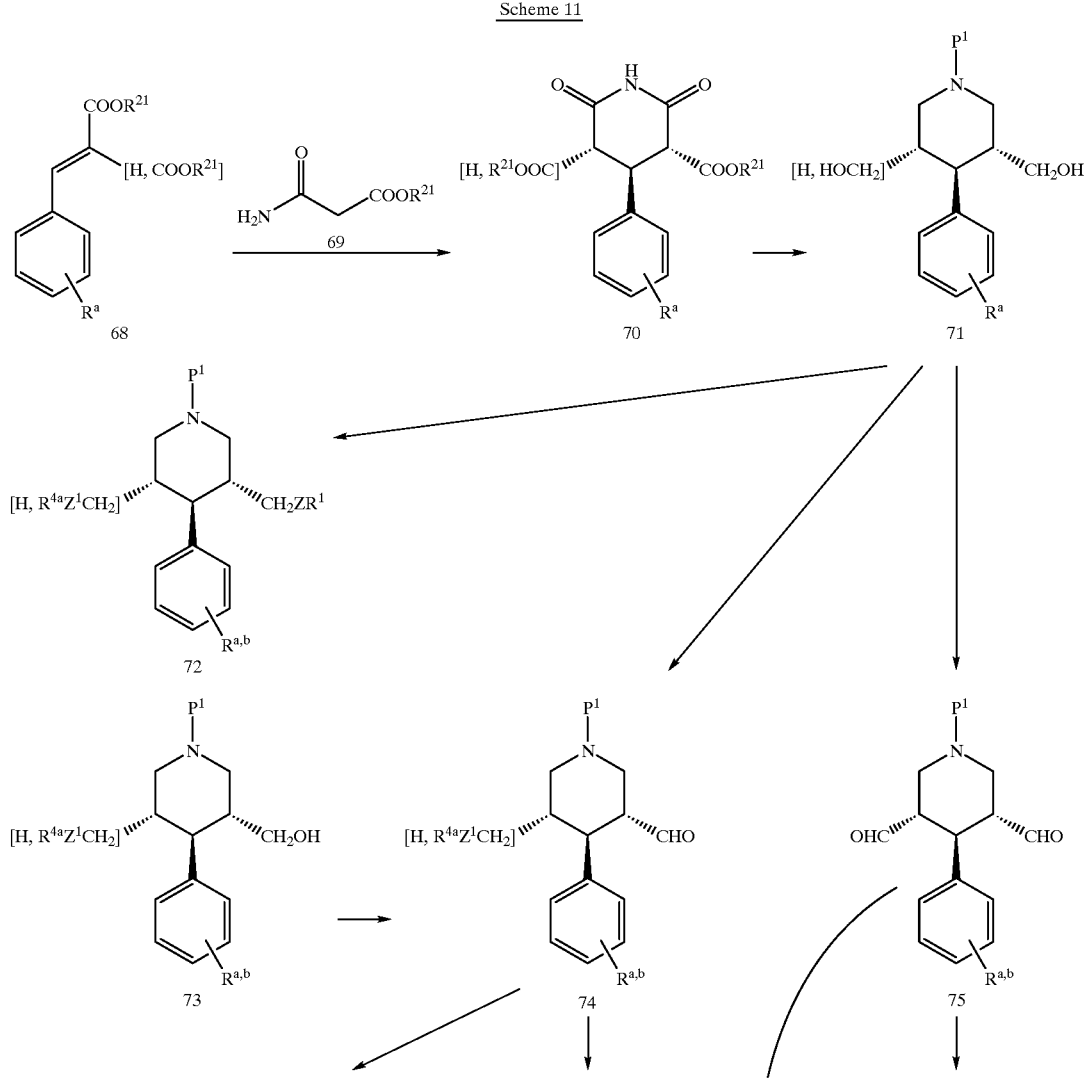

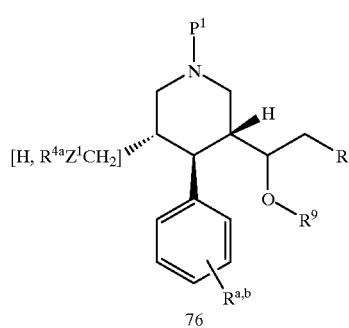
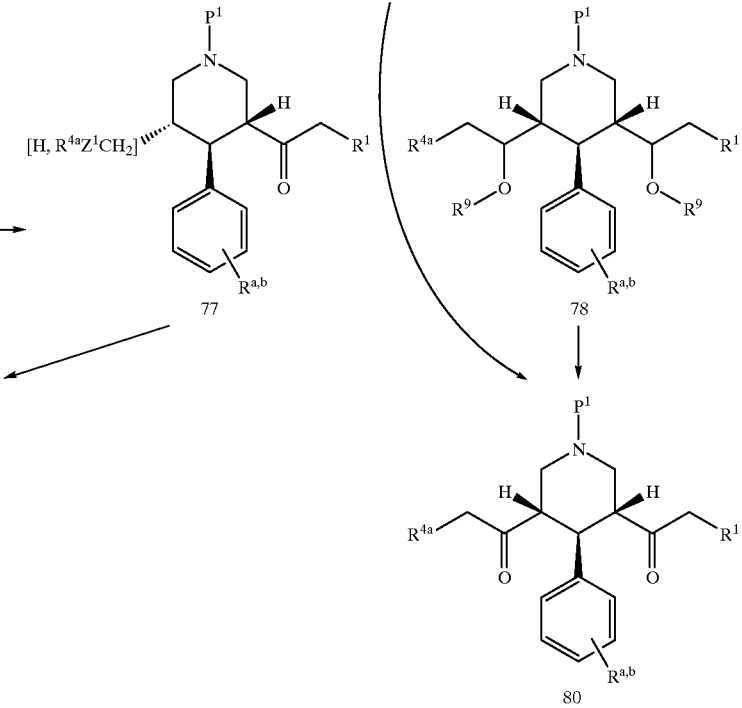

In accordance with Scheme 11 cinnamic acid derivatives 68, which are known from the literature, can be converted with malonic acid monoester monoamides 69 in protic solvents such as ethanol or methanol or aprotic solvents such as N,N-dimethylformamide, dimethyl sulphoxide, tetrahydrofuran or acetonitrile using bases such as, for example, potassium tert-butylate or sodium hydride at temperatures between room temperature and 130° C. into cyclic imides 70. Reduction of these imides 70 with hydride reducing reagents such as lithium aluminium hydride, diisobutyl aluminium hydride or sodium dihydrido-bis-(2-methoxyethoxy)aluminate in aprotic solvents such as ethers, tetrahydrofuran or dioxan at temperatures between room temperature and 120° C. yields the piperidine mono- and dimethanols 71, which can be provided at the piperidine nitrogen with a suitable protecting groups. Mono- and dihydroxy compounds of general formula 71 can now be selectively functionalized stepwise in an analogous manner to that described earlier for mono- and dihydroxy compounds 7, 10, 62, 63, 64 or by conversion into the corresponding bromo, chloro or iodo compounds or aryl- or alkylsulphonic acid esters and subsequent nucleophilic substitution with alcoholates, phenolates or thiophenolates according to conventional methods. Thereby, $ZR^1$, $Z^1R^{4a}$ can are substituents as defined earlier in general formula I or suitable precursors, which are inert under the reaction conditions or in which reactive groups are present in appropriately protected form, preferably chosen such that, if desired, it is possible to synthesize another desired substituent at a suitable later stage of the reaction sequence. $R^a$ and $R^b$ correspond to the definitions set forth above. Alternatively, monohydroxy compounds 71, dihydroxy compounds 71 or derivatives 73 of the dihydroxy compounds 71, the hydroxy function of which has been structurally modified, can be converted into the aldehydes 74 by oxidation, for example according to Swern (dimethyl sulphoxide, oxalyl choride) [J. Org. Chem. 43, 2480 (1978)]. Addition of a Grignard compound or lithium compound according to known methodology in an inert solvent such as tetrahydrofuran or 1,2-dimethoxyethane at temperatures between −78° C. and room temperature then yields the alcohols 76 ($R^9$=H), which can be optionally alkylated, acylated or again oxidized, for example according to Swern, and thus give derivatives 76 ($R^9$ other than H) or, respectively ketones 77. Compounds of general formula 78 and 80 can be obtained starting from dihydroxy compounds 71 by simultaneous conversion of both hydroxy functions analogously to that described above via dialdehydes 75. The transformation of aldehydes 74, 75 into ketones 77, 80 can also be effected via an oxidation to the acids [for example with sodium chlorite, amidosulphonic acid and isopropenyl acetate in a solvent such as acetone/water at 0° C. to room temperature according to J. Am. Chem Soc. 110, 2242 (1988)], subsequent amide coupling to N-methyl-N-methoxy amides with N,O-dimethylhydroxylamine according to known methods as well as reaction thereof with organolithium or organomagnesium compounds in an inert solvent such as tetrahydrofuran or 1,2-dimethoxyethane at temperatures between −78° C. and room temperature as described, for example, in [Synthesis 1986, 944]. Ketones 77 can be converted into oximes 79 in which $R^{10}$ can have the significance defined in general formula I by reaction with optionally substituted hydroxylamine derivatives in a solvent such as pyridine in the presence of catalytic or stoichiometric amounts of a strong acid at temperatures between room temperature and 120° C.

Scheme 12

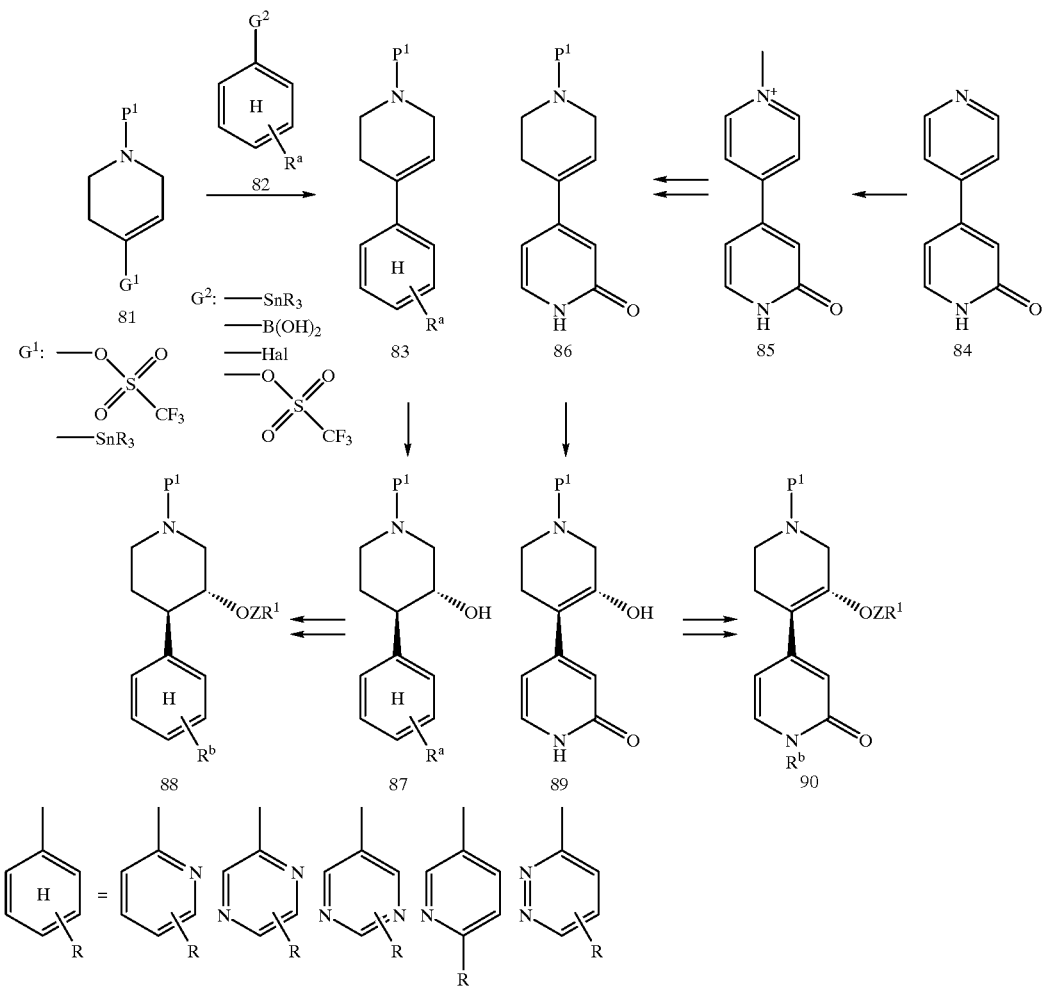

Compounds of general formulae 88 and 90, which contain heterocyclic substituents in the 4-position of the piperidine ring, can be synthesized stepwise in accordance with Scheme 12, e.g., as described hereinafter.

4-Heteroaryl-1,2,3,6-tetrahydro-pyridine derivatives 83 can be obtained, for example, from 1,2,3,6-tetrahydro-pyridine derivatives 81 activated in the form of an enol triflate by condensation with suitable functionalized heteroaromatic compounds activated, for example, in the form of tin compounds. Coupling reactions of this type are preferably carried out in an inert solvent such as 1,2-dimethoxyethane, tetrahydrofuran or N,N-dimethylformamide using a catalyst such as tetrakis-(triphenylphosphine)-palladium at temperatures up to 130° C. In place of tin compounds there can also be used analogous boric acid derivatives 82 under comparable reaction conditions or a vinyl-tin compound 81 which is analogous to the enol triflate 81 can be reacted with heterocyclic halo compounds or triflates 82 likewise under comparable conditions; in both cases the reactions lead to the same products. 4-Heteroaryl-1,2,3,6-tetrahydro-pyridine derivatives 86 can, however, also be obtained from pyridyl-heteroaryl-biaryl derivatives such as 84 according to known methods: N-methylation, partial hydrogenation of the methylated pyridine ring with a suitable hydride reagent such as sodium borohydride and subsequent conversion of the N-methyl function into a suitable protecting group by demethylating carbamoylation [as described, for example, in J. Org. Chem. 49, 2081 (1984)].

Compounds of general formulae 87 and 89 can be obtained by hydroboration and subsequent basic oxidative working-up of compounds of general formulae 83 and 86. The hydroboration can be effected according to methods known per se, for example in a solvent which is inert under the reaction conditions, such as an ether, e.g., 1,2-dimethoxyethane, at a temperature between about 0° C. and 70° C., and with a reagent which contains or liberates diborane, such as, e.g., borane in tetrahydrofuran, borane-dimethyl sulphide or a mixture of sodium borohydride and boron trifluoride etherate. The carboboranes which are formed as intermediates can be converted into the secondary alcohols of general formula 87 and 89 by reaction with bases, e.g., potassium hydroxide, and an oxidizing agent, e.g., hydrogen peroxide, sodium perborate or sodium percarbonate, with a combination of base and oxidizing agent or with trimethylamine N-oxide without the addition of base at a temperature between about room temperature and 120° C.

Compounds of general formulae 88 and 90 in which —$ZR^1$ is a substituent containing an aryl or heteroaryl function can be obtained from compounds of general formulae 87 and 89 by alkylation with a compound which yields the group —ZR¹. Alkylation of the secondary alcohol is effected according to methods known per se, for example in a solvent which is inert under the reaction conditions, such as an ether, e.g., tetrahydrofuran or 1,2-dimethoxyethane, or dimethylformamide, with the aid of an alcoholate-forming base, e.g., sodium hydride, at a temperature between about 0° C. and 40° C. and using a halide, preferably a chloride or bromide, or a sulphonic acid ester, e.g., a mesylate or tosylate, as the compound which yields —ZR¹. The group $R^a$ can be structurally modified prior to or after the alkylation described above. Modification reactions of group $R^a$ to $R^b$, a group of the general formula -$T^1$-$L^2$-$T^2$-$L^3$-$T^3$-$L^4$-$T^4$-U, include usual transformation reactions such as removal and re-introduction of a functional group, alkylation and acylation of alcohol and amine functions, oxidations of sulphides to sulphoxides and sulphones as well as other transformation reactions which are well documented in the literature. Examples of specific structural transformations of group $R^a$ to group $R^b$ are compiled in Scheme 13:

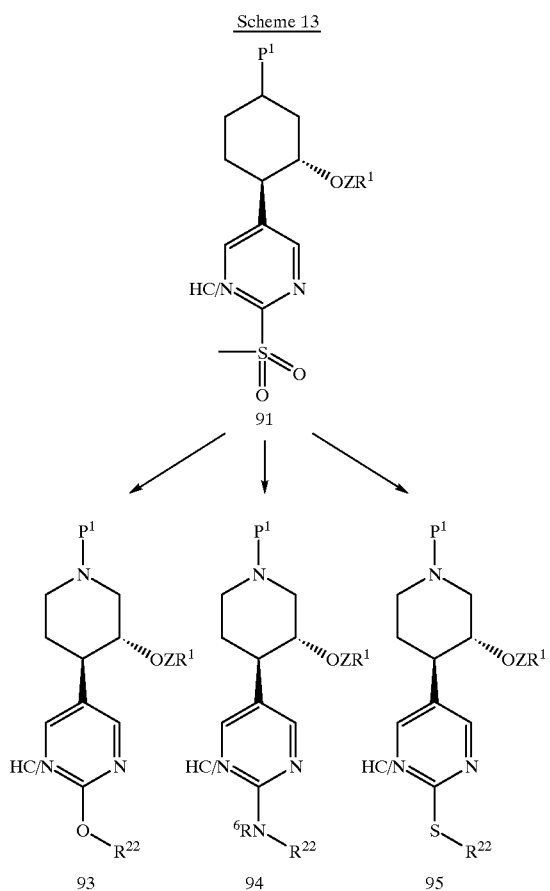

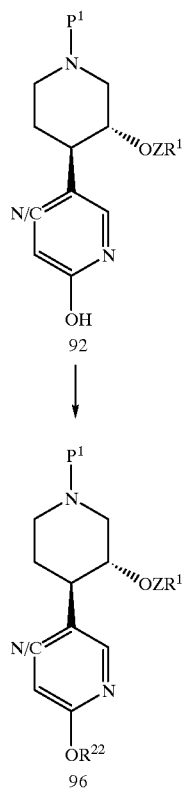

2-Methylsulphonyl pyridine and pyrimidine derivatives 91, which are already appropriately substituted in the 3-position of the piperidine, can be converted into the correspondingly substituted heteroaryl compounds with alcoholates, thiolates and amines in tetrahydrofuran, 1,2-dimethoxyethane, dimethylformamide or dimethyl sulphoxide at temperatures between room temperature and about 150° C. Phenolic pyridine or pyrazine derivatives 92, which have a OH or OZR¹ function in the 3-position of the piperidine, can be alkylated at the phenolic O function using a base and an alkylating agent according to known methods, in which case varying amounts of N-alkylation products can result. On the other hand, when the reaction is carried out with an alcohol in the presence of triphenylphosphine and an azodicarboxylic acid ester in a solvent such as tetrahydrofuran or 1,2-dimethoxyethane according to Mitsunobu [Synthesis 1981, 1], then O-alkylation products are formed almost exclusively. Accordingly, in the reaction products of general formulae 93–96—OR²², —R⁶NR²² and —SR²² each are a group -$T^1$-$L^2$-$T^2$-$L^3$-$T^3$-$L^4$-$T^4$-U, which $T^1$=oxygen, nitrgen or sulphur.

Scheme 14
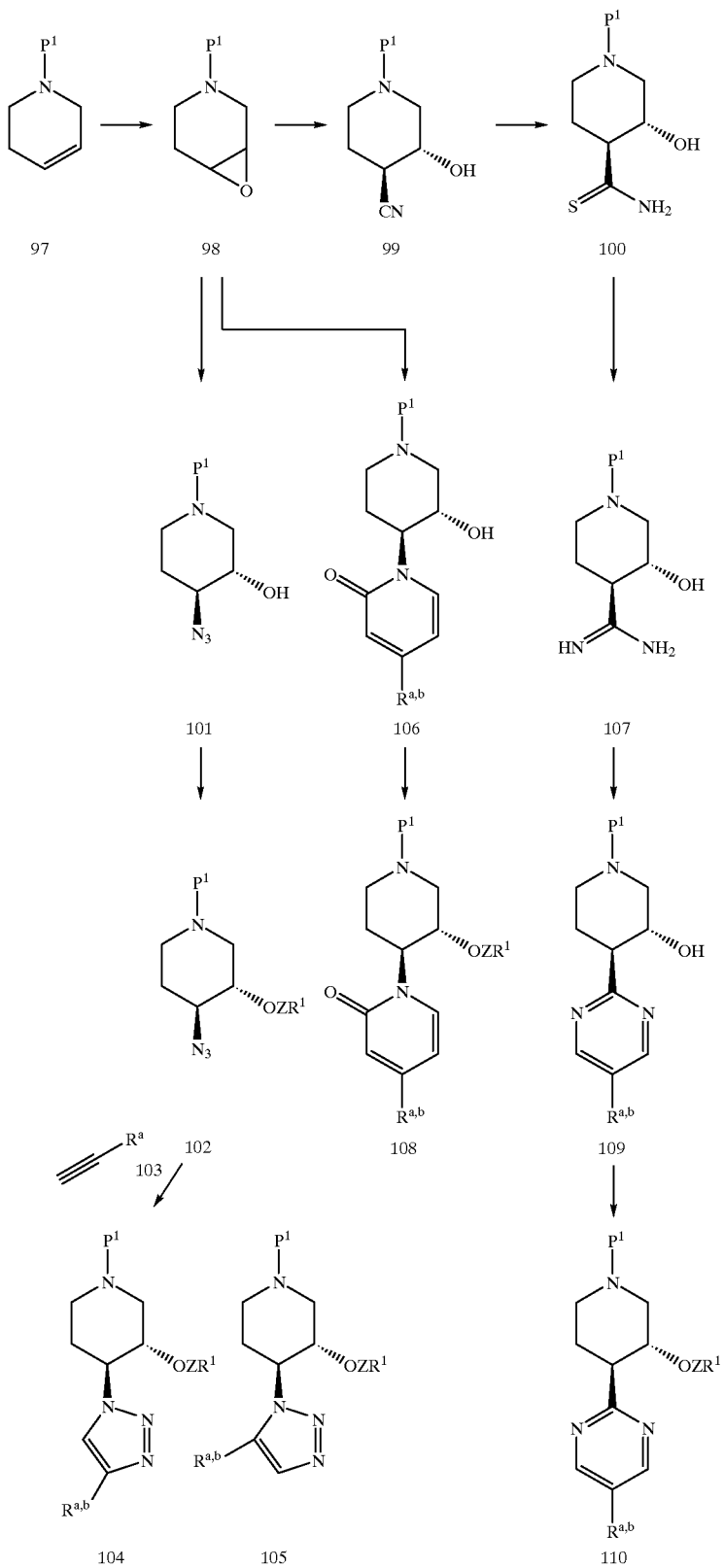

Compounds of general formulae 104, 105 as well as 108 to 110 can be obtained from oxirane compounds 98 in accordance with Scheme 14. Oxirane compounds 98 can be obtained by oxidation of the corresponding olefins by means of peracids such as peracetic acid or perbenzoic acid, preferably 3-chloro-perbenzoic acid. They can be converted into azido compounds 101 with azide anions in protic solvents such as ethanol or methanol or in aprotic solvents such as N,N-dimethylformamide, acetonitrile or dimethyl sulphoxide with or without the addition of Lewis acids such as lithium perchlorate or magnesium sulphate at temperatures between 50° C. and 150° C., with varying amounts of epoxide-opened products having the azido function in the 3-position and the OH function in the 4-position of the piperidine ring being formed. The undesired isomeric compounds having the azido function in the 3-position of the piperidine ring can be separated, for example, by chromatography on silica gel. After the introduction of a suitable ether function in the 3-position the azido compounds can be converted by condensation with a suitable acetylene compound 103, such as, for example, propargyl alcohol in an apolar solvent such as toluene or xylene at temperatures between 60° C. and 160° C., into the two isomeric N-triazolyl compounds of general formulae 104 and 105. Both give potent renin inhibitors after the introduction of a suitable side-chain on the substituents of the triazole ring using specific modification reactions of group $R^a$ to $R^b$ such as removal and re-introduction of a functional group, alkylation and acylation of alcohol and amine functions, oxidations of sulphides to sulphoxides and sulphones as well as other transformations which are well documented in the literature and after cleavage of the protecting group on the nitrogen atom of the piperidine ring. Compounds of general formula 106 can be synthesized by the nucleophilic opening of oxiranes of general formula 98 with an anion obtained from the substituted pyridone. The nucleophilic opening can be effected according to methods known per se, for example in a solvent which is inert under the reaction conditions, such as, e.g., acetonitrile, 1,2-dimethoxyethane or N,N-dimethylformamide, at a temperature between about room temperature and 120° C. and using a catalyst, e.g., ammonium chloride or lithium perchlorate, with the isomeric epoxide-opened product which occurs in varying amounts conveniently being separated by chromatography on silica gel. Compounds of general formula 109 can be obtained starting from compounds of general formula 98 by firstly performing a nucleophilic opening of the oxiranes by means of cyanide ions to give compounds of formula 99. The nucleophilic opening can be effected according to methods known per se, for example in a solvent which is inert under the reaction conditions, such as, e.g., acetonitrile, 1,2-dimethoxyethane or N,N-dimethylformamide, at a temperature between about room temperature and 120° C. and using a catalyst, e.g., ammonium chloride, zinc trifluoroacetate or lithium tetrafluoroborate, especially lithium perchlorate, with the isomeric epoxide-opened product which occurs in varying amounts conveniently being separated by chromatography on silica gel. Compounds of general formula 107 can be obtained from compounds of general formula 99 by the direct addition of ammonia or via the corresponding thioamides of general formula 100. The addition can be effected according to methods known per se, for example by reacting the nitrile under pressure with ammonia and ammonium chloride or by reacting sulphuretted hydrogen, preferably in the form of a hydrogen sulphide, with the nitrile to give the thioamide of general formula 100. This can be further converted, e.g., according to the procedure described in Helv.Chim.Acta Vol. 69, 1224 (1986), by alkylation with methyl iodide or ethyl iodide into the corresponding sulphonium derivative, ammonolysis of which, e.g., with ammonium chloride, leads to the amidine of general formula 107. Compounds of general formula 109 can be prepared by a ring-closure reaction of the amidine of general formula 107 with a corresponding malondialdehyde. The synthesis of the pyrimidine unit can be effected according to procedures known per se, for example by reaction of the amidine with a diacetal or enamine of the 2-substituted malondialdehyde in a solvent which is inert under the reaction conditions, such as, e.g., methanol, at a temperature between about room temperature and 120° C.

Depending on the target molecule under preparation, starting from compounds 106 and 109 firstly —$ZR^1$ can be introduced and subsequently group $R^a$ can be modified to $R^b$ or a reversed synthetic route can be used.

Scheme 15

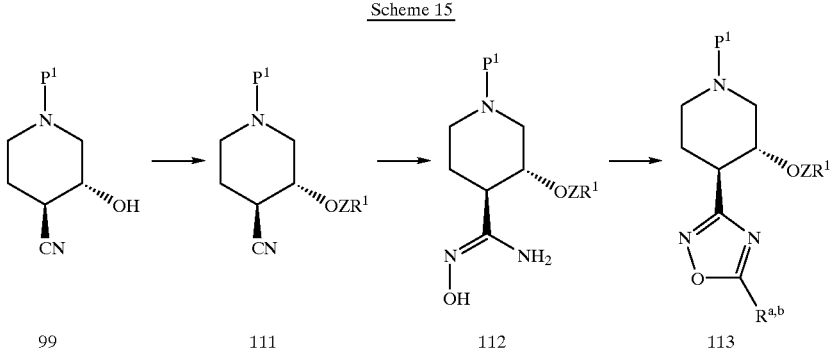

99    111    112    113

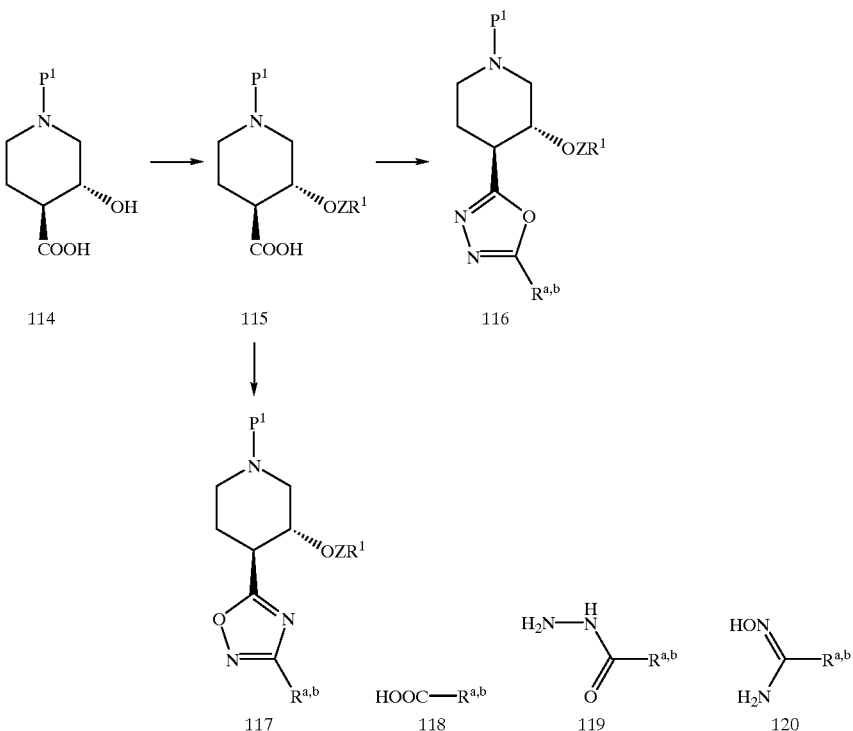

Compounds of general formula 113 can be obtained from compounds of general formula 99 in accordance with Scheme 15 by firstly alkylating the secondary alcohol with a compound which yields the group Z—$R^1$, whereby, if desired, the further synthesis of the desired substituents can be effected at a later stage of the reaction sequence. The alkylation of the secondary alcohol is effected according to procedures known per se, for example in a solvent which is inert under the reaction conditions, such as an ether, e.g., tetrahydrofuran or 1,2-dimethoxyethane, or dimethylformamide, with the aid of an alcoholate-forming base, e.g., sodium hydride, at a temperature between about 0° C. and 40° C. and using a halide, preferably a chloride or bromide, or a sulphonic acid ester, e.g., a mesylate or tosylate, as the compound which yields Z—$R^1$.

The reaction of compounds of general formula 111 with hydroxylamine in the presence of a base such as, e.g., sodium methylate, conveniently at temperatures between 40° C. and 100° C., gives amidoxines of general formula 112. Compounds of general formula 113 are obtained by reacting a reactive functional derivative of a carboxylic acid of general formula 118 with an amidoxime of formula 112. The reaction is conveniently effected by heating for several hours to about 70° C. to 130° C. in an inert solvent, e.g., in dimethylformamide. The non-cyclized condensation product which is formed as an intermediate cyclizes spontaneously under the given reaction conditions. As reactive functional derivatives of carboxylic acids of general formula 118 there can be used the corresponding imidazolides, which can be prepared from the corresponding free carboxylic acids according to procedures known per se, e.g., by reaction with 1,1'-carbonyldiimidazole in an inert organic solvent, e.g., in dimethylformamide. Furthermore, as reactive functional derivatives of the carboxylic acids there can also be used carboxylic acid chlorides which can be prepared from the corresponding free carboxylic acids by means of thionyl chloride or oxalyl chloride.

Compounds of general formula 116 can be obtained from compounds of general formula 114 firstly, as mentioned above, by alkylating compounds of general formula 115. These are then converted into reactive, functional derivatives of the carboxylic acid and reacted with hydrazides of general formula 119. The reaction is conveniently effected at room temperature to 50° C. in an inert organic solvent, e.g., in dimethylformamide. The non-cyclized condensation product which thereby results can be isolated and then cyclized to compounds of general formula 116 by heating for several hours with polyphosphoric acid at about 100° C.

Compounds of general formula 117 can be obtained from compounds of general formula 115 in accordance with Scheme 15 by reacting reactive, functional derivates of the carboxylic acids with amidoximes of general formula 120. The reaction is conveniently effected by heating for several hours to about 70° C. to 130° C. in an inert solvent, e.g., in dimethylformaide. The non-cyclized condensation product which is formed as an intermediate cyclises spontaneously under the given reaction conditions.

The compounds of general formulae 114 and 118–120 belong to generally known classes of compound and will therefore be readily accessible to any person skilled in the art.

Furthermore, compounds of general formula II in which $R^2$ has the meaning of a 5-membered aromatic group can also be prepared very similarly to the synthesis route described in Scheme 12, in which the specifically functionalized 6-membered aromatic synthone 82 must be replaced by a corresponding 5-membered aromatic synthone.

Piperidines of general formula I can also exist in optically pure form. Separation into antipodes can be effected according to methods known per se, either preferably at an early stage of the synthesis by salt formation with an optically active acid such as, for example, (+)- or (−)- mandelic acid and separation of the diastereomeric salts by fractional crystallization or preferably at a later stage by derivatization with a chiral auxilary substance such as, for example, (+)- or (−)- camphamoyl chloride and separation of the diastereomeric products by chromatography and/or crystallization and subsequent cleavage of the bond to the chiral auxilary substance. In order to determine the absolute configuration of the piperidine obtained, the pure diastereomeric salts and derivatives can be analyzed by conventional spectroscopic methods, with X-ray spectroscopy on single crystals being an especially suitable method.

The compounds of the invention have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases blood pressure not only directly by arterial constriction, but also indirectly by the liberation of the sodium ion-retaining hormone aldosterone from the adrenal gland, with which is associated an increase in the extracellular fluid volume. This increase in blood pressure is attributed to the action of agiotensin II itself or to the hepapeptide angiotensin III which is formed therefrom as a cleavage product. Inhibitors of the enzymatic activity of renin bring about a decrease in the formation of angiotensin I and as a consequence of this the formation of a smaller amount of angiotensin II. The reduced concentration of this active peptide hormone is the direct reason for the known blood pressure-lowering activity of renin inhibitors.

The in-vivo potency of renin inhibitors can, as described by W. Fischli et al. in Hypertension, Vol. 18 (1), 22–31 (1991) or Hypertension Vol. 22 (1), 9–17 (1993), be demonstrated experimentally by means of the tests described hereinafter. The tests can be carried out in analogy to those described by D. T. Pals et al. in Hypertension Vol 8, 1105–1112 (1986) or J.Boger et al. in J.Med.Chem. 28, 1779–1790 (1985) or J. F.Dellaria et al. in J.Med.Chem. 30, 2137–2144 (1987) or T.Kokubu et al. in Biochem.Biophys-.Res.Commun. 118, 929–933 (1984).

In vitro Test with Pure Human Renin

The test is carried out in Eppendorf test tubes. The incubation mixture consists of (1) 100 μl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2–3 ng of angiotensin l/ml/hr.; (2) 145 μl of buffer A: (3) 30 μl of 10 mM human tetradecapeptide renin substrate (hTD) in 10 mM hydrochloric acid: (4) 15 ml of dimethyl sulphoxide with or without inhibitor and (5) 10 μl of a 0.03 molar solution of hydroxyquinoline sulphate in water.

The samples are incubated for three hours at 37° C. and, respectively, 4° C. in triplicate. 2×100 μl samples per test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the test at 37° C. and that at 4° C.

The following controls are carried out:
(a) Incubation of hTD samples without renin and without inhibitor at 37° C. and 4° C. The difference between these two values gives the base value of the angiotensin I production.
(b) Incubation of hTD samples with renin, but without inhibitor at 37° C. and 4° C. The difference between these values gives the maximum value of the angiotensin I production.

In each sample the base value of the angiotensin I production is subtracted from the angiotensin I production which is determined. The difference between the maximum value and the base value gives the value of the maximum substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ values in μMol/l |
|---|---|
| A | 0.011 |
| B | 0.026 |
| C | 0.070 |
| D | 0.040 |
| E | 0.041 |
| F | 0.057 |
| G | 0.033 |
| H | 0.073 |
| I | 0.317 |
| J | 0.017 |
| K | 2.600 |
| L | 3.080 |
| M | 0.008 |
| N | 0.012 |
| O | 0.017 |
| P | 0.006 |
| Q | 0.005 |
| R | 0.003 |
| S | 0.002 |
| T | 0.005 |
| U | 0.024 |
| V | 0.002 |
| W | 0.002 |
| X | 0.003 |
| Y | 0.003 |
| Z | 0.001 |
| AA | 0.001 |
| BB | 0.003 |
| CC | 0.002 |
| DD | 0.001 |
| EE | 0.0004 |
| FF | 0.0006 |
| GG | 0.001 |
| HH | 0.006 |
| II | 0.002 |
| JJ | 0.002 |
| KK | 0.012 |
| LL | 0.001 |
| MM | 0.0005 |
| NN | 0.001 |
| OO | 0.006 |
| PP | 0.002 |
| QQ | 0.002 |
| RR | 0.270 |
| SS | 132 |
| TT | 0.0005 |
| UU | 0.0001 |
| VV | 0.002 |
| WW | 0.009 |
| XX | 0.0008 |
| YY | 0.0005 |
| ZZ | 0.00003 |

A = (3RS,4RS)-2-[4-(3-Naphthalen-2-ylmethoxy-piperidin-4-yl)-phenoxy]-ethyl thiophene-2-carboxylate hydrochloride (Example 58-4)
B = (3RS,4RS)-2-[4-(3-Naphthalen-2-ylmethoxy-piperidin-4-yl)-phenoxy]-ethyl 2-chloro-benzoate hydrochloride (Example 54-2)
C = (3RS,4RS)-2-[4-[3-[4-(2-methoxy-benzyloxy)-naphthalen-2-ylmethoxy]-piperidin-4-yl]-phenoxy]-ethyl benzoate hydrochloride (Example 55-2)
D = (3RS,4RS)-4-[4-(3-Benzyloxy-propoxy)-phenyl]-3-(2,3-dihydro-benzo[1,4]dioxin-6-ylmethoxy)-piperidine (Example 86-54)

TABLE-continued

E = (3RS,4RS)-3-(Naphthalen-2-ylmethoxy)-4-[4-(3-phenyl-[1,2,4]oxadiazol-5-ylmethoxy)-phenyl]-piperidine trifluoroacetate (Example 86-34)
F = (3RS,4RS)-3-(Naphthalen-2-ylmethoxy)-4-[4-(3-phenyl-isoxazol-5-ylmethoxy)-phenyl]-piperidine trifluoroacetate (Example 86-36)
G = (3RS,4RS)-3-(Naphthalen-2-ylmethoxy)-4-[4-(3-phenylsulphanyl-propyl)-phenyl]-piperidine (Example 86-19)
H = (3RS,4RS)-3-[4-[4-[2-(Benzothiazol-2-ylsulphanyl)-ethyl]-phenyl]-piperidin-3-yloxymethyl]-naphthalen-1-ol (Example 86-23)
I = (3RS,4RS,5SR)-3-(4-Benzyloxy-naphthalen-2-ylmethoxy)-4-(4-fluoro-phenyl)-5-propyl-piperidine (Example 64)
J = (3SR,4RS,5RS)-4-(4-Benzyloxymethyl-phenyl)-3-methoxymethyl-5-(naphthalen-2-ylmethoxy)-piperidine (Example 86-60)
K = (SR)- or (RS)-1-[(3RS,4SR)-4-(4-fluoro-phenyl)-piperidin-3-yl]-2-naphthalen-2-yl-ethyl benzoate hydrochloride (Example 75 b)
L = (1RS,2RS,3RS,5SR)-2-(4-Benzyloxy-naphthalen-2-ylmethoxy)-3-(4-fluoro-phenyl)-8-aza-bicyclo[3.2.1]octane (Example 84 e)
M = (3RS,4RS)-4-[4-(3-Benzyloxy-propoxy)-phenyl]-3-(naphthalen-2-ylmethoxy)-piperidine
N = 4-[2-[7-[(3RS,4RS)-4-[4-(3-Benzyloxy-propoxy)-phenyl]-piperidin-3-yloxymethyl]-naphthalen-2-yloxy]-ethyl]-morpholine hydrochloride (1:2) (Example 90-07)
O = Mixture of (RS)- and (SR)-3-[7-[(3RS,4RS)-4-[4-(3-benzyloxy-propoxy)-phenyl]-piperidin-3-yloxymethyl]-naphthalen-2-yloxy]-propane-1,2-diol (Example 90-08)
P = Mixture of (RS)- and (SR)-3-[2-[7-[(3RS,4RS)-4-[4-(3-benzyloxy-propoxy)-phenyl]-piperidin-3-yloxymethyl]-naphthalen-2-yloxy]-ethoxy]-propane-1,2-diol hydrochloride(1:1) (Example 98)
Q = 1-[2-[7-[(3RS,4RS)-4-[4-(3-Benzyloxy-propoxy)-phenyl]-piperidin-3-yloxymethyl]-naphthalen-2-yloxy]-ethyl]-4-methyl-piperazine hydrochloride (1:3) (Example 90-13)
R = 1-[(3RS,4SR)-4-[4-(3-Benzyloxy-propoxy)-phenyl]-piperidin-3-yl]-2-naphthalen-2-yl-ethanone hydrochloride (1:1) (Example 100)
S = (3RS,4SR,5SR)-4-[4-(3-Benzyloxy-propoxy)-phenyl]-3-(1,4-dimethoxy-naphthalen-2-ylmethoxy)-piperidin-5-ol (Example 109-04)
T = Mixture of (3RS,4RS)- and (3SR,4SR)-4-[4-(3-benzyloxy-propoxy)-phenyl]-3-[7-[(RS)-2,3-dihydroxy-propoxymethyl]-naphthalen-2-ylmethoxy]-piperidine (Example 106-02)
U = Mixture of (3RS,4RS)- and (3SR,4SR)-4-[4-(3-benzyloxy-propoxy)-phenyl]-3-[6-[(RS)-2,3-dihydroxy-propoxymethyl]-naphthalen-2-ylmethoxy]-piperidine (Example 106-01)
V = 4-[(3RS,4SR,5SR)-4-[4-(3-Benzyloxy-propoxy)-phenyl]-3-(naphthalen-2-ylmethoxy)-piperidin-5-yloxy]-butan-1-ol (Example 110-08)
W = 3-[(3RS,4SR,5SR)-4-[4-(3-Benzyloxy-propoxy)-phenyl]-3-(naphthalen-2-ylmethoxy)-piperidin-5-yloxy]-propan-1-ol (Example 110-07)
X = 1-{2-[(3RS,4RS,5SR)-4-[4-(3-Benzyloxy-propoxy)-phenyl]-3-(naphthalen-2-ylmethoxy)-piperidin-5-yloxy]-ethyl}-4-methyl-piperazine (Example 110-02)
Y = 4-{2-[(3RS,4RS,5SR)-4-[4-(3-Benzyloxy-propoxy)-phenyl]-3-(naphthalen-2-ylmethoxy)-piperidin-5-yloxy]-ethyl}-morpholine (Example 110-09)
Z = (3RS,4SR,5SR)-4-[4-(3-Benzyloxy-propoxy)-phenyl]-3-(4-methoxy-benzyloxy)-piperidin-5-ol (Example 109-28)
AA = (3R,4s,5S)-4-[4-(3-Benzyloxy-propoxy)-phenyl]-3, 5-bis-(4-methoxy-benzyloxy)-piperidine (Example 109-27)
BB = (3SR,4RS,5RS)-4-[2-[4-[4-(3-Benzyloxy-propoxy)-phenyl]-5-(naphthalen-2-ylmethoxy)-piperidin-3-ylmethoxy]-ethyl]-morpholine (Example 149-04)
CC = (3SR,4RS,5RS)-4-[4-(3-Benzyloxy-propoxy)-phenyl]-3-methoxymethyl-5-(naphthalen-2-ylmethoxy)-piperidine (Example 148)
DD = (3SR,4RS,5RS)-4-[4-(3-Benzyloxy-propoxy)-phenyl]-5-(naphthalen-2-ylmethoxy)-piperidin-3-ylmethyl [3-(4-methyl-piperazin-1-yl)-propyl]-carbamate (Example 150-01)
EE = (3SR,4RS,5RS)-4-[4-(3-Benzyloxy-propoxy)-phenyl]-5-(naphthalen-2-ylmethoxy)-piperidin-3-ylmethylsulphanyl]-pyridine (Example 149-02)
FF = 2-(4-Cyclohexyl-butoxy)-5-[(3RS,4RS)-3-(1,4-dimethoxy-naphthalen-2-ylmethoxy)-piperidin-4-yl]-pyrimidine (Example 139-03)
GG = (3'RS,4'RS)-6-(3-Cyclohexyl-propoxy)-3'-(1,4-dimethoxy-naphthalen-2-ylmethoxy)-1',2',3',4',5',6'-hexahydro-[3,4']bipyridine (Example 140-01)
HH = (3SR,4RS,5RS)-[4-[4-(3-Benzyloxy-propoxy)-phenyl]-5-(naphthalen-2-ylmethoxy)-piperidin-3-yl]-methanol hydrochloride (Example 149-01)
II = (3SR,4RS,5RS)-N-[4-[4-(3-Benzyloxy-propoxy)-phenyl]-5-(naphthalen-2-ylmethoxy)-piperidin-3-ylmethyl]-N,N',N'-trimethyl-ethane-1,2-diamine (Example 149-06)
JJ = (3SR,4RS,5RS)-[4-[4-(3-Benzyloxy-propoxy)-phenyl]-5-(naphthalen-2-ylmethoxy)-piperidin-3-ylmethyl]-diethyl-amine (Example 149-05)
KK = 1-[(3RS,4SR,5SR)-4-[4-(3-Benzyloxy-propoxy)-phenyl]-5-(2-morpholin-4-yl-ethoxymethyl)-piperidin-3-yl]-2-naphthalen-2-yl-ethanone (Example 101)
LL = (3RS,4RS)-3-(1,4-Dimethoxy-naphthalen-2-ylmethoxy)-4-[4-[3-(2-methoxy-phenoxy)-propoxy]-phenyl]-piperidine (Example 123-27)

TABLE-continued

MM = (3R,4s,5S)-4-[4-(3-Benzyloxy-propoxy)-phenyl]-3,5-bis-(3,4,5-trimethoxy-benzyloxy)-piperidine (Example 109-29)
NN = (3RS,4RS,5SR)-4-[4-(3-Benzyloxy-propoxy)-phenyl]-3-(naphthalen-2-ylmethoxy)-5-[1,2,4]triazol-1-ylmethyl-piperidine hydrochloride (Example 149-07)
OO = (3RS,4RS)-4-[4-[3-(2-Methoxy-benzyloxy)-propoxy]-phenyl]-3-(quinolin-7-ylmethoxy)-piperidine (Example 120-07)
PP = 2-(7-{(3RS,4RS)-4-[4-(3-Benzyloxy-propoxy)-phenyl]-piperidin-3-yloxymethyl}-naphthalen-2-ylmethoxy)-ethanol (Example 106-03)
QQ = 7-{(3RS,4RS)-4-[4-(3-Benzyloxy-propoxy)-phenyl]-piperidin-3-yloxymethyl}-naphthalen-2-ylmethyl)-dimethyl-amine (Example 106-03)
RR = (3R,4R)-3-(4-Benzyloxy-naphthalen-2-ylmethoxy)-4-(4-fluoro-phenyl)-piperidine (Example 154-06)
SS = (3S,4S)-3-(4-Benzyloxy-naphthalen-2-ylmethoxy)-4-(4-fluoro-phenyl)-piperidine (Example 154-07)
TT = (3'RS,4'RS)-3'-(1,4-Dimethoxy-naphthalen-2-ylmethoxy)-6-[3-(2-methoxybenzyloxy)-propoxy]-1',2',3',4',5',6'-hexahydro-[3,4']bipyridine (Example 140.02)
UU = (3RS,4RS)-3-(1,4-Dimethoxy-naphthalen-2-ylmethoxy)-4-[4-[3-(2-methoxy-benzyloxy)-propoxy]-phenyl]-piperidine (Example 123.32)
VV = (3SR,4RS,5RS)-1-[4-[4-(3-Benzyloxy-propoxy)-phenyl]-5-(naphthalen-2-ylmethoxy)-piperidin-3-ylmethyl]-imidazolidin-2-one (Example 149.08)
WW = (3RS,4RS)-4-[4-[3-(2-Methoxy-benzyloxy)-propoxy]-phenyl]-3-(2-oxo-1,2-dihydro-quinolin-7-ylmethoxy)-piperidine (Example 120.10)
XX = (3RS,4RS)-3-(Isoquinolin-7-ylmethoxy)-4-[4-[3-(2-methoxy-benzyloxy)-propoxy]-phenyl]-piperidine (Example 120.11)
YY = (3RS,4RS)-4-[4-[3-(2-Methoxy-benzyloxy)-propoxy]-phenyl]-3-(1,2,3,4-tetrahydro-quinolin-7-ylmethoxy)-piperidine (Example 120.12)
ZZ = (3RS,4SR,5SR)-3-(1,4-Dimethoxy-naphthalen-2-ylmethoxy)-4-[4-[3-(2-methoxy-benzyloxy)-propoxy]-phenyl]-piperidin-5-ol (Example 112-11)

The compounds of formula I as well as their pharmaceutically usable salts can be used as medicaments, e.g., in the form of pharmaceutical preparations. The pharmaceutical preparations can be administered enterally such as orally, e.g., in the form of tablets, coated tablets, dragées, hard and soft gelatine capsules, solutions, emulsions or suspensions, nasally, e.g., in the form of nasal sprays, or rectally, e.g., in the form of suppositories. However, the administration can also be effected parenterally such as intramuscularly or intravenously, e.g., in the form of injection solutions.

The compounds of formula I as well as their pharmaceutically usable salts can be processed with pharmaceutically inert, inorganic or organic excipients for the production of tablets, coated tablets, dragées and hard gelatine capsules. Lactose, corn starch or derivatives thereof, talc, stearic acid or its salts etc can be used, e.g., as such excipients for tablets, dragees and hard gelatine capsules.

Suitable excipients for soft gelatine capsules are, e.g., vegetable oils, waxes, fats, semi-solid and liquid polyols etc.

Suitable excipients for the production of solutions and syrups are, e.g., water, polyols, sucrose, invert sugar, glucose etc.

Suitable excipients for injection solutions are, e.g., water, alcohols, polyols, glycerol, vegetable oils bile acids, lecithin etc.

Suitable excipients for suppositories are, e.g., natural or hardened oils, waxes, fats, semi-liquid or liquid polyols etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other thereapeutically valuable substances.

In accordance with the invention the compounds of general formula I as well as their pharmaceutically usable salts can be used in the control or prevention of high blood pressure and cardiac insufficiency, as well as glaucoma, cardiac infarct, kidney insufficiency and restenosis.

The compounds in accordance with the invention can also be administered in combination with one or more agents having cardiovascular activity, e.g., α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclane, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane synthetase inhibitors; angio-tensin II antagonists; as well as diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyldopa, clonidine, guanabenz, reserpine; and other agents which are suitable for the treatment of high blood pressure, cardiac insufficiency or vascular disorders in humans and animals associated with diabetes or kidney disorders such as acute or chronic kidney failure. Such combinations can be used separately or in preparations which contain several components.

The dosage can vary within wide limits and will, of course, be fitted to the individual requirements in each particular case. In general, in the case of oral administration a daily dosage of about 3 mg to about 3 g, preferably about 10 mg to about 1 g, e.g., approximately 300 mg per adult person (70 kg), divided into preferably 1–3 individual doses which, e.g., can be of equal amount, should be sufficient, although the upper limit given can also be exceeded when this is found to be indicated. Usually, children receive a reduced dose appropriate to their age and body weight.

The following Examples are intended to illustrate the present invention, but they are not intended to be limiting in any manner. All temperatures are given in degrees Celsius. The following abbreviations are used:
BOC: tert-Butoxycarbonyl
DME: 1,2-Dimethoxyethane
DMF: Dimethylformamide
TBAF: Tetrabutylammonium fluoride
EDC: N-Ethyl-N'-(3-dimethylaminopropyl)-carbodiimide hydrochloride
THP: Tetrahydropyranyl
TROC: Trichloroethoxycarbonyl.
TPTU: O-(1,2-Dihydro-2-oxo-1-pyridyl)-N,N,N'N'-tetramethyluronium-tetrafluoroborate
HBTU: O-(1H-Benzotriazol-1-yl)-N,N,N'N'-tetramethyluronium-hexafluorophosphate
SEM: 2-(Trimethylsilyl)-ethoxymethyl

EXAMPLE 1

(a) A solution of 23.6 g (100 mmol) of 1,3-dibromobenzene in 250 ml of absolute ether was cooled to −75° C. A solution of 62.5 ml (100 mmol) of n-butyllithium (1.6M in hexane) was added dropwise within 45 minutes. The resulting suspension was stirred at −75° C. for 2.5 hours. Subsequently, a solution of 19.0 g (100 mmol) of 1-benzyl-4-piperidone in 100 ml of absolute ether was added dropwise within 30 minutes at −70° C. to −75° C. and thereafter the mixture was stirred for 2 hours. Subsequently, the mixture was partitioned between ether and saturated ammonium chloride solution, the organic phase was dried over magnesium sulphate and finally the solvent was removed under reduced pressure. The crude product was purified by chromatography on silica gel with a 1:1 mixture of methylene chloride and hexane as the eluent. There were obtained 28.3 g (82% of theory) of 1-benzyl-4-(3-bromophenyl)-piperidin-4-ol as a yellow oil; MS: 345, 347 (M)$^+$.

(b) A solution of 28.2 g (81.4 mmol) of 4-(3-bromophenyl)-piperidin-4-ol in 600 ml of toluene was treated with 30 g (157 mmol) of p-toluenesulphonic acid monohydrate and heated to reflux on a water separator for 4 hours. Subsequently, the reaction mixture was cooled to room temperature and adjusted to pH 10 with 3N sodium hydroxide solution. Thereafter, it was firstly extracted three times with 500 ml of methylene chloride. The combined organic phases were washed three times with 200 ml of water each time, dried over magnesium sulphate and then evaporated under reduced pressure. The crude product was purified by chromatography on silica gel with a 1:1 mixture of methylene chloride and hexane as the eluent. There were obtained 9.5 g (36% of theory) of 1-benzyl-4-(3-bromophenyl)-1,2,3,6-tetrahydro-pyridine as a light yellow oil; MS: 327, 329 (M+H)$^+$.

(c) 3.15 g (83.3 mmol) of sodium borohydride were added portionwise at room temperature to a suspension of 9.5 g (28.9 mmol) of 1-benzyl-4-(3-bromophenyl)-1,2,3,6-tetrahydro-pyridine in 65 ml of absolute dimethoxyethane (DME). Thereafter, a solution of 17.7 ml (20.0 g 140.9 mmol) of boron trifluoride etherate in 11 ml of DME was added dropwise at 15–200° C. and the mixture was stirred at room temperature for 2 hours. Subsequently, a solution of 18.3 g (326 mmol) of potassium hydroxide in 100 ml of water was added dropwise within 30 minutes at 20–25° C. Finally, 55 ml of 30% hydrogen peroxide solution were added dropwise within 30 minutes at 20–25° C. The mixture was stirred at room temperature for 30 minutes and heated to reflux for 3 hours. After cooling the reaction mixture the separated boric acid was filtered off. Subsequently, the filtrate was partitioned between methylene chloride and water, the organic phase was dried over magnesium sulphate and the solvent was removed under reduced pressure. The crude product was purified by chromatography on silica gel with a 1:1 mixture of ethyl acetate and methylene chloride as the eluent. There were obtained 6.3 g (63% of theory) of (3RS,4RS)-1-benzyl-4-(3-bromophenyl)-piperidin-3-ol as a colourless oil. MS: 345, 347 (M)$^+$.

(d) A solution of 691 mg (2.00 mmol) of (3RS,4RS)-1-benzyl-4-(3-bromophenyl)-piperidin-3-ol in 3 ml of absolute tetrahydrofuran was treated with 163 mg (2.20 mmol) of lithium carbonate and cooled to −50° C. A solution of 722 mg (4.00 mmol) of β-trimethylsilylethyl chloroformate [Synthesis 346 (1987)] in 4 ml of toluene was added dropwise thereto at −50° C. The reaction mixture was warmed to room temperature and stirred for 24 hours. Subsequently, the mixture was partitioned between methylene chloride and water, the organic phase was dried over magnesium sulphate and finally the solvent was removed under reduced pressure. The crude product (0.8 g) was purified by chromatography on silica gel with methylene chloride as the eluent. There were obtained 470 mg (43% of theory) of 2-trimethylsilylethyl (3RS,4RS)-4-(3-bromophenyl)-3-(2-trimethylsilyl-ethoxycarbonyloxy)-piperidine-1-carboxylate as light yellow oil, which was used directly in the next step.

(e) A solution of 470 mg (0.863 mmol) of 2-trimethylsilylethyl (3RS,4RS)-4-(3-bromophenyl)-3-(2-trimethylsilyl-ethoxycarbonyloxy)-piperidine-1-carboxylate in 3 ml of absolute tetrahydrofuran was treated with 2.65 ml (2.91 mmol) of tetrabutylammonium fluoride solution (1.1M in THF) and stirred at room temperature for 2.5 hours. Subsequently, the mixture was partitioned between methylene chloride and saturated sodium carbonate solution, the organic phase was dried over magnesium sulphate and finally the solvent was removed under reduced pressure. The crude product (440 mg) was purified by chromatography on silica gel with a 6.5:1:0.1 mixture of methylene chloride, MeOH and 25% ammonia as the eluent. There were obtained 180 mg (81% of theory) of (3RS,4RS)-4-(3-bromophenyl)-piperidin-3-ol as a light yellow oil. MS: 255, 257 (M)$^+$.

(f) A solution of 180 mg (0.702 mmol) of (3RS,4RS)-4-(3-bromophenyl)-piperidin-3-ol in 1 ml of absolute dimethylformamide was treated at 0° C. with 0.1 ml (73 mg, 0.72 mmol) of triethylamine. A solution of 167 mg (76.5 mmol) of di-tert-butyl dicarbonate in 0.5 ml of dimethylformamide was added thereto at 0° C. The mixture was warmed to room temperature and stirred for 20 hours. The solvent was distilled off at 50–55° C. at 0.1 mm Hg. Subsequently, the residue obtained was partitioned between methylene chloride and water, the organic phase was dried over magnesium sulphate and finally the solvent was removed under reduced pressure. The crude product was purified by chromatography on silica gel with a 4:1 mixture of methylene chloride and ethyl acetate. There were obtained 220 mg (92% of theory) of tert-butyl (3RS,4RS)-4-(3-bromophenyl)-3-hydroxy-piperidine-1-carboxylate as a colourless solid; MS: 299, 301 (M-C$_4$H$_8$)$^+$.

(g) A solution of 168 mg (0.47 mmol) of tert-butyl (3RS,4RS)-4-(3-bromophenyl)-3-hydroxy-piperidine-1-carboxylate and 157 mg (0.71 mmol) of 2-bromomethylnaphthalene in 2 ml of dimethylformamide was treated with 28 mg (0.7 mmol) of sodium hydride (60% dispersion in refined oil) and the mixture was stirred at room temperature for 3 hours. Subsequently, the reaction mixture was partitioned between ethyl acetate and water, the organic phase was dried over magnesium sulphate and finally the solvent was removed under reduced pressure. The crude product was purified by chromatography on silica gel with a 1:4 mixture of ethyl acetate and hexane as the eluent. There were obtained 173 mg (74% of theory) of tert-butyl (3RS,4RS)-4-(3-bromophenyl)-3-(naphthalen-2-ylmethoxy)-piperidine-1-carboxylate as a light yellow oil; MS: 439, 441 (M-C$_4$H$_8$)$^+$.

(h) A solution of 173 mg (0.35 mmol) of tert-butyl (3RS,4RS)-4-(3-bromophenyl)-3-(naphthalen-2-ylmethoxy)-piperidine-1-carboxylate in 6 ml of methanol was treated with 6 ml of a 2N solution of hydrogen chloride in MeOH and stirred at 50° C. for 4 hours. Subsequently, the mixture was partitioned between ethyl acetate and a 5% sodium hydrogen carbonate solution, the organic phase was dried over magnesium sulphate and finally the solvent was removed under reduced pressure. The crude product was purified by chromatography on silica gel with a 10:1:0.1 mixture of methylene chloride, MeOH and 25% ammonia and the eluent. There were obtained 126 mg (91% of theory) of (3RS,4RS)-4-(3-bromophenyl)-3-(naphthalen-2-ylmethoxy)-piperidine as a light yellow oil. MS: 396, 398 (M+H)$^+$.

EXAMPLE 2

The following compounds were obtained by cleavage of the BOC group in an analogous manner to that described in Example 1(h):

1) (3RS,4RS)-3-(4-Methoxy-benzyloxy)-4-phenyl-piperidine as a light yellow oil, MS: 298 (M+H)$^+$, from tert-butyl (3RS,4RS)-3-(4-methoxy-benzyloxy)-4-phenyl-piperidine-1-carboxylate;
2) (3RS,4RS)-4-(4-bromophenyl-3-(4-methoxy-benzyloxy)-piperidine as a colourless oil, MS: 376, 378 (M+H)$^+$, from tert-butyl (3RS,4RS)-4-(4-bromophenyl-3-(4-methoxy-benzyloxy)-piperidine-1-carboxylate;
3) (3RS,4RS)-3-(4-methoxy-benzyloxy)-4-(3-trifluoromethylphenyl)-piperidine as a colourless oil, MS: 366 (M+H)$^+$, from tert-butyl (3RS,4RS)-3-(4-methoxy-benzyloxy)-4-(3-trifluoromethylphenyl)-piperidine-1-carboxylate;
4) (3RS,4RS)-3-(4-methoxy-benzyloxy)-4-p-tolyl-piperidine as a colourless solid, MS: 312 (M+H)$^+$, from tert-butyl (3RS,4RS)-3-(4-methoxy-benzyloxy)-4-p-tolyl-piperidine-1-carboxylate;
5) (3RS,4RS)-3-(naphthalen-2-ylmethoxy)-4-phenyl-piperidine as a light yellow oil, MS: 318 (M+H)$^+$, from tert-butyl (3RS,4RS)-3-(naphthalen-2-ylmethoxy)-4-phenyl-piperidine-1-carboxylate;
6) (3RS,4RS)-4-(4-bromophenyl)-3-(naphthalen-2-ylmethoxy)-piperidine as a colourless solid, MS: 396, 398 (M+H)$^+$, from tert-butyl (3RS,4RS)-4-(4-bromophenyl)-3-(naphthalen-2-ylmethoxy)-piperidine-1-carboxylate;
7) (3RS,4RS)-3-(naphthalen-2-ylmethoxy)-4-(3-trifluoromethyl-phenyl)-piperidine as a colourless oil, MS: 386 (M+H)$^+$, from tert-butyl (3RS,4RS)-3-(naphthalen-2-ylmethoxy)-4-(3-trifluoromethyl-phenyl)-piperidine-1-carboxylate;
8) (3RS,4RS)-4-cyclohexyl-3-(naphthalen-2-ylmethoxy)-piperidine as a light yellow oil, MS: 324 (M+H)$^+$, from tert-butyl (3RS,4RS)-4-cyclohexyl-3-(naphthalen-2-ylmethoxy)-piperidine-1-carboxylate;
9) (3RS,4RS)-3-(naphthalen-2-ylmethoxy)-4-p-tolyl-piperidine as a colourless solid, MS: 332 (M+H)$^+$, from tert-butyl (3RS,4RS)-3-(naphthalen-2-ylmethoxy)-4-p-tolyl-piperidine-1-carboxylate;
10) (3RS,4RS)-4-naphthalen-2-yl-3-(naphthalen-2-ylmethoxy)-piperidine as a colourless oil, MS: 367 (M)$^+$, from tert-butyl (3RS,4RS)-4-naphthalen-2-yl-3-(naphthalen-2-ylmethoxy)-piperidine-1-carboxylate;
11) (3RS,4RS)-3-(naphthalen-2-ylmethoxy)-4-(5,6,7,8-tetrahydro-naphthalen-2-yl)-piperidine as a colourless oil, MS: 372 (M+H)$^+$, from tert-butyl (3RS,4RS)-3-(naphthalen-2-ylmethoxy)-4-(5,6,7,8-tetrahydro-naphthalen-2-yl)-piperidine-1-carboxylate;
12) (3RS,4RS)-4-naphthalen-1-yl-3-(naphthalen-2-ylmethoxy)-piperidine as a colourless solid, MS: 367 (M)$^+$, from tert-butyl (3RS,4RS)-4-naphthalen-1-yl-3-(naphthalen-2-ylmethoxy)-piperidine-1-carboxylate;
13) (3RS,4RS)-4-(3,4-dimethoxy-phenyl)-3-(naphthalen-2-ylmethoxy)-piperidine as a colourless resin, MS: 377 (M)$^+$, from tert-butyl (3RS,4RS)-4-(3,4-dimethoxy-phenyl)-3-(naphthalen-2-ylmethoxy)-piperidine-1-carboxylate;
14) (3RS,4RS)-4-acenaphthen-5-yl-3-(naphthalen-2-ylmethoxy)-piperidine as a colourless solid, MS: 394 (M+H)$^+$, from tert-butyl (3RS,4RS)-4-acenaphthen-5-yl-3-(naphthalen-2-ylmethoxy)-piperidine-1-carboxylate;
15) (3RS,4RS)-4-(4-chlorophenyl)-3-(3-phenoxy-benzyloxy)-piperidine as a colourless solid, MS: 394, 396 (M+H)$^+$, from tert-butyl (3RS,4RS)-4-(4-chlorophenyl)-3-(3-phenoxy-benzyloxy)-piperidine-1-carboxylate;
16) (3RS,4SR)-3-(naphthalen-2-ylmethoxy)-4-phenyl-piperidine hydrochloride as a colourless powder, MS: 318 (M+H)$^+$, from tert-butyl (3RS,4SR)-3-(naphthalen-2-ylmethoxy)-4-phenyl-piperidine-1-carboxylate.

The BOC compounds used as the starting materials were prepared as follows:

The following compounds were obtained in an analogous manner to that described in Example 1(b)–(c) and (f)–(g):
(a) From 4-phenyl-piperidin-4-ol there was obtained by elimination 4-phenyl-1,2,3,6-tetrahydro-pyridine as a light yellow oil; MS: 159 (M)$^+$. Subsequent hydroboration gave (3RS,4RS)-4-phenyl-piperidin-3-ol as a colourless solid; MS: 177 (M)⁺. Introduction of the BOC group yielded tert-butyl (3RS,4RS)-3-hydroxy-4-phenyl-piperidine-1-carboxylate as a colourless solid; MS: 277 (M)⁺. After alkylation with 4-methoxybenzyl bromide there was obtained tert-butyl (3RS,4RS)-3-(4-methoxy-benzyloxy)-4-phenyl-piperidine-1-carboxylate as a colourless solid; MS: 340 (M-C₄H₉)⁺.

(b) From 4-(4-bromophenyl)-piperidin-4-ol there was obtained by elimination 4-(4-bromophenyl)-1,2,3,6-tetrahydro-pyridine as a light yellow solid; MS: 237, 239 (M)⁺. Subsequent hydroboration gave (3RS,4RS)-4-(4-bromophenyl)-piperidin-3-ol as a colourless solid; MS: 255, 257 (M)⁺. Introduction of the BOC group yielded tert-butyl (3RS,4RS)-4-(4-bromophenyl)-3-hydroxy-piperidine-1-carboxylate as a colourless solid; MS: 299, 301 (M-C₄H₈)⁺. After alkylation with 4-methoxybenzyl bromide there was obtained tert-butyl (3RS,4RS)-4-(4-bromophenyl)-3-(4-methoxy-benzyloxy)-piperidine-1-carboxylate as a light yellow oil; MS: 418, 420 (M-C₄H₉)⁺.

(c) From 4-(3-trifluoromethylphenyl)-piperidin-4-ol there was obtained by elimination 4-(3-trifluoromethylphenyl)-1,2,3,6-tetrahydro-pyridine as a colourless solid; MS: 227 (M)⁺. Subsequent hydroboration gave (3RS,4RS)-4-(3-trifluoromethylphenyl)-piperidin-3-ol as a colourless solid; MS: 245 (M)⁺. Introduction of the BOC group yielded tert-butyl (3RS,4RS)-3-hydroxy-4-(3-trifluoromethylphenyl)-piperidine-1-carboxylate as a colourless solid; MS: 289 (M-C₄H₈)⁺. After alkylation with 4-methoxybenzyl bromide there was obtained tert-butyl (3RS,4RS)-3-(4-methoxy-benzyloxy)-4-(3-trifluoromethylphenyl)-piperidine-1-carboxylate as a light yellow oil; MS: 408 (M-C₄H₉)⁺.

(d) From 1-benzyl-4-(p-tolyl)-piperidin-4-ol there was obtained by elimination 1-benzyl-4-(p-tolyl)-1,2,3,6-tetrahydro-pyridine as a light yellow solid; MS: 263 (M)⁺. Subsequent hydroboration gave (3RS,4RS)-1-benzyl-4-(p-tolyl)-piperidin-3-ol as a colourless solid; MS: 281 (M)⁺.

(e) A solution of 2.5 g (8.9 mmol) of (3RS,4RS)-1-benzyl-4-(p-tolyl)-piperidin-3-ol in 100 ml of methanol was hydrogenated at 5 bar at room temperature for 18 hours using a palladium (10%)-carbon catalyst. For the working up, the catalyst was filtered off, washed with methanol and the solution obtained was evaporated under reduced pressure. For purification, the residue was chromatographed on silica gel using a 5:1:0.1 mixture of methylene chloride, methanol and ammonia as the eluent. There were obtained 1.15 g (68% of theory) of (3RS,4RS)-4-(p-tolyl)-piperidin-3-ol as a colourless solid; MS: 191 (M)⁺.

(f) From (3RS,4RS)-4-(p-tolyl)-piperidin-3-ol by introduction of the BOC group there was obtained tert-butyl (3RS,4RS)-3-hydroxy-4-(p-tolyl)-piperidine-1-carboxylate as a colourless solid; MS: 291 (M)⁺. After alkylation [with] 4-methoxybenzyl bromide there was obtained tert-butyl (3RS,4RS)-3-(4-methoxy-benzyloxy)-4-(p-tolyl)-piperidine-1-carboxylate as a colourless oil; MS: 354 (M-C₄H₉)⁺.

The following compounds were obtained in an analogous manner to that described in Example 1 (g):

(g) By alkylating tert-butyl (3RS,4RS)-3-hydroxy-4-phenyl-piperidine-1-carboxylate with 2-bromomethylnaphthalene there was obtained tert-butyl (3RS,4RS)-3-(napththalen-2-ylmethoxy)-4-phenyl-piperidine-1-carboxylate as a light yellow oil; MS: 417 (M)⁺.

(h) By alkylating tert-butyl (3RS,4RS)-4-(4-bromophenyl)-3-hydroxy-piperidine-1-carboxylate with 2-bromomethyl-naphthalene there was obtained tert-butyl (3RS,4RS)-4-(4-bromophenyl)-3-(naphthalen-2-ylmethoxy)-piperidine-1-carboxylate as a colourless solid; MS: 495, 497 (M)⁺.

(i) By alkylating tert-butyl (3RS,4RS)-3-hydroxy-4-(3-trifluoromethylphenyl)-piperidine-1-carboxylate with 2-bromomethylnaphthalene there was obtained tert-butyl (3RS,4RS)-3-(naphthalen-2-ylmethoxy)-4-(3-trifluoromethyl-phenyl)-piperidine-1-carboxylate as a light yellow oil; MS: 485 (M)⁺.

(j) A solution of 4.0 g tert-butyl (13.8 mmol) of tert-butyl (3RS,4RS)-3-hydroxy-4-phenyl-piperidine-1-carboxylate in 100 ml of methanol was hydrogenated at 150 bar at 100° C. for 18 hours using a rhodium(5%)-aluminium oxide catalyst. For the working up, the catalyst was filtered off, washed with methanol and the solution obtained was evaporated under reduced pressure. For purification, the residue was chromatographed on silica gel using a 4:1 mixture of hexane and ethyl acetate as the eluent. There were obtained 2.32 g (59% of theory) of tert-butyl (3RS,4RS)-4-cyclohexyl-3-(naphthalen-2-ylmethoxy)-piperidine-1-carboxylate as a colourless solid; MS: 283 (M)⁺.

(k) By alkylating tert-butyl (3RS,4RS)-4-cyclohexyl-3-(naphthalen-2-yl-methoxy)-piperidine-1-carboxylate with 2-bromomethylnaphthalene there was obtained tert-butyl (3RS,4RS)-4-cyclohexyl-3-(naphthalen-2-ylmethoxy)-piperidine-1-carboxylate as a light yellow oil; MS: 423 (M)⁺.

(l) By alkylating tert-butyl (3RS,4RS)-3-hydroxy-4-(p-tolyl)-piperidine-1-carboxylate with 2-bromomethylnaphthalene there was obtained tert-butyl (3RS,4RS)-3-(naphthalen-2-ylmethoxy)-4-p-tolyl-piperidine-1-carboxylate as a colourless oil; MS: 431 (M)⁺.

The remaining starting materials were obtained as follows:

(m) From 2-bromonaphthalene and 1-benzyl-4-piperidone there was obtained in an analogous manner to Example 1(a) 1-benzyl-4-naphthalen-2-yl-piperidin-4-ol as a light yellow oil; MS: 317 (M)⁺. Elimination in an analogous manner to that described in Example 1(b) yielded 1-benzyl-4-naphthalen-2-yl-1,2,3,6-tetrahydro-pyridine as a light brown oil; MS: 299 (M)⁺. Subsequent cleavage of the benzyl group analogously to Example 1(d) gave 2-trimethylsilylethyl 4-naphthalen-2-yl-1,2,3,6-tetrahydro-pyridine-1-carboxylate as a colourless solid; 4-MS: 325 (M-C₂H₄)⁺. By treatment with tetrabutylammonium fluoride in tetrahydrofuran analogously to Example 1(e) there was obtained 4-naphthalen-2-yl-1,2,3,6-tetrahydro-pyridine as a colourless solid; MS: 209 (M)⁺. Subsequent hydroboration in an analogous manner to that described in Example 1(c) gave (3RS,4RS)-naphthalen-2-yl-4-piperidin-3-ol as a colourless solid; MS: 227 (M)⁺. Introduction of the BOC group in analogy to Example 1(f) yielded tert-butyl (3RS,4RS)-3-hydroxy-4-naphthalen-2-yl-piperidine-1-carboxylate as a colourless oil; MS: 327 (M)⁺. After alkylation with 2-bromomethylnaphthalene in an analogous manner to the procedure described in Example 1(g) there was obtained tert-butyl (3RS,4RS)-4-naphthalen-2-yl-3-(naphthalen-2-ylmethoxy)-piperidine-1-carboxylate as a colourless oil; MS: 467 (M)⁺.

(n) In an analogous manner to that described in Example 2(e), by catalytically hydrogenating (3RS,4RS)-1-benzyl-4-naphthalen-2-yl-piperidin-3-ol there was obtained (3RS,4RS)-4-(5,6,7,8-tetrahydro-naphthalen-2-yl)-piperidin-3-ol as a colourless solid; MS: 231 (M)⁺. Introduction of the BOC group in an analogous manner to that described in Example 1(f) yielded tert-butyl (3RS,4RS)-3-hydroxy-4-(5,6,7,8-tetrahydro-naphthalen-2-yl)-piperidine-1-carboxylate as a colourless oil; MS: 331 (M)⁺. After alkylation with 2-bromomethylnaphthalene in an analogous manner to the procedure described in Example 1(g) there was obtained tert-butyl (3RS,4RS)-3-(naphthalen-2-ylmethoxy)-4-(5,6,7,8-tetrahydro-naphthalen-2-yl)-piperidine-1-carboxylate as a colourless oil; MS: 471 (M)$^+$.

(o) From 1-benzyl-4-naphthalen-1-yl-1,2,3,6-tetrahydro-pyridine (EP-A-372 776) by hydroboration in an analogous manner to Example 1(c) there was obtained (3RS,4RS)-1-benzyl-4-naphthalen-1-yl-piperidin-3-ol as a colourless solid; MS: 317 (M)$^+$. The benzyl group was removed by catalytic hydrogenation [palladium (10%)-charcoal, ethanol, 80° C., 24 hours, 50 bar, 21% of theory] in an analogous manner to that described in Example 2(e). (3RS,4RS)-4-Naphthalen-1-yl-piperidin-3-ol was obtained as a beige solid; MS: 227 (M)$^+$. Introduction of the BOC group in an analogous manner to that described in Example 1(f) yielded tert-butyl (3RS,4RS)-3-hydroxy-4-naphthalen-1-yl-piperidine-1-carboxylate as a colourless solid; MS: 327 (M)$^+$. After alkylation with 2-bromomethylnaphthalene, in analogy to the procedure described in Example 1(g) there was obtained tert-butyl (3RS,4RS)-4-naphthalen-1-yl-3-(naphthalen-2-ylmethoxy)-piperidine-1-carboxylate as a colourless solid; MS: 467 (M)$^+$.

(p) From 1-benzyl-4-(3,4-dimethoxy-phenyl)-1,2,3,6-tetrahydro-pyridine (JP 60 146 872) by hydroboration in an analogous manner to that described in Example 1(c) there was obtained (3RS,4RS)-1-benzyl-(3,4-dimethoxy-phenyl)-piperidin-3-ol as a colourless solid; MS: 327 (M)$^+$. The benzyl group was removed by catalytic hydrogenation [palladium (10%)-charcoal, methanol, room temperature, 18 hours, 5 bar, 81% of theory] in an analogous manner to that described in Example 2(e). (3RS,4RS)-4-(3,4-Dimethoxy-phenyl)-piperidin-3-ol was obtained as a colourless solid; MS: 237 (M)$^+$. Introduction of the BOC group in an analogous manner to that described in Example 1(f) yielded tert-butyl (3RS,4RS)-3-hydroxy-4-(3,4-dimethoxy-phenyl)-piperidine-1-carboxylate as a light yellow oil; MS: 337 (M)$^+$. After alkylation with 2-bromomethylnaphthalene in analogy to the procedure described in Example 1(g) there was obtained tert-butyl (3RS,4RS)-4-(3,4-dimethoxy-phenyl)-3-(naphthalen-2-ylmethoxy)-piperidine-1-carboxylate as a light yellow oil; MS: 477 (M)$^+$.

(q) From 5-bromo-acenaphthene and 1-benzyl-4-piperidone there was obtained in an analogous manner to Example 1(a) 4-acenaphthen-5-yl-1-benzyl-piperidin-4-ol as a yellow oil; MS: 343 (M)$^+$. Elimination in an analogous manner to that described in Example 1(b) yielded 4-acenaphthen-5-yl-1-benzyl-1,2,3,6-tetrahydro-pyridine as a light brown oil; MS: 325 (M)$^+$. Subsequent hydroboration in an analogous manner to that described in Example 1(c) gave (3RS,4RS)-1-benzyl-acenaphthen-5-yl-4-piperidin-3-ol as a yellow oil; MS: 343 (M)$^+$. The benzyl group was removed by catalytic hydrogenation [palladium (10%)-charcoal, methanol, room temperature, 18 hours, 5 bar, 95% of theory] in an analogous manner to that described in Example 2(e). (3RS,4RS)-4-Acenaphthen-5-yl-piperidin-3-ol was obtained as a colourless solid; MS: 253 (M)$^+$. Introduction of the BOC group in an analogous manner to that described in Example 1(f) yielded tert-butyl (3RS,4RS)-4-acenaphthen-5-yl-3-hydroxy-piperidine-1-carboxylate as a colourless solid; MS: 353 (M)$^+$. After alkylation with 2-bromomethylnaphthalene in analogy to the procedure described in Example 1(g) there was obtained tert-butyl (3RS,4RS)-4-acenaphthen-5-yl-3-(naphthalen-2-ylmethoxy)-piperidine-1-carboxylate as a yellow solid; MS: 493 (M)$^+$.

(r) From 4-(4-chlorophenyl)-piperidin-4-ol by elimination in an analogous manner to that described in Example 1(b) there was obtained 4-(4-chlorophenyl)-1,2,3,6-tetrahydro-pyridine as a light yellow solid; MS: 193, 195 (M)$^+$. Hydroboration in an analogous manner as Example 1(c) gave (3RS,4RS)-4-(4-chlorophenyl)-piperidin-3-ol as a colourless solid; MS: 211, 213 (M)$^+$. Introduction of the BOC group in an analogous manner to that described in Example 1(f) yielded tert-butyl (3RS,4RS)-4-(4-chlorophenyl)-3-hydroxy-piperidine-1-carboxylate as a colourless solid; MS: 255, 257 (M-C$_4$H$_8$)$^+$. After alkylation with 4-phenoxybenzyl chloride in analogy to the procedure described in Example 1(g) there was obtained tert-butyl (3RS,4RS)-4-(4-chlorophenyl)-3-(4-phenoxy-benzyloxy)-piperidine-1-carboxylate as a colourless oil; MS: 437, 439 (M-C$_4$H$_9$)$^+$.

(s) From (3RS,4SR)-4-phenyl-piperidin-3-ol [J. A.Gauthier et al., U.S. Pat. No. 4,132,710] by introduction of the BOC group there was obtained tert-butyl (3RS,4SR)- 3-hydroxy-4-phenyl-piperidine-1-carboxylate as a colourless solid; m.p.: 134–134.5° C. Subsequent alkylation with 2-bromomethylnaphthalene gave tert-butyl (3RS,4SR)-3-(naphthalen-2-ylmethoxy)-4-phenyl-piperidine-1-carboxylate as a colourless solid; MS: 417 (M)$^+$.

EXAMPLE 3

130 mg (0.31 mmol) of tert-butyl (3RS,4RS)-4-(4-fluorophenyl)-3-(4-methoxy-benzyloxy)-piperidine-1-carboxylate were dissolved in 5 ml of methanol, treated with 5 ml of a 2N solution of hydrogen chloride in methanol and stirred at 50° C. for 4 hours. Subsequently, the mixture was partitioned between ethyl acetate and aqueous 5% sodium hydrogen carbonate solution, the organic phase was dried over magnesium sulphate and finally the solvent was distilled off under reduced pressure. For purification, the crude product was chromatographed on silica gel with a 10:1:0.1 mixture of methylene chloride, methanol and ammonia as the eluent. There were obtained 76 mg (78% of theory) of (3RS,4RS)-4-(4-fluorophenyl)-3-(4-methoxy-benzyloxy)-piperidine as a colourless oil. MS: 316 (M+H)$^+$.

The tert-butyl (3RS,4RS)-4-(4-fluorophenyl)-3-(4-methoxy-benzyloxy)-piperidine-1-carboxylate used as the starting material was prepared as follows:

(a) 20.0 g (93.6 mmol) of (3RS,4RS)-4-(4-fluorophenyl)-1,2,3,6-tetrahydropyridine hydrochloride were suspended in 160 ml of absolute dimethoxyethane. 10.6 g (280 mmol) of sodium borohydride were added portionwise at room temperature. Thereafter, a solution of 62 ml (500 mmol) of boron trifluoride etherate in 30 ml of dimethoxyethane was added dropwise at 15–20° C. and the mixture was stirred at room temperature for 2.5 hours. Subsequently, a solution of 65 g (1.16 mmol) of potassium hydroxide in 340 ml of water was added dropwise at 20–25° C. within 60 minutes. 55 ml of hydrogen peroxide solution (30%) were then added dropwise at 20–25° C. within 30 minutes. The mixture was stirred at room temperature for 30 minutes and boiled under reflux for 3 hours. After cooling the reaction mixture the precipitated boric acid was filtered off. Subsequently, the filtrate was partitioned between methylene chloride and water, the organic phase was dried over magnesium sulphate and the solvent was distilled off under reduced pressure. The crude product was purified by chromatography on silica gel with a 3:1:0.1 mixture of methylene chloride, methanol and ammonia as the eluent. There were obtained 9.1 g (50% of theory) of (3RS,4RS)-4-(4-fluorophenyl)-piperidin-3-ol as a colourless oil. MS: 195 (M)$^+$.

(b) 4.10 g (21.0 mmol) of (3RS,4RS)-4-(4-fluorophenyl)-piperidin-3-ol were dissolved in 35 ml of absolute dimethylformamide. Thereto there were added at 0° C. 3.2 ml (23.0 mmol) of triethylamine and subsequently dropwise a solution of 5.04 g (23.1 mmol) of di-tert-butyl dicarbonate in 15 ml of dimethylformamide. The mixture was warmed to room temperature and stirred for 20 hours. The solvent was distilled off at 0.1 mm Hg at 50–55° C. Subsequently, the residue obtained was partitioned between methylene chloride and water, the organic phase was dried over magnesium sulphate and finally the solvent was removed under reduced pressure. The crude product (7.09 g) was purified by chromatography on silica gel with a 2:3 mixture of ethyl acetate and hexane as the eluent. There were obtained 5.45 mg (88% of theory) of tert-butyl (3RS,4RS)-4-(4-fluorophenyl)-3-hydroxy-piperidine-1-carboxylate; MS: 239 $(M-C_4H_8)^+$.

(c) 200 mg (0.68 mmol) of tert-butyl (3RS,4RS)-4-(4-fluorophenyl)-3-hydroxy-piperidine-1-carboxylate and 159 mg (1.01 mmol) of 4-methoxybenzyl chloride were dissolved in 3 ml of dimethylformamide. 40 mg (1.01 mmol) of a 60% sodium hydride suspension were added and the mixture was stirred at room temperature for 3 hours. Subsequently, the reaction mixture was partitioned between ethyl acetate and water, the organic phase was dried over magnesium sulphate and finally the solvent was removed under reduced pressure. The crude product was purified by chromatography on silica gel with a 1:3 mixture of ethyl acetate and hexane as the eluent. There were obtained 250 mg (90% of theory) of tert-butyl (3RS,4RS)-4-(4-fluorophenyl)-3-(4-methoxy-benzyloxy)-piperidine-1-carboxylate as a light yellow oil; MS: 358 $(M-C_4H_9)^+$.

EXAMPLE 4

The following compounds were prepared in an analogous manner to that described in Example 3:

1) (3RS,4RS)-4-(4-fluorophenyl)-3-(naphthalen-2-ylmethoxy)-piperidine as a colourless oil, MS: 336 $(M+1)^+$, from tert-butyl (3RS,4RS)-4-(4-fluorophenyl)-3-(naphthalen-2-yl-methoxy)-piperidine-1-carboxylate;

2) (3RS,4RS)-3-(3-benzyloxy-benzyloxy)-4-(4-fluorophenyl)-piperidine as a colourless solid, MS: 392 $(M+1)^+$, from tert-butyl (3RS,4RS)-3-(3-benzyloxy-benzyloxy)-4-(4-fluorophenyl)-piperidine-1-carboxylate;

3) (3RS,4RS)-4-(4-fluorophenyl)-3-(4-methoxy-quinazolin-2-ylmethoxy)-piperidine as a colourless solid, MS: 368 $(M+1)^+$, from tert-butyl (3RS,4RS)-4-(4-fluorophenyl)-3-(4-methoxy-quinazolin-2-ylmethoxy)-piperidine-1-carboxylate;

4) (3RS,4RS)-3-(benzo[b]thiophen-5-ylmethoxy)-4-(4-fluoro-phenyl)-piperidine as a colourless solid, MS: 342 $(M+1)^+$, from tert-butyl (3RS,4RS)-3-(benzo[b]thiophen-5-ylmethoxy)-4-(4-fluoro-phenyl)-piperidine-1-carboxylate;

5) (3RS,4RS)-4-(4-fluorophenyl)-3-(indan-5-ylmethoxy)-piperidine as a colourless solid, MS: 326 $(M+1)^+$, from tert-butyl (3RS,4RS)-4-(4-fluorophenyl)-3-(indan-5-ylmethoxy)-piperidine-1-carboxylate, 6) (3RS,4RS)-4-(4-fluoro-phenyl)-3-(5,6,7,8-tetrahydro-naphthalen-2-ylmethoxy)-piperidine as a colourless solid, MS: 340 $(M+1)^+$, from tert-butyl (3RS,4RS)-4-(4-fluorophenyl)-3-(5,6,7,8-tetra-hydronaphthalen-2-ylmethoxy)-piperidine-1-carboxylate;

7) (3RS,4RS)-4-(4-fluoro-phenyl)-3-(isoquinolin-6-ylmethoxy)-piperidine as a colourless solid, MS: 337 $(M+1)^+$, from tert-butyl (3RS,4RS)-4-(4-fluoro-phenyl)-3-(isoquinolin-6-ylmethoxy)-piperidine-1-carboxylate.

The BOC derivatives used as the starting materials were obtained as follows in an analogous manner to the alkylation procedure described in Example 3(c):

tert-Butyl (3RS,4RS)-4-(4-fluorophenyl)-3-(naphthalen-2-yl-methoxy)-piperidine-1-carboxylate as a light yellow oil, MS: 436 $(M+1)^+$, from tert-butyl (3RS,4RS)-4-(4-fluorophenyl)-3-hydroxy-piperidine-1-carboxylate and 2-naphthylmethyl bromide;

tert-butyl (3RS,4RS)-3-(3-benzyloxy-benzyloxy)-4-(4-fluorophenyl)-piperidine-1-carboxylate as a colourless solid, MS: 492 $(M+1)^+$, from tert-butyl (3RS,4RS)-4-(4-fluorophenyl)-3-hydroxy-piperidine-1-carboxylate and 3-benzyloxy-benzyl chloride [J. Med. Chem. 31(3), 606 (1988)];

tert-butyl (3RS,4RS)-4-(4-fluorophenyl)-3-(4-methoxy-quinazolin-2-ylmethoxy)-piperidine-1-carboxylate as a colourless solid, MS: 492 $(M+1)^+$, from tert-butyl (3RS,4RS)-4-(4-fluorophenyl)-3-hydroxy-piperidine-1-carboxylate and 2-bromo-methyl-4-methoxy-quinazoline;

tert-butyl (3RS,4RS)-3-(benzo[b]thiophen-5-ylmethoxy)-4-(4-fluoro-phenyl)-piperidine-1-carboxylate as a light yellow resin, MS: 442 $(M+1)^+$, from tert-butyl (3RS,4RS)-4-(4-fluorophenyl)-3-hydroxy-piperidine-1-carboxylate and 5-bromomethyl-benzo[b]thiophene [J. Med. Chem. 34(1), 65(1991)];

tert-butyl (3RS,4RS)-4-(4-fluorophenyl)-3-(indan-5-ylmethoxy)-piperidine-1-carboxylate as a colourless solid, MS: 426 $(M+1)^+$, from tert-butyl (3RS,4RS)-4-(4-fluorophenyl)-3-hydroxy-piperidine-1-carboxylate and 5-chloromethylindane [Recl. Trav. Chim. Pays-Bas 77, 792 (1988)];

tert-butyl (3RS,4RS)-4-(4-fluorophenyl)-3-(5,6,7,8-tetrahydro-naphthalen-2-ylmethoxy)-piperidine-1-carboxylate as a light yellow resin, MS: 440 $(M+1)^+$, from tert-butyl (3RS,4RS)-4-(4-fluorophenyl)-3-hydroxy-piperidine-1-carboxylate and 6-chloromethyl-1,2,3,4-tetrahydro-naphthalene [J. Chem. Soc. 684 (1941)];

tert-butyl (3RS,4RS)-4-(4-fluoro-phenyl)-3-(isoquinolin-6-ylmethoxy)-piperidine-1-carboxylate as a light yellow resin, MS: 437 $(M+1)^+$, from tert-butyl (3RS,4RS)-4-(4-fluorophenyl)-3-hydroxy-piperidine-1-carboxylate and 6-bromomethylisoquinoline hydrobromide.

2-Bromomethyl-4-methoxy-quinazoline (a) By brominating 2-methyl-4-methoxy-quinazoline [Recl. Trav. Chim. Pays-Bas 76, 401 (1957)] with N-bromosuccinimide in carbon tetrachloride in an analogous manner to the procedure described for the preparation of 6-bromomethylquinoxaline [J. Het. Chem. 11, 595(1974)] from 6-methylquinoxaline there was obtained 2-bromomethyl-4-methoxy-quinazoline as a light yellow solid; MS: 252, 254 $(M)^+$.

6-Bromomethyl-isoquinoline hydrobromide (b) From isoquinoline-6-carboxylic acid [J.Am.Chem.Soc. 61, 183(1939)] by esterification with ethanol/sulphuric acid there was obtained ethyl isoquinoline-6-carboxylate as a colourless solid; MS: 201 $(M)^+$. Subsequent reduction yielded 6-isoquinoline-methanol as a yellow solid which was used directly in the next step.

(c) A solution of 190 mg (1.19 mmol) of 6-isoquinoline-methanol in 1 ml of glacial acetic acid was treated with 2 ml of 30% HBr in glacial acetic acid and the mixture was heated at 70° C. for 45 minutes. The reaction mixture was cooled, treated with 20 ml of diethyl ether and stirred at 0° C. for 30 min. The resulting solid was filtered off, washed with diethyl ether and dried in a high vacuum. There was obtained 6-bromomethyl-isoquinoline hydrobromide (73% of theory) as a light brown solid; MS: 221, 223 $(M)^+$.

EXAMPLE 5

70 mg (0.141 mmol) of β-trimethylsilylethyl (3RS,4RS)-4-(4-fluorophenyl)-3-(4-hydroxy-naphthalen-2-ylmethoxy)- piperidine-1-carboxylate were dissolved in 1.0 ml of tetrabutylammonium fluoride solution (1M in tetrahydrofuran) and stirred at room temperature for one hour. Subsequently, the mixture was partitioned between methylene chloride and aqueous 5% sodium hydrogen carbonate solution, then the organic phase was dried over magnesium sulphate and finally the solvent was distilled off under reduced pressure. The crude product (72 mg) was purified by chromatography on silica gel with a 10:1:0.1 mixture of methylene chloride, methanol and ammonia as the eluent. There were obtained 41 mg (83% of theory) of (3RS,4RS)-4-(4-fluorophenyl)-3-(4-hydroxy-naphthalen-2-ylmethoxy)-piperidine as a colourless solid. MS: 352 (M+H)$^+$.

The 62 -trimethylsilylethyl (3RS,4RS)-4-(4-fluorophenyl)-3-(4-hydroxy-naphthalen-2-ylmethoxy)-piperidine-1-carboxylate used as the starting material was prepared as follows:

(a) 17.87 g (82.64 mmol) of ethyl 4-hydroxy-naphthalene-2-carboxylate [J.Agric.Chem Soc.Japan 24, 313 (1950)] were suspended in 900 ml of methylene chloride, the suspension was cooled to 0–5° C. and subsequently treated with 17.9 ml (91.02 mmol) of 2-(trimethylsilyl)-ethoxymethyl chloride (SEM chloride) and 28.3 ml (165.31 mmol) of N-ethyldiisopropylamine. The yellow solution was warmed to room temperature and stirred for 2 hours. The solvent was distilled off under reduced pressure and the crude product (58 g), without further purification, was chromatographed on silica gel using a 3:2 mixture of methylene chloride and hexane as the eluent. There were obtained 15.81 g (99% of theory) of ethyl 4-(2-trimethyl-silylethoxy-methoxy)-naphthalene-2-carboxylate as a light yellow oil; MS: 322, 324 (M)$^+$.

(b) A solution of 28.31 g (81.70 mmol) of ethyl 4-(2-trimethyl-silylethoxy-methoxy)-naphthalene-2-carboxylate in 480 ml of diethyl ether was added dropwise within 90 minutes at −5 to 0° C. under argon to a suspension of 3.29 g (86.69 mmol) of lithium aluminium hydride in 230 ml of diethyl ether. The reaction mixture was warmed to room temperature and stirred for 2 hours. For the working-up, the mixture was cooled to 0° C., treated dropwise with 25 ml of ethyl acetate and with 50 ml of saturated potassium sodium tartrate solution. A light yellowish solution containing a white precipitate resulted. The solution was warmed to room temperature [and] decanted off from the precipitate. The residue was suspended three times with diethyl ether and the solvent was decanted off each time. The combined organic phases were washed with water, the organic phase was dried over magnesium sulphate and finally the solvent was removed under reduced pressure. The crude product (26.4 g) was chromatographed on silica gel using a 3:7 mixture of ethyl acetate and hexane. There were obtained 23.72 g (95% of theory) of [4-(2-trimethylsilyl-ethoxymethoxy)-naphthalen-2-yl]-methanol as a light yellow oil; MS: 304 (M)$^+$.

(c) 23.72 g (77.91 mmol) of [4-(2-trimethylsilyl-ethoxymethoxy)-naphthalen-2-yl]-methanol were dissolved in 350 ml of carbon tetrachloride and the solution was cooled to 0° C. Thereupon, 350 ml of acetonitrile and 26.54 g (1.012 mmol) of triphenylphosphine were added. The light yellow solution was stirred at 0° C. for 30 minutes, warmed to room temperature and stirred for a further 2 hours. A further 10.14 g (38.7 mmol) of triphenylphosphine were added and the reaction mixture was stirred at room temperature for 90 minutes. Subsequently, the mixture was partitioned between methylene chloride and water, the organic phase was dried over magnesium sulphate and finally the solvent was removed under reduced pressure. The crude product was chromatographed on silica gel using a 3:7 mixture of methylene chloride and hexane as the eluent. There were obtained 15.81 g (63% of theory) of 2-chloromethyl-4-(p-trimethylsilyl-ethoxymethoxy)-naphthalene as a light yellow oil; MS: 322, 324 (M)$^+$.

(d) A solution of 4.00 g (20.5 mmol) of (3RS,4RS)-4-(4-fluorophenyl)-piperidin-3-ol in 150 ml of ethanol was treated with 2.80 g (26.4 mmol) of sodium carbonate and refluxed. A solution of 2.50 ml (21.1 mmol) of benzyl bromide in 50 ml of ethanol was added dropwise within one hour and thereafter the mixture was held at reflux temperature for 2 hours. The pale brownish suspension was filtered and the filtrate was concentrated under reduced pressure. Subsequently, the residue was partitioned between methylene chloride and water, the organic phase was dried over magnesium sulphate and finally the solvent was distilled off under reduced pressure. The crude product was chromatographed on silica gel using a 2:3 mixture of ethyl acetate and hexane as the eluent. There were obtained 4.34 g (74% of theory) of (3RS,4RS)-1-benzyl-4-(4-fluoro-phenyl)-piperidin-3-ol as a colourless solid; MS: 285 (M)$^+$.

(e) In an analogous manner to that described in Example 1(g), by alkylating (3RS,4RS)-1-benzyl-4-(4-fluorophenyl)-piperidin-3-ol with 2-chloromethyl-4-(β-trimethylsilylethoxymethoxy)-naphthalene there was obtained (3RS,4RS)- 1-benzyl-4-(4-fluoro-phenyl)-3-[4-(2-trimethylsilyl-ethoxymethoxy)-naphthalen-2-ylmethoxy]-piperidine as a light yellow oil; MS: 572 (M+H)$^+$.

(f) In an analogous manner to that described in Example 1(d) by cleavage of the benzyl group by means of β-trimethylsilylethyl chloroformate from (3RS,4RS)-1-benzyl-4-(4-fluoro-phenyl)-3-[4-(2-trimethylsilyl-ethoxymethoxy)-naphthalen-2-ylmethoxy]-piperidine there was obtained β-trimethylsilylethyl (3RS,4RS)-4-(4-fluorophenyl)-3-[4-(2-trimethylsilyl-ethoxymethoxy)-naphthalen-2-yl-methoxy]-piperidine-1-carboxylate as a light yellow oil; MS: 626 (M+H)$^+$.

(g) 4.65 g (7.43 mmol) of β-trimethylsilylethyl (3RS,4RS)-4-(4-fluorophenyl)-3-[4-(2-trimethylsilyl-ethoxymethoxy)-naphthalen-2-ylmethoxy]-piperidin-1-carboxylate were dissolved in 40 ml of methanol, treated with 40 ml of a 2N solution of hydrogen chloride in methanol and stirred at 50° C. for 90 minutes. Subsequently, the mixture was partitioned between methylene chloride and aqueous 5% sodium hydrogen carbonate solution, the organic phase was dried over magnesium sulphate and finally the solvent was distilled off under reduced pressure. The crude product (6.8 g) was purified by chromatography on silica gel with a 3:7 mixture of ethyl acetate and hexane. There were obtained 2.93 g (80% of theory) of p-trimethylsilylethyl (3RS,4RS)-4-(4-fluorophenyl)-3-(4-hydroxy-naphthalen-2-ylmethoxy)-piperidine-1-carboxylate as a colourless solid; MS: 496 (M+H)$^+$.

EXAMPLE 6

The following compounds were obtained in an analogous manner to that described in Example 5:

1) 4-(4-Fluoro-phenyl)-3-(1-hydroxy-naphthalen-2-ylmethoxy)-piperidine as a light brown solid, MS: 351 (M)$^+$, from β-trimethylsilylethyl (3RS,4RS)-4-(4-fluorophenyl)-3-(1-hydroxy-naphthalen-2-ylmethoxy)-piperidine-1-carboxylate;

2) -4-(4-fluoro-phenyl)-3-(5-hydroxy-naphthalen-2-ylmethoxy)-piperidine as a colourless solid, MS: 351 (M)$^+$, from β-trimethylsilylethyl (3RS,4RS)-4-(4-fluorophenyl)-3-(5-hydroxy-naphthalen-2-ylmethoxy)-piperidine-1-carboxylate;

3) -4-(4-fluoro-phenyl)-3-(6-hydroxy-naphthalen-2-ylmethoxy)-piperidine as a colourless solid, MS: 351 (M)⁺, from β-trimethylsilylethyl (3RS,4RS)-4-(4-fluorophenyl)-3-(6-hydroxy-naphthalen-2-ylmethoxy)-piperidine-1-carboxylate;
4) -4-(4-fluoro-phenyl)-3-(7-hydroxy-naphthalen-2-ylmethoxy)-piperidine as a light brown solid, MS: 351 (M)⁺, from β-trimethylsilylethyl (3RS,4RS)-4-(4-fluorophenyl)-3-(7-hydroxy-naphthalen-2-ylmethoxy)-piperidine-1-carboxylate;
5) -4-(4-fluoro-phenyl)-3-(8-hydroxy-naphthalen-2-ylmethoxy)-piperidine as a light yellow resin, MS: 352 (M+H)⁺, from β-trimethylsilylethyl (3RS,4RS)-4-(4-fluorophenyl)-3-(8-hydroxy-naphthalen-2-ylmethoxy)-piperidine-1-carboxylate.

The trimethylsilylethyl carbamates used as the starting materials were obtained as follows in analogy to the procedure described in Example 5(a)–(f):

(a) From methyl 1-hydroxy-naphthalene-2-carboxylate [J. Chem. Soc. 309 (1948)] by introducing the protecting group there was obtained methyl 1-(2-trimethylsilylethoxymethoxy)-naphthalene-2-carboxylate as a light yellow oil, MS: 333 (M+H)⁺.
(b) Reduction of methyl 1-(2-trimethylsilyl-ethoxymethoxy)-naphthalene-2-carboxylate gave [1-(2-trimethyl-silylethoxy-methoxy)-naphthalen-2-yl]-methanol as a light yellow oil, MS: 305 (M+H)⁺.
(c) Chlorination of [1-(2-trimethylsilylethoxy-methoxy)-naphthalen-2-yl]-methanol yielded 2-chloro-methyl-1-(β-trimethylsilylethoxymethoxy)-naphthalene as a colourless oil, MS: 322, 324 (M)⁺.
(d) Alkylation of (3RS,4RS)-1-benzyl-4-(4-fluoro-phenyl)-piperidin-3-ol with 2-chloromethyl-1-(β-trimethylsilylethoxy-methoxy)-naphthalene yielded (3RS,4RS)- 1-benzyl-3-(4-fluorophenyl)-3-[1-(2-trimethylsilylethoxy-methoxy)-naphthalen-2-ylmethoxy]-piperidine as a light yellow oil, MS: 572 (M+H)⁺.
(e) Cleavage of the N-benzyl group from (3RS,4RS)-1-benzyl-3-(4-fluorophenyl)-3-[1-(2-trimethylsilylethoxy-methoxy)-naphthalen-2-ylmethoxy]-piperidine with β-trimethylsilylethyl chloroformate gave β-trimethylsilylethyl (3RS,4RS)-4-(4-fluorophenyl)-3-[1-(2-trimethylsilyl-ethoxymethoxy)-naphthalen-2-ylmethoxy]-piperidine-1-carboxylate as a colourless oil, MS: 626 (M+H)⁺.
(f) Cleavage of the SEM group from β-trimethylsilylethyl (3RS,4RS)-4-(4-fluorophenyl)-3-[1-(2-trimethylsilyl-ethoxymethoxy)-naphthalen-2-ylmethoxy]-piperidine-1-carboxylate yielded β-trimethylsilylethyl (3RS,4RS)-4-(4-fluorophenyl)-3-(1-hydroxy-naphthalen-2-ylmethoxy)-piperidine-1-carboxylate as a colourless oil, MS: 494 (M–H)⁻.
(g) From 5-hydroxy-naphthalene-2-carboxylic acid [Bull. Soc. Chim. Fr., 857 (1953)] there was obtained firstly by esterification with methanol/sulphuric acid methyl 5-hydroxy-naphthalene-2-carboxylate as a light yellow solid, MS: 202 (M)⁺. By introducing the protecting group there was obtained methyl 5-(2-trimethylsilyl-ethoxymethoxy)-naphthalene-2-carboxylate as a light yellow oil, MS: 333 (M+H)⁺.
(h) Reduction of methyl 5-(2-trimethylsilyl-ethoxymethoxy)-naphthalene-2-carboxylate gave [5-(2-trimethylsilyl-ethoxymethoxy)-naphthalen-2-yl]-methanol as a light yellow oil, MS: 305 (M+H)⁺.
(i) Chlorination of [5-(2-trimethylsilyl-äthoxymethoxy)-naphthalen-2-yl]-methanol yielded 2-chloro-methyl-5-(β-trimethyl-silylethoxy-methoxy)-naphthalene as a colourless oil, MS: 322, 324 (M)⁺.
(j) Alkylation of (3RS,4RS)-1-benzyl-4-(4-fluoro-phenyl)-piperidin-3-ol with 2-chloromethyl-5-(β-trimethyl-silylethoxy-methoxy)-naphthalene yielded (3RS,4RS)-1-benzyl-3-(4-fluoro-phenyl)-3-[5-(2-tri-methylsilyl-ethoxymethoxy)-naphthalen-2-ylmethoxy]-piperidine as a light yellow oil, MS: 572 (M+H)⁺.
(k) Cleavage of the N-benzyl group from (3RS,4RS)-1-benzyl-3-(4-fluoro-phenyl)-3-[5-(2-trimethylsilyl-ethoxymethoxy)-naphthalen-2-ylmethoxy]-piperidine with β-trimethylsilylethyl chloroformate gave β-trimethylsilylethyl (3RS,4RS)-4-(4-fluorophenyl)-3-[5-(2-trimethylsilyl-ethoxymethoxy)-naphthalen-2-ylmethoxy]-piperidine-1-carboxylate as a colourless oil, MS: 626 (M+H)⁺.
(l) Cleavage of the SEM group in β-trimethylsilylethyl (3RS,4RS)-4-(4-fluorophenyl)-3-[5-(2-trimethylsilyl-ethoxymethoxy)-naphthalen-2-ylmethoxy]-piperidine-1-carboxylate yielded β-trimethylsilylethyl (3RS,4RS)-4-(4-fluoro-phenyl)-3-(5-hydroxy-naphthalen-2-ylmethoxy)-piperidine-1-carboxylate as a colourless oil, MS: 494 (M–H)⁻.
(m) From ethyl 6-hydroxy-naphthalene-2-carboxylate [J. Chem. Soc. 123, 1654 (1923)] by introducing the protecting group there was obtained ethyl 6-(2-trimethylsilyl-ethoxymethoxy)-naphthalene-2-carboxylate as a light yellow oil, MS: 346 (M)⁺.
(n) Reduction of ethyl 6-(2-trimethylsilyl-ethoxymethoxy)-naphthalene-2-carboxylate gave [6-(2-trimethylsilyl-ethoxy-methoxy)-naphthalen-2-yl]-methanol as a colourless solid, MS: 304 (M)⁺.
(o) Chlorination of [6-(2-trimethylsilyl-ethoxy-methoxy)-naphthalen-2-yl]-methanol yielded 6-chloromethyl-1-(-trimethylsilylethoxymethoxy)-naphthalene as a colourless oil, MS: 322, 324 (M)⁺.
(p) Alkylation of (3RS,4RS)-1-benzyl-4-(4-fluoro-phenyl)-piperidin-3-ol with 6-chloromethyl-1-(β-trimethylsilylethoxymethoxy)-naphthalene yielded (3RS, 4RS)-1-benzyl-3-(4-fluorophenyl)-3-[6-(2-trimethyl-silylethoxy-methoxy)-naphthalen-2-ylmethoxy]-piperidine as a light yellow oil, MS: 572 (M+H)⁺.
(q) Cleavage of the N-benzyl group from (3RS,4RS)-1-benzyl-3-(4-fluorophenyl)-3-[6-(2-trimethyl-silylethoxy-methoxy)-naphthalen-2-ylmethoxy]-piperidine with β-trimethylsilylethyl chloroformate gave β-trimethylsilylethyl (3RS,4RS)-4-(4-fluorophenyl)-3-[6-(2-trimethylsilylethoxy-methoxy)-naphthalen-2-yl-methoxy]-piperidine-1-carboxylate as a colourless oil, MS: 626 (M+H)⁺.
(r) Cleavage of the SEM group from β-trimethylsilylethyl (3RS,4RS)-4-(4-fluorophenyl)-3-[6-(2-trimethylsilylethoxy-methoxy)-naphthalen-2-yl-methoxy]-piperidine-1-carboxylate yielded β-trimethylsilylethyl (3RS,4RS)-4-(4-fluorophenyl)-3-(6-hydroxy-naphthalen-2-ylmethoxy)-piperidine-1-carboxylate as a colourless resin, MS: 495 (M)⁺.
(s) From 7-hydroxy-naphthalene-2-carboxylic acid [Bull. Soc. Chim. Fr., 573 (1952)] there was firstly obtained by esterification with methanol/sulphuric acid methyl 7-hydroxy-naphthalene-2-carboxylate as a colourless solid, MS: 202 (M)⁺. Introduction of the protecting group yielded methyl 7-(2-trimethylsilyl-ethoxymethoxy)-naphthalene-2-carboxylate as a light yellow oil, MS: 332 (M)⁺.
(t) Reduction of methyl 7-(2-trimethylsilyl-ethoxymethoxy)-naphthalene-2-carboxylate gave [7-(2- trimethylsilyl-ethoxymethoxy)-naphthalen-2-yl]-methanol as a light yellow oil, MS: 304 (M)+.
(u) Chlorination of [7-(2-trimethylsilyl-ethoxy-methoxy)-naphthalen-2-yl]-methanol yielded 2-chloromethyl-7-(β-trimethyl-silylethoxymethoxy)-naphthalene as a light yellow oil, MS: 322, 324 (M)+.
(v) Alkylation of (3RS,4RS)-1-benzyl-4-(4-fluoro-phenyl)-piperidin-3-ol with 2-chloromethyl-7-(β-trimethyl-silylethoxymethoxy)-naphthalene yielded (3RS,4RS)-1-benzyl-3-(4-fluoro-phenyl)-3-[7-(2-trimethylsilyl-ethoxymethoxy)-naphthalen-2-ylmethoxy]-piperidine as a light yellow oil, MS: 572 (M+H)+.
(w) Cleavage of the N-benzyl group from (3RS,4RS)-1-benzyl-3-(4-fluoro-phenyl)-3-[7-(2-trimethylsilyl-ethoxymethoxy)-naphthalen-2-ylmethoxy]-piperidine with β-trimethylsilylethyl chloroformate yielded β-trimethylsilylethyl (3RS,4RS)-4-(4-fluorophenyl)-3-[7-(2-trimethylsilyl-ethoxymethoxy)-naphthalen-2-ylmethoxy]-piperidine-1-carboxylate as a colourless oil, MS: 626 (M+H)+.
(x) Cleavage of the SEM group from β-trimethylsilylethyl (3RS,4RS)-4-(4-fluorophenyl)-3-[7-(2-trimethylsilyl-ethoxymethoxy)-naphthalen-2-ylmethoxy]-piperidine-1-carboxylate yielded β-trimethylsilylethyl (3RS,4RS)-4-(4-fluorophenyl)-3-(7-hydroxy-naphthalen-2-ylmethoxy)-piperidine-1-carboxylate as a light yellow oil, MS: 495 (M)+.
(y) From 8-hydroxy-naphthalene-2-carboxylic acid [Bull. Soc. Chim. Fr., 857 (1953)] there was firstly obtained by esterification with methanol/sulphuric acid methyl 8-hydroxy-naphthalene-2-carboxylate as a light yellow solid, MS: 202 (M)+. Introduction of the protecting group yielded methyl 8-(2-trimethylsilyl-ethoxymethoxy)-naphthalene-2-carboxylate as a colourless solid, MS: 274 [M-($C_2H_4$+$CH_2O$)]+.
(z) Reduction of methyl 8-(2-trimethylsilyl-ethoxymethoxy)-naphthalene-2-carboxylate gave [8-(2-trimethylsilyl-ethoxymethoxy)-naphthalen-2-yl]-methanol as a colourless oil, MS: 304 (M)+.
(aa) Chlorination of [8-(2-trimethylsilyl-ethoxymethoxy)-naphthalen-2-yl]-methanol yielded 2-chloromethyl-8-(2-trimethylsilylethoxy-methoxy)-naphthalene as a light yellow oil, MS: 322, 324 (M)+.
(bb) Alkylation of (3RS,4RS)-1-benzyl-4-(4-fluoro-phenyl)-piperidin-3-ol with 2-chloromethyl-8-(2-trimethylsilylethoxy-methoxy)-naphthalene yielded (3RS,4RS)-1-benzyl-3-(4-fluoro-phenyl)-3-[8-(2-trimethylsilylethoxy-methoxy)-naphthalen-2-ylmethoxy]-piperidine as a light yellow oil, MS: 572 (M+H)+.
(cc) Cleavage of the N-benzyl group from (3RS,4RS)-1-benzyl-3-(4-fluoro-phenyl)-3-[8-(2-trimethylsilylethoxy-methoxy)-naphthalen-2-ylmethoxyl-piperidine with β-trimethylsilylethyl chloroformate gave β-trimethylsilylethyl (3RS,4RS)-4-(4-fluorophenyl)-3-[8-(2-trimethylsilyl-ethoxymethoxy)-naphthalen-2-yl-methoxy]-piperidine-1-carboxylate as a colourless oil, MS: 626 (M+H)+.
(dd) Cleavage of the SEM group from β-trimethylsilylethyl (3RS,4RS)-4-(4-fluorophenyl)-3-[8-(2-trimethylsilyl-ethoxymethoxy)-naphthalen-2-yl-methoxy]-piperidine-1-carboxylate yielded β-trimethylsilylethyl (3RS,4RS)-4-(4-fluorophenyl)-3-(8-hydroxy-naphthalen-2-ylmethoxy)-piperidine-1-carboxylate as a colourless oil, MS: 494 (M-H)−.

EXAMPLE 7

The following compounds were prepared in an analogous manner to that described in Examples 3 and 5:

1) (3RS,4RS)-4-(4-Fluorophenyl)-3-(3-hydroxy-naphthalen-2-ylmethoxy)-piperidine

In an analogous manner to that described in Examples 3 and 5(g), by cleaving off the two protecting groups with methanolic hydrochloric acid from tert-butyl (3RS,4RS)-4-(4-fluorophenyl)-3-[3-(2-trimethylsilyl-ethoxymethoxy)-naphthalen-2-yl-methoxy]-piperidine-1-carboxylate there was obtained (3RS,4RS)-4-(4-fluorophenyl)-3-(3-hydroxy-naphthalen-2-yl-methoxy)-piperidine as a colourless solid, MS: 351 (M)+.

The tert-butyl (3RS,4RS)-4-(4-fluorophenyl)-3-[3-(2-trimethylsilyl-ethoxymethoxy)-naphthalen-2-ylmethoxy]-piperidine-1-carboxylate used as the starting material was prepared as follows:
(a) In an analogous manner to that described in Example 5(a), from methyl 3-hydroxy-naphthalene-2-carboxylate by introducing the protecting group there was obtained methyl 3-(2-trimethylsilyl-ethoxy-methoxy)-naphthalene-2-carboxylate as a light yellow oil, MS: 274 (M-($C_2H_4$+$CH_2O$)]+.
(b) In an analogous manner to that described in Example 5(b), reduction of methyl 3-(2-trimethylsilyl-ethoxy-methoxy)-naphthalene-2-carboxylate gave [3-(2-trimethylsilylethoxy-methoxy)-naphthalen-2-yl]-methanol as a light yellow oil, MS: 304 (M)+.
(c) 400 mg (1.30 mmol) of [3-(2-trimethylsilylethoxy-methoxy)-naphthalen-2-yl]-methanol and 462 mg (1.81 mmol) of carbon tetrabromide were dissolved in 5 ml of absolute acetonitrile and the solution was cooled to 0° C. A solution of 446 mg (1.68 mmol) of triphenylphosphine in 6 ml of absolute acetonitrile was added dropwise thereto at 0° C. within 10 minutes and thereafter the mixture was stirred at 0° C. for a further 30 minutes. Subsequently, the solvent was distilled off under reduced pressure and, for purification, the crude product was chromatographed, without further working up, on silica gel using a 2:3 mixture of methylene chloride and hexane as the eluent. There were obtained 314 mg (65% of theory) of 2-bromomethyl-3-(2-trimethylsilylethoxymethoxy)-naphthalene as a light yellow oil; MS: 366, 368 (M)+.
(d) In an analogous manner to that described in Example 3(c), by alkylating tert-butyl (3RS,4RS)-4-(4-fluorophenyl)-3-hydroxy-piperidine-1-carboxylate with 2-bromomethyl-3-(2-trimethylsilylethoxy-methoxy)-naphthalene there was obtained tert-butyl (3RS,4RS)-4-(4-fluorophenyl)-3-[3-(2-trimethylsilyl-ethoxy-methoxy)-naphthalen-2-ylmethoxy]-piperidine-1-carboxylate as a light yellow oil; MS: 523 [M-($C_2H_4$+$CH_2O$)]+.

2) (3RS,4RS)-4-(4-Fluorophenyl)-3-(1-methoxy-naphthalen-2-yl-methoxy)-piperidine In an analogous manner to that described in Example 3, by cleavage of the BOC protecting group from tert-butyl (3RS,4RS)-4-(4-fluorophenyl)-3-[1-methoxy-naphthalen-2-ylmethoxy]-piperidine-1-carboxylate there was obtained (3RS,4RS)-4-(4-fluorophenyl)-3-(1-methoxy-naphthalen-2-yl-methoxy)-piperidine as a light yellow oil; MS: 365 (M)+.

The tert-butyl (3RS,4RS)-4-(4-fluorophenyl)-3-[1-methoxy-naphthalen-2-ylmethoxy]-piperidine-1-carboxylate used as the starting material was obtained as follows:
(e) In an analogous manner to that described in Example 5(b), by reducing methyl 1-methoxy-naphthalene-2-carboxylate [J. Chem. Soc. 121,1657 (1922)] there was obtained [1-methoxy)-naphthalen-2-yl]-methanol as a colourless solid; MS: 188 (M)+.

(f) In an analogous manner to that described in Example 7(c), by brominating [1-methoxy)-naphthalen-2-yl]-methanol there was obtained 2-bromomethyl-1-methoxy-naphthalene as a colourless solid; MS: 250, 252 (M)⁺.

(g) In an analogous manner to that described in Example 3(c), by alkylating tert-butyl (3RS,4RS)-4-(4-fluorophenyl)-3-hydroxy-piperidine-1-carboxylate [Example 3(b)] with 2-bromomethyl-1-methoxy-naphthalene there was obtained tert-butyl (3RS,4RS)-4-(4-fluorophenyl)-3-[1-methoxy-naphthalen-2-yl-methoxy]-piperidine-1-carboxylate as a colourless resin; MS: 465 (M)⁺.

3) (3RS,4RS)-4-(4-Fluorophenyl)-3-(3-methoxy-naphthalen-2-yl-methoxy)-piperidine In an analogous manner to that described in Example 3, by cleavage of the BOC protecting group from tert-butyl (3RS,4RS)-4-(4-fluorophenyl)-3-[3-methoxy-naphthalen-2-ylmethoxy)-piperidine-1-carboxylate there was obtained (3RS,4RS)-4-(4-fluorophenyl)-3-(3-methoxy-naphthalen-2-yl-methoxy)-piperidine as a light yellow oil; MS: 365 (M)⁺.

The tert-butyl (3RS,4RS)-4-(4-fluorophenyl)-3-[3-methoxy-naphthalen-2-ylmethoxy]-piperidine-1-carboxylate used as the starting material was obtained as follows:

(h) In an analogous manner to that described in Example 5(b), by reducing methyl 3-methoxy-naphthalene-2-carboxylate [J. Chem. Soc. 2351 (1950)] there was obtained [3-methoxy)-naphthalen-2-yl]-methanol as a colourless solid; MS: 188 (M)⁺.

(i) In an analogous manner to that described in Example 7(c), by brominating [3-methoxy)-naphthalen-2-yl]-methanol there was obtained 2-bromomethyl-3-methoxy-naphthalene as a colourless solid; MS: 250, 252 (M)⁺.

(j) In an analogous manner to that described in Example 3(c), by alkylating tert-butyl (3RS,4RS)-4-(4-fluorophenyl)-3-hydroxy-piperidine-1-carboxylate [Example 3(b)] with 2-bromomethyl-3-methoxy-naphthalene there was obtained tert-butyl (3RS,4RS)-4-(4-fluorophenyl)-3-[3-methoxy-naphthalen-2-yl-methoxy]-piperidine-1-carboxylate as a colourless resin; MS: 465 (M)⁺.

EXAMPLE 8

(a) To 1.46 g of magnesium shavings, which had previously been covered with tetrahydrofuran, was added dropwise a solution of 12.06 g (60 mmol) of 5-bromo-benzo[1,3]dioxol in 30 ml of absolute tetrahydrofuran, followed by 11.35 g (60 mmol) of 1-benzyl-4-piperidone. The reaction mixture was stirred at 50° C. for 1 hour, then poured on to ice and ammonium chloride solution. The 4-benzo[1,3]dioxol-5-yl-1-benzyl-piperidin-4-ol formed was extracted with ethyl acetate and crystallized upon concentration of the solution. There were obtained 10.85 g (58% of theory) of white crystals; m.p.: 144° C.

(b) In an analogous manner to that described in Example 2(e), from 4-benzo[1,3]dioxol-5-yl-1-benzyl-piperidin-4-ol by catalytic hydrogenation at normal pressure within 4 hours there was obtained 4-benzo[1,3]dioxol-5-yl-piperidin-4-ol as a colourless solid in quantitative yield; MS: 221 (M)⁺.

(c) In an analogous manner to that described in Example 1(b), from 4-benzo[1,3]dioxol-5-yl-piperidin-4-ol by elimination there was obtained 4-benzo[1,3]dioxol-5-yl-1,2,3,6-tetrahydro-pyridine as a beige coloured solid; MS: 203 (M)⁺.

(d) In an analogous manner to that described in Example 1(f), from 4-benzo[1,3]dioxol-5-yl-1,2,3,6-tetrahydro-pyridine by introducing the BOC group there was obtained tert-butyl 4-benzo[1,3]dioxol-5-yl-3,6-dihydro-2H-pyridine-1-carboxylate as a colourless oil; MS: 304 (M+H)⁺.

(e) In an analogous manner to that described in Example 1(c), by hydroborating tert-butyl 4-benzo[1,3]dioxol-5-yl-3,6-dihydro-2H-pyridine-1-carboxylate there was obtained tert-butyl (3RS,4RS)-4-benzo[1,3]dioxol-5-yl-3-hydroxy-piperidine-1-carboxylate as white crystals; m.p.: 112° C.

(f) In an analogous manner to that described in Example 1(g), by alkylating tert-butyl (3RS,4RS)-4-benzo[1,3]dioxol-5-yl-3-hydroxy-piperidine-1-carboxylate with 2-bromomethylnaphthalene there was obtained tert-butyl (3RS,4RS)-4-benzo[1,3]dioxol-5-yl-3-(naphthalen-2-ylmethoxy)-piperidine-1-carboxylate as white crystals after crystallization from hexane; m.p.: 128–129° C.

(g) A solution of 190 mg (0.41 mmol) of tert-butyl (3RS,4RS)-4-benzo[1,3]dioxol-5-yl-3-(naphthalen-2-ylmethoxy)-piperidine-1-carboxylate in a mixture of 5 ml of methanol and 25% aqueous hydrochloric acid was heated under reflux for 1 hour. Subsequently, the solvent mixture was distilled off under reduced pressure. After recrystallization of the residue from a mixture of methanol and ether there were obtained 130 mg (73% of theory) of (3RS,4RS)-4-(1,3-benzodioxol-5-yl)-3-naphthalen-2-ylmethoxy-piperidine hydrochloride as a white powder; MS: 362 (M+H)⁺.

EXAMPLE 9

The following compounds were obtained in an analogous manner to that described in Example 8(g) by cleavage of the BOC group using acid:

1) Pyridine-3-carboxylic acid (3RS,4RS)-2-(4-phenyl-piperidin-3-yloxymethyl)-benzylamide hydrochloride as a beige coloured powder, MS: 402 (M+H)⁺, from tert-butyl (3RS,4RS)-4-phenyl-3-(2-{[(pyridine-3-carbonyl)-amino]-methyl}-benzyloxy)-piperidine-1-carboxylate;

2) (3RS,4RS)-2-(4-[1,3]benzodioxol-5-yl-piperidin-3-yloxymethyl)-benzamide hydrochloride as a white powder, MS: 355 (M+H)⁺, from tert-butyl (3RS,4RS)-4-benzo[1,3]dioxol-5-yl-3-(2-carbamoyl-benzyloxy)-piperidine-1-carboxylate.

The BOC derivatives used as the starting materials were prepared as follows:

(a) In an analogous manner to that described in Example 1(g), by alkylating tert-butyl (3RS,4RS)-3-hydroxy-4-phenyl-piperidine-1-carboxylate [Example 2(a)] with 2-bromomethylbenzonitrile there was obtained tert-butyl (3RS,4RS)-3-(2-cyano-benzyloxy)-4-phenyl-piperidine-1-carboxylate as a colourless oil; MS: 393 (M+H)⁺.

(b) 528 mg (1.35 mmol) of tert-butyl (3RS,4RS)-3-(2-cyano-benzyloxy)-4-phenyl-piperidine-1-carboxylate were reduced with 0.3 ml of borane-dimethyl sulphide complex in analogy to the process described by H. C.Brown et al. in Synthesis 1981, 605. There were obtained 480 mg (90% of theory) of tert-butyl (3RS,4RS)-3-(2-aminomethyl-benzyloxy)-4-phenyl-piperidine-1-carboxylate as a colourless solid; 397 (M+H)⁺.

(c) A solution of 150 mg (0.38 mmol) of tert-butyl (3RS,4RS)-3-(2-aminomethyl-benzyloxy)-4-phenyl-piperidine-1-carboxylate in 2 ml of methylene chloride was treated with 229 mg (2.26 mmol) of triethylamine, 139 mg (1.05 mmol) of nicotinic acid, 216 mg (1.13 mmol) of EDC and 10 mg (0.08 mmol) of 4-dimethylaminopyridine and the mixture was stirred at room temperature for 24 hours. Thereafter, the reaction solution was diluted with methylene chloride and washed with a saturated sodium hydrogen carbonate solution. The organic phase was separated, dried over sodium sulphate and evaporated under reduced pressure. The residue was chromatographed on silica gel using ethyl acetate as the eluent. There were obtained 100 mg (53% of theory) of tert-butyl (3RS,4RS)-4-phenyl-3-(2-{[(pyridine-3-carbonyl)-amino]-methyl}-benzyloxy)-piperidine-1-carboxylate as a colourless solid; MS: 502 (M+H)$^+$.

(d) In an analogous manner to that described in Example 1(g), by alkylating tert-butyl (3RS,4RS)-4-benzo[1,3]dioxol-5-yl-3-(naphthalen-2-ylmethoxy)-piperidine-1-carboxylate [Example 8(f)] with 2-bromomethyl-benzonitrile there was obtained tert-butyl (3RS,4RS)-4-benzo[1,3]dioxol-5-yl-3-(2-cyano-benzyloxy)-piperidine-1-carboxylate as colourless crystals; MS: 455 (M+H)$^+$.

(e) 0.5 ml of hydrogen peroxide (33%) and 0.2 ml of 2N sodium hydroxide solution were added to a solution of 236 mg (0.54 mmol) of tert-butyl (3RS,4RS)-4-benzo[1,3]dioxol-5-yl-3-(2-cyano-benzyloxy)-piperidine1-carboxylate in 5 ml of methanol. The reaction solution was heated under reflux for 2 hours. Subsequently, the same amounts of hydrogen peroxide and sodium hydroxide solution were again added and the solution was heated for a further 2 hours. Thereafter, the solution was cooled and evaporated under reduced pressure. For purification, the residue was chromatographed on silica gel using a 9:1 mixture of methylene chloride and ether as the eluent. There were obtained 140 mg (57% of theory) of tert-butyl (3RS,4RS)-4-benzo[1,3]dioxol-5-yl-3-(2-carbamoyl-benzyloxy)-piperidine-1-carboxylate as a colourless solid; MS: 455 (M+H)$^+$.

EXAMPLE 10

(a) In an analogous manner to that described in Example 1(g), by alkylating tert-butyl (3RS,4RS)-4-(4-fluorophenyl)-3-hydroxy-piperidine-1-carboxylate with 6-chloromethyl-2,3-dihydro-benzo[1,4]dioxin [Brit. Pat. 566732 (1943)] there was obtained tert-butyl (3RS,4RS)-3-(2,3-dihydro-benzo[1,4]dioxin-6-ylmethoxy)-4-(4-fluorophenyl)-piperidine-1-carboxylate as a colourless solid; MS: 444 (M+H)$^+$;

(b) A solution of 280 mg (0.63 mmol) of tert-butyl (3RS,4RS)-3-(2,3-dihydro-benzo[1,4]dioxin-6-ylmethoxy)-4-(4-fluorophenyl)-piperidine-1-carboxylate in 5 ml of dry methylene chloride was treated with 808 mg (1.89 mmol) of anhydrous zinc bromide and the mixture was stirred at room temperature for 5 hours. Subsequently, the solvent was distilled off under reduced pressure, the residue was taken up in 10 ml of methanol, treated with 2 ml of 2N sodium hydroxide solution and the solid was separated. The filtrate was evaporated under reduced pressure and the residue was partitioned between methylene chloride and water. The organic phase was separated and evaporated under reduced pressure. There were obtained 220 mg (98% of theory) of (3RS,4RS)-3-(2,3-dihydrobenzo[1,4]dioxin-6-yl-methoxy)-4-(4-fluorophenyl)-piperidine as a yellowish solid; MS: 344 (M+H)$^+$.

EXAMPLE 11

In an analogous manner to that described in Example 10(b), from tert-butyl (3RS,4RS)-3-(benzo[b]furan-5-ylmethoxy)-4-(4-fluoro-phenyl)-piperidine-1-carboxylate there was obtained (3RS,4RS)-3-(benzo[b]furan-5-ylmethoxy)-4-(4-fluorophenyl)-piperidine as a colourless solid; MS: 326 (M+1)$^+$;

The tert-butyl (3RS,4RS)-3-(benzo[b]furan-5-ylmethoxy)-4-(4-fluoro-phenyl)-piperidine-1-carboxylate used as the starting material was obtained as a colourless solid, MS: 426 (M+H)$^+$, analogously to the procedure described in Example 1(g) by alkylating tert-butyl (3RS,4RS)-4-(4-fluorophenyl)-3-hydroxy-piperidine-1-carboxylate.

The 5-bromomethyl-benzo[b]furan used as the alkylating agent was prepared as follows:

By brominating 5-methyl-benzo[b]furan[Synth. Commun. 19, 257(1989)] with N-bromosuccinimide in carbon tetrachloride in an analogous manner to the procedure for the preparation of 5-bromomethyl-benzo[b]thiophene [J. Med. Chem. 34(1), 65(1991)] from 5-methyl-benzo[b]thiophene there was obtained 5-bromomethyl-benzo[b]furan as a light yellow solid; MS: 210, 212 (M)$^+$.

EXAMPLE 12

(a) In an analogous manner to that described in Example 1(c), from 4-(4-chloro-phenyl)-1-methyl-1,2,3,6-tetrahydropyridine [U.S. Pat. No. 3,320,265] by hydroboration using borane in tetrahydrofuran there was obtained (3RS,4RS)-4-(4-chloro-phenyl)-1-methyl-piperidin-3-ol which, after recrystallization from a mixture of methylene chloride and hexane, formed colourless crystals of m.p.: 99–100° C.

(b) A solution of 1.12 g (5 mmol) of (3RS,4RS)-4-(4-chloro-phenyl)-1-methyl-piperidine-3-ol in 5 ml of tetrahydrofuran was added dropwise to a suspension of 0.264 g (5 mmol) of sodium hydride (50% dispersion in refined oil) in 8 ml of tetrahydrofuran and the mixture was stirred at 50° C. for 60 minutes. Subsequently, it was cooled to room temperature and treated with 1.10 g (5 mmol) of 2-bromomethyl-naphthalene in 5 ml of tetrahydrofuran. After 2 hours at 50° C. the reaction solution was poured into 60 ml of ice-water and extracted three times with 25 ml of ethyl acetate each time. The organic phases were washed with saturated sodium chloride solution, dried over magnesium sulphate, filtered and evaporated. The residue was chromatographed on silica gel using a 95:5 mixture of methylene chloride and ethanol as the eluent. There was obtained 0.53 g (28% of theory) of (3RS,4RS)-4-(4-chloro-phenyl)-1-methyl-3-(naphthalen-2-ylmethoxy)-piperidine as a pale yellow oil; MS: 366 (M)$^+$.

(c) A solution of 0.526 g (1.43 mmol) of (3RS,4RS)-4-(4-chloro-phenyl)-1-methyl-3-(naphthalen-2-ylmethoxy)-piperidine in 12 ml of toluene was treated with 100 mg of potassium carbonate and heated to 100°. Subsequently, 0.423 g (0.288 ml, 2 mmol) of 2,2,2-trichloroethyl chloroformate was added thereto and the mixture was stirred at 100° for 12 hours. The reaction solution was evaporated, taken up in 50 ml of ethyl acetate and washed with 20 ml of water and 20 ml of saturated sodium hydrogen carbonate solution. Drying over magnesium sulphate, filtration (sic) and evaporation yielded a colourless oil which was chromatographed on silica gel using a 3:2 mixture of hexane and ethyl acetate as the eluent. There was obtained 0.426 g (57% of theory) of 2,2,2-trichloroethyl 4-(4-chloro-phenyl)-3-(naphthalen-2-ylmethoxy)-piperidine-1-carboxylate as a colourless oil; R$_f$: 0.31 (silica gel, hexane/ethyl acetate: 3/2).

(d) A suspension of 0.420 g (0.8 mmol) of 2,2,2-trichloroethyl 4-(4-chloro-phenyl)-3-(naphthalen-2-ylmethoxy)-piperidine-1-carboxylate and 300 mg of zinc in 10 ml of acetic acid was stirred at room temperature for 12 hours. The reaction solution was diluted with 40 ml of water and extracted four times with 30 ml of methylene chloride. The organic phase was washed twice with 40 ml of 1N sodium hydroxide solution each time, dried over sodium sulphate, filtered and evaporated. The residue was chromatographed on silica gel using a 9:1 mixture of methylene chloride and methanol as the eluent. There was obtained 0.210 g (74% of theory) of (3RS,4RS)-4-(4-chloro-phenyl)-3-(naphthalen-2-ylmethoxy)-piperidine, MS: 210 (M-$C_{11}H_9$)$^+$, which was converted into the hydrochloride of m.p. 159–161° C. (dec.) with a solution of hydrogen chloride in methanol.

EXAMPLE 13

The following compounds were prepared in an analogous manner to that described in Example 12(b)–(d) by alkylation and subsequent cleavage of the N-methyl group:

1) from (3RS,4RS)-4-(4-chloro-phenyl)-1-methyl-piperidin-3-ol and 1-bromomethylnaphthalene, (3RS,4RS)-4-(4-chloro-phenyl)-3-(naphthalene-1-ylmethoxy)-piperidine, MS: 210 (M-$C_{11}H_9$)$^+$, which was converted with a solution of hydrogen chloride in ethanol into the hydrochloride of m.p. 210–213° C. (dec.).

2) from (3RS,4RS)-4-(4-chloro-phenyl)-1-methyl-piperidin-3-ol and 1-bromomethyl-4-tert-butylbenzene, (3RS,4RS)-3-(4-tert.butyl-benzyloxy)-4-(4-chloro-phenyl)-piperidine, MS: 358 (M)$^+$, which was converted with a solution of hydrogen chloride in ethanol into the hydrochloride of m.p. 164–166° C. (dec.).

3) from (3RS,4RS)-4-(4-chloro-phenyl)-1-methyl-piperidin-3-ol and 5-chloromethyl-benzo[1.3]dioxol, (3RS,4RS)-3-(benzo[1.3]dioxol-5-yl-methoxy)-4-(4-chloro-phenyl)-piperidine, MS: 210 (M-$C_8H_7O_2$)$^+$, which was converted with methanesulphonic acid in a mixture of dioxan and water and subsequent lyophilization into the corresponding methanesulphonate; $R_f$: 0.45 (silica gel, methylene chloride/methanol: 9/1).

4) from (3RS,4RS)-4-(4-chloro-phenyl)-1-methyl-piperidin-3-ol and 1,2-dichloro4-chloromethylbenzene, (3RS,4RS)-4-(4-chloro-phenyl)-3-(3,4-dichlorobenzyloxy)-piperidine, MS: 370 (M)$^+$, which was converted with a solution of hydrogen chloride in ethanol into the hydrochloride of m.p. 156–158° C. (dec.).

5) from (3RS,4RS)-4-(4-chloro-phenyl)-1-methyl-piperidin-3-ol and 2,4-dichloro-1-chloromethylbenzene, (3RS,4RS)-4-(4-chloro-phenyl)-3-(2,4-dichloro-benzyloxy)-piperidine of m.p. 83–84° C.; MS: 370 (M)$^+$.

6) from (3RS,4RS)-4-(4-chloro-phenyl)-1-methyl-piperidin-3-ol and 1-chloro-4-chloromethylbenzene, (3RS,4RS)-3-(4-chlorobenzyloxy)-4-(4-chloro-phenyl)-piperidine, MS: 210 (M-$C_7H_6Cl$)$^+$, which was converted with a solution of hydrogen chloride in ethanol into the hydrochloride of m.p. 128–130° C. (dec.).

7) from (3RS,4RS)-4-(4-chloro-phenyl)-1-methyl-piperidin-3-ol and 1-chloromethyl-3-methoxy-benzene, (3RS,4RS)-(4-chloro-phenyl)-3-(2-methoxy-benzyloxy)-piperidine, MS: 332 (M)$^+$, which was converted with a solution of hydrogen chloride in ethanol into the hydrochloride of m.p. 116–118° C. (dec.).

8) from (3RS,4RS)-4-(4-chloro-phenyl)-1-methyl-piperidin-3-ol and 1-chloro-2-chloromethyl-benzene, (3RS,4RS)-3-(2-chlorobenzyloxy)-4-(4-chloro-phenyl)-piperidine, MS: 210 (M-$C_7H_6Cl$)$^+$, which was converted with a solution of hydrogen chloride in ethanol into the hydrochloride of m.p. 145–147° C. (dec.).

9) from (3RS,4RS)-4-(4-chloro-phenyl)-1-methyl-piperidin-3-ol and 4-chloromethyl-biphenyl, (3RS,4RS)-3-(biphenyl-4-ylmethoxy)-4-(4-chloro-phenyl)-piperidine, MS: 210 (M-$C_{13}H_{11}$)$^+$, which was converted with a solution of hydrogen chloride in ethanol into the hydrochloride of m.p. 177–180° C. (dec.).

10) from (3RS,4RS)-4-(4-chloro-phenyl)-1-methyl-piperidin-3-ol and 2-chloromethyl-quinoline, (3RS,4RS)-2-[4-(4-chloro-phenyl)-piperidin-3-yloxy-methyl] quinoline, MS: 353 (M)$^+$ of m.p. 109–110° C.

11) from (3RS,4RS)-4-(4-chloro-phenyl)-1-methyl-piperidin-3-ol and 3-chloro-methyl-benzofuran [J.Am. Chem. Soc. 73, 4400 (1951)], (3RS,4RS)-3-(benzofuran-2-ylmethoxy)-4-(4-chloro-phenyl)-piperidine, MS: 341 (M)$^+$, which was converted with a solution of hydrogen chloride in ethanol into the hydrochloride of m.p. 144–146° C. (dec.).

12) from (3RS,4RS)-4-(4-chloro-phenyl)-1-methyl-piperidin-3-ol and 2-chloromethyl-benzo[b]thiophene [J. Am.Chem. Soc. 71, 2856 (1949)], (3RS,4RS)-3-(benzo[b]thiophen-2-ylmethoxy)-4-(4-chloro-phenyl)-piperidine, MS: 210 (M-$C_8H_7S$)$^+$, which was converted with a solution of hydrogen chloride in ethanol into the hydrochloride of m.p. 141–144° C. (dec.).

13) from (3RS,4RS)-4-(4-chloro-phenyl)-1-methyl-piperidin-3-ol and methyl 4'-bromomethyl-biphenyl-2-carboxylate [J. Med. Chem. 34, 2525 (1991)], methyl (3RS ,4RS)-4'-[4-(4-chloro-phenyl)piperidin-3-yloxymethyl]-biphenyl-2-carboxylate, MS: 436 (M)$^+$ which was converted with hydrochloric acid in ethanol into the hydrochloride of m.p. 95–99° C. (dec.).

14) from (3RS,4RS)-4-(4-chloro-phenyl)-1-methyl-piperidin-3-ol and 3-chloromethyl-pyridine [J. Am. Chem. Soc. 77,1054 (1955)], (3RS,4RS)-3-[4-(4-chloro-phenyl-piperidin-3-yloxymethyl]-pyridine, MS: 303 (M)$^+$, which was converted with a solution of hydrogen chloride in ethanol into the hydrochloride of m.p. 78–81° C. (dec.).

15) from (3RS,4RS)-4-(4-chloro-phenyl)-1-methyl-piperidin-3-ol and 6-chloromethyl-1,1,4,4,-tetramethyl-1,2,3,4-tetrahydronaphthalene, (3RS,4RS)-4-(4-chloro-phenyl)-3-(5,5,8,8,-tetramethyl-5,6,7,8-tetrahydronaphthalene-2-ylmethoxy)-piperidine, MS: 412 (M)$^+$, which was converted with a solution of hydrogen chloride in ethanol into the hydrochloride of m.p. 118–121° C. (dec.).

16) from (3RS,4RS)-4-(3-chloro-phenyl)-1-methyl-piperidin-3-ol [U.S. Pat. No. 4,132,710 (1976)] and 4-methoxybenzyl chloride, (3RS,4RS)-3-(4-methoxy-benzyloxy)-4-(3-chloro-phenyl)-piperidine; MS: 332 (M)$^+$.

EXAMPLE 14

The following compounds were prepared in analogy to the procedure described in Example 1(e) by cleavage of the 2-trimethylsilyl-ethoxycarbonyl group with tetrabutylammonium fluoride in tetrahydrofuran:

1) (3RS,4RS)-4-(4-fluorophenyl)-3-(4-methoxy-naphthalen-2-ylmethoxy)-piperidine as a colourless solid, MS: 365 (M)$^+$, from β-trimethyl-silylethyl (3RS,4RS)-4-(4-fluorophenyl)-3-(4-methoxy-naphthalen-2-ylmethoxy)-piperidine-1-carboxylate;

2) (3RS,4RS)-4-(4-fluorophenyl)-3-(5-methoxy-naphthalen-2-ylmethoxy)-piperidine as a colourless solid, MS: 365 (M)$^+$, from β-trimethyl-silylethyl (3RS,4RS)-4-(4-fluorophenyl)-3-(5-methoxy-naphthalen-2-ylmethoxy)-piperidine-1-carboxylate;

3) (3RS,4RS)-4-(4-fluorophenyl)-3-(6-methoxy-naphthalen-2-ylmethoxy)-piperidine as a colourless solid, MS: 365 (M)$^+$, from β-trimethyl-silylethyl (3RS,4RS)-4-(4-fluorophenyl)-3-(6-methoxy-naphthalen-2-ylmethoxy)-piperidine-1-carboxylate;

4) (3RS,4RS)-4-(4-fluorophenyl)-3-(7-methoxy-naphthalen-2-ylmethoxy)-piperidine as a colourless solid, MS: 365 (M)$^+$, from -trimethyl-silylethyl (3RS,4RS)-4-(4-fluorophenyl)-3-(7-methoxy-naphthalen-2-ylmethoxy)-piperidine-1-carboxylate;

5) (3RS,4RS)-4-(4-fluorophenyl)-3-(8-methoxy-naphthalen-2-ylmethoxy)-piperidine as a colourless resin, MS: 366 (M+H)⁺, from β-trimethyl-silylethyl (3RS,4RS)-4-(4-fluorophenyl)-3-(8-methoxy-naphthalen-2-ylmethoxy)-piperidine-1-carboxylate;

6) (3RS,4RS)-4-(4-fluorophenyl)-3-[4-(pyridin-2-ylmethoxy)-naphthalen-2-ylmethoxy]-piperidine as a colourless solid, MS: 442 (M)⁺, from β-trimethyl-silylethyl (3RS,4RS)-4-(4-fluorophenyl)-3-[4-(pyridin-2-ylmethoxy)-naphthalen-2-ylmethoxy]-piperidine-1-carboxylate;

7) (3RS,4RS)-4-(4-fluorophenyl)-3-[4-(pyridin-3-ylmethoxy)-naphthalen-2-ylmethoxy]-piperidine as a colourless solid, MS: 443 (M+H)⁺, from β-trimethyl-silylethyl (3RS,4RS)-4-(4-fluorophenyl)-3-[4-(pyridin-3-ylmethoxy)-naphthalen-2-ylmethoxy]-piperidine-1-carboxylate;

8) (3RS,4RS)-4-(4-fluorophenyl)-3-[4-(pyridin-4-ylmethoxy)-naphthalen-2-ylmethoxy]-piperidine as a colourless solid, MS: 442 (M)⁺, from β-trimethyl-silylethyl (3RS,4RS)-4-(4-fluorophenyl)-3-[4-(pyridin-4-ylmethoxy)-naphthalen-2-ylmethoxy]-piperidine-1-carboxylate;

9) (3RS,4RS)-3-(4-allyloxy-naphthalen-2-ylmethoxy)-4-(4-fluorophenyl)-piperidine as a colourless solid, MS: 391 (M)⁺, from β-trimethyl-silylethyl (3RS,4RS)-3-(4-allyloxy-naphthalen-2-ylmethoxy)-4-(4-fluorophenyl)-piperidine-1-carboxylate;

10) (3RS,4RS)-3-(6-allyloxy-naphthalen-2-ylmethoxy)-4-(4-fluorophenyl)-piperidine as a colourless solid, MS: 391 (M)⁺, from β-trimethyl-silylethyl (3RS,4RS)-3-(6-allyloxy-naphthalen-2-ylmethoxy)-4-(4-fluorophenyl)-piperidine-1-carboxylate;

11) (3RS,4RS)-4-(4-fluorophenyl)-3-(4-isobutyloxy-naphthalen-2-ylmethoxy)-piperidine as a colourless solid, MS: 407 (M)⁺, from β-trimethyl-silylethyl (3RS,4RS)-4-(4-fluorophenyl)-3-(4-isobutoxy-naphthalen-2-ylmethoxy)-piperidine-1-carboxylate;

12) (3RS,4RS)-3-(1-benzyloxy-naphthalen-2-ylmethoxy)-4-(4-fluorophenyl)-piperidine as a light yellow oil, MS: 441 (M)⁺, from β-trimethyl-silylethyl (3RS,4RS)-3-(1-benzyloxy-naphthalen-2-ylmethoxy)-4-(4-fluorophenyl)-piperidine-1-carboxylate;

13) (3RS,4RS)-3-(4-benzyloxy-naphthalen-2-ylmethoxy)-4-(4-fluorophenyl)-piperidine as a colourless solid, MS: 441 (M)⁺, from β-trimethyl-silylethyl (3RS,4RS)-3-(4-benzyloxy-naphthalen-2-ylmethoxy)-4-(4-fluorophenyl)-piperidine-1-carboxylate;

14) (3RS,4RS)-3-(5-benzyloxy-naphthalen-2-ylmethoxy)-4-(4-fluorophenyl)-piperidine as a light yellow oil, MS: 442 (M+H)⁺, from β-trimethyl-silylethyl (3RS,4RS)-3-(5-benzyloxy-naphthalen-2-ylmethoxy)4-(4-fluorophenyl)-piperidine-1-carboxylate;

15) (3RS,4RS)-3-(7-benzyloxy-naphthalen-2-ylmethoxy)-4-(4-fluorophenyl)-piperidine as a colourless solid, MS: 441 (M)⁺, from 3-trimethyl-silylethyl (3RS,4RS)-3-(7-benzyloxy-naphthalen-2-ylmethoxy)-4-(4-fluorophenyl)-piperidine-1-carboxylate;

16) (3RS,4RS)-3-(8-benzyloxy-naphthalen-2-ylmethoxy)-4-(4-fluorophenyl)-piperidine as a light yellow resin, MS: 442 (M+H)⁺, from β-trimethyl-silylethyl (3RS,4RS)-3-(8-benzyloxy-naphthalen-2-ylmethoxy)-4-(4-fluorophenyl)-piperidine-1-carboxylate;

17) (3RS,4RS)4-(4-fluorophenyl)-3-[4-(2-methoxy-ethoxy)-naphthalen-2-ylmethoxy]-piperidine as a colourless solid, MS: 410 (M+H)⁺, from β-trimethyl- silylethyl (3RS,4RS)4-(4-fluorophenyl)-3-[4-(2-methoxy-ethoxy)-naphthalen-2-yl-methoxy)-piperidine-1-carboxylate;

18) 4-(4-fluorophenyl)-3-[4-(3-methoxy-propoxy)-naphthalen-2-ylmethoxy]-piperidine as a light yellow solid, MS: 424 (M+H)⁺, from β-trimethyl-silylethyl 4-(4-fluorophenyl)-3-[4-(3-methoxy-propoxy)-naphthalen-2-ylmethoxy]-piperidine-1-carboxylate;

19) (3RS,4RS) 3-(4-butoxy-naphthalen-2-ylmethoxy)-4-(4-fluorophenyl)-piperidine as a colourless solid, MS: 408 (M+H)⁺, from β-trimethyl-silylethyl (3RS,4RS) 3-(4-butoxy-naphthalen-2-ylmethoxy)-4-(4-fluorophenyl)-piperidine-1-carboxylate;

20) (3RS,4RS)-4-(4-fluorophenyl)-3-(4-(2-methoxy-benzyloxy)-naphthalen-2-ylmethoxy)-piperidine as a colourless resin, MS: 472 (M+H)⁺, from β-trimethyl-silylethyl (3RS,4RS)-4-(4-fluorophenyl)-3-(4-(2-methoxy-benzyloxy)-naphthalen-2-ylmethoxy)-piperidine-1-carboxylate;

21) (3RS,4RS)-4-(4-fluorophenyl)-3-(4-(3-methoxy-benzyloxy)-naphthalen-2-ylmethoxy)-piperidine as a colourless solid, MS: 471 (M)⁺, from β-trimethyl-silylethyl (3RS,4RS)-4-(4-fluorophenyl)-3-(4-(3-methoxy-benzyloxy)-naphthalen-2-ylmethoxy)-piperidine-1-carboxylate;

22) (3RS,4RS)-4-(4-fluorophenyl)-3-(4-(2-methoxy-benzyloxy)-naphthalen-2-ylmethoxy)-piperidine as a colourless oil, MS: 471 (M)⁺, from β-trimethyl-silylethyl (3RS,4RS)-4-(4-fluorophenyl)-3-(4-methoxy-benzyloxy)-naphthalen-2-ylmethoxy)-piperidine-1-carboxylate;

23) (3RS,4RS)-4-(4-fluorophenyl)-3-(1-phenethyloxy-naphthalen-2-ylmethoxy)-piperidine as a light yellow oil, MS: 456 (M+H)⁺, from β-trimethyl-silylethyl (3RS,4RS)-4-(4-fluorophenyl)-3-(1-phenethyloxy-naphthalen-2-ylmethoxy)-piperidine-1-carboxylate;

24) (3RS,4RS)-4-(4-fluorophenyl)-3-(4-phenethyloxy-naphthalen-2-ylmethoxy)-piperidine as a colourless solid, MS: 456 (M+H)⁺, from β-trimethyl-silylethyl (3RS,4RS)-4-(4-fluorophenyl)-3-(4-phenethyloxy-naphthalen-2-ylmethoxy)-piperidine-1-carboxylate;

25) (3RS,4RS)-3-[4-(2-[1,3]dioxolan-2-yl-ethoxy)-naphthalen-2-ylmethoxy]-4-(4-fluorophenyl)-piperidine as a light yellow oil, MS: 451 (M)⁺, from β-trimethyl-silylethyl (3RS,4RS)-3-[4-(2-[1,3]dioxolan-2-yl-ethoxy)-naphthalen-2-ylmethoxy]-4-(4-fluorophenyl)-piperidine-1-carboxylate;

26) (3RS,4RS)-3-[1-(2-[1,3]dioxolan-2-yl-ethoxy)-naphthalen-2-ylmethoxy]-4-(4-fluorophenyl)-piperidine as a light yellow oil, MS: 452 (M+H)⁺, from β-trimethyl-silylethyl (3RS,4RS)-3-[1-(2-[1,3]dioxolan-2-yl-ethoxy)-naphthalen-2-ylmethoxy]-4-(4-fluorophenyl)-piperidine-1-carboxylate;

27) (3RS,4RS)-3-[4-(benzo[1,3]dioxol-5-ylmethoxy)-naphthalen-2-ylmethoxy]-4-(4-fluorophenyl)-piperidine as a colourless resin, MS: 485 (M)⁺, from β-trimethyl-silylethyl (3RS,4RS)-3-[4-(benzo[1,3]dioxol-5-ylmethoxy)-naphthalen-2-ylmethoxy]-4-(4-fluorophenyl)-piperidine-1-carboxylate;

28) (3RS,4RS)-3-[4-(2-cyclopropyl-ethoxy)-naphthalen-2-ylmethoxy]-4-(4-fluorophenyl)-piperidine as a colourless solid, MS: 419 (M)⁺, from β-trimethyl-silylethyl (3RS,4RS)-3-[4-(2-cyclopropyl-ethoxy)-naphthalen-2-ylmethoxy]-4-(4-fluorophenyl)-piperidine-1-carboxylate;

29) (3RS,4RS)-4-(4-fluorophenyl)-3-[4-(2-hydroxy-ethoxy)-naphthalen-2-ylmethoxy]-piperidine as a colourless solid, MS: 395 (M)⁺, from β-trimethyl-silylethyl (3RS,4RS)-4-(4-fluorophenyl)-3-[4-(2-hydroxy-ethoxy)-naphthalen-2-yl-methoxy]-piperidine-1-carboxylate;

The compounds used as starting materials were prepared as follows:

(a) 99 mg (0.20 mmol) of β-trimethyl-silylethyl (3RS,4RS)-4-(4-fluorophenyl)-3-(4-hydroxy-naphthalen-2-ylmethoxy)-piperidine-1-carboxylate were dissolved in 1 ml of dimethylformamide, treated with 69 mg (0.50 mmol) of anhydrous potassium carbonate and 19 μl (43 mg, 0.30 mmol) of methyl iodide and stirred at room temperature for 4 hours. Subsequently, the mixture was partitioned between methylene chloride and water, the organic phase was dried over magnesium sulphate and finally the solvent was distilled off under reduced pressure. For purification, the crude product was chromatographed on silica gel with a 4:1 mixture of hexane and methylene chloride as the eluent. There were obtained 85 mg (83% of theory) of β-trimethyl-silylethyl (3RS,4RS)-4-(4-fluorophenyl)-3-(4-methoxy-naphthalen-2-ylmethoxy)-piperidine-1-carboxylate as a light yellow oil; MS: 509 (M)$^+$.

The following compounds were prepared in an analogous manner to the previously described procedure:

from β-trimethylsilylethyl (3RS,4RS)-4-(4-fluorophenyl)-3-(5-hydroxy-naphthalen-2-ylmethoxy)-piperidine-1-carboxylate and methyl iodide, β-trimethylsilylethyl (3RS,4RS)-4-(4-fluorophenyl)-3-(5-methoxy-naphthalen-2-ylmethoxy)-piperidine-1-carboxylate, which was used in crude form in the next step;

from β-trimethylsilylethyl (3RS,4RS)-4-(4-fluorophenyl)-3-(6-hydroxy-naphthalen-2-ylmethoxy)-piperidine-1-carboxylate and methyl iodide, β-trimethylsilylethyl (3RS,4RS)-4-(4-fluorophenyl)-3-(6-methoxy-naphthalen-2-ylmethoxy)-piperidine-1-carboxylate as a light yellow oil; MS: 509 (M)$^+$;

from β-trimethylsilylethyl (3RS,4RS)-4-(4-fluorophenyl)-3-(7-hydroxy-naphthalen-2-ylmethoxy)-piperidine-1-carboxylate and methyl iodide, β-trimethylsilylethyl (3RS,4RS)-4-(4-fluorophenyl)-3-(7-methoxy-naphthalen-2-ylmethoxy)-piperidine-1-carboxylate, which was used in crude form in the next step;

from β-trimethylsilylethyl (3RS,4RS)-4-(4-fluorophenyl)-3-(8-hydroxy-naphthalen-2-ylmethoxy)-piperidine-1-carboxylate and methyl iodide, β-trimethylsilylethyl (3RS,4RS)-4-(4-fluorophenyl)-3-(8-methoxy-naphthalen-2-ylmethoxy)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 2-pyridylmethyl chloride, β-trimethylsilylethyl (3RS,4RS)-4-(4-fluorophenyl)-3-[4-(pyridin- 2-ylmethoxy)-naphthalen-2-ylmethoxy]-piperidine-1-carboxylate as a light yellow oil; MS: 587 (M+H)$^+$;

from β-trimethylsilylethyl (3RS,4RS)-4-(4-fluorophenyl)-3-(4-hydroxy-naphthalen-2-ylmethoxy)-piperidine-1-carboxylate and 3-pyridylmethyl chloride, β-trimethylsilylethyl (3RS,4RS)-4-(4-fluorophenyl)-3-[4-(pyridin-3-ylmethoxy)-naphthalen-2-ylmethoxy]-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 4-pyridylmethyl chloride, β-trimethylsilylethyl (3RS,4RS)-4-(4-fluorophenyl)-3-[4-(pyridin-4-ylmethoxy)-naphthalen-2-ylmethoxy]-piperidine-1-carboxylate as a light yellow oil; MS: 587 (M+H)$^+$;

from β-trimethylsilylethyl (3RS,4RS)-4-(4-fluorophenyl)-3-(4-hydroxy-naphthalen-2-ylmethoxy)-piperidine-1-carboxylate and allyl bromide, β-trimethylsilylethyl (3RS,4RS)-3-(4-allyloxy-naphthalen-2-ylmethoxy)-4-(4-fluorophenyl)-piperidine-1-carboxylate, which was used in crude form in the next step;

from β-trimethylsilylethyl (3RS,4RS)-4-(4-fluorophenyl)-3-(6-hydroxy-naphthalen-2-ylmethoxy)-piperidine-1-carboxylate and allyl bromide, β-trimethylsilylethyl (3RS,4RS)-3-(6-allyloxy-naphthalen-2-ylmethoxy)-4-(4-fluorophenyl)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and iso-butyl bromide, β-trimethylsilylethyl (3RS,4RS)-4-(4-fluorophenyl)-3-(4-isobutoxy-naphthalen-2-ylmethoxy)-piperidine-1-carboxylate, which was used in crude form in the next step;

from β-trimethylsilylethyl (3RS,4RS)-4-(4-fluorophenyl)-3-(1-hydroxy-naphthalen-2-ylmethoxy)-piperidine-1-carboxylate and benzyl bromide, β-trimethylsilylethyl (3RS,4RS)-4-(4-fluorophenyl)-3-(1-benzyloxy-naphthalen-2-ylmethoxy)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and benzyl bromide, β-trimethylsilylethyl (3RS,4RS)-3-(4-benzyloxy-naphthalen-2-ylmethoxy)-4-(4-fluorophenyl)-piperidine-1-carboxylate as a light yellow oil; MS: 586 (M+H)$^+$;

from β-trimethylsilylethyl (3RS,4RS)-4-(4-fluorophenyl)-3-(7-hydroxy-naphthalen-2-ylmethoxy)-piperidine-1-carboxylate and benzyl bromide, β-trimethylsilylethyl (3RS,4RS)-3-(7-benzyloxy-naphthalen-2-ylmethoxy)-4-(4-fluorophenyl)-piperidine-1-carboxylate as a light yellow oil; MS: 585 (M)$^+$;

from β-trimethylsilylethyl (3RS,4RS)-4-(4-fluorophenyl)-3-(5-hydroxy-naphthalen-2-ylmethoxy)-piperidine-1-carboxylate and benzyl bromide, 2-trimethylsilanyl-ethyl (3RS,4RS)-3-(5-benzyloxy-naphthalen-2-ylmethoxy)-4-(4-fluoro-phenyl)-piperidine-1-carboxylate as a colourless oil; MS: 585 (M)$^+$;

from β-trimethylsilylethyl (3RS,4RS)-4-(4-fluorophenyl)-3-(8-hydroxy-naphthalen-2-ylmethoxy)-piperidine-1-carboxylate and benzyl bromide, β-trimethylsilylethyl (3RS,4RS)-3-(8-benzyloxy-naphthalen-2-ylmethoxy)-4-(4-fluorophenyl)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 2-methoxyethyl bromide, 2-trimethylsilanyl-ethyl (3RS,4RS)-4-(4-fluoro-phenyl)-3-[4-(2-methoxy-ethoxy)- naphthalen-2-ylmethoxy]-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 3-methoxypropyl chloride [J. Org. Chem. 16, 704(1951)], 2-trimethylsilanyl-ethyl (3RS,4RS)-4-(4-fluoro-phenyl)-3-[4-(3-methoxy-propoxy)-naphthalen-2-ylmethoxy]-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and butyl bromide, 2-trimethylsilanyl-ethyl (3RS,4RS)-3-(4-butyl-naphthalen-2-ylmethoxy)-4-(4-fluoro-phenyl)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 2-methoxybenzyl chloride, 2-trimethylsilanyl-ethyl (3RS,4RS)-4-(4-fluoro-phenyl)-3-[4-(2-methoxy-benzyloxy)-naphthalen-2-ylmethoxy)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 3-methoxybenzyl chloride, 2-trimethylsilanyl-ethyl (3RS,4RS)-4-(4-fluoro-phenyl)-3-[4-(3-methoxy-benzyloxy)-naphthalen-2-ylmethoxy)-piperidine-1-carboxylate as a light yellow oil; MS: 615 (M)$^+$;

from β-trimethylsilylethyl (3RS,4RS)-4-(4-fluorophenyl)-3-(4-hydroxy-naphthalen-2-ylmethoxy)-piperidine-1-carboxylate and 4-methoxybenzyl chloride, 2-trimethylsilanyl-ethyl (3RS,4RS)-4-(4-fluoro-phenyl)-3-[4-(4-methoxy-benzyloxy)-naphthalen-2-ylmethoxy)-piperidine-1-carboxylate as a light yellow oil; MS: 616 (M+H)$^+$;

from β-trimethylsilylethyl (3RS,4RS)-4-(4-fluorophenyl)-3-(4-hydroxy-naphthalen-2-ylmethoxy)-piperidine-1-carboxylate and phenethyl bromide, β-trimethylsilylethyl (3RS,4RS)-4-(4-fluorophenyl)-3-(4-phenethyloxy-naphthalen-2-ylmethoxy)-piperidine-1-carboxylate, which was used in crude form in the next step;

from β-trimethylsilylethyl (3RS,4RS)-4-(4-fluorophenyl)-3-(1-hydroxy-naphthalen-2-ylmethoxy)-piperidine-1-carboxylate and phenethyl bromide, 2-trimethylsilanyl-ethyl (3RS,4RS)-4-(4-fluoro-phenyl)-3-(1-phenethyloxy-naphthalen-2-ylmethoxy)-piperidine-1-carboxylate as a light yellow oil; MS: 600 (M+H)$^+$;

from β-trimethylsilylethyl (3RS,4RS)-4-(4-fluorophenyl)-3-(4-hydroxy-naphthalen-2-ylmethoxy)-piperidine-1-carboxylate and 2-(2-bromoethyl)-1,3-dioxolan, 2-trimethylsilanyl-ethyl (3RS,4RS)-3-[4-(2-[1,3]dioxolan-2-yl-ethoxy)-naphthalen-2-ylmethoxy]-4-(4-fluoro-phenyl)-piperidine-1-carboxylate, which was used in crude form in the next step;

from β-trimethylsilylethyl (3RS,4RS)-4-(4-fluorophenyl)-3-(1-hydroxy-naphthalen-2-ylmethoxy)-piperidine-1-carboxylate and 2-(2-bromoethyl)-1,3-dioxolan, β-trimethylsilylethyl (3RS,4RS)-3-[1-(2-[1,3]dioxolan-2-yl-ethoxy)-naphthalen-2-ylmethoxy]-4-(4-fluorophenyl)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 3,4-methylenedioxybenzyl chloride, β-trimethyl-silylethyl (3RS,4RS)-3-[4-(benzo[1,3]dioxol-5-ylmethoxy)-naphthalen-2-ylmethoxy]-4-(4-fluorophenyl)-piperidine-1-carboxylate, which was used in crude form in the next step;

from β-trimethylsilylethyl (3RS,4RS)-4-(4-fluorophenyl)-3-(4-hydroxy-naphthalen-2-ylmethoxy)-piperidine-1-carboxylate and 2-cyclopropyl-ethyl chloride [Justus Liebigs Ann. Chem. 759, 132 (1972)], β-trimethylsilylethyl (3RS,4RS)-3-[4-(2-cyclopropyl-ethoxy)-naphthalen-2-ylmethoxy]-4-(4-fluorophenyl)-piperidine-1-carboxylate as a light pink coloured oil; MS: 564 (M+H)$^+$;

from β-trimethylsilylethyl (3RS,4RS)-4-(4-fluorophenyl)-3-(4-hydroxy-naphthalen-2-ylmethoxy)-piperidine-1-carboxylate and 2-(2-bromoethoxy)-tetrahydropyran, a mixture of β-trimethyl-silanylethyl (3RS,4RS)-4-(4-fluorophenyl)-3-{4-[2-[(RS)- and (SR)-tetrahydro-pyran-2-yloxy]-ethoxy]-naphthalen-2-ylmethoxy}-piperidine-1-carboxylate as a colourless oil; MS: 624 (M+H)$^+$.

Subsequent cleavage of the THP protecting group with a 1M solution of hydrogen chloride in methanol (10 minutes, room temperature) yielded β-trimethyl-silylethyl (3RS,4RS)-4-(4-fluorophenyl)-3-[4-(2-hydroxy-ethoxy)-naphthalen-2-ylmethoxy]-piperidine-1-carboxylate as a colourless solid; MS: 540 (M+H)$^+$.

EXAMPLE 15

(a) A solution of 63 mg (0.116 mmol) of β-trimethyl-silylethyl (3RS,4RS)-4-(4-fluorophenyl)-3-[4-(2-hydroxy-ethoxy)-naphthalen-2-ylmethoxy]-piperidine-1-carboxylate in 2 ml of methylene chloride was treated with 38 mg (0.58 mmol) of sodium cyanate. 44 μl (67 mg, 0.58 mmol) of trifluoroacetic acid were added to this suspension at 0° C. and the reaction mixture was stirred at room temperature for 2 hours. Subsequently, the mixture was partitioned between methylene chloride and a 5% sodium hydrogen carbonate solution, the organic phase was dried over magnesium sulphate and finally the solvent was distilled off under reduced pressure. The crude β-trimethyl-silylethyl (3RS,4RS)-3-[4-(2-carbamoyloxy-ethoxy)-naphthalen-2-ylmethoxy]-4-(4-fluorophenyl)-piperidine-1-carboxylate obtained was used in the following step without further purification and characterization.

(b) From the crude β-trimethyl-silylethyl (3RS,4RS)-3-[4-(2-carbamoyloxy-ethoxy)-naphthalen-2-ylmethoxy]-4-(4-fluorophenyl)-piperidine-1-carboxylate there was obtained by cleavage of the protecting group with tetrabutylammonium fluoride in tetrahydrofuran in analogy to the procedure described in Example 1(e) (3RS,4RS)-3-[4-(2-carbamoyloxy-ethoxy)-naphthalen-2-ylmethoxy]-4-(4-fluorophenyl)-piperidine as a light yellow oil; MS: 438 (M)$^+$.

EXAMPLE 16

The following compounds were obtained in an analogous manner to that described in Example 1(e) by cleavage of the protecting group with tetrabutylammonium fluoride in tetrahydrofuran:

1) 4-(4-Fluorophenyl)-3-[4-[2-(pyridin-2-ylcarbamoyloxy)-ethoxy]-naphthalen-2-ylmethoxy]-piperidine as a colourless solid, MS: 395 [M-(PyNCO)]$^+$, from β-trimethyl-silylethyl 4-(4-fluorophenyl)-3-[4-[2-(pyridin-2-ylcarbamoyloxy)-ethoxy]-naphthalen-2-ylmethoxy]-piperidine-1-carboxylate;

2) (3RS,4RS)-3-[4-(2-benzoyloxy-ethoxy)-naphthalen-2-ylmethoxy]-4-(4-fluorophenyl)-piperidine as a colourless resin, MS: 500 (M+H)$^+$, from β-trimethyl-silylethyl (3RS, 4RS)-3-[4-(2-benzoyloxy-ethoxy)-naphthalen-2-ylmethoxy]-4-(4-fluorophenyl)-piperidine-1-carboxylate.

The β-trimethyl-silylethyl carbamates used as the starting materials were obtained as follows:

(a) A solution of 54 mg (0.10 mmol) of β-trimethyl-silylethyl (3RS,4RS)-4-(4-fluorophenyl)-3-[4-(2-hydroxy-ethoxy)-naphthalen-2-ylmethoxy]-piperidine-1-carboxylate in 5 ml of toluene was treated with 30 mg (0.20 mmol) of 2-pyridylcarbonyl azide [Monatsh. Chem. 33, 397 (1912)] and 5 mg of 4-dimethyl-aminopyridine. The solution was heated to reflux under argon for 2 hours. The mixture was cooled and the solvent was removed under reduced pressure. The residue was partitioned between methylene chloride and saturated sodium chloride solution, the organic phase was dried over magnesium sulphate and finally the solvent was removed under reduced pressure. The crude product (103 mg) was purified by chromatography on silica gel with a 1:2 mixture of ethyl acetate and hexane as the eluent. There were obtained 65 mg (99% of theory) of β-trimethyl-silylethyl (3RS,4RS)-4-(4-fluorophenyl)-3-[4-[2-(pyridin-2-ylcarbamoyloxy)-ethoxy]-naphthalen-2-ylmethoxy]-piperidine-1-carboxylate as a colourless solid; MS: 660 $(M+H)^+$.

(b) A solution of 108 mg (0.20 mmol) of β-trimethyl-silylethyl (3RS,4RS)-4-(4-fluorophenyl)-3-[4-(2-hydroxy-ethoxy)-naphthalen-2-ylmethoxy]-piperidine-1-carboxylate in 2 ml of methylene chloride was treated with 56 μl (41 mg, 0.40 mmol) of triethylamine. 36 μl (42 mg, 0.30 mmol) of benzoyl chloride were added thereto. The reaction mixture was stirred at room temperature for 6 hours and at 50° C. for one hour. Subsequently, the mixture was partitioned between methylene chloride and a 5% sodium hydrogen carbonate solution, the organic phase was dried over magnesium sulphate and finally the solvent was removed under reduced pressure. The crude β-trimethyl-silylethyl (3RS,4RS)-3-[4-(2-benzoyloxy-ethoxy)-naphthalen-2-ylmethoxy]-4-(4-fluorophenyl)-piperidine-1-carboxylate was used directly in the next step.

EXAMPLE 17

The following compound was obtained in an analogous manner to that described in Example 5:

The procedure was carried out as follows in analogy to Example 5(a)–(d):

(a) From methyl salicylate there was obtained by introduction of the SEM group methyl 2-(2-trimethylsilylethoxymethoxy)-benzoate as a colourless oil; MS 224 $[M-(C_2H_4+CH_2O)]^+$.

(b) Reduction of methyl 2-(2-trimethylsilyl-ethoxymethoxy)-benzoate gave [2-(2-trimethylsilylethoxy-methoxy)-phenyl]-methanol as a light yellow oil; MS: 226 $[M-(C_2H_4)]^+$.

(c) Chlorination of [2-(2-trimethylsilylethoxy-methoxy)-phenyl]-methanol yielded 1-chloromethyl-(2-trimethylsilyl-ethoxymethoxy)-benzene as a colourless oil; MS: 214, 216 $[M-(C_2H_4+CH_2O)]^+$.

(d) Alkylation of β-trimethyl-silylethyl (3RS,4RS)-4-(4-fluorophenyl)-3-(4-hydroxy-naphthalen-2-ylmethoxy)-piperidine-1-carboxylic acid [Example 5(g)] with 1-chloromethyl-(2-trimethylsilyl-ethoxymethoxy)-benzene yielded β-trimethylsilylethyl (3RS,4RS)-4-(4-fluorophenyl)-3-[4-[2-(2-trimethylsilyl-ethoxymethoxy)-benzyloxy]-naphthalen-2-ylmethoxy]-piperidine-1-carboxylate as a colourless oil; MS: 749 $(M+NH_4)^+$;

(e) From β-trimethylsilylethyl (3RS,4RS)-4-(4-fluorophenyl)-3-[4-[2-(2-trimethylsilyl-ethoxymethoxy)-benzyloxy]-naphthalen-2-ylmethoxy]-piperidine-1-carboxylate by cleaving the β-trimethylsilylethyl carbamate with tetrabutyl-ammonium fluoride in tetrahydrofuran in analogy to the procedure described in Example 5 there was obtained (3RS,4RS)-4-(4-fluorophenyl)-3-[4-[2-(2-trimethylsilyl-ethoxymethoxy)-benzyloxyl-naphthalen-2-ylmethoxy]-piperidine as a rose coloured oil; MS: 588 $(M+H)^+$.

(f) Cleavage of the SEM group from (3RS,4RS)-4-(4-fluorophenyl)-3-[4-[2-(2-trimethylsilyl-ethoxymethoxy)-benzyloxy]-naphthalen-2-ylmethoxy]-piperidine using a 2N solution of hydrogen chloride in methanol analogously to the procedure described in Example 5(g) yielded (3RS,4RS)-4-(4-fluorophenyl)-3-[4-[2-hydroxy-benzyloxy]-naphthalen-2-ylmethoxy]-piperidine as a colourless resin; MS: 458 $(M+H)^+$.

EXAMPLE 18

The following compounds were obtained in an analogous manner to that described in Example 12(d) by cleavage of the 2,2,2-trichloroethyl carbamate:

1) (3RS,4RS)-4-(2-Fluorophenyl)-3-(naphthalen-2-ylmethoxy)-piperidine as a light yellow oil, MS: 336 $(M+H)^+$, from 2,2,2-trichloroethyl (3RS,4RS)-4-(2-fluorophenyl)-3-(naphthalen-2-ylmethoxy)-piperidine-1-carboxylate;

2) (3RS,4RS)-4-(3-fluorophenyl)-3-(naphthalen-2-ylmethoxy)-piperidine as a light yellow oil, MS: 336 $(M+H)^+$, from 2,2,2-trichloroethyl (3RS,4RS)-4-(3-fluorophenyl)-3-(naphthalen-2-ylmethoxy)-piperidine-1-carboxylate;

3) (3RS,4RS)-4-(3-hydroxyphenyl)-3-(naphthalen-2-ylmethoxy)-piperidine as a beige solid, MS: 333 $(M)^+$, from 2,2,2-trichloroethyl (3RS,4RS)-3-(naphthalen-2-ylmethoxy)-4-[3-(2,2,2-trichloro-ethoxycarbonyloxy)-phenyl]-piperidine-1-carboxylate.

The 2,2,2-trichloroethyl carbamates used as the starting materials were prepared as follows:

(a) The following procedure was carried out in an analogous manner to that described in Example 1(a)–(c):

From 2-bromofluorobenzene and 1-benzyl-4-piperidone there was obtained 1-benzyl-4-(2-fluorophenyl)-piperidin-4-ol as a yellow oil; MS: 285 $(M)^+$. Subsequent elimination yielded 1-benzyl-4-(2-fluorophenyl)-1,2,3,6-tetrahydro-pyridine as a light yellow oil; MS: 267 $(M)^+$. Hydroboration subsequently gave (3RS,4RS)-1-benzyl-4-(2-fluorophenyl)-piperidin-3-ol as a colourless solid; MS: 285 $(M)^+$.

(b) In an analogous manner to that described in Example 1(g), by alkylating (3RS,4RS)-1-benzyl-4-(2-fluorophenyl)-piperidin-3-ol with 2-bromomethylnaphthalene there was obtained (3RS,4RS)-1-benzyl-4-(2-fluorophenyl)-3-(naphthalen-2-ylmethoxy)-piperidine as a yellow oil; MS: 284 $(M-C_{11}H_9)^+$. By cleavage of the benzyl protecting group with 2,2,2-trichloroethyl chloroformate in an analogous manner to that described in Example 12(c) there was obtained 2,2,2-trichloroethyl (3RS,4RS)-4-(2-fluorophenyl)-3-(naphthalen-2-ylmethoxy)-piperidine-1-carboxylate as a yellow oil; MS: 509 $(M)^+$.

(c) The following procedure was carried out in an analogous manner to that described in Example 1(a)–(c):

From 3-bromofluorobenzene and 1-benzyl-4-piperidone there was obtained 1-benzyl-4-(3-fluorophenyl)-piperidin-4-ol as a colourless solid; MS: 285 $(M)^+$. Subsequent elimination yielded 1-benzyl-4-(3-fluorophenyl)-1,2,3,6-tetrahydro-pyridine as a light yellow oil; MS: 267 $(M)^+$. Hydroboration subsequently gave (3RS,4RS)-1-benzyl-4-(3-fluorophenyl)-piperidin-3-ol as a colourless oil; MS: 285 $(M)^+$.

(d) In an analogous manner to that described in Example 1(g), by alkylating (3RS,4RS)-1-benzyl-4-(3-fluorophenyl)-piperidin-3-ol with 2-bromomethylnaphthalene there was obtained (3RS,4RS)-1-benzyl-4-(3-fluorophenyl)-3-(naphthalen-2-ylmethoxy)-piperidine as a colourless oil; MS: 426 (M+H)$^+$. By cleavage of the benzyl protecting group with 2,2,2-trichloroethyl chloroformate in an analogous manner to that described in Example 12(c) there was obtained 2,2,2-trichloroethyl (3RS,4RS)-4-(3-fluorophenyl)-3-(naphthalen-2-ylmethoxy)-piperidine-1-carboxylate as a yellow oil; MS: 510 (M+H)$^+$.

(e) The following procedure was carried out in an analogous manner to that described in Example 1(a)–(c):

From 3-benzyloxy-iodobenzene [J. Chem. Soc. 2857 (1932)] and 1-benzyl-4-piperidone there was obtained 1-benzyl-4-(3-benzyloxy-phenyl)-piperidin-4-ol as a light yellow oil; MS: 373 (M)$^+$. Subsequent elimination yielded 1-benzyl-4-(3-benzyloxy-phenyl)-1,2,3,6-tetrahydro-pyridine as a colourless solid; MS: 355 (M)$^+$. Hydroboration subsequently gave (3RS,4RS)-1-benzyl-4-(3-benzyloxy-phenyl)-piperidin-3-ol as a colourless solid; MS: 373 (M)$^+$.

(f) In an analogous manner to that described in Example 1(g), by alkylating (3RS,4RS)-1-benzyl-4-(3-benzyloxy-phenyl)-piperidin-3-ol with 2-bromomethylnaphthalene there was obtained (3RS,4RS)-1-benzyl-4-(3-benzyloxy-phenyl)-3-(naphthalen-2-ylmethoxy)-piperidine as a colourless resin; MS: 514 (M+H)$^+$.

(g) A solution of 250 mg (0.487 mmol) of (3RS,4RS)-1-benzyl-4-(3-benzyloxy-phenyl)-3-(naphthalen-2-ylmethoxy)-piperidine in 1.1 ml of methylene chloride was treated at room temperature with 247 μl (236 mg, 1.946 mmol, 4 eq.) of N,N-dimethylaniline and 195 mg (1.46 mmol, 3.0 eq.) of aluminium trichloride and stirred at room temperature for 2.5 hours. Subsequently, the mixture was partitioned between methylene chloride and 5% sodium hydrogen carbonate solution, the organic phase was dried over magnesium sulphate and finally the solvent was removed under reduced pressure. The crude product was purified by chromatography on silica gel with a 4:1 mixture of methylene chloride and hexane as the eluent. There were obtained 65 mg (32% of theory) of (3RS,4RS)-1-benzyl-4-(3-hydroxyphenyl)-3-(naphthalen-2-ylmethoxy)-piperidine as a beige coloured solid; MS: 423 (M)$^+$.

(h) In an analogous manner to that described in Example 12(c), by cleavage of the benzyl group with 2,2,2-trichloroethyl chloroformate there was obtained 2,2,2-trichloroethyl (3RS,4RS)-3-(naphthalen-2-ylmethoxy)-4-[3-(2,2,2-trichloro-ethoxycarbonyloxy)-phenyl]-piperidine-1-carboxylate, which was used directly as the crude product in the next step.

EXAMPLE 19

In analogy to the procedure described in Example 2(e), by catalytically hydrogenating (3RS,4RS)-1-benzyl-4-(3-fluorophenyl)-piperidin-3-ol there was obtained (3RS,4RS)-4-(3-fluorophenyl)-piperidin-3-ol as a colourless solid; MS: 196 (M+H)$^+$. Introduction of the BOC group in an analogous manner to that described in Example 1(f) yielded tert-butyl (3RS,4RS)-4-(3-fluorophenyl)-3-hydroxy-piperidine-1-carboxylate as a colourless solid; MS: 296 (M+H)$^+$. Subsequent alkylation with 4-benzyloxy-2-chloromethyl-naphthalene in analogy to the procedure described in Example 1(g) gave tert-butyl (3RS,4RS)-3-(4-benzyloxy-naphthalen-2-ylmethoxy)-4-(3-fluorophenyl)-piperidine-1-carboxylate as a colourless solid; MS: 541 (M)$^+$. Cleavage of the BOC group using a solution of hydrogen chloride in methanol analogously to the procedure described in Example 1(h) finally led to (3RS,4RS)-3-(4-benzyloxy-naphthalen-2-ylmethoxy)-4-(3-fluorophenyl)-piperidine, which was obtained as a colourless solid; MS: 442 (M+H)$^+$.

The 4-benzyloxy-2-chloromethyl-naphthalene used as the starting compound was obtained as follows:

(a) By alkylating ethyl 4-hydroxy-naphthalene-2-carboxylate [J. Agric. Chem Soc. Japan 24, 313 (1950)] with benzyl bromide in an analogous manner to that described in Example 14(a) there was obtained ethyl 4-benzyloxy-naphthalene-2-carboxylate as an almost colourless solid; MS: 216 (M)$^+$.

(b) Reduction of ethyl 4-benzyloxy-naphthalene-2-carboxylate analogously to Example 5(b) yielded (4-benzyloxy-naphthalen-2-yl)-methanol as a colourless solid; MS: 264 (M)$^+$.

(c) Chlorination of (4-benzyloxy-naphthalen-2-yl)[-methanol] using carbon tetrachloride analogously to Example 7(c) yielded 4-benzyloxy-2-chloromethyl-naphthalene as a colourless solid; MS: 282 (M)$^+$.

EXAMPLE 20

The following compounds were obtained in an analogous manner to that described in Example 1(h) by cleavage of the BOC group using a solution of hydrogen chloride in methanol:

1) (3RS,4RS)-4-(4-Cyano-phenyl)-3-(naphthalen-2-ylmethoxy)-piperidine as a light yellow solid, MS: 342 (M+H)$^+$, from tert-butyl (3RS,4RS)-4-(4-cyano-phenyl)-3-(naphthalen-2-ylmethoxy)-piperidine-1-carboxylate;

2) (3RS,4RS)-4-[4-(phenylsulphonylamino-methyl)-phenyl]-3-(naphthalen-2-ylmethoxy)-piperidine as a colourless solid, MS: 485 (M–H)$^-$, from tert-butyl 4-[4-(phenylsulphonylamino-methyl)-phenyl]-3-(naphthalen-2-ylmethoxy)-piperidine-1-carboxylate;

3) (3RS,4RS)-4-[4-(4-methoxy-benzoylamino)-methyl]-phenyl-3-(naphthalen-2-ylmethoxy)-piperidine as a colourless resin, MS: 481 (M+H)$^+$, from tert-butyl (3RS,4RS)-4-[4-(4-methoxy-benzoylamino)-methyl]-phenyl-3-(naphthalen-2-ylmethoxy)-piperidine-1-carboxylate;

4) (3RS,4RS)-3-(naphthalen-2-ylmethoxy)-4-[4-(phenylacetyl-aminomethyl)-phenyl]-piperidine as a colourless resin, MS: 465 (M+H)$^+$, from tert-butyl (3RS,4RS)-3-(naphthalen-2-ylmethoxy)-4-[4-(phenylacetylamino-methyl)-phenyl]-piperidine-1-carboxylate;

5) (3RS,4RS)-4-[4-(benzoylamino-methyl)-phenyl]-3-(4-hydroxy-naphthalen-2-ylmethoxy)-piperidine as a light orange coloured solid, MS: 467 (M+H)$^+$, from tert-butyl (3RS,4RS)-4-[4-(benzoylamino-methyl)-phenyl]-3-[4-(2-trimethylsilyl-ethoxymethoxy)-naphthalen-2-ylmethoxy]-piperidine-1-carboxylate by simultaneous cleavage of the BOC and SEM groups analogously to that described in Example 3 and 5(g).

The BOC compounds used as the starting materials were prepared as follows:

(a) A suspension of 20 mg (0.30 mmol) of activated zinc powder, 76 mg (1.17 mmol) of potassium cyanide, 52 mg (0.20 mmol) of triphenylphosphine and 74 mg (0.10 mmol) of bis(triphenylphosphine)-nickel(II) dibromide in 2 ml of acetonitrile was heated at 60° C. under argon for 5 minutes. 356 mg (1.00 mmol) of tert-butyl (3RS,4RS)-4-(4-bromophenyl)-3-hydroxy-piperidine-1-carboxylate in solid form were added thereto. The green suspension was stirred at 60° C. under argon for 20 hours. The resulting dark brown suspension was filtered over Speedex and the insoluble material was washed with methylene chloride. The filtrate was partitioned between methylene chloride and 5% sodium hydrogen carbonate solution, the organic phase was dried over magnesium sulphate and finally the solvent was removed under reduced pressure. The crude product (416 mg) was purified by chromatography on silica gel with a 1:1 mixture of ethyl acetate and hexane as the eluent. There were obtained 168 mg (56% of theory) of tert-butyl (3RS,4RS)-4-(4-cyano-phenyl)-3-hydroxy-piperidine-1-carboxylate as a colourless solid; MS: 302 (M)$^+$.

(b) In analogy to the procedure described in Example 1(g), by alkylating tert-butyl (3RS,4RS)-4-(4-cyano-phenyl)-3-hydroxy-piperidine-1-carboxylate with 2-bromomethylnaphthalene there was obtained tert-butyl (3RS,4RS)-4-(4-cyano-phenyl)-3-(naphthalen-2-ylmethoxy)-piperidine-1-carboxylate as a light yellow resin; MS: 443 (M+H)$^+$.

(c) A solution of 133 mg (0.301 mmol) of tert-butyl (3RS,4RS)-4-(4-cyano-phenyl)-3-(naphthalen-2-ylmethoxy)-piperidine-1-carboxylate in 0.5 ml of tetrahydrofuran was treated with 1.5 ml (1.5 mmol) of a 1M borane-tetrahydrofuran complex solution in tetrahydrofuran and the mixture was heated to reflux under argon for 6 hours. The reaction mixture was partitioned between methylene chloride and water, the organic phase was dried over magnesium sulphate and finally the solvent was removed under reduced pressure. The crude product (163 mg) was purified by chromatography on silica gel with a 14:1:0.1 mixture of methylene chloride, methanol and a 25% ammonia solution as the eluent. There were obtained 106 mg (79% of theory) of tert-butyl (3RS,4RS)-4-(4-aminomethyl-phenyl)-3-(naphthalen-2-ylmethoxy)-piperidine-1-carboxylate as a colourless resin; MS: 447 (M+H)$^+$.

(d) A solution of 47 mg (0.105 mmol) of tert-butyl (3RS,4RS)-4-(4-aminomethyl-phenyl)-3-(naphthalen-2-ylmethoxy)-piperidine-1-carboxylate in 2 ml of methylene chloride was treated with 18 μl (12.7 mg, 0.126 mmol, 1.2 eq.) of triethylamine and cooled to 0° C. 15 μl (20.4 mg, 0.116 mmol, 1.1 eq.) of benzenesulphonyl chloride were added dropwise, the mixture was warmed to room temperature and stirred for 1 hour. The reaction mixture was partitioned between methylene chloride and 5% sodium hydrogen carbonate solution, the organic phase was dried over magnesium sulphate and finally the solvent was removed under reduced pressure. There were obtained 47 mg of crude tert-butyl (3RS,4RS)-4-[4-(phenylsulphonyl-amino-methyl)-phenyl]-3-(naphthalen-2-ylmethoxy)-piperidine-1-carboxylate, which was used in the following step without further purification and characterization.

(e) In an analogous manner to the procedure described under (d), from tert-butyl (3RS,4RS)-4-(4-aminomethyl-phenyl)-3-(naphthalen-2-ylmethoxy)-piperidine-1-carboxylate by acylation with p-anisoyl chloride there was obtained crude tert-butyl (3RS,4RS)-4-[4-(4-methoxy-benzoylamino)-methyl]-phenyl-3-(naphthalen-2-ylmethoxy)-piperidine-1-carboxylate, which was used in the following step without further purification and characterization.

(f) In an analogous manner to the procedure described under (d), from tert-butyl (3RS,4RS)-4-(4-aminomethyl-phenyl)-3-(naphthalen-2-ylmethoxy)-piperidine-1-carboxylate by acylation with phenylacetyl chloride there was obtained crude tert-butyl (3RS,4RS)-3-(naphthalen-2-ylmethoxy)-4-[4-(phenyl-acetylamino-methyl)-phenyl]-piperidine-1-carboxylate, which was used in the following step without further purification and characterization.

(g) In an analogous manner to that described in Example 1(g), by alkylating tert-butyl (3RS,4RS)-4-(4-cyano-phenyl)-3-hydroxy-piperidine-1-carboxylate with 2-chloromethyl-4-(β-trimethylsilyl-ethoxymethoxy)-naphthalene there was obtained tert-butyl (3RS,4RS)-4-(4-cyano-phenyl)-3-[4-(2-trimethylsilyl-ethoxy-methoxy)-naphthalen-2-ylmethoxy]-piperidine-1-carboxylate as a light yellow oil; MS: 530 [M-(C$_2$H$_4$+CH$_2$O)$^+$.

(h) In analogy to the procedure described under (c), by reducing the nitrile group in tert-butyl (3RS,4RS)-4-(4-cyano-phenyl)-3-[4-(2-trimethylsilyl-ethoxymethoxy)-naphthalen-2-ylmethoxy]-piperidine-1-carboxylate there was obtained tert-butyl (3RS,4RS)-4-(4-aminomethyl-phenyl)-3-[4-(2-trimethylsilyl-ethoxymethoxy)-naphthalen-2-ylmethoxy]-piperidine-1-carboxylate as a light yellow oil; MS: 593 (M+H)$^+$.

(i) In analogy to the procedure described under (d), from tert-butyl (3RS,4RS)-4-(4-aminomethyl-phenyl)-3-[4-(2-trimethylsilyl-ethoxymethoxy)-naphthalen-2-ylmethoxy]-piperidine-1-carboxylate by acylation with benzoyl chloride there was obtained crude tert-butyl (3RS,4RS)-4-[4-(benzoylamino-methyl)-phenyl]-3-[4-(2-trimethylsilyl-ethoxymethoxy)-naphthalen-2-ylmethoxy]-piperidine-1-carboxylate, which was used in the following step without further purification and characterization.

EXAMPLE 21

The following compounds were obtained in an analogous manner to that described in Example 1(h) by cleavage of the BOC group using a solution of hydrogen chloride in methanol:

1) (3RS,4RS)-4-(4-Chlorophenyl)-4-hydroxy-3-(4-methoxy-benzyloxy)-piperidine as a colourless solid, MS: 348 (M+H)$^+$, from tert-butyl (3RS,4RS)-4-(4-chlorophenyl)-4-hydroxy-3-(4-methoxy-benzyloxy)-piperidine-1-carboxylate;

2) (3RS,4RS)-4-(4-chlorophenyl)-4-hydroxy-3-(naphthalen-2-ylmethoxy)-piperidine as a colourless solid, MS: 226, 228 [M-(C$_{11}$H$_9$)]$^+$, from tert-butyl (3RS,4RS)-4-(4-chlorophenyl)-4-hydroxy-3-(naphthalen-2-ylmethoxy)-piperidine-1-carboxylate.

The compounds used as the starting materials were prepared as follows:

(a) A solution of 3.0 g (15.5 mmol) of 4-(4-chlorophenyl)-1,2,3,6-tetrahydro-pyridine in 20 ml of absolute dimethylformamide was treated with 2.37 ml (1.72 g, 17.0 mmol) of triethylamine and cooled to 0° C. A solution of 3.7 g (17.0 mmol) of di-tert-butyl dicarbonate in 8 ml of absolute dimethylformamide was added dropwise at 0° C. The mixture was warmed to room temperature and stirred for 20 hours. The solvent was distilled off at 50–55° C. at 0.1 mm Hg. Subsequently, the residue obtained was partitioned between methylene chloride and water, the organic phase was dried over magnesium sulphate and finally the solvent was removed under reduced pressure. The crude product (5.0 g) was purified by chromatography on silica gel with a 95:5 mixture of methylene chloride and ethyl acetate as the eluent. There were obtained 4.5 g (99% of theory) of tert-butyl 4-(4-chlorophenyl)-1,2,3,6-tetrahydro-pyridine-1-carboxylate as a colourless oil; MS: 236, 238 [M-(C$_4$H$_9$)]$^+$.

(b) A solution of 2.5 g (8.5 mmol) of tert-butyl 4-(4-chlorophenyl)-1,2,3,6-tetrahydro-pyridine-1-carboxylate in 20 ml of acetone was treated with 0.425 ml (0.0085 mmol, 0.01 eq.) of osmium tetroxide solution (0.02M in tert-butanol) and 8.6 ml of hydrogen peroxide solution (30% in water) and the mixture was stirred at room temperature for 18 hours. The mixture was partitioned between ethyl acetate and water, the organic phase was washed with 10% sodium bisulphite solution and water, dried over magnesium sulphate and finally the solvent was removed under reduced pressure. The crude product (2.2 g) was purified by chromatography on silica gel with a 3:1 mixture of methylene chloride and ethyl acetate as the eluent. There were obtained 544 mg (20% of theory) of tert-butyl (3RS,4RS)-4-(4-chlorophenyl)-3,4-dihydroxy-piperidine-1-carboxylate as a colourless resin; MS: 270, 272 [M-($C_4H_9$)]$^+$.

(c) A solution of 128 mg (0.392 mmol) of tert-butyl (3RS,4RS)-4-(4-chlorophenyl)-3,4-dihydroxy-piperidine-1-carboxylate in 1.5 ml of dimethyl sulphoxide was added dropwise to a suspension of 16 mg (0.4 mmol) of sodium hydride (60% dispersion in refined oil) in 3 ml of dimethyl sulphoxide. After 15 minutes a solution of 61 mg (0.39 mmol) of p-methoxybenzyl chloride in 1 ml of dimethyl sulphoxide was added dropwise at room temperature within 10 minutes and the mixture was stirred for 18 hours. Subsequently, the reaction mixture was partitioned between ethyl acetate and water, the organic phase was dried over magnesium sulphate and finally the solvent was removed under reduced pressure. The crude product (200 mg) was purified by chromatography on silica gel with a 3:1 mixture of hexane and ethyl acetate as the eluent. There were obtained (in addition to starting material and bisalkylated product) 63 mg (38% of theory) of tert-butyl (3RS,4RS)-4-(4-chlorophenyl)-4-hydroxy-3-(4-methoxy-benzyloxy)-piperidine-1-carboxylate as a colourless oil; MS: 448, 450 [M+H]$^+$.

(d) In an analogous manner to the procedure described under (c), by alkylating tert-butyl (3RS,4RS)-4-(4-chlorophenyl)-3,4-dihydroxy-piperidine-1-carboxylate with 2-bromomethylnaphthalene there was obtained tert-butyl (3RS,4RS)-4-(4-chlorophenyl)-4-hydroxy-3-(naphthalen-2-ylmethoxy)-piperidine-1-carboxylate as a light yellow oil; MS: 411, 413 [M-($C_4H_8$)]$^+$.

EXAMPLE 22

(a) 400 ml of a 1.2M solution of n-BuLi in hexane were added dropwise within 45 minutes to a solution, cooled to −70° C., of 112.5 g (0.48 mol) of 1,4-dibromobenzene in 1200 ml of diethyl ether in such a manner that the temperature did not rise above −60° C. After completion of the addition the mixture was stirred at −70° C. for 2.5 hours. Thereafter, a solution of 90.84 g (0.48 mol) of 1-benzyl-4-piperidone in 300 ml of ether was added dropwise at −70 to −65° C. during one hour. After the dropwise addition the mixture was stirred at −70° C. for 2 hours. For the working-up, the cold reaction mixture was poured into 1200 ml of a 15% ammonium chloride solution, the mixture was transferred to a separating funnel and the organic phase was separated. The aqueous phase was extracted twice with ether and subsequently the combined organic phases were extracted twice with water and saturated sodium chloride solution. Then, the organic phase was dried over magnesium sulphate evaporated under reduced pressure, with the crude product separating as a yellowish solid. For purification, this was dissolved in hot methylene chloride, the solution was treated with hexane until turbidity began and cooled to room temperature while stirring. The resulting precipitate was filtered off under suction and dried. There were obtained 121.65 g (73% of theory) of 1-benzyl-(4-bromo-phenyl)-piperidin-4-ol as a yellowish solid; m.p.: 106° C., MS: 346, 348 (M+H)$^+$.

(b) A mixture of 121.6 g (0.35 mol) of 1-benzyl-4-(4-bromo-phenyl)-piperidin-4-ol and 121.6 g of p-toluenesulphonic acid monohydrate (0.64 mol) in 1200 ml of toluene was heated to reflux on a water separator for 4.5 hours. Subsequently, the reaction mixture was cooled to room temperature and adjusted to pH 10 with 3N sodium hydroxide solution. Thereafter, the mixture was extracted firstly with 200 ml and then with 500 ml of methylene chloride. The combined organic phases were washed twice with 100 ml of water each time, dried over magnesium sulphate and then evaporated under reduced pressure. There were obtained 109.1 g (99% of theory) of 1-benzyl-4-(4-bromo-phenyl)-1,2,3,6-tetrahydro-pyridine as a yellowish solid; MS: 328, 330 (M+H)$^+$.

(c) 16.9 g of sodium borohydride were added to a solution of 51.1 g (0.156 mol) of 1-benzyl-4-(4-bromo-phenyl)-1,2,3,6-tetrahydro-pyridine in 350 ml of dimethoxyethane and the reaction mixture was stirred at room temperature for 15 minutes. Thereafter, 95.2 ml of boron trifluoride etherate were added dropwise at 25–30° C. during 30 minutes, the reaction mixture was subsequently stirred at room temperature for 2 hours. Thereafter, firstly a solution of 98.4 g of potassium hydroxide in 530 ml of water was slowly added dropwise and thereafter within 15 minutes 80.7 ml of a 30% hydrogen peroxide solution were added. Subsequently, the mixture was boiled under reflux for 2 hours. For the working-up, the cooled reaction mixture was filtered over Dicalit and this was rinsed with methylene chloride. The solution obtained was treated with 700 ml of methylene chloride, the organic phase was separated and then the aqueous phase was back-extracted with 300 ml of methylene chloride. The combined organic phases were washed twice with 200 ml of water each time, dried over magnesium sulphate and evaporated under reduced pressure. Crystallization of the crude product from acetone yielded 31 g (57% of theory) of (3RS,4RS)-1-benzyl-4-(4-bromo-phenyl)-piperidin-3-ol as colourless crystals; m.p.: 125–129° C.

(d) A Schlenk tube was charged under argon with 74.9 mg (0.29 mmol) of $PdCl_2(CH_3CN)_2$, 168.0 mg (0.303 mmol) of 1,1'-bis(diphenylphosphino)ferrocene and 10 ml of methanol (distilled under argon) and the reaction mixture was stirred at room temperature for 30 minutes. The red-brown suspension was transferred under argon into a 185 ml steel autoclave fitted with a glass insert. Thereafter, 10.0 g (29 mmol) of (3RS,4RS)-1-benzyl-4-(4-bromo-phenyl)-piperidin-3-ol (pre-treated with active charcoal), 60 ml of methanol and 6 ml (43 mmol) of triethylamine (sic) were added. The autoclave was sealed, pressurized to 15 bar with carbon monoxide and the reaction mixture was stirred at 110° for 20 hours under constant pressure. After cooling the autoclave and releasing the gases the orange coloured reaction mixture was evaporated under reduced pressure. The solid, orange coloured residue was dissolved in 20 ml of methylene chloride, the solution was washed twice with 100 ml of 5% sodium carbonate solution each time and, respectively, with 100 ml of water and then evaporated under reduced pressure. For purification, the yellow-brown solid residue was chromatographed on silica gel using a 1:1 mixture of ethyl acetate and hexane as the eluent. There were obtained 7.74 g (82% of theory) of methyl (3RS,4RS)-4-(1-benzyl-3-hydroxy-piperidin-4-yl)-benzoate as a white solid; m.p.: 103–104° C.; MS: 326 (M+H)$^+$.

(e) A solution of 5.0 g (15.3 mmol) of methyl (3RS,4RS)-4-(1-benzyl-3-hydroxy-piperidin-4-yl)-benzoate in 50 ml of tetrahydrofuran was treated at room temperature with 720 mg (32.9 mmol) of lithium borohydride. Subsequently, the reaction mixture was heated to 60° C. for 15 hours. For the working-up, the reaction mixture was treated with 20 ml of water while cooling with ice and thereafter extracted twice with 50 ml of ethyl acetate each time. The organic phases were combined, dried over sodium sulphate and evaporated under reduced pressure. The crude (3RS,4RS)-1-benzyl-4-(4-hydroxymethyl-phenyl)-piperidine-3-ol obtained (Rf: 0.23, methylene chloride:methanol:ammonia=95:5:0.1) was used in the following step without further purification.

(f) A solution of 2.0 g (6.72 mmol) of (3RS,4RS)-1-benzyl-4-(4-hydroxymethyl-phenyl)-piperidin-3-ol in 100 ml of ethanol was hydrogenated at room temperature and 3 bar for 4 hours in the presence of 1.0 g of palladium oxide/charcoal (20%). For the working-up, the catalyst was filtered off under suction over Dicalit and the residue was washed twice with 50 ml of ethanol each time. The ethanol solution was evaporated under reduced pressure and the residue was chromatographed on silica gel using a 65:10:1 mixture of methylene chloride, methanol and ammonia as the eluent. There were obtained 1.1 g (79% of theory) of (3RS,4RS)-4-(4-hydroxymethyl-phenyl)-piperidin-3-ol as a colourless solid; MS: 207 (M)$^+$.

(g) A solution of 1.10 g (5.31 mmol) of (3RS,4RS)-4-(4-hydroxymethyl-phenyl)-piperidin-3-ol in 20 ml of dimethylformamide was treated at 0° C. with 0.59 g (5.82 mmol) of triethylamine and 1.22 g (5.57 mmol) of di-tert-butyl dicarbonate and the mixture was stirred at room temperature for 15 hours. Subsequently, the dimethylformamide was distilled off in an oil pump vacuum and, for purification, the residue was chromatographed on silica gel using a 98:2 mixture of methylene chloride and methanol as the eluent. There were obtained 1.51 g (92% of theory) of tert-butyl (3RS,4RS)-3-hydroxy-4-(4-hydroxymethyl-phenyl)-piperidine-1-carboxylate as a colourless foam; MS: 233 (M-C$_4$H$_{10}$O)$^+$.

(h) A solution of 1.50 g (5.14 mmol) of tert-butyl (3RS, 4RS)-3-hydroxy-4-(4-hydroxymethyl-phenyl)-piperidine-1-carboxylate, 1.73 g (6.16 mmol) of triphenylchloromethane and 674 mg (6.68 mmol) of triethylamine in 20 ml of methylene chloride was stirred at room temperature for 5 hours. For the working-up, the reaction mixture was washed with 10 ml of water and 10 ml of saturated sodium hydrogen carbonate solution, the organic phase was dried over sodium sulphate and evaporated under reduced pressure. The crude product was chromatographed on silica gel using a 95:5 mixture of toluene and ethyl acetate as the eluent. There were obtained 2.08 g (77.5% of theory) of tert-butyl (3RS, 4RS)-3-hydroxy-4-(4-trityloxymethyl-phenyl)-piperidine-1-carboxylate as a colourless foam; MS: 567 (M+NH$_4$)$^+$.

(i) 290 mg (6.05 mmol) of sodium hydride (50% dispersion in refined oil) were added to a solution of 2.08 g (3.78 mmol) of tert-butyl (3RS,4RS)-3-hydroxy-4-(4-trityloxymethyl-phenyl)-piperidine-1-carboxylate and 1.0 g (4.54 mmol) of 2-bromomethylnaphthalene in 30 ml of dimethylformamide and the reaction mixture was stirred at room temperature for 2 hours. For the working-up, the reaction mixture was evaporated in an oil pump vacuum, the residue was partitioned between 100 ml of saturated ammonium chloride solution and 100 ml of ethyl acetate and thereafter the separated aqueous phase was extracted twice with 50 ml of ethyl acetate each time. The combined ethyl acetate extracts were dried over sodium sulphate and evaporated under reduced pressure. For purification, the crude product was chromatographed on silica gel using a 4:1 mixture of methylene chloride and hexane as the eluent. There were obtained 2.27 g (87% of theory) of tert-butyl (3RS,4RS)-3-naphthalen-2-ylmethoxy-4-(4-trityloxymethyl-phenyl)-piperidine-1-carboxylate as a colourless solid; MS: 707 (M+NH$_4$)$^+$.

(j) A solution of 1.07 g (1.48 mmol) of tert-butyl (3RS, 4RS)-3-naphthalen-2-ylmethoxy-4-(4-trityloxymethyl-phenyl)-piperidine-1-carboxylate in 15 ml of methylene chloride was treated at room temperature with 2 ml of 2N hydrogen chloride in methanol and the mixture was stirred at room temperature for 15 minutes. Subsequently, the solution was poured into 30 ml of saturated sodium carbonate solution and this was extracted twice with 50 ml of ethyl acetate each time. The combined organic phases were dried over sodium sulphate and evaporated under reduced pressure. For purification, the crude product was chromatographed on silica gel using a 99:1 mixture of methylene chloride and methanol as the eluent. There were obtained 580 mg (82% of theory) of tert-butyl (3RS,4RS)-4-(4-hydroxymethyl-phenyl)-3-(naphthalen-2-ylmethoxy)-piperidine-1-carboxylate as a colourless oil; MS: 447 (M)$^+$.

(k) A solution of 45 mg (0.1 mmol) of tert-butyl (3RS,4RS)-4-(4-hydroxymethyl-phenyl)-3-(naphthalen-2-ylmethoxy)-piperidine-1-carboxylate, 12 mg (0.12 mmol) of triethylamine and 12 mg (0.1 mmol) of pivaloyl chloride in 5 ml of methylene chloride was stirred at room temperature for 15 hours. For the working-up, the reaction solution was diluted with 10 ml of methylene chloride, then washed with 5 ml of water, dried over sodium sulphate and evaporated under reduced pressure. The residue was chromatographed on silica gel using a 4:1 mixture of hexane and ethyl acetate as the eluent. There were obtained 39 mg (73% of theory) of tert-butyl (3RS,4RS)-4-[4-(2,2-dimethyl-propionyloxymethyl)-phenyl]-3-(naphthalen-2-ylmethoxy)-piperidine-1-carboxylate as a colourless oil; MS: 549 (M+NH$_4$)$^+$.

(l) A solution of 35 mg (0.07 mmol) of tert-butyl (3RS, 4RS)-4-[4-(2,2-dimethyl-propionyloxymethyl)-phenyl]-3-(naphthalen-2-ylmethoxy)-piperidine-1-carboxylate in 2 ml of 2M hydrogen chloride in methanol was stirred at room temperature for 4.5 hours. Subsequently, the reaction solution was evaporated under reduced pressure. The residue was taken up in diethyl ether, with a part (15 mg, 49% of theory) of the (3RS,4RS)-4-(3-naphthalen-2-ylmethoxy-piperidin-4-yl)-benzyl 2,2-dimethyl-propionate hydrochloride being obtained in the form of white crystals; MS: 432 (M+H)$^+$.

EXAMPLE 23

A solution of 1.10 g (1.59 mmol) of tert-butyl (3RS,4RS)-3-naphthalen-2-ylmethoxy-4-(4-trityloxymethyl-phenyl)-piperidine-1-carboxylate in 50 ml of methanol was treated at room temperature with 30 ml of a 2M solution of hydrogen chloride in methanol and the mixture was stirred at room temperature for 4 hours. Subsequently, the solution was evaporated under reduced pressure and the residue was partitioned between 30 ml of saturated sodium carbonate solution and 50 ml of ethyl acetate. The aqueous phase was again extracted with 50 ml of ethyl acetate, thereafter the organic phases were combined, dried over sodium sulphate and evaporated under reduced pressure. For purification, the crude product was chromatographed on silica gel using a 90:10 mixture of methylene chloride and methanol as the eluent. There were obtained 462 mg (83% of theory) of (3RS,4RS)-[4-[3-(naphthalen-2-ylmethoxy)-piperidin-4-yl]-phenyl}-methanol as a colourless solid; MS: 348 (M+H)$^+$.

EXAMPLE 24

The following compounds were obtained in an analogous manner to that in Example 22(l) by cleavage of the BOC group using acid 1) (3RS,4RS)-4-[3-(Naphthalen-2-ylmethoxy)-piperidin-4-yl]-benzyl benzoate as a colourless foam, MS: 452 (M+H)$^+$, from tert-butyl (3RS,4RS)-4-(4-benzoyloxymethyl-phenyl)-3-(naphthalen-2-ylmethoxy)-piperidine-1-carboxylate;

2) (3RS,4RS)-4-(3-naphthalen-2-ylmethoxy-piperidin-4-yl)-benzyl 3-methoxy-benzoate hydrochloride as a colourless solid, MS: 482 (M+H)⁺, from tert-butyl (3RS,4RS)-4-[4-(3-methoxy-benzoyloxymethyl)-phenyl]-3-naphthalen-2-ylmethoxy-piperidine-1-carboxylate;

3) (3RS,4SR)-4-(3-naphthalen-2-ylmethoxy-piperidin-4-yl)-benzyl 3,5-dimethoxy-benzoate hydrochloride as a colourless solid, MS: 512 (M+H)⁺, from tert-butyl (3RS,4RS)-4-[4-(3,5-dimethoxy-benzoyloxymethyl)-phenyl]-3-(naphthalen-2-ylmethoxy)-piperidine-1-carboxylate;

4) (3RS,4RS)-4-[3-(naphthalen-2-ylmethoxy)-piperidin-4-yl]-benzyl cyclohexanecarboxylate trifluoroacetate as a colourless solid, MS: 458 (M+H)⁺, from tert-butyl (3RS,4RS)-4-(4-cyclohexanecarbonyloxymethyl-phenyl)-3-(naphthalen-2-ylmethoxy)-piperidine-1-carboxylate using trifluoroacetic acid in methylene chloride;

5) (4RS,3RS)-4-(3-naphthalen-2-ylmethoxy-piperidin-4-yl)-benzyl 2-chloro-benzoate trifluoroacetate as a colourless solid, MS: 486 (M+H)⁺, from tert-butyl (3RS,4RS)-[4-(2-chloro-benzoyloxymethyl)-phenyl]-3-naphthalen-2-ylmethoxy-piperidine-1-carboxylate using trifluoroacetic acid in methylene chloride;

6) carbonic acid methyl ester (3RS,4RS)-4-(naphthalen-2-ylmethoxy-piperidin-4-yl)-benzyl ester hydrochloride as a colourless oil, MS: 406 (M+H)⁺, from tert-butyl (3RS,4RS)-4-(4-methoxycarbonyloxymethyl-phenyl)-3-(naphthalen-2-ylmethoxy)-piperidine-1-carboxylate;

7) (3RS,4RS)-4-[3-(naphthalen-2-ylmethoxy)-piperidin-4-yl]-benzyl pyridine-4-carboxylate hydrochloride as a yellow oil, MS: 453 (M+H)⁺, from (3RS,4RS)-4-(1-tert-butoxycarbonyl-3-naphthalen-2-ylmethoxy-piperidin-4-yl)-benzyl pyridine-4-carboxylate;

8) (3RS,4RS)-4-(3-naphthalen-2-ylmethoxy-piperidin-4-yl)-benzyl pyrazine-2-carboxylate hydrochloride as a colourless solid, MS: 454 (M+H)⁺, from (3RS,4RS)-4-[1-tert-butoxycarbonyl-3-(naphthalen-2-ylmethoxy)-piperidin-4-yl]-benzyl pyrazine-2-carboxylate;

9) (3RS,4RS)-4-[3-(1-methoxy-naphthalen-2-ylmethoxy)-piperidin-4-yl]-benzyl 2-chloro-benzoate trifluoroacetate as a colourless solid, MS: 516 (M+H)⁺, from tert-butyl (3RS,4RS)-4-[4-(2-chloro-benzoyloxymethyl)-phenyl]-3-(1-methoxy-naphthalen-2-ylmethoxy)-piperidine-1-carboxylate using trifluoroacetic acid in methylene chloride;

10) (3RS,4RS)-4-(3-naphthalen-2-ylmethoxy-piperidin-4-yl)-benzyl 4-hydroxy-benzoate hydrochloride as a yellowish solid, MS: 468 (M+H)⁺, from tert-butyl (3RS,4RS)-4-[4-(4-hydroxy-benzoyloxymethyl)-phenyl]-3-(naphthalen-2-ylmethoxy)-piperidine-1-carboxylate using trifluoroacetic acid in methylene chloride and simultaneous cleavage of the acetal group;

11) (3RS,4RS)-4-[3-(naphthalen-2-ylmethoxy)-piperidin-4-yl]-benzyl pyridin-2-yl-carbamate hydrochloride as a colourless foam, R$_f$: 0.15 (methylene chloride:methanol ammonia=90:10:0.1), from tert-butyl (3RS,4RS)-3-(naphthalen-2-ylmethoxy)-4-[4-(pyridin-2-ylcarbamoyloxymethyl)-phenyl]-piperidine-1-carboxylate;

12) (3RS,4RS)-4-[4-(3-methoxy-propenyl)-phenyl]-3-(naphthalen-2-ylmethoxy)-piperidine as a yellow oil, MS: 388 (M+H)⁺, from tert-butyl (3RS,4RS)-4-[4-(3-hydroxy-propenyl)-phenyl]-3-(naphthalen-2-ylmethoxy)-piperidine-1-carboxylate;

13) (3RS,4RS)-4-[4-(3-benzoyloxy-propenyl)-phenyl]-3-(naphthalen-2-ylmethoxy)-piperidine as a yellow oil, MS: 478 (M+H)⁺, from tert-butyl (3RS,4RS)-4-[4-(3-benzoyloxy-propenyl)-phenyl]-3-(naphthalen-2-ylmethoxy)-piperidine-1-carboxylate;

14) 3-[4-[3-(naphthalen-2-ylmethoxy)-piperidin-4-yl]-phenyl]-propyl (3RS,4RS)-2-chloro-benzoate as a yellowish oil, MS: 514, 516 (M+H)⁺, from tert-butyl (3RS,4RS)-4-[4-[3-(2-chloro-benzoyloxy)-propyl]-phenyl]-3-(naphthalen-2-ylmethoxy)-piperidine-1-carboxylate.

The starting materials were obtained as follows analogously to the procedure described in Example 22(k):

(a) tert-Butyl (3RS,4RS)-4-(4-benzoyloxymethyl-phenyl)-3-(naphthalen-2-ylmethoxy)-piperidine-1-carboxylate as a colourless oil, MS: 552 (M+H)⁺, from tert-butyl (3RS,4RS)-4-(4-hydroxymethyl-phenyl)-3-(naphthalen-2-ylmethoxy)-piperidine-1-carboxylate and benzoyl chloride.

(b) tert-Butyl (3RS,4RS)-4-[4-(3-methoxy-benzoyloxymethyl)-phenyl]-3-naphthalen-2-ylmethoxy-piperidine-1-carboxylate as a colourless oil, MS: 582 (M+H)⁺, from tert-butyl (3RS,4RS)-4-(4-hydroxymethyl-phenyl)-3-(naphthalen-2-ylmethoxy)-piperidine-1-carboxylate and 3-methoxybenzoyl chloride.

c) tert-Butyl (3RS,4RS)-4-[4-(3,5-dimethoxy-benzoyloxymethyl)-phenyl]-3-(naphthalen-2-ylmethoxy)-piperidine-1-carboxylate as a colourless oil, MS: 612 (M+H)⁺, from tert-butyl (3RS,4RS)-4-(4-hydroxymethyl-phenyl)-3-(naphthalen-2-ylmethoxy)-piperidine-1-carboxylate and 3,5-dimethoxybenzoyl chloride.

(d) tert-Butyl (3RS,4RS)-4-(4-cyclohexanecarbonyloxymethyl-phenyl)-3-(naphthalen-2-ylmethoxy)-piperidine-1-carboxylate as a colourless oil, MS: 558 (M+H)⁺, from tert-butyl (3RS,4RS)-4-(4-hydroxymethyl-phenyl)-3-(naphthalen-2-ylmethoxy)-piperidine-1-carboxylate and cyclohexanecarbonyl chloride.

(e) tert-Butyl (3RS,4RS)-[4-(2-chloro-benzoyloxymethyl)-phenyl]-3-naphthalen-2-ylmethoxy-piperidine-1-carboxylate as a colourless oil, MS: 586 (M+H)⁺, from tert-butyl (3RS,4RS)-4-(4-hydroxymethyl-phenyl)-3-(naphthalen-2-ylmethoxy)-piperidine-1-carboxylate and 2-chlorobenzoyl chloride.

(f) tert-Butyl (3RS,4RS)-4-(4-methoxycarbonyloxymethyl-phenyl)-3-(naphthalen-2-ylmethoxy)-piperidine-1-carboxylate as a colourless oil from tert-butyl (3RS,4RS)-4-(4-hydroxymethyl-phenyl)-3-(naphthalen-2-ylmethoxy)-piperidine-1-carboxylate and methyl chloroformate.

(g) A solution of 60 mg (0.13 mmol) of tert-butyl (3RS,4RS)-4-(4-hydroxymethyl-phenyl)-3-(naphthalen-2-ylmethoxy)-piperidine--carboxylate, 16 mg (0.13 mmol) of isonicotinic acid, 34 mg (0.26 mmol) of ethyidiisopropylamine and 58 mg (0.13 mmol) of benzotriazol-1-yl-oxy-tris-(dimethylamino)-phosphonium hexafluorophosphate (BOP) in 5 ml of acetonitrile was stirred at room temperature for 2 hours. Subsequently, the reaction mixture was evaporated under reduced pressure and the residue, without further working-up, was chromatographed on silica gel using a 3:1 mixture of hexane and ethyl acetate as the eluent. There were obtained 15 mg (21% of theory) of (3RS,4RS)-4-(1-tert-butoxycarbonyl-3-naphthalen-2-ylmethoxy-piperidin-4-yl)-benzyl pyridine-4-carboxylate as a colourless solid; MS: 552 (M)⁺.

(h) In an analogous manner to that described under (g) by condensing tert-butyl (3RS,4RS)-4-(4-hydroxymethyl-phenyl)-3-(naphthalen-2-ylmethoxy)-piperidine-1-carboxylate and pyrazinecarboxylic acid using 1,1-carbonyldiimidazole as the condensation agent there was obtained 4-[1-tert-butoxycarbonyl-3-(naphthalen-2-ylmethoxy)-piperidin-4-yl]-benzyl (3RS,4RS)-pyrazine-2-carboxylate; MS: 554 (M+H)⁺.

Processing was carried out as follows in an analogous manner to that described in Example 22(i)–(k):

(i) Alkylation of methyl (3RS,4RS)-4-(1-benzyl-3-hydroxy-piperidin-4-yl)-benzoate with 2-bromomethyl-1-methoxy-naphthalene gave tert-butyl (3RS,4RS)-3-(1-methoxynaphthalen-2-ylmethoxy)-4-(4-trityloxymethyl-phenyl)-piperidine-1-carboxylate as a colourless oil; MS: 720 (M+H)⁺.

(j) Cleavage of the trityl group from tert-butyl (3RS,4RS)-3-(1-methoxy-naphthalen-2-ylmethoxy)-4-(4-trityloxymethyl-phenyl)-piperidine-1-carboxylate yielded tert-butyl (3RS,4RS)-4-(4-hydroxymethyl-phenyl)-3-(1-methoxy-naphthalen-2-ylmethoxy)-piperidine-1-carboxylate as a colourless oil; MS: 478 (M+H)⁺.

(k) Acylation of tert-butyl (3RS,4RS)-4-(4-hydroxymethyl-phenyl)-3-(1-methoxy-naphthalen-2-ylmethoxy)-piperidine-1-carboxylate with 2-chlorobenzoyl chloride gave tert-butyl (3RS,4RS)-4-[4-(2-chloro-benzoyloxymethyl)-phenyl]-3-(1-methoxy-naphthalen-2-ylmethoxy)-piperidine-1-carboxylate as a colourless oil; MS: 615 (M+H)⁺.

(l) In an analogous manner to that described under (g) by condensing tert-butyl (3RS,4RS)-4-(4-hydroxymethyl-phenyl)-3-(naphthalen-2-ylmethoxy)-piperidine-1-carboxylate and 4-(2-trimethylsilanyl-ethoxymethoxy)-benzoic acid using N-ethyl-N'-(3-dimethylaminopropyl)-carbodiimide hydrochloride (EDC) as the condensation agent there was obtained tert-butyl (3RS,4RS)-3-(naphthalen-2-ylmethoxy)-4-{4-[4-(2-trimethylsilanyl-ethoxymethoxy)-benzoyloxymethyl]-phenyl}-piperidine-1-carboxylate; MS: 715 (M+NH₄)⁺.

The 4-(2-trimethylsilanyl-ethoxymethoxy)-benzoic acid was obtained as a colourless solid in an analogous manner to that described in Example 5 by reaction of methyl 4-hydroxybenzoate with 2-(trimethylsilyl)-ethoxymethyl chloride and subsequent basic saponification of the ester.

(m) A solution of 57 mg (0.13 mmol) of tert-butyl (3RS, 4RS)-4-(4-hydroxymethyl-phenyl)-3-(naphthalen-2-ylmethoxy)-piperidine-1-carboxylate, 20 mg (0.14 mmol) of pyridine-2-carbonyl azide [H.Saikachi and T.Kitgawa, Chem.Pharm.Bull. 25 (7), 1651–1657 (1977)] and 3 mg of 4-dimethylaminopyridine in 3 ml of toluene was heated to 90° C. for 3 hours. Subsequently, the toluene was evaporated under reduced pressure, the residue was taken up in 15 ml of methylene chloride and the solution was washed with 5 ml of water. The organic phase was thereafter dried over sodium sulphate and evaporated under reduced pressure. The oily residue was taken up with a mixture of ether and hexane and crystallized. There were obtained 64 mg (88% of theory) of tert-butyl (3RS,4RS)-3-(naphthalen-2-ylmethoxy)-4-[4-(pyridin-2-ylcarbamoyloxymethyl)-phenyl]-piperidine-1-carboxylate as a colourless solid; MS: 568 (M+H)⁺.

(n) A Schlenk tube was charged under argon with 25.6 mg (0.114 mmol) of Pd(OAc)₂, 69.6 mg (0.229 mmol) of tri(o-tolyl)phosphine and 20 ml of DMF (distilled under argon) and the reaction mixture was stirred at room temperature for 15 minutes. A 200 ml sulphonation flask was charged under argon and while stirring with 8.15 g (22.9 mmol) of tert-butyl (3RS,4RS)-4-(4-bromo-phenyl)-3-hydroxy-piperidine-1-carboxylate [Example 25(c)], 100 ml of DMF, 3.73 ml (34.3 mmol) of ethyl acrylate, 2.25 g (27.5 mmol) of sodium acetate and the yellow catalyst solution. The reaction mixture was stirred at 120° C. for 6 hours. In order to complete the reaction, a solution of 5.1 mg Pd(OAc)₂ and 14.3 mg of tri(o-tolyl)phosphine in 5 ml of DMF was added after 5 hours. The dark reaction mixture was evaporated on a rotary evaporator. The grey solid residue was taken up in ether and the turbid solution was washed three times with water, dried over sodium sulphate and evaporated under reduced pressure. The yellow solid residue was chromatographed on 250 g of silica gel using a 2:1 mixture of hexane and ethyl acetate as the eluent. After crystallization from ethyl acetate there were obtained 6.66 g (77% of theory) of tert-butyl (3RS,4RS)-4-[4-(2-ethoxycarbonyl-vinyl)-phenyl]-3-hydroxy-piperidine-1-carboxylate as colourless crystals; MS: 376 (M+H)⁺.

(o) Alkylation of tert-butyl (3RS,4RS)-4-[4-(2-ethoxycarbonyl-vinyl)-phenyl]-3-hydroxy-piperidine-1-carboxylate with 2-bromomethylnaphthalene analogously to the procedure described in Example 22(i) gave tert-butyl (3RS,4RS)-4-[4-(2-ethoxycarbonyl-vinyl)-phenyl]-3-(naphthalen-2-ylmethoxy)-piperidine-1-carboxylate as a light yellow resin; MS: 516 (M+H)⁺.

(p) 5 ml (5 mmol) of a solution of diisobutylaluminium hydride (DIBAH) (1M in hexane) were added dropwise at −50° C. to a solution of 698 mg (1.35 mmol) of tert-butyl (3RS,4RS)-4-[4-(2-ethoxycarbonyl-vinyl)-phenyl]-3-(naphthalen-2-ylmethoxy)-piperidine-1-carboxylate in 15 ml of toluene and the mixture was stirred at −50° C. for 30 minutes. Subsequently, the reaction mixture was treated dropwise at −50° C. with 10 ml of ethanol and warmed to room temperature. For the working-up, the reaction mixture was treated with 20 ml of water and 20 ml of saturated potassium sodium tartrate solution while cooling with ice and thereafter extracted three times with 50 ml of ethyl acetate each time. The organic phases were combined, dried over sodium sulphate and evaporated under reduced pressure. The crude product was chromatographed on silica gel using a 6:4 mixture of hexane and ethyl acetate as the eluent. There were obtained 354 mg (55% of theory) of tert-butyl (3RS,4RS)-4-[4-(3-hydroxy-propenyl)-phenyl]-3-(naphthalen-2-ylmethoxy)-piperidine-1-carboxylate as a colourless solid; MS: 474 (M+H)⁺.

(q) Acylation of tert-butyl (3RS,4RS)-4-[4-(3-hydroxy-propenyl)-phenyl]-3-(naphthalen-2-ylmethoxy)-piperidine-1-carboxylate with benzoyl chloride analogously to the procedure described in Example 22(k) yielded tert-butyl (3RS,4RS)-4-[4-(3-benzoyloxy-propenyl)-phenyl]-3-(naphthalen-2-ylmethoxy)-piperidine-1-carboxylate as a colourless resin; MS: 578 (M+H)⁺.

(r) A solution of 2.0 g (5.35 mmol) of tert-butyl (3RS,4RS)-4-[4-(2-ethoxycarbonyl-vinyl)-phenyl]-3-hydroxy-piperidine-1-carboxylate in 100 ml of ethanol was treated with 200 mg of palladium/charcoal (Type E101R) and hydrogenated at room temperature for 1 hour. Subsequently, the catalyst was filtered off and rinsed with ethanol. The filtrate was evaporated under reduced pressure and the light grey residue (1.97 g) was combined with those from three analogous hydrogenation batches (total 3.08 g). For purification, the crude product was chromatographed on silica gel using a 2:1 mixture of hexane and ethyl acetate as the eluent and thereafter crystallized from ethyl acetate/hexane. There were obtained 2.67 g (87% of theory) of tert-butyl (3RS,4RS)-4-[4-(2-ethoxycarbonyl-ethyl)-phenyl]-3-hydroxy-piperidine-1-carboxylate as colourless crystals; MS: 378 (M+H)⁺.

(s) Analogously to the procedure described in Example 22(i), by alkylating tert-butyl (3RS,4RS)-4-[4-(2-ethoxycarbonyl-ethyl)-phenyl]-3-hydroxy-piperidine-1-carboxylic acid with 2-bromomethylnaphthalene there was obtained tert-butyl (3RS,4RS)-4-[4-(2-ethoxycarbonyl-ethyl)-phenyl]-3-(naphthalen-2-ylmethoxy)-piperidine-1-carboxylate; MS: 518 (M+H)⁺.

(t) Analogously to the procedure described in Example 22(e), by reducing tert-butyl (3RS,4RS)-4-[4-(2-ethoxycarbonyl-ethyl)-phenyl]-3-(naphthalen-2-ylmethoxy)-piperidine-1-carboxylate using lithium borohydride there was obtained tert-butyl (3RS,4RS)-4-[4-(3- hydroxy-propyl)-phenyl]-3-(naphthalen-2-ylmethoxy)-piperidine-1-carboxylate as a colourless solid; MS: 476 (M+H)$^+$.

(u) Acylation of tert-butyl (3RS,4RS)-4-[4-(3-hydroxy-propyl)-phenyl]-3-(naphthalen-2-ylmethoxy)-piperidine-1-carboxylate with 2-chloro-benzoyl chloride analogously to the procedure described in Example 22(k) gave tert-butyl (3RS,4RS)-4-[4-[3-(2-chloro-benzoyloxy)-propyl]-phenyl]-3-(naphthalen-2-ylmethoxy)-piperidine-1-carboxylate as a colourless, amorphous solid; MS: 614.6, 616 (M+H)$^+$.

EXAMPLE 25

(a) A mixture of 1.0 g (2.9 mmol) of (3RS,4RS)-1-benzyl-4-(4-bromo-phenyl)-piperidin-3-ol [Example 22(c)], 1.36 ml (10.2 mmol) of 2,2,2-trichloroethyl chloroformate and 0.90 g (12.6 mmol) of lithium carbonate in 20 ml of toluene was heated to 105° C. for 18 hours. For the working-up, the cooled reaction mixture was poured into 200 ml of ice-water and subsequently extracted three times with 25 ml of ethyl acetate each time. The combined organic phases were dried over sodium sulphate and evaporated under reduced pressure. For purification, the crude material obtained was chromatographed on silica gel using a 2:3 mixture of methylene chloride and hexane as the eluent. There were obtained 1.3 g (76% of theory) of 2,2,2-trichloroethyl (3RS,4RS)-4-(4-bromo-phenyl)-3-(2,2,2-trichloro-ethoxycarbonyloxy)-piperidine-1-carboxylate as a colourless solid; R$_f$: 0.17 (methylene chloride:hexane=1:1), MS: 622, 624, 626 (M+NH$_4$)$^+$.

(b) A mixture of 1.3 g (2.1 mmol) of 2,2,2-trichloroethyl (3RS,4RS)-4-(4-bromo-phenyl)-3-(2,2,2-trichloro-ethoxycarbonyloxy)-piperidine-1-carboxylate 1.54 g of activated zinc in 20 ml of glacial acetic acid was stirred at room temperature for 5 hours. For the working-up, the zinc was filtered off, the residue was rinsed with glacial acetic acid and the solution was subsequently evaporated to dryness under reduced pressure. The residue was partitioned between 20 ml of saturated sodium carbonate solution and 30 ml of ethyl acetate, thereafter the separated aqueous phase was extracted twice with 30 ml of ethyl acetate each time. The combined organic phases were dried over sodium sulphate and evaporated under reduced pressure. Crystallization of the residue using a 1:2 mixture of ethyl acetate and hexane yielded 250 mg (46% of theory) of (3RS,4RS)-4-(4-bromo-phenyl)-piperidin-3-ol as a colourless solid; MS: 255, 257 (M)$^+$. The mother liquor was purified by chromatography on silica gel using a 4:1 mixture of methylene chloride and methanol as the eluent. A further 101 mg (18% of theory) were obtained.

(c) A solution of 351 mg (1.37 mmol) of (3RS,4RS)-4-(4-bromo-phenyl)-piperidin-3-ol in 12 ml of dimethylformamide was treated with 139 mg (1.37 mmol) of triethylamine and 300 mg (1.37 mg) of di-tert-butyl dicarbonate and the mixture was stirred at room temperature for 15 hours. Subsequently, the dimethylformamide was distilled off in an oil pump vacuum and the residue was crystallized from a 1:1 mixture of ether and hexane. There were obtained 318 mg (65% of theory) of tert-butyl (3RS,4RS)-4-(4-bromo-phenyl)-3-hydroxy-piperidine-1-carboxylate as a colourless solid; MS: 299, 301 (M-C$_4$H$_8$)$^+$. Chromatography of the mother liquor on silica gel using a 98:2 mixture of methylene chloride and methanol as the eluent yielded a further 96 mg (19% of theory) of the product.

(d) In an analogous manner to that described in Example 22(d), by carbonylating tert-butyl (3RS,4RS)-4-(4-bromo-phenyl)-3-hydroxy-piperidine-1-carboxylate using PdCl$_2$(CH$_3$CN)$_2$ and 1,3-bis(diphenylphosphino)-propane as the catalyst in the presence of triethylamine under 10 bar of carbon monoxide at 100° C. for 40 hours there was obtained tert-butyl (3RS,4RS)-3-hydroxy-4-(4-methoxycarbonyl-phenyl)-piperidine-1-carboxylate as white crystals; m.p.: 145.5–146° C., MS: 279 (M-C$_4$H$_8$)$^+$.

(e) In an analogous manner to that described in Example 22(i), by alkylating tert-butyl (3RS,4RS)-3-hydroxy-4-(4-methoxycarbonyl-phenyl)-piperidine-1-carboxylate with 2-bromomethylnaphthalene there was obtained tert-butyl (3RS,4RS)-4-(4-methoxycarbonyl-phenyl)-3-naphthalen-2-ylmethoxy-piperidine-1-carboxylate as a colourless oil; MS: 476 (M+H)$^+$.

(f) In an analogous manner to that described in Example 22(l), after cleavage of the BOC group from tert-butyl (3RS,4RS)-4-(4-methoxycarbonyl-phenyl)-3-naphthalen-2-ylmethoxy-piperidine-1-carboxylate there was obtained methyl (3RS,4RS)-4-(3-naphthalen-2-ylmethoxy-piperidin-4-yl)-benzoate hydrochloride as a colourless solid; MS: 344 (M-OCH$_3$)$^+$.

EXAMPLE 26

The following compounds were obtained in an analogous manner to that described in Example 22(l) by cleavage of the BOC group:

1) (3RS,4RS)-[3-[3-(4-Benzyloxy-naphthalen-2-ylmethoxy)-piperidin-4-yl]-phenyl}-methanol as a colourless amorphous powder, MS: 454 (M+H)$^+$, from tert-butyl (3RS,4RS)-3-(4-benzyloxy-naphthalen-2-ylmethoxy)-4-(3-hydroxymethyl-phenyl)-piperidine-1-carboxylate;

2) (3RS,4RS)-3-(3-naphthalen-2-ylmethoxy-piperidin-4-yl)-benzyl benzoate hydrochloride as a colourless solid, MS: 452 (M+H)$^+$, from tert-butyl (3RS,4RS)-4-(3-benzoyloxymethyl-phenyl)-3-naphthalen-2-ylmethoxy-piperidine-1-carboxylate.

The BOC derivatives used as the starting materials were obtained as follows:

(a) In an analogous manner to that described in Example 22(a)–(d), starting from 3-bromophenyllithium and 1-benzyl-4-piperidone there was obtained methyl (3RS,4RS)-3-(1-benzyl-3-hydroxy-piperidin-4-yl)-benzoate as a light yellow resin; MS: 325 (M)$^+$.

(b) The benzyl group was cleaved off from methyl (3RS,4RS)-3-(1-benzyl-3-hydroxy-piperidin-4-yl)-benzoate by catalytic hydrogenation in an analogous manner to that described in Example 2(e). The methyl (3RS,4RS)-3-(3-hydroxy-piperidine-4-yl)-benzoate was converted, without further purification and characterization, with di-tert-butyl dicarbonate analogously to Example 22(g) into tert-butyl (3RS,4RS)-3-hydroxy-4-(3-methoxycarbonyl-phenyl)-piperidine-1-carboxylate, MS: 304 (M-OCH$_3$)$^+$.

(c) In an analogous manner to that described in Example 22(i), by alkylating tert-butyl (3RS,4RS)-3-hydroxy-4-(3-methoxycarbonyl-phenyl)-piperidine-1-carboxylate with 1-benzyloxy-3-chloromethylnaphthalene there was obtained tert-butyl (3RS,4RS)-3-(4-benzyloxy-naphthalen-2-ylmethoxy)-4-(3-methoxycarbonyl-phenyl)-piperidine-1-carboxylate as a pale yellow amorphous powder; MS: 582 (M+H)$^+$.

(d) In an analogous manner to that described in Example 22(e), by reducing tert-butyl (3RS,4RS)-3-(4-benzyloxy-naphthalen-2-ylmethoxy)-4-(3-methoxycarbonyl-phenyl)-piperidine-1-carboxylate with lithium borohydride there was obtained tert-butyl (3RS,4RS)-3-(4-benzyloxy-naphthalen-2-ylmethoxy)-4-(3-hydroxymethyl-phenyl)-piperidine-1-carboxylate as a colourless solid; MS: 554 (M+H)$^+$.

(e) In an analogous manner to that described in Example 22(i), by alkylating tert-butyl (3RS,4RS)-3-hydroxy-4-(3- methoxycarbonyl-phenyl)-piperidine-1-carboxylate with 2-bromomethylnaphthalene there was obtained tert-butyl (3RS,4RS)-4-(3-methoxycarbonyl-phenyl)-3-naphthalen-2-ylmethoxy-piperidine-1-carboxylate as a colourless oil; MS: 493 (M+NH$_4$)$^+$.

(f) In an analogous manner to that described in Example 22(e), by reducing tert-butyl (3RS,4RS)-4-(3-methoxycarbonyl-phenyl)-3-naphthalen-2-ylmethoxy-piperidine-1-carboxylate with lithium borohydride there was obtained tert-butyl 4-(3-hydroxymethyl-phenyl)-3-(naphthalen-2-ylmethoxy)-piperidine-1-carboxylate as a colourless oil; MS: 448 (M+H)$^+$.

(g) In an analogous manner to that described in Example 22(k), by acylating tert-butyl (3RS,4RS)-4-(3-hydroxymethyl-phenyl)-3-(naphthalen-2-ylmethoxy)-piperidine-1-carboxylate with benzoyl chloride there was obtained tert-butyl (3RS,4RS)-4-(3-benzoyloxymethyl-phenyl)-3-naphthalen-2-ylmethoxy-piperidine-1-carboxylate as a colourless oil; MS: 569 (M+NH$_4$)$^+$.

EXAMPLE 27

The following compounds were obtained in an analogous manner to that described in Example 22(l) by cleavage of the BOC group:
1) Methyl (3RS,4RS)-3-[3-(4-benzyloxy-naphthalen-2-ylmethoxy)-piperidin-4-yl]-benzoate as a colourless amorphous powder, MS: 482 (M+H)$^+$, from tert-butyl (3RS,4RS)-3-(4-benzyloxy-naphthalen-2-ylmethoxy)-4-(3-methoxycarbonyl-phenyl)-piperidine-1-carboxylate;
2) methyl (3RS,4RS)-3-[3-(naphthalen-2-ylmethoxy)-piperidin-4-yl]-benzoate as a colourless oil, MS: 376 (M+H)$^+$, from tert-butyl (3RS,4RS)-4-(3-methoxycarbonyl-phenyl)-3-naphthalen-2-ylmethoxy-piperidine-1-carboxylate.

EXAMPLE 28

By cleavage of the BOC group from 57 mg of crude tert-butyl (3RS,4RS)-3-(4-benzyloxy-naphthalen-2-ylmethoxy)-4-(3-fluoromethyl-phenyl)-piperidine-1-carboxylate in an analogous manner to that described in Example 22 there was obtained (3RS,4RS)-3-(4-benzyloxy-naphthalen-2-ylmethoxy)-4-(3-fluoromethyl-phenyl)-piperidine as a light yellow resin; MS: 456 (M+H)$^+$.

The tert-butyl (3RS,4RS)-3-(4-benzyloxy-naphthalen-2-ylmethoxy)-4-(3-fluoromethyl-phenyl)-piperidine-1-carboxylate used as the starting material was prepared as follows:

A solution of 18 mg (0.106 mmol) of diethylaminosulphur trifluoride (DAST) in 1 ml of methylene chloride was cooled to −65° C. and a solution of 56 mg (0.101 mmol) of tert-butyl (3RS,4RS)-3-(4-benzyloxy-naphthalen-2-ylmethoxy)-4-(3-hydroxymethyl-phenyl)-piperidine-1-carboxylate in 1 ml of methylene chloride was added dropwise thereto at −60° C. to −65° C. within 3 minutes. The resulting yellow solution was warmed to room temperature and stirred for one hour. Subsequently, the mixture was partitioned between methylene chloride and 5% sodium hydrogen carbonate solution, the organic phase was dried over magnesium sulphate and finally the solvent was distilled off under reduced pressure. There were obtained 57 mg of crude tert-butyl (3RS,4RS)-3-(4-benzyloxy-naphthalen-2-ylmethoxy)-4-(3-fluoromethyl-phenyl)-piperidine-1-carboxylate, which was used in the next step without further purification and characterization.

EXAMPLE 29

(a) In an analogous manner to that described in Example 22(a), starting from 1-benzyl-4-piperidone and 2-[2-(4-bromo-phenyl)-ethoxy]-tetrahydropyran there was obtained (RS)-1-benzyl-4-[4-[2-(tetrahydro-pyran-2-yloxy)-ethyl]-phenyl]-piperidin-4-ol as a yellow oil; MS: 396 (M+H)$^+$.

(b) A solution of 78 g (197 mmol) of (RS)-1-benzyl-4-[4-[2-(tetrahydro-pyran-2-yloxy)-ethyl]-phenyl]-piperidin-4-ol in 400 ml of methanol was treated with 470 ml of 2N hydrochloric acid and stirred at room temperature for 5 hours. For the working-up, the reaction solution was poured into 1500 ml of saturated sodium hydrogen carbonate solution and subsequently extracted three times with 1000 ml of ethyl acetate each time. The combined organic phases were dried over sodium sulphate and evaporated under reduced pressure. For purification of the crude substance, a flash chromatography on silica gel using a 95:5 mixture of methylene chloride and methanol as the eluent was carried out. There were obtained 51.6 g (84% of theory) of 1-benzyl-4-[4-(2-hydroxy-ethyl)-phenyl]-piperidin-4-ol as a yellowish solid; MS: 312 (M+H)$^+$.

(c) In an analogous manner to that described in Example 22(b), by an elimination reaction from 1-benzyl-4-[4-(2-hydroxy-ethyl)-phenyl]-piperidin-4-ol using p-toluenesulphonic acid there was obtained 2-[4-(1-benzyl-1,2,3,6-tetrahydro-pyridin-4-yl)-phenyl]-ethanol as a colourless oil; MS: 293 (M)$^+$.

(d) In an analogous manner to that described in Example 22(c), from 2-[4-(1-benzyl-1,2,3,6-tetrahydro-pyridin-4-yl)-phenyl]-ethanol by hydroboration there was obtained (3RS,4RS)-1-benzyl-4-[4-(2-hydroxy-ethyl)-phenyl]-piperidin-3-ol as a colourless oil; MS: 311 (M)$^+$.

(e) In an analogous manner to that described in Example 2(e) and Example 22(g), by catalytically hydrogenating (3RS,4RS)-1-benzyl-4-[4-(2-hydroxy-ethyl)-phenyl]-piperidin-3-ol there was obtained (3RS,4RS)-4-[4-(2-hydroxy-ethyl)-phenyl]-piperidin-3-ol, which, without further purification and characterization, was converted with di-tert-butyl dicarbonate into tert-butyl (3RS,4RS)-3-hydroxy-4-[4-(2-hydroxy-ethyl)-phenyl]-piperidine-1-carboxylate; colourless oil, MS: 322 (M+H)$^+$.

(f) In an analogous manner to that described in Example 22(h), from tert-butyl (3RS,4RS)-3-hydroxy-4-[4-(2-hydroxy-ethyl)-phenyl]-piperidine-1-carboxylate by introduction of the trityl group there was obtained tert-butyl (3RS,4RS)-3-hydroxy-4-[4-(2-trityloxy-ethyl)-phenyl]-piperidine-1-carboxylate as a colourless foam; MS: 581 (M+NH$_4$)$^+$.

(g) In an analogous manner to that described in Example 22(i), from tert-butyl (3RS,4RS)-3-hydroxy-4-[4-(2-trityloxy-ethyl)-phenyl]-piperidine-1-carboxylate by alkylation with 2-bromomethylnaphthalene there was obtained tert-butyl (3RS,4RS)-3-(naphthalen-2-ylmethoxy)-4-[4-(2-trityloxy-ethyl)-phenyl]-piperidine-1-carboxylate as a colourless oil; MS: 721 (M+H)$^+$.

(h) In an analogous manner to that described in Example 22(j), from tert-butyl (33RS,4RS)-3-(naphthalen-2-ylmethoxy)-4-[4-(2-trityloxy-ethyl)-phenyl]-piperidine-1-carboxylate by cleavage of the trityl group there was obtained tert-butyl (3RS,4RS)-4-[4-(2-hydroxy-ethyl)-phenyl]-3-naphthalen-2-ylmethoxy-piperidine-1-carboxylate as a colourless solid; MS: 462 (M+H)$^+$.

(i) In an analogous manner to that described in Example 22(k), by acylating tert-butyl (3RS,4RS)-4-[4-(2-hydroxy-ethyl)-phenyl]-3-naphthalen-2-ylmethoxy-piperidine-1-carboxylate with cyclopropanecarbonyl chloride there was obtained tert-butyl (3RS,4RS)-4-[4-(2-cyclopropylcarbonyloxy-ethyl)-phenyl]-3-naphthalen-2-ylmethoxy-piperidine-1-carboxylate as a colourless oil; MS: 572 (M+H)$^+$.

(j) In an analogous manner to that described in Example 22(l), by cleavage of the BOC group from tert-butyl (3RS,4RS)-4-[4-(2-cyclopropylcarbonyloxy-ethyl)-phenyl]-3-naphthalen-2-ylmethoxy-piperidine-1-carboxylate using trifluoroacetic acid in methylene chloride there was obtained (3RS,4RS)-2-[4-(3-naphthalen-2-ylmethoxy-piperidin-4-yl)-phenyl]-ethyl cyclopropanecarboxylate trifluoroacetate as a white solid; MS: 430 (M+H)$^+$.

EXAMPLE 30

The following compound was obtained in an analogous manner to that described in Example 23 by simultaneous cleavage of the BOC and trityl groups:

(3RS,4RS)-2-{4-[3-(naphthalen-2-ylmethoxy)-piperidin-4-yl]-phenyl}-ethanol hydrochloride as a white powder, MS: 362 (M+H)$^+$, from tert-butyl (3RS,4RS)-3-(naphthalen-2-ylmethoxy)-4-[4-(2-trityloxy-ethyl)-phenyl]-piperidine-1-carboxylate.

EXAMPLE 31

The following compounds were obtained in an analogous manner to that in Example 22(l) by cleavage of the BOC group using acid:

1) (3RS,4RS)-2-[4-(3-Naphthalen-2-ylmethoxy-piperidin-4-yl)-phenyl]-ethyl benzoate hydrochloride as a white solid, MS: 466 (M+H)$^+$, from tert-butyl (3RS,4RS)-4-[4-(2-benzoyloxy-ethyl)-phenyl]-3-(naphthalen-2-ylmethoxy)-piperidine-1-carboxylate;

2) (3RS,4RS)-2-[4-(3-naphthalen-2-ylmethoxy-piperidin-4-yl)-phenyl]-ethyl 3-methoxy-benzoate hydrochloride as a colourless oil, MS: 496 (M+H)$^+$, from tert-butyl (3RS,4RS)-4-{4-[2-(3-methoxy-benzoyloxy)-ethyl]-phenyl}-3-(naphthalen-2-ylmethoxy)-piperidine-1-carboxylate;

3) (3RS,4RS)-2-[4-(3-naphthalen-2-ylmethoxy-piperidin-4-yl)-phenyl]-ethyl 2-methoxy-benzoate hydrochloride as a colourless solid, MS: 496 (M+H)$^+$, from tert-butyl (3RS,4RS)-4-{4-[2-(2-methoxy-benzoyloxy)-ethyl]-phenyl}-3-(naphthalen-2-ylmethoxy)-piperidine-1-carboxylate;

4) (3RS,4RS)-2-[4-(3-naphthalen-2-ylmethoxy-piperidin-4-yl)-phenyl]-ethyl benzyloxy-acetate hydrochloride as a colourless solid, MS: 510 (M+H)$^+$, from tert-butyl (3RS,4RS)-4-[4-(2-benzyloxyacetoxy-ethyl)-phenyl]-3-naphthalen-2-ylmethoxy-piperidine-1-carboxylate;

5) (3RS,4RS)-2-[4-(3-naphthalen-2-yl-methoxy)-piperidin-4-yl]-phenyl]-ethyl (4-methoxy-phenyl)-acetate trifluoroacetate as a colourless solid, MS: 510 (M+H)$^+$, from tert-butyl (3RS,4RS)-4-[4-2-[(4-methoxy-phenyl)-acetoxy]-ethyl]-phenyl]-3-naphthalen-2-ylmethoxy-piperidine-1-carboxylate using trifluoroacetic acid in methylene chloride;

6) (3RS,4RS)-2-[4-(3-naphthalen-2-ylmethoxy-piperidin-4-yl)-phenyl]-ethyl cyclohexanecarboxylate trifluoroacetate as a colourless solid, MS: 472 (M+H)$^+$, from tert-butyl (3RS,4RS)-4-[4-(2-cyclohexylcarbonyloxy-ethyl)-phenyl]-3-naphthalen-2-ylmethoxy-piperidine-1-carboxylate using trifluoroacetic acid in methylene chloride;

7) (3RS,4RS)-2-[4-(3-naphthalen-2-ylmethoxy-piperidin-4-yl)-phenyl]-ethyl 2,6-dichloro-benzoate trifluoroacetate as a colourless solid (sic), MS: 534 (M+H)$^+$, from tert-butyl (3RS,4RS)-4-{4-[2-(2,6-dichloro-benzoyloxy)-ethyl]-phenyl}-3-(naphthalen-2-ylmethoxy)-piperidine-1-carboxylate using trifluoroacetic acid in methylene chloride;

8) (3RS,4RS)-2-[4-(3-naphthalen-2-ylmethoxy-piperidin-4-yl)-phenyl]-ethyl 2,6-dimethoxy-benzoate trifluoroacetate as a colourless solid, MS: 526 (M+H)$^+$, from tert-butyl (3RS,4RS)-4-[4-[2-(2,6-dimethoxy-benzoyloxy)-ethyl]-phenyl]-3-naphthalen-2-ylmethoxy-piperidine-1-carboxylate using trifluoroacetic acid in methylene chloride;

9) (3RS,4RS)-2-[4-(3-naphthalen-2-ylmethoxy-piperidin-4-yl)-phenyl]-ethyl 2-acetoxy-benzoate trifluoroacetate as a colourless solid, MS: 524 (M+H)$^+$, from tert-butyl (3RS,4RS)-[4-[4-[2-(2-acetoxy-benzoyloxy)-ethyl]-phenyl]-3-naphthalen-2-ylmethoxy-piperidine]-1-carboxylate using trifluoroacetic acid in methylene chloride;

10) (3RS,4RS)-2-[4-(3-naphthalen-2-ylmethoxy-piperidin-4-yl)-phenyl]-ethyl 2-chloro-benzoate trifluoroacetate as a colourless solid, MS: 500 (M+H)$^+$, from tert-butyl (3RS,4RS)-[4-[2-(2-chloro-benzoyloxy)-ethyl]-phenyl]-3-naphthalen-2-ylmethoxy-piperidine-1-carboxylate using trifluoroacetic acid in methylene chloride;

11) (3RS,4RS)-2-[4-(3-naphthalen-2-ylmethoxy-piperidin-4-yl)-phenyl]-ethyl pyridin-2-yl-carbamate hydrochloride as a colourless foam, MS: 482 (M+H)$^+$, from tert-butyl (3RS,4RS)-3-naphthalen-2-ylmethoxy-4-[4-(2-pyridin-2-ylcarbamoyloxy-ethyl)-phenyl]-piperidine-1-carboxylate;

12) (3RS,4RS)-2-[4-(3-naphthalen-2-ylmethoxy-piperidin-4-yl)-phenyl]-ethyl phenyl-carbamate hydrochloride as a colourless solid, MS: 598 (M+H)$^+$, from tert-butyl (3RS,4RS)-3-naphthalen-2-ylmethoxy-4-[4-(2-phenylcarbamoyloxy-ethyl)-phenyl]-3-piperidine-1-carboxylate;

13) (3RS,4SR)-2-[4-(3-naphthalen-2-ylmethoxy-piperidin-4-yl)-phenyl]-ethyl pyridine-3-carboxylate hydrochloride as a colourless solid, MS: 467 (M+H)$^+$, from tert-butyl (3RS,4RS)-3-naphthalen-2-ylmethoxy-4-[4-(2-pyridin-3-ylcarbonyloxy-ethyl)-phenyl]-piperidine-1-carboxylate;

14) (3RS,4RS)-2-[4-(3-naphthalen-2-ylmethoxy-piperidin-4-yl)-phenyl]-ethyl pyridine-2-carboxylate as a colourless oil, MS: 467 (M+H)$^+$, from 2-{4-[1-tert-butoxycarbonyl-3-(naphthalen-2-ylmethoxy)-piperidin-4-yl]-phenyl}-ethyl (3RS,4RS)-pyridine-2-carboxylate;

15) (3RS,4RS)-2-[4-(3-naphthalen-2-ylmethoxy-piperidin-4-yl)-phenyl]-ethyl thiophene-3-carboxylate trifluoroacetate as a colourless solid, MS: 472 (M+H)$^+$, from tert-butyl (3RS,4RS)-3-naphthalen-2-ylmethoxy-4-[4-(2-thiophen-3-ylcarbonyloxy-ethyl)-phenyl]-piperidine-1-carboxylate using trifluoroacetic acid in methylene chloride;

16) (3RS,4RS)-2-[4-(3-naphthalen-2-ylmethoxy-piperidin-4-yl)-phenyl]-ethyl thiophen-2-ylacetate trifluoroacetate as a colourless solid, MS: 486 (M+H)$^+$, from tert-butyl (3RS,4RS)-3-naphthalen-2-ylmethoxy-4-[4-(2-thiophen-3-ylacetoxy-ethyl)-phenyl]-piperidine-1-carboxylate using trifluoroacetic acid in methylene chloride;

17) (3RS,4RS)-2-[4-(3-naphthalen-2-ylmethoxy-piperidin-4-yl)-phenyl]-ethyl imidazole-2-carboxylate trifluoroacetate as a colourless solid, MS: 456 (M+H)$^+$, from tert-butyl (3RS,4RS)-4-[4-(2-imidazol-2-ylcarbonyloxy-ethyl)-phenyl]-3-naphthalen-2-ylmethoxy]-piperidine-1-carboxylate using trifluoroacetic acid in methylene chloride;

18) (3RS,4RS)-2-[4-[3-(4-benzyloxy-naphthalen-2-ylmethoxy)-piperidin-4-yl]-phenyl]-ethyl benzoate hydrochloride as a yellowish solid, MS: 572 (M+H)$^+$, from tert-butyl (3RS,4RS)-4-[4-(2-benzyloxy-ethyl)-phenyl-3-(4-benzyloxy-naphthalen-2-ylmethoxy)-piperidine-1-carboxylate.

The following starting materials were obtained analogously to the procedure described in Example 22(k):

(a) tert-Butyl (3RS,4RS)-4-[4-(2-benzoyloxy-ethyl)-phenyl]-3-(naphthalen-2-ylmethoxy)-piperidine-1-carboxylate as a colourless oil, MS: 583 (M+NH$_4$)$^+$, from tert-butyl (3RS,4RS)-4-[4-(2-hydroxy-ethyl)-phenyl]-3-naphthalen-2-ylmethoxy-piperidine-1-carboxylate and benzoyl chloride;

(b) tert-butyl (3RS,4RS)-4-{4-[2-(3-methoxy-benzoyloxy)-ethyl]-phenyl}-3-(naphthalen-2-ylmethoxy)-piperidine-1-carboxylate as a colourless oil, MS: 593 (M+H)$^+$, from tert-butyl (3RS,4RS)-4-[4-(2-hydroxy-ethyl)-phenyl]-3-naphthalen-2-ylmethoxy-piperidine-1-carboxylate and 3-methoxybenzoyl chloride;

(c) tert-butyl (3RS,4RS)-4-{4-[2-(2-methoxy-benzoyloxy)-ethyl]-phenyl}-3-(naphthalen-2-ylmethoxy)-piperidine-1-carboxylate as a colourless oil, R$_f$: 0.35 (SiO$_2$, hexane:ethyl acetate=2:1), from tert-butyl (3RS,4RS)-4-[4-(2-hydroxy-ethyl)-phenyl]-3-naphthalen-2-ylmethoxy-piperidine-1-carboxylate and 2-methoxybenzoyl chloride;

(d) tert-butyl (3RS,4RS)-4-[4-(2-benzyloxyacetoxy-ethyl)-phenyl]-3-naphthalen-2-ylmethoxy-piperidine-1-carboxylate as a colourless oil, MS: 627 (M+NH$_4$)$^+$, from tert-butyl (3RS,4RS)-4-[4-(2-hydroxy-ethyl)-phenyl]-3-naphthalen-2-ylmethoxy-piperidine-1-carboxylate and benzyloxyacetyl chloride;

(e) tert-butyl (3RS,4RS)-4-[4-[2-[(4-methoxy-phenyl)-acetoxy]-ethyl]-phenyl]-3-naphthalen-2-ylmethoxy-piperidine-1-carboxylate as a colourless oil, MS: 627 (M+NH$_4$)$^+$, from tert-butyl (3RS,4RS)-4-[4-(2-hydroxy-ethyl)-phenyl]-3-naphthalen-2-ylmethoxy-piperidine-1-carboxylate and 4-methoxyphenylacetyl chloride;

(f) tert-butyl (3RS,4RS)-4-[4-(2-cyclohexylcarbonyloxy-ethyl)-phenyl]-3-naphthalen-2-ylmethoxy-piperidine-1-carboxylate as a colourless oil, MS: 572 (M+H)$^+$, from tert-butyl (3RS,4RS)-4-[4-(2-hydroxy-ethyl)-phenyl]-3-naphthalen-2-ylmethoxy-piperidine-1-carboxylate and cyclohexanecarbonyl chloride;

(g) tert-butyl (3RS,4RS)-4-{4-[2-(2,6-dichloro-benzoyloxy)-ethyl]-phenyl{-3-(naphthalen-2-ylmethoxy)-piperidine-1-carboxylate as a colourless oil, MS: 651 (M+NH$_4$)$^+$, from tert-butyl (3RS,4RS)-4-[4-(2-hydroxy-ethyl)-phenyl]-3-naphthalen-2-ylmethoxy-piperidine-1-carboxylate and 2,6-dichlorobenzoyl chloride;

(h) tert-butyl (3RS,4RS)-4-[4-[2-(2,6-dimethoxy-benzoyloxy)-ethyl]-phenyl]-3-naphthalen-2-ylmethoxy-piperidine-1-carboxylate as a colourless amorphous solid, MS: 643 (M+NH$_4$)$^+$, from tert-butyl (3RS,4RS)-4-[4-(2-hydroxy-ethyl)-phenyl]-3-naphthalen-2-ylmethoxy-piperidine-1-carboxylate and 2,6-dimethoxybenzoyl chloride;

(i) tert-butyl (3RS,4RS)-[4-[4-[2-(2-acetoxy-benzoyloxy)-ethyl]-phenyl]-3-naphthalen-2-ylmethoxy-piperidine]-1-carboxylate as a colourless oil, MS: 641 (M+NH$_4$)$^+$, from tert-butyl (3RS,4RS)-4-[4-(2-hydroxy-ethyl)-phenyl]-3-naphthalen-2-ylmethoxy-piperidine-1-carboxylate and O-acetylsalicyloyl chloride;

(j) tert-butyl (3RS,4RS)-[4-[2-(2-chloro-benzoyloxy)-ethyl]-phenyl]-3-naphthalen-2-ylmethoxy-piperidine-1-carboxylate as a colourless oil, MS: 617 (M+NH$_4$)$^+$; from tert-butyl (3RS,4RS)-4-[4-(2-hydroxy-ethyl)-phenyl]-3-naphthalen-2-ylmethoxy-piperidine-1-carboxylate and 2-chlorobenzoyl chloride;

(k) In an analogous manner to that described in Example 24(m), by reacting tert-butyl (3RS,4RS)-4-[4-(2-hydroxy-ethyl)-phenyl]-3-naphthalen-2-ylmethoxy-piperidine-1-carboxylate with pyridine-2-carbonyl azide there was obtained tert-butyl (3RS,4RS)-3-naphthalen-2-ylmethoxy-4-[4-(2-pyridin-2-ylcarbamoyloxy-ethyl)-phenyl]-piperidine-1-carboxylate as colourless crystals, MS: 582 (M+H)$^+$.

(l) In an analogous manner to that described in Example 24(m), by reacting tert-butyl (3RS,4RS)-4-[4-(2-hydroxy-ethyl)-phenyl]-3-naphthalen-2-ylmethoxy-piperidine-1-carboxylate with phenyl isocyanate there was obtained tert-butyl (3RS,4RS)-3-naphthalen-2-ylmethoxy-4-[4-(2-phenylcarbamoyloxy-ethyl)-phenyl]-piperidine-1-carboxylate as a colourless oil, MS: 481 (M+H)$^+$.

(m) In an analogous manner to that described in Example 24(g), by condensing tert-butyl (3RS,4RS)-4-[4-(2-hydroxy-ethyl)-phenyl]-3-naphthalen-2-ylmethoxy-piperidine-1-carboxylate and nicotinic acid there was obtained tert-butyl (3RS,4RS)-3-naphthalen-2-ylmethoxy-4-[4-(2-pyridin-3-ylcarbonyloxy-ethyl)-phenyl]-piperidine-1-carboxylate as a colourless oil, MS: 567 (M+H)$^+$.

(n) In an analogous manner to that described in Example 24(g), by condensing tert-butyl (3RS,4RS)-4-[4-(2-hydroxy-ethyl)-phenyl]-3-naphthalen-2-ylmethoxy-piperidine-1-carboxylate and pyridine-2-carboxylic acid using 1,1-carbonyldiimidazole as the condensation agent there was obtained 2-{4-[1-tert-butoxycarbonyl-3-(naphthalen-2-ylmethoxy)-piperidin-4-yl]-phenyl}-ethyl (3RS,4RS)-pyridine-2-carboxylate as a colourless oil, MS: 467 (M+H)$^+$.

(o) In an analogous manner to that described in Example 24(g), by condensing tert-butyl (3RS,4RS)-4-[4-(2-hydroxy-ethyl)-phenyl]-3-naphthalen-2-ylmethoxy-piperidine-1-carboxylate and thiophene-3-carboxylic acid using 1,1-carbonyldiimidazole as the condensation agent there was obtained tert-butyl (3RS,4RS)-3-naphthalen-2-ylmethoxy-4-[4-(2-thiophen-3-ylcarbonyloxy-ethyl)-phenyl]-piperidine-1-carboxylate as white crystals, MS: 572 (M+H)$^+$.

(p) In an analogous manner to that described in Example 24(g), by condensing tert-butyl (3RS,4RS)-4-[4-(2-hydroxy-ethyl)-phenyl]-3-naphthalen-2-ylmethoxy-piperidine-1-carboxylate and 3-thiopheneacetic acid using 1,1-carbonyldiimidazole as the condensation agent there was obtained tert-butyl (3RS,4RS)-3-naphthalen-2-ylmethoxy-4-[4-(2-thiophen-3-ylacetoxy-ethyl)-phenyl]-piperidine-1-carboxylate as a colourless solid, MS: 603 (M+NH$_4$)$^+$.

(q) In an analogous manner to that described in Example 24(g), by condensing tert-butyl (3RS,4RS)-4-[4-(2-hydroxy-ethyl)-phenyl]-3-naphthalen-2-ylmethoxy-piperidine-1-carboxylate and imidazole-2-carboxylic acid using 1,1-carbonyldiimidazole as the condensation agent there was obtained tert-butyl (3RS,4RS)-4-[4-(2-imidazol-2-ylcarbonyloxy-ethyl)-phenyl]-3-naphthalen-2-ylmethoxy]-piperidine-1-carboxylate as a colourless solid, MS: 556 (M+H)$^+$.

The following procedure was carried out in an analogous manner to that described in Example 22(i)–(k):

(r) Alkylation of tert-butyl (3RS,4RS)-3-hydroxy-4-[4-(2-trityloxy-ethyl)-phenyl]-piperidine-1-carboxylate with 1-benzyloxy-3-chloromethyl-naphthalene gave tert-butyl (3RS,4RS)-3-(4-benzyloxy-naphthalen-2-ylmethoxy)-4-[4-(2-trityloxy-ethyl)-phenyl]-piperidine-1-carboxylate as a colourless oil, MS: 827 (M+NH$_4$)$^+$.

(s) Cleavage of the trityl group from tert-butyl (3RS,4RS)-3-(4-benzyloxy-naphthalen-2-ylmethoxy)-4-[4-(2-trityloxy-ethyl)-phenyl]-piperidine-1-carboxylate yielded tert-butyl (3RS,4RS)-3-(4-benzyloxy-naphthalen-2-ylmethoxy)-4-[4-(2-hydroxy-ethyl)-phenyl]-piperidine-1-carboxylate as a colourless oil, MS: 568 (M+H)$^+$.

(t) Acylation of tert-butyl (3RS,4RS)-3-(4-benzyloxy-naphthalen-2-yl-methoxy)-4-[4-(2-hydroxy-ethyl)-phenyl]-piperidine-1-carboxylate with benzoyl chloride gave (3RS, 4RS)-4-[4-(2-benzyloxy-ethyl)-phenyl-3-(4-benzyloxy-naphthalen-2-ylmethoxy)-piperidine-1-carboxylate as a colourless oil, MS: 689 (M+NH$_4$)$^+$.

EXAMPLE 32

The following compounds were obtained in an analogous manner to that described in Example 22(l) by cleavage of the BOC group using acid:
1) (3RS,4RS)-3-Naphthalen-2-ylmethoxy-4-(4-naphthalen-2-ylmethoxymethyl-phenyl)-piperidine hydrochloride as a colourless solid, MS: 488 (M+H)$^+$, from tert-butyl (3RS,4RS)-3-(naphthalen-2-ylmethoxy)-4-[4-(naphthalen-2-ylmethoxymethyl)-phenyl]-piperidine-1-carboxylate;
2) (3RS,4RS)-4-[4-(4-methoxy-phenoxymethyl)-phenyl]-3-naphthalen-2-ylmethoxy-piperidine as a yellow foam, MS: 454 (M+H)$^+$, from tert-butyl (3RS,4RS)-4-[4-(4-methoxy-phenoxymethyl)-phenyl]-3-naphthalen-2-ylmethoxy-piperidine-1-carboxylate;
3) (3RS,4RS)-3-(1-methoxy-naphthalen-2-ylmethoxy)-4-[4-(2-phenoxy-ethyl)-phenyl]-piperidine trifluoroacetate as a colourless oil, MS: 468 (M+H)$^+$, from tert-butyl (3RS,4RS)-3-(1-methoxy-naphthalen-2-ylmethoxy)-4-[4-(2-phenoxy-ethyl)-phenyl]-piperidine-1-carboxylate using trifluoroacetic acid in methylene chloride;
4) (3RS,4RS)-4-[4-(2-methoxy-ethyl)-phenyl]-3-naphthalen-2-ylmethoxy]-piperidine as a colourless solid, MS: 376 (M+H)$^+$, from tert-butyl (3RS,4RS)-4-[4-(2-methoxy-ethyl)-phenyl]-3-naphthalen-2-ylmethoxy]-piperidine-1-carboxylate.

The BOC derivatives use as the starting materials were prepared as follows:
(a) In an analogous manner to that described in Example 22(i), by alkylating tert-butyl (3RS,4RS)-3-hydroxy-4-(4-hydroxymethyl-phenyl)-piperidine-1-carboxylate with 2-bromomethylnaphthalene there was obtained tert-butyl (3RS,4RS)-3-(naphthalen-2-ylmethoxy)-4-[4-(naphthalen-2-ylmethoxymethyl)-phenyl]-piperidine-1-carboxylate as a colourless oil, R$_f$: 0.31 (SiO$_2$, hexane:ethyl acetate=2:1).
b) A solution of 200 mg (0.45 mmol) of tert-butyl (3RS,4RS)-4-(4-hydroxymethyl-phenyl)-3-(naphthalen-2-ylmethoxy)-piperidine-1-carboxylate in 10 ml of tetrahydrofuran was treated in sequence with 143 mg (0.58 mmol) of triphenylphosphine, 94 mg (0.58 mmol) of diethylazo dicarboxylate and 166 mg (1.35 mmol) of hydroquinone monomethyl ether and the reaction mixture was stirred at room temperature for 15 hours. For the working-up, the reaction mixture was diluted with 20 ml of methylene chloride and extracted with 20 ml of saturated sodium carbonate solution. The organic phase was dried over sodium sulphate and evaporated under reduced pressure. For purification, the crude product was chromatographed on silica gel using methylene chloride as the eluent. There were obtained 245 mg of colourless oil which contained tert-butyl (3RS,4RS)-4-(4-hydroxymethyl-phenyl)-3-(naphthalen-2-ylmethoxy)-piperidine-1-carboxylate in addition to tert-butyl (3RS,4RS)-4-[4-(4-methoxy-phenoxymethyl)-phenyl]-3-naphthalen-2-ylmethoxy-piperidine-1-carboxylate, R$_f$: 0.08 (methylene chloride).

The following procedure was carried out in an analogous manner to that described in Example 22(i)–(j):
(c) Alkylation of tert-butyl (3RS,4RS)-3-hydroxy-4-[4-(2-trityloxy-ethyl)-phenyl]-piperidine-1-carboxylate with 2-bromomethyl-1-methoxy-naphthalene gave tert-butyl (3RS,4RS)-3-(1-methoxy-naphthalen-2-ylmethoxy)-4-[4-(2-trityloxy-ethyl)-phenyl]-piperidine-1-carboxylate from which, after cleavage of the trityl group there was obtained tert-butyl (3RS,4RS)-4-[4-(2-hydroxy-ethyl)-phenyl]-3-(1-methoxy-naphthalen-2-ylmethoxy)-piperidine-1-carboxylate and, after reaction with phenol, analogously to the procedure described under (b), tert-butyl (3RS,4RS)-3-(1-methoxy-naphthalen-2-ylmethoxy)-4-[4-(2-phenoxy-ethyl)-phenyl]-piperidine-1-carboxylate as a colourless oil; R$_f$: 0.34 (SiO$_2$, hexane:ethyl acetate=2:1).
(d) In an analogous manner to that described in Example 22(i) by alkylating tert-butyl (3RS,4RS)-4-[4-(2-hydroxy-ethyl)-phenyl]-3-naphthalen-2-ylmethoxy-piperidine-1-carboxylate with methyl iodide there was obtained tert-butyl (3RS,4RS)-4-[4-(2-methoxy-ethyl)-phenyl]-3-naphthalen-2-ylmethoxy]-piperidine-1-carboxylate as a colourless oil; MS: 493 (M+NH$_4$)$^+$.

EXAMPLE 33

The following compounds were obtained in an analogous manner to that described in Example 22(l) by cleavage of the BOC group by means of acid:
1) (3RS,4RS)-3-naphthalen-2-ylmethoxy-4-[4-(2-phenylsulphanyl-ethyl)-phenyl]-piperidine hydrochloride as white crystals, MS: 454 (M+H)$^+$, from tert-butyl (3RS,4RS)-3-naphthalen-2-ylmethoxy-4-[4-(2-phenylsulphanyl-ethyl)-phenyl]-piperidine-1-carboxylate;
2) a mixture of (3RS,4RS)-3-naphthalen-2-ylmethoxy-4-[4-[(RS)- and -[(SR)-2-phenylsulphinyl-ethyl]-phenyl]-piperidine as a colourless amorphous solid, MS: 470 (M+H)$^+$, from a mixture of tert-butyl (3RS,4RS)-3-naphthalen-2-yl-methoxy-4-[4-[(RS)- and -[(SR)-2-phenylsulphinyl-ethyl]-phenyl]-piperidine-1-carboxylate;
3) (3RS,4RS)-3-naphthalen-2-ylmethoxy-4-[4-(2-phenylsulphonyl-ethyl)-phenyl]-piperidine hydrochloride as white crystals, MS: 486 (M+H)$^+$, from tert-butyl (3RS,4RS)-3-naphthalen-2-ylmethoxy-4-[4-(2-phenylsulphonyl-ethyl)-phenyl]-piperidine-1-carboxylate;
4) (3RS,4RS)-4-[4-(2-benzothiazol-2-ylsulphanyl-ethyl)-phenyl]-3-naphthalen-2-ylmethoxy-piperidine as a colourless foam, MS: 511 (M+H)$^+$, from tert-butyl (3RS,4RS)-4-[4-(2-benzothiazol-2-ylsulphanyl-ethyl)-phenyl]-3-naphthalen-2-ylmethoxy-piperidine-1-carboxylate;
5) (3RS,4RS)-2-[4-(3-naphthalen-2-ylmethoxy-piperidin-4-yl)-benzylsulphanyl]-benzothiazole as a yellow foam, MS: 497 (M+H)$^+$, from tert-butyl (3RS,4RS)-4-[4-(benzothiazol-2-ylsulphanylmethyl)-phenyl]-3-naphthalen-2-ylmethoxy-piperidine-1-carboxylate;
6) (3RS,4RS)-3-naphthalen-2-ylmethoxy-4-[4-(1-phenyl-1H-tetrazol-5-ylsulphanylmethyl)-phenyl]-piperidine hydrochloride as a colourless oil, MS: 508 (M+H)$^+$, from tert-butyl (3RS,4RS)-3-naphthalen-2-ylmethoxy-4-[4-(1-phenyl-1H-tetrazol-5-ylsulphanylmethyl)-phenyl]-piperidine-1-carboxylate;
7) (3RS,4RS)-3-(naphthalen-2-ylmethoxy)-4-[4-(2-phenoxy-ethyl)-phenyl]-piperidine as a yellowish foam, MS: 438 (M+H)$^+$, from tert-butyl (3RS,4RS)-3-(naphthalen-2-ylmethoxy)-4-[4-(2-phenoxy-ethyl)-phenyl]-piperidine-1-carboxylate.

The BOC derivatives used as the starting materials were prepared as follows:
(a) A mixture of 200 mg (0.43 mmol) of tert-butyl (3RS,4RS)-4-[4-(2-hydroxy-ethyl)-phenyl]-3-naphthalen-2-ylmethoxy-piperidine-1-carboxylate, 263 mg (1.29 mmol) of tributylphosphine and 284 mg (1.29 mmol) of diphenyl sulphide in 1 ml of pyridine was stirred at room temperature for 18 hours. Subsequently, the reaction mixture was evaporated under reduced pressure and the residue, without further working-up, was chromatographed directly on silica gel using methylene chloride as the eluent. The tert-butyl (3RS, 4RS)-3-naphthalen-2-yl-methoxy-4-[4-(2-phenylsulphanyl-ethyl)-phenyl]-piperidine-1-carboxylate was obtained as a colourless oil in quantitative yield; MS: 554 (M+H)$^+$.

(b) A solution of 216 mg (0.23 mmol) of tetrabutylammonium ozone was added dropwise very slowly at room temperature to a solution of 128 mg (0.23 mmol) of tert-butyl (3RS,4RS)-3-naphthalen-2-ylmethoxy-4-[4-(2-phenylsulphanyl-ethyl)-phenyl]-piperidine-1-carboxylate in 10 ml of methylene chloride. After 6 hours the reaction solution was evaporated under reduced pressure and the crude product was chromatographed on silica gel using a 2:1 mixture of hexane and ethyl acetate as the eluent in order to separate the sulphone which had already formed. There were obtained 100 mg (76% of theory) of a mixture of tert-butyl (3RS,4RS)-3-naphthalen-2-ylmethoxy-4-[4-[(RS)- and -[(SR)-2-phenylsulphinyl-ethyl]-phenyl]-piperidine-1-carboxylate as a colourless oil which gradually crystallized out; MS: 570 (M+H)$^+$.

(c) In an analogous manner to that described under (b), starting from tert-butyl (3RS,4RS)-3-naphthalen-2-ylmethoxy-4-[4-(2-phenylsulphanyl-ethyl)-phenyl]-piperidine-1-carboxylate using an excess of tetrabutylammonium oxone there was obtained tert-butyl (3RS,4RS)-3-naphthalen-2-ylmethoxy-4-[4-(2-phenylsulphonyl-ethyl)-phenyl]-piperidine-1-carboxylate as a colourless foam; MS: 603 (M+NH$_4$)$^+$.

(d) In an analogous manner to that described under (a), by reacting tert-butyl (3RS,4RS)-4-[4-(2-hydroxy-ethyl)-phenyl]-3-naphthalen-2-ylmethoxy-piperidine-1-carboxylate with bis-(benzothiazol-2-yl) disulphide there was obtained tert-butyl (3RS,4RS)-4-[4-(2-benzothiazol-2-ylsulphanyl-ethyl)-phenyl]-3-naphthalen-2-ylmethoxy-piperidine-1-carboxylate as a yellowish solid; MS: 611 (M+H)$^+$.

(e) In an analogous manner to that described under (a), by reacting tert-butyl (3RS,4RS)-4-(4-hydroxymethyl-phenyl)-3-(naphthalen-2-ylmethoxy)-piperidine-1-carboxylate with (benzothiazol-2-yl) disulphide there was obtained tert-butyl (3RS,4RS)-4-[4-(benzothiazol-2-ylsulphanylmethyl)-phenyl]-3-naphthalen-2-ylmethoxy-piperidine-1-carboxylate as a yellowish foam; MS: 597 (M+H)$^+$.

(f) In an analogous manner to that described under (a), by reacting tert-butyl (3RS,4RS)-4-(4-hydroxymethyl-phenyl)-3-(naphthalen-2-ylmethoxy)-piperidine-1-carboxylate with bis-(1-phenyl-1H-tetrazol-5-yl) disulphide there was obtained tert-butyl (3RS,4RS)-3-naphthalen-2-ylmethoxy-4-[4-(1-phenyl-1H-tetrazol-5-ylsulphanylmethyl)-phenyl]-piperidine-1-carboxylate as a colourless foam; MS: 630 (M+Na)$^+$.

(g) In an analogous manner to that described in Example 32(b), from tert-butyl (3RS,4RS)-4-[4-(2-hydroxy-ethyl)-phenyl]-3-naphthalen-2-ylmethoxy-piperidine-1-carboxylate there was obtained tert-butyl (3RS,4RS)-3-(naphthalen-2-ylmethoxy)-4-[4-(2-phenoxy-ethyl)-phenyl]-piperidine-1-carboxylate as a colourless oil; MS: 555 (M+NH$_4$)$^+$.

EXAMPLE 34

(a) To a solution of 100 mg (0.22 mmol) of tert-butyl (3RS,4RS)-4-(4-hydroxymethyl-phenyl)-3-(naphthalen-2-ylmethoxy)-piperidine-1-carboxylate in 10 ml of tetrahydrofuran were added 68 mg (0.66 mmol) of triethylamine and thereafter dropwise at 0° C. 25 mg (0.26 mmol) of methanesulphonyl chloride. The reaction solution was stirred at room temperature for 90 minutes, thereafter 38 mg (0.33 mmol) of 2-mercaptopyrimidine were added and the mixture was stirred at room temperature for a further 18 hours. For the working-up, the reaction mixture was evaporated under reduced pressure, the residue was taken up in 20 ml of methylene chloride and then extracted with 10 ml of water. The organic phase was dried over sodium sulphate and subsequently evaporated under reduced pressure. For purification, the crude product was chromatographed on silica gel using a 5:1 mixture of hexane and ethyl acetate as the eluent. There were obtained 100 mg (82% of theory) of tert-butyl (3RS,4RS)-3-naphthalen-2-ylmethoxy-4-[4-(pyrimidin-2-ylsulphanylmethyl)-phenyl]-piperidine-1-carboxylate as a yellowish oil; MS: 542 (M+H)$^+$.

(b) In an analogous manner to that described in Example 22(l), by cleavage of the BOC group there was obtained (3RS,4RS)-2-[4-(3-naphthalen-2-ylmethoxy-piperidin-4-yl)-benzylsulphanyl]-pyrimidine as a yellow foam; MS: 442 (M+H)$^+$.

EXAMPLE 35

The following compounds were obtained in an analogous manner to that described in Example 22(l) by cleavage of the BOC group using acid:

1) (3RS,4RS)-2-[4-(3-naphthalen-2-ylmethoxy-piperidin-4-yl)-benzylsulphanyl]-6-nitro-benzothiazole hydrochloride as a yellowish foam, MS: 542 (M+H)$^+$, from tert-butyl (3RS,4RS)-3-naphthalen-2-ylmethoxy-4-[4-(6-nitro-benzothiazol-2-ylsulphanylmethyl)-phenyl]-piperidine-1-carboxylate;

2) (3RS,4RS)-3-{4-[3-(naphthalen-2-ylmethoxy)-piperidin-4-yl]-phenyl}-propionitrile trifluoroacetate as a white powder, MS: 371 (M+H)$^+$, from tert-butyl (3RS,4RS)-4-[4-(2-cyano-ethyl)-phenyl]-3-naphthalen-2-ylmethoxy-piperidine-1-carboxylate using trifluoroacetic acid in methylene chloride.

The BOC derivatives used as the starting materials were obtained as follows:

(a) In an analogous manner to that described in Example 34(a), by reacting tert-butyl (3RS,4RS)-4-(4-hydroxymethyl-phenyl)-3-(naphthalen-2-ylmethoxy)-piperidine-1-carboxylate with 6-nitro-2-mercaptobenzothiazole there was obtained, via the mesylate prepared in situ, tert-butyl (3RS,4RS)-3-naphthalen-2-ylmethoxy-4-[4-(6-nitro-benzothiazol-2-ylsulphanylmethyl)-phenyl]-piperidine-1-carboxylate as a yellow solid; MS: 642 (M+H)$^+$.

(b) In an analogous manner to that described in Example 34(a), by reacting tert-butyl (3RS,4RS)-4-[4-(2-hydroxy-ethyl)-phenyl]-3-naphthalen-2-ylmethoxy-piperidine-1-carboxylate with potassium cyanide in dimethylformamide there was obtained, via the corresponding mesylate, tert-butyl (3RS,4RS)-4-[4-(2-cyano-ethyl)-phenyl]-3-naphthalen-2-ylmethoxy-piperidine-1-carboxylate as a white powder, MS: 471 (M+H)$^+$.

EXAMPLE 36

(a) 6.95 g (44 mmol) of powdered potassium permanganate dissolved in a mixture of 100 ml of water and 100 ml of glacial acetic acid as well as 0.73 g (2 mmol) of tetrabutylammonium iodide were added to a solution of 5.0 g (10.83 mmol) of tert-butyl (3RS,4RS)-4-[4-(2-hydroxy-ethyl)-phenyl]-3-naphthalen-2-ylmethoxy-piperidine-1-carboxylate in 500 ml of benzene. The reaction mixture was stirred intensively for 48 hours. For the working-up, the phases were separated. The organic phase was washed with 100 ml of saturated sodium thiosulphate solution. The aqueous phase was decolorized by the addition of saturated sodium thiosulphate solution and subsequently extracted twice with 100 ml of ethyl acetate and 100 ml of methylene chloride each time. The organic phases were combined, dried over sodium sulphate and evaporated under reduced pressure. For purification, the crude material was chromatographed on silica gel using a 9:1 mixture of methylene chloride and methanol as the eluent after the column had previously been prepared with a 90:10:0.1 mixture of methylene chloride, methanol and ammonia. There were obtained 2.6 g (50% of theory) of (3RS,4RS)-[4-(1-tert-butoxycarbonyl-3-naphthalen-2-ylmethoxy-piperidin-4-yl)-phenyl]-acetic acid as a colourless, amorphous solid; MS: 476 (M+H)$^+$.

(b) A solution of 150 mg (0.32 mmol) of (3RS,4RS)-[4-(1-tert-butoxycarbonyl-3-naphthalen-2-ylmethoxy-piperidin-4-yl)-phenyl]-acetic acid and 55 mg (0.32 mmol) of 2-amino-1-phenyl-ethanone in 5 ml of dimethylformamide was treated in sequence with 44.6 µl (0.32 mmol) of triethylamine and 96 mg (0.32 mmol) of O-(1,2-dihydro-2-oxo-1-pyridyl)-N,N,N',N'-tetramethyluronium tetrafluoroborate (TPTU) and the mixture was stirred at room temperature for 18 hours. For the working-up, the reaction was evaporated in an oil pump vacuum, the residue was taken up in 20 ml of methylene chloride and washed with 5 ml of water. The organic phase was dried over sodium sulphate and evaporated under reduced pressure. For purification, the crude material was chromatographed on silica gel using a 95:5 mixture of methylene chloride and methanol as the eluent. There were obtained 120 mg (64% of theory) of tert-butyl (3RS,4RS)-3-(naphthalen-2-ylmethoxy)-4-{4-[(2-oxo-2-phenyl-ethylcarbamoyl)-methyl]-phenyl}-piperidine-1-carboxylate as a colourless oil; MS: 615 (M+Na)$^+$.

(c) In an analogous manner to that described in Example 22(l), starting from tert-butyl (3RS,4RS)-3-(naphthalen-2-ylmethoxy)-4-{4-[(2-oxo-2-phenyl-ethylcarbamoyl)-methyl]-phenyl}-piperidine-1-carboxylate by cleavage of the BOC group using trifluoroacetic acid in methylene chloride there was obtained (3RS,4RS)-2-{4-[3-(naphthalen-2-ylmethoxy)-piperidin-4-yl]-phenyl}-N-(2-oxo-2-phenyl-ethyl)-acetamide trifluoroacetate as a white powder; MS: 493 (M+H)$^+$.

EXAMPLE 37

The following compounds were obtained in an analogous manner to that described in Example 36(b)–(c):

1) From (3RS,4RS)-[4-(1-tert-butoxycarbonyl-3-naphthalen-2-ylmethoxy-piperidin-4-yl)-phenyl]-acetic acid and 3-amino-1-phenyl-propan-1-one [H.Zinner and G.Brossmann, J. Prakt. Chem. 5, 91 (1958)] there was obtained tert-butyl (3RS,4RS)-3-(naphth-alen-2-ylmethoxy)-4-{4-[(3-oxo-3-phenyl-propylcarbamoyl)-methyl]-phenyl}-piperidine-1-carboxylate, MS: 607 (M+H)$^+$, 15154B66, which, after cleavage of the BOC group, gave (3RS,4RS)-2-[4-[3-(naphthalen-2-ylmethoxy)-piperidin-4-yl]-phenyl]-N-(3-oxo-3-phenyl-propyl)-acetamide trifluoroacetate as a white powder; MS: 507 (M+H)$^+$;

2) from (3RS,4RS)-[4-(1-tert-butoxycarbonyl-3-naphthalen-2-ylmethoxy-piperidin-4-yl)-phenyl]-acetic acid and 2-hydroxy-1-phenyl-ethanone with 1,1-carbonyldiimidazole as the condensation agent there was obtained tert-butyl (3RS,4RS)-3-(naphthalen-2-ylmethoxy)-4-[4-(2-oxo-2-phenyl-ethoxycarbonyl-methyl)-phenyl]-piperidine-1-carboxylate which, after cleavage of the BOC group, gave 2-oxo-2-phenyl-ethyl (3RS,4RS)-[4-[3-(naphthalen-2-ylmethoxy)-piperidin-4-yl]-phenyl]-acetate trifluoroacetate as a white powder; MS: 494 (M+H)$^+$;

3) from (3RS,4RS)-[4-(1-tert-butoxycarbonyl-3-naphthalen-2-ylmethoxy-piperidin-4-yl)-phenyl]-acetic acid and phenol with 1,1-carbonyldiimidazole as the condensation agent there was obtained tert-butyl (3RS,4RS)-3-(naphthalen-2-ylmethoxy)-4-(4-phenoxycarbonylmethyl-phenyl)-piperidine-1-carboxylate which, after cleavage of the BOC group, gave phenyl (3RS,4RS)-[4-(3-naphthalen-2-ylmethoxy-piperidin-4-yl)-phenyl]-acetate trifluoroacetate as white crystals; MS: 452 (M+H)$^+$.

EXAMPLE 38

(a) A solution of 100 mg (0.21 mmol) of (3RS,4RS)-[4-(1-tert-butoxycarbonyl-3-naphthalen-2-ylmethoxy-piperidin-4-yl)-phenyl]-acetic acid in 5 ml of dimethylformamide was treated with 50 mg (0.31 mmol) of 1,1-carbonyldiimidazole and the mixture was stirred at 50° C. for one hour. Subsequently, the mixture was cooled to room temperature, a solution of 45 mg (0.33 mmol) of benzamidoxime in 2 ml of dimethylformamide was added and the mixture was stirred at 50° C. for one hour. For the working-up, the mixture was cooled to room temperature and the dimethylformamide was distilled off in an oil pump vacuum. The residue was chromatographed on silica gel using a 98:2:0.1 mixture of methylene chloride, methanol and ammonia as the eluent. There were obtained 90 mg (72% of theory) of the benzamidoxime ester as a colourless foam; MS: 594 (M+H)$^+$, R$_f$: 0.68 (SiO$_2$, methylene chloride:methanol:ammonia=95:5:0.1)

(b) A solution of 90 mg (0.15 mmol) of the benzamidoxime ester in 10 ml of dimethylformamide was heated to 130° C. for 18 hours. For the working-up, the mixture was evaporated under reduced pressure and the residue was chromatographed on silica gel using a 4:1 mixture of hexane and ethyl acetate as the eluent. There were obtained 63 mg (72% of theory) of tert-butyl (3RS,4RS)-3-(naphthalen-2-ylmethoxy)-4-[4-(3-phenyl-[1,2,4]oxadiazol-5-ylmethyl)-phenyl]-piperidine-1-carboxylate as a colourless oil; MS: 592 (M+NH$_4$)$^+$.

(c) In an analogous manner to that described in Example 22(l), starting from tert-butyl (3RS,4RS)-3-(naphthalen-2-ylmethoxy)-4-[4-(3-phenyl-[1,2,4]oxadiazol-5-ylmethyl)-phenyl]-piperidine-1-carboxylate by cleavage of the BOC group using trifluoroacetic acid in methylene chloride there was obtained (3RS,4RS)-3-(3-naphthalen-2-ylmethoxy)-4-[4-(3-phenyl-[1,2,4]oxadiazol-5-ylmethyl)-phenyl]-piperidine trifluoroacetate as a white powder; MS: 476 (M+H)$^+$.

EXAMPLE 39

(a) A solution of 100 mg (0.21 mmol) of (3RS,4RS)-[4-(1-tert-butoxycarbonyl-3-naphthalen-2-ylmethoxy-piperidin-4-yl)-phenyl]-acetic acid in 5 ml of methylene chloride was treated with 1 ml of ethereal diazomethane solution at room temperature and stirred for a further 2 hours. The reaction solution was evaporated under reduced pressure and the tert-butyl (3RS,4RS)-4-(4-methoxycarbonylmethyl-phenyl)-3-(naphthalen-2-ylmethoxy)-piperidine-1-carboxylate, R$_f$: 0.5 (hexane:ethyl acetate=2:1), obtained in quantitative yield, was used in the following step without further purification and characterization.

(b) A solution of 102 mg (0.21 mmol) of tert-butyl (3RS, 4RS)-4-(4-methoxycarbonylmethyl-phenyl)-3-(naphthalen-2-ylmethoxy)-piperidine-1-carboxylate in 0.5 ml of hydrazine hydrate was heated to 120° C. for 18 hours. For the working-up, the reaction mixture was cooled to room temperature, treated with 3 ml of ice-water and extracted twice with 5 ml of methylene chloride each time. The combined organic phases were dried over sodium sulphate and evaporated under reduced pressure. There were obtained 63 mg (63% of theory) of tert-butyl (3RS,4RS)-4-(4-hydrazinocarbonylmethyl-phenyl)-3-(naphthalen-2-ylmethoxy)-piperidine-1-carboxylate as a colourless foam; $R_f$: 0.22 (SiO2, methylene chloride:methanol:ammonia=95:5:0.1).

(c) A mixture of 60 mg (0.12 mmol) of tert-butyl (3RS,4RS)-4-(4-hydrazinocarbonylmethyl-phenyl)-3-(naphthalen-2-ylmethoxy)-piperidine-1-carboxylate and 27.7 μl (0.12 mmol) of triethyl orthobenzoate in 5 ml of ethanol was boiled under reflux for 18 hours. After cooling the mixture was evaporated under reduced pressure and the residue was chromatographed on silica gel using a 2:1 mixture of hexane and ethyl acetate as the eluent. There were obtained 30 mg (44% of theory) or tert-butyl (3RS,4RS)-3-(naphthalen-2-ylmethoxy)-4-[4-(5-phenyl-[1,3,4]oxadiazol-2-ylmethyl)-phenyl]-piperidine-1-carboxylate as a colourless foam; MS: 575 (M+H)$^+$.

(d) In an analogous manner to that described in Example 22(l), starting from tert-butyl (3RS,4RS)-3-(naphthalen-2-ylmethoxy)-4-[4-(5-phenyl-[1,3,4]oxadiazol-2-ylmethyl)-phenyl]-piperidine-1-carboxylate by cleavage of the BOC group using trifluoroacetic acid in methylene chloride there was obtained (3RS,4RS)-3-naphthalen-2-ylmethoxy-4-[4-(5-phenyl-[1,3,4]oxadiazol-2-ylmethyl)-phenyl]-piperidine trifluoroacetate as a white powder; MS: 476 (M+H)$^+$.

EXAMPLE 40

(a) 70 mg (0.51 mmol) of phenylmagnesium chloride were added using a syringe to a solution of 80 mg (0.17 mmol) of tert-butyl (3RS,4RS)-4-[4-(2-cyano-ethyl)-phenyl]-3-naphthalen-2-ylmethoxy-piperidine-1-carboxylate (Example 35) in 10 ml of toluene. The reaction mixture was boiled under reflux for 3 hours, thereafter cooled to room temperature and hydrolyzed with 4 ml of 1N hydrochloric acid. The mixture was subsequently stirred at 80° C. for 1 hour, then cooled to room temperature and extracted twice with ethyl acetate. The combined organic phases were dried over sodium sulphate and evaporated under reduced pressure. The residue was chromatographed on silica gel using a 90:10:0.1 mixture of methylene chloride, methanol and ammonia as the eluent. The resulting mixture of (3RS,4RS)-3-[4-(3-naphthalen-2-ylmethoxy-piperidin-4-yl)-phenyl]-1-phenyl-propan-1-one and (3RS,4RS)-3-{4-[3-(naphthalen-2-ylmethoxy)-piperidin-4-yl]-phenyl}-propionic acid was converted into the corresponding BOC derivative in an analogous manner to that described in Example 1(f) and subsequently chromatographed on silica gel using a 2:1 mikxture of hexane and ethyl acetate as the eluent. There were obtained 13 mg (14% of theory) of tert-butyl (3RS,4RS)-3-(naphthalen-2-ylmethoxy)-4-[4-(3-oxo-3-phenyl-propyl)-phenyl]-piperidine-1-carboxylate as a colourless foam; $R_f$: 0.38 (hexane:=2:1).

(b) In an analogous manner to that described in Example 22(l), starting from tert-butyl (3RS,4RS)-3-(naphthalen-2-ylmethoxy)-4-[4-(3-oxo-3-phenyl-propyl)-phenyl]-piperidine-1-carboxylate by cleavage of the BOC group using trifluoroacetic acid in methylene chloride there was obtained (3RS,4RS)-3-[4-(3-naphthalen-2-ylmethoxy-piperidin-4-yl)-phenyl]-1-phenyl-propan-1-one trifluoroacetate as a white powder; MS: 450 (M+H)$^+$.

EXAMPLE 41

(a) A solution of 60 mg (0.13 mmol) of tert-butyl (3RS,4RS)-4-(3-methoxycarbonyl-phenyl)-3-naphthalen-2-ylmethoxy-piperidine-1-carboxylate [Example 26(e)] and 0.26 ml (0.26 mmol) of 1N sodium hydroxide solution in 2 ml of methanol was stirred at 30° C. for 18 hours. For the working-up, the reaction mixture was neutralized with 1N hydrochloric acid and extracted twice with 10 ml of methylene chloride each time. The organic phases were combined, dried over sodium sulphate and evaporated under reduced pressure. The residue was crystallized from a mixture of hexane and diethyl ether. There were obtained 45 mg (75% of theory) of (3RS,4RS)-3-(1-tert-butoxycarbonyl-3-naphthalen-2-ylmethoxy-piperidin-4-yl)-benzoic acid as colourless crystals; MS: 462 (M+H)$^+$.

(b) In an analogous manner to that described in Example 36(b), by condensing (3RS,4RS)-3-(1-tert-butoxycarbonyl-3-naphthalen-2-ylmethoxy-piperidin-4-yl)-benzoic acid with benzylamine using 1,1-carbonyldiimidazole as the condensation agent there was obtained tert-butyl (3RS,4RS)-4-(3-benzyl-carbamoyl-phenyl)-3-(naphthalen-2-ylmethoxy)-piperidine-1-carboxylate as a colourless oil; MS: 551 (M+H)$^+$.

(c) In an analogous manner to that described in Example 22(l), by cleavage of the BOC group from tert-butyl (3RS,4RS)-4-(3-benzylcarbamoyl-phenyl)-3-(naphthalen-2-ylmethoxy)-piperidine-1-carboxylate there was obtained (3RS,4RS)-N-benzyl-3-(3-naphthalen-2-ylmethoxy-piperidin-4-yl)-benzamide hydrochloride as a white powder; MS: 451 (M+H)$^+$.

EXAMPLE 42

The following compounds were obtained in an analogous manner to that described in Example 11(l) by cleavage of the BOC group using trifluoroacetic acid in methylene chloride:

1) (3RS,4RS)-N-benzyl-4-[3-(naphthalen-2-ylmethoxy)-piperidin-4-yl]-benzamide as a white powder, MS: 453 (M+H)$^+$, from tert-butyl (3RS,4RS)4-(4-benzylcarbamoyl-phenyl)-3-(naphthalen-2-ylmethoxy)-piperidine-1-carboxylate;

2) (3RS,4RS)-4-[3-(naphthalen-2-ylmethoxy)-piperidin-4-yl]-N-(3-oxo-3-phenyl-propyl)-benzamide trifluoroacetate as a white powder, MS: 493 (M+H)$^+$, from tert-butyl (3RS,4RS)-3-(naphthalen-2-ylmethoxy)-4-[4-(3-oxo-3-phenyl-propylcarbamoyl)-phenyl]-piperidine-1-carboxylate;

3) (3RS,4RS)-4-[3-(naphthalen-2-ylmethoxy)-piperidin-4-yl]-N-(2-oxo-2-phenyl-ethyl)-benzamide trifluoroacetate as a white powder, MS: 479 (M+H)$^+$, from tert-butyl (3RS,4RS)-3-(naphthalen-2-ylmethoxy)-4-[4-(2-oxo-2-phenyl-ethylcarbamoyl)-phenyl]-piperidine-1-carboxamide.

The BOC derivatives used as the starting materials were obtained as follows:

(a) In an analogous manner to that described in Example 41(b), by the alkaline saponification of tert-butyl (3RS,4RS)-4-(4-methoxycarbonyl-phenyl)-3-naphthalen-2-ylmethoxy-piperidine-1-carboxylate there was obtained (3RS,4RS)-4-(1-tert-butoxycarbonyl-3-naphthalen-2-ylmethoxy-piperidin-4-yl)-benzoic acid as a colourless solid; MS: 461 (M)$^+$.

(b) In an analogous manner to that described in Example 36(b), by condensing (3RS,4RS)-4-(1-tert-butoxycarbonyl-3-naphthalen-2-ylmethoxy-piperidin-4-yl)-benzoic acid with benzylamine there was obtained tert-butyl (3RS,4RS)-4-(4-benzylcarbamoyl-phenyl)-3-(naphthalen-2-ylmethoxy)-piperidine-1-carboxylate as a colourless foam; MS: 551 (M+H)$^+$.

(c) In an analogous manner to that described in Example 36(b), by condensing (3RS,4RS)-4-(1-tert-butoxycarbonyl-3-naphthalen-2-ylmethoxy-piperidin-4-yl)-benzoic acid with 3-amino-1-phenyl-propan-1-one there was obtained tert-butyl (3RS,4RS)-3-(naphthalen-2-ylmethoxy)-4-[4-(3-oxo-3-phenyl-propylcarbamoyl)-phenyl]-piperidine-1-carboxylate as a colourless foam; MS: 593 (M+H)⁺.

(d) In an analogous manner to that described in Example 36(b), by condensing (3RS,4RS)-4-(1-tert-butoxycarbonyl-3-naphthalen-2-ylmethoxy-piperidin-4-yl)-benzoic acid with 2-amino-1-phenyl-ethanone there was obtained tert-butyl (3RS,4RS)-3-(naphthalen-2-ylmethoxy)-4-[4-(2-oxo-2-phenyl-ethylcarbamoyl)-phenyl]-piperidine-1-carboxylate as a colourless foam; MS: 579 (M+H)⁺.

EXAMPLE 43

(a) A solution of 1.0 g (3 mmol) of tert-butyl (3RS,4RS)-3-hydroxy-4-(4-methoxycarbonyl-phenyl)-piperidine-1-carboxylate in 100 ml of methanol was treated with 100 mg of rhodium (5%) on aluminium oxide and hydrogenated for 5 hours at 50° C. under 10 bar of hydrogen. Thereafter, the reaction mixture was filtered over 30 g of Dicalit, the filter aid was rinsed with 200 ml of methanol and the solution obtained was evaporated under reduced pressure. There was obtained in quantitative yield a 2:1 or 1:2 mixture of tert-butyl (3RS,4RS)-3-hydroxy-4-(trans- and -(cis-4-methoxycarbonyl-cyclohexyl)-piperidine-4-carboxylate as a colourless solid; MS: 342 (M+H)⁺.

The following procedure was carried out in an analogous manner to that described in Example 22(e) and (h)–(l):

(b) From a 2:1 or 1:2 mixture of tert-butyl (3RS,4RS)-3-hydroxy-4-(trans- and -(cis-4-methoxycarbonyl-cyclohexyl)-piperidin-4-carboxylate by reduction using lithium borohydride there was obtained a 2:1 or 1:2 mixture of tert-butyl (3RS,4RS)-cis- and -trans-3-hydroxy-4-(4-hydroxymethyl-cyclohexyl)-piperidine-1-carboxylate as a colourless foam; MS: 314 (M+H)⁺.

(c) From a 2:1 or 1:2 mixture of tert-butyl (3RS,4RS)-cis- and -trans-3-hydroxy-4-(4-hydroxymethyl-cyclohexyl)-piperidine-1-carboxylate there was obtained by introduction of the trityl group a 2:1 or 1:2 mixture of tert-butyl (3RS,4RS)-cis- and -trans-3-hydroxy-4-(4-trityloxymethyl-cyclohexyl)-piperidine-1-carboxylate as a colourless foam; MS: 573 (M+H)⁺.

(d) Alkylation of a 2:1 or 1:2 mixture of tert-butyl (3RS,4RS)-cis- and -trans-3-hydroxy-4-(4-trityloxymethyl-cyclohexyl)-piperidine-1-carboxylate with 2-bromomethylnaphthalene gave a 2:1 or 1:2 mixture of tert-butyl (3RS,4RS)-cis- and -trans-3-naphthalen-2-ylmethoxy-4-(4-trityloxymethyl-cyclohexyl)-piperidine-1-carboxylate as a colourless foam: MS: 713 (M+NH₄)⁺.

(e) From a 2:1 or 1:2 mixture of tert-butyl (3RS,4RS)-cis- and -trans-3-naphthalen-2-ylmethoxy-4-(4-trityloxymethyl-cyclohexyl)-piperidine-1-carboxylate by cleavage of the trityl group using hydrogen chloride in methanol there was obtained a 2:1 or 1:2 mixture of tert-butyl (3RS,4RS)-cis- and -trans-3-naphthalen-2-ylmethoxy-4-(4-hydroxymethyl-cyclohexyl)-piperidine-1-carboxylate as a colourless foam; MS: 453 (M+H)⁺.

(f) Acylation of a 2:1 or 1:2 mixture of tert-butyl (3RS,4RS)-cis- and -trans-3-naphthalen-2-ylmethoxy-4-(4-hydroxymethyl-cyclohexyl)-piperidine-1-carboxylate with benzoyl chloride yielded a 2:1 or 1:2 mixture of tert-butyl (3RS,4RS)-cis- and -trans-4-(4-benzoyloxymethyl-cyclohexyl)-3-naphthalen-2-ylmethoxy-piperidine-1-carboxylate as a colourless oil; MS: 558 (M+H)⁺.

(g) From a 2:1 or 1:2 mixture of tert-butyl (3RS,4RS)-cis- and -trans-4-(4-benzoyloxymethyl-cyclohexyl)-3-naphthalen-2-ylmethoxy-piperidine-1-carboxylate by cleavage of the BOC group using hydrogen chloride in methanol there was obtained a 2:1 or 1:2 mixture of (3RS,4RS)-cis- and -trans 4-(3-naphthalen-2-ylmethoxy-piperidin-4-yl)-cyclohexylmethyl benzoate as a colourless foam; MS: 458 (M+H)⁺.

EXAMPLE 44

The following procedure was carried out in an analogous manner to that described in Example 22(a)–(c):

(a) 1-Benzyl-4-(4-methoxy-phenyl)-piperidin-4-ol was obtained as a colourless solid, MS: 298 (M+H)⁺, from 1-benzyl-4-piperidone and 4-iodoanisole.

(b) 1-Benzyl-4-(4-methoxy-phenyl)-1,2,3,6-tetrahydro-pyridine was obtained as a beige solid, MS: 280 (M+H)⁺, from 1-benzyl-4-(4-methoxy-phenyl)-piperidin-4-ol by elimination.

(c) Hydroboration of 1-benzyl-4-(4-methoxy-phenyl)-1,2,3,6-tetrahydro-pyridine gave (3RS,4RS)-1-benzyl-4-(4-methoxy-phenyl)-piperidin-3-ol as colourless crystals; MS: 297 (M)⁺.

(d) 49.6 ml (49.6 mmol, 2 eq.) of an approximately 1M boron tribromide solution in methylene chloride was added dropwise at 3–7° C. within 10 minutes to a solution of 7.38 g (24.82 mmol) of (3RS,4RS)-1-benzyl-4-(4-methoxy-phenyl)-piperidin-3-ol in 248 ml of methylene chloride. This suspension was stirred at room temperature for 3 hours. Subsequently, the reaction mixture was poured into 750 ml of an ice/water mixture, brought to pH 8 with 2N sodium hydroxide solution and extracted three times with 500 ml of methylene chloride each time. The organic phases were washed with a small amount of water, dried over magnesium sulphate, evaporated under reduced pressure and dried in a high vacuum. This yielded 6.42 g of (3RS,4RS)-1-benzyl-4-(4-hydroxy-phenyl)-piperidin-3-ol in the form of a white foam; MS: 283 (M)⁺.

(e) A solution of 3.0 g, (10.6 mmol) of (3RS,4RS)-1-benzyl-4-(4-hydroxy-phenyl)-piperidin-3-ol in 75 ml of ethyl methyl ketone was treated in succession with 10.84 g (42.4 mmol, 4.8 eq) of 2-(2-iodo-ethoxy)-tetrahydro-pyran and 5.25 g (53 mmol, 5 eq) of potassium carbonate. This mixture was stirred at 95° C. for 25 hours. Subsequently, it was concentrated to a few millilitres, poured into 200 ml of an ice/water mixture and extracted three times with 300 ml of methylene chloride each time. The combined organic phases were washed once with a small amount of water, dried over magnesium sulphate, evaporated under reduced pressure and dried in a high vacuum. The thus-obtained crude product (11.81 g) was separated on silica gel using a 99:1 mixture of methylene chloride and methanol as the eluent and yielded 3.2 g (73% of theory) of a mixture of (3RS,4RS)-1-benzyl-4-[4-[2-[(RS)- and -[(SR)-tetrahydro-pyran-2-yloxy]-ethoxy]-phenyl]-piperidin-3-ol as a colourless oil; $R_f$: 0.55 ($SiO_2$, methylene chloride:methanol=9:1).

(f) In an analogous manner to that described in Example 22(i), by alkylating a mixture of (3RS,4RS)-1-benzyl-4-[4-[2-[(RS)- and -[(SR)-tetrahydro-pyran-2-yloxy]-ethoxy]-phenyl]-piperidin-3-ol with 2-bromomethylnaphthalene there was obtained a mixture of (3RS,4RS)-1-benzyl-3-(naphthalen-2-ylmethoxy)-4-[4-[2-[(RS)- and -[(SR)-tetrahydro-pyran-2-yloxy]-ethoxy]-phenyl]-piperidine as a colourless oil; $R_f$: 0.46 ($SiO_2$, methylene chloride:=1:1).

(g) In an analogous manner to that described Example 25(a), by cleavage of the benzyl group using 2,2,2-trichloroethyl chloroformate and potassium carbonate there was obtained a mixture of 2,2,2-trichloro-ethyl (3RS,4RS)-3-(naphthalen-2-ylmethoxy)-4-[4-[2-[(RS)- and -[(SR)-tetrahydro-pyran-2-yloxy]-ethoxy]-phenyl]-piperidine-1-carboxylate as a colourless oil; MS: 653.3, 655 (M+H)⁺.

(h) A solution of 500 mg (0.785 mmol) of a mixture of 2,2,2-trichloro-ethyl (3RS,4RS)-3-(naphthalen-2-ylmethoxy)-4-[4-[2-[(RS)- and -[(SR)-tetrahydro-pyran-2-yloxy]-ethoxy]-phenyl]-piperidine-1-carboxylate in 10 ml of methanol was treated with 1 ml of water and 1.120 g (5.888 mmol) of p-toluenesulphonic acid monohydrate. This suspension was stirred at room temperature for 1.5 hours, then concentrated to half of the volume under reduced pressure and extracted four times with methylene chloride against water. The organic phases were each washed once with saturated sodium hydrogen carbonate solution and saturated sodium chloride solution, dried over magnesium sulphate, evaporated under reduced pressure and dried in a high vacuum. The crude product (465 mg) was separated on silica gel using a 9:1 mixture of methylene chloride and methanol as the eluent. This yielded 344 mg (79% of theory) of 2,2,2-trichloroethyl (3RS,4RS)-4-[4-(2-hydroxy-ethoxy)-phenyl]-3-(naphthalen-2-ylmethoxy)-piperidine-1-carboxylate as a colourless, amorphous powder; MS: 569.3, 571 $(M+NH_4)^+$.

(i) In an analogous manner to that described in Example 24(m), from 2,2,2-trichloroethyl (3RS,4RS)-4-[4-(2-hydroxy-ethoxy)-phenyl]-3-(naphthalen-2-ylmethoxy)-piperidine-1-carboxylate and pyridine-2-carbonyl azide there was obtained 2,2,2-trichloro-ethyl (3RS,4RS)-3-(naphthalen-2-ylmethoxy)-4-[4-(2-pyridin-2-ylcarbamoyloxy-ethoxy]-phenyl]-piperidine-1-carboxylate as a colourless oil; MS: 672.2, 674 $(M+H)^+$.

(j) In an analogous manner to that described in Example 25(b), by treating 2,2,2-trichloroethyl (3RS,4RS)-3-(naphthalen-2-ylmethoxy)-4-[4-(2-pyridin-2-ylcarbamoyloxy-ethoxy]-phenyl]-piperidine-1-carboxylate with zinc in glacial acetic acid there was obtained (3RS,4RS)-2-[4-[3-(naphthalen-2-ylmethoxy)-piperidin-4-yl]-phenoxy]-ethyl pyridine-2-yl-carbamate as a colourless solid; MS: 498 $(M+H)^+$.

EXAMPLE 45

The following compounds were obtained in an analogous manner to that described in Example 25(b):

1) (3RS,4RS)-2-[4-[3-(Naphthalen-2-ylmethoxy)-piperidin-4-yl]-phenoxy]-ethyl carbamate as a colourless oil, MS: 421 $(M+H)^+$, from 2,2,2-trichloro-ethyl (3RS,4RS)-4-[4-(2-carbamoyloxy-ethoxy)-phenyl]-3-(naphthalen-2-ylmethoxy)-piperidine-1-carboxylate;

2) (3RS,4RS)-2-[4-[3-(naphthalen-2-ylmethoxy)-piperidin-4-yl]-phenoxy]-ethyl morpholine-4-carboxylate as a colourless oil, MS: 491 $(M+H)^+$, from 2,2,2-trichloro-ethyl (3RS,4RS)-4-[4-[2-(morpholin-4-ylcarbonyloxy)-ethoxy]-phenyl]-3-(naphthalen-2-ylmethoxy)-piperidine-1-carboxylate;

3) (3RS,4RS)-4-(4-methoxy-phenyl)-3-(naphthalen-2-ylmethoxy)-piperidine as a colourless oil, MS: 348 $(M+H)^+$, from 2,2,2-trichloro-ethyl (3RS,4RS)-4-(4-methoxy-phenyl)-3-(naphthalen-2-ylmethoxy)-piperidine-1-carboxylate;

4) (3RS,4RS)-2-[4-[3-(naphthalen-2-ylmethoxy)-piperidin-4-yl]-phenoxy]-ethanol as a colourless, amorphous solid, MS: 378 $(M+H)^+$, from a mixture of 2,2,2-trichloro-ethyl (3RS,4RS)-3-(naphthalen-2-ylmethoxy)-4-[4-[2-[(RS)- and -[(SR)-tetrahydro-pyran-2-yloxy]-ethoxy]-phenyl]-piperidine-1-carboxylate with simultaneous cleavage of the THP group.

The derivatives used as the starting materials were obtained as follows:

(a) In an analogous manner to that described in Example 24 (m), from 2,2,2-trichloroethyl (3RS,4RS)-4-[4-(2-hydroxy-ethoxy)-phenyl]-3-(naphthalen-2-ylmethoxy)-piperidine-1-carboxylate and sodium isocyanate there was obtained 2,2,2-trichloro-ethyl (3RS,4RS)-4-[4-(2-carbamoyloxy-ethoxy)-phenyl]-3-(naphthalen-2-ylmethoxy)-piperidine-1-carboxylate as a colourless oil; $R_f$: 0.28 (SiO$_2$, methylene chloride:acetone=1:1).

(b) A solution of 250 mg (0.56 mmol) of 2,2,2-trichloroethyl (3RS,4RS)-4-[4-(2-hydroxy-ethoxy)-phenyl]-3-(naphthalen-2-ylmethoxy)-piperidine-1-carboxylate in 20 ml of toluene was treated in succession with 250 ml (2.8 mmol, 5.0 eq.) of morpholine-4-carbonyl chloride, 375 mg (3.08 mmol, 5.5 eq.) of 4-dimethylaminopyridine and 20 µl (0.075 mmol, 0.13 eq.) of dibutyltin diacetate. This mixture was boiled under reflux for 64 hours. In the course of the reaction a further 125 ml (1.40 mmol, 5.0 eq.) of morpholine-4-carbonyl chloride and 188 mg (1.56 mmol, 2.3 eq.) of 4-dimethylaminopyridine were added and the mixture was boiled under reflux for a further 24 hours. The reaction mixture, cooled to room temperature, was poured into 100 ml of an ice/water mixture, stirred for 5 minutes and extracted three times with methylene chloride. The organic phases were each washed once with water and saturated sodium chloride solution, dried over magnesium sulphate, evaporated under reduced pressure and dried in a high vacuum. The crude product (546 mg) was separated on silica gel using a 9:1 mixture of hexane and acetone as the eluent. There were obtained 42 mg (14% of theory) of 2,2,2-trichloro-ethyl (3RS,4RS)-4-[4-[2-(morpholin-4-ylcarbonyloxy)-ethoxy]-phenyl]-3-(naphthalen-2-ylmethoxy)-piperidine-1-carboxylate as a colourless oil; MS: 665.3, 667 $(M+H)^+$.

(c) In an analogous manner to that described in Example 12(b), by alkylating (3RS,4RS)-1-benzyl-4-(4-methoxy-phenyl)-piperidin-3-ol [Example 44(c)] with 2-bromomethylnaphthalene there was obtained (3RS,4RS)-1-benzyl-4-(4-methoxy-phenyl)-3-(naphthalen-2-ylmethoxy)-piperidine as a beige coloured solid; MS: 437 $(M)^+$. Subsequent reaction with 2,2,2-trichloroethyl chloroformate gave 2,2,2-trichloro-ethyl (3RS,4RS)-4-(4-methoxy-phenyl)-3-(naphthalen-2-ylmethoxy)-piperidine-1-carboxylate as a yellowish oil; MS: 539, 541 $(M+NH_4)^+$.

EXAMPLE 46

(a) In an analogous manner to that described in Example 2(e), by hydrogenolytic cleavage of the benzyl group from (3RS,4RS)-1-benzyl-4-(4-hydroxy-phenyl)-piperidin-3-ol [Example 44(d)] there was obtained (3RS,4RS)-4-(4-hydroxy-phenyl)-piperidin-3-ol as a colourless solid; MS: 194 $(M+H)^+$.

b) In an analogous manner to that described in Example 22(g), from (3RS,4RS)-4-(4-hydroxy-phenyl)-piperidin-3-ol by introduction of the BOC group there was obtained tert-butyl (3RS,4RS)-3-hydroxy-4-(4-hydroxy-phenyl)-piperidine-1-carboxylate as a colourless foam; MS: 237 $(M-C_4H_8)^+$.

(c) A mixture of 4.5 g (15.3 mmol) of tert-butyl (3RS,4RS)-3-hydroxy-4-(4-hydroxy-phenyl)-piperidine-1-carboxylate, 20.8 g (91.8 mmol, 6.0 eq.) of 2-(3-chloropropyl)-2-phenyl-[1,3]dioxolane [J. Med. Chem. 34, 12 (1991)], 14.6 g (105.5 mmol, 6.9 eq.) of potassium carbonate and 2.0 g (0.012 mmol, 0.078 eq.) of potassium iodide in 50 ml of methyl ethyl ketone were stirred in a sealed, pressure-tight vessel at a bath temperature of 100° C. for 60 hours. The reaction mixture was poured into an ice/water mixture and extracted three times with ethyl acetate. The organic phases were each washed once with water and saturated sodium chloride solution, dried over magnesium sulphate, concentrated under reduced pressure and dried in a high vacuum. The yellow oil (25.72 g) was separated on silica gel using an elution gradient of 4:1 to 1:1 of a mixture of hexane and ethyl acetate as the eluent. This yielded 5.34 g (72% of theory) of white, crystalline tert-butyl (3RS,4RS)-3-hydroxy-4-[4-[3-(2-phenyl-[1,3]dioxolan-2-yl)-propoxy]-phenyl]-piperidine-1-carboxylate; MS: 484 $(M+H)^+$.

(d) In an analogous manner to that described in Example 22(i), by alkylating tert-butyl (3RS,4RS)-3-hydroxy-4-[4-[3-(2-phenyl-[1,3]dioxolan-2-yl)-propoxy]-phenyl]-piperidine-1-carboxylate with 2-bromomethylnaphthalene there was obtained tert-butyl (3RS,4RS)-3-(naphthalen-2-ylmethoxy)-4-[4-[3-(2-phenyl-[1,3]dioxolan-2-yl)-propoxy]-phenyl]-piperidine-1-carboxylate as white crystals; MS: 624 (M+H)$^+$.

(e) A solution of 193 mg (0.31 mmol) of tert-butyl (3RS,4RS)-3-(naphthalen-2-ylmethoxy)-4-[4-[3-(2-phenyl-[1,3]dioxolan-2-yl)-propoxy]-phenyl]-piperidine-1-carboxylate in 3 ml of tetrahydrofuran and 3 ml of 2N hydrochloric acid was stirred at room temperature for 12 hours and at 50° C. for 24 hours. Subsequently, the reaction mixture was poured into a 1:1 mixture of water and saturated sodium hydrogen carbonate solution and extracted three times with ethyl acetate. The organic phases were each washed once with water and saturated sodium chloride solution, dried over magnesium sulphate, concentrated under reduced pressure and dried in a high vacuum. The colourless oil (165 mg) was separated on silica gel using a 9:1 mixture of methylene chloride and methanol (extr. against 5 vol. % conc. NH$_4$OH). This yielded 127.4 mg of (3RS,4RS)-4-[4-(3-naphthalen-2-ylmethoxy-piperidin-4-yl)-phenoxy]-1-phenyl-butan-1-one in the form of a colourless oil; MS: 502 (M+Na)$^+$.

EXAMPLE 47

The following compounds were obtained in an analogous manner to that described in Example 46(d)–(e) and, respectively, 3(c)–(e):

1) From tert-butyl (3RS,4RS)-3-hydroxy-4-[4-[3-(2-phenyl-[1,3]dioxolan-2-yl)-propoxy]-phenyl]-piperidine-1-carboxylate by alkylation with 5-bromomethyl-benzo[b]thiophene there was obtained tert-butyl (3RS,4RS)-3-(benzo[b]thiophen-5-ylmethoxy)-4-{4-[3-(2-phenyl-[1,3]dioxolan-2-yl)-propoxy]-phenyl}-piperidine-1-carboxylate, MS: 630 (M+H)$^+$, as a light yellow resin. Subsequent cleavage of the BOC and acetal groups yielded (3RS,4RS)-4-[4-[3-(benzo[b]thiophen-5-ylmethoxy)-piperidin-4-yl]-phenoxy]-1-phenyl-butan-1-one as a colourless resin; MS: 486 (M+H)$^+$.

2) From tert-butyl (3RS,4RS)-3-hydroxy-4-[4-[3-(2-phenyl-[1,3]dioxolan-2-yl)-propoxy]-phenyl]-piperidine-1-carboxylate by alkylation with 5-(chloromethyl)indane there was obtained tert-butyl (3RS,4RS)-3-(indan-5-ylmethoxy)-4-{4-[3-(2-phenyl-[1,3]dioxolan-2-yl)-propoxy]-phenyl}-piperidine-1-carboxylate, MS: 614 (M+H)$^+$, as a light yellow resin. Subsequent cleavage of the BOC and acetyl groups yielded (3RS,4RS)-4-[4-[3-indan-5-ylmethoxy)-piperidin-4-yl]-phenoxy]-1-phenyl-butan-1-one as a colourless resin; MS: 470 (M+H)$^+$.

3) From tert-butyl (3RS,4RS)-3-hydroxy-4-[4-[3-(2-phenyl-[1,3]dioxolan-2-yl)-propoxy]-phenyl]-piperidine-1-carboxylate by alkylation with 3-chloromethyl-1-(2-trimethylsilanyl-ethoxymethyl)-naphthalene there was obtained tert-butyl (3RS,4RS)-4-[4-[3-(2-phenyl-[1,3]dioxolan-2-yl)-propoxy]-phenyl]-3-[4-(2-trimethylsilanyl-ethoxymethoxy)-naphthalen-2-ylmethoxy]-piperidine-1-carboxylate, MS: 770 (M+H)$^+$, as a colourless resin. Subsequent cleavage of the BOC group and of the two acetal groups yielded (3RS,4RS)-4-[4-[3-(4-hydroxy-naphthalen-2-ylmethoxy)-piperidin-4-yl]-phenoxy]-1-phenyl-butan-1-one as a colourless resin; R$_f$: 0.17 (SiO$_2$, methylene chloride:methanol=9:1, extracted against 5% ammonia).

4) From tert-butyl (3RS,4RS)-3-hydroxy-4-(4-hydroxy-phenyl)-piperidine-1-carboxylate by alkylation with 1-bromo-4-(2-bromoethyl)-benzene analogously to Example 46(c) there was obtained tert-butyl (3RS,4RS)-4-[4-[2-(4-bromo-phenoxy)-ethoxy]-phenyl]-3-hydroxy-piperidine-1-carboxylate as a colourless resin. Further alkylation with 2-bromomethylnaphthalene gave tert-butyl (3RS,4RS)-4-[4-[2-(4-bromo-phenoxy)-ethoxy]-phenyl]-3-(naphthalen-2-ylmethoxy)-piperidine-1-carboxylate, from which by cleavage of the BOC group there was obtained (3RS,4RS)-4-[4-[2-(4-bromo-phenoxy)-ethoxy]-phenyl]-3-(naphthalen-2-ylmethoxy)-piperidine as a colourless resin; MS: 532, 534M+H)$^+$.

5) From tert-butyl (3RS,4RS)-3-hydroxy-4-(4-hydroxy-phenyl)-piperidine-1-carboxylate by alkylation with 2-bromomethyl-5-phenyl-[1,3,4]oxadiazole analogously to Example 44(e) there was obtained tert-butyl (3RS,4RS)-3-hydroxy-4-[4-(5-phenyl-[1,3,4]oxadiazol-2-ylmethoxy)-phenyl]-piperidine-1-carboxylate as a yellowish, amorphous solid. Further alkylation with 2-bromomethylnaphthalene gave tert-butyl (3RS,4RS)-3-(naphthalen-2-ylmethoxy)-4-[4-(5-phenyl-[1,3,4]oxadiazol-2-ylmethoxy)-phenyl]-piperidine-1-carboxylate, from which by cleavage of the BOC group there was obtained (3RS,4RS)-3-(naphthalen-2-ylmethoxy)-4-[4-(5-phenyl-[1,3,4]oxadiazol-2-ylmethoxy)-phenyl]piperidine as a colourless solid; MS: 492 (M+H)$^+$.

6) From (3RS,4RS)-3-hydroxy-4-(4-hydroxy-phenyl)-piperidine-1-carboxylate by alkylation with β-bromophenethol analogously to Example 46(c) there was obtained tert-butyl (3RS,4RS)-3-hydroxy-4-[4-(2-phenoxy-ethoxy)-phenyl]-piperidine-1-carboxylate; MS: 414 (M+H)$^+$. Further alkylation with 2-bromomethylnaphthalene gave tert-butyl (3RS,4RS)-3-(naphthalen-2-ylmethoxy)-4-(2-phenoxy-ethoxy)-phenyl]-piperidine-1-carboxylate, MS: 554 (M+H)$^+$, from which by cleavage of the BOC group there was obtained (3RS,4RS)-3-(naphthalen-2-ylmethoxy)-4-[4-(2-phenoxy-ethoxy)-phenyl]-piperidine; MS: 454 (M+H)$^+$.

7) From tert-butyl (3RS,4RS)-3-hydroxy-4-[4-(2-phenoxy-ethoxy)-phenyl]-piperidine-1-carboxylate by alkylation with 2-chloromethyl-O-SEM there was obtained tert-butyl (3RS,4RS)-4-[4-(2-phenoxy-ethoxy)-phenyl]-3-[4-(2-trimethylsilanyl-ethoxymethoxy)-naphthalen-2-ylmethoxy]-piperidine-1-carboxylate; MS: 700 (M+H)$^+$. Subsequent cleavage of the BOC and acetal groups yielded (3RS,4RS)-3-{4-[4-(2-phenoxy-ethoxy)-phenyl]-piperidin-3-yloxymethyl}-naphthalen-1-ol; MS: 470 (M+H)$^+$.

EXAMPLE 48

A solution of 18.7 mg (0.494 mmol, 6.7 eq.) of sodium borohydride in 0.35 ml of water was added using a syringe to a solution of 44 mg (0.074 mmol) of (3RS,4RS)-4-[4-[3-(4-hydroxy-naphthalen-2-ylmethoxy)-piperidin-4-yl]-phenoxy]-1-phenyl-butan-1-one in 1.5 ml of dioxan. The mixture was stirred at room temperature for 1.5 hours. Subsequently, the reaction solution was treated with the same amount by volume of ice-water and the mixture was brought to pH 1 with 2N hydrochloric acid. After stirring at room temperature for 5–10 minutes the mixture was adjusted to pH 9 with concentrated ammonia and the aqueous solution was extracted three times with one equivalent by volume of methylene chloride each time. The combined organic phases were dried over magnesium sulphate, concentrated at 45° C. under reduced pressure and dried in a high vacuum. The brownish solid (40.1 mg) was separated on silica gel using a 9:1 mixture of methylene chloride and methanol (extr. against 5 vol. % conc. NH₃ aq.) as the eluent. This yielded 13 mg (35% of theory) of (3RS,4RS)-3-[4-[4-(4-hydroxy-4-phenyl-butoxy)-phenyl]-piperidin-4-yloxymethyl]-naphthalen-1-ol (configuration unknown in the butanol part) as a colourless oil; MS: 498 (M+H)⁺.

EXAMPLE 49

The following alcohols were obtained in an analogous manner to that described in Example 48 by reduction of the ketones:

1) The 2:1 or 1:2 mixture of (RS)- and (SR)-4-[4-[(3RS,4RS)-3-(indan-5-ylmethoxy)-piperidin-4-yl]-phenoxy]-1-phenyl-butan-1-ol as a colourless resin, MS: 472 (M+H)⁺, from (3RS,4RS)-4-[4-[3-indan-5-ylmethoxy)-piperidin-4-yl]-phenoxy]-1-phenyl-butan-1-one;
2) The mixture of (RS)- and (SR)-4-[4-[(3RS,4RS)-3-(benzo[b]thiopen-5-ylmethoxy)-piperidin-4-yl]-phenoxy]-1-phenyl-butan-1-ol as a colourless resin, MS: 488 (M+H))⁺, from (3RS,4RS)-4-[4-[3-(benzo[b]thiophen-5-ylmethoxy)-piperidin-4-yl]-phenoxy]-1-phenyl-butan-1-one;
3) 4-[4-[(3RS,4RS)-3-naphthalen-2-ylmethoxy-piperidin-4-yl]-phenoxy]-1-phenyl-butan-1-ol (configuration unknown in the butanol part) as a colourless resin, MS: 482 (M+H)⁺, from (3RS,4RS)-4-[4-(3-naphthalen-2-ylmethoxy-piperidin-4-yl)-phenoxy]-1-phenyl-butan-1-one.

EXAMPLE 50

(a) In an analogous manner to that described in Example 22(g), from (3RS,4RS)-4-[4-(3-naphthalen-2-ylmethoxy-piperidin-4-yl)-phenoxy]-1-phenyl-butan-1-one by introducing the BOC group there was obtained tert-butyl (3RS,4RS)-3-(naphthalen-2-ylmethoxy)-4-[4-(4-oxo-4-phenyl-butoxy)-phenyl]-piperidine-1-carboxylate as a colourless solid; MS : 580 (M+H)⁺.

(b) Reduction of tert-butyl (3RS,4RS)-3-(naphthalen-2-ylmethoxy)-4-[4-(4-oxo-4-phenyl-butoxy)-phenyl]-piperidine-1-carboxylate analogously to Example 48 yielded tert-butyl (3RS,4RS)-4-[4-(4-hydroxy-4-phenyl-butoxy)-phenyl]-3-naphthalen-2-ylmethoxy-piperidine-1-carboxylate (configuration unknown in the butoxy part) as a colourless solid; MS: 582 (M+H)⁺.

(c) Alkylation of tert-butyl (3RS,4RS)-4-[4-(4-hydroxy-4-phenyl-butoxy)-phenyl]-3-naphthalen-2-ylmethoxy-piperidine-1-carboxylate with methyl iodide analogously to Example 22(i) gave tert-butyl (3RS,4RS)-4-[4-(4-methoxy-4-phenyl-butoxy)-phenyl]-3-(naphthalen-2-ylmethoxy)-piperidine-1-carboxylate (configuration unknown in the butoxy part) as a colourless oil; R_f: 0.61 (SiO₂, hexane:ethyl acetate=2:1).

(d) In an analogous manner to that described in Example 22(l), from tert-butyl (3RS,4RS)-4-[4-(4-methoxy-4-phenyl-butoxy)-phenyl]-3-(naphthalen-2-ylmethoxy)-piperidine-1-carboxylate by cleavage of the BOC group there was obtained (3RS,4RS)-4-[4-(4-methoxy-4-phenyl-butoxy)-phenyl]-3-(naphthalen-2-ylmethoxy)-piperidine (configuration unknown in the butoxy part) as a colourless resin; MS: 496 (M+H)⁺.

EXAMPLE 51

A solution of 30 mg (0.052 mmol) of tert-butyl (3RS,4RS)-4-[4-(4-hydroxy-4-phenyl-butoxy)-phenyl]-3-naphthalen-2-ylmethoxy-piperidine-1-carboxylate (configuration unknown in the butoxy part), 25.5 µl (0.186 mmol, 3.6 eq.) of triethylamine and 1.7 ml of methylene chloride was treated in succession with 21.6 µl (0.186 mmol, 3.6 eq.) of benzoyl chloride and 2 mg (0.016 mmol) of 4-dimethylaminopyridine. This reaction solution was stirred at room temperature for 10 hours, then poured into 5 ml of water and extracted three times with 10 ml of ethyl acetate each time. The combined organic phases were dried over magnesium sulphate, evaporated under reduced pressure and dried in a high vacuum. The light yellow resin (62 mg) was dissolved in 1 ml of methanol, again concentrated, dried in a high vacuum. Without further purification and characterization the product obtained was reacted with hydrogen chloride in methanol analogously to the procedure described in Example 22(l). The brown-yellow resin (56 mg) was separated on silica gel using a 95:5 mixture of methylene chloride and methanol (extracted against 5 vol. % conc. ammonia) as the eluent. There were obtained 15 mg (50% of theory) of 4-[4-[(3RS,4RS)-3-naphthalen-2-ylmethoxy-piperidin-4-yl]-phenoxy]-1-phenyl-butyl benzoate (configuration unknown in the butoxy part) as a colourless resin; MS: 586 (M+H)⁺.

EXAMPLE 52

A mixture of 600 mg (0.962 mmol) of tert-butyl (3RS,4RS)-3-(naphthalen-2-ylmethoxy)-4-{4-[3-(2-phenyl-[1,3]dioxolan-2-yl)-propoxy]-phenyl}-piperidine-1-carboxylate in 3.0 ml of methylene chloride and 433 mg (1.92 mmol, 2.0 eq.) of zinc bromide was stirred at room temperature for 4 hours. The reaction mixture was poured into water and extracted three times with ethyl acetate. The organic phases were washed in each case once with water and with saturated sodium chloride solution, dried over magnesium sulphate, evaporated under reduced pressure and dried in a high vacuum. The amorphous, slightly yellow crude product was separated on silica gel using a 95:5:0.1 mixture of methylene chloride, methanol and ammonia. There were obtained 355 mg (71% of theory) of (3RS,4RS)-3-(naphthalen-2-ylmethoxy)-4-[4-[3-(2-phenyl-[1,3]dioxolan-2-yl)-propoxy]-phenyl]-piperidine as a colourless resin; MS: 524 (M+H)⁺.

EXAMPLE 53

(a) In an analogous manner to that described in Example 44(e)–(f), by alkylating tert-butyl (3RS,4RS)-3-hydroxy-4-(4-hydroxy-phenyl)-piperidine-1-carboxylate with 2-(2-iodo-ethoxy)-tetrahydro-pyran there was obtained a mixture of tert-butyl (3RS,4RS)-3-hydroxy-4-[4-[2-[(RS)- and -[(SR)-tetrahydro-pyran-2-yloxy]-ethoxy]-phenyl]-piperidine-1-carboxylate as a yellow oil; R_f: 0.45 (SiO₂, hexane:ethyl acetate=1:1).

b) In an analogous manner to that described in Example 22(i), by alkylating the mixture of tert-butyl (3RS,4RS)-3-hydroxy-4-[4-[2-[(RS)- and -[(SR)-tetrahydro-pyran-2-yloxy]-ethoxy]-phenyl]-piperidine-1-carboxylate with 2-bromomethylnaphthalene there was obtained a mixture of tert-butyl (3RS,4RS)-3-(naphthalen-2-ylmethoxy)-4-[4-[2-[(RS)- and -[(SR)-tetrahydro-pyran-2-yloxy]-ethoxy]-phenyl]-piperidine-1-carboxylate as a colourless solid; MS: 579 (M+H)⁺.

(c) A solution of 1.99 g (3.54 mmol) of a mixture of tert-butyl (3RS,4RS)-3-(naphthalen-2-ylmethoxy)-4-[4-[2-[(RS)- and -[(SR)-tetrahydro-pyran-2-yloxy]-ethoxy]-phenyl]-piperidine-1-carboxylate in 11.3 ml of methanol was treated with 11.3 ml of 2N hydrogen chloride in methanol and the mixture was stirred at room temperature for 5 minutes. The reaction mixture was poured into 200 ml of a mixture of ice and saturated sodium hydrogen carbonate solution and extracted three times with ethyl acetate. The organic phases were washed with saturated sodium chloride solution, dried over magnesium sulphate, evaporated under reduced pressure and dried in a high vacuum. The yellow resin (1.80 g) was recrystallized from hexane. There were obtained 950 mg (56%) of tert-butyl (3RS,4RS)-4-[4-(2-hydroxy-ethoxy)-phenyl]-3-(naphthalen-2-ylmethoxy)-piperidine-1-carboxylate as a colourless solid; MS: 478 (M+H)⁺.

d) In an analogous manner to that described in Example 22(k), by acylating tert-butyl (3RS,4RS)-4-[4-(2-hydroxy-ethoxy)-phenyl]-3-(naphthalen-2-ylmethoxy)-piperidine-1-carboxylate with 4-chlorobenzoyl chloride there was obtained tert-butyl (3RS,4RS)-4-[4-[2-(4-chloro-benzoyloxy)-ethoxy]-phenyl]-3-(naphthalen-2-ylmethoxy)-piperidine-1-carboxylate as a colourless oil; MS: 616 (M+H)⁺.

(e) In an analogous manner to that described in Example 22(l), from tert-butyl (3RS,4RS)-4-[4-[2-(4-chloro-benzoyloxy)-ethoxy]-phenyl]-3-(naphthalen-2-ylmethoxy)-piperidine-1-carboxylate by cleavage of the BOC group there was obtained (3RS,4RS)-2-[4-(3-napthalen-2-ylmethoxy-piperidin-4-yl)-phenoxy]-ethyl 4-chloro-benzoate hydrochloride as a colourless solid; MS: 516 (M+H)⁺.

EXAMPLE 54

The following compounds were obtained in an analogous manner to that described in Example 22(l) by cleavage of the BOC group using acid:

1) (3RS,4RS)-2-[4-[3-(Naphthalen-2-ylmethoxy)-piperidin-4-yl]-phenoxy]-ethyl 4-methoxy-benzoate hydrochloride as a colourless solid, MS: 512 (M+H)⁺, from tert-butyl (3RS,4RS)-4-[4-[2-(4-methoxy-benzoyloxy)-ethoxy]-phenyl]-3-(naphthalen-2-ylmethoxy)-piperidine-1-carboxylate;

2) (3RS,4RS)-2-[4-(3-napthalen-2-ylmethoxy-piperidin-4-yl)-phenoxy]-ethyl 2-chloro-benzoate hydrochloride as a colourless solid, MS: 516 (M+H)⁺, from tert-butyl (3RS,4RS)-4-[4-[2-(2-chloro-benzoyloxy)-ethoxy]-phenyl]-3-(naphthalen-2-ylmethoxy)-piperidine-1-carboxylate;

3) (3RS,4RS)-2-[4-[3-(naphthalen-2-yloxy)-piperidin-4-yl]-phenoxy]-ethyl benzoate as a colourless, amorphous solid, MS: 340 (M-naphthylmethyl)⁺, from tert-butyl (3RS,4RS)-4-[4-(2-benzoyloxy-ethoxy)-phenyl]-3-(naphthalen-2-ylmethoxy)-piperidine-1-carboxylate;

4) (3RS,4RS)-2-[4-[3-(naphthalen-2-ylmethoxy)-piperidin-4-yl]-phenoxy]-ethyl 2-benzoyloxymethyl-benzoate hydrochloride as a colourless solid, MS: 616 (M+H)⁺, from tert-butyl (3RS,4RS)-4-[4-[2-(2-benzoyloxymethyl-benzoyloxy)-ethoxy]-phenyl]-3-(naphthalen-2-ylmethoxy)-piperidine-1-carboxylate;

5) (3RS,4RS)-3-(naphthalen-2-ylmethoxy)-4-[4-(2-phenylsulphanyl-ethoxy)-phenyl]-piperidine hydrochloride as a colourless solid, MS: 470 (M+H)⁺, from tert-butyl (3RS,4RS)-3-(naphthalen-2-ylmethoxy)-4-[4-(2-phenylsulphanyl-ethoxy)-phenyl]-piperidine-1-carboxylate;

6) (3RS,4RS)-3-naphthalen-2-ylmethoxyxy-4-[4-(2-phenylsulphonyl-ethoxy)-phenyl]-piperidine as a yellowish foam, MS: 502 (M+H)⁺, from tert-butyl (3RS,4RS)-3-(naphthalen-2-ylmethoxy)-4-[4-(2-phenylsulphonyl-ethoxy)-phenyl]-piperidine-1-carboxylate;

7) (3RS,4RS)-N-[2-[4-[3-(naphthalen-2-yloxy)-piperidin-4-yl]-phenoxy]-ethyl-benzamide as a colourless, amorphous solid, MS: 481 (M+H)⁺, from tert-butyl (3RS,4RS)-4-[4-(2-benzoylamino-ethoxy)-phenyl]-3-(naphthalen-2-ylmethoxy)-piperidine-1-carboxylate;

8) (3RS,4RS)-3-(naphthalen-2-ylmethoxy)-4-[4-(2-[1,2,4]triazol-1-yl-ethoxy)-phenyl]-piperidine hydrochloride as a white powder, MS: 428 (M)⁺, from tert-butyl (3RS,4RS)-3-naphthalen-2-ylmethoxy-4-[4-(2-[1,2,4]triazol-1-yl-ethoxy)-phenyl]-piperidine-1-carboxylate;

9) (3RS,4RS)-4-[4-(2-benzyloxy-ethoxy)-phenyl]-3-(naphthalen-2-ylmethoxy)-piperidine, MS: 468 (M+H)⁺, from tert-butyl (3RS,4RS)-4-[4-(2-benzyloxy-ethoxy)-phenyl]-3-(naphthalen-2-ylmethoxy)-piperidine-1-carboxylate.

The BOC derivatives used as the starting materials were prepared as follows:

a) A solution of 150 mg (0.314 mmol) of tert-butyl (3RS,4RS)-4-[4-(2-hydroxy-ethoxy)-phenyl]-3-(naphthalen-2-ylmethoxy)-piperidine-1-carboxylate, 3.7 mg (0.031 mmol, 0.1 eq.) of 4-dimethylaminopyridine, 65.9 mg (0.375 mmol, 1.2 eq.) of 4-methoxy-benzoyl chloride and 51.7 µl of triethylamine in 10 ml of methylene chloride was stirred at room temperature for 15 hours. This reaction solution was poured into 50 ml of an ice/water mixture and extracted three times with ethyl acetate. The organic phases were washed once with water and once with saturated sodium chloride solution, dried over magnesium sulphate, evaporated under reduced pressure and dried in a high vacuum. The crude product (208 mg) was separated on silica gel using a 95:5 mixture of hexane and acetone as the eluent. There were obtained 104 mg (51% of theory) of tert-butyl (3RS,4RS)-4-[4-[2-(4-methoxy-benzoyloxy)-ethoxy]-phenyl]-3-(naphthalen-2-ylmethoxy)-piperidine-1-carboxylate as a colourless oil; MS: 612 (M+H)⁺.

(b) In an analogous manner to that described in Example 22(k), by acylating (3RS,4RS)-4-[4-(2-hydroxy-ethoxy)-phenyl]-3-(naphthalen-2-ylmethoxy)-piperidine-1-carboxylate with 2-chlorobenzoyl chloride there was obtained tert-butyl (3RS,4RS)-4-[4-[2-(2-chloro-benzoyloxy)-ethoxy]-phenyl]-3-(naphthalen-2-ylmethoxy)-piperidine-1-carboxylate as a yellow oil; MS: 616 (M+H)⁺.

c) In an analogous manner to that described in Example 22(k), by acylating tert-butyl (3RS,4RS)-4-[4-(2-hydroxy-ethoxy)-phenyl]-3-(naphthalen-2-ylmethoxy)-piperidine-1-carboxylate with benzoyl chloride there was obtained tert-butyl (3RS,4RS)-4-[4-(2-benzoyloxy-ethoxy)-phenyl]-3-(naphthalen-2-ylmethoxy)-piperidine-1-carboxylate as a colourless, amorphous solid; $R_f$: 0.61 (SiO₂, hexane:acetone=95:5).

(d) In an analogous manner to that described in Example 22(k), by acylating tert-butyl (3RS,4RS)-4-[4-(2-hydroxy-ethoxy)-phenyl]-3-(naphthalen-2-ylmethoxy)-piperidine-1-carboxylate with 2-chlorocarbonyl-benzyl benzoate there was obtained tert-butyl (3RS,4RS)-4-[4-[2-(2-benzoyloxymethyl-benzoyloxy)-ethoxy]-phenyl]-3-(naphthalen-2-ylmethoxy)-piperidine-1-carboxylate as a colourless solid; MS: 716 (M+H)⁺.

(e) In an analogous manner to that described in Example 33(a), from tert-butyl (3RS,4RS)-4-[4-(2-hydroxy-ethoxy)-phenyl]-3-(naphthalen-2-ylmethoxy)-piperidine-1-carboxylate and diphenyl sulphide there was obtained tert-butyl (3RS,4RS)-3-(naphthalen-2-ylmethoxy)-4-[4-(2-phenylsulphanyl-ethoxy)-phenyl]-piperidine-1-carboxylate as a colourless solid; MS: 570 (M+H)⁺.

(f) In an analogous manner to that described in Example 33(c), by oxidizing tert-butyl (3RS,4RS)-3-(naphthalen-2-ylmethoxy)-4-[4-(2-phenylsulphanyl-ethoxy)-phenyl]-piperidine-1-carboxylate there was obtained tert-butyl (3RS,4RS)-3-(naphthalen-2-ylmethoxy)-4-[4-(2-phenylsulphonyl-ethoxy)-phenyl]-piperidine-1-carboxylate as a colourless foam; MS: 619 (M+NH₄)⁺.

(g) A solution of 478 mg (1.00 mmol) of tert-butyl (3RS,4RS)-4-[4-(2-hydroxy-ethoxy)-phenyl]-3-(naphthalen-2- ylmethoxy)-piperidine-1-carboxylate and 93 ml of mesyl chloride in 5 ml of pyridine was stirred at room temperature for 2 hours. Subsequently, the reaction solution was poured into 50 ml of an ice/water mixture and extracted three times with methylene chloride. The organic phases were washed twice with water, dried over magnesium sulphate, evaporated under reduced pressure and dried in a high vacuum. This yielded 569 mg of crude tert-butyl (3RS,4RS)-4-[4-(2-methylsulphonyloxy-ethoxy)-phenyl]-3-(naphthalen-2-ylmethoxy)-piperidine-1-carboxylate, which was used in the following step without further purification and characterization.

(h) A mixture of 569 mg of crude tert-butyl (3RS,4RS)-4-[4-(2-methylsulphonyloxy-ethoxy)-phenyl]-3-(naphthalen-2-ylmethoxy)-piperidine-1-carboxylate and 650 mg of sodium azide in 20 ml of dimethyl sulphoxide was stirred at 80° C. for 3.5 hours. Subsequently, this reaction solution was poured into 50 ml of an ice/water mixture and extracted three times with ethyl acetate. The organic phases were washed with water, dried over magnesium sulphate, evaporated under reduced pressure and dried in a high vacuum. The yellow oil (670 mg) was separated on silica gel using a 9:1 mixture of hexane and ethyl acetate as the eluent. There were obtained 271 mg (54% of theory over both steps) of tert-butyl (3RS,4RS)-4-[4-(2-azido-ethoxy)-phenyl]-3-(naphthalen-2-ylmethoxy)-piperidine-1-carboxylate as a colourless solid; MS: 503 (M+H)+.

(i) A mixture of 115.9 mg (0.231 mmol) of tert-butyl (3RS,4RS)-4-[4-(2-azido-ethoxy)-phenyl]-3-(naphthalen-2-ylmethoxy)-piperidine-1-carboxylate, 87.4 mg (0.330 mmol, 1.43 eq.) of triphenylphosphine and 6.1 μl (6.1 mg, 0.339 mmol, 1.47 eq.) of deionized water was stirred at room temperature for 4 hours. Subsequently, 3 ml of acetic acid were added and the mixture was stirred at room temperature for 17 hours. This reaction mixture was poured into an ice/water mixture, made basic with saturated sodium hydrogen carbonate solution and extracted three times with ethyl acetate. The organic phases were washed once with water and once with saturated sodium chloride solution, dried over magnesium sulphate, evaporated under reduced pressure and dried in a high vacuum. This yielded 192.3 mg of crude tert-butyl (3RS,4RS)-4-[4-(2-amino-ethoxy)-phenyl]-3-(naphthalen-2-ylmethoxy)-piperidine-1-carboxylate, which was used in the following reaction without further purification; R$_f$: 0.10 (SiO$_2$, methylene chloride:acetone=95:5+0.1% ammonia)

j) A solution of 192.4 mg of crude tert-butyl (3RS,4RS)-4-[4-(2-amino-ethoxy)-phenyl]-3-(naphthalen-2-ylmethoxy)-piperidine-1-carboxylate in 3 ml of methylene chloride was treated at 0° C. with 51.7 ml of triethylamine and 64.9 mg (0.462 mmol, 2.0 eq.) of benzoyl chloride and the mixture was stirred at 0° C. for 0.75 hr and at room temperature for 3 hours. The reaction mixture was poured into an ice/water mixture, made basic with saturated sodium hydrogen carbonate solution and extracted three times with ethyl acetate. The organic phases were washed once with water and once with saturated sodium chloride solution, dried over magnesium sulphate, evaporated under reduced pressure and dried in a high vacuum. The colourless oil was separated on silica gel using a 95:5 mixture of methylene chloride and acetone as the eluent. There were obtained 44.9 mg (33% of theory) of tert-butyl (3RS,4RS)-4-[4-(2-benzoylamino-ethoxy)-phenyl]-3-(naphthalen-2-ylmethoxy)-piperidine-1-carboxylate in the form of a light yellow oil; MS: 581 (M+H)+.

(k) A solution of 110 mg (0.2 mmol) of crude tert-butyl (3RS,4RS)-4-[4-(2-methylsulphonyloxy-ethoxy)-phenyl]-3-(naphthalen-2-ylmethoxy)-piperidine- 1-carboxylate in 5 ml of dimethylformamide was treated with 70 mg (1.0 mmol) of 1,2,4-triazole sodium salt and the reaction mixture was heated to 100° C. for 6 hours. Subsequently, the mixture was cooled to room temperature and the dimethylformamide was distilled off in an oil pump vacuum. The residue was taken up in 10 ml of methylene chloride, washed with 2 ml of water, the organic phase was dried over sodium sulphate and evaporated under reduced pressure. The residue was chromatographed on silica gel using a 95:5:0.1 mixture of methylene chloride, methanol and ammonia as the eluent. There were obtained 90 mg (85% of theory) of tert-butyl (3RS,4RS)-3-naphthalen-2-ylmethoxy-4-[4-(2-[1,2,4] triazol-1-yl-ethoxy)-phenyl]-piperidine-1-carboxylate as a colourless oil; MS: 529 (M+H)+.

(l) In analogy to the procedure described in Example 3(c), by alkylating tert-butyl (3RS,4RS)-4-[4-(2-hydroxy-ethoxy)-phenyl]-3-(naphthalen-2-ylmethoxy)-piperidine-1-carboxylate with benzyl bromide there was obtained tert-butyl (3RS,4RS)-4-[4-(2-benzyloxy-ethoxy)-phenyl]-3-(naphthalen-2-ylmethoxy)-piperidine-1-carboxylate; MS: 568 (M+H)+.

EXAMPLE 55

The following compounds were obtained in an analogous manner to that described in Example 22(l):

1) (3RS,4RS)-2-{4-[3-(4-Hydroxy-naphthalen-2-ylmethoxy)-piperidin-4-yl]-phenoxy}-ethyl 2-chloromethyl-benzoate as a colourless oil from tert-butyl (3RS,4RS)-4-[2-(2-chloromethyl-benzoyloxy)-ethoxy]-phenyl]-3-[4-(2-trimethylsilanyl-ethoxymethoxy)-naphthalen-2-ylmethoxy]-piperidine-1-carboxylate by simultaneous cleavage of the BOC and acetal groups;

2) (3RS,4RS)-2-[4-[3-[4-(2-methoxy-benzyloxy)-naphthalen-2-ylmethoxy]-piperidin-4-yl]-phenoxy]-ethyl benzoate hydrochloride as a colourless solid, MS: 618 (M+H)+, from tert-butyl (3RS,4RS)-4-[4-(2-benzoyloxy-ethoxy)-phenyl]-3-[4-(2-methoxy-benzyloxy)-naphthalen-2-ylmethoxy]-piperidine-1-carboxylate;

3) (3RS,4RS)-4-[4-(2-benzyloxy-ethoxy)-phenyl]-3-(4-benzyloxy-naphthalen-2-ylmethoxy)-piperidine, MS: 574 (M+H)+, from tert-butyl (3RS,4RS)-4-[4-(2-benzyloxy-ethoxy)-phenyl]-3-(4-benzyloxy-naphthalen-2-ylmethoxy)-piperidine-1-carboxylate.

The BOC derivatives used as the starting materials were prepared as follows:

(a) In an analogous manner to that described in Example 44(e), by alkylating a mixture of tert-butyl (3RS,4RS)-3-hydroxy-4-[4-[2-[(RS)- and -[(SR)-tetrahydro-pyran-2-yloxy]-ethoxy]-phenyl]-piperidine-1-carboxylate with 3-chloromethyl-1-(2-trimethylsilanyl-ethoxymethoxy)-naphthalene there was obtained a mixture of tert-butyl (3RS,4RS)-4-[4-[2-[(RS)- and -[(SR)-tetrahydro-pyran-2-yl]-ethoxy]-phenyl]-3-[4-(2-trimethylsilanyl-ethoxymethoxy)-naphthalen-2-ylmethoxy]-piperidine-1-carboxylate as a colourless oil; MS: 725 (M+NH$_4$)+.

(b) In an analogous manner to that described in Example 53(c), from a mixture of tert-butyl (3RS,4RS)-4-[4-[2-[(RS)- and -[(SR)-tetrahydro-pyran-2-yl]-ethoxy]-phenyl]-3-[4-(2-trimethylsilanyl-ethoxymethoxy)-naphthalen-2-ylmethoxy]-piperidine-1-carboxylate there was obtained tert-butyl (3RS,4RS)-4-[4-(2-hydroxy-ethoxy)-phenyl]-3-[4-(2-trimethylsilanyl-ethoxymethoxy)-naphthalen-2-ylmethoxy]-piperidine-1-carboxylate as a colourless solid; MS: 624 (M+H)+.

(c) In an analogous manner to that described in Example 22(k), by acylating tert-butyl (3RS,4RS)-4-[4-(2-hydroxyethoxy)-phenyl]-3-[4-(2-trimethylsilanyl-ethoxymethoxy)-naphthalen-2-ylmethoxy]-piperidine-1-carboxylate with 2-chloromethyl-benzoyl chloride there was obtained tert-butyl (3RS,4RS)-4-[4-[2-(2-chloromethyl-benzoyloxy)-ethoxy]-phenyl]-3-[4-(2-trimethylsilanyl-ethoxymethoxy)-naphthalen-2-ylmethoxy]-piperidine-1-carboxylate as a colourless solid; MS: 776 (M+H)$^+$.

(d) 200 mg (0.28 mmol) of a mixture of tert-butyl (3RS,4RS)-4-[4-[2-[(RS)- and -[(SR)-tetrahydro-pyran-2-yl]-ethoxy]-phenyl]-3-[4-(2-trimethylsilanyl-ethoxy-methoxy)-naphthalen-2-ylmethoxy]-piperidine-1-carboxylate were dissolved in 7.6 ml 0.1M hydrogen chloride in methanol and the mixture was stirred at room temperature for 2 hours. Subsequently, a further 0.36 ml of 2M hydrogen chloride in methanol was added and the mixture was stirred at room temperature for a further 2 hours. This reaction solution was poured into semi-saturated sodium hydrogen carbonate solution and extracted three times with ethyl acetate. The organic phases were washed once with water and once with saturated sodium chloride solution, dried over magnesium sulphate, evaporated under reduced pressure and dried in a high vacuum. The yellowish oil (204 mg) was separated on silica gel using a 1:1 mixture of hexane and ethyl acetate (extracted against concentrated ammonia). This yielded 111 mg (80% of theory) of tert-butyl (3RS,4RS)-4-[4-(2-hydroxy-ethoxy)-phenyl]-3-(4-hydroxy-naphthalen-2-ylmethoxy)-piperidine-1-carboxylate in the form of a colourless oil; $R_f$: 0.26 (SiO$_2$, hexane:ethyl acetate=1:1).

(e) In an analogous manner to that described in Example 44(e), by alkylating tert-butyl (3RS,4RS)-4-[4-(2-hydroxy-ethoxy)-phenyl]-3-(4-hydroxy-naphthalen-2-ylmethoxy)-piperidine-1-carboxylate with 2-methoxybenzyl chloride there was obtained tert-butyl (3RS,4RS)-4-[4-(2-hydroxy-ethoxy)-phenyl]-3-[4-(2-methoxy-benzyloxy)-naphthalen-2-ylmethoxy]-piperidine-1-carboxylate as a colourless oil; MS: 652 (M+K)$^+$.

(f) In an analogous manner to that described in Example 22(k), by acylating tert-butyl (3RS,4RS)-4-[4-(2-hydroxy-ethoxy)-phenyl]-3-[4-(2-methoxy-benzyloxy)-naphthalen-2-ylmethoxy]-piperidine-1-carboxylate with benzoyl chloride there was obtained tert-butyl (3RS,4RS)-4-[4-(2-benzoyloxy-ethoxy)-phenyl]-3-[4-(2-methoxy-benzyloxy)-naphthalen-2-ylmethoxy]-piperidine-1-carboxylate as a colourless oil; MS: 736 (M+H)$^+$.

(g) In an analogous manner to that described in Example 1(g), by two-fold alkylation of tert-butyl (3RS,4RS)-4-[4-(2-hydroxy-ethoxy)-phenyl]-3-(4-hydroxy-naphthalen-2-ylmethoxy)-piperidine-1-carboxylate with benzyl bromide there was obtained tert-butyl (3RS,4RS)-4-[4-(2-benzyloxy-ethoxy)-phenyl]-3-(4-benzyloxy-naphthalen-2-ylmethoxy)-piperidine-1-carboxylate.

EXAMPLE 56

The following compounds were obtained in an analogous manner to that described in Example 22(l) by simultaneous cleavage of the BOC and SEM groups using acid:

1) (3RS,4RS)-2-[4-(3-Naphthalen-2-ylmethoxy-piperidin-4-yl)-phenoxy]-ethyl 4-hydroxy-benzoate hydrochloride as a colourless solid, MS: 498 (M+H)$^+$, from tert-butyl (3RS,4RS)-3-(naphthalen-2-ylmethoxy)-4-[4-[2-[4-(2-trimethylsilanyl-ethoxymethoxy)-benzoyloxy]-ethoxyl-phenyl]-piperidine-1-carboxylate;

2) (3RS,4RS)-3-[4-[4-(2-benzyloxy-ethoxy)-phenyl]-piperidin-3-yloxymethyl}-naphthalen-1-ol, MS: 484 (M+H)$^+$, from tert-butyl (3RS,4RS)-4-[4-(2-benzyloxy-ethoxy)-phenyl]-3-(4-hydroxy-naphthalen-2-ylmethoxy)-piperidine-1-carboxylate.

The BOC derivatives used as the starting materials were prepared as follows:

(a) In an analogous manner to that described under Example 24(l), from tert-butyl (3RS,4RS)-4-[4-(2-hydroxy-ethoxy)-phenyl]-3-(naphthalen-2-ylmethoxy)-piperidine-1-carboxylate and 4-(2-trimethylsilanyl-ethoxymethoxy)-benzoic acid using N-ethyl-N'-(3-dimethylaminopropyl)-carbodiimide hydrochloride (EDC) as the condensation agent there was obtained tert-butyl (3RS,4RS)-3-(naphthalen-2-ylmethoxy)-4-[4-[2-[4-(2-trimethylsilanyl-ethoxymethoxy)-benzoyloxy]-ethoxy]-phenyl]-piperidine-1-carboxylate as a colourless, amorphous solid; MS: 728 (M+H)$^+$.

(b) In an analogous manner to that described in Example 1(g), by alkylating tert-butyl (3RS,4RS)-4-[4-(2-hydroxy-ethoxy)-phenyl]-3-[4-(2-trimethylsilanyl-ethoxymethoxy)-naphthalen-2-ylmethoxy]-piperidine-1-carboxylate with benzyl bromide there was obtained tert-butyl (3RS,4RS)-4-[4-(2-benzyloxy-ethoxy)-phenyl]-3-(4-hydroxy-naphthalen-2-ylmethoxy)-piperidine-1-carboxylate.

EXAMPLE 57

(a) In an analogous manner to that described in Example 44(e), by alkylating tert-butyl (3RS,4RS)-3-hydroxy-4-(4-hydroxy-phenyl)-piperidine-1-carboxylate with 2-(3-bromo-propoxy)-tetrahydro-pyran there was obtained a mixture of tert-butyl (3RS,4RS)-3-hydroxy-4-[4-[3-[(RS)- and -[(SR)-tetrahydro-pyran-2-yloxy]-propoxy]-phenyl]-piperidine-1-carboxylate as a colourless solid; $R_f$: 0.23 (SiO$_2$, hexane:ethyl acetate=4:1).

(b) Alkylation of a mixture of tert-butyl (3RS,4RS)-3-hydroxy-4-[4-[3-[(RS)- and -[(SR)-tetrahydro-pyran-2-yloxy]-propoxy]-phenyl]-piperidine-1-carboxylate with 2-bromomethylnaphthalene analogously to the procedure described in Example 22(i) gave a mixture of tert-butyl (3RS,4RS)-3-(naphthalen-2-ylmethoxy)-4-[4-[3-[(RS)- and -[(SR)-tetrahydro-pyran-2-yloxy]-propoxy]-phenyl]-piperidine-1-carboxylate as a yellow oil; $R_f$: 0.35 (SiO$_2$, hexane:acetone=4:1).

(c) A solution of 5.22 g of the crude mixture of tert-butyl (3RS,4RS)-3-(naphthalen-2-ylmethoxy)-4-[4-[3-[(RS)- and -[(SR)-tetrahydro-pyran-2-yloxy]-propoxy]-phenyl]-piperidine-1-carboxylate in 30 ml of tetrahydrofuran and 30 ml of 2N hydrochloric acid was stirred at room temperature for 14 hours and at 40° C. for 2 hours. The tetrahydrofuran was subsequently distilled off under reduced pressure and the residual aqueous phase was extracted three times with methylene chloride. The organic phase was dried over magnesium sulphate and thereafter the solvent was distilled off under reduced pressure. The resulting yellow oil (2.9 g) was chromatographed on silica gel using a 9:1 mixture of methylene chloride and ethyl acetate as the eluent. There were obtained 1.08 g (34% of theory over both steps) of tert-butyl (3RS,4RS)-4-[4-(3-hydroxy-propoxy)-phenyl]-3-(naphthalen-2-ylmethoxy)-piperidine-1-carboxylate in the form of a white amorphous solid; MS: 491 (M)$^+$.

(d) Reaction of tert-butyl (3RS,4RS)-4-[4-(3-hydroxy-propoxy)-phenyl]-3-(naphthalen-2-ylmethoxy)-piperidine-1-carboxylate with mesyl chloride analogously to the procedure described in Example 54(h) gave tert-butyl (3RS,4RS)-4-[4-(3-methylsulphonyloxy-propoxy)-phenyl]-3-(naphthalen-2-yl-methoxy)-piperidine-1-carboxylate as a yellow oil; $R_f$: 0.50 (SiO$_2$, hexane:ethyl acetate=1:1).

(e) A solution of 850 mg of crude tert-butyl (3RS,4RS)-4-[4-(3-methylsulphonyloxy-propoxy)-phenyl]-3-(naphthalen-2-ylmethoxy)-piperidine-1-carboxylate in 6.1 ml (48.98 mmol, 32.4 eq.) of a 33% methylamine solution in ethanol was stirred at room temperature for 14 hours.

Thereupon, the solution was evaporated under reduced pressure. The yellow solid (932 mg) was chromatographed on silica gel using a 90:10:0.1 mixture of methylene chloride, methanol and ammonia as the eluent. This yielded 610 mg (80% of theory over both steps) of tert-butyl (3RS,4RS)-4-[4-(3-methylamino-propoxy)-phenyl]-3-(naphthalen-2-ylmethoxy)-piperidine-1-carboxylate as a colourless solid; MS: 505 (M+H)$^+$.

(f) Acylation of tert-butyl (3RS,4RS)-4-[4-(3-methylamino-propoxy)-phenyl]-3-(naphthalen-2-ylmethoxy)-piperidine-1-carboxylate with benzoyl chloride analogously to the procedure described in Example 22(k) gave tert-butyl (3RS,4RS)-4-[4-[3-(benzoyl-methyl-amino)-propoxy]-phenyl]-3-(naphthalen-2-ylmethoxy)-piperidine-1-carboxylate as a colourless oil; MS: 609 (M+H)$^+$.

(g) In an analogous manner to the procedure described in Example 22(l), from tert-butyl (3RS,4RS)-4-[4-[3-(benzoyl-methyl-amino)-propoxy]-phenyl]-3-(naphthalen-2-ylmethoxy)-piperidine-1-carboxylate by cleavage of the BOC group there was obtained (3RS,4RS)-N-methyl-N-[3-[4-[3-(naphthalen-2-yloxy)-piperidine-4-yl]-phenoxy]-propyl]-benzamide as a colourless solid; MS: 509 (M+H)$^+$.

EXAMPLE 58

The following compounds were obtained in analogy to the procedure described in Example 8(g) by cleavage of the BOC group using hydrochloric acid in methanol:

1) (3RS,4RS)-2-[4-(3-Naphthalen-2-ylmethoxy-piperidin-4-yl)-phenoxy]-ethyl pyridine-3-carboxylate hydrochloride as a colourless solid, MS: 483 (M+H)$^+$, from 2-[4-[1-tert-butoxycarbonyl-3-(naphthalen-2-ylmethoxy)-piperidin-4-yl]-phenoxy}-ethyl (3RS,4RS)-nicotinate;

2) (3RS,4RS)-2-[4-(3-naphthalen-2-ylmethoxy-piperidin-4-yl)-phenoxy]-ethyl 1,3-benzodioxole-5-carboxylate hydrochloride as a colourless solid, MS: 526 (M+H)$^+$, from tert-butyl (3RS,4RS)-4-{4-[2-(benzo[1,3]dioxol-5-carbonyloxy)-ethoxy]-phenyl}-3-(naphthalen-2-ylmethoxy)-piperidine-1-carboxylate;

3) (3RS,4RS)-2-[4-(3-naphthalen-2-ylmethoxy-piperidin-4-yl)-phenoxy]-ethyl thiophene-3-carboxylate hydrochloride as a colourless solid, MS: 488 (M+H)$^+$, from tert-butyl (3RS,4RS)-3-(naphthalen-2-ylmethoxy)-4-{4-[2-(thiophene-3-carbonyloxy)-ethoxy]-phenyl}-piperidine-1-carboxylate;

4) (3RS,4RS)-2-[4-(3-naphthalen-2-ylmethoxy-piperidin-4-yl)-phenoxy]-ethyl thiophene-2-carboxylate hydrochloride as a colourless solid, MS: 488 (M+H)$^+$, from tert-butyl (3RS,4RS)-3-(naphthalen-2-ylmethoxy)-4-[4-[2-(thiophene-2-carbonyloxy)-ethoxy]-phenyl]-piperidine-1-carboxylate;

5) 2-[(3RS,4RS)-4-[3-(naphthalen-2-ylmethoxy)-piperidin-4-yl]-phenoxy]-ethyl furan-3-carboxylate hydrochloride as a colourless solid, MS: 472 (M+H)$^+$, from tert-butyl 4-[4-[2-(furan-3-carbonyloxy)-ethoxy]-phenyl]-3-(naphthalen-2-ylmethoxy)-piperidin-1-carboxylate;

6) 2-[(3RS,4RS)-4-[3-(naphthalen-2-ylmethoxy)-piperidin-4-yl]-phenoxy]-ethyl furan-2-carboxylate hydrochloride as a colourless solid, MS: 472 (M+H)$^+$, from tert-butyl 4-[4-[2-(furan-2-carbonyloxy)-ethoxy]-phenyl}-3-(naphthalen-2-ylmethoxy)-piperidine-1-carboxylate;

7) a mixture of (3RS,4RS)-2-[4-(2-naphthalen-2-ylmethoxy-piperidin-4-yl)-phenoxy]-ethyl (RS)- and (SR)-methoxy-phenylacetate hydrobromide as a brownish solid, MS: 526 (M+H)$^+$, from a mixture of tert-butyl (3RS,4RS)-4-[4-[2-[(RS)- and (SR)-methoxyphenyl-acetoxy]ethoxy]phenyl]-3-(naphthalen-2-ylmethoxy)-piperidine-1-carboxylate;

8) (3RS,4RS)-2-[4-(3-naphthalen-2-yl-methoxy-piperidin-4-yl)-phenoxy]-ethyl 2-methylsulphanyl-benzoate hydrochloride as a beige coloured solid, MS: 528 (M+H)$^+$, from tert-butyl (3RS,4RS)-4-[4-[2-(2-methylsulphanyl-benzoyloxy)-ethoxy]-phenyl]-3-(naphthalen-2-ylmethoxy)-piperidine-1-carboxylate;

9) (3RS,4RS)-2-[4-(2-naphthalen-2-ylmethoxy-piperidin-4-yl)-phenoxy]-ethyl (RS)- and (SR)-2-methylsulphinyl-benzoate hydrochloride as a colourless solid, MS: 544 (M+H)$^+$, from tert-butyl (3RS,4RS))-4-{4-[2-[(RS)- and (SR)-2-methylsulphinyl-benzoyloxy]-ethoxy]-phenyl}-3-(naphthalen-2-ylmethoxy)-piperidine-1-carboxylate.

The BOC derivatives used as the starting materials were prepared as follows in an analogous manner to that described under Example 24(l) using N-ethyl-N'-(3-dimethylaminopropyl)-carbodiimide hydrochloride (EDC) as the condensation agent:

(a) 2-[4-[1-tert-Butoxycarbonyl-3-(naphthalen-2-ylmethoxy)-piperidin-4-yl]-phenoxy}-ethyl (3RS,4RS)-nicotinate as a colourless solid, MS: 481 (M-C$_4$H$_9$COO)$^+$, from tert-butyl (3RS,4RS)-4-[4-(2-hydroxy-ethoxy)-phenyl]-3-(naphthalen-2-ylmethoxy)-piperidine-1-carboxylate and pyridine-3-carboxylic acid.

(b) tert-Butyl (3RS,4RS)-4-{4-[2-(benzo[1,3]dioxol-5-carbonyloxy)-ethoxy]-phenyl}-3-(naphthalen-2-ylmethoxy)-piperidine-1-carboxylate as a colourless solid, MS: 626 (M+H)$^+$, from tert-butyl (3RS,4RS)-4-[4-(2-hydroxy-ethoxy)-phenyl]-3-(naphthalen-2-ylmethoxy)-piperidine-1-carboxylate and piperonylic acid.

(c) tert-Butyl (3RS,4RS)-3-(naphthalen-2-ylmethoxy)-4-{4-[2-(thiophen-3-carbonyloxy)-ethoxy]-phenyl}-piperidine-1-carboxylate as a colourless solid, MS: 587 (M)$^+$, from tert-butyl (3RS,4RS)-4-[4-(2-hydroxy-ethoxy)-phenyl]-3-(naphthalen-2-ylmethoxy)-piperidine-1-carboxylate and thiophene-3-carboxylic acid.

(d) tert-Butyl (3RS,4RS)-3-(naphthalen-2-ylmethoxy)-4-[4-[2-(thiophen-2-carbonyloxy)-ethoxy]-phenyl]-piperidine-1-carboxylate as a colourless solid, MS: 588 (M+H)$^+$, from tert-butyl (3RS,4RS)-4-[4-(2-hydroxy-ethoxy)-phenyl]-3-(naphthalen-2-ylmethoxy)-piperidine-1-carboxylate and thiophene-2-carboxylic acid.

(e) tert-Butyl 4-[4-[2-(furan-3-carbonyloxy)-ethoxy]-phenyl]-3-(naphthalen-2-ylmethoxy)-piperidine-1-carboxylate as a colourless solid, MS: 572 (M+H)$^+$, from tert-butyl (3RS,4RS)-4-[4-(2-hydroxy-ethoxy)-phenyl]-3-(naphthalen-2-ylmethoxy)-piperidine-1-carboxylate and furan-3-carboxylic acid.

(f) tert-Butyl 4-[4-[2-(furan-2-carbonyloxy)-ethoxy]-phenyl}-3-(naphthalen-2-ylmethoxy)-piperidine-1-carboxylate as a colourless solid, MS: 572 (M+H)$^+$, from tert-butyl (3RS,4RS)-4-[4-(2-hydroxy-ethoxy)-phenyl]-3-(naphthalen-2-ylmethoxy)-piperidine-1-carboxylate and furan-2-carboxylic acid.

(g) tert-Butyl (3RS,4RS)-4-[4-[2-(methoxy-phenyl-acetoxy)-ethoxy]-phenyl]-3-(naphthalen-2-ylmethoxy)-piperidine-1-carboxylate as a colourless oil, MS: 648 (M+Na)$^+$, from tert-butyl (3RS,4RS)-4-[4-(2-hydroxy-ethoxy)-phenyl]-3-(naphthalen-2-ylmethoxy)-piperidine-1-carboxylate and (RS)-α-methoxy-phenylacetic acid.

(h) tert-Butyl (3RS,4RS)-4-[4-[2-(2-methylsulphanyl-benzoyloxy)-ethoxy]-phenyl]-3-(naphthalen-2-ylmethoxy)-piperidine-1-carboxylate as a colourless solid, MS: 628 (M+H)$^+$, from tert-butyl (3RS,4RS)-4-[4-(2-hydroxy-ethoxy)-phenyl]-3-(naphthalen-2-ylmethoxy)-piperidine-1-carboxylate and 2-methylsulphanylbenzoic acid.

(i) A solution of 170 mg (0.8 mmol) of sodium metaperiodate in 2 ml of water was added to a solution of 250 mg (0.4 mmol) of tert-butyl (3RS,4RS)-4-[4-[2-(2-methylsulphanyl-benzoyloxy)-ethoxy]-phenyl]-3-(naphthalen-2-ylmethoxy)-piperidine-1-carboxylate in 25 ml of methanol. The resulting reaction mixture was stirred at 50° C. for 8 hours. Thereafter, the solvent was distilled off under reduced pressure, the residue was partitioned between ethyl acetate and water, the organic phase was dried over sodium sulphate and evaporated under reduced pressure. There were obtained 230 mg (90% of theory) of crude tert-butyl (3RS,4RS))-4-{4-[2-[(RS)- and (SR)-2-methylsulphinyl-benzoyloxy]-ethoxy]-phenyl}-3-(naphthalen-2-ylmethoxy)-piperidine-1-carboxylate as a colourless solid; MS : 644 (M+H)$^+$.

EXAMPLE 59

The following compounds were obtained in an analogous manner to that described in Example 22(l) by cleavage of the BOC group:

1) (3RS,4RS)-4-[4-(3-Morpholin-4-yl-propoxy)-phenyl]-3-(naphthalen-2-ylmethoxy)-piperidine as a colourless solid, MS: 461 (M+H)$^+$, from tert-butyl (3RS,4RS)-4-[4-(3-morpholin-4-yl-propoxy)-phenyl]-3-(naphthalen-2-ylmethoxy)-piperidine-1-carboxylate;
2) (3RS,4RS)-3-[4-(3-naphthalen-2-ylmethoxy-piperidin-4-yl)-phenoxy]-propyl 2,2-dimethyl-propionate as a colourless, amorphous solid, MS: 476 (M+H)$^+$, from tert-butyl (3RS,4RS)-4-[4-[3-(2,2-dimethyl-propionyloxy)-propoxy]-phenyl]-3-(naphthalen-2-ylmethoxy)-piperidine-1-carboxylate;
3) (3RS,4RS)-3-[4-(3-napthalen-2-ylmethoxy-piperidin-4-yl)-phenoxy]-propyl benzoate hydrochloride as a colourless solid, MS: 496 (M+H)$^+$, from tert-butyl (3RS,4RS)-4-[4-(3-benzoyloxy-propoxy)-phenyl]-3-(naphthalen-2-ylmethoxy)-piperidine-1-carboxylate;
4) (3RS,4RS)-4-(4-benzyloxy-phenyl)-3-(naphthalen-2-yloxy)-piperidine as a colourless, amorphous solid, MS: 424 (M+H)$^+$, from tert-butyl (3RS,4RS)-4-(4-benzyloxy-phenyl)-3-(naphthalen-2-yloxy)-piperidine-1-carboxylate;
5) (3RS,4RS)-3-(2-methoxy-benzyloxy)-4-(4-naphthalen-2-ylmethoxy-phenyl)-piperidine hydrochloride as a colourless solid, MS: 454 (M+H)$^+$, from tert-butyl (3RS,4RS)-3-(2-methoxy-benzyloxy)-4-[4-(naphthalen-2-ylmethoxy)-phenyl]-piperidine-1-carboxylate The BOC derivatives used as the starting materials were prepared as follows:

(a) A solution of 200 mg (0.35 mmol) of tert-butyl 3RS,4RS)-4-[4-(3-methylsulphonyloxy-propoxy)-phenyl]-3-(naphthalen-2-ylmethoxy)-piperidine-1-carboxylate in 1 ml of ethyl acetate was treated with 60 μl of morpholine and boiled under reflux for 3 hours. Subsequently, the reaction solution was diluted with 5 ml of ethyl acetate and extracted twice with 1 ml of saturated sodium hydrogen carbonate solution each time. The organic phases were dried over magnesium sulphate, evaporated under reduced pressure and dried in a high vacuum. The colourless oil (169 mg) was chromatographed on silica gel using ethyl acetate and the eluent. There were obtained 142 mg of tert-butyl (3RS,4RS)-4-[4-(3-morpholin-4-yl-propoxy)-phenyl]-3-(naphthalen-2-ylmethoxy)-piperidine-1-carboxylate in the form of white crystals; MS: 561 (M+H)$^+$.

(b) In an analogous manner to that described in Example 22(k), by acylating tert-butyl (3RS,4RS)-4-[4-(3-hydroxy-propoxy)-phenyl]-3-(naphthalen-2-ylmethoxy)-piperidine-1-carboxylate with pivaloyl chloride there was obtained tert-butyl (3RS,4RS)-4-[4-[3-(2,2-dimethyl-propionyloxy)-propoxy]-phenyl]-3-(naphthalen-2-ylmethoxy)-piperidine-1-carboxylate as a colourless oil; MS: 576 (M+H)$^+$.

(c) In an analogous manner to that described in Example 22(k), by acylating (3RS,4RS)-4-[4-(3-hydroxy-propoxy)-phenyl]-3-(naphthalen-2-ylmethoxy)-piperidine-1-carboxylate with benzoyl chloride there was obtained tert-butyl (3RS,4RS)-4-[4-(3-benzoyloxy-propoxy)-phenyl]-3-(naphthalen-2-ylmethoxy)-piperidine-1-carboxylate as a colourless oil; R$_f$: 0.84 (SiO$_2$, hexane:ethyl acetate=1:1).

(d) A mixture of 1.0 g (3.41 mmol) of tert-butyl (3RS,4RS)-3-hydroxy-4-(4-hydroxy-phenyl)-piperidine-1-carboxylate, 471 mg (34.1 mmol, 10 eq.) of potassium carbonate and 607 ml (5.11 mmol, 1.5 eq.) of benzyl bromide in 30 ml of dimethylformamide was stirred at room temperature for 2 hours and at 80° C. for 15 hours. Subsequently, 471 mg (34.1 mmol, 10 eq.) of potassium carbonate and 607 ml (5.11 mmol, 1.5 eq.) of benzyl bromide were again added and the mixture was stirred at 80° C. for a further 6 hours. The reaction mixture, cooled to room temperature, was poured into 300 ml of an ice/water mixture and extracted three times with 250 ml of ethyl acetate. The organic phases were washed once with water and once with saturated sodium chloride solution, dried over magnesium sulphate, evaporated under reduced pressure and dried in a high vacuum. The yellow oil (1.82 g) was separated on silica gel using an eluent gradient of 4:1 to 3:2 of a mixture of hexane and ethyl acetate as the eluent. There were obtained 620 mg (72% of theory) of tert-butyl (3RS,4RS)-4-(4-benzyloxy-phenyl)-3-hydroxy-piperidine-1-carboxylate which, after recrystallization from a mixture of methylene chloride and hexane, gave 361 mg (28% of theory) as a white, crystalline product; MS: 383 (M)$^+$.

(e) In an analogous manner to that described in Example 22(i), by alkylating tert-butyl (3RS,4RS)-4-(4-benzyloxy-phenyl)-3-hydroxy-piperidine-1-carboxylate with 2-bromomethylnaphthalene there was obtained tert-butyl (3RS,4RS)-4-(4-benzyloxy-phenyl)-3-(naphthalen-2-yloxy)-piperidine-1-carboxylate as a colourless, amorphous solid; MS: 523 (M)$^+$.

(f) In analogy to the procedure described in Example 14, by alkylating tert-butyl (3RS,4RS)-3-hydroxy-4-(4-hydroxy-phenyl)-piperidine-1-carboxylate with 2-bromomethylnaphthalene in the presence of potassium carbonate there was obtained tert-butyl (3RS,4RS)-3-hydroxy-4-[4-(naphthalen-2-ylmethoxy)-phenyl]-piperidine-1-carboxylate as a colourless solid; MS: 434 (M+H)$^+$.

(g) In analogy to the procedure described in Example 3(c), by alkylating tert-butyl (3RS,4RS)-3-hydroxy-4-[4-(naphthalen-2-ylmethoxy)-phenyl]-piperidine-1-carboxylate with 2-methoxybenzyl chloride there was obtained tert-butyl (3RS,4RS)-3-(2-methoxy-benzyloxy)-4-[4-(naphthalen-2-ylmethoxy)-phenyl]-piperidine-1-carboxylate as a colourless solid; MS: 554 (M+H)$^+$.

EXAMPLE 60

The following compounds were obtained in an analogous manner to that described in Example 25(b) by cleavage of the 2,2,2-trichloroethyl carbamate by treatment with zinc in glacial acetic acid:

1) 3-{4-[3-(Naphthalen-2-ylmethoxy)-piperidin-4-yl]-phenoxy}-propyl (3RS,4RS)-carbamate as a colourless solid, MS: 435 (M+H)$^+$, from 2,2,2-trichloro-ethyl (3RS,4RS)-4-[4-(3-carbamoyloxy-propoxy)-phenyl]-3-(naphthalen-2-ylmethoxy)-piperidine-1-carboxylate;
2) 3-{4-[3-(naphthalen-2-ylmethoxy)-piperidin-4-yl]-phenoxy}-propyl (3RS,4RS)-pyridin-2-yl-carbamate as a colourless oil, MS: 512 (M+H)$^+$, from 2,2,2-trichloro-ethyl (3RS,4RS)-3-(naphthalen-2-ylmethoxy)-4-{4-[3-

(pyridin-2-ylcarbamoyloxy)-propoxy]-phenyl}-piperidine-1-carboxylate;
3) (3RS,4RS)-2-[3-[3-(naphthalen-2-ylmethoxy)-piperidin-4-yl]-phenoxy]-ethyl pyridin-2-yl-carbamate as a colourless oil, MS: 498 (M+H)⁺, from 2,2,2-trichloro-ethyl (3RS,4RS)-3-(naphthalen-2-ylmethoxy)-4-[3-(2-pyridin-2-ylcarbamoyloxy-ethoxy]-phenyl]-piperidine-1-carboxylate;
4) (3RS,4RS)-2-[3-[3-(naphthalen-2-ylmethoxy)-piperidin-4-yl]-phenoxy]-ethyl carbamate as a colourless, amorphous solid, MS: 421 (M+H)⁺, from 2,2,2-trichloro-ethyl (3RS,4RS)-4-[3-(2-carbamoyloxy-ethoxy)-phenyl]-3-(naphthalen-2-ylmethoxy)-piperidine-1-carboxylate;
5) (3RS,4RS)-2-[3-[3-(naphthalen-2-ylmethoxy)-piperidin-4-yl]-phenoxy]-ethanol as a colourless, amorphous solid, MS: 378 (M+H)⁺, from the mixture of 2,2,2-trichloro-ethyl (3RS,4RS)-3-(naphthalen-2-ylmethoxy)-4-[3-[2-[(RS)- and -[(SR)-tetrahydro-pyran-2-yloxy]-ethoxy]-phenyl]-piperidine-1-carboxylate with simultaneous cleavage of the THP group;
6) (3RS,4RS)-2-[4-(3-naphthalen-2-ylmethoxy-piperidin-4-yl]-phenoxy]-ethyl benzoate as a colourless, amorphous solid, MS: 482 (M+H)⁺, from 2,2,2-trichloroethyl (3RS,4RS)-4-[3-(2-benzoyloxy-ethoxy)-phenyl]-3-(naphthalen-2-ylmethoxy)-piperidine-1-carboxylate;
7) 3-{3-[3-(naphthalen-2-ylmethoxy)-piperidin-4-yl]-phenoxy}-propyl (3RS,4RS)-pyridin-2-yl-carbamate as a colourless, amorphous solid, MS: 512 (M+H)⁺, from 2,2,2-trichloroethyl (3RS,4RS)-3-(naphthalen-2-ylmethoxy)-4-{3-[3-(pyridin-2-ylcarbamoyloxy)-propoxy]-phenyl}-piperidine-1-carboxylate;
8) (3RS,4RS)-4-[3-[3-(naphthalen-2-yloxy)-piperidin-4-yl]-phenoxy]-butyl benzoate as a colourless, amorphous solid, MS: 510 (M+H)⁺, from 2,2,2-trichloro-ethyl (3RS,4RS)-4-[3-(4-benzoyloxy-butoxy)-phenyl]-3-(naphthalen-2-ylmethoxy)-piperidine-1-carboxylate.

The 2,2,2-trichloroethyl carbamates used as the starting materials were prepared as follows:

The following procedure was carried out in an analogous manner to that described in Example 22(a)–(c):
(a) 1-Benzyl-4-(3-methoxy-phenyl)-piperidin-4-ol was obtained as a colourless solid, $R_f$: 0.18 (SiO₂, methylene chloride:ethyl acetate=1:1), from 1-benzyl-4-piperidone and 3-iodoanisole. Subsequent elimination with p-toluenesulphonic acid yielded 1-benzyl-4-(3-methoxy-phenyl)-1,2,3,6-tetrahydro-pyridine as a colourless solid, MS: 279 (M)⁺. Hydroboration which followed gave 1-benzyl-4-(3-methoxy-phenyl)-piperidin-3-ol as a colourless powder, MS: 297 (M)⁺.

The following procedure was followed in an analogous manner to that described in Example 44 (d)–(i):
(b) From 1-benzyl-4-(3-methoxy-phenyl)-piperidin-3-ol by cleavage of the methyl ether (RS)- and (SR)-methoxy-phenyl-acetate boron tribromide in methylene chloride there was obtained (3RS,4RS)-1-benzyl-4-(3-hydroxy-phenyl)-piperidin-3-ol as a pale yellow solid; MS: 283 (M)⁺. Alkylation with rac.-2-(2-iodo-ethoxy)-tetrahydro-pyran in the presence of potassium carbonate gave a mixture of (3RS,4RS)-1-benzyl-4-[3-[2-[(RS)- and -[(SR)-tetrahydro-pyran-2-yloxy]-ethoxy]-phenyl]-piperidin-3-ol as a colourless oil; MS: 410 (M−H)⁺. By subsequent alkylation with 2-bromomethylnaphthalene in an analogous manner to that described in Example 22(i) there was obtained a mixture of (3RS,4RS)-1-benzyl-3-(naphthalen-2-ylmethoxy)-4-[3-[2-[(RS)- and -[(SR)-tetrahydro-pyran-2-yloxy]-ethoxy]-phenyl]-piperidine as a colourless oil; MS: 552 (M)⁺. Then, by cleavage of the benzyl group using 2,2,2-trichloroethyl chloroformate and potassium carbonate in an analogous manner to that described in Example 25(a) there was obtained a mixture of 2,2,2-trichloroethyl (3RS,4RS)-3-(naphthalen-2-ylmethoxy)-4-[3-[2-[(RS)- and -[(SR)-tetrahydro-pyran-2-yloxy]-ethoxy]-phenyl]-piperidine-1-carboxylate; $R_f$: 0.60 (SiO₂, methylene chloride:ethyl acetate=2:1). By subsequent cleavage of the THP group using p-toluenesulphonic acid there was obtained 2,2,2-trichloro-ethyl (3RS,4RS)-4-[3-(2-hydroxy-ethoxy)-phenyl]-3-(naphthalen-2-ylmethoxy)-piperidine-1-carboxylate. Finally, by reaction with pyridine-2-carbonyl azide in an analogous manner to that described in Example 24(m) there was obtained 2,2,2-trichloro-ethyl (3RS,4RS)-3-(naphthalen-2-ylmethoxy)-4-[3-(2-pyridin-2-ylcarbamoyloxy-ethoxy]-phenyl]-piperidine-1-carboxylate; $R_f$: 0.45 (SiO₂, methylene chloride:ethyl acetate=9:1).

(c) In an analogous manner to that described in Example 44(e), by alkylating (3RS,4RS)-1-benzyl-4-(4-hydroxy-phenyl)-piperidin-3-ol with rac.-2-(3-bromo-propoxy)-tetrahydro-pyran there was obtained (3RS,4RS)-1-benzyl-4-{4-[3-[(RS)-and (SR)-tetrahydro-pyran-2-yloxy]-propoxy]-phenyl}-piperidin-3-ol as a colourless solid; MS: 426 (M+H)⁺. Subsequent alkylation with 2-bromomethyl-naphthalene according to the procedure described in Example 12(b) gave (3RS,4RS)-1-benzyl-3-(naphthalen-2-ylmethoxy)-4-{4-[3-[(RS)- and (SR)-tetrahydro-pyran-2-yloxy]-propoxy]-phenyl}-piperidine as a colourless solid; MS: 566 (M+H)⁺. Further reaction with 2,2,2-trichloroethyl chloroformate analogously to Example 12(c) yielded 2,2,2-trichloro-ethyl (3RS,4RS)-3-(naphthalen-2-ylmethoxy)-4-{4-[3-[(RS)- and (SR)-tetrahydro-pyran-2-yloxy]-propoxy]-phenyl}-piperidine-1-carboxylate as a colourless solid; MS: 672 (M+Na)⁺. Cleavage of the THP group using p-toluenesulphonic acid analogously to Example 44(h) gave 2,2,2-trichloro-ethyl (3RS,4RS)-4-[4-(3-hydroxy-propoxy)-phenyl]-3-(naphthalen-2-ylmethoxy)-piperidine-1-carboxylate as a colourless solid; MS: 583 (M+NH₄)⁺. Finally, by reaction with sodium isocyanate in an analogous manner to that described in Example 24(m) there was obtained 2,2,2-trichloro-ethyl (3RS, 4RS)-4-[4-(3-carbamoyloxy-propoxy)-phenyl]-3-(naphthalen-2-ylmethoxy)-piperidine-1-carboxylate as a colourless solid; MS: 609 (M+H)⁺.

(d) In an analogous manner to that described in Example 24(m), by reacting 2,2,2-trichloro-ethyl (3RS,4RS)-4-[4-(3-hydroxy-propoxy)-phenyl]-3-(naphthalen-2-ylmethoxy)-piperidine-1-carboxylate with pyridine-2-carbonyl azide there was obtained 2,2,2-trichloro-ethyl (3RS,4RS)-3-(naphthalen-2-ylmethoxy)-4-{4-[3-(pyridin-2-ylcarbamoyloxy)-propoxy]-phenyl}-piperidine-1-carboxylate as a colourless solid.

e) In an analogous manner to that described in Example 24(m), by reacting 2,2,2-trichloro-ethyl (3RS,4RS)-4-[3-(2-hydroxy-ethoxy)-phenyl]-3-(naphthalen-2-ylmethoxy)-piperidine-1-carboxylate with sodium isocyanate there was obtained 2,2,2-trichloro-ethyl (3RS,4RS)-4-[3-(2-carbamoyloxy-ethoxy)-phenyl]-3-(naphthalen-2-ylmethoxy)-piperidine-1-carboxylate as a colourless solid; $R_f$: 0.40 (SiO₂, methylene chloride:methanol=9:1).

(f) In an analogous manner to that described in Example 22(k), by acylating 2,2,2-trichloro-ethyl (3RS,4RS)-4-[3-(2-hydroxy-ethoxy)-phenyl]-3-(naphthalen-2-ylmethoxy)-piperidine-1-carboxylate with benzoyl chloride there was obtained 2,2,2-trichloroethyl (3RS,4RS)-4-[3-(2-benzoyloxy-ethoxy)-phenyl]-3-(naphthalen-2-ylmethoxy)-piperidine-1-carboxylate as a colourless oil.

(g) In an analogous manner to that described in Example 14, by alkylating (3RS,4RS)-1-benzyl-4-(3-hydroxy-phenyl)- piperidin-3-ol with rac.-2-(3-bromo-propoxy)-tetrahydro-pyran in the presence of potassium carbonate there was obtained a mixture of the diastereomeric racemates of (3RS,4RS)-1-benzyl-4-{3-[3-(tetrahydro-pyran-2-yloxy)-propoxy]-phenyl}-piperidin-3-ol as a colourless oil; $R_f$: 0.38 (hexane:acetone=1:1). Subsequent alkylation with 2-bromomethylnaphthalene analogously to Example 12(b) gave a mixture of the diastereomeric racemates of 1-benzyl-3-(naphthalen-2-ylmethoxy)-4-{3-[3-(tetrahydro-pyran-2-yloxy)-propoxy]-phenyl}-piperidine as a colourless oil; MS: 566 (M+H)$^+$. Subsequent reaction with 2,2,2-trichloroethyl (sic) chloroformate analogously to Example 12(c) yielded a mixture of the diastereomeric racemates of 2,2,2-trichloroethyl 3-(naphthalen-2-ylmethoxy)-4-{3-[3-(tetrahydro-pyran-2-yloxy)-propoxy]-phenyl}-piperidine-1-carboxylate which, without further purification and characterization, was reacted with p-toluenesulphonic acid analogously to Example 53(c) to give 2,2,2-trichloroethyl (3RS,4RS)-4-[3-(3-hydroxy-propoxy)-phenyl]-3-(naphthalen-2-ylmethoxy)-piperidine-1-carboxylate. Finally, by reaction with pyridine-2-carbonyl azide in an analogous manner to that described in Example 24(m) there was obtained 2,2,2-trichloroethyl (3RS,4RS)-3-(naphthalen-2-ylmethoxy)-4-{3-[3-(pyridin-2-ylcarbamoyloxy)-propoxy]-phenyl}-piperidine-1-carboxylate as a colourless oil; $R_f$: 0.55 (methylene chloride:ethyl acetate=1:1).

(h) In an analogous manner to that described in Example 14, by alkylating (3RS,4RS)-1-benzyl-4-(3-hydroxy-phenyl)-piperidin-3-ol with rac.-2-(4-bromo-butoxy)-tetrahydro-pyran [S. W.Baldwin et al., J.Org.Chem. 1985, 50, 4432–4439] and further reacting as described under (g) there was obtained 2,2,2-trichloro-ethyl (3RS,4RS)-4-[3-(4-hydroxy-butoxy)-phenyl]-3-(naphthalen-2-ylmethoxy)-piperidine-1-carboxylate as a colourless solid; $R_f$: 0.50 (methylene chloride:ethyl acetate=9:1). Subsequent acylation with benzoyl chloride analogously to Example 22(k) yielded 2,2,2-trichloro-ethyl (3RS,4RS)-4-[3-(4-benzoyloxy-butoxy)-phenyl]-3-(naphthalen-2-ylmethoxy)-piperidine-1-carboxylate as a colourless solid; $R_f$: 0.85 (SiO$_2$, methylene chloride:ethyl acetate=95:5)

EXAMPLE 61

The following compounds were obtained in analogy to the procedure described in Example 10(b) by cleavage of the BOC group using zinc bromide in methylene chloride:

1) (3RS,4RS)-2-[4-[3-(Naphthalen-2-yloxy)-piperidin-4-yl]-phenoxy]-1-phenyl-ethanone hydrobromide as a colourless solid, MS: 452 (M+H)$^+$, from tert-butyl (3RS,4RS)-3-(naphthalen-2-ylmethoxy)-4-[4-(2-oxo-2-phenyl-ethoxy)-phenyl]-piperidine-1-carboxylate;
2) (3RS,4RS)-2-[4-[3-(2-methoxy-benzyloxy)-piperidin-4-yl]-phenoxy]-ethyl benzoate hydrobromide as a beige coloured solid, MS: 462 (M+H)$^+$, from tert-butyl (3RS,4RS)-4-[4-(2-benzoyloxy-ethoxy)-phenyl]-3-(2-methoxy-benzyloxy)-piperidine-1-carboxylate;
3) (3RS,4RS)-4-(4-[1,3]dioxolan-2-ylmethoxy-phenyl)-3-(naphthalen-2-ylmethoxy)-piperidine as a yellowish solid, MS: 420 (M+H)$^+$, from tert-butyl (3RS,4RS)-4-[4-([1,3]dioxolan-2-ylmethoxy)-phenyl]-3-(naphthalen-2-ylmethoxy)-piperidine-1-carboxylate.

The BOC derivatives used as the starting materials were obtained as follows:

(a) In an analogous manner to the procedure described in Example 14, by alkylating tert-butyl (3RS,4RS)-3-hydroxy-4-(4-hydroxy-phenyl)-piperidine-1-carboxylate with allyl bromide in the presence of potassium carbonate there was obtained tert-butyl (3RS,4RS)-4-(4-allyloxy-phenyl)-3-hydroxy-piperidine-1-carboxylate as a colourless solid; m.p.: 113° C. (hexane).

(b) In analogy to the procedure described in Example 3(c) by alkylating tert-butyl (3RS,4RS)-4-(4-allyloxy-phenyl)-3-hydroxy-piperidine-1-carboxylate with 2-bromomethylnaphthalene there was obtained tert-butyl (3RS,4RS)-4-(4-allyloxy-phenyl)-3-(naphthalen-2-ylmethoxy)-piperidine-1-carboxylate as a colourless oil; MS: 474 (M+H)$^+$.

(c) A mixture of 400 mg (0.8 mmol) of tert-butyl (3RS,4RS)-4-(4-allyloxy-phenyl)-3-(naphthalen-2-ylmethoxy)-piperidine-1-carboxylate, 0.2 ml of triethylamine, 0.5 ml of water and 78 mg of tris-(triphenylphosphine)rhodium(I) chloride in 10 ml of ethanol was stirred at reflux for 1 hour. The tert-butyl (3RS,4RS)-4-(4-hydroxy-phenyl)-3-(naphthalen-2-ylmethoxy)-piperidine-1-carboxylate formed in part (30% of theory), MS: 434 (M+H)$^+$, was separated by chromatography and was used in the following step.

(d) In an analogous manner to the procedure described in Example 14, by alkylating tert-butyl (3RS,4RS)-4-(4-hydroxy-phenyl)-3-(naphthalen-2-ylmethoxy)-piperidine-1-carboxylate with phenacyl bromide in the presence of potassium carbonate there was obtained tert-butyl (3RS,4RS)-3-(naphthalen- 2-ylmethoxy)-4-[4-(2-oxo-2-phenyl-ethoxy)-phenyl]-piperidine-1-carboxylate as a yellowish solid; MS: 551 (M)$^+$.

(e) In analogy to the procedure described in Example 3(c), by alkylating a mixture of tert-butyl (3RS,4RS)-3-hydroxy-4-[4-[2-[(RS)- and -[(SR)-tetrahydro-pyran-2-yloxy]-ethoxy]-phenyl]-piperidine-1-carboxylate [Example 53(a)] with 2-methoxybenzyl chloride there was obtained tert-butyl (3RS,4RS)-3-(2-methoxy-benzyloxy)-4-{4-[2-[(RS)- and [(SR)-tetrahydro-pyran-2-yloxy]-ethoxy]-phenyl}-piperidine-1-carboxylate as a colourless oil.

(f) In analogy to the procedure described in Example 53(c), by cleaving the THP ether from tert-butyl (3RS,4RS)-3-(2-methoxy-benzyloxy)-4-{4-[2-[(RS)- and [(SR)-tetrahydro-pyran-2-yloxy]-ethoxy]-phenyl}-piperidine-1-carboxylate there was obtained tert-butyl (3RS,4RS)-4-[4-(2-hydroxy-ethoxy)-phenyl]-3-(2-methoxy-benzyloxy)-piperidine-1-carboxylate.

(g) In analogy to the procedure described in Example 22(k), by acylating tert-butyl (3RS,4RS)-4-[4-(2-Hydroxy-ethoxy)-phenyl]-3-(2-methoxy-benzyloxy)-piperidine-1-carboxylate there was obtained tert-butyl (3RS,4RS)-4-[4-(2-benzoyloxy-ethoxy)-phenyl]-3-(2-methoxy-benzyloxy)-piperidine-1-carboxylate as a colourless, viscous liquid; MS: 562 (M+H)$^+$.

(h) In an analogous manner to the procedure described in Example 14, by alkylating tert-butyl (3RS,4RS)-3-hydroxy-4-(4-hydroxy-phenyl)-piperidine-1-carboxylate with 2-bromomethyl-1,3-dioxolane in the presence of potassium carbonate there was obtained tert-butyl (3RS,4RS)-4-[4-([1,3]dioxolan-2-ylmethoxy)-phenyl]-3-hydroxy-piperidine-1-carboxylate as a colourless solid; m.p.: 136–137° C. (hexane).

(i) In analogy to the procedure described in Example 3(c), by alkylating tert-butyl (3RS,4RS)-4-[4-([1,3]dioxolan-2-ylmethoxy)-phenyl]-3-hydroxy-piperidine-1-carboxylate with 2-bromomethylnaphthalene there was obtained tert-butyl (3RS,4RS)-4-[4-([1,3]dioxolan-2-ylmethoxy)-phenyl]-3-(naphthalen-2-ylmethoxy)-piperidine-1-carboxylate as a colourless solid; MS: 520 (M+H)$^+$.

EXAMPLE 62

A solution of 210 mg (0.425 mmol) of tert-butyl (3RS,4RS,5SR)-4-(4-chloro-phenyl)-3-naphthalen-2-ylmethoxy- 5-propyl-piperidine-1-carboxylate in 18 ml of methanol was treated with 12 ml of 1N hydrochloric acid and stirred at 50° C. overnight. Subsequently, the solution was evaporated under reduced pressure, the residue was taken up in warm toluene and again evaporated, the product beginning to separate out. There were obtained 153 mg (84% of theory) of (3RS,4RS,5SR)-4-(4-chloro-phenyl)-3-naphthalen-2-ylmethoxy-5-propyl-piperidine as a colourless solid. MS: 252 (M-naphthylmethyl)$^+$.

The tert-butyl (3RS,4RS,5SR)-4-(4-chloro-phenyl)-3-naphthalen-2-ylmethoxy-5-propyl-piperidine-1-carboxylate used as the starting material was prepared as follows:

(a) In an analogous manner to the procedure described by A. Ziering et al. in J. Org. Chem. 22, 1521–1528 (1957) for the preparation of piperidin-4-ones from the corresponding acrylic acid esters by reaction with methylamine or benzylamine, reaction with ethyl acrylate or methyl acrylate, cyclization and finally decarboxylation, starting from ethyl 2-propyl-acrylate and methylamine there was obtained (3RS)-1-methyl-3-propyl-piperidin-4-one as a colourless oil; $R_f$: 0.38 (SiO$_2$, methylene chloride:methanol=95:5).

(b) 83.8 ml (134 mmol) of n-BuLi (1.6N in hexane) were added dropwise within 30 minutes to a solution, cooled to −78° C., of 25.68 g (134 mmol) of 1-bromo-4-chloro-benzene in 250 ml of tert-butyl methyl ether. After completion of the addition the mixture was stirred at −78° C. for 1 hour. Thereafter, a solution of 10.41 g (67.05 mmol) of (3RS)-1-methyl-3-propyl-piperidin-4-one in 100 ml of tert-butyl methyl ether was added dropwise at −70 to −65° C. After the dropwise addition the mixture was stirred at −78° C. for 2 hours. For the working-up, the reaction mixture was poured on to ice, transferred to a separating funnel and the organic phase was separated. The aqueous phase was extracted with ethyl acetate and subsequently the combined organic phases were dried over sodium sulphate and evaporated under reduced pressure. For purification, the crude product was chromatographed on silica gel using a 95:5:0.1 mixture of methylene chloride, methanol and ammonia as the eluent. There were obtained 15.9 g (88% of theory) of (3RS,4RS)- and (3RS,4SR)-4-(4-chloro-phenyl)-1-methyl-3-propyl-piperidin-4-ol as a colourless solid; MS: 267 (M)$^+$.

(c) A solution of 13.68 g (51.06 mmol) of (3RS,4RS)- and (3RS,4SR)-4-(4-chloro-phenyl)-1-methyl-3-propyl-piperidin-4-ol in 67 ml of trifluoroacetic acid was boiled under reflux for 18 hours. Thereafter, the reaction solution was evaporated under reduced pressure. The residue was partitioned between a saturated sodium carbonate solution and ether, the separated aqueous phase was back-extracted with ether and finally the combined organic phases were dried over sodium sulphate and evaporated under reduced pressure. For purification of the crude product and separation of isomeric olefins, [the residue] was chromatographed on silica gel using a 96:4 mixture of methylene chloride and methanol as the eluent. There were obtained 9.71 g (76% of theory) of (RS)-4-(4-chloro-phenyl)-1-methyl-3-propyl-1,2,3,6-tetrahydro-pyridine, MS: 249 (M)$^+$, and 1.74 g of 4-(4-chloro-phenyl)-1-methyl-5-propyl-1,2,3,6-tetrahydro-pyridine, MS: 248 (M−H)$^+$, each as a yellowish oil.

(d) 2.23 g (60 mmol) of sodium borohydride were added spatula-wise to a suspension of 9.7 g (39 mmol) of (RS)-4-(4-chloro-phenyl)-1-methyl-3-propyl-1,2,3,6-tetrahydro-pyridine in 80 ml of 1,2-dimethoxyethane in such a manner that the temperature did not rise above 35° C. Subsequently, 13.2 ml of boron trifluoride etherate dissolved in 15 ml of 1,2-dimethoxyethane were added dropwise during 45 minutes and thereafter the reaction mixture was stirred at room temperature for 2 hours. Subsequently, firstly a solution of 15.65 g (277 mmol) of potassium hydroxide dissolved in 60 ml of water was slowly added dropwise at about 30° C. and thereafter within 15 minutes 11.2 ml of a 30% hydrogen peroxide solution was added, with the temperature rising to 40° C. Subsequently, the mixture was boiled under reflux for 2.5 hours. For the working-up, the cooled reaction mixture was filtered over Dicalit and this was rinsed with ethyl acetate. The solution obtained was treated with 100 ml of ethyl acetate and 100 ml of water, the organic phase was separated and then the aqueous phase was back-extracted with 100 ml of ethyl acetate. The combined organic phases were dried over sodium sulphate and evaporated under reduced pressure. For purification, the crude product was chromatographed on silica gel using a 95:5 mixture of methylene chloride and methanol as the eluent. There were obtained 8.64 g (73% of theory) of (3RS,4SR,5RS)-4-(4-chloro-phenyl)-1-methyl-5-propyl-piperidin-3-ol as a colourless solid; MS: 267 (M)$^+$.

(e) A mixture of 7.19 g (26.85 mmol) of (3RS,4SR,5RS)-4-(4-chloro-phenyl)-1-methyl-5-propyl-piperidin-3-ol, 5.96 g (80.7 mmol) of lithium carbonate and 14.22 g (67.1 mmol) of 2,2,2-trichloroethyl chloroformate in 200 ml of toluene was stirred at 105° C. for 8 hours. For the working-up, the cooled reaction mixture was treated with aqueous sodium carbonate solution and ethyl acetate. The organic phase was separated, dried over sodium sulphate and evaporated under reduced pressure. For purification, the crude product was chromatographed on silica gel using a 1:1 mixture of methylene chloride and hexane as the eluent. There were obtained 13.05 g (80% of theory) of 2,2,2-trichloro-ethyl (3RS,4SR,5SR)-4-(4-chloro-phenyl)-3-propyl-5-(2,2,2-trichloro-ethoxycarbonyloxy)-piperidine-1-carboxylate as a yellowish oil; MS: 621 (M+NH$_4$)$^+$.

(f) A mixture of 13.05 g (21.6 mmol) of 2,2,2-trichloro-ethyl (3RS,4SR,5SR)-4-(4-chloro-phenyl)-3-propyl-5-(2,2,2-trichloro-ethoxycarbonyloxy)-piperidine-1-carboxylate and 14.5 g of zinc in 200 ml of glacial acetic acid was treated in an ultrasound bath for 15 hours. In order to complete the reaction, a further 5 g of zinc were subsequently added and the mixture was left in the ultrasound bath for a further 5 hours. For the working-up, the zinc was filtered off under suction, the residue was rinsed with glacial acetic acid and the solution was evaporated to dryness under reduced pressure. The residue was partitioned between 1N NaOH and ethyl acetate, the separated aqueous phase was then again extracted with ethyl acetate and finally the combined organic phases were evaporated under reduced pressure. The crude product obtained was crystallized from diethyl ether and gave 3.0 g (55% of theory) of (3RS,4RS,5SR)-4-(4-chloro-phenyl)-5-propyl-piperidin-3-ol as colourless crystals; MS: 253 (M)$^+$. For purification, the mother liquor was chromatographed on silica gel using a 90:10:0.1 mixture of methylene chloride, methanol and ammonia as the eluent. There were obtained a further 1.1 g (20% of theory) of (3RS,4RS,5SR)-4-(4-chloro-phenyl)-5-propyl-piperidin-3-ol.

(g) A solution of 3.05 g (12.0 mmol) of (3RS,4RS,5SR)-4-(4-chloro-phenyl)-5-propyl-piperidin-3-ol in 20 ml of dimethylformamide was treated at 0° C. with 1.34 g (13.2 mmol) of triethylamine and 3.02 g (13.8 mmol) of di-tert-butyl dicarbonate and the mixture was stirred at room temperature for 15 hours. Subsequently, the dimethylformamide was distilled off in an oil pump vacuum and, for purification, the residue was chromatographed on silica gel using a 99:1 mixture of methylene chloride and methanol as the eluent. There were obtained 3.92 g (92% of theory) of tert-butyl (3RS,4RS,5SR)-4-(4-chloro-phenyl)-3-hydroxy-5-propyl-piperidine-1-carboxylate as a colourless solid; MS: 297 (M-C$_4$H$_8$)$^+$.

(h) 37 mg (0.85 mmol) of sodium hydride (55% dispersion in refined oil) were added to a solution of 200 mg (0.56 mmol) of tert-butyl (3RS,4RS,5SR)-4-(4-chloro-phenyl)-3-hydroxy-5-propyl-piperidine-1-carboxylate and 188 mg (0.85 mmol) of 2-bromomethylnaphthalene in 10 ml of dimethylformamide and the reaction mixture was stirred at room temperature for 5 hours. For the working-up, the reaction mixture was evaporated in an oil pump vacuum, the residue was partitioned between water and ether and thereafter the separated aqueous phase was extracted five times with 50 ml of ether each time. The combined ether extracts were washed with saturated sodium chloride solution, dried over sodium sulphate and evaporated under reduced pressure. For purification, the crude product was chromatographed on silica gel using a 96:4 mixture of toluene and ethyl acetate as the eluent. There were obtained 215 mg (77% of theory) of tert-butyl (3RS,4RS,5SR)-4-(4-chloro-phenyl)-3-naphthalen-2-ylmethoxy-5-propyl-piperidine-1-carboxylate as a colourless oil; MS: 494 (M+H)$^+$.

EXAMPLE 63

The following compounds were obtained in an analogous manner to that described in Example 62:
1) (3RS,4RS,5SR)-4-(4-Chloro-phenyl)-3-(4-methoxy-benzyloxy)-5-propyl-piperidine as a yellowish oil, MS: 252 (M-methoxybenzyl)$^+$, from tert-butyl (3RS,4RS,5SR)-4-(4-chloro-phenyl)-3-(4-methoxy-benzyloxy)-5-propyl-piperidine-1-carboxylate;
2) (3RS,4RS,5SR)-4-(4-chloro-phenyl)-3-(1-ethyl-1H-benzimidazol-2-ylmethoxy)-5-propyl-piperidine hydrochloride as a colourless solid, MS: 412 (M+H)$^+$, from tert-butyl (3RS,4RS,5SR)-4-(4-chloro-phenyl)-3-(1-ethyl-1H-benzimidazol-2-ylmethoxy)-5-propyl-piperidine-1-carboxylate.

The BOC derivatives used as the starting materials were obtained as follows:

In an analogous manner to that described in Example 62(h), by alkylating tert-butyl (3RS,4RS,5SR)-4-(4-chloro-phenyl)-3-hydroxy-5-propyl-piperidine-1-carboxylate with 4-methoxybenzyl chloride there was obtained tert-butyl (3RS,4RS,5SR)-4-(4-chloro-phenyl)-3-(4-methoxy-benzyloxy)-5-propyl-piperidine-1-carboxylate as a colourless solid, MS: 416 (M-C$_4$H$_9$)$^+$.

In an analogous manner to that described in Example 62(h), by alkylating tert-butyl (3RS,4RS,5SR)-4-(4-chloro-phenyl)-3-hydroxy-5-propyl-piperidine-1-carboxylate with 2-chloromethyl-1-ethyl-1H-benzoimidazole [Acta Pol. Pharm. 1977, 34(4), 359–369] there was obtained tert-butyl (3RS,4RS,5SR)-4-(4-chloro-phenyl)-3-(1-ethyl-1H-benzimidazol-2-ylmethoxy)-5-propyl-piperidine-1-carboxylate as a colourless oil, MS: 495 (M+H)$^+$.

EXAMPLE 64

In an analogous manner to that described in Example 5, by treating 2-trimethylsilanylethyl (3RS,4RS,5SR)-3-(4-benzyloxy-naphthalen-2-ylmethoxy)-4-(4-fluoro-phenyl)-5-propyl-piperidine-1-carboxylate with tetrabutylammonium fluoride solution there was obtained (3RS,4RS,5SR)-3-(4-benzyloxy-naphthalen-2-ylmethoxy)-4-(4-fluoro-phenyl)-5-propyl-piperidine as an almost colourless solid, MS: 484 (M+H)$^+$.

The 2-trimethylsilanylethyl (3RS,4RS,5SR)-3-(4-benzyloxy-naphthalen-2-ylmethoxy)-4-(4-fluoro-phenyl)-5-propyl-piperidine-1-carboxylate used as the starting substance was obtained as follows:
(a) In an analogous manner to that described in Example 62(a)–(d), starting from (RS)-1-benzyl-3-propyl-piperidin-4-one, MS: 231 (M)$^+$, and 1-bromo-4-fluorobenzene there was obtained (3RS,4RS,5SR)-1-benzyl-4-(4-fluoro-phenyl)-5-propyl-piperidin-3-ol as a colourless solid, MS: 327 (M)$^+$.
(b) In an analogous manner to that described in Example 62(h), by alkylating (3RS,4RS,5SR)-1-benzyl-4-(4-fluoro-phenyl)-5-propyl-piperidin-3-ol with 1-benzyloxy-3-chloromethyl-naphthalene there was obtained (3RS,4RS,5SR)-1-benzyl-3-(4-benzyloxy-naphthalen-2-ylmethoxy)-4-(4-fluoro-phenyl)-5-propyl-piperidine as a yellow resin, MS (ISP): 574 (M+H)$^+$.
(c) In an analogous manner to that described in Example 1(d), by reacting (3RS,4RS,5SR)-1-benzyl-3-(4-benzyloxy-naphthalen-2-ylmethoxy)-4-(4-fluoro-phenyl)-5-propyl-piperidine with β-trimethylsilylethyl chloroformate [Synthesis 346 (1987)] there was obtained 2-trimethylsilanylethyl (3RS,4RS,5SR)-3-(4-benzyloxy-naphthalen-2-ylmethoxy)-4-(4-fluoro-phenyl)-5-propyl-piperidine-1-carboxylate as a pale yellow syrup, MS: 628 (M+H)$^+$.

The 1-benzyloxy-3-chloromethyl-naphthalene used as the starting material was obtained as follows:
(a) In an analogous manner to that described in Example 14(a), by alkylating ethyl 4-hydroxy-naphthalene-2-carboxylate [J. Agric. Chem Soc. Japan 24, 313 (1950)] with benzyl bromide there was obtained ethyl 4-benzyloxy-naphthalene-2-carboxylate as an almost colourless solid, R$_f$: 0.53 (SiO$_2$, hexane:ethyl acetate=4:1).
(b) Reduction of ethyl 4-benzyloxy-naphthalene-2-carboxylate analogously to Example 7(b) yielded (4-benzyloxy-naphthalen-2-yl)-methanol as a colourless solid, R$_f$: 0.42 (SiO$_2$, hexane:ethyl acetate=2:1).
(c) Chlorination of (4-benzyloxy-naphthalen-2-yl)-methanol analogously to Example 7(c) yielded 1-benzyloxy-3-chloromethyl-naphthalene as a colourless solid, MS: 282 (M)$^+$.

EXAMPLE 65

The following compounds were prepared in an analogous manner to that described in Example 62:
1) (3RS,4RS,5SR)-4-(4-Chloro-phenyl)-5-isopropyl-3-(naphthalen-2-ylmethoxy)-piperidine hydrochloride as a colourless solid, MS: 394 (M+H)$^+$, from tert-butyl (3RS,4RS,5SR)-4-(4-chloro-phenyl)-5-isopropyl-3-naphthalen-2-ylmethoxy-piperidine-1-carboxylate;
2) (3RS,4RS,5SR)-4-(4-bromo-phenyl)-5-isobutyl-3-naphthalen-2-ylmethoxy-piperidine hydrochloride as a colourless solid, MS: 310 (M-naphthylmethyl)$^+$, from tert-butyl (3RS,4RS,5SR)-4-(4-bromo-phenyl)-5-isobutyl-3-naphthalen-2-ylmethoxy-piperidine-1-carboxylate;
3) (3RS,4RS,5SR)-4-(4-fluoro-phenyl)-5-methyl-3-naphthalen-2-ylmethoxy-piperidine hydrochloride as a colourless solid, R$_f$: 0.37 (SiO$_2$, methylene chloride:methanol:ammonia=95:5:0.1), from tert-butyl (3RS,4RS,5SR)-4-(4-fluoro-phenyl)-5-methyl-3-naphthalen-2-ylmethoxy-piperidine-1-carboxylate;
4) (3RS,4RS,5SR)-5-benzyl-4-(4-fluoro-phenyl)-3-naphthalen-2-ylmethoxy-piperidine hydrochloride as a colourless solid, MS: 426 (M+H)$^+$, from tert-butyl (3RS,4RS,5SR)-5-benzyl-4-(4-fluoro-phenyl)-3-(naphthalen-2-ylmethoxy)-piperidine-1-carboxylate.

The BOC derivatives used as the starting materials were obtained as follows:

The following procedure was carried out in an analogous manner to that described in Example 62(a)–(h):
(a) Starting from ethyl 2-isopropyl-acrylate and methylamine there was obtained (3RS)-1-methyl-3-isopropylpiperidin-4-one as a colourless oil; MS: 155 (M)⁺. By reaction with 1-bromo-4-chlorobenzene there was obtained (3RS,4RS)- and (3RS,4SR)-4-(4-chloro-phenyl)-3-isopropyl-1-methyl-piperidin-4-ol as a colourless solid; MS: 267 (M)⁺. Following elimination using trifluoroacetic acid and subsequent chromatographic separation gave the two isomeric olefins, (RS)-4-(4-chloro-phenyl)-3-isopropyl-1-methyl-1,2,3,6-tetrahydro-pyridine, MS: 249 (M)⁺, and 4-(4-chloro-phenyl)-5-isopropyl-1-methyl-1,2,3,6-tetrahydro-pyridine, each as a colourless oil. Hydroboration of (RS)-4-(4-chloro-phenyl)-3-isopropyl-1-methyl-1,2,3,6-tetrahydro-pyridine gave (3RS,4RS,5SR)-4-(4-chloro-phenyl)-5-isopropyl-1-methyl-piperidin-3-ol as a colourless solid; MS: 267 (M)⁺. Further reaction with 2,2,2-trichloroethyl chloroformate yielded 2,2,2-trichloroethyl (3SR,4RS,5RS)-4-(4-chloro-phenyl)-3-isopropyl-5-(2,2,2-trichloro-ethoxycarbonyloxy)-piperidine-1-carboxylate as a yellowish oil; MS: 619, 621, 623, 625 (M+NH₄)⁺. Cleavage of the TROC group with zinc in glacial acetic acid gave (3RS,4RS, 5SR)-4-(4-chloro-phenyl)-5-isopropyl-piperidin-3-ol as a colourless solid: MS: 253 (M)⁺. By introduction of the BOC group there was obtained therefrom tert-butyl (3RS,4RS,5SR)-4-(4-chloro-phenyl)-3-hydroxy-5-isopropyl-piperidine-1-carboxylate as a colourless solid; MS: 297 (M-C₄H₈)⁺. Finally, alkylation with 2-bromomethylnaphthalene yielded tert-butyl (3RS,4RS,5SR)-4-(4-chloro-phenyl)-5-isopropyl-3-naphthalen-2-ylmethoxy-piperidine-1-carboxylate as a colourless solid; MS: 437 (M-C₄H₈)⁺.

The following procedure was carried out in an analogous manner to that described in Example 62(a)–(h):

(b) Starting from methyl 2-isobutyl-acrylate and benzylamine there was obtained (3RS)-1-benzyl-3-isobutyl-piperidin-4-one as a yellowish oil; MS: 245 (M)⁺. By reaction with 1,4-dibromobenzene and subsequent elimination using trifluoroacetic acid as well as chromatographic separation there were obtained the two isomeric olefins, (RS)-1-benzyl-4-(4-bromo-phenyl)-3-isobutyl-1,2,3,6-tetrahydro-pyridine, MS: 383 (M)⁺, and 1-benzyl-4-(4-bromo-phenyl)-5-isobutyl-1,2,3,6-tetrahydro-pyridine, each as a brownish oil. Subsequent hydroboration of (RS)-1-benzyl-4-(4-bromo-phenyl)-3-isobutyl-1,2,3,6-tetrahydro-pyridine gave (3RS,4RS,5SR)-1-benzyl-4-(4-bromo-phenyl)-5-isobutyl-piperidin-3-ol as a colourless solid; MS: 401 (M)⁺. Further reaction with 2,2,2-trichloroethyl chloroformate yielded 2,2,2-trichloro-ethyl (3RS,4R,5SR)-4-(4-bromo-phenyl-5-isobutyl-3-(2,2,2-trichloro-ethoxycarbonyloxy)-piperidine-1-carboxylate as a colourless solid; R$_f$: 0.25 (SiO₂, methylene chloride:hexane 1:1). Cleavage of the TROC group with zinc in glacial acetic acid gave (3RS,4RS,5SR)-4-(4-bromo-phenyl)-5-isobutyl-piperidine-3-ol as a colourless solid: MS: 311 (M)⁺. By introduction of the BOC group there was obtained therefrom tert-butyl (3RS,4RS,5SR)-4-(4-bromo-phenyl)-3-hydroxy-5-isobutyl-piperidine-1-carboxylate as a colourless solid; MS: 412 (M+H)⁺. Finally, alkylation with 2-bromomethylnaphthalene yielded tert-butyl (3RS,4RS,5SR)-4-(4-bromo-phenyl)-5-isobutyl-3-naphthalen-2-ylmethoxy-piperidine-1-carboxylate as a colourless foam; MS: 552 (M+H)⁺.

The following procedure was carried out in an analogous manner to that described in Example 62(b)–(d):

(c) From (RS)-1-benzyl-3-methyl-piperidin-4-one and 1-bromo-4-fluorobenzene there was obtained (3RS,4RS)- and (3RS, 4SR)-1-benzyl-4-(4-fluoro-phenyl)-3-methyl-piperidine-4-ol as a colourless solid; MS: 299 (M)⁺. By elimination using trifluoroacetic acid and subsequent chromatographic separation there were obtained the two isomeric olefins, (RS)-1-benzyl-4-(4-fluoro-phenyl)-3-methyl-1,2,3,6-tetrahydro-pyridine, MS: 281 (M)⁺, and 1-benzyl-4-(4-fluoro-phenyl)-5-methyl-1,2,3,6-tetrahydro-pyridine, MS: 281 (M)⁺, each as a brownish oil. Subsequent hydroboration of the (RS)-1-benzyl-4-(4-fluoro-phenyl)-3-methyl-1,2,3,6-tetrahydro-pyridine gave (3RS,4RS,5SR)-1-benzyl-4-(4-fluoro-phenyl)-5-methyl-piperidine-3-ol as a colourless solid; MS: 299 (M)⁺.

(d) A solution of 600 mg (2 mmol) of (3RS,4RS,5SR)-1-benzyl-4-(4-fluoro-phenyl)-5-methyl-piperidin-3-ol in 20 ml of methanol was hydrogenated with 60 mg of palladium/charcoal (10%) at room temperature under normal pressure. For the working-up, the catalyst was filtered off, stirred in warm methanol and again filtered off. The combined methanol solutions were evaporated under reduced pressure. The resulting crude product (410 mg) was used without further purification in the following step. For analytical purposes, a sample was recrystallized from ether/hexane. The (3RS, 4RS,5SR)-4-(4-fluoro-phenyl)-5-methyl-piperidin-3-ol hydrochloride was obtained in the form of colourless crystals; MS: 209 (M)⁺.

e) From (3RS,4RS,5SR)-4-(4-fluoro-phenyl)-5-methyl-piperidin-3-ol hydrochloride by introduction of the BOC protecting group there was obtained tert-butyl (3RS,4RS,5SR)-4-(4-fluoro-phenyl)-3-hydroxy-5-methyl-piperidine-1-carboxylate as a colourless oil; MS: 253 (M-C₄H₈)⁺. Finally, alkylation with 2-bromomethylnaphthalene yielded tert-butyl (3RS,4RS,5SR)-4-(4-fluoro-phenyl)-5-methyl-3-naphthalen-2-ylmethoxy-piperidine-1-carboxylate as a colourless solid; MS: 393 (M-C₄H₈)⁺.

The following procedure was carried out in an analogous manner to that described in Example 62(a)–(d) and (g)–(h):

(a) Starting from ethyl 2-benzyl-acrylate and benzylamine there was obtained (3RS)-1,3-dibenzyl-piperidin-4-one as a yellowish oil; MS: 279 (M)⁺. By reaction with 1-bromo-4-fluorobenzene there was obtained (3RS,4RS)- and (3RS, 4SR)-1,3 dibenzyl-4-(4-fluoro-phenyl)-piperidin-4-ol as a colourless solid; MS: 375 (M)⁺. By elimination using trifluoroacetic acid and subsequent chromatographic separation there were obtained the two isomeric olefins, (RS)-1,3-dibenzyl-4-(4-fluoro-phenyl)-1,2,3,6-tetrahydro-pyridine as a yellow solid, MS: 357 (M)⁺, and 1,5-dibenzyl-4-(4-fluoro-phenyl)-1,2,3,6-tetrahydro-pyridine. Subsequent hydroboration of the (RS)-1,3-dibenzyl-4-(4-fluoro-phenyl)-1,2,3,6-tetrahydro-pyridine gave (3RS,4RS,5SR)-1,5-dibenzyl-4-(4-fluoro-phenyl)-piperidin-3-ol as a colourless solid; MS: 375 (M)⁺. Cleavage of the benzyl group was effected using catalytic hydrogenation in an analogous manner to that described in the above Example and yielded (3RS,4RS,5SR)-5-benzyl-4-(4-fluoro-phenyl)-piperidin-3-ol as a colourless solid; MS: 285 (M)⁺. By introduction of the BOC group there was obtained therefrom tert-butyl (3RS,4SR,5SR)-3-benzyl-4-(4-fluoro-phenyl)-5-hydroxy-piperidine-1-carboxylate as a colourless solid; MS: 329 (M-C₄H₈)⁺. Finally, alkylation with 2-bromomethylnaphthalene yielded tert-butyl (3RS,4RS,5SR)-5-benzyl-4-(4-fluoro-phenyl)-3-(naphthalen-2-ylmethoxy)-piperidine-1-carboxylate as a colourless foam; R$_f$: 0.32 (SiO₂, toluene:ethyl acetate=95:5).

EXAMPLE 66

40 mg (0.08 mmol) of tert-butyl (3SR,4RS,5RS)-4-(4-chloro-phenyl)-3-(1-ethyl-propyl)-5-(naphthalen-2-ylmethoxy)-piperidine-carboxylate were dissolved in 5 ml of dry methylene chloride and treated with 35 mg (0.16 mmol) of anhydrous zinc bromide in an analogous manner to the procedure described by A. Mann et al. in Synth.

Comm. 19(18), 3139–3142 (1989). The reaction mixture was stirred at room temperature for 5 hours. For the working-up, the reaction mixture was evaporated under reduced pressure and the crude product obtained was purified by chromatography on silica gel using a 90:10:0.1 mixture of methylene chloride, methanol and ammonia as the eluent. There were obtained 28 mg (86% of theory) of (3SR,4RS,5RS)-4-(4-chloro-phenyl)-3-(1-ethyl-propyl)-5-(naphthalen-2-ylmethoxy)-piperidine as a colourless oil; MS: 422 (M+H)$^+$.

The tert-butyl (3SR,4RS,5RS)-4-(4-chloro-phenyl)-3-(1-ethyl-propyl)-5-(naphthalen-2-ylmethoxy)-piperidine-carboxylate used as the starting material was obtained as follows in an analogous manner to that described in Example 62(a)–(h):

Starting from methyl 2-(1-ethyl-propyl)-acrylate and methylamine there was obtained (3RS)-3-(1-ethyl-propyl)-1-methyl-piperidin-4-one as a colourless oil; MS: 183 (M)$^+$. By reaction with 1-bromo-4-chlorobenzene there was obtained therefrom (3RS,4RS)- and (3RS,4SR)-4-(4-chloro-phenyl)-3-(1-ethyl-propyl)-1-methyl-piperidin-4-ol as a colourless solid; MS: 295 (M)$^+$. Subsequent elimination using trifluoroacetic acid and chromatographic separation gave the two isomeric olefins, (RS)-4-(4-chloro-phenyl)-3-(1-ethyl-propyl)-1-methyl-1,2,3,6-tetrahydro-pyridine, MS: 277 (M)$^+$, and 4-(4-chloro-phenyl)-5-(1-ethyl-propyl)-1-methyl-1,2,3,6-tetrahydro-pyridine, each as a colourless oil. Subsequent hydroboration of the (RS)-4-(4-chloro-phenyl)-3-(1-ethyl-propyl)-1-methyl 1,2,3,6-tetrahydro-pyridine gave (3RS,4RS,5SR)-4-(4-chloro-phenyl)-5-(1-ethyl-propyl)-1-methyl-piperidin-3-ol as a colourless solid; MS: 296 (M+H)$^+$. Further reaction with 2,2,2-trichloroethyl chloroformate yielded 2,2,2-trichloro-ethyl (3SR,4RS,5RS)-4-(4-chloro-phenyl)-3-(1-ethyl-propyl)-5-(2,2,2-trichloro-ethoxycarbonyloxy)-piperidine-1-carboxylate as a colourless oil; MS: 653 (M+Na)$^+$. Cleavage of the TROC group with zinc in glacial acetic acid gave (3RS,4RS,5SR)-4-(4-chloro-phenyl)-5-(1-ethyl-propyl)-piperidin-3-ol as a colourless solid: MS: 281 (M)$^+$. By introduction of the BOC protecting group there was obtained therefrom tert-butyl (3SR,4RS,5RS)-4-(4-chloro-phenyl)-3-(1-ethyl-propyl)-5-hydroxy-piperidine-1-carboxylate as a colourless oil; MS: 325 (M-C$_4$H$_8$)$^+$. Finally, alkylation with 2-bromomethylnaphthalene yielded tert-butyl (3SR,4RS,5RS)-4-(4-chloro-phenyl)-3-(1-ethyl-propyl)-5-(naphthalen-2-yl-methoxy)-piperidine-carboxylate; R$_f$: 0.41 (SiO$_2$, toluene:ethyl acetate=95:5).

EXAMPLE 67

In an analogous manner to that described in Example 66, from tert-butyl (3SR,4RS,5RS)-4-(4-chloro-phenyl)-3-isopropyl-5-(4-methoxy-benzyloxy)-piperidine-carboxylate there was obtained (3SR,4RS,5RS)-4-(4-chloro-phenyl)-3-isopropyl-5-(4-methoxy-benzyloxy)-piperidine as a colourless oil; R$_f$: 0.21 (SiO$_2$, methylene chloride:methanol:ammonia=95:5:0.1.

The tert-butyl (3SR,4RS,5RS)-4-(4-chloro-phenyl)-3-isopropyl-5-(4-methoxy-benzyloxy)-piperidine-carboxylate used as the starting material was obtained in an analogous manner to that described in Example 62(h) by alkylating tert-butyl (3RS,4RS,5SR)-4-(4-chloro-phenyl)-3-hydroxy-5-isopropyl-piperidine-1-carboxylate (Example 65) with 4-methoxy-benzyl chloride; R$_f$: 0.39 (SiO$_2$, toluene:ethyl acetate=9:1).

EXAMPLE 68

A solution of 60 mg (0.11 mg) of tert-butyl (3RS,4RS,5SR)-4-(4-bromo-phenyl)-5-methoxymethyl-3-naphthalen-2-yl-methoxy-piperidine-1-carboxylate in 5 ml of methylene chloride was treated with 2 ml of 2N hydrogen chloride in methanol and stirred at room temperature for 2 hours. For the working-up, the reaction solution was evaporated under reduced pressure. The residue was recrystallized from diethyl ether and gave 53 mg (98% of theory) of (3RS,4RS,5SR)-4-(4-bromo-phenyl)-5-methoxymethyl-3-naphthalen-2-yl-methoxy-piperidine hydrochloride as a colourless solid; MS: 442 (M+H)$^+$.

The tert-butyl (3RS,4RS,5SR)-4-(4-bromo-phenyl)-5-methoxymethyl-3-naphthalen-2-ylmethoxy-piperidine-1-carboxylate used as the starting substance was obtained as follows:

(a) A solution of 7.45 g (33.7 mmol) of (3RS,4RS)-1-benzyl-3-hydroxymethyl-piperidin-4-ol and (3SR,4RS)-1-benzyl-3-hydroxymethyl-piperidin-4-ol [E. Jaeger and J. H. Biel, J. Org. Chem. 30(3), 740–744 (1965)], 10.89 g (39.6 mmol) of tert-butyldiphenylchlorosilane, 3.44 g (50.5 mmol) of imidazole and 0.2 g (1.6 mmol) of 4-dimethylaminopyridine in 80 ml of dimethylformamide was stirred at room temperature for 4 days in the presence of molecular sieve (4 Å). For the working-up, the molecular sieve was filtered off under suction and the solution was evaporated in an oil pump vacuum. The residue was digested four times in a mixture of ether and methylene chloride, the solutions obtained were combined, dried over sodium sulphate and evaporated under reduced pressure. For purification, the crude product was chromatographed on silica gel using a 98:2 mixture of methylene chloride and methanol as the eluent. There were obtained 8.23 g (53% of theory) of a mixture of (3RS,4RS)- and (3RS,4SR)-1-benzyl-3-(tert-butyl-diphenyl-silanyloxymethyl)-piperidin-4-ol as a colourless oil; MS: 459 (M)$^+$.

(b) A solution of 2.45 g (19.33 mmol) of oxalyl chloride in 60 ml of methylene chloride was cooled to −70° C., then treated dropwise with 3.02 g (38.66 mmol) of dimethyl sulphoxide and stirred at −70° for 5 minutes. A solution of 8.08 g (17.6 mmol) of a mixture of (3RS,4RS)- and (3RS,4SR)-1-benzyl-3-(tert-butyl-diphenyl-silanyloxymethyl)-piperidin-4-ol in 15 ml of methylene chloride was added dropwise thereto, the mixture was then stirred for 15 minutes. Subsequently, 8.86 g (87.6 mmol) of triethylamine were added dropwise at −70° C. After warming the reaction mixture to room temperature (about 15 minutes) it was hydrolyzed in ice-water and thereafter extracted three times with 200 ml of methylene chloride each time. The combined organic phases were dried over sodium sulphate and evaporated under reduced pressure. For purification, the crude product was chromatographed on silica gel using methylene chloride as the eluent. There were obtained 6.5 g (81% of theory) of (3RS)-1-benzyl-3-(tert-butyl-diphenyl-silanyloxymethyl)-piperidin-4-one as a colourless oil; MS: 458 (M+H)$^+$.

(c) In an analogous manner to that described in Example 62(b), from (3RS)-1-benzyl-3-(tert-butyl-diphenyl-silanyloxymethyl)-piperidin-4-one and 1,4-dibromobenzene there was obtained (3RS,4RS)- and/or (3RS,4SR)-1-benzyl-4-(4-bromo-phenyl)-3-(tert-butyl-diphenyl-silanyloxymethyl)-piperidin-4-ol as a colourless foam; MS: 616 (M+H)$^+$.

(d) In an analogous manner to that described in Example 62(c), from (3RS,4RS)- and/or (3RS,4SR)-1-benzyl-4-(4-bromo-phenyl)-3-(tert-butyl-diphenyl-silanyloxymethyl)-piperidin-4-ol by eliminating the tert. alcohol and simultaneous cleavage of the silyl group using trifluoroacetic acid there was obtained (3RS)-[1-benzyl-4-(4-bromo-phenyl)-1,2,3,6-tetrahydro-pyridin-3-yl]-methanol as a colourless solid; MS: 360 (M+H)$^+$.

(e) In an analogous manner to that described in Example 62(d), by hydroborating (3RS)-[1-benzyl-4-(4-bromo-phenyl)-1,2,3,6-tetrahydro-pyridin-3-yl]-methanol there was obtained a mixture of (3RS,4RS,5SR)-1-benzyl-4-(4-bromo-phenyl)-5-hydroxymethyl-piperidin-3-ol and (3RS, 4RS)- and/or (3RS,4SR)-1-benzyl-4-(4-bromo-phenyl)-3-hydroxymethyl-piperidin-4-ol as a colourless foam.

(f) In an analogous manner to that described in (e), by treating the above mixture with 2,2,2-trichloroethyl chloroformate there was obtained a mixture of 2,2,2-trichloro-ethyl (3RS,4RS,5SR)-4-(4-bromo-phenyl)-3-(2,2,2-trichloro-ethoxycarbonyloxy)-5-(2,2,2-trichloro-ethoxycarbonyloxymethyl)-piperidine-1-carboxylate and 2,2,2-trichloro-ethyl (3RS,4RS)- and/or (3RS,4SR)-4-(4-bromo-phenyl)-4-(2,2,2-trichloro-ethoxycarbonyloxy)-3-(2,2,2-trichloro-ethoxycarbonyl-oxymethyl)-piperidine-1-carboxylate as a colourless foam.

(g) In an analogous manner to that described in Example 62(f), by reacting the above mixture with zinc in glacial acetic acid there was obtained a 4:1 mixture of (3RS,4RS,5RS)-4-(4-bromo-phenyl)-5-hydroxymethyl-piperidin-3-ol and (3RS,4RS)- and/or (3RS,4SR)-4-(4-bromo-phenyl)-3-hydroxymethyl-piperidin-4-ol as a colourless foam.

(h) In an analogous manner to that described in Example 62(g), by introducing the BOC group and subsequent chromatographic separation there was obtained the mixture of tert-butyl (3RS,4RS,5SR)-4-(4-bromo-phenyl)-3-hydroxy-5-hydroxymethyl-piperidine-1-carboxylate as a colourless foam, MS: 386 (M+H)$^+$, and tert-butyl (3RS,4RS)- and/or (3RS,4SR)-4-(4-bromo-phenyl)-4-hydroxy-3-hydroxymethyl-piperidine-1-carboxylate as a colourless solid, MS: 386 (M+H)$^+$.

(i) A solution of 735 mg (1.91 mmol) of tert-butyl (3RS,4RS,5SR)-4-(4-bromo-phenyl)-3-hydroxy-5-hydroxymethyl-piperidine-1-carboxylate, 766 mg (2.75 mmol) of triphenylchloromethane and 324 mg (3.20 mmol) of triethylamine in 8 ml of methylene chloride was stirred at room temperature for 15 hours. For the working-up, the reaction mixture was evaporated under reduced pressure and the crude product was chromatographed directly on silica gel using methylene chloride as the eluent. There were obtained 1.01 g (84.5% of theory) of tert-butyl (3RS,4RS,5SR)-4-(4-bromo-phenyl)-3-hydroxy-5-trityloxymethyl-piperidine-1-carboxylate as a colourless foam; MS: 646 (M+NH$_4$)$^+$.

(j) In an analogous manner to that described in Example 62(h), by alkylating tert-butyl (3RS,4RS,5SR)-4-(4-bromo-phenyl)-3-hydroxy-5-trityloxymethyl-piperidine-1-carboxylate with 2-bromomethylnaphthalene there was obtained tert-butyl (3RS,4RS,5SR)-4-(4-bromo-phenyl)-3-naphthalen-2-ylmethoxy-5-trityl-oxymethyl-piperidine-1-carboxylate as a colourless foam; MS: 785 (M+NH$_4$)$^+$.

(k) A solution of 990 mg (1.29 mmol) of tert-butyl (3RS,4RS,5SR)-4-(4-bromo-phenyl)-3-naphthalen-2-ylmethoxy-5-trityloxymethyl-piperidine-1-carboxylate and 4 ml of 2N hydrogen chloride/methanol in 5 ml of methylene chloride was stirred at room temperature for 45 minutes. For the working-up, the reaction solution was poured into 40 ml of saturated sodium carbonate solution and this was extracted twice with 40 ml of methylene chloride each time. The combined organic phases were dried over sodium sulphate and evaporated under reduced pressure. For purification and separation, the product obtained was chromatographed on silica gel: firstly with a 98:2 mixture of methylene chloride and methanol as the eluent. There were thus obtained 360 mg (54% of theory) of tert-butyl (3RS,4RS,5SR)-4-(4-bromo-phenyl)-5-hydroxymethyl-3-naphthalen-2-ylmethoxy-piperidine-1-carboxylate as a colourless solid; MS: 528 (M+H)$^+$. Then with a 90:10:1 mixture of methylene chloride, methanol and ammonia, with (3SR,4RS,5RS)-4-(4-bromo-phenyl)-5-naphthalen-2-ylmethoxy-piperidin-3-yl]-methanol being obtained as a colourless solid; MS: 426 (M+H)$^+$.

(l) In an analogous manner to that described in Example 62(h), by alkylating (3SR,4RS,5RS)-4-(4-bromo-phenyl)-5-naphthalen-2-ylmethoxy-piperidin-3-yl]-methanol with methyl iodide there was obtained tert-butyl (3RS,4RS,5SR)-4-(4-bromo-phenyl)-5-methoxymethyl-3-naphthalen-2-yl-methoxy-piperidine-1-carboxylate as a colourless solid; MS: 540 (M+H)$^+$.

EXAMPLE 69 a) A solution of 32.5 g (163 mmol) of tert-butyl 4-oxo-piperidine-1-carboxylate in 200 ml of chloroform was treated with 24.0 g (168 mmol) of disodium hydrogen phosphate and cooled to 5° C. A solution of 27.9 g (175 mmol) of bromine in 75 ml of chloroform was added dropwise during 1 hour, thereafter the reaction mixture was warmed to room temperature and stirred for 18 hours. The reaction mixture was worked-up by extraction with ice-water and methylene chloride, the organic phase was dried over magnesium sulphate, filtered and the solvent was distilled off in a water-jet vacuum. The crude product (38 g) was chromatographed on silica gel with methylene chloride and ethyl acetate as the eluent. The thus-obtained product was recrystallized from ethyl acetate and n-hexane. There were obtained 19.1 g (42% of theory) of tert-butyl 3-bromo-4-oxo-piperidine-1-carboxylate as a pale yellow solid; MS: 277, 279 (M)$^+$.

b) A solution of 2.78 g (10 mmol) of tert-butyl 3-bromo-4-oxo-piperidine-1-carboxylate and 2.09 g (12 mmol) of 2-mercaptomethylnaphthalene in 100 ml of absolute acetonitrile was treated with 13.8 g (100 mmol) of anhydrous potassium carbonate and thereafter the mixture was stirred at room temperature for 18 hours. The reaction mixture was filtered, the filtrate was poured on to ice-water and adjusted to pH 2–3 with concentrated hydrochloric acid; the aqueous phase was extracted three times with 200 ml of ethyl acetate each time, the organic phase was washed once with 200 ml of water, dried over magnesium sulphate, filtered and concentrated in a water-jet vacuum. The crude product (5.5 g) was chromatographed on silica gel with hexane and ethyl acetate as the eluent. The product was recrystallized from ethyl acetate and hexane. There were obtained 2.27 g (61% of theory) of tert-butyl (3RS)-3-(naphthalen-2-ylmethylthio)-4-oxo-piperidine-1-carboxylate as a colourless solid; MS: 371 (M)$^+$.

c) 0.31 g (12.8 mg atoms) of magnesium shavings were suspended in 5 ml of absolute tetrahydrofuran under argon, then reacted at reflux with a solution of 1.75 g (10 mmol) of 4-bromo-fluorobenzene in 10 ml of tetrahydrofuran. After the reaction had died down a solution of 1.86 g (5 mmol) of tert-butyl (3RS)-3-(naphthalen-2-ylmethylthio)-4-oxo-piperidine-1-carboxylate in 10 ml of tetrahydrofuran was added dropwise at room temperature and the mixture was then stirred for a further 4 hours. After hydrolysis with 10 ml of water the reaction mixture was worked-up by extraction with ethyl acetate. The organic phase was dried over magnesium sulphate, filtered and the solvent was distilled off in a water-jet vacuum. The crude product (2.6 g) was chromatographed on silica gel with hexane and ethyl acetate as the eluent. There were obtained 1.45 g (62% of theory) of tert-butyl (3RS,4SR or 3RS,4RS)-4-(4-fluorophenyl)-4-hydroxy-3-(naphthalen-2-ylmethylthio)-piperidine-1-carboxylate as a colourless solid, MS: 468 (M+H)$^+$, and 0.37 g (16% of theory) of tert-butyl (3RS,4RS or 3RS,4SR)-4-(4-fluorophenyl)-4-hydroxy-3-(naphthalen-2-ylmethylthio)-piperidine-1-carboxylate as a colourless solid; MS: 468 (M+H)$^+$.

d) A solution of 0.23 g (0.5 mmol) of tert-butyl (3RS,4SR or 3RS,4RS)-4-(4-fluorophenyl)-4-hydroxy-3-(naphthalen-2-ylmethylthio)-piperidine-1-carboxylate in 5 ml of absolute methanol was treated with 1 ml of hydrochloric acid in methanol (1.4 molar) and thereafter stirred at 50° C. for 3 hours. After distillation of the solvent in a water-jet vacuum the product was recrystallized from methanol. There was thus obtained 0.18 g (89% of theory) of (3RS,4SR or 3RS,4RS)-4-(4-fluorophenyl)-4-hydroxy-3-(naphthalen-2-ylmethylthio)-piperidine hydrochloride as a pale yellow solid; MS: 368 (M+H)$^+$.

EXAMPLE 70

A solution of 0.23 g (0.5 mmol) of tert-butyl (3RS,4RS or 3RS,4SR)-4-(4-fluorophenyl)-4-hydroxy-3-(naphthalen-2-ylmethylthio)-piperidine-1-carboxylate [Example 70(c)] in 5 ml of absolute methanol was treated with 1 ml of hydrochloric acid in methanol (1.4 molar) and thereafter stirred at 50° C. for 3 hours. After distillation of the solvent in a water-jet vacuum the residue was partitioned between methylene chloride and water, neutralized with saturated sodium bicarbonate solution and extracted; the organic phase was dried over magnesium sulphate, filtered and concentrated. The crude product (0.15 g) was chromatographed on silica gel with methylene chloride and methanol as the eluent. There was thus obtained 0.041 g (22% of theory) of (3RS,4RS or 3RS,4SR)-4-(4-fluorophenyl)-4-methoxy-3-(naphthalen-2-ylmethylthio)-piperidine as a yellow oil, MS: 381 (M)$^+$, and 0.067 g (37% of theory) of (3RS,4RS or 3RS,4SR)-4-(4-fluorophenyl)-4-hydroxy-3-(naphthalen-2-ylmethylthio)-piperidine as a pale yellow solid; MS: 367 (M)$^+$.

EXAMPLE 71

(a) 2.33 g (10.0 mmol) of benzyl rac-3-aza-7-oxa-bicyclo[4.1.0]heptane-3-carboxylate [S. V. D'Andrea et al., J. Org. Chem. (1991), 56(9), 3133–3137] and 1.88 g (20.0 mmol, 2 eq.) of phenol were dissolved in 30 ml of acetonitrile and treated at room temperature with 10.0 ml of 2N sodium hydroxide solution. This solution was stirred at 95° C. for 5 hours. Subsequently, the solution, cooled to room temperature, was treated with 60 ml of water and extracted three times with methylene chloride. The organic phases were washed with 100 ml of 2N sodium hydroxide solution and twice with water, dried over magnesium sulphate, evaporated under reduced pressure and dried in a high vacuum. The crude product (3.05 g) was separated on silica gel using a 7:3 mixture of hexane and ethyl acetate as the eluent. This yielded 2.06 g (63% of theory) of benzyl (3RS,4RS)-3-hydroxy-4-phenoxy-piperidine-1-carboxylate as a colourless oil; MS: 327 (M)$^+$.

(b) A dispersion of 262 mg (6.0 mmol, 2 eq.) of sodium hydride (60% dispersion in refined oil) in 40 ml of dimethyl sulphoxide was treated with a solution of 982 mg (3.0 mmol, 1 eq.) of benzyl (3RS,4RS)-3-hydroxy-4-phenoxy-piperidine-1-carboxylate in 67 ml of dimethyl sulphoxide. This mixture was stirred at 40° C. for 2 hours, then cooled to room temperature and treated drop-wise with a solution of 1326 mg (6.0 mmol, 2 eq.) of 2-bromomethylnaphthalene in 40 ml of dimethyl sulphoxide and stirred at room temperature for 4 hours. The mixture was poured into 1 l of an ice/water mixture, stirred for 10 minutes and extracted three times with diethyl ether. The organic phases were washed once with water and once with saturated sodium chloride solution, dried over magnesium sulphate, evaporated under reduced pressure and dried in a high vacuum. The pale yellow oil (1.75 g) was separated on silica gel using a 4:1 mixture of hexane and ethyl acetate as the eluent. This yielded 647 mg (46% of theory) of benzyl (3RS,4RS)-3-(naphthalen-2-ylmethoxy)-4-phenoxy-piperidine-1-carboxylate as an amorphous solid; MS: 476 (M-benzyl)$^+$.

(c) 30 mg, 0.065 mmol) of benzyl (3RS,4RS)-3-(naphthalen-2-ylmethoxy)-4-phenoxy-piperidine-1-carboxylate were dissolved in 1.6 ml of tetrahydrofuran, cooled to 0° C. and treated in succession within 25 minutes with a solution of 95 ml (0.32 mmol, approximately 5 eq.) of a 70% sodium dihydrido-bis-(2-methoxyethoxy)-aluminate solution (SDMA) in toluene and 1.6 ml of tetrahydrofuran. This reaction solution was stirred at 0° C. for 2.5 hours. Subsequently, it was poured into a mixture of saturated potassium sodium tartrate solution and ice and extracted four times with 50 ml of methylene chloride each time. The organic phases were washed twice with water, evaporated under reduced pressure and dried in a high vacuum. The orange coloured resin was separated on silica gel using a 95:5 mixture of methylene chloride and methanol as the eluent. There were obtained 10 mg (47% of theory) of (3RS,4RS)-3-(naphthalen-2-ylmethoxy)-4-phenoxy-piperidine as a colourless, amorphous solid; R$_f$: 0.38 (SiO$_2$, methylene chloride:methanol=9:1).

EXAMPLE 72

The following compounds were obtained in an analogous manner to that described in Example 71 by cleavage of the benzyloxycarbonyl group:

1) (3RS,4RS)-4-(4-Bromophenoxy)-3-(naphthalen-2-ylmethoxy)-piperidine as a colourless, amorphous solid, MS: 412.4, 414 (M+H)$^+$, from benzyl (3RS,4RS)-4-(4-bromo-phenyl)-3-(naphthalen-2-ylmethoxy)-piperidine-1-carboxylate;

2) (3RS,4RS)-4-(4-chlorophenylsulphanyl)-3-(naphthalen-2-ylmethoxy)-piperidine as a colourless, amorphous solid, MS: 384 (M+H)$^+$, from benzyl (3RS,4RS)-4-(4-chloro-phenylsulphanyl)-3-(naphthalen-2-ylmethoxy)-piperidine-1-carboxylate.

The derivatives used as the starting materials were obtained as follows:

(a) In an analogous manner to that described in Example 71(a)–(b), from benzyl rac-3-aza-7-oxa-bicyclo[4.1.0]heptane-3-carboxylate by reaction with 4-bromophenol there was obtained (3RS,4RS)-1-[4-(4-bromo-phenoxy)-3-hydroxy-piperidin-1-yl]-2-phenyl-ethanone as a colourless solid [R$_f$: 0.40 (SiO$_2$, methylene chloride:ethyl acetate= 2:1)], alkylation of which with 2-bromomethylnaphthalene gave benzyl (3RS,4RS)-4-(4-bromo-phenyl)-3-(naphthalen-2-ylmethoxy)-piperidine-1-carboxylate as a colourless solid; MS: 454, 456 (M-benzyl)$^+$.

(b) A mixture of 2.33 g (10.0 mmol) of benzyl rac-3-aza-7-oxa-bicyclo[4.1.0]heptane-3-carboxylate, 2.89 g (20.0 mmol, 2 eq.) of p-chlorothiophenol and 10.0 ml of 2N sodium hydroxide solution in 20.5 ml of acetonitrile was boiled under reflux for 4 hours. Subsequently, the solution, cooled to room temperature, was treated with 25 ml of water and extracted three times with methylene chloride. The organic phases were washed once with 1N sodium hydroxide solution and twice with water, dried over magnesium sulphate, evaporated under reduced pressure and dried in a high vacuum. The crude product (3.55 g) was separated on silica gel using a 9:1 mixture of methylene chloride and ethyl acetate as the eluent. This yielded 1.89 g (46% of theory) of benzyl (3RS,4RS)-4-(4-chloro-phenylsulphanyl)-3-hydroxy-piperidine-1-carboxylate as a colourless solid, MS: 377 (M)⁺, and 169 mg (4%) of benzyl (3RS,4SR)-4-(4-chloro-phenylsulphanyl)-3-hydroxy-piperidine-1-carboxylate.

(c) In an analogous manner to that described in Example 71(b), from benzyl (3RS,4RS)-4-(4-chloro-phenylsulphanyl)-3-hydroxy-piperidine-1-carboxylate by alkylation with 2-bromomethylnaphthalene there was obtained benzyl (3RS,4RS)-4-(4-chloro-phenylsulphanyl)-3-(naphthalen-2-ylmethoxy)-piperidine-1-carboxylate as a colourless solid; MS: 518 (M+H)⁺.

EXAMPLE 73 a) A solution of 5.0 g (16.9 mmol) of tert-butyl (3RS,4RS)-4-(4-fluoro-phenyl)-3-hydroxy-piperidine-1-carboxylate in 50 ml of methylene chloride was treated with 240 mg (1.96 mmol) of 4-dimethylamino-pyridine and 4.2 ml (29 mmol) of triethylamine and cooled to 0° C. Subsequently, 4.65 g (24.4 mmol) of 2-naphthoyl chloride were added portionwise and the reaction mixture was stirred at room temperature for 18 hours. Thereupon, the reaction mixture was treated with ice-water and extracted with methylene chloride. The combined methylene chloride phases were dried over magnesium sulphate, filtered and the solvent was distilled off in a water-jet vacuum. The crude product was chromatographed on silica gel with methylene chloride as the eluent. The thus-obtained product fractions were recrystallized from ether and n-hexane. There were obtained 7.4 g (97% of theory) of tert-butyl (3RS,4RS)-4-(4-fluoro-phenyl)-3-(naphthalen-2-ylcarbonyloxy)-piperidine-1-carboxylate as a colourless solid; MS: 450 (M+H)⁺.

b) A solution of 2.7 ml (24.6 mmol) of titanium tetrachloride in 18 ml of methylene chloride was added dropwise at 0° C. under argon and with the exclusion of moisture to 30 ml of tetrahydrofuran, a yellow suspension resulting. After warming to room temperature 15 ml (95 mmol) of tetramethyl-ethylenediamine were added and the reaction mixture was stirred for 10 minutes. After the addition of 3.6 g (55 mmol) of zinc dust the mixture was stirred at room temperature for a further 30 minutes. Thereupon, a solution of 2.1 ml (30 mmol) of dibromomethane and 2.7 g (6.0 mmol) of tert-butyl (3RS,4RS)-4-(4-fluoro-phenyl)-3-(naphthalen-2-ylcarbonyloxy)-piperidine-1-carboxylate dissolved in 30 ml of tetrahydrofuran was added dropwise in such a manner that the temperature did not rise above 36° C. Subsequently, the reaction mixture was stirred at room temperature for 60 hours, then poured into saturated ammonium chloride solution and extracted with ether. The combined ether phases were dried over magnesium sulphate, concentrated and the residue was chromatographed on silica gel using a 99:1 mixture of methylene chloride and triethylamine as the eluent. Therefrom there were obtained 1.23 g (46% of theory) of tert-butyl (3RS,4RS)-4-(4-fluoro-phenyl)-3-(1-naphthalen- 2-yl-vinyloxy)-piperidine-1-carboxylate as an amorphous colourless solid; MS: 448 (M+H)⁺.

c) A solution of 70 mg (0.156 mmol) of tert-butyl (3RS,4RS)-4-(4-fluoro-phenyl)-3-(1-naphthalen-2-yl-vinyloxy)-piperidine-1-carboxylate in 10 ml of tetrahydrofuran was treated with 0.2 ml of triethylamine and 100 mg of palladium on charcoal and hydrogenated in a hydrogen atmosphere at room temperature and normal pressure. Subsequently, the reaction mixture was suction filtered over a 0.8 μ cellulose filter and the solvent was evaporated in a water-jet vacuum. There were obtained 68.4 mg (97% of theory) of a mixture of tert-butyl (3RS,4RS)-4-(4-fluoro-phenyl)-3-[(RS)- and -[(SR)-1-naphthalen-2-yl-ethoxy]-piperidine-1-carboxylate as an amorphous colourless solid; MS: 450 (M+H)⁺.

d) 69 mg (0.153 mmol) of a mixture of tert-butyl (3RS,4RS)-4-(4-fluoro-phenyl)-3-[(RS)- and -[(SR)-1-naphthalen-2-yl-ethoxy]-piperidine-1-carboxylate were dissolved in 2 ml of methylene chloride, treated with 104 mg (0.46 mmol) of anhydrous zinc bromide and stirred at room temperature for 2.5 hours. Thereupon, the reaction mixture was poured into aqueous sodium carbonate solution and this was extracted with methylene chloride. The combined methylene chloride phases were dried over magnesium sulphate, concentrated and the thus-obtained residue was chromatographed on silica gel with a 9:1 mixture of methylene chloride and methanol as the eluent. There were thus obtained 22.1 mg (41% of theory) of (3RS,4RS)-4-(4-fluoro-phenyl)-3-[(RS)- or -[(SR)-1-naphthalen-2-yl-ethoxy]-piperidine as an amorphous yellowish solid; MS: 350 (M+H)⁺, and 13.6 mg (25% of theory) of (3RS,4RS)-4-(4-fluoro-phenyl)-3-[(SR)- or -[(RS)-1-naphthalen-2-yl-ethoxy]-piperidine as an amorphous colourless solid; MS: 350 (M+H)⁺.

EXAMPLE 74 a) 13.8 g (100 mmol) of potassium carbonate were added to a solution of 10.0 g (46.8 mmol) of 4-(4-fluoro-phenyl)-1,2,3,6-tetrahydro-pyridine hydrochloride in 400 ml of ethanol and the reaction mixture was subsequently heated to reflux temperature. A solution of 5.8 ml (49 mmol) of benzyl bromide in 100 ml of ethanol was added dropwise within one hour and thereafter the mixture was stirred at this temperature for a further 1 hour. The reaction mixture was cooled to room temperature and filtered, the filtrate was extracted with water and ethyl acetate and finally the organic phase was dried over magnesium sulphate. After evaporation in a water-jet vacuum the crude product obtained was chromatographed on silica gel with hexane and ethyl acetate as the eluent. There were obtained 8.90 g (71% of theory) of 1-benzyl-4-(4-fluoro-phenyl)-1,2,3,6-tetrahydro-pyridine; MS: 267 (M)⁺.

b) 4.5 g (16.8 mmol) of 1-benzyl-4-(4-fluoro-phenyl)-1,2,3,6-tetrahydro-pyridine were suspended in 55 ml of water, then partially dissolved by the addition of 70 ml of concentrated hydrochloric acid, 1.36 g (45.3 mmol) of paraformaldehyde were added and the mixture was stirred at 100° C. for 5 hours. After cooling to room temperature the mixture was adjusted to pH 5–6 with sodium hydroxide solution and the product was extracted twice with 100 ml of ethyl acetate. The organic phases were washed once with 100 ml of water, dried over magnesium sulphate, filtered and concentrated in a water-jet vacuum. The thus-obtained crude product was chromatographed on silica gel with hexane and ethyl acetate as the eluent (sic). There were obtained 3.91 g (78% of theory) of (RS)-[1-benzyl-4-(4-fluoro-phenyl)-1,2,3,6-tetrahydro-pyridin-3-yl]-methanol; MS: 297 (M)⁺.

c) 58 ml (203 mmol) of sodium dihydrido-bis-(2-methoxyethoxy)aluminate (70% in toluene) were added dropwise under argon at room temperature while stirring to a solution of 17.4 g (58.5 mmol) of (RS)-[1-benzyl-4-(4-fluoro-phenyl)-1,2,3,6-tetrahydro-pyridin-3-yl]-methanol in 580 ml of absolute toluene. Subsequently, the mixture was stirred at 80° C. for 4 hours. 100 ml of water were added dropwise to the reaction mixture at room temperature, with working-up thereafter being carried out by extraction with water and ethyl acetate. The crude product was chromatographed on silica gel with hexane and ethyl acetate as the eluent. There were obtained 3.90 g (44% of theory) of (3RS,4SR)-[1-benzyl-4-(4-fluoro-phenyl)-piperidin-3-yl]-methanol; MS: 300 (M+H)⁺.

d) 6.86 g (22.9 mmol) of (3RS,4SR)-[1-benzyl-4-(4-fluoro-phenyl)-piperidin-3-yl]-methanol were hydrogenated at room temperature in 70 ml of methanol with the addition of 1.5 g of Pd-charcoal (10%). After filtration of the catalyst the solvent was distilled off in a water-jet vacuum. There were thus obtained 4.79 g (100% of theory) of (3RS,4SR)-[4-(4-fluoro-phenyl)-piperidin-3-yl]-methanol; MS: 210 (M+H)$^+$.

e) 4.20 g (50 mmol) of sodium hydrogen carbonate and 20 ml of water were added to a solution of 4.89 g (23.4 mmol) of (3RS,4SR)-[4-(4-fluoro-phenyl)-piperidin-3-yl]-methanol in 60 ml of dioxan, then 6.10 g (28 mmol) of di-tert-butyl dicarbonate were introduced portionwise and the mixture was stirred at room temperature for 4 hours. The reaction mixture was poured on to ice-water and the product was extracted twice with 200 ml of ethyl acetate each time; the organic phases were washed once with 300 ml of water, dried over magnesium sulphate, filtered and concentrated in a water-jet vacuum. The thus-obtained crude product was chromatographed on silica gel with methylene chloride and methanol as the eluent. There were obtained 7.03 g (97% of theory) of tert-butyl (3RS,4SR)-4-(4-fluoro-phenyl)-3-hydroxymethyl-piperidine-1-carboxylate; MS: 309 (M)$^+$.

f) 3.28 ml (46.2 mmol) of dimethyl sulphoxide were added dropwise at −70° C. under argon to a solution of 2.34 ml (27.3 mmol) of oxalyl chloride in 250 ml of methylene chloride. After 30 minutes 6.50 g (21 mmol) of tert-butyl (3RS,4SR)-4-(4-fluoro-phenyl)-3-hydroxymethyl-piperidine-1-carboxylate dissolved in 75 ml of methylene chloride were added dropwise and the mixture was stirred at −70° C. for 2 hours. Subsequently, 7.25 ml (52.5 mmol) of triethylamine were added dropwise. The reaction mixture was warmed to room temperature during 3 hours and subsequently extracted with water and methylene chloride. After drying over magnesium sulphate and evaporation in a water-jet vacuum the product was purified by recrystallization from n-hexane. There were thus obtained 5.51 g (85% of theory) of tert-butyl (3RS,4SR)-4-(4-fluoro-phenyl)-3-formyl-piperidine-1-carboxylate; MS: 279 (M-CO)$^+$.

g) 28.0 ml (54 mmol) of hexabutyldistannate were placed in 150 ml of tetrahydrofuran at 0° C. under argon. Thereto there were added dropwise 31.3 ml (50 mmol) of n-butyllithium solution (1.6M in n-hexane). After 30 minutes a solution of 11.1 g (50 mmol) of 2-bromomethyl-naphthalene in 50 ml of tetra-hydrofuran were added dropwise and thereafter the mixture was stirred at room temperature. After 2 hours the solvent was distilled off in a water-jet vacuum and the residue was chromatographed on silica gel using hexane and ethyl acetate as the eluent. There were obtained 16.8 g (78% of theory) of tributyl-naphthalen-2-ylmethyl-stannate; MS: 432 (M+H)$^+$.

h) 16.8 g (38.9 mmol) of tributyl-naphthalen-2-ylmethyl-stannate were dissolved in 150 ml of tetrahydrofuran under argon. Thereafter, 12.5 ml (20 mmol) of n-butyllithium solution (1.6M in n-hexane) were added dropwise at −78° C. After 30 minutes a solution of 4.80 g (15.6 mmol) of tert-butyl (3RS,4SR)-4-(4-fluoro-phenyl)-3-formyl-piperidine-1-carboxylate in 70 ml of tetrahydrofuran was added dropwise at −78° C. and the reaction mixture was stirred for a further 2 hours. Subsequently, the mixture was warmed to room temperature for 3 hours and stirred for a further 18 hours. After distillation of the solvent in a water-jet vacuum the reaction mixture was partitioned between water and methylene chloride, the organic phase was dried over magnesium sulphate and concentrated. The crude product was chromatographed on silica gel with hexane and ethyl acetate as the eluent. There were obtained 5.50 g (78% of theory) of a mixture of tert-butyl (3RS,4SR)-4-(4-fluoro-phenyl-3-[(RS)- and -[(SR)-1-hydroxy-2-naphthalen-2-yl-ethyl]-piperidine-1-carboxylate; MS: 450 (M+H)$^+$.

i) 0.45 g (1 mmol) of the mixture of tert-butyl (3RS,4SR)-4-(4-fluoro-phenyl-3-[(RS)- and -[(SR)-1-hydroxy-2-naphthalen-2-yl-ethyl]-piperidine-1-carboxylate was dissolved in 10 ml of methanol. 2.0 ml (2.8 mmol) of HCl in methanol were added to the solution and the reaction mixture was stirred at 50° C. for 1 hour. After distillation of the solvent in a water-jet vacuum the residue was recrystallized from methanol and ether. There was obtained 0.16 g (42% of theory) of a mixture of (RS)- and (SR)-1-[(3RS,4SR)-4-(4-fluoro-phenyl)-piperidin-3-yl]-2-naphthalen-2-yl-ethanol hydrochloride (1:1) in the form of colourless crystals; MS: 350 (M+H)$^+$.

EXAMPLE 75 a) 0.45 g (1 mmol) of a mixture of tert-butyl (3RS,4SR)-4-(4-fluoro-phenyl-3-[(RS)- and -[(SR)-1-hydroxy-2-naphthalen-2-yl-ethyl]-piperidine-1-carboxylate was dissolved in 5 ml of dimethylformamide under argon, then treated in succession with 0.16 g (1.2 mmol) of 4-dimethylamino-pyridine and 0.14 ml (1.2 mmol) of benzoyl chloride and stirred at room temperature for 16 hours. The reaction mixture was subsequently worked-up by extraction with ice-water and methylene chloride. The thus-obtained crude product was chromatographed on silica gel with hexane and ethyl acetate as the eluent. There were obtained 0.27 g (49% of theory) of tert-butyl (3RS,4SR)-3-[(RS)- or -[(SR)-1-benzoyloxy-2-naphthalen-2-yl-ethyl]-4-(4-fluoro-phenyl)-piperidine-1-carboxylate, MS: 554 (M+H)$^+$, and 0.19 g (34% of theory) of tert-butyl (3RS,4SR)-3-[(SR)- or -[(RS)-1-benzoyloxy-2-naphthalen-2-yl-ethyl]-4-(4-fluoro-phenyl)-piperidine-1-carboxylate, MS: 554 (M+H)$^+$.

b) 0.15 g (0.27 mmol) of tert-butyl (3RS,4SR)-3-[(SR)- or -[(RS)-1-benzoyloxy-2-naphthalen-2-yl-ethyl]-4-(4-fluoro-phenyl)-piperidine-1-carboxylate was stirred at 50° C. for 1 hour in 10 ml of methanol with the addition of 1.0 ml (1.4 mmol) of HCl in methanol. After distillation of the solvent in a water-jet vacuum and subsequent drying in a high vacuum there was obtained 0.12 g (91 % of theory) of (SR)- or (RS)-1-[(3RS,4SR)-4-(4-fluoro-phenyl)-piperidin-3-yl]-2-naphthalen-2-yl-ethyl benzoate hydrochloride (1:1) as a colourless foam; MS: 454 (M+H)$^+$.

EXAMPLE 76 a) 0.25 g (0.45 mmol) of tert-butyl (3RS,4SR)-3-[(RS)- or -[(SR)-1-benzoyloxy-2-naphthalen-2-yl-ethyl]-4-(4-fluoro-phenyl)-piperidine-1-carboxylate was reacted with 1.2 ml (1.68 mmol) of HCl in methanol in analogy to Example 75(b). There was thus obtained 0.21 g (95% of theory) of (RS)- or (SR)-1-[(3RS,4SR)-4-(4-fluoro-phenyl)-piperidin-3-yl]-2-naphthalen-2-yl-ethyl benzoate hydrochloride (1:1) as a colourless foam; MS: 454 (M+H)$^+$.

EXAMPLE 77 a) 0.45 g (1 mmol) of a mixture of tert-butyl (3RS,4SR)-4-(4-fluoro-phenyl-3-[(RS)- and -[(SR)-1-hydroxy-2-naphthalen-2-yl-ethyl]-piperidin-1-carboxylate was reacted with 0.09 ml (1.26 mmol) of acetyl chloride and 0.16 g (1.3 mmol) of 4-dimethylamino-pyridine in analogy to Example 75(a). There was thus obtained 0.38 g (77% of theory) of a mixture of tert-butyl (3RS,4SR)-3[(RS)- and -[(SR)-1-acetyloxy-2-naphthalen-2-yl-ethyl]-4-(4-fluoro-phenyl)-piperidine-1-carboxylate, which was used directly in the next step.

b) 0.15 g (0.31 mmol) of the mixture of tert-butyl (3RS, 4SR)-3[(RS)- and -[(SR)-1-of acetyloxy-2-naphthalen-2-yl-ethyl]-4-(4-fluoro-phenyl)-piperidine-1-carboxylate was treated in 10 ml of methylene chloride which 0.5 ml (6.5 mmol) of trifluoroacetic acid and the mixture was stirred at room temperature for 16 hours. After distillation of the solvent in a water-jet vacuum and subsequent drying in a high vacuum there was obtained 0.15 g (96% of theory) of a mixture of (RS)- and (SR)-1-[(3RS,4SR)-4-(4-fluoro-phenyl)-piperidin-3-yl]-2-naphthalen-2-yl-ethyl acetate trifluoroacetate (1:1) as a colourless foam; MS: 392 (M+H)$^+$.

EXAMPLE 78 a) 0.45 g (1 mmol) of a mixture of tert-butyl (3RS,4SR)-4-(4-fluoro-phenyl-3-[(RS)- and -[(SR)-1-hydroxy-2-naphthalen-2-yl-ethyl]-piperidine-1-carboxylate was dissolved in 10 ml of dimethylformamide under argon and 0.07 g (1.6 mmol) of sodium hydride dispersion (55% in mineral oil) was added thereto at room temperature while stirring. After 1 hour 0.14 ml (1.2 mmol) of benzyl bromide was added dropwise and the reaction mixture was stirred at room temperature for 18 hours. Subsequently, the mixture was worked-up by extraction with ice-water and methylene chloride. The thus-obtained crude product was chromatographed on silica gel with hexane and ethyl acetate as the eluent. There were obtained 0.21 g (39% of theory) of tert-butyl (3RS,4SR)-3-[(RS)- or -[(SR)-1-benzyloxy-2-naphthalen-2-yl-ethyl]-4-(4-fluoro-phenyl)-piperidine-1-carboxylate, MS: 540 (M+H)$^+$, and 0.17 g (31% of theory) of tert-butyl (3RS,4SR)-3-[(SR)- or -[(RS)-1-benzyloxy-2-naphthalen-2-yl-ethyl]-4-(4-fluoro-phenyl)-piperidine-1-carboxylate, MS: 540 (M+H)$^+$.

b) 0.12 g (0.22 mmol) of tert-butyl 3RS,4SR)-3-[(RS)- or -[(SR)-1-benzyloxy-2-naphthalen-2-yl-ethyl]-4- (4-fluoro-phenyl)-piperidine-1-carboxylate was reacted with 1.0 ml (1.40 mmol) of HCl in methanol in analogy to Example 75(b). There was thus obtained 0.10 g (95% of theory) of (3RS,4SR)-3-[(RS)- or -[(SR)- 1-benzyloxy-2-naphthalen-2-yl-ethyl]-4-(4-fluoro-phenyl)-piperidine hydrochloride (1:1) as a colourless foam; MS: 440 (M+H)$^+$.

EXAMPLE 79 a) 0.16 g (0.3 mmol) of tert-butyl (3RS,4SR)-3-[(SR)- or -[(RS)-1-benzyloxy-2-naphthalen-2-yl-ethyl]-4- (4-fluoro-phenyl)-piperidine-1-carboxylate was reacted with 1.0 ml (1.40 mmol) of HCl in methanol in analogy to Example 75(b). After distillation of the solvent in a water-jet vacuum the residue was recrystallized from methanol and diethyl ether. There was thus obtained 0.085 g (60% of theory) of (3RS,4SR)-3-[(SR)- or -[(RS)-1-benzyloxy-2-naphthalen-2-yl-ethyl]-4-(4-fluoro-phenyl)-piperidine hydrochloride (1:1) as a white solid; MS: 440 (M+H)$^+$.

EXAMPLE 80 a) 0.45 g (1 mmol) of a mixture of tert-butyl (3RS,4SR)-4-(4-fluoro-phenyl-3-[(RS)- and -[(SR)-1-hydroxy-2-naphthalen-2-yl-ethyl]-piperidine-1-carboxylate was dissolved in 10 ml of dimethylformamide under argon, then 0.07 g (1.6 mmol) of sodium hydride dispersion (55% in mineral oil) was added at room temperature while stirring. After 1 hour 0.27 g (1.2 mmol) of 2-(bromomethyl)-naphthalene was added and the mixture was stirred at room temperature for 72 hours. Subsequently, the mixture was extracted with ice-water and ethyl acetate, the organic phase was dried over magnesium sulphate and subsequently evaporated in a water-jet vacuum. The thus-obtained crude product was chromatographed on silica gel with hexane and ethyl acetate as the eluent. There was obtained 0.19 g (32% of theory) of tert-butyl (3RS,4SR)-4-(4-fluoro-phenyl)-3-[(SR)- or (RS)-2-naphthalen-2-yl-1-(naphthalen-2-ylmethoxy)-ethyl]-piperidine-1-carboxylate, which was used directly in the next step, and 0.09 g (15% of theory) of tert-butyl (3RS,4SR)-4-(4-fluoro-phenyl)-3-[(RS)- or (SR)-2-naphthalen-2-yl-1-(naphthalen-2-ylmethoxy)-ethyl]-piperidine-1-carboxylate, which was likewise used directly in the next step.

b) 0.19 g (0.32 mmol) of tert-butyl (3RS,4SR)-4-(4-fluoro-phenyl)-3-[(SR)- or (RS)-2-naphthalen-2-yl-1-(naphthalen-2-ylmethoxy)-ethyl]-piperidine-1-carboxylate was reacted with 1.0 ml (1.40 mmol) of HCl in methanol in analogy to Example 75(b). The reaction solution was poured on to ice-water, neutralized with saturated sodium hydrogen carbonate solution, the product was then extracted twice with 50 ml of methylene chloride. The organic phases were dried over magnesium sulphate, filtered and the solvent was distilled off in a water-jet vacuum. The thus-obtained crude product was chromatographed on silica gel with methylene chloride and methanol as the eluent. There was thus obtained 0.28 g (18% of theory) of (3RS,4SR)-4-(4-fluoro-phenyl)-3-[(SR)- or (RS)-2-naphthalen-2-yl-1-(naphthalen-2-ylmethoxy)-ethyl]-piperidine as an amorphous, colourless solid; MS: 490 (M+H)$^+$.

EXAMPLE 81 a) 0.09 g (0.15 mmol) of tert-butyl (3RS,4SR)-4-(4-fluoro-phenyl)-3-[(RS)- or (SR)-2-naphthalen-2-yl-1-(naphthalen-2-ylmethoxy)-ethyl]-piperidine-1-carboxylate was reacted with 1.0 ml (1.40 mmol) of HCl in methanol in analogy to Example 75(b). The reaction solution was poured on to ice-water (sic), neutralized with saturated sodium hydrogen carbonate solution, then the product was extracted twice with 50 ml of methylene chloride. The organic phases were dried over magnesium sulphate, filtered and the solvent was distilled off in a water-jet vacuum. The thus-obtained crude product was chromatographed on silica gel with methylene chloride and methanol as the eluent. There was thus obtained 0.036 g (49% of theory) of (3RS,4SR)-4-(4-fluoro-phenyl)-3-[(RS)- or (SR)-2-naphthalen-2-yl-1-(naphthalen-2-ylmethoxy)-ethyl]-piperidine as an amorphous, colourless solid; MS: 490 (M+H)$^+$.

EXAMPLE 82 a) A solution of 1.08 g (4.3 mmol) of (1RS,2RS,3RS,5SR)-3-(4-chloro-phenyl)-8-methyl-8-aza-bicyclo[3.2.1]octan-2-ol [J. Org. Chem. 35, 802, 1970)] in 5 ml of tetrahydrofuran was added dropwise to a suspension of 0.206 g (4.3 mmol) of sodium hydride (50% dispersion in refined oil) in 6 ml of tetrahydrofuran and the mixture was stirred at 50° C. for 60 minutes. Subsequently, the mixture was cooled to room temperature and treated with 0.95 g (4.3 mmol) of 2-bromomethylnaphthalene in 5 ml of tetrahydrofuran. After 2 hours at 50° C. the reaction solution was poured into 60 ml of ice-water and extracted three times with 25 ml of ethyl acetate. The organic phases were washed with saturated sodium chloride solution, dried over magnesium sulphate, filtered and evaporated. The residue was chromatographed on silica gel using a 95:5 mixture of methylene chloride and methanol as the eluent and yielded 1.04 g (62% of theory) of (1RS,2RS,3RS,5SR)-3-(4-chloro-phenyl)-8-methyl-2-(naphthalen-2-ylmethoxy)-8-aza-bicyclo[3.2.1]octane as a light yellow oil, R$_f$: 0.43 (silica gel, methylene chloride;methanol=95:5), MS: 392 (M)$^+$.

(b) A solution of 1.02 g (2.6 mmol) of (1RS,2RS,3RS,5SR)-3-(4-chloro-phenyl)-8-methyl-2-(naphthalen-2-ylmethoxy)-8-aza-bicyclo[3.2.1]octane in 40 ml of toluene was treated with 150 mg of potassium carbonate and heated to 100° C. Subsequently, 0.635 g (0.400 ml) (3 mmol) of 2,2,2-trichloroethyl chloro-formate was added thereto and the mixture was stirred at 100° C. for 12 hours. The reaction solution was evaporated under reduced pressure, the residue was taken up in 70 ml of ethyl acetate and washed with 30 ml of water and 30 ml of saturated sodium hydrogen carbonate solution. Drying over magnesium sulphate, filtration and evaporation yielded a colourless oil which was chromatographed on silica gel using a 3:2 mixture of hexane and ethyl acetate. There were obtained 1.14 g (79% of theory) of 2,2,2-trichloroethyl (1RS,2RS,3RS,5SR)-3-(4-chloro-phenyl)-2-(naphthalen-2-ylmethoxy)-8-aza-bicyclo[3.2.1]octane-8-carboxylate as a colourless oil, $R_f$: 0.38 (silica gel, hexane:ethyl acetate=3:2).

(c) A suspension of 1.14 g (2.06 mmol) of 2,2,2-trichloroethyl (1RS,2RS,3RS,5SR)-3-(4-chloro-phenyl)-2-(naphthalen-2-ylmethoxy)-8-aza-bicyclo[3.2.1]octane-8-carboxylate and 400 mg of zinc in 10 ml of acetic acid was stirred at room temperature for 12 hours. The reaction solution was diluted with 50 ml of water and extracted four times with 40 ml of methylene chloride. The organic phase was washed twice with 50 ml of 1N sodium hydroxide solution, dried over sodium sulphate, filtered and evaporated. The residue was chromatographed on silica gel using a 9:1 mixture of methylene chloride and methanol as the eluent. There was obtained 0.480 g (61% of theory) of (1RS,2RS,3RS,5SR)-3-(4-chloro-phenyl)-2-(naphthalen-2-ylmethoxy)-8-aza-bicyclo[3.2.1]octane of m.p. 184–185°; MS: 379 (M+H)$^+$.

EXAMPLE 83

The following compounds were prepared in an analogous manner to that described in Example 82(a)–(c):

1) From (1RS,2RS,3RS,5SR)-3-(4-chloro-phenyl)-8-methyl-8-aza-bicyclo[3.2.1]octan-2-ol and 4-chloromethyl-biphenyl, (1RS,2RS,3RS,5SR)-2-(biphenyl-4-ylmethoxy)-3-(4-chloro-phenyl)-8-aza-bicyclo[3.2.1]octane, MS: 236 (M-C$_{13}$H$_{11}$)$^+$, which was converted with hydrogen chloride in ethanol into the hydrochloride of m.p. 175–177°(dec.);

2) from (1RS,2RS,3RS,5SR)-3-(4-chloro-phenyl)-8-methyl-8-aza-bicyclo[3.2.1]octane-2-ol and 3,4-dichloro-1-chloromethylbenzene, 3-(4-chloro-phenyl)-2-(3,4-dichloro-benzyloxy)-8-aza-bicyclo[3.2.1]octane, MS: 236 (M-C$_7$H$_5$Cl$_2$)$^+$, which was converted with hydrogen chloride in ethanol into the hydrochloride of m.p. 211–213°;

3) from (1RS,2RS,3RS,5SR)-3-(4-chloro-phenyl)-8-methyl-8-aza-bicyclo[3.2.1]octane-2-ol and 1-chloro-methyl-4-methoxy-benzene, (1RS,2RS,3RS,5SR)-3-(4-chloro-phenyl)-2-(4-methoxy-benzyloxy)-8-aza-bicyclo[3.2.1]octane, MS: 358 (M+H)$^+$, which was converted with methanesulphonic acid in dioxan/water and subsequent lyophilization into the corresponding methanesulphonate, $R_f$: 0.26 (silica gel, methylene chloride: methanol:ammonia=200:10:1);

4) from (1RS,2RS,3RS,5SR)-3-(4-chloro-phenyl)-8-methyl-8-aza-bicyclo[3.2.1]octane-2-ol and 3-chloromethyl-benzo[b]thiophene (J. Am. Chem. Soc. 71, 2856 (1949), 2-(benzo[b]thiophen-2-ylmethoxy)-3-(4-chloro-phenyl)-8-aza-bicyclo[3.2.1]octane, MS: 236 (M-C$_8$H$_7$S)$^+$, which was converted with hydrogen chloride in ethanol into the hydrochloride of m.p. 196–198° C. (dec.);

5) from (1RS,2RS,3RS,5SR)-3-(4-chloro-phenyl)-8-methyl-8-aza-bicyclo[3.2.1]octane-2-ol and methyl 4'-bromomethyl-biphenyl-2-carboxylate [J. Med. Chem. 34, 2525 (1991), methyl (1RS,2RS,3RS,5SR)-4'-[3-(4-chloro-phenyl)-8-aza-bicyclo[3.2.1]oct-2-yloxymethyl]-biphenyl-2-carboxylate, MS: 236 (M-C$_{15}$H$_{13}$O$_2$)$^+$, which was converted with hydrogen chloride in ethanol into the hydrochloride of m.p. 101–103° C. (dec.);

6) from (1RS,2RS,3RS,5SR)-3-(4-chloro-phenyl)-8-methyl-8-aza-bicyclo[3.2.1]octane-2-ol and 6-chloromethyl-1,1,4,4,-tetramethyl-1,2,3,4-tetrahydronaphthalene, (1RS,2RS,3RS,5SR)-3-(4-chloro-phenyl)-2-(5,5,8,8-tetramethyl-5,6,7,8-tetrahydro-naphthalen-2-ylmethoxy)-8-aza-bicyclo[3.2.1]octane, MS: 437 (M)$^+$, which was converted with hydrogen chloride in ethanol into the hydrochloride of m.p. 87–90° C. (dec.).

EXAMPLE 84

(a) Cleavage of the N-methyl group by reacting 2,2,2-trichloroethyl chloroformate with (1RS,2RS,3RS,5SR)-3-(4-fluoro-phenyl)-8-methyl-8-aza-bicyclo[3.2.1]octane-2-ol, obtained analogously to the 4-chloro-phenyl derivative [J. Org. Chem. 35, 802, 1970)], was effected in an analogous manner to the procedure described in Example 12(c). There was thus obtained 2,2,2-trichloro-ethyl (1RS,2RS,3RS,5RS)-3-(4-fluoro-phenyl)-2-(2,2,2-trichloro-ethoxycarbonyloxy)-8-aza-bicyclo[3.2.1]octane-8-carboxylate as a yellowish solid; MS: 587, 589, 591, 593 (M+NH$_4$)$^+$.

(b) By cleavage of the 2,2,2-trichloroethyl carbamate and 2,2,2-trichloroethyl carbonate from 2,2,2-trichloro-ethyl (1RS,2RS,3RS,5RS)-3-(4-fluoro-phenyl)-2-(2,2,2-trichloro-ethoxycarbonyloxy)-8-aza-bicyclo[3.2.1]octane-8-carboxylate in an analogous manner to that described in Example 12(d) there was obtained (1RS,2RS,3RS,5RS)-3-(4-fluoro-phenyl)-8-aza-bicyclo[3.2.1]octan-2-ol as a colourless solid; MS: 221 (M)$^+$.

(c) In analogy to the procedure described in Example 1(f), from (1RS,2RS,3RS,5RS)-3-(4-fluoro-phenyl)-8-aza-bicyclo[3.2.1]octane-2-ol by introduction of the BOC group there was obtained tert-butyl (1RS,2RS,3RS,5RS)-3-(4-fluoro-phenyl)-2-hydroxy-8-aza-bicyclo[3.2.1]octane-8-carboxylate as a colourless foam; MS: 265 (M-C$_4$H$_8$)$^+$.

(d) Alkylation of tert-butyl (1RS,2RS,3RS,5RS)-3-(4-fluoro-phenyl)-2-hydroxy-8-aza-bicyclo[3.2.1]octane-8-carboxylate with 1-benzyloxy-3-chloromethyl-naphthalene (Example 19) analogously to the procedure described in Example 1 (g) yielded tert-butyl (1RS,2RS,3RS,5RS)-2-(4-benzyloxy-naphthalen-2-yl-methoxy)-3-(4-fluoro-phenyl)-8-aza-bicyclo[3.2.1]octane-8-carboxylate as a colourless solid; MS: 568 (M+H)$^+$.

(e) Cleavage of the BOC group using hydrogen chloride in ethanol analogously to the procedure described in Example 22(1) gave (1RS,2RS,3RS,5SR)-2-(4-benzyloxy-naphthalen-2-ylmethoxy)-3-(4-fluoro-phenyl)-8-aza-bicyclo[3.2.1]octane as a beige coloured solid; MS: 468 (M+H)$^+$.

EXAMPLE 85

A solution of 0.330 g (0.71 mmol) of methyl (1RS,2RS,3RS,5SR)-4'-[3-(4-chloro-phenyl)-8-aza-bicyclo[3.2.1]oct-2-yloxymethyl]-biphenyl-2-carboxylate in 10 ml of ether was slowly added dropwise to a suspension of 33 mg of lithium aluminium hydride in 5 ml of ether and the mixture was stirred at room temperature for 4 hours. After the addition of aqueous ether and subsequently water the phases were separated, the organic phase was washed with saturated sodium chloride solution, dried over sodium sulphate, filtered and evaporated. The residue was chromatographed on silica gel using a 140:10:1 mixture of methylene chloride, methanol and ammonia as the eluent. There was obtained 0.210 g (68% of theory) of [4'-[3-(4-chloro-phenyl)-8-aza-bicyclo[3.2.1]oct-2-yloxymethyl]-biphenyl-2-yl]-ethanol as a colourless foam, $R_f$: 0.18 (methylene chloride:methanol:ammonia=140:10:1), MS: 434 (M+H)$^+$.

EXAMPLE 86

The following compounds were prepared by cleavage of the BOC group:

1) From tert-butyl (3RS,4RS)-3-(naphthalen-2-ylmethoxy)-4-(4-prop-2-ynyloxy-phenyl)-piperidine-1-carboxylate with trifluoroacetic acid, (3RS,4RS)-3-(naphthalen-2-ylmethoxy)-4-[4-(prop-2-ynyloxy)-phenyl]-piperidine trifluoro-acetate as a colourless solid; m.p.: 186° C. (dec.);
2) from tert-butyl (3RS,4RS)-4-(4-allyloxy-phenyl)-3-(naphthalen-2-ylmethoxy)-piperidine-1-carboxylate with hydrochloric acid in methanol, (3RS,4RS)-4-(4-allyloxy-phenyl)-3-naphthalen-2-ylmethoxy-piperidine as a light oil; MS: 374 (M+H)$^+$;
3) from a mixture of tert-butyl (3RS,4RS)- and (3SR,4SR)-4-[4-[(RS)-2,2-dimethyl-[1,3]dioxolan-4-ylmethoxy]-phenyl]-3-(naphthalen-2-ylmethoxy)-piperidine-1-carboxylate with hydrochloric acid in methanol with simultaneous cleavage of the isopropylidene group, a mixture of (RS)- and (SR)-3-[(3RS,4RS)-4-[3-(naphthalen-2-ylmethoxy)-piperidin-4-yl]-phenoxy]-propane-1,2-diol as a yellowish solid; MS: 408 (M+H)$^+$;
4) from a mixture of tert-butyl (3RS,4RS)- and (3SR,4SR)-4-[4-[(RS)-2-hydroxy-3-phenoxy-propoxy]-phenyl]-3-(naphthalen-2-ylmethoxy)-piperidine-1-carboxylate with trifluoroacetic acid, a mixture of (RS)- and (SR)-1-[4-[(3RS,4RS)-3-(naphthalen-2-ylmethoxy)-piperidin-4-yl]-phenoxy]-3-phenoxy-propan-2-ol trifluoroacetate as a white solid; MS: 484 (M+H)$^+$;
5) from a mixture of tert-butyl (3RS,4RS)- and (3SR,4SR)-4-[4-[(RS)-2-benzyloxy-3-methoxy-propoxy]-phenyl]-3-(naphthalen-2-ylmethoxy)-piperidine-1-carboxylate with trifluoroacetic acid, a mixture of (RS)- and (SR)-4-[(3RS,4RS)-4-(2-benzyloxy-3-methoxy-propoxy)-phenyl]-3-(naphthalen-2-ylmethoxy)-piperidine trifluoroacetate as a white solid; m.p.: 138–139° C.
6) from a mixture of tert-butyl (3RS,4RS)- and (3SR,4SR)-4-[4-[(RS)-2-hydroxy-3-phenylsulphanyl-propoxy]-phenyl]-3-(naphthalen-2-ylmethoxy)-piperidine-1-carboxylate with trifluoroacetic acid, a mixture of (RS)- and (SR)-1-[(3RS,4RS)-4-[3-(naphthalen-2-yloxymethyl)-piperidine-4-yl]-phenoxy]-3-phenylsulphanyl-propan-2-ol trifluoroacetate as a white solid; MS: 500 (M+H)$^+$;
7) from a mixture of tert-butyl (3RS,4RS)- and (3SR,4SR)-4-[4-[(RS)-2-methoxy-3-phenoxy-propoxy)-phenyl]-3-(naphthalen-2-ylmethoxy)-piperidine-1-carboxylate with trifluoroacetic acid, a mixture of (3RS,4RS)-4-[4-[(RS) and [(SR)-2-methoxy-3-phenoxy-propoxy]-phenyl]-3-(naphthalen-2-ylmethoxy)-piperidine trifluoroacetate as a white solid; MS: 498 (M+H)$^+$;
8) from a mixture of tert-butyl (3RS,4RS)- and (3SR,4SR)-4-[4-[(RS)-2-benzoyloxy-3-methoxy-propoxy]-phenyl]-3-(naphthalen-2-ylmethoxy)-piperidine-1-carboxylate with trifluoroacetic acid, a mixture of (RS)- and (SR)-1-methoxymethyl-2-[4-[(3RS,4RS)-3-(naphthalen-2-ylmethoxy)-piperidin-4-yl]-phenoxy]-ethyl benzoate trifluoroacetate as a white solid; MS: 526 (M+H)$^+$;
9) from a mixture of tert-butyl (3RS,4RS)-4-[4-[(RS)- and [(SR)-(3-benzyloxy-2-methoxy-propoxy)-phenyl]-3-(naphthalen-2-ylmethoxy)-piperidine-1-carboxylate, a mixture of (3RS,4RS)-4-[4-[(RS)- and -[(SR)-3-benzyloxy-2-methoxypropoxy]-phenyl]-3-(naphthalen-2-ylmethoxy)-piperidine trifluoroacetate as a white solid; MS: 512 (M+H)$^+$;
10) from tert-butyl (3RS,4RS)-3-(naphthalen-2-ylmethoxy)-4-{4-[2-(pyridin-3-ylmethoxy)-ethoxy]-phenyl}-piperidine-1-carboxylate with hydrogen chloride in methanol, (3RS,4RS)-3-(2-[4-[3-(naphthalen-2-ylmethoxy)-piperidine-4-yl]-phenoxy]-ethoxymethyl)-pyridine as a colourless resin; MS: 469 (M+H)$^+$;
11) from tert-butyl (3RS,4RS)-4-{4-[2-(pyridin-3-ylmethoxy)-ethoxy]-phenyl}-3-[4-(2-trimethylsilanyl-ethoxymethoxy)-naphthalen-2-ylmethoxy]-piperidine-1-carboxylate with hydrogen chloride in methanol with simultaneous cleavage of the SEM group, (3RS,4RS)-3-(4-[4-[2-(pyridin-3-ylmethoxy)-ethoxy]-phenyl]-piperidin-3-yloxymethyl)-naphthalen-1-ol as a colourless resin; MS: 485(M+H)$^+$;
12) from tert-butyl (3RS,4RS)-3-(naphthalen-2-ylmethoxy)-4-{4-[2-(pyridin-4-ylmethoxy)-ethoxy]-phenyl}-piperidine-1-carboxylate with hydrogen chloride in methanol, (3RS,4RS)-4-(2-{4-[3-(naphthalen-2-ylmethoxy)-piperidin-4-yl]-phenoxy}-ethoxymethyl)-pyridine as a colourless resin; MS: 469 (M+H)$^+$;
13) from tert-butyl (3RS,4RS)-3-(naphthalen-2-ylmethoxy)-4-{4-[2-(pyridin-2-ylmethoxy)-ethoxy]-phenyl}-piperidine-1-carboxylate with hydrogen chloride in methanol, (3RS,4RS)-2-(2-{4-[3-(naphthalen-2-ylmethoxy)-piperidin-4-yl]-phenoxy}-ethoxymethyl)-pyridine as a colourless resin; MS: 469 (M+H)$^+$;
14) from tert-butyl (3RS,4RS)-4-[4-(3-benzyloxy-propoxy)-phenyl]-3-(naphthalen-2-ylmethoxy)-piperidine-1-carboxylate with hydrogen chloride in methanol, (3RS,4RS)-4-[4-(3-benzyloxy-propoxy)-phenyl]-3-(naphthalen-2-ylmethoxy)-piperidine as a colourless resin; MS: 482 (M+H)$^+$;
15) from tert-butyl (3RS,4RS)-3-(naphthalen-2-ylmethoxy)-4-[4-[3-(pyridin-2-ylmethoxy)-propoxy]-phenyl]-piperidine-1-carboxylate with hydrogen chloride in methanol, (3RS,4RS)-2-(3-{4-[3-(naphthalen-2-ylmethoxy)-piperidin-4-yl]-phenoxy}-propoxymethyl)-pyridine as a colourless solid; MS: 483 (M+H)$^+$;
16) from tert-butyl (3RS,4RS)-3-(naphthalen-2-ylmethoxy)-4-[4-[3-(pyridin-2-ylmethoxy)-propyl]-phenyl]-piperidine-1-carboxylate with hydrogen chloride in methanol, (3RS,4RS)-2-[3-[4-[3-(naphthalen-2-ylmethoxy)-piperidin-4-yl]-phenyl]-propoxymethyl]-pyridine as a colourless amorphous solid; MS: 467 (M+H)$^+$;
17) from tert-butyl (3RS,4RS)-4-[4-[3-(benzyl-methyl-amino)-propoxy]-phenyl]-3-(naphthalen-2-ylmethoxy)-piperidine-1-carboxylate with hydrogen chloride in methanol, (3RS,4RS)-benzyl-methyl-(3-{4-[3-(naphthalen-2-ylmethoxy)-piperidin-4-yl]-phenoxy}-propyl)-amine as a colourless solid; MS: 495 (M+H)$^+$;
18) from tert-butyl (3RS,4RS)-4-[4-[3-(benzothiazol-2-ylsulphonyl)-propoxy]-phenyl]-3-(1-methoxy-naphthalen-2-ylmethoxy)-piperidine-1-carboxylate with hydrogen chloride in methanol, (3RS,4RS)-2-[3-[4-[3-(1-methoxy-naphthalen-2-ylmethoxy)-piperidin-4-yl]-phenoxy]-propylsulphonyl]-benzothiazole as a colourless foam; MS: 571 (M+H)$^+$;
19) from tert-butyl (3RS,4RS)-3-(naphthalen-2-ylmethoxy)-4-[4-(3-phenylsulphanyl-propyl)-phenyl]-piperidine-1-carboxylate with hydrogen chloride in methanol, (3RS,4RS)-3-(naphthalen-2-ylmethoxy)-4-[4-(3-phenylsulphanyl-propyl)-phenyl]-piperidine as a white solid; MS: 468 (M+H)$^+$;
20) from tert-butyl (3RS,4RS)-4-{4-[3-(benzothiazol-2-ylsulphanyl)-propyl]-phenyl}-3-(naphthalen-2-ylmethoxy)-piperidine-1-carboxylate with hydrogen chloride in methanol, (3RS,4RS)-2-(3-{4-[3-(naphthalen-2-ylmethoxy)-piperidin-4-yl]-phenyl}-propylsulphanyl)-benzothiazole as a white solid; MS: 525 (M+H)$^+$;

21) from tert-butyl (3RS,4RS)-4-{4-[2-(pyrimidin-2-ylsulphanyl)-ethyl]-phenyl}-3-[4-(2-trimethylsilanyl-ethoxymethoxy)-naphthalen-2-ylmethoxy]-piperidine-1-carboxylate with hydrogen chloride in methanol with simultaneous cleavage of the SEM group, (3RS,4RS)-3-[4-[4-[2-(pyrimidin-2-ylsulphanyl)-ethyl]-phenyl]-piperidin-3-yloxymethyl]-naphthalen-1-ol as colurless foam; MS: 472 (M+H)$^+$;

22) from tert-butyl (3RS,4RS)-4-{4-[2-(pyridin-2-ylsulphanyl)-ethyl]-phenyl}-3-[4-(2-trimethylsilanyl-ethoxymethoxy)-naphthalen-2-ylmethoxy]-piperidine-1-carboxylate with hydrogen chloride in methanol with simultaneous cleavage of the SEM group, (3RS,4RS)-3-(4-{4-[2-(pyridin-2-ylsulphanyl)-ethyl]-phenyl}-piperidin-3-yloxymethyl)-naphthalen-1-ol; MS: 471 (M+H)$^+$;

23) from tert-butyl (3RS,4RS)-4-[4-[2-(benzothiazol-2-ylsulphanyl)-ethyl]-phenyl]-3-[4-(2-trimethylsilanyl-ethoxymethoxy)-naphthalen-2-ylmethoxy]-piperidine-1-carboxylate with hydrogen chloride in methanol with simultaneous cleavage of the SEM group, (3RS,4RS)-3-[4-[4-[2-(benzothiazol-2-ylsulphanyl)-ethyl]-phenyl]-piperidin-3-yloxymethyl]-naphthalen-1-ol as a colourless solid MS: 527 (M+H)$^+$;

24) from tert-butyl (3RS,4RS)-3-(naphthalen-2-ylmethoxy)-4-[4-(pyridin-3-ylmethoxymethyl)-phenyl]-piperidine-1-carboxylate with hydrogen chloride in methanol, (3RS,4RS)-3-[4-[3-(naphthalen-2-ylmethoxy)-piperidin-4-yl]-benzyloxymethyl]-pyridine as a colourless foam; MS: 438 (M)$^+$;

25) from a mixture of tert-butyl (3RS,4RS)-4-(4-{2-[(RS)-2- and (SR)-2-(4-fluoro-phenyl)-3-methyl-butyryloxy]-ethoxy}-phenyl)-3-(naphthalen-2-ylmethoxy)-piperidine-1-carboxylate with zinc bromide in methylene chloride, a mixture of (3RS,4RS)-2-[4-(3-naphthalen-2-ylmethoxy-piperidin-4-yl)-phenoxy]-ethyl (RS)- and (SR)-2-(4-fluoro-phenyl)-3-methyl-butyrate hydrobromide as a white solid; MS: 556 (M+H)$^+$;

26) from tert-butyl (3RS,4RS)-4-[4-[2-(1-methyl-1H-pyrrol-2-carbonyloxy)-ethoxy]-phenyl]-3-(naphthalen-2-ylmethoxy)-piperidine-1-carboxylate with zinc bromide in methylene chloride, (3RS,4RS)-[4-[3-(naphthalen-2-ylmethoxy)-piperidin-4-yl]-phenoxy]-ethyl 1-methyl-1H-pyrrole-2-carboxylate hydrobromide as a beige solid; MS: 485 (M+H)$^+$;

27) from tert-butyl (3RS,4RS)-4-[4-(3-benzoyloxy-propyl)-phenyl]-3-(naphthalen-2-ylmethoxy)-piperidine-1-carboxylate with hydrogen chloride in methanol, (3RS,4RS)-3-{4-[3-(naphthalen-2-ylmethoxy)-piperidin-4-yl]-phenyl}-propyl benzoate as a yellow syrup; MS: 480 (M+H)$^+$;

28) from tert-butyl (3RS,4RS)-4-{4-[3-(3-methoxy-benzoyloxy)-propyl]-phenyl}-3-(naphthalen-2-ylmethoxy)-piperidine-1-carboxylate with hydrogen chloride in methanol, (3RS,4RS)-3-{4-[3-(naphthalen-2-ylmethoxy)-piperidin-4-yl]-phenyl}-propyl 3-methoxy-benzoate as a yellow solid; MS: 510 (M+H)$^+$;

29) from tert-butyl (3RS,4RS)-4-[4-(3-methoxy-benzoyloxymethyl)-phenyl]-3-[1-(2-trimethylsilanyl-ethoxymethoxy)-naphthalen-2-ylmethoxy]-piperidine-1-carboxylate with hydrogen chloride in methanol with simultaneous cleavage of the SEM group, (3RS,4RS)-4-[3-(1-hydroxy-naphthalen-2-ylmethoxy)-piperidin-4-yl]-benzyl 3-methoxy-benzoate as a colourless foam; MS: 498 (M+H)$^+$;

30) from tert-butyl (3RS,4RS)-4-(4-ethoxycarbonylmethoxy-phenyl)-3-(naphthalen-2-ylmethoxy)-piperidine-1-carboxylate with trifluoroacetic acid, ethyl (3RS,4RS)-[4-[3-(naphthalen-2-ylmethoxy)-piperidin-4-yl]-phenoxy]-acetate trifluoroacetate as a white solid; MS: 420 (M+H)$^+$;

31) from tert-butyl (3RS,4RS)-4-[4-(benzylcarbamoyl-methoxy)-phenyl]-3-(naphthalen-2-ylmethoxy)-piperidine-1-carboxylate with trifluoroacetic acid, (3RS,4RS)-N-benzyl-2-[4-[3-(naphthalen-2-ylmethoxy)-piperidin-4-yl]-phenoxy]-acetamide trifluoroacetate as a white solid; m.p.: 185° C.;

32) from tert-butyl (3RS,4RS)-3-(naphthalen-2-ylmethoxy)-4-[4-(pyridin-2-ylcarbamoyloxy)-phenyl]-piperidine-1-carboxylate with trifluoroacetic acid, (3RS,4RS)-4-[3-(naphthalen-2-ylmethoxy)-piperidin-4-yl]-3-phenyl pyridin-2-yl-carbamate trifluoroacetate as a white solid; m.p.: 158° C.;

33) from tert-butyl (3RS,4RS)-4-(4-carboxymethoxy-phenyl)-3-(naphthalen-2-ylmethoxy)-piperidine-1-carboxylate [Example 86(ee)] with trifluoroacetic acid, (3RS,4RS)-[4-[3-(naphthalen-2-ylmethoxy)-piperidin-4-yl]-phenoxy]-acetic acid trifluoroacetate as a white colourless solid; m.p.: 183–184° C.;

34) from tert-butyl (3RS,4RS)-3-(naphthalen-2-ylmethoxy)-4-[4-(2-oxo-3-phenoxypropoxy)-phenyl]-piperidine-1-carboxylate with trifluoroacetic acid, (3RS,4RS)-1-[4-[3-(naphthalen-2-ylmethoxy)-piperidin-4-yl]-phenoxy]-3-phenoxy-propan-2-one trifluoroacetate as a white solid; m.p.: 145–146° C.;

35) from tert-butyl (3RS,4RS)-4-[4-(2-ethoxycarbonyl-ethyl)-phenyl]-3-(naphthalen-2-ylmethoxy)-piperidine-1-carboxylate [Example 24(s)] with zinc bromide in methylene chloride, ethyl (3RS,4RS)-3-{4-[3-(naphthalen-2-yl-methoxy)-piperidin-4-yl]-phenyl}-propionate as a yellow syrup; MS: 418 (M+H)$^+$;

36) from a mixture of tert-butyl (3RS,4RS)-4-[4-[(RS)-2- and [(SR)-2-hydroxy-2-phenyl-ethyl]-phenyl]-3-(naphthalen-2-ylmethoxy)-piperidine-1-carboxylate with hydrogen chloride in methanol, a mixture of (RS)- and (SR)-2-[4-[(3RS,4RS)-3-naphthalen-2-ylmethoxy-piperidin-4-yl]-phenyl]-1-phenyl-ethanol hydrochloride; MS: 438 (M+H)$^+$;

37) from tert-butyl (3RS,4RS)-4-(4-fluoro-phenyl)-3-(2-{[(pyridin-2-carbonyl)-amino]-methyl}-benzyloxy)-piperidine-1-carboxylate with hydrogen chloride in methanol, pyridine-2-carboxylic acid (3RS,4RS)-2-[4-(4-fluoro-phenyl)-piperidin-3-yloxymethyl]-benzylamide dihydrochloride as a white solid; MS: 420 (M+H)$^+$;

38) from tert-butyl (3RS,4RS)-3-(3-benzoyl-benzyloxy)-4-(4-fluoro-phenyl)-piperidine-1-carboxylate with hydrogen chloride in methanol, (3RS,4RS)-[3-[4-(4-fluoro-phenyl)-piperidin-3-yloxymethyl]-phenyl]-phenyl-methanone hydrochloride as a white, amorphous solid; MS: 390 (M+H)$^+$;

39) from tert-butyl (3RS,4RS)-3-(naphthalen-2-ylmethoxy)-4-[4-[2-(5-phenyl-[1,2,4]oxadiazol-3-yl)-ethyl]-phenyl]-piperidine-1-carboxylate with hydrogen chloride in methanol, (3RS,4RS)-3-(naphthalen-2-ylmethoxy)-4-[4-[2-(5-phenyl-[1,2,4]oxadiazol-3-yl)-ethyl]-phenyl]-piperidine as a white solid; MS: 490 (M+H)$^+$;

40) from tert-butyl (3RS,4RS)-3-(naphthalen-2-ylmethoxy)-4-[4-[2-(3-phenyl-[1,2,4]oxadiazol-5-yl)-ethyl]-phenyl]-piperidine-1-carboxylate with hydrogen chloride in methanol, (3RS,4RS)-3-(naphthalen-2-ylmethoxy)-4-[4-[2-(3-phenyl-[1,2,4]oxadiazol-5-yl)-ethyl]-phenyl]-piperidine as a white solid; MS: 490 (M+H)$^+$;

41) from tert-butyl (3RS,4RS)-3-(naphthalen-2-ylmethoxy)-4-[4-(3-phenyl-[1,2,4]oxadiazol-5-ylmethoxy)-phenyl]- piperidine-1-carboxylate with trifluoroacetic acid, (3RS, 4RS)-3-(naphthalen-2-ylmethoxy)-4-[4-(3-phenyl-[1,2,4]oxadiazol-5-ylmethoxy)-phenyl]-piperidine trifluoroacetate as a white solid; m.p.: 195–196° C.;

42) from tert-butyl (3RS,4RS)-3-(naphthalen-2-ylmethoxy)-4-[4-(3-pyridin-3-yl-[1,2,4]oxadiazol-5-ylmethoxy)-phenyl]-piperidine-1-carboxylate with trifluoroacetic acid, (3RS,4RS)-3-(5-[4-[3-(naphthalen-2-ylmethoxy)-piperidin-4-yl]-phenoxymethyl]-[1,2,4]oxadiazol-3-yl)-pyridine trifluoroacetate as a white solid; MS: 493 (M+H)+;

43) from tert-butyl (3RS,4RS)-3-(naphthalen-2-ylmethoxy)-4-[4-(3-phenyl-isoxazol-5-ylmethoxy)-phenyl]-piperidine-1-carboxylate with trifluoroacetic acid, (3RS, 4RS)-3-(naphthalen-2-ylmethoxy)-4-[4-(3-phenyl-isoxazol-5-ylmethoxy)-phenyl)-piperidine trifluoroacetate as a white solid; MS: 491 (M+H)+;

44) from tert-butyl (3RS,4RS)-4-[4-(3-benzyloxy-propoxy)-phenyl]-3-(3-methoxy-benzyloxy)-piperidine-1-carboxylate by means of hydrogen chloride in methanol, (3RS,4RS)-4-[4-(3-benzyloxy-propoxy)-phenyl]-3-(3-methoxy-benzyloxy)-piperidine hydrochloride as a colourless oil; MS: 462 (M+H)+;

45) from tert-butyl (3RS,4RS)-4-[4-(3-benzyloxy-propoxy)-phenyl]-3-[3-(2-trimethylsilanyl-ethoxymethoxy)-benzyloxy]-piperidine-1-carboxylate with hydrogen chloride in methanol with simultaneous cleavage of the SEM group, (3RS,4RS)-3-{4-[4-(3-benzyloxy-propoxy)-phenyl]-piperidin-3-yloxymethyl}-phenol as a colourless oil; MS: 448 (M+H)+;

46) from tert-butyl (3RS,4RS)-4-[4-(3-benzyloxy-propoxy)-phenyl]-3-(3-chloro-4-methoxy-benzyloxy)-piperidine-1-carboxylate with zinc bromide in methylene chloride, (3RS,4RS)-4-[4-(3-benzyloxy-propoxy)-phenyl]-3-(3-chloro-4-methoxy-benzyloxy)-piperidine hydrobromide as a colourless oil; MS: 497 (M+H)+;

47) from tert-butyl (3RS,4RS)-4-[4-(3-benzyloxy-propoxy)-phenyl]-3-(3,4-dichloro-benzyloxy)-piperidine-1-carboxylate by means of hydrogen chloride in methanol, (3RS,4RS)-4-[4-(3-benzyloxy-propoxy)-phenyl]-3-(3,4-dichloro-benzyloxy)-piperidine hydrochloride as a colourless oil; MS: 500 (M)+;

48) from tert-butyl (3RS,4RS)-4-[4-(3-benzyloxy-propoxy)-phenyl]-3-(2,5-dichloro-benzyloxy)-piperidine-1-carboxylate by means of hydrogen chloride in methanol, (3RS,4RS)-4-[4-(3-benzyloxy-propoxy)-phenyl]-3-(2,5-dichloro-benzyloxy)-piperidine hydrochloride as a colourless oil; MS: 500 (M)+;

49) from tert-butyl (3RS,4RS)-3-benzyloxy-4-[4-(3-benzyloxy-propoxy)-phenyl]-piperidine-1-carboxylate with zinc bromide in methylene chloride, (3RS,4RS)-3-benzyloxy-4-[4-(3-benzyloxy-propoxy)-phenyl]-piperidine hydrobromide as a colourless solid; MS: 432 (M+H)+;

50) from tert-butyl (3RS,4RS)-4-[4-(3-benzyloxy-propoxy)-phenyl]-3-(2,5-dimethyl-benzyloxy)-piperidine-1-carboxylate with zinc bromide in methylene chloride, (3RS,4RS)-4-[4-(3-benzyloxy-propoxy)-phenyl]-3-(2,5-dimethyl-benzyloxy)-piperidine hydrobromide as a colourless oil; MS: 460 (M+H)+;

51) from tert-butyl (3RS,4RS)-4-[4-(3-benzyloxy-propoxy)-phenyl]-3-(4-ethyl-benzyloxy)-piperidine-1-carboxylate with zinc bromide in methylene chloride, (3RS,4RS)-4-[4-(3-benzyloxy-propoxy)-phenyl]-3-(4-ethyl-benzyloxy)-piperidine as a colourless oil; MS: 460 (M+H)+;

52) from a mixture of tert-butyl (3RS,4RS)-4-[4-(3-benzyloxy-propoxy)-phenyl]-3-(3- and 4-vinyl-benzyloxy)-piperidine-1-carboxylate with zinc bromide in methylene chloride, a mixture of (3RS,4RS)-4-[4-(3-benzyloxy-propoxy)-phenyl]-3-(3 and 4-vinyl-benzyloxy)-piperidine hydrobromide as a colourless solid; MS: 458 (M+H)+;

53) from tert-butyl (3RS,4RS)-4-[4-(3-benzyloxy-propoxy)-phenyl]-3-(2,3-dihydro-benzo[1,4]dioxin-6-ylmethoxy)-piperidine-1-carboxylate with zinc bromide in methylene chloride, (3RS,4RS)-4-[4-(3-benzyloxy-propoxy)-phenyl]-3-(2,3-dihydro-benzo[1,4]dioxin-6-ylmethoxy)-piperidine as a colourless resin; MS: 490 (M+H)+;

54) from tert-butyl (3RS,4RS)-4-[4-(3-benzyloxy-propoxy)-phenyl]-3-(5,6,7,8-tetrahydro-naphthalen-2-ylmethoxy)-piperidine-1-carboxylate with zinc bromide in methylene chloride, (3RS,4RS)-4-[4-(3-benzyloxy-propoxy)-phenyl]-3-(5,6,7,8-tetrahydro-naphthalen-2-ylmethoxy)-piperidine as a colourless resin; MS: 486 (M+H)+;

55) from tert-butyl (3RS,4RS)-4-[4-(3-benzyloxy-propoxy)-phenyl]-3-[4-(2-carboxylate with hydrogen chloride in methanol with simultaneous cleavage of the SEM group, (3RS,4RS)-3-{4-[4-(3-benzyloxy-propoxy)-phenyl]-piperidin-3-yloxymethyl}-naphthalen-1-ol as a colourless resin; MS: 498 (M+H)+;

56) from tert-butyl (3RS,4RS)-4-[4-(4-benzyloxy-butoxy)-phenyl]-3-(naphthalen-2-ylmethoxy)-piperidine-1-carboxylate with hydrogen chloride in methanol, (3RS, 4RS)-4-[4-(4-benzyloxy-butoxy)-phenyl]-3-(naphthalen-2-ylmethoxy)-piperidine as a colourless oil; MS: 496 (M+H)+;

57) from tert-butyl (3SR,4RS,5RS)-4-[4-(2-chloro-benzoyloxymethyl)-phenyl]-3-methoxymethyl-5-(naphthalen-2-ylmethoxy)-piperazine-1-carboxylate with hydrogen chloride in methanol, (3SR,4RS,5RS)-4-[3-methoxymethyl-5-(naphthalen-2-ylmethoxy)-piperidin-4-yl]-benzyl 2-chloro-benzoate as a colourless foam; MS: 530 (M+H)+;

58) from tert-butyl (3SR,4RS,5RS)-4-(4-methoxycarbonyl-phenyl)-3-methoxymethyl-5-(naphthalen-2-ylmethoxy)-piperidine-1-carboxylate with hydrogen chloride in methanol, methyl (3SR,4RS,5RS)-4-[3-methoxymethyl-5-naphthalen-2-ylmethoxy-piperidin-4-yl]-benzoate as a colourless solid; MS: 420 (M+H)+;

59) from tert-butyl (3SR,4RS,5RS)-4-(4-benzyloxymethyl-phenyl)-3-methoxymethyl-5-(naphthalen-2-ylmethoxy)-piperidine-1-carboxylate with hydrogen chloride in methanol, (3SR,4RS,5RS)-4-(4-benzyloxymethyl-phenyl)-3-methoxymethyl-5-(naphthalen-2-ylmethoxy)-piperidine as a colourless foam; MS: 482 (M+H)+;

60) from tert-butyl (1RS,2RS,3RS,5SR)-3-[4-(2-benzyloxy-propoxymethyl)-phenyl]-2-(naphthalen-2-ylmethoxy)-8-aza-bicyclo[3.2.1]octane-8-carboxylate with hydrogen chloride in methanol, (1RS,2RS,3RS,5SR)-2-(naphthalen-2-ylmethoxy)-3-[4-(3-phenoxy-propoxymethyl)phenyl]-8-azabicyclo[3.2.1]octane as a colourless oil; MS: 508 (M+H)+.

The BOC derivatives used as starting materials were prepared as follows:

(a) In an analogous manner to that described in Example 44(e), by alkylating tert-butyl (3RS,4RS)-3-hydroxy-4-(4-hydroxy-phenyl)-piperidine-1-carboxylate [Example 46(b)] with propargyl bromide in the presence of potassium carbonate in acetone there was obtained tert-butyl (3RS,4RS)-3-hydroxy-4-(4-prop-2-ynyloxy-phenyl)-piperidine-1-carboxylate, alkylation of which with 2-bromomethylnaphthalene in analogy to Example 1(g) gave tert-butyl (3RS,4RS)-3-(naphthalen-2-ylmethoxy)-4-(4-prop-2-ynyloxy-phenyl)-piperidine-1-carboxylate as a pale yellow solid; MS: 472 (M+H)+.

(b) In an analogous manner to that described in Example 44(e), by alkylating tert-butyl (3RS,4RS)-3-hydroxy-4-(4-hydroxy-phenyl)-piperidine-1-carboxylate [Example 46(b)] with allyl bromide in the presence of potassium carbonate in acetone there was obtained tert-butyl (3RS,4RS)-4-(4-allyloxy-phenyl)-3-hydroxy-piperidine-1-carboxylate, alkylation of which with 2-bromomethylnaphthalene in analogy to Example 1(g) gave tert-butyl (3RS,4RS)-4-(4-allyloxy-phenyl)-3-(naphthalen-2-ylmethoxy)-piperidine-1-carboxylate as a colourless resin; MS: 474 (M+H)$^+$.

(c) In an analogous manner to that described in Example 1(g), by alkylating tert-butyl (3RS,4RS)-3-hydroxy-4-(4-hydroxy-phenyl)-piperidine-1-carboxylate [Example 46(b)] with (RS)-2,2-dimethyl-[1,3]dioxolan-4-ylmethyl methanesulphonate in the presence of sodium hydride there was obtained a mixture of tert-butyl (3RS,4RS)- and (3SR,4SR)-4-[4-[(RS)-2,2-dimethyl-[1,3]dioxolan-4-ylmethoxy]-phenyl]-3-hydroxy-piperidine-1-carboxylate, alkylation of which with 2-bromomethylnaphthalene in analogy to Example 1(g) gave a mixture of tert-butyl (3RS,4RS)- and (3SR,4SR)-4-[4-[(RS)-2,2-dimethyl-[1,3]dioxolan-4-ylmethoxy]-phenyl]-3-(naphthalen-2-ylmethoxy)-piperidine-1-carboxylate as a white solid; MS: 547 (M)$^+$.

(d) In an analogous manner to that described in Example 1(g), by alkylating tert-butyl (3RS,4RS)-3-hydroxy-4-(4-hydroxy-phenyl)-piperidine-1-carboxylate [Example 46(b)] with (RS)-2,3-epoxypropyl p-toluenesulphonate in the presence of sodium hydride there was obtained a mixture of tert-butyl (3RS,4RS)- and (3SR,4SR)-3-hydroxy-4-[(RS)-4-oxiranylmethoxy-phenyl]-piperidine-1-carboxylate, alkylation of which with 2-bromomethylnaphthalene in analogy to Example 1(g) gave a mixture of tert-butyl (3RS,4RS)- and (3SR,4SR)-3-(naphthalen-2-ylmethoxy)-4-[(RS)-4-oxiranylmethoxy-phenyl]-piperidine-1-carboxylate. Subsequent epoxide opening with potassium phenolate in analogy to Example 71(a) yielded a mixture of tert-butyl (3RS,4RS)- and (3SR,4SR)-4-[4-[(RS)-2-hydroxy-3-phenoxy-propoxy]-phenyl]-3-(naphthalen-2-ylmethoxy)-piperidine-1-carboxylate as a white solid; MS: 584 (M+H)$^+$.

(e) Epoxide opening of a mixture of tert-butyl (3RS,4RS)- and (3SR,4SR)-3-(naphthalen-2-ylmethoxy)-4-[(RS)-4-oxiranylmethoxy-phenyl]-piperidine-1-carboxylate [Example 86(d)] with sodium methylate in N,N-dimethylformamide yielded a mixture of tert-butyl (3RS,4RS)- and (3SR,4SR)-4-[4-[(RS)-2-hydroxy-3-methoxy-propoxy]-phenyl]-3-(naphthalen-2-ylmethoxy)-piperidine-1-carboxylate, alkylation of which with benzyl bromide analogously to Example 1(g) gave a mixture of tert-butyl (3RS,4RS)- and (3SR,4SR)-4-[4-[(RS)-2-benzyloxy-3-methoxy-propoxy]-phenyl]-3-(naphthalen-2-ylmethoxy)-piperidine-1-carboxylate as a colourless resin; MS: 612 (M+H)$^+$.

(f) Epoxide opening of a mixture of tert-butyl (3RS,4RS)- and (3SR,4SR)-3-(naphthalen-2-ylmethoxy)-4-[(RS)-4-oxiranylmethoxy-phenyl]-piperidine-1-carboxylate [Example 86(d)] with sodium thiophenolate in analogy to Example 71(a) gave a mixture of tert-butyl 3RS,4RS)- and (3SR,4SR)-4-[4-[(RS)-2-hydroxy-3-phenylsulphanyl-propoxy]-phenyl]-3-(naphthalen-2-ylmethoxy)-piperidine-1-carboxylate as a white solid; MS: 600 (M+H)$^+$.

(g) Alkylation of a mixture of tert-butyl (3RS,4RS)- and (3SR,4SR)-4-[4-[(RS)-2-hydroxy-3-phenoxy-propoxy]-phenyl]-3-(naphthalen-2-ylmethoxy)-piperidine-1-carboxylate [Example 86(d)] with methyl iodide in analogy to Example 1(g) yielded a mixture of tert-butyl (3RS,4RS)- and (3SR,4SR)-4-[4-[(RS)-2-methoxy-3-phenoxy-propoxy)-phenyl]-3-(naphthalen-2-ylmethoxy)-piperidine-1-carboxylate as a colourless resin; MS: 598 (M+H)$^+$.

(h) In analogy to Example 22(k), by benzoylating a mixture of tert-butyl (3RS,4RS)- and (3SR,4SR)-4-[4-[(RS)-2-hydroxy-3-methoxy-propoxy]-phenyl]-3-(naphthalen-2-ylmethoxy)-piperidine-1-carboxylate [Example 86(e)] there was obtained a mixture of tert-butyl (3RS,4RS)- and (3SR, 4SR)-4-[4-[(RS)-2-benzoyloxy-3-methoxy-propoxy]-phenyl]-3-(naphthalen-2-ylmethoxy)-piperidine-1-carboxylate as a colourless resin; MS: 626 (M+H)$^+$.

(i) Epoxide opening of a mixture of tert-butyl (3RS,4RS)- and (3SR,4SR)-3-(naphthalen-2-ylmethoxy)-4-[(RS)-4-oxiranylmethoxy-phenyl]-piperidine-1-carboxylate [Example 86(d)] with sodium benzylate in N,N-dimethylformamide gave a mixture of tert-butyl (3RS,4RS)- and (3SR,4SR)-4-[4-[(RS)-3-Benzyloxy-2-hydroxy-propoxy]-phenyl]-3-(naphthalen-2-ylmethoxy)-piperidine-1-carboxylate, alkylation of which with methyl iodide analogously to Example 1(g) yielded a mixture of tert-butyl (3RS,4RS)- and (3SR,4SR)-4-[4-[(RS)-3-benzyloxy-2-methoxypropoxy]-phenyl]-3-(naphthalen-2-ylmethoxy)-piperidine-1-carboxylate as a colourless resin; MS: 612 (M+H)$^+$.

(j) In an analogous manner to that described in Example 1(g) by alkylating tert-butyl (3RS,4RS)-4-[4-(2-hydroxy-ethoxy)-phenyl]-3-(naphthalen-2-ylmethoxy)-piperidine-1-carboxylate [Example 53(c)] with 3-chloromethyl-pyridine there was obtained tert-butyl (3RS,4RS)-3-(naphthalen-2-ylmethoxy)-4-{4-[2-(pyridin-3-ylmethoxy)-ethoxy]-phenyl}-piperidine-1-carboxylate; MS: 569 (M+H)$^+$.

(k) In an analogous manner to that described in Example 1(g), by alkylating tert-butyl (3RS,4RS)-4-[4-(2-hydroxy-ethoxy)-phenyl]-3-[4-(2-trimethylsilanyl-ethoxymethoxy)-naphthalen-2-ylmethoxy]-piperidine-1-carboxylate [Example 55(b)] with 3-chloromethyl-pyridine there was obtained tert-butyl (3RS,4RS)-4-{4-[2-(pyridin-3-ylmethoxy)-ethoxy]-phenyl}-3-[4-(2-trimethylsilanyl-ethoxymethoxy)-naphthalen-2-ylmethoxy]-piperidine-1-carboxylate.

(l) In an analogous manner to that described in Example 1(g), by alkylating tert-butyl (3RS,4RS)-4-[4-(2-hydroxy-ethoxy)-phenyl]-3-(naphthalen-2-ylmethoxy)-piperidine-1-carboxylate [Example 53(c)] with 4-chloromethyl-pyridine there was obtained tert-butyl (3RS,4RS)-3-(naphthalen-2-ylmethoxy)-4-{4-[2-(pyridin-4-ylmethoxy)-ethoxy]-phenyl}-piperidine-1-carboxylate as a colourless oil.

(m) In an analogous manner to that described in Example 1(g), by alkylating tert-butyl (3RS,4RS)-4-[4-(2-hydroxy-ethoxy)-phenyl]-3-(naphthalen-2-ylmethoxy)-piperidine-1-carboxylate [Example 53(c)] with 2-chloromethyl-pyridine there was obtained tert-butyl (3RS,4RS)-3-(naphthalen-2-ylmethoxy)-4-{4-[2-(pyridin-2-ylmethoxy)-ethoxy]-phenyl}-piperidine-1-carboxylate as a colourless oil.

(n) In an analogous manner to that described in Example 44(e), by alkylating tert-butyl (3RS,4RS)-3-hydroxy-4-(4-hydroxy-phenyl)-piperidine-1-carboxylate [Example 46(b)] with benzyl 3-bromopropyl ether in the presence of potassium carbonate in butan-2-one there was obtained tert-butyl (3RS,4RS)-4-[4-(3-benzyloxy-propoxy)-phenyl]-3-hydroxy-piperidine-1-carboxylate, alkylation of which with 2-bromomethyl-naphthalene analogously to Example 1(g) gave tert-butyl (3RS,4RS)-4-[4-(3-benzyloxy-propoxy)-phenyl]-3-(naphthalen-2-ylmethoxy)-piperidine-1-carboxylate as a colourless oil; MS: 582 (M+H)$^+$.

(o) In an analogous manner to that described in Example 1(g), by alkylating tert-butyl (3RS,4RS)-4-[4-(3-hydroxy-propoxy)-phenyl]-3-(naphthalen-2-ylmethoxy)-piperidine-1-carboxylate [Example 57(c)] with 2-chloromethylpyridine there was obtained tert-butyl (3RS,4RS)-3-(naphthalen-2-ylmethoxy)-4-[4-[3-(pyridin-2-ylmethoxy)-propoxy]-phenyl]-piperidine-1-carboxylate as a colourless resin; MS: 583 (M+H)$^+$.

(p) In an analogous manner to that described in Example 1(g), by alkylating tert-butyl (3RS,4RS)-4-[4-(3-hydroxy-propyl)-phenyl]-3-(naphthalen-2-ylmethoxy)-piperidine-1-carboxylate [Example 24(t)] with 2-chloromethyl-pyridine there was obtained tert-butyl (3RS,4RS)-3-(naphthalen-2-ylmethoxy)-4-[4-[3-(pyridin-2-ylmethoxy)-propyl]-phenyl]-piperidine-1-carboxylate as a colourless, amorphous solid, which was used in the following step without further purification and characterization.

(q) In an analogous manner to that described in Example 44(e), by alkylating tert-butyl (3RS,4RS)-4-[4-(3-methylamino-propoxy)-phenyl]-3-(naphthalen-2-ylmethoxy)-piperidine-1-carboxylate [Example 57(e)] with benzyl bromide there was obtained tert-butyl (3RS,4RS)-4-[4-[3-(benzyl-methyl-amino)-propoxy]-phenyl]-3-(naphthalen-2-ylmethoxy)-piperidine-1-carboxylate as a colourless solid; MS: 595 (M+H)$^+$.

(r) In an analogous manner to that described in Example 1(g), by alkylating a mixture of tert-butyl (3RS,4RS)- and (3SR,4SR)-3-hydroxy-4-[4-[3-[(RS)-tetrahydro-pyran-2-yloxy]-propoxy]-phenyl]-piperidine-1-carboxylate [Example 57(a)] with 1-methoxy-2-bromomethyl-naphthalene [Example 7(f)] there was obtained a mixture of tert-butyl (3RS,4RS)- and (3SR,4SR)-3-(1-methoxy-naphthalen-2-ylmethoxy)-4-[4-[3-[(RS)-tetrahydro-pyran-2-yloxy]-propoxy]-phenyl]-piperidine-1-carboxylate. Cleavage of the THP group by means of pyridinium (toluene-4-sulphonate) in ethanol analogously to Example 53(c) gave tert-butyl (3RS,4RS)-4-[4-(3-hydroxy-propoxy)-phenyl]-3-(1-methoxy-naphthalen-2-ylmethoxy)-piperidine-1-carboxylate, reaction of which with bis-(benzothiazol-2-yl) disulphide analogously to Example 33(a) gave tert-butyl (3RS,4RS)-4-[4-[3-(benzothiazol-2-ylsulphonyl)-propoxy]-phenyl]-3-(1-methoxy-naphthalen-2-ylmethoxy)-piperidine-1-carboxylate as a colourless liquid; MS: 671 (M+H)$^+$.

(s) In an analogous manner to that described in Example 33(a), by reacting tert-butyl (3RS,4RS)-4-[4-(3-hydroxy-propyl)-phenyl]-3-(naphthalen- 2-ylmethoxy)-piperidine-1-carboxylate [Example 24(t)] with diphenyl disulphide there was obtained tert-butyl (3RS,4RS)-3-(naphthalen-2-ylmethoxy)-4-[4-(3-phenylsulphanyl-propyl)-phenyl]-piperidine-1-carboxylate as a colourless, amorphous solid; MS: 568 (M+H)$^+$.

(t) In an analogous manner to that described in Example 33(a), by reacting tert-butyl (3RS,4RS)-4-[4-(3-hydroxy-propyl)-phenyl]-3-(naphthalen-2-ylmethoxy)-piperidine-1-carboxylate [Example 24(t)] with bis-(benzothiazol-2-yl) disulphide there was obtained tert-butyl (3RS,4RS)-4-{4-[3-(benzothiazol-2-ylsulphanyl)-propyl]-phenyl}-3-(naphthalen-2-ylmethoxy)-piperidine-1-carboxylate, which was used in the following step without further purification and characterization.

(u) (α) In an analogous manner to that described in Example 1(g), by alkylating tert-butyl (3RS,4RS)-3-hydroxy-4-[4-(2-trityloxy-ethyl)-phenyl]-piperidine-1-carboxylate [Example 29(t)] with 3-chloromethyl-1-(2-trimethylsilanyl-ethoxymethoxy)-naphthalene [Example 5(c)] there was obtained tert-butyl (3RS,4RS)-3-[4-(2-trimethylsilanyl-ethoxymethoxy)-naphthalen-2-ylmethoxy]-4-[4-(2-trityloxy-ethyl)-phenyl]-piperidine-1-carboxylate.

(β) Selective cleavage of the trityl group was effected analogously to the procedure published by E. Krainer et al. in Tetrahedron Letters 1993, 1713–1716 by treating a solution of 780 mg (0.92 mmol) of tert-butyl (3RS,4RS)-3-[4-(2-trimethylsilanyl-ethoxymethoxy)-naphthalen-2-ylmethoxy]-4-[4-(2-trityloxy-ethyl)-phenyl]-piperidine-1-carboxylate in 15 ml of methylene chloride with a solution of 436 mg (3.68 mmol) of trifluoroacetic acid and 803 mg (3.68 mmol) of trifluoroacetic anhydride in 2 ml of methylene chloride. After 30 seconds the reaction mixture was cooled to 0° C. and treated with 4 ml of triethylamine. After 5 minutes 10 ml of methanol were added and the mixture was stirred for 10 minutes. Subsequently, the mixture was washed with saturated sodium hydrogen carbonate solution and the aqueous phase was thereafter back-extracted with 10 ml of methylene chloride. The combined organic phases were dried over sodium sulphate and then evaporated under reduced pressure. The crude product was chromatographed on silica gel using a 4:1 mixture of hexane and ethyl acetate as the eluent. There were obtained 553 mg of tert-butyl (3RS,4RS)-4-[4-( 2-hydroxy-ethyl)-phenyl]-3-[4-(2-trimethylsilanyl-ethoxymethoxy)-naphthalen-2-ylmethoxy]-piperidine-1-carboxylate as a colourless oil.

(γ) In an analogous manner to that described in Example 34, from tert-butyl (3RS,4RS)-4-[4-(2-hydroxy-ethyl)-phenyl]-3-[4-(2-trimethylsilanyl-ethoxymethoxy)-naphthalen-2-ylmethoxy]-piperidine-1-carboxylate via the corresponding mesylate by reaction with 2-mercaptopyrimidine there was obtained tert-butyl (3RS,4RS)-4-{4-[2-(pyrimidin-2-ylsulphanyl)-ethyl]-phenyl}-3-[4-(2-trimethylsilanyl-ethoxymethoxy)-naphthalen-2-ylmethoxy]-piperidine-1-carboxylate as a colourless oil, which was used in the following step without further purification and characterization.

(v) In an analogous manner to that described in Example 33(a), from tert-butyl (3RS,4RS)-4-[4-(2-hydroxy-ethyl)-phenyl]-3-[4-(2-trimethylsilanyl-ethoxymethoxy)-naphthalen-2-ylmethoxy]-piperidine-1-carboxylate by reaction with 2,2'-dithiopyridine there was obtained tert-butyl (3RS,4RS)-4-{4-[2-(pyridin-2-ylsulphanyl)-ethyl]-phenyl}-3-[4-(2-trimethylsilanyl-ethoxymethoxy)-naphthalen-2-ylmethoxy]-piperidine-1-carboxylate as a colourless oil, which was used in the following step without further purification and characterization.

(w) In an analogous manner to that described in Example 33(a), from tert-butyl (3RS,4RS)-4-[4-(2-hydroxy-ethyl)-phenyl]-3-[4-(2-trimethylsilanyl-ethoxymethoxy)-naphthalen-2-ylmethoxy]-piperidine-1-carboxylate by reaction with bis-(benzothiazol-2-yl) disulphide there was obtained tert-butyl (3RS,4RS)-4-[4-[2-(benzothiazol-2-ylsulphanyl)-ethyl]-phenyl]-3-[4-(2-trimethylsilanyl-ethoxymethoxy)-naphthalen-2-ylmethoxy]-piperidine-1-carboxylate as a colourless foam; MS: 757 (M+H)$^+$.

(x) In an analogous manner to that described in Example 1(g), by alkylating tert-butyl (3RS,4RS)-4-(4-hydroxymethyl-phenyl)-3-(naphthalen-2-ylmethoxy)-piperidine-1-carboxylate [Example 22(j)] with 3-chloromethyl-pyridine there was obtained tert-butyl (3RS,4RS)-3-(naphthalen-2-ylmethoxy)-4-[4-(pyridin-3-yl-methoxymethyl)-phenyl]-piperidine-1-carboxylate as a colourless oil; MS: 539 (M+H)$^+$.

(y) In an analogous manner to that described in Example 9(c), by esterifying tert-butyl (3RS,4RS)-4-[4-(2-hydroxy-ethoxy)-phenyl]-3-(naphthalen-2-ylmethoxy)-piperidine-1-carboxylate [Example 53(c)] with (RS)-2-(4-fluoro-phenyl)-3-methyl-butyric acid (DE 2365555) in the presence of EDC there was obtained a mixture of tert-butyl (3RS,4RS)- and (3SR,4SR)-4-(4-2-[(RS)-2-(4-fluoro-phenyl)-3-methyl-butyryloxy]-ethoxy)-phenyl)-3-(naphthalen-2-ylmethoxy)-piperidine-1-carboxylate as a colourless solid; MS: 656 (M+H)$^+$.

(z) In an analogous manner to that described in Example 9(c), by esterifying tert-butyl (3RS,4RS)-4-[4-(2-hydroxy-ethoxy)-phenyl]-3-(naphthalen-2-ylmethoxy)-piperidine-1-carboxylate [Example 53(c)] with 1-methyl-pyrrole-2-carboxylic acid in the presence of EDC there was obtained tert-butyl (3RS,4RS)-4-[4-[2-(1-methyl-1H-pyrrol-2-carbonyloxy)-ethoxy]-phenyl]-3-(naphthalen-2-ylmethoxy)-piperidine-1-carboxylate as a colourless oil; MS: 585 (M+H)$^+$.

(aa) In an analogous manner to that described in Example 22(k), by acylating tert-butyl (3RS,4RS)-4-[4-(3-hydroxy-propyl)-phenyl]-3-(naphthalen-2-ylmethoxy)-piperidine-1-carboxylate [Example 24(t)] with benzoyl chloride there was obtained tert-butyl (3RS,4RS)-4-[4-(3-benzoyloxy-propyl)-phenyl]-3-(naphthalen-2-ylmethoxy)-piperidine-1-carboxylate as an almost colourless solid; MS: 580 (M+H)$^+$.

(bb) In an analogous manner to that described in Example 22(k), by acylating tert-butyl (3RS,4RS)-4-[4-(3-hydroxy-propyl)-phenyl]-3-(naphthalen-2-ylmethoxy)-piperidine-1-carboxylate [Example 24(t)] with 3-methoxy-benzoyl chloride there was obtained tert-butyl (3RS,4RS)-4-{4-[3-(3-Methoxy-benzoyloxy)-propyl]-phenyl}-3-(naphthalen-2-ylmethoxy)-piperidine-1-carboxylate as a colourless, amorphous solid; MS: 610 (M+H)$^+$.

(cc) In an analogous manner to that described in Example 1(g), by alkylating tert-butyl (3RS,4RS)-3-hydroxy-4-(4-trityloxymethyl-phenyl)-piperidine-1-carboxylate [Example 22(h)] with 2-chloromethyl-1-(2-trimethylsilanyl-ethoxymethoxy)-naphthalene [Example 6(c)] there was obtained tert-butyl (3RS,4RS)-3-[1-(2-trimethylsilanyl-ethoxymethoxy)-naphthalen-2-ylmethoxy]-4-(4-trityloxymethyl-phenyl)-piperidine-1-carboxylate. Selective cleavage of the trityl group analogously to Example 86(u) (β) gave tert-butyl (3RS,4RS)-4-(4-hydroxymethyl-phenyl)-3-[1-(2-trimethylsilanyl-ethoxymethoxy)naphthalen-2-ylmethoxy]-piperidine-1-carboxylate, acylation of which with 3-methoxy-benzoyl chloride analogously to Example 22(k) gave tert-butyl (3RS,4RS)-4-[4-(3-methoxy-benzoyloxymethyl)-phenyl]-3-[1-(2-trimethylsilanyl-ethoxymethoxy)-naphthalen-2-ylmethoxy]-piperidine-1-carboxylate as a colourless oil, MS: 745 (M+NH$_4$)$^+$.

(dd) In an analogous manner to that described in Example 44(e), by alkylating tert-butyl (3RS,4RS)-4-(4-hydroxy-phenyl)-3-(naphthalen-2-ylmethoxy)-piperidine-1-carboxylate [Example 61(c)] with ethyl bromoacetate there was obtained tert-butyl (3RS,4RS)-4-(4-ethoxycarbonylmethoxy-phenyl)-3-(naphthalen-2-ylmethoxy)-piperidine-1-carboxylate as a colourless solid; MS: 520 (M+H)$^+$.

(ee) Saponification of tert-butyl (3RS,4RS)-4-(4-ethoxycarbonylmethoxy-phenyl)-3-(naphthalen-2-ylmethoxy)-piperidine-1-carboxylate [Example 86(dd)] with 1N sodium hydroxide in methanol yielded tert-butyl (3RS,4RS)-4-(4-carboxymethoxy-phenyl)-3-(naphthalen-2-ylmethoxy)-piperidine-1-carboxylate, condensation of which with benzylamine in the presence of HBTU analogously to Example 36(b) gave tert-butyl (3RS,4RS)-4-[4-(benzylcarbamoyl-methoxy)-phenyl]-3-(naphthalen-2-ylmethoxy)-piperidine-1-carboxylate as a yellowish solid; MS: 598 (M+NH$_4$)$^+$.

(ff) In an analogous manner to that described in Example 24(m), by reacting tert-butyl (3RS,4RS)-4-(4-hydroxy-phenyl)-3-(naphthalen-2-ylmethoxy)-piperidine-1-carboxylate with 2-pyridyl isocyanate there was obtained tert-butyl (3RS,4RS)-3-(naphthalen-2-ylmethoxy)-4-[4-(pyridin-2-ylcarbamoyloxy)-phenyl]-piperidine-1-carboxylate as a white solid; MS: 554 (M+H)$^+$.

(gg) In an analogous manner to that described in Example 68(b), by Swern oxidation of a mixture of tert-butyl (3RS,4RS)- and (3SR,4SR)-4-[4-[(RS)-2-hydroxy-3-phenoxy-propoxy]-phenyl]-3-(naphthalen-2-ylmethoxy)-piperidine-1-carboxylate there was obtained tert-butyl (3RS,4RS)-3-(naphthalen-2-ylmethoxy)-4-[4-(2-oxo-3-phenoxypropoxy)-phenyl]-piperidine-1-carboxylate as a white solid; MS: 582 (M+H)$^+$.

(hh) (α) A solution of 5 mg (0.04 mmol) of potassium bromide and 20 mg (0.24 mmol) of sodium hydrogen carbonate in 10 ml of water was added at room temperature and while stirring to a solution of 0.270 g (0.58 mmol) of tert-butyl (3RS,4RS)-4-[4-(2-hydroxy-ethyl)-phenyl]-3-naphthalen-2-ylmethoxy-piperidine-1-carboxylate [Example 29(h)] in 10 ml of methylene chloride under argon. The reaction mixture was cooled to 0° C. and treated with 2 mg (0.01 mmol) of 2,2,6,6-tetramethyl-1-piperidinyloxyl (TEMPO). Then, 1 ml (0.658 mmol) of Javelle water was sprayed into the reaction mixture while stirring continuously. After the addition the reaction mixture was stirred at 0° C. for about 30 minutes. For the working-up, 20 ml of a 1:1 mixture of methylene chloride and water were added, the reaction mixture was washed with 10 ml of saturated sodium chloride solution and the aqueous phase was back-extracted with 10 ml of methylene chloride. The combined organic phases were dried over sodium sulphate and evaporated under reduced pressure. The crude product was purified by flash chromatography on silica gel with a 2:1 mixture of hexane and ethyl acetate as the eluent. There were obtained 200 mg (75% of theory) of tert-butyl (3RS,4RS)-3-(naphthalen-2-ylmethoxy)-4-[4-(2-oxo-ethyl)-phenyl]-piperidine-1-carboxylate as a foam; MS: 460 (M+H)$^+$.

(β) In an analogous manner to that described in Example 40(a), by a Grignard reaction of tert-butyl (3RS,4RS)-3-(naphthalen-2-ylmethoxy)-4-[4-(2-oxo-ethyl)-phenyl]-piperidine-1-carboxylate with phenylmagnesium chloride there was obtained a mixture of tert-butyl (3RS,4RS)-4-[4-[(RS)-2- and [(SR)-2-hydroxy-2-phenyl-ethyl]-phenyl]-3-(naphthalen-2-ylmethoxy)-piperidine-1-carboxylate as a colourless oil.

(ii) In an analogous manner to that described in Example 9(a)–(c), by alkylating tert-butyl (3RS,4RS)-4-(4-fluoro-phenyl)-3-hydroxy-piperidine-1-carboxylate [Example 3(b)] with 2-bromomethylbenzonitrile there was obtained tert-butyl (3RS,4RS)-3-(2-cyano-benzyloxy)-4-(4-fluoro-phenyl)-piperidine-1-carboxylate, reduction of which using borane-dimethyl sulphide complex gave tert-butyl (3RS,4RS)-3-(2-aminomethyl-benzyloxy)-4-(4-fluoro-phenyl)-piperidine- 1-carboxylate. Subsequent acylation with pyridine-2-carboxylic acid in the presence of EDC yielded tert-butyl (3RS,4RS)-4-(4-fluoro-phenyl)-3-(2-{[(pyridine-2-carbonyl)-amino]-methyl}-benzyloxy)-piperidine-1-carboxylate as a white solid.

(jj) In an analogous manner to that described in Example 1(g), by alkylating tert-butyl (3RS,4RS)-4-(4-fluoro-phenyl)-3-hydroxy-piperidine-1-carboxylate [Example 3(b)] with (3-bromomethyl-phenyl)-phenyl-methanone [J.Med.Chem. 1984, 27 (12), 1682–1690] there was obtained tert-butyl (3RS,4RS)-3-(3-benzoyl-benzyloxy)-4-(4-fluoro-phenyl)-piperidine-1-carboxylate as a yellowish liquid; MS: 490 (M+H)$^+$.

(kk) (α) A solution of 470 mg (1.0 mmol) of tert-butyl (3RS,4RS)-4-[4-(2-cyano-ethyl)-phenyl]-3-naphthalen-2-ylmethoxy-piperidine-1-carboxylate [Example 35(b)] and 348 mg (5.0 mmol) of hydroxylamine hydrochloride in 6 ml of a 1M sodium methylate solution in methanol was stirred at 65° C. for 5 hours. For working-up, the mixture was partitioned between 40 ml of ethyl acetate and 40 ml of water and thereafter the organic phase was separated. The aqueous phase was extracted twice with 40 ml of ethyl acetate each time. The combined organic phases were dried over magnesium sulphate and finally the solvent was distilled off under reduced pressure. The crude product (550 mg) was purified by chromatography on silica gel with a 20:1:0.1 mixture of methylene chloride, methanol and 28% ammonia solution. There were obtained 501 mg (99% of theory) of tert-butyl (3RS,4RS)-4-{4-[2-(N-hydroxycarbamimidoyl)-ethyl]-phenyl}-3-(naphthalen-2-ylmethoxy)-piperidine-1-carboxylate as a yellow oil, which was used directly in the next step.

(b) In an analogous manner to that described in Example 38, by condensing tert-butyl (3RS,4RS)-4-{4-[2-(N-hydroxycarbamimidoyl)-ethyl]-phenyl}-3-(naphthalen-2-ylmethoxy)-piperidine-1-carboxylate with benzoic acid in the presence of EDC and subsequent cyclization there was obtained tert-butyl (3RS,4RS)-3-(naphthalen-2-ylmethoxy)-4-[4-[2-(5-phenyl-[1,2,4]oxadiazol-3-yl)-ethyl]-phenyl]-piperidine-1-carboxylate; MS: 590 (M+H)$^+$.

(II) By alkaline saponification of tert-butyl (3RS,4RS)-4-[4-(2-ethoxycarbonyl-ethyl)-phenyl]-3-(naphthalen-2-ylmethoxy)-piperidine-1-carboxylate [Example 24(s)] with aqueous sodium hydroxide in tetrahydrofuran there was obtained tert-butyl (3RS,4RS)-4-[4-(2-carboxy-ethyl)-phenyl]-3-(naphthalen-2-ylmethoxy)piperidine-1-carboxylate, condensation of which with N-hydroxy-benzamidine in the presence of EDC in an analogous manner to that described in Example 38 gave the corresponding N-hydroxy-benzamidine ester and cyclization of the latter yielded tert-butyl (3RS,4RS)-3-(naphthalen-2-ylmethoxy)-4-[4-[2-(3-phenyl-[1,2,4]oxadiazol-5-yl)-ethyl]-phenyl]-piperidine-1-carboxylate as a yellowish, amorphous solid; MS: 590 (M+H)$^+$.

(mm) Saponification of tert-butyl (3RS,4RS)-4-(4-ethoxycarbonylmethoxy-phenyl)-3-(naphthalen-2-ylmethoxy)-piperidine-1-carboxylate [Example 86(dd)] with 1N sodium hydroxide in methanol yielded tert-butyl (3RS,4RS)-4-(4-carboxymethoxy-phenyl)-3-(naphthalen-2-ylmethoxy)-piperidine-1-carboxylate, condensation of which with N-hydroxy-benzamidine in the presence of HBTU in an analogous manner to that described in Example 38 gave the corresponding N-hydroxy-benzamidine ester and cyclization of the latter gave tert-butyl (3RS,4RS)-3-(naphthalen-2-ylmethoxy)-4-[4-(3-phenyl-[1,2,4]oxadiazol-5-ylmethoxy)-phenyl]-piperidine-1-carboxylate as a colourless oil; MS: 592 (M+H)$^+$.

(nn) In an analogous manner to that described in Example 38, by condensing tert-butyl (3RS,4RS)-4-(4-carboxymethoxy-phenyl)-3-(naphthalen-2-ylmethoxy)-piperidine-1-carboxylate [Example 86(mm)] with 3-pyridinamidoxime in the presence of HBTU and subsequent cyclization there was obtained tert-butyl (3RS,4RS)-3-(naphthalen-2-ylmethoxy)-4-[4-(3-pyridin-3-yl-[1,2,4]oxadiazol-5ylmethoxy)-phenyl]-piperidine-1-carboxylate as a yellowish solid; MS: 593 (M+H)$^+$.

(oo) In an analogous manner to that described in Example 44(e), by alkylating tert-butyl (3RS,4RS)-4-(4-hydroxy-phenyl)-3-(naphthalen-2-ylmethoxy)-piperidine-1-carboxylate [Example 61(c)] with 5-hydroxymethyl-3-phenyl-4,5-dihydro-isoxazole mesylate, prepared according to a generally known procedure, there was obtained tert-butyl (3RS,4RS)-3-(naphthalen-2-ylmethoxy)-4-[4-(3-phenyl-isoxazol-5-ylmethoxy)-phenyl]-piperidine-1-carboxylate as a colourless solid; MS: 591 (M+H)$^+$.

The following BOC derivatives were obtained in an analogous manner to that described in Example 1(g) by alkylating tert-butyl (3RS,4RS)-4-[4-(3-benzyloxy-propoxy)-phenyl]-3-hydroxy-piperidine-1-carboxylate [Example 86(n)] as follows:

(pp) with 3-methoxybenzyl chloride to give tert-butyl (3RS,4RS)-4-[4-(3-benzyloxy-propoxy)-phenyl]-3-(3-methoxy-benzyloxy)-piperidine-1-carboxylate, which was obtained as a colourless oil; MS: 579 (M+NH$_4$)$^+$.

(qq) with 1-chloromethyl-3-(2-trimethylsilanyl-ethoxymethoxy)-benzene to give tert-butyl (3RS,4RS)-4-[4-(3-benzyloxy-propoxy)-phenyl]-3-[3-(2-trimethylsilanyl-ethoxymethoxy)-benzyloxy]-piperidine-1-carboxylate, which was obtained as a colourless oil; MS: 695 (M+NH$_4$)$^+$.

The 1-chloromethyl-3-(2-trimethylsilanyl-ethoxymethoxy)-benzene used as the alkylating agent was prepared in analogy to Example 5(a)–(d) by converting methyl 3-hydroxybenzoate into methyl 3-(2-trimethylsilanyl-ethoxymethoxy)-benzoate by introduction of the SEM group. Subsequent reduction with lithium aluminium hydride gave [3-(2-trimethylsilanylethoxy-methoxy)-phenyl]-methanol and chlorination of the latter gave 1-chloromethyl-3-(2-trimethylsilanyl-ethoxymethoxy)-benzene as a colourless oil; MS: 272 (M)$^+$.

(rr) with 3-chloro-4-methoxy-benzyl chloride to give tert-butyl (3RS,4RS)-4-[4-(3-benzyloxy-propoxy)-phenyl]-3-(3-chloro-4-methoxy-benzyloxy)-piperidine-1-carboxylate, which was used in the following step without further purification and characterization;

(ss) with 3,4-dichloro-benzyl chloride to give tert-butyl (3RS,4RS)-4-[4-(3-benzyloxy-propoxy)-phenyl]-3-(3,4-dichloro-benzyloxy)-piperidine-1-carboxylate, which was used in the following step without further purification and characterization;

(tt) with 2,5-dichloro-benzyl chloride to give tert-butyl (3RS,4RS)-4-[4-(3-benzyloxy-propoxy)-phenyl]-3-(2,5-dichloro-benzyloxy)-piperidine-1-carboxylate, which was used in the following step without further purification and characterization;

(uu) with benzyl chloride to give tert-butyl (3RS,4RS)-3-benzyloxy-4-[4-(3-benzyloxy-propoxy)-phenyl]-piperidine-1-carboxylate, which was used in the following step without further purification and characterization;

(vv) with 2,5-dimethyl-benzyl chloride to give tert-butyl (3RS,4RS)-4-[4-(3-benzyloxy-propoxy)-phenyl]-3-(2,5-dimethyl-benzyloxy)-piperidine-1-carboxylate, which was used in the following step without further purification and characterization;

(ww) with 4-ethyl-benzyl chloride to give tert-butyl (3RS,4RS)-4-[4-(3-benzyloxy-propoxy)-phenyl]-3-(4-ethyl-benzyloxy)-piperidine-1-carboxylate, which was used in the following step without further purification and characterization;

(xx) with a mixture of 3- and 4-vinyl-benzyl chloride to give a mixture of tert-butyl (3RS,4RS)-4-[4-(3-benzyloxy-propoxy)-phenyl]-3-(3- and 4-vinyl-benzyloxy)-piperidine-1-carboxylate, which was used in the following step without further purification and characterization;

(yy) with 6-chloromethyl-2,3-dihydro-benzo[1,4]dioxin to give tert-butyl (3RS,4RS)-4-[4-(3-benzyloxy-propoxy)-phenyl]-3-(2,3-dihydro-benzo[1,4]dioxin-6-ylmethoxy)-piperidine-1-carboxylate, which was obtained as a colourless resin; MS: 607 (M+NH$_4$)$^+$;

(zz) with 6-chloromethyl-1,2,3,4-tetrahydro-naphthalene to give tert-butyl (3RS,4RS)-4-[4-(3-benzyloxy-propoxy)-phenyl]-3-(5,6,7,8-tetrahydro-naphthalen-2-ylmethoxy)-piperidine-1-carboxylate, which was obtained as a colourless resin; MS: 603 (M+NH$_4$)$^+$;

(aaa) with 3-chloromethyl-1-(2-trimethylsilanyl-ethoxymethoxy)-naphthalene [Example 5(c)] to give tert-butyl (3RS,4RS)-4-[4-(3-benzyloxy-propoxy)-phenyl]-3-[4-(2-trimethylsilanyl-ethoxymethoxy)-naphthalen-2-ylmethoxy]-piperidine-1-carbxylate, which was obtained as a colourless resin; MS: 745 (M+NH$_4$)$^+$.

(bbb) In an analogous manner to that described in Example 44(e), by alkylating tert-butyl (3RS,4RS)-3-hydroxy-4-(4-hydroxy-phenyl)-piperidine-1-carboxylate [Example 46(b)] with 2-(4-chloro-butoxy)-tetrahydro-2H-pyran there was obtained a mixture of tert-butyl (3RS,4RS)- and (3SR,4SR)-3-hydroxy-4-[4-[4-[(RS)-tetrahydropyran-2-yloxy]-butoxy]-phenyl]-piperidine-1-carboxylate, alkylation of which with 2-bromomethyl-naphthalene analogously to Example 1 10(g) gave a mixture of (3RS,4RS)- and (3SR,4SR)-3-(naphthalen-2-ylmethoxy)-4-[4-[4-[(RS)-tetrahydro-pyran-2-yloxy]-butoxy]-phenyl]-piperidine-1-carboxylate. Cleavage of the THP group with hydrogen chloride in methanol analogously to Example 53(c) yielded tert-butyl (3RS,4RS)-4-[4-(4-hydroxy-butoxy)-phenyl]-3-(naphthalen-2-ylmethoxy)-piperidine1-carboxylate, alkylation of which with benzyl bromide analogously to Example 1(g) gave tert-butyl (3RS,4RS)-4-[4-(4-benzyloxy-butoxy)-phenyl]-3-(naphthalen-2-ylmethoxy)-piperidine-1-carboxylate as a colourless oil; MS: 613 (M+NH$_4$)$^+$.

(ccc) In an analogous manner to that described in Example 22(d), from tert-butyl (3RS,4RS,5SR)-4-(4-bromo-phenyl)-5-methoxymethyl-3-naphthalen-2-yl-methoxy-piperidine-1-carboxylate [Example 68(l)] by a palladium-catalyzed carbonylation with carbon monoxide in methanol there was obtained tert-butyl (3SR,4RS,5RS)-4-(4-methoxycarbonyl-phenyl)-3-methoxymethyl-5-(naphthalen-2-ylmethoxy)-piperidine-1-carboxylate, reduction of which with lithium borhydride analogously to Example 22(e) yielded tert-butyl (3SR,4RS,5RS)-4-(4-hydroxymethyl-phenyl)-3-methoxymethyl-5-(naphthalen-2-yl-methoxy)-piperidine-1-carboxylate. Subsequent acylation with 2-chlorobenzoyl chloride analogously to Example 22(k) gave tert-butyl (3SR,4RS,5RS)-4-[4-(2-chloro-benzoyl-oxymethyl)-phenyl]-3-methoxymethyl-5-(naphthalen-2-ylmethoxy)-piperidine-1-carboxylate as a colourless foam; MS: 630 (M+H)$^+$.

(ddd) In an analogous manner to that described in Example 1(g), by alkylating tert-butyl (3SR,4RS,5RS)-4-(4-hydroxymethyl-phenyl)-3-methoxymethyl-5-(naphthalen-2-yl-methoxy)-piperidine-1-carboxylate with benzyl bromide there was obtained tert-butyl (3SR,4RS,5RS)-4-(4-benzyloxymethyl-phenyl)- 3-methoxymethyl-5-(naphthalen-2-ylmethoxy)-piperidine-1-carboxylate as a colourless oil; MS: 582 (M+H)$^+$.

(eee) In an analogous manner to that described in Example 12(c)–(d), cleavage of the N-methyl group from (1RS,2RS,3RS,5SR)-3-(4-bromo-phenyl)-8-methyl-8-aza-bicyclo[3.2.1]octan-2-ol, obtained analogously to the 4-chlorophenyl derivative [J.Org.Chem. 35, 802 (1970)], was effected by firstly synthesizing (1RS,2RS,3RS,5SR)-3-(4-bromo-phenyl)-2-(2,2,2-trichloro-ethoxycarbonyloxy)-8-aza-bicyclo[3.2.1]octane-8-carboxylate by reaction with 2,2,2-trichloroethyl chloroformate and subsequently reacting with zinc in glacial acetic acid to give (1RS,2RS,3RS,5SR)-3-(4-bromo-phenyl)-8-aza-bicyclo[3.2.1]octan-2-ol. Subsequent introduction of the BOC group analogously to Example 1(f) gave tert-butyl (1RS,2RS,3RS,5SR)-3-(4-bromo-phenyl)-2-hydroxy-8-aza-bicyclo[3.2.1]octane-8-carboxylate, palladium-catalyzed carbonylation of which with carbon monoxide in methanol analogously to Example 22(d) yielded tert-butyl (1RS,2RS,3RS,5SR)-2-hydroxy-3-(4-methoxycarbonyl-phenyl)-8-aza-bicyclo[3.2.1]octane-8-carboxylate. Subsequent reduction with lithium borohydride analogously to Example 22(e) gave tert-butyl (1RS,2RS,3RS,5SR)-2-hydroxymethyl-phenyl)-8-aza-bicyclo[3.2.1]octane-8-carboxylate, reaction of which with trityl chloride analogously to Example 22(h) gave tert-butyl (1RS,2RS,3RS,5SR)-2-hydroxy-3-(4-trityloxymethyl)-phenyl)-8-aza-bicyclo[3.2.1]octane-8-carboxylate. Further reaction with 2-bromomethyl-naphthalene analogously to Example 1(g) gave tert-butyl (1RS,2RS,3RS,5SR)-2-(naphthalen-2-ylmethoxy)-3-(4-trityloxymethyl-phenyl)-8-aza-bicyclo[3.2.1]octane-8-carboxylate. In an analogous manner to that described in Example 86(u)(b), by cleavage of the trityl group with a mixture of trifluoroacetic acid and trifluoroacetic anhydride there was obtained tert-butyl (1RS,2RS,3RS,5SR)-3-(4-hydroxymethyl-phenyl)-2-(naphthalen-2-ylmethoxy)-8-aza-bicyclo[3.2.1]octane-8-carboxylate, alkylation of which with benzyl 3-bromopropyl ether analogously to Example 44(e) gave tert-butyl (1RS,2RS,3RS,5SR)-3-[4-(2-benzyloxy-propoxymethyl)-phenyl]-2-(naphthalen-2-ylmethoxy)-8-aza-bicyclo[3.2.1]octane-8-carboxylate as a colourless oil.

EXAMPLE 87

The following compounds were obtained in an analogous manner to that described in Example 73(d) by cleavage of the BOC group using anhydrous zinc bromide:

1) From tert-butyl (3RS,4RS)-3-(naphthalen-2-carbonyloxy)-4-[4-(2-phenoxy-ethoxy)-phenyl]-piperidine-1-carboxylate, (3RS,4RS)-4-[4-(2-phenoxy-ethoxy)-phenyl]-piperidin-3-yl naphthalene-2-carboxylate as a colourless solid; MS: 468 (M+H)$^+$;

2) from a mixture of tert-butyl (3RS,4RS)-4-(4-fluoro-phenyl)-3-[(RS)- and (SR)-2-hydroxy-1-naphthalen-2-yl-ethoxy]-piperidine-1-carboxylate, a mixture of (RS)- and (SR)-2-[(3RS,4RS)-4-(4-fluoro-phenyl)-piperidine-3-yloxy]-2-naphthalen-2-yl-ethanol as a colourless, amorphous solid; MS: 366 (M+H)$^+$.

The BOC derivatives used as the starting materials were prepared as follows:

(a) 250 mg of 4-dimethylamino-pyridine and 2.5 ml of triethylamine were added to a solution of 5.50 g (13.3 mmol) of tert-butyl (3RS,4RS)-3-hydroxy-4-[4-(2-phenoxy-ethoxy)-phenyl]-piperidine-1-carboxylate (Example 47.6) in 50 ml of methylene chloride and 2.77 g (14.5 mmol) of solid 2-naphthoyl chloride were subsequently added while cooling with ice. Thereupon, the reaction mixture was stirred at room temperature for 20 hours, partitioned between water and methylene chloride, the combined methylene chloride phases were dried over magnesium sulphate and concentrated, and the thus-obtained residue was chromatographed on silica gel with methylene chloride/ether (95:5). There were thus obtained 7.3 g (97% of theory) of tert-butyl (3RS,4RS)-3-(naphthalen-2-carbonyloxy)-4-[4-(2-phenoxy-ethoxy)-phenyl]-piperidine-1-carboxylate in the form of an amorphous, colourless solid; MS: 568 (M+H)$^+$.

(b) Under argon and with the exclusion of moisture, 255 mg (0.57 mmol) of tert-butyl (3RS,4RS)-4-(4-fluoro-phenyl)-3-(1-naphthalen-2-yl-vinyloxy)-piperidine-1-carboxylate [Example 73(b)] were dissolved in 3 ml of tetrahydrofuran, treated at 0° C. with 50 mg of triethylamine followed by 0.11 ml (about 1.1 mmol) of borane-dimethyl sulphide complex and stirred at room temperature for 30 minutes. Thereupon, again while cooling with ice, 1.5 ml of 50% KOH solution in water followed by 1.5 ml of 30% hydrogen peroxide solution in water were added and the reaction mixture was heated under reflux for 1.5 hours. Now, the reaction solution was partitioned between water and methylene chloride, the combined methylene chloride phases were dried over magnesium sulphate, concentrated and the thus-obtained residue was chromatographed on silica gel with hexane/ethyl acetate (1:1). There were thus obtained 30 mg (11% of theory) of a mixture of tert-butyl (3RS,4RS)-4-(4-fluoro-phenyl)-3-[(RS)- and (SR)-2-hydroxy-1-naphthalen-2-yl-ethoxy]-piperidine-1-carboxylate in the form of an amorphous, colourless solid; MS: 466 (M+H)$^+$.

EXAMPLE 88

(a) 25.23 g (91 mmol) of tert-butyl 4-(4-fluoro-phenyl)-1,2,3,6-tetrahydro-pyridine-1-carboxylate [prepared from 4-(4-fluorophenyl)-1,2,3,6-tetrahydro-pyridine and di-tert-butyl dicarbonate in analogy to Example 1(f)] were suspended in 200 ml of 1,2-dimethoxyethane, 5.1 g (135 mmol) of sodium borohydride were added thereto at 20° C. and subsequently a solution of 22.85 ml (182 mmol) of boron trifluoride ethyl etherate in 35 ml of 1,2-dimethoxyethane was added dropwise during 45 minutes while cooling occasionally at 20° C. After stirring at room temperature for 2½ hours a solution of 82 g (1.26 mmol) of potassium hydroxide (86%) in 430 ml of distilled water was added dropwise at room temperature during 1 hour while stirring intensively. Thereupon, 69.3 ml (0.68 mmol) of hydrogen peroxide (30%) were added dropwise at room temperature within 30 minutes and then the mixture was stirred at reflux for 3 hours. After cooling to room temperature the mixture was poured on to ice-water, the product was extracted 3 times with 200 ml of ethyl acetate each time, the organic phases were washed twice with 300 ml of distilled water each time, then dried over magnesium sulphate, filtered and concentrated in a water-jet vacuum. After drying in a high vacuum at room temperature for 90 minutes there were thus obtained 24.4 g (91% of theory) of tert-butyl (3RS,4RS)-4-(4-fluoro-phenyl)-3-hydroxy-piperidine-1-carboxylate in the form of colourless crystals; MS: 296 (M+H)$^+$.

(b) 39.2 g (0.2 mol) of 3-methylbenzophenone and 38.4 g (0.24 mol) of bromine were stirred at reflux in 1 l of carbon tetrachloride for 8 hours. After distillation of the solvent in a water-jet vacuum the crude product obtained was chromatographed on 500 g of silica gel with hexane and methylene chloride. The thus-purified product was recrystallized from n-hexane. There were thus obtained 21.76 g (40% of theory) of (3-bromomethyl-phenyl)-phenyl-methanone in the form of colourless crystals; MS: 274, 276 (M)$^+$.

(c) 0.29 g (1 mmol) of tert-butyl (3RS,4RS)-4-(4-fluoro-phenyl)-3-hydroxy-piperidine-1-carboxylate and 0.30 g (1.1 mmol) of (3-bromomethyl-phenyl)-phenyl-methanone were dissolved in 10 ml of dimethylformamide under argon at room temperature, then treated with 0.056 g (1.3 mmol) of sodium hydride dispersion (55% in mineral oil) with the addition of 0.25 g (1.5 mmol) of potassium iodide and stirred at room temperature for 18 hours. The reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.42 g (86% of theory) of tert-butyl (3RS,4RS)-3-(3-benzoyl-benzyloxy)-4-(4-fluoro-phenyl)-piperidine-1-carboxylate as a colourless oil; MS: 490 (M+H)$^+$.

(d) In an analogous manner to that described in Example 22(l), from tert-butyl (3RS,4RS)-3-(3-benzoyl-benzyloxy)-4-(4-fluoro-phenyl)-piperidine-1-carboxylate by cleavage of the BOC group with hydrogen chloride in methanol there was obtained [3-[(3RS,4RS)-4-(4-fluoro-phenyl)-piperidin-3-yloxymethyl]-phenyl]-phenyl-methanone hydrochloride (1:1) in the form of colourless crystals; MS: 390 (M+H)$^+$.

EXAMPLE 89

The following compounds were obtained in an analogous manner to that described in Example 73(d) by cleavage of the BOC group using anhydrous zinc bromide:
1) From tert-butyl (E)-(3RS,4RS)-4-(4-fluoro-phenyl)-3-(3-phenyl-allyloxy)-piperidine-1-carboxylate, (E)-(3RS,4RS)-4-(4-fluoro-phenyl)-3-(3-phenyl-allyloxy)-piperidine as a pale yellow oil; MS: 312 (M+H)$^+$;
2) from tert-butyl (3R,4s,5S)-4-[4-(3-benzyloxy-propoxy)-phenyl]-3,5-bis-(4,5-dimethoxy-pyrimidin-2-yloxymethyl)-piperidine-1-carboxylate, 2-[(3R,4s,5S)-4-[4-(3-benzyloxy-propoxy)-phenyl]-5-(4,5-dimethoxy-pyrimidin-2-yloxymethyl)-piperidine-3-ylmethoxy)-4,5-dimethoxy-pyrimidine as a pale yellow resin; MS: 662 (M+H)$^+$;
3) from tert-butyl (3R,4s,5S)-4-[4-(3-benzyloxy-propoxy)-phenyl]-3,5-bis-(4-methoxy-phenoxymethyl)-piperidine-1-carboxylate, (3R,4S,5S)-4-[4-(3-benzyloxy-propoxy)-phenyl]-3,5-bis-(4-methoxy-phenoxymethyl)-piperidine as a pale yellow oil; MS: 598 (M+H)$^+$;
4) from tert-butyl (3R,4s,5S)-4-[4-(3-benzyloxy-propoxy)-phenyl]-3,5-bis-p-tolylsulphanylmethyl-piperidine-1-carboxylate, (3R,4s,5S)-4-[4-(3-benzyloxy-propoxy)-phenyl]-3,5-bis-p-tolylsulphanylmethyl-piperidine as a pale yellow oil; MS: 598 (M+H)$^+$.
5) from (3RS,4RS)-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidin-1-carboxylic acid tert-butylester, 1-[2-[7-[(3RS,4RS)-4-[4-[3-(2-methoxy-benzyloxy)-propoxy]-piperidin-3-yloxymethyl]-naphthalen-2-yloxy]-ethyl]-4-methyl-piperazine as a amorphous, colourless solid; MS: 654 (M+H)$^+$.

The BOC derivatives used as the starting materials were prepared as follows:
1.48 g (5 mmol) of tert-butyl (3RS,4RS)-4-(4-fluoro-phenyl)-3-hydroxy-piperidine-1-carboxylate [Example 88(a)] and 1.08 g (5.5 mmol) of 3-bromo-1-phenyl-propene were dissolved in 10 ml of dimethylformamide under argon at room temperature, then treated with 0.284 g (6.5 mmol) of sodium hydride dispersion (55% in mineral oil) with the addition of 1.25 g (7.5 mmol) of potassium iodide and stirred at room temperature for 18 hours. The reaction mixture was poured on to ice-water, the product was extracted 3 times with methylene chloride, the organic phases were washed twice with distilled water, dried over magnesium sulphate, filtered and concentrated in a water-jet vacuum. The thus-obtained crude product was chromatographed on silica gel with methylene chloride and methanol. There were thus obtained 1.01 g (49% of theory) of tert-butyl (E)-(3RS,4RS)-4-(4-fluoro-phenyl)-3-(3-phenyl-allyloxy)-piperidine-1-carboxylate as a colourless oil; MS: 412 (M+H)$^+$.

(b) 0.49 g (1 mmol) of tert-butyl (3R,4s,5S)-4-[4-(3-benzyloxy-propoxy)-phenyl]-3,5-bis-hydroxymethyl-piperidine-1-carboxylate [Example 101(f)] and 0.45 g (2 mmol) of 4,5-dimethoxy-2-methylsulphonyl-pyrimidine [prepared from 4,5-dimethoxy-2-methylsulphanyl-pyrimidine by oxidation with m-chloroperbenzoic acid in an analogous manner to that described in Example 129(c)] were placed in 5 ml of dimethylformamide under argon at 5° C., treated while stirring with 0.10 g (2.2 mmol) of sodium hydride dispersion (55% in mineral oil) and stirred at room temperature for 2 hours. The reaction mixture was thereupon poured on to ice-water, the product was extracted 3 times with methylene chloride, the organic phases were washed twice with distilled water, dried over magnesium sulphate, filtered and concentrated in a water-jet vacuum. The thus-obtained crude product was chromatographed on silica gel with methylene chloride and methanol. There was thus obtained 0.47 g (61% of theory) of tert-butyl (3R,4s,5S)-4-[4-(3-benzyloxy-propoxy)-phenyl]-3,5-bis-(4,5-dimethoxy-pyrimidin-2-yloxymethyl)-piperidine-1-carboxylate as a colourless oil; MS: 762 (M+H)+.

(c) (α) 2.91 g (6 mmol) of tert-butyl (3R,4s,5S)-4-[4-(3-benzyloxy-propoxy)-phenyl]-3,5-bis-hydroxymethyl-piperidine-1-carboxylate [Example 101(f)] and 1.93 ml (24 mmol) of pyridine were placed in 30 ml of acetonitrile under argon at 5° C., 8.00 g (18 mmol) of triphenylphosphine dibromide were introduced portionwise while stirring and the mixture was thereafter stirred at room temperature. After 90 minutes the reaction mixture was poured on to ice-water, the product was then extracted 3 times with ethyl acetate, the organic phases were washed twice with distilled water, dried over magnesium sulphate, filtered and concentrated in a water-jet vacuum. The thus-obtained crude product was chromatographed on silica gel with n-hexane and ethyl acetate. There were thus-obtained 2.81 g (77% of theory) of tert-butyl (3R,4s,5S)-4-[4-(3-benzyloxy-propoxy)-phenyl]-3,5-bis-bromomethyl-piperidine-1-carboxylate as a colourless oil; MS: 610 (M+H)+.

(c) (β) 0.30 g (0.5 mmol) of tert-butyl (3R,4s,5S)-4-[4-(3-benzyloxy-propoxy)-phenyl]-3,5-bis-bromomethyl-piperidine-1-carboxylate and 0.19 g (1.5 mmol) of hydroquinone monomethyl ether were stirred at reflux under argon for 18 hours with the addition of 0.69 g (5 mmol) of anhydrous potassium carbonate in 15 ml of acetonitrile. After cooling to room temperature the reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.15 g (43% of theory) of tert-butyl (3R,4s,5S)-4-[4-(3-benzyloxy-propoxy)-phenyl]-3,5-bis-(4-methoxy-phenoxymethyl)-piperidine-1-carboxylate as pale yellow crystals; MS: 518 (M+H)+.

(d) In an analogous manner to that described in Example 89(c)(β), from tert-butyl (3R,4s,5S)-4-[4-(3-benzyloxy-propoxy)-phenyl]-3,5-bis-bromomethyl-piperidine-1-carboxylate and 4-methyl-thiophenol there was obtained tert-butyl (3R,4s,5S)-4-[4-(3-benzyloxy-propoxy)-phenyl]-3,5-bis-p-tolylsulphanylmethyl-piperidine1-carboxylate in the form of a colourless oil; MS: 698 (M+H)+.

(e) in an analogeous manner as described in Example 95(a) there was obtained from (3RS,4RS)-3-hydroxy-4-[4-[3-(2-methoxy-benzyloxy)-propoxy]-phenyl]-piperidin-1-carboxylic acid tert-butylester [Example 120(g) (α)] and 2-chloromethyl-7-(2-trimethylsilanyl-ethoxymethoxy)-naphthalene [Example 6(u)] (3RS,4RS)-4-[4-[3-(2-methoxy-benzyloxy)-propoxy-phenyl]-3-[7-(2-trimethylsilanyl-ethoxymethoxy)-naphthalen-2-ylmethoxy]-piperidin-1-carboxylic acid tert-butylester as a pale yellow oil; MS: 758 (M+H)+. Then, (3RS,4RS)-4-[4-[3-(2-methoxy-benzyloxy)-propoxy]-phenyl]-3-[7-(2-trimethylsilanyl-ethoxymethoxy)-naphthalen-2-ylmethoxy]-piperidin-1-carboxylic acid tert-butylester was reacted in analogy to Example 95(b) by cleaving of the SEM protecting group to afford (3RS,4RS)-4-[4-[3-( 2-methoxy-benzyloxy)-propoxy]-phenyl]-3-(7-hydroxy-naphthalen-2-ylmethoxy)-piperidin-1-carboxylic acid tert-butylester [yellow oil; MS: 628 (M+H)+] which, on alkylation with 1-(2-chloro-ethyl)-4-methyl-piperazine hydrochloride (1:2) [Chim. Ther. 4, 283 (1969)] in analogy to Example 90(n) gave (3RS,4RS)-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidin-1-carboxylic acid tert-butylester as a light brown oil; MS: 754 (M+H)+.

EXAMPLE 90

The following compounds were obtained in an analogous manner to that described in Example 22(l) by cleavage of the BOC group using hydrogen chloride in methanol:

1) From a mixture of tert-butyl (3RS,4SR)-4-(4-fluoro-phenyl)-3-[(RS)- and -[(SR)-1-[4-(2-morpholin-4-yl-ethoxy)-benzoyloxy]-2-naphthalen-2-yl-ethyl]-piperidine-1-carboxylate, a mixture of (RS)- and (SR)-1-[(3RS,4SR)-4-(4-fluoro-phenyl)-piperidin-3-yl]-2-naphthalen-2-yl-ethyl 4-(2-morpholin-4-ylethoxy)-benzoate as a colourless oil; MS: 583 (M+H)+;

2) from tert-butyl (3RS,4SR)-4-(4-fluoro-phenyl)-3-(naphthalen-2-yl-acetyl)-piperidine-1-carboxylate, 1-[(3RS,4SR)-4-(4-fluoro-phenyl)-piperidin-3-yl]-2-naphthalen-2-yl-ethanone hydrochloride (1:1) in the form of colourless crystals; MS: 348 (M+H)+;

3) from a mixture of tert-butyl (E)- and (Z)-(3RS,4SR)-3-(1-carboxymethoxyimino-2-naphthalen-2-yl-ethyl)-4-(4-fluoro-phenyl)-piperidine-1-carboxylate, a 3:1 mixture of methyl (E)- and (Z)-[1-[(3RS,4SR)-4-(4-fluoro-phenyl)-piperidine-3-yl]-2-naphthalen-2-yl-ethylidene-aminooxy]-acetate as a yellow oil; MS: 435 (M+H)+;

4) from tert-butyl (3RS,4RS)-3-[2-(3H-benzoimidazol-5-yloxy)-ethoxy]-4-[4-(3-benzyloxy-propoxy)-phenyl]-piperidine-1-carboxylate, 6-[2-[(3RS,4RS)-4-[4-(3-benzyloxy-propoxy)-phenyl]-piperidin-3-yloxy]-ethoxy]-1H-benzoimidazole as a yellow oil; MS: 502 (M+H)+;

5) from tert-butyl 3RS,4RS)-4-[4-(3-benzyloxy-propoxy)-phenyl]-3-[2-(2-oxo-2,3-dihydro-1H-benzoimidazol-5-yloxy)-ethoxy]-piperidine-1-carboxylate, 5-[2-[(3RS, 4RS)-4-[4-(3-benzyloxy-propoxy)-phenyl]-piperidin-3-yloxy]-ethoxy]-1,3-dihydro-benzoimidazol-2-one in the form of yellow crystals; MS: 518 (M+H)+;

6) from tert-butyl (3RS,4RS)-4-[4-(3-benzyloxy-propoxy)-phenyl]-3-[2-(3,4-dinitro-phenoxy)-ethoxy]-piperidine-1-carboxylate [Example 94(d)], (3RS,4RS)-4-[4-(3-benzyloxy-propoxy)-phenyl]-3-[2-(3,4-dinitro-phenoxy)-ethoxy]-piperidine as an amorphous, yellow foam; MS: 552 (M+H)+;

7) from tert-butyl (3RS,4RS)-4-[4-(3-benzyloxy-propoxy)-phenyl]-3-[7-(2-morpholin-4-yl-ethoxy)-naphthalen-2-ylmethoxy]-piperidine-1-carboxylate, 4-[2-[7-[(3RS, 4RS)-4-[4-(3-benzyloxy-propoxy)-phenyl]-piperidin-3-yloxymethyl]-naphthalen-2-yloxy]-ethyl]-morpholine hydrochloride (1:2) in the form of beige crystals; MS: 611 (M+H)+;

8) from a mixture of tert-butyl (3RS,4RS)- and (3SR,4SR)-4-[4-(3-benzyloxy-propoxy)-phenyl]-3-[7-[(RS)-2,2-dimethyl-[1,3]dioxolan-4-ylmethoxy]-naphthalen-2-ylmethoxy]-piperidine-1-carboxylate, a mixture of (RS)- and (SR)-3-[7-[(3RS,4RS)-4-[4-(3-benzyloxy-propoxy)-phenyl]-piperidin-3-yloxymethyl]-naphthalen-2-yloxy]-propane-1,2-diol as a colourless oil; MS: 572 (M+H)+;

9) from tert-butyl (3RS,4RS)-4-[4-(3-benzyloxy-propoxy)-phenyl]-3-[6-(2-trimethylsilanyl-ethoxymethoxy)-naphthalen-2-ylmethoxy]-piperidine-1-carboxylate [Example 97(a)], 6-[(3RS,4RS)-4-[4-(3-benzyloxy-propoxy)-phenyl]-piperidin-3-yloxymethyl]-naphthalen-2-ol hydrochloride (1:1) in the form of colourless crystals; MS: 498 (M+H)+;

10) from a mixture of tert-butyl [3RS,4RS]- and [3SR,4SR]-4-[4-(3-benzyloxy-propoxy)-phenyl]-3-[6-[(RS)-2,2- dimethyl-[1,3]dioxolan-4-ylmethoxy)-naphthalen-2-ylmethoxy]-piperidine-1-carboxylate with simultaneous cleavage of the dioxolane protecting group, a mixture of (RS)- and (SR)-3-[6-[(3RS,4RS)-4-[4-(3-benzyloxy-propoxy)-phenyl]-piperidin-3-yloxymethyl]-naphthalen-2-yloxy]-propane-1,2-diol hydrochloride (1:1) in the form of pale brown crystals; MS: 572 (M+H)$^+$;

11) from a mixture of tert-butyl (3RS,4RS)- and (3SR,4SR)-4-[4-(3-benzyloxy-propoxy)-phenyl]-3-[6-[2-[(RS)-2,2-dimethyl-[1,3]dioxolan-4-ylmethoxy]-ethoxy]-naphthalen-2-ylmethoxy]-piperidine-1-carboxylate with simultaneous cleavage of the dioxolane protecting group, a mixture of [RS]- and [SR]-3-[2-[6-[(3RS,4RS)-4-[4-(3-benzyloxy-propoxy)-phenyl]-piperidin-3-yloxymethyl]-naphthalen-2-yloxy]-ethoxy]-propane-1,2-diol hydrochloride (1:1) in the form of colourless crystals; MS: 616 (M+H)$^+$;

12) from a mixture of tert-butyl (3RS,4SR)-4-[4-(3-benzyloxy-propoxy)-phenyl]-3-[(RS)- and -[(SR) 1-hydroxy-2-naphthalen-2-yl-ethyl]-piperidine-1-carboxylate [Example 100(b)], a mixture of (RS)- and (SR)-1-[(3RS,4SR)-4-[4-(3-benzyloxy-propoxy)-phenyl]-piperidin-3-yl]-2-naphthalen-2-yl-ethanol hydrochloride (1:1) in the form of beige crystals; MS: 496 (M+H)$^+$;

13) from tert-butyl (3RS,4RS)-4-[4-(3-benzyloxy-propoxy)-phenyl]-3-[7-[2-(4-methyl-piperazin-1-yl)-ethoxy]-naphthalen-2-ylmethoxy]-piperidine-1-carboxylate, 1-[2-[7-[(3RS,4RS)-4-[4-(3-benzyloxy-propoxy)-phenyl]-piperidin-3-yloxymethyl]-naphthalen-2-yloxy]-ethyl]-4-methyl-piperazine hydrochloride (1:3) in the form of colourless crystals; MS: 624 (M+H)$^+$;

14) from a mixture of tert-butyl (E)- and (Z)-(3RS,4SR)-4-[4-(3-benzyloxy-propoxy)-phenyl]-3-(1-methoxycarbonyl-methoxyimino-2-naphthalen-2-yl-ethyl)-piperidine-1-carboxylate, a mixture of methyl (E)- and (Z)-(1-[(3RS,4SR)-4-[4-(3-benzyloxy-propoxy)-phenyl]-piperidin-3-yl]-2-naphthalen-2-yl-ethylidene-aminooxy)-acetate as a pale yellow oil; MS: 581 (M+H)$^+$;

15) from tert-butyl (3R,4s,5S)-4-[4-(3-benzyloxy-propoxy)-phenyl]-3,5-bis-(2-morpholin-4-yl-ethoxymethyl)-piperidine-1-carboxylate [Example 101(g)], (3R,4s,5S)-4-[4-(3-benzyloxy-propoxy)-phenyl]-3,5-bis-(2-morpholin-4-yl-ethoxymethyl)-piperidine as a yellow oil; MS: 612 (M+H)$^+$.

The BOC derivatives used as the starting materials were prepared as follows:

(a) 0.45 g (1 mmol) of a mixture of tert-butyl (3RS,4SR)-4-(4-fluoro-phenyl)-3-[(RS)- and -[(SR)-1-hydroxy-2-naphthalen-2-yl-ethyl]-piperidine-1-carboxylate[Example 74(h)] and 0.28 g (1.1 mmol) of 4-(2-morpholin-4-yl-ethoxy)-benzoic acid (prepared by alkylating methyl 4-hydroxybenzoate with 4-(2-chloroethyl)-morpholine in dimethylformamide in the presence of potassium carbonate at 100° C. and subsequently saponifying with base were dissolved in 15 ml of methylene chloride under argon, 0.23 g (1.2 mmol) of N-ethyl-N'-(3-dimethylaminopropyl)-carbodiimide hydrochloride and 0.04 g (0.33 mmol) of 4-dimethylamino-pyridine were then added and the mixture was stirred at room temperature for 70 hours. After distillation of the solvent in a water-jet vacuum the crude product was chromatographed on silica gel with n-hexane, methylene chloride and methanol. There was thus obtained 0.54 g (79% of theory) of a mixture of tert-butyl (3RS,4SR)-4-(4-fluoro-phenyl)-3-[(RS)- and -[(SR)-1-[4-(2-morpholin-4-yl-ethoxy)-benzoyloxy]-2-naphthalen-2-yl-ethyl]-piperidine-1-carboxylate as a pale yellow oil; MS: 683 (M+H)$^+$.

(b) In an analogous manner to that described in Example 74(f), from a mixture of tert-butyl (3RS,4SR)-4-(4-fluoro-phenyl)-3-[(RS)- and -[(SR)-1-hydroxy-2-naphthalen-2-yl-ethyl]-piperidine-1-carboxylate [Example 74(h)] by oxidation with dimethyl sulphoxide/oxalyl chloride in methylene chloride there was obtained tert-butyl (3RS,4SR)-4-(4-fluoro-phenyl)-3-(naphthalen-2-yl-acetyl)-piperidine-1-carboxylate as a yellow oil; MS: 447 (M)$^+$.

(c) 0.22 g (0.5 mmol) of tert-butyl (3RS,4SR)-4-(4-fluoro-phenyl)-3-(naphthalen-2-yl-acetyl)-piperidine-1-carboxylate and 0.11 g (1 mmol) of aminooxy-acetic acid hydrochloride (1:0.5) [Organic Synthesis Collect. Vol. III, 172 (1955)] were stirred at 60° C. in 2 ml of pyridine for 18 hours under argon. The reaction mixture was thereupon poured on to ice-water, the product was extracted 3 times with ethyl acetate, the organic phases were washed twice with distilled water, dried over magnesium sulphate, filtered and concentrated in a water-jet vacuum. The thus-obtained crude product was chromatographed on silica gel with methylene chloride and methanol. There was thus obtained 0.24 g (92% of theory) of a mixture of tert-butyl (E)- and (Z)-(3RS,4SR)-3-(1-carboxymethoxyimino-2-naphthalen-2-yl-ethyl)-4-(4-fluoro-phenyl)-piperidine-1-carboxylate as a pale yellow oil; MS: 521 (M+H)$^+$.

(d) 0.55 g (0.93 mmol) of tert-butyl (3RS,4RS)-4-[4-(3-benzyloxy-propoxy)-phenyl]-3-[2-(3,4-diamino-phenoxy)-ethoxy]-piperidine-1-carboxylate (Example 94(e)] was stirred at 50° C. in 5 ml of triethyl orthoformate for 1 hour under argon. The reaction mixture was poured on to ice-water, the product was extracted 3 times with methylene chloride, the organic phases were washed twice with distilled water, then dried over potassium carbonate, filtered and concentrated in a water-jet vacuum. The thus-obtained crude product was chromatographed on silica gel with methylene chloride and methanol. There was thus obtained 0.38 g (68% of theory) of tert-butyl 3-[2-(3H-benzoimidazol-5-yloxy)-ethoxy]-4-[(3RS,4RS)-4-(3-benzyloxy-propoxy)-phenyl]-piperidine-1-carboxylate as a pale brown oil; MS: 602 (M+H)$^+$.

(e) 0.60 g (1.0 mmol) of tert-butyl (3RS,4RS)-4-[4-(3-benzyloxy-propoxy)-phenyl]-3-[2-(3,4-diamino-phenoxy)-ethoxy]-piperidine-1-carboxylate [Example 94(e)] was dissolved in 5 ml of dimethylformamide under argon a room temperature and then 0.18 g (1.1 mmol) of 1,1'-carbonyldiimidazole was added. After 1 hour the reaction mixture was poured on to ice to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.46 g (74% of theory) of tert-butyl (3RS,4RS)-4-[4-(3-benzyloxy-propoxy)-phenyl]-3-[2-(2-oxo-2,3-dihydro-1H-benzo-imidazol-5-yloxy)-ethoxy]-piperidine-1-carboxylate as a yellow oil; MS: 618 (M+H)$^+$.

(g) 0.30 g (0.5 mmol) of tert-butyl (3RS,4RS)-4-[4-(3-benzyloxy-propoxy)-phenyl]-3-(7-hydroxy-naphthalen-2-ylmethoxy)-piperidine-1-carboxylate [Example 95(b)] and 0.13 g (0.7 mmol) of 4-(2-chloroethyl)-morpholine hydrochloride were stirred at 60° C. under argon for 18 hours in 15 ml of dimethyl-formamide with the addition of 0.69 g (5 mmol) of potassium carbonate (anhydrous). The reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.32 g (90% of theory) of tert-butyl (3RS,4RS)-4-[4-(3-benzyloxy-propoxy)-phenyl]-3-[7-(2-morpholin-4-yl-ethoxy)-naphthalen-2-ylmethoxy]-piperidine-1-carboxylate as a colourless oil; MS: 711 (M+H)⁺.

(h) 0.33 g (0.54 mmol) of tert-butyl (3RS,4RS)-4-[4-(3-benzyloxy-propoxy)-phenyl]-3-(7-hydroxy-naphthalen-2-ylmethoxy)-piperidine-1-carboxylate [Example 95(b)] and 0.20 g (0.70 mmol) of D,L-α,β-isopropylideneglycerol γ-tosylate were stirred at reflux for 3 hours under argon in 15 ml of dimethyl-formamide with the addition of 0.69 g (5 mmol) of potassium carbonate (anhydrous). The reaction mixture was thereupon poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.32 g (83% of theory) of a mixture of tert-butyl (3RS,4RS)- and (3SR,4SR)-4-[4-(3-benzyloxy-propoxy)-phenyl]-3-[7-[(RS)-2,2-dimethyl-[1,3]dioxolan-4-ylmethoxy]-naphthalen-2-ylmethoxy]-piperidine-1-carboxylate as a colourless oil; MS: 712 (M+H)⁺.

(k) In an analogous manner to that described in Example 90(h), from tert-butyl (3RS,4RS)-4-[4-(3-benzyloxy-propoxy)-phenyl]-3-(6-hydroxy-naphthalen-2-ylmethoxy)-piperidine-1-carboxylate [Example 97(b)] there was obtained a mixture of tert-butyl [3RS,4RS]- and [3SR,4SR]-4-[4-(3-benzyloxy-propoxy)-phenyl]-3-[6-[(RS)-2,2-dimethyl-[1,3]dioxolan-4-ylmethoxy]-naphthalen-2-ylmethoxy]-piperidine-1-carboxylate in the form of colourless crystals; MS: 712 (M+H)⁺.

(l) In an analogous manner to that described in Example 90(g), from tert-butyl (3RS,4RS)-4-[4-(3-benzyloxy-propoxy)-phenyl]-3-(6-hydroxy-naphthalen-2-ylmethoxy)-piperidine-1-carboxylate [Example 97(b)] and (RS)-2-(2,2-dimethyl-[1,3]dioxolan-4-ylmethoxy)-ethyl toluene 4-sulphonate [Example 98(a)] there was obtained a mixture of tert-butyl (3RS,4RS)- and (3SR,4SR)-4-[4-(3-benzyloxy-propoxy)-phenyl]-3-[6-[2-[(RS)-2,2-dimethyl-[1,3]dioxolan-4-ylmethoxy]-ethoxy]-naphthalen-2-ylmethoxy]-piperidine-1-carboxylate in the form of colourless crystals; MS: 773 (M+NH₄)⁺.

(n) 0.30 g (0.5 mmol) of tert-butyl (3RS,4RS)-4-[4-(3-benzyloxy-propoxy)-phenyl]-3-(7-hydroxy-naphthalen-2-yl-methoxy)-piperidine-1-carboxylate [Example 95(b)] and 0.47 g (2 mmol) of 1-(2-chloro-ethyl)-4-methyl-piperazine hydrochloride (1:2) [Chim. Ther. 4, 283 (1969)] were dissolved in 5 ml of dimethylformamide under argon at room temperature and then stirred at 100° C. for 3 hours with the addition of 0.05 g (0.3 mmol) of potassium iodide and 0.22 g (5 mmol) of sodium hydride dispersion (55% in mineral oil). The reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.20 g (55% of theory) of tert-butyl (3RS,4RS)-4-[4-(3-benzyloxy-propoxy)-phenyl]-3-[7-[2-(4-methyl-piperazin-1-yl)-ethoxy]-naphthalen-2-ylmethoxy]-piperidine-1-carboxylate as a pale yellow oil; MS: 724 (M+H)⁺.

(o) In an analogous manner to that described in Example 102(a), from tert-butyl (3RS,4SR)-4-[4-(3-benzyloxy-propoxy)-phenyl]-3-(naphthalen-2-yl-acetyl)-piperidine-1-carboxylate [Example 100(c)] and methyl aminooxy-acetate hydrochloride [J. Med. Chem. 28, 1447 (1985)] there was obtained a mixture of tert-butyl (E)- und (Z)-(3RS,4SR)-4-[4-(3-benzyloxy-propoxy)-phenyl]-3-(1-methoxycarbonylmethoxyimino-2-naphthalen-2-yl-ethyl)-piperidine-1-carboxylate as a colourless oil; MS: 698 (M+NH₄)⁺.

EXAMPLE 91

(a) 0.90 g (2 mmol) of a mixture of tert-butyl (3RS,4SR)-4-(4-fluoro-phenyl)-3-[(RS)- and -[(SR)-1-hydroxy-2-naphthalen-2-yl-ethyl]-piperidine-1-carboxylate [Example 74(h)] and 0.55 g (2.2 mmol) of 4-(2-morpholin-4-yl-ethoxy]-benzoic acid (prepared by alkylating methyl 4-hydroxybenzoate with 4-( 2-chloroethyl)morpholine in dimethylformamide in the presence of potassium carbonate at 100° C. and subsequently saponifying with base) were dissolved in 30 ml of tetrahydrofuran under argon, then 0.44 ml (2.8 mmol of diethyl azodicarboxylate was added dropwise after the addition of 0.66 g (2.5 mmol) of triphenylphosphine and the mixture was subsequently stirred at room temperature for 18 hours. After distillation of the solvent in a water-jet vacuum the crude product was purified on silica gel with n-hexane and ethyl acetate. There was thus obtained 0.31 g (23% of theory) of tert-butyl (E)-(3RS,4SR)-4-(4-fluoro-phenyl)-3-(2-naphthalen-2-yl-vinyl)-piperidine-1-carboxylate as a pale yellow resin; MS: 432 (M+H)⁺.

(b) In an analogous manner to that described in Example 22(l), by cleaving off the BOC group using hydrogen chloride in methanol from tert-butyl (E)-(3RS,4SR)-4-(4-fluoro-phenyl)-3-(2-naphthalen-2-yl-vinyl)-piperidine-1-carboxylate there was obtained (E)-(3RS,4SR)-4-(4-fluoro-phenyl)-3-(2-naphthalen-2-yl-vinyl)-piperidine as a pale yellow oil; MS: 331 (M)⁺.

(c) 0.060 g (0.18 mmol) of (E)-(3RS,4SR)-4-(4-fluoro-phenyl)-3-(2-naphthalen-2-yl-vinyl)-piperidine was hydrogenated under normal conditions in 3 ml of methanol with the addition of 30 mg of Pd-C (10%). After filtering off the catalyst the solvent was distilled off in a water-jet vacuum. There was thus obtained 0.055 g (92% of theory) of (3RS,4SR)-4-(4-fluoro-phenyl)-3-(2-naphthalen-2-yl-ethyl)-piperidine as a pale yellow oil; MS: 334 (M+H)⁺.

EXAMPLE 92

(a) 2.95 g (10 mmol) of tert-butyl (3RS,4RS)-4-(4-fluoro-phenyl)-3-hydroxy-piperidine-1-carboxylate [Example 88(a)] and 3.82 g (11 mmol) of tert-butyl 4'-bromomethyl-biphenyl-2-carboxylate [J. Med. Chem. 34, 2525 (1991)] were dissolved in 100 ml of dimethylformamide under argon at room temperature, then firstly 2.49 g (15 mmol) of potassium iodide and thereafter 0.57 g (13 mmol) of sodium hydride dispersion (55% in mineral oil) were added. After stirring at room temperature for 4 hours the reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with n-hexane and ethyl acetate. There were thus obtained 5.08 g (90% of theory) of tert-butyl (3RS,4RS)-3-(2'-tert-butoxycarbonyl-biphenyl-4-ylmethoxy)-4-(4-fluoro-phenyl)-piperidine-1-carboxylate as an amorphous, colourless foam.

(b) 2.25 g (4 mmol) of tert-butyl (3RS,4RS)-3-(2'-tert-butoxycarbonyl-biphenyl-4-ylmethoxy)-4-(4-fluoro-phenyl)-piperidine-1-carboxylate were stirred at reflux for 18 hours in 50 ml of ethylene glycol monomethyl ether with the addition of 8 ml (36 mmol) of sodium hydroxide solution (14%). After distillation of the solvent in a water-jet vacuum the residue was dissolved in ice-water, then adjusted to pH 3 with 2N hydrochloric acid and the product was extracted 3 times with methylene chloride, the organic phases were washed twice with distilled water, then dried over magnesium sulphate, filtered and concentrated in a water-jet vacuum. The thus-obtained product was chromatographed on silica gel with methylene chloride and methanol. There were thus obtained 1.66 g (82% of theory) of tert-butyl (3RS,4RS)-3-(2'-carboxy-biphenyl-4-ylmethoxy)-4-(4-fluoro-phenyl)-piperidine-1-carboxylate as an amorphous, colourless foam; MS: 504 (M–H)$^+$.

(c) 0.51 g (1 mmol) of tert-butyl (3RS,4RS)-3-(2'-carboxy-biphenyl-4-ylmethoxy)-4-(4-fluoro-phenyl)-piperidine-1-carboxylate and 0.18 g (1 mmol) of 2-chloro-4,6-dimethoxy-1,3,5-triazine were dissolved in a mixture of 3.5 ml of dimethylformamide and 5 ml of acetonitrile under argon, 0.22 ml (2 mmol) of N-methylmorpholine was added dropwise thereto at 0° C. and the mixture was stirred at 0° C. for 2 hours. Now, a solution of 0.08 ml (1 mmol) of (RS)-3-amino-1,2-propanediol in 6 ml of acetonitrile was added dropwise and thereafter the mixture was stirred at room temperature for 18 hours. The reaction mixture was poured on to ice-water, the product was extracted 3 times with methylene chloride, the organic phases were washed twice with distilled water, then dried over magnesium sulphate, filtered and concentrated in water-jet vacuum. The thus-obtained crude product was chromatographed on silica gel with methylene chloride and methanol. There was thus obtained 0.29 g (50% of theory) of a mixture of tert-butyl (3RS,4RS)- and (3SR,4SR)-3-[2'[(RS)-( 2,3-dihydroxy-propyl-carbamoyl]-biphenyl-4-ylmethoxy]-4-(4-fluoro-phenyl)-piperidine-1-carboxylate as an amorphous, colourless foam; MS: 579 (M+H)$^+$.

(d) In an analogous manner to that described in Example 22(l), from a mixture of tert-butyl (3RS,4RS)- and (3SR,4SR)-3-[2'[(RS)-(2,3-dihydroxy-propyl-carbamoyl]-biphenyl-4-ylmethoxy]-4-(4-fluoro-phenyl)-piperidine-1-carboxylate by cleavage of the BOC protecting group with hydrogen chloride in methanol there was obtained a mixture of 4'-[(3RS,4RS)-4-(4-fluoro-phenyl)-piperidin-3-yloxymethyl]-biphenyl-2-carboxylic acid (RS)- and (SR)-(2,3-dihydroxy-propyl)-amide hydrochloride (1:1) as an amorphous, colourless foam: MS: 479 (M+H)$^+$.

EXAMPLE 93

(a) 0.050 g (0.12 mmol) of a 3:1 mixture of methyl (E)- and (Z)-[1-[(3RS,4SR)-4-(4-fluoro-phenyl)-piperidin-3-yl]-2-naphthalen-2-yl-ethylideneaminooxy]-acetate {Example 90.03] was stirred at 50° C. for 18 hours in 3 ml of methanol with the addition of 1.0 ml of 1N sodium hydroxide solution. After cooling to room temperature 1.0 ml of 1N hydrochloric acid was added dropwise and thereafter the mixture was concentrated in a water-jet vacuum. The residue was suspended in ethanol, then filtered, 0.025 ml (0.3 mmol) of hydrochloric acid (37%) was added to the filtrate and the mixture was again concentrated in a water-jet vacuum. This residue was now dried at room temperature in a high vacuum for 2 hours. There was thus obtained 0.040 g (73% of theory) of a mixture of (E)- and (Z)-(3RS,4SR)-(1-[4-(4-fluoro-phenyl)-piperidin-3-yl]-2-naphthalen-2-yl-ethylideneaminooxy)-acetic acid hydrochloride (1:1) as an amorphous, pale yellow foam; MS: 421 (M+H)$^+$.

EXAMPLE 94

(a) 4.30 g (9.7 mmol) of tert-butyl (3RS,4RS)-4-[4-(3-benzyloxy-propoxy)-phenyl]-3-hydroxy-piperidine-1-carboxylate [Example 86(n)] were placed in 215 ml of tetrahydrofuran at 0° C. under argon and 1.23 g (28.1 mmol) of sodium hydride dispersion (55% in mineral oil) were added while stirring. After 30 minutes a solution of 1.86 ml (12.7 mmol) of tert-butyl bromoacetate in 10 ml of tetrahydrofuran were added dropwise and the mixture was warmed to room temperature. The reaction mixture was poured on to ice-water, the product was extracted 3 times with ethyl acetate, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 4.77 g (88% of theory) of tert-butyl (3RS,4RS)-4-[4-(3-benzyloxy-propoxy)-phenyl]-3-tert-butoxycarbonylmethoxy-piperidine-1-carboxylate as a yellow oil; MS: 556 (M+H)$^+$.

(b) 0.36 g (16.5 mmol) of lithium borohydride was placed in 55 ml of tetrahydrofuran at room temperature under argon and a solution of 4.58 g (8.24 mmol) of tert-butyl (3RS,4RS)-4-[4-(3-benzyloxy-propoxy)-phenyl]-3-tert-butoxycarbonylmethoxy-piperidine-1-carboxylate in 55 ml of tetrahydrofuran was added dropwise while stirring and the mixture was subsequently heated under reflux. After 4 hours the reaction mixture was poured on to ice-water, adjusted to pH 3 with hydrochloric acid (2N) and then the product was extracted 3 times with ethyl acetate. The organic phases were thereupon washed twice with distilled water, dried over magnesium sulphate, filtered and concentrated in a water-jet vacuum. There were thus obtained 3.95 g (99% of theory) of tert-butyl (3RS,4RS)-4-[4-(3-benzyloxy-propoxy)-phenyl]-3-(2-hydroxy-ethoxy)-piperidine-1-carboxylate as a yellow oil; MS: 486 (M+H)$^+$.

(c) 5.56 g (13.2 mmol) of triphenylphosphine dibromide were dissolved in 20 ml of acetonitrile under argon, then 1.06 ml (13.2 mmol) of pyridine were added dropwise at 0° C.; this solution was added dropwise to a solution of 3.95 g (8.1 mmol) of tert-butyl (3RS,4RS)-4-[4-(3-benzyloxy-propoxy)-phenyl]-3-(2-hydroxy-ethoxy)-piperidine-1-carboxylate in 20 ml of acetonitrile at 0° C. and subsequently the mixture was stirred at room temperature for 18 hours. The reaction mixture was poured on to ice-water, the product was then extracted 3 times with ethyl acetate, the organic phases were washed twice with distilled water, then dried over magnesium sulphate, filtered and concentrated in a water-jet vacuum. The thus-obtained crude product was chromatographed on silica gel with n-hexane and ethyl acetate. There were thus obtained 3.14 g (71% of theory) of tert-butyl (3RS,4RS)-4-[4-(3-benzyloxy-propoxy)-phenyl]-3-(2-bromo-ethoxy)-piperidine-1-carboxylate as a yellow oil; MS: 548,550 (M+H)$^+$.

(d) 3.14 g (5.72 mmol) of tert-butyl (3RS,4RS)-4-[4-(3-benzyloxy-propoxy)-phenyl]-3-(2-bromo-ethoxy)-piperidine-1-carboxylate and 2.53 g (13.76 mmol) of 3,4-dinitrophenol in 230 ml of acetonitrile were stirred at reflux under argon for 22 hours with the addition of 7.9 g (57.2 mmol) of potassium carbonate (anhydrous). After distillation of the solvent in a water-jet vacuum the residue was poured on to ice-water and the product was extracted 3 times with methylene chloride, the organic phases were washed twice with distilled water, then dried over magnesium sulphate, filtered and concentrated in a water-jet vacuum. The thus-obtained crude product was chromatographed on silica gel with n-hexane and ethyl acetate. There were thus obtained 2.57 g (69% of theory) of tert-butyl (3RS,4RS)-4-[4-(3-benzyloxy-propoxy)-phenyl]-3-[2-(3,4-dinitro-phenoxy)-ethoxy]-piperidine-1-carboxylate as a brown oil; MS: 652 (M+H)$^+$.

(e) 1.63 g (2.5 mmol) of tert-butyl (3RS,4RS)-4-[4-(3-benzyloxy-propoxy)-phenyl]-3-[2-(3,4-dinitro-phenoxy)-ethoxy]-piperidine-1-carboxylate were hydrogenated under normal conditions for 2 hours in 80 ml of ethyl acetate with the addition of 0.50 g of platinum oxide. The catalyst was filtered off over a Dicalite pad and the solvent was distilled off in a water-jet vacuum. There were thus obtained 1.44 g (97% of theory) of tert-butyl (3RS,4RS)-4-[4-(3-benzyloxy-propoxy)-phenyl]-3-[2-(3,4-diamino-phenoxy)-ethoxy]-piperidine-1-carboxylate as a violet oil; MS: 592 $(M+H)^+$.

(f) In an analogous manner to that described in Example 22(l), from tert-butyl (3RS,4RS)-4-[4-(3-benzyloxy-propoxy)-phenyl]-3-[2-(3,4-diamino-phenoxy)-ethoxy]-piperidine-1-carboxylate by cleavage of the BOC protecting group with hydrogen chloride in methanol there was obtained 4-[2-[(3RS,4RS)-4-[4-(3-benzyloxy-propoxy)-phenyl]-piperidin-3-yloxy]-ethoxy]-benzene-1,2-diamine hydrochloride (1:3) as pale violet crystals; MS: 492 $(M+H)^+$.

EXAMPLE 95

(a) 4.37 g (9.9 mmol) of (3RS,4RS)-4-[4-(3-benzyloxy-propoxy)-phenyl]-3-hydroxy-piperidine-1-carboxylate [Example 86(n)] and 3.20 g (9.9 mmol) of 2-chloromethyl-7-(2-trimethylsilanyl-ethoxymethoxy)-naphthalene [Example 6(u)] were dissolved in 35 ml of dimethylformamide under argon and then 0.46 g (10.5 mmol) of sodium hydride dispersion (55% in mineral oil) was added. Subsequently, the mixture was stirred at room temperature for 18 hours. The reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 7.15 g (99% of theory) of tert-butyl (3RS,4RS)-4-[4-(3-benzyloxy-propoxy)-phenyl]-3-[7-(2-trimethylsilanyl-ethoxymethoxy)-naphthalen-2-ylmethoxy]-piperidine-1-carboxylate as a pale yellow oil; MS: 728 $(M+H)^+$.

(b) 6.72 g (9.23 g) of tert-butyl (3RS,4RS)-4-[4-(3-benzyloxy-propoxy)-phenyl]-3-[7-(2-trimethylsilanyl-ethoxymethoxy)-naphthalen-2-ylmethoxy]-piperidine-1-carboxylate were placed in 140 ml of abs. methanol at 0° C., then 2.8 ml (19.4 mmol) of hydrochloric acid in methanol (7.0 molar) were added dropwise at 5° C. max. and thereafter the mixture was warmed to room temperature. After 90 minutes the reaction mixture was poured into ice-cold sodium hydrogen carbonate solution and the product was extracted three times with methylene chloride, the organic phases were washed once with distilled water, then dried over magnesium sulphate, filtered and concentrated in a water-jet vacuum. The thus-obtained crude product was chromatographed on silica gel with methylene chloride and methanol. There were thus obtained 4.92 g (89% of theory) of tert-butyl (3RS,4RS)-4-[4-(3-benzyloxy-propoxy)-phenyl]-3-(7-hydroxy-naphthalen-2-ylmethoxy)-piperidine-1-carboxylate as a yellow oil; MS: 598 $(M+H)^+$.

(c) In an analogous manner to that described in Example 22(l), from tert-butyl (3RS,4RS)-4-[4-(3-benzyloxy-propoxy)-phenyl]-3-(7-hydroxy-naphthalen-2-ylmethoxy)-piperidine-1-carboxylate by cleavage of the BOC protecting group with hydrogen chloride in methanol there was obtained 7-[(3RS,4RS)-4-[4-(3-benzyloxy-propoxy)-phenyl]-piperidine-3-yloxymethyl]-naphthalen-2-ol hydrochloride (1:1) as an amorphous, beige foam; MS: 498 $(M+H)^+$.

EXAMPLE 96

(a) 0.33 g (0.54 mmol) of tert-butyl (3RS,4RS)-4-[4-(3-benzyloxy-propoxy)-phenyl]-3-(7-hydroxy-naphthalen-2-ylmethoxy)-piperidine-1-carboxylate [Example 95(b)] and 0.27 g (0.7 mmol) of di-O-isopropylidene-1-O-(4-methyl-phenylsulphonyl)-D-arabinitol [Liebigs Ann. Chem. 1992, 1131] were stirred at reflux under argon for 2 hours in 15 ml of dimethylformamide with the addition of 0.69 g (5 mmol) of potassium carbonate (anhydrous). The reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.34 g (78% of theory) of a 1:1 mixture of tert-butyl (3R,4R)- and (3S,4S)-4-[4-(3-benzyloxy-propoxy)-phenyl]-3-[7-[(4S,4'R,5R)-2,2,2',2'-tetramethyl-[4,4']bi[[1,3]dioxolan-5-ylmethoxy]-naphthalen-2-ylmethoxy]-piperidine-1-carboxylate as a colourless oil; MS: 829 $(M+NH_4)^+$.

(b) 0.10 g (0.12 mmol) of a 1:1 mixture of tert-butyl (3R,4R)- and (3S,4S)-4-[4-(3-benzyloxy-propoxy)-phenyl]-3-[7-[(4S,4'R,5R)-2,2,2',2'-tetramethyl-[4,4']bi[[1,3]dioxolan-5-ylmethoxy]-naphthalen-2-ylmethoxy]-piperidine-1-carboxylate was dissolved in 5 ml of abs. ethanol, 1 ml of hydrochloric acid in ethanol (5.6 molar) was added thereto and the mixture was stirred at 50° C. under argon for 90 hours. After distillation of the solvent in a water-jet vacuum the residue was dried over phosphorus pentoxide at 50° C. in a high vacuum for 3 hours. There was thus obtained 0.07 g (87% of theory) of a 1:1 mixture of (2R,3R,4R)-5-[7-[(3R,4R)- and (3S,4S)-4-[4-(3-benzyloxy-propoxy)-piperidin-3-yloxymethyl]-naphthalen-2-yloxy]-pentane-1,2,3,4-tetraol hydrochloride (1:1) in the form of pale yellow crystals; MS: 632 $(M+H)^+$.

EXAMPLE 97

(a) 4.77 g (10.8 mmol) of tert-butyl (3RS,4RS)-4-[4-(3-benzyloxy-propoxy)-phenyl]-3-hydroxy-piperidine-1-carboxylate [Example 86(n)] and 3.49 g (10.8 mmol) of 2-chloromethyl-6-(2-trimethylsilanyl-ethoxymethoxy)-naphthalene [Example 6(o)] were dissolved in 35 ml of dimethylformamide at room temperature under argon, then 0.50 g (11.5 mmol) of sodium hydride dispersion (55% in mineral oil) was added and the mixture was stirred at room temperature for 18 hours. The reaction mixture was poured on to ice-water, the product was extracted three times with methylene chloride, the organic phases were washed twice with distilled water, then dried over magnesium sulphate, filtered and concentrated in a water-jet vacuum. The thus-obtained crude product was chromatographed on silica gel with n-hexane and methylene chloride. There were thus obtained 6.74 g (83% of theory) of tert-butyl (3RS,4RS)-4-[4-(3-benzyloxy-propoxy)-phenyl]-3-[6-(2-trimethylsilany-ethoxymethoxy)-naphthalen-2-ylmethoxy]-piperidine-1-carboxylate as a pale yellow oil: MS: 728 $(M+H)^+$.

(b) In an analogous manner to that described in Example 95(b), from tert-butyl (3RS,4RS)-4-[4-(3-benzyloxy-propoxy)-phenyl]-3-[6-(2-trimethylsilanyl-ethoxymethoxy)-naphthalen-2-ylmethoxy]-piperidine-1-carboxylate there was obtained tert-butyl (3RS,4RS)-4-[4-(3-benzyloxy-propoxy)-phenyl]-3-(6-hydroxy-naphthalen-2-ylmethoxy)-piperidine-1-carboxylate as an amorphous, colourless foam; MS: 598 $(M+H)^+$.

(c) In an analogous manner to that described in Example 90(g), from tert-butyl (3RS,4RS)-4-[4-(3-benzyloxy-propoxy)-phenyl]-3-(6-hydroxy-naphthalen-2-ylmethoxy)-piperidine-1-carboxylate there was obtained tert-butyl (3RS,4RS)-4-[4-(3-benzyloxy-propoxy)-phenyl]-3-[6-(2-morpholin-4-yl-ethoxy)-naphthalen-2-ylmethoxy]-piperidine-1-carboxylate as a pale yellow oil; MS: 711 $(M+H)^+$.

(d) In an analogous manner to that described in Example 22(l), from tert-butyl (3RS,4RS)-4-[4-(3-benzyloxy-propoxy)-phenyl]-3-[6-(2-morpholin-4-yl-ethoxy)-naphthalen-2-ylmethoxy]-piperidine-1-carboxylate by cleavage of the BOC protecting group with hydrogen chloride in methanol there was obtained 4-[2-[6-[(3RS,4RS)-4-[4-(3-benzyloxy-propoxy)-phenyl]-piperidin-3-yloxymethyl]-naphthalen-2-yloxy]-ethyl]-morpholine hydrochloride (1:2) in the form of colourless crystals; M: 611 (M+H)$^+$.

EXAMPLE 98

(a) 4.10 g (21.5 mmol) of p-toluenesulphonyl chloride were placed in 20 ml of abs. pyridine at 5° C. under argon, 0.06 g (0.5 mmol) of 4-dimethylaminopyridine was added and a solution of 3.58 g (20.3 mmol) of (RS)-2-[(2,2-dimethyl-1,3-dioxolan-4-yl)methoxy]-ethanol [J. Chem. Soc. 1965, 2968] in 20 ml of abs. pyridine was added dropwise while stirring. After stirring at room temperature for 6 hours the reaction mixture was poured on to ice-water, the product was extracted three times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 1.72 g (26% of theory) of (RS)-2-(2,2-dimethyl-[1,3]dioxolan-4-ylmethoxy)-ethyl toluene-4-sulphonate as a colourless oil; MS: 315 (M-CH3).

(b) In an analogous manner to that described in Example 90(g), from (RS)-2-(2,2-dimethyl-[1,3]dioxolan-4-ylmethoxy)-ethyl toluene-4-sulphonate and tert-butyl (3RS,4RS)-4-[4-(3-benzyloxy-propoxy)-phenyl]-3-(7-hydroxy-naphthalen-2-ylmethoxy)-piperidine-1-carboxylate [Example 95(b)] there was obtained a mixture of tert-butyl (3RS,4RS)- and (3SR,4SR)-4-[4-(3-benzyloxy-propoxy)-phenyl]-3-[7-[2-[(RS)-2,2-dimethyl-[1,3]dioxolan-4-ylmethoxy]-ethoxy]-naphthalen-2-ylmethoxy]-piperidine-1-carboxylate in the form of colourless crystals; MS: 773 (M+NH$_4$)$^+$.

(c) In an analogous manner to that described in Example 22(l), from a mixture of tert-butyl (3RS,4RS)- and (3SR,4SR)-4-[4-(3-benzyloxy-propoxy)-phenyl]-3-[7-[2-[(RS)-2,2-dimethyl-[1,3]dioxolan-4-ylmethoxy]-ethoxy]-naphthalen-2-ylmethoxy]-piperidine-1-carboxylate by cleavage of the BOC protecting group with hydrogen chloride in methanol there was obtained a mixture of (RS)- and (SR)-3-[2-[7-[(3RS,4RS)-4-[4-(3-benzyloxy-propoxy)-phenyl]-piperidin-3-yloxymethyl]-naphthalen-2-yloxy]-ethoxy]-propane-1,2-diol hydrochloride (1:1) as an amorphous, beige foam; MS: 616 (M+H)$^+$.

EXAMPLE 99 a) 9.92 g (227.4 mmol) of sodium hydride dispersion (55% in mineral oil) were placed in 220 ml of abs. tetrahydrofuran at 5° C. under argon, a solution of 68.3 ml (341.1 mmol) of triethyl phosphonoacetate in 220 ml of abs. tetrahydrofuran was added dropwise thereto at 5° C. during 1 hour and the mixture was subsequently stirred at room temperature for 1 hour. Now, again at 5° C., a solution of 24.1 g (113.7 mmol) of 4-benzyloxy-benzaldehyde in 220 ml of tetrahydrofuran was added dropwise during 30 minutes and thereafter the mixture was stirred at 5° C. for 2 hours. The reaction mixture was treated with 300 ml of ice-water and the solvent was distilled off in a water-jet vacuum; the aqueous suspension of the product was extracted 3 times with ethyl acetate, the organic phases were washed twice with distilled water, then dried over magnesium sulphate, filtered and concentrated in a water-jet vacuum. The thus-obtained crude product was chromatographed on silica gel with n-hexane and ethyl acetate. There were thus obtained 30.8 g (96% of theory) of ethyl (E)-3-(4-benzyloxy-phenyl)-acrylate as a colourless solid; MS: 282 (M)$^+$.

(b) 17.85 g (136.1 mmol) of malonic acid monoethyl ester monoamide in 350 ml of abs. ethanol were treated under argon with 15.3 g (136.1 mmol) of potassium tert-butylate, then 19.2 g (68.1 mmol) of ethyl (E)-3-(4-benzyloxy-phenyl)-acrylate were added at room temperature while stirring and the mixture was stirred at reflux for 1 hour. After cooling to 10° C. 15.4 ml (269.7 mmol) of glacial acetic acid were added dropwise. The reaction mixture was poured on to ice-water, the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 17.2 g (69% of theory) of ethyl (3RS,4SR)-4-(4-benzyloxy-phenyl)-2,6-dioxo-piperidine-3-carboxylate as a colourless solid; MS: 367 (M)$^+$.

(c) 4.33 g (114.2 mmol) of lithium aluminium hydride were suspended in 200 ml of tetrahydrofuran under argon, then a solution of 18.31 g (49.8 mmol) of ethyl (3RS,4SR)-4-(4-benzyloxy-phenyl)-2,6-dioxo-piperidine-3-carboxylate in 200 ml of tetrahydrofuan was added dropwise at room temperature and the mixture was subsequently stirred at reflux for 2 hours. 100 ml of distilled water were cautiously added dropwise to the reaction mixture at 5–10° C. and the precipitate which thereby formed was filtered off. The filtrate was thereupon extracted 3 times with ethyl acetate, the organic phases were washed twice with distilled water, dried over magnesium sulphate, filtered and concentrated in a water-jet vacuum. The thus-obtained crude product was recrystallized from methylene chloride and n-hexane. There were thus obtained 11.14 g (75% of theory) of (3RS,4SR)-[4-(4-benzyloxy-phenyl)-piperidin-3-yl]-methanol in the form of colourless crystals; MS: 297 (M)$^+$.

(d) 11.14 g (37.5 mmol) of (3RS,4SR)-[4-(4-benzyloxy-phenyl)-piperidin-3-yl]-methanol were dissolved in 140 ml of dioxan under argon, then a solution of 6.72 g (80 mmol) of sodium hydrogen carbonate in 45 ml of water was added at room temperature and 9.78 g (44.8 mmol) of di-tert-butyl dicarbonate were introduced portionwise. After stirring at room temperature for 18 hours the reaction mixture was extracted 3 times with ethyl acetate, the organic phases were washed twice with distilled water, then dried over magnesium sulphate, filtered and concentrated in a water jet vacuum. The thus-obtained crude product was chromatographed on silica gel with methylene chloride and methanol. There were thus obtained 13.38 g (90% of theory) of tert-butyl (3RS,4SR)-4-(4-benzyloxy-phenyl)-3-hydroxymethyl-piperidine-1-carboxylate as an amorphous, colourless foam; MS: 398 (M+H)$^+$.

(e) 3.92 ml (45.6 mmol) of oxalyl chloride were placed in 400 ml of methylene chloride at −70° C. under argon, 5.48 ml (77.2 mmol) of dimethyl sulphoxide were added dropwise thereto and the mixture was stirred for 30 minutes. Now, a solution of 13.95 g (35.1 mmol) of tert-butyl (3RS,4SR)-4-(4-benzyloxy-phenyl)-3-hydroxymethyl-piperidine-1-carboxylate in 200 ml of methylene chloride was added dropwise at −70° C. and thereafter the mixture was stirred at this temperature for 2 hours. Subsequently, 12.2 ml (87.7 mmol) of triethylamine were added dropwise to the reaction mixture and thereafter it was warmed to room temperature. After stirring at this temperature for 18 hours the mixture was poured on to ice-water and the product was extracted 3 times with methylene chloride, the organic phases were washed twice with distilled water, then dried over magnesium sulphate, filtered and concentrated in a water-jet vacuum. The thus-obtained crude product was recrystallized from n-hexane. There were thus obtained 11.31 g (81% of theory) of tert-butyl (3RS,4SR)-4-(4-benzyloxy-phenyl)-3-formyl-piperidine-1-carboxylate in the form of colourless crystals; MS: 395 (M)$^+$.

(f) 11.04 g (25.6 mmol) of tributyl-naphthalen-2-yl-stannate [Example 74(g)] were placed in 100 ml of tetrahydrofuran at −70° C. under argon and 12.0 ml (19.2 mmol) of n-butyllithium solution (1.6 molar in n-hexane) were added dropwise thereto. After stirring at this temperature for 30 minutes a solution of 5.94 g (15 mmol) of tert-butyl (3RS,4SR)-4-(4-benzyloxy-phenyl)-3-formyl-piperidine-1-carboxylate in 45 ml of tetrahydrofuran was added dropwise and the mixture was stirred at −70° C. for a further 1 hour. Now, the mixture was warmed to room temperature and, after 18 hours, poured on to ice-water and the product was extracted 3 times with ethyl acetate; the organic phases were washed twice with distilled water, then dried over magnesium sulphate, filtered and concentrated in a water-jet vacuum. The thus-obtained crude product was chromatographed on silica gel with n-hexane and ethyl acetate. There were thus obtained 6.88 g (85% of theory) of a mixture of tert-butyl (3RS,4SR)-4-(4-benzyloxy-phenyl)-3-[(RS)- and -[(SR)-1-hydroxy-2-naphthalen-2-yl-ethyl]-piperidine-1-carboxylate in the form of yellow crystals; MS: 538 (M+H)$^+$.

(g) In an analogous manner to that described in Example 22(l), from a mixture of tert-butyl (3RS,4SR)-4-(4-benzyloxy-phenyl)-3-[(RS)- and -[(SR)-1-hydroxy-2-naphthalen-2-yl-ethyl]-piperidine-1-carboxylate by cleavage of the BOC protecting group with hydrogen chloride in methanol there was obtained a mixture of (RS)- and (SR)-1-[(3RS,4SR)-4-(4-benzyloxy-phenyl)-piperidin-3-yl]-2-naphthalen-2-yl-ethanol hydrochloride (1:1) in the form of beige crystals; MS: 438 (M+H)$^+$.

EXAMPLE 100

(a) 6.36 g (11.8 mmol) of a mixture of tert-butyl (3RS,4SR)-4-(4-benzyloxy-phenyl)-3-[(RS)- and -[(SR)-1-hydroxy-2-naphthalen-2-yl-ethyl]-piperidine-1-carboxylate [Example 99(f)] were hydrogenated under normal conditions for 4 hours in 50 ml of methanol with the addition of 2.0 g of palladium-charcoal (10%). After filtration of the catalyst over a Dicalite pad and distillation of the 35 solvent in a water-jet vacuum there were obtained 4.97 g (94% of theory) of a mixture of tert-butyl (3RS,4SR)-4-(4-hydroxy-phenyl)-3-[(RS)-and-(SR)-1-hydroxy-2-naphthalen-2-yl-ethyl]-piperidine-1-carboxylate as an amorphous, pale yellow foam; MS: 448 (M+H)$^+$.

(b) 3.97 g (8.9 mmol) of a mixture of tert-butyl (3RS,4SR)-4-(4-hydroxy-phenyl)-3-[(RS)- and -(SR)-1-hydroxy-2-naphthalen-2-yl-ethyl]-piperidine-1-carboxylate were placed in 60 ml of methyl ethyl ketone at room temperature under argon, then 4.90 g (35.5 mmol) of potassium carbonate (anhydrous) and 4.54 ml (27.7 mmol) of benzyl 3-bromo-propyl ether were added and thereafter the mixture was stirred at reflux for 8 hours. After cooling to room temperature the reaction mixture was poured on to ice-water and the product was extracted 3 times with ethyl acetete, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 5.13 g (97% of theory) of a mixture of tert-butyl (3RS,4SR)-4-[4-(3-benzyloxy-propoxy)-phenyl]-3-[(RS)- and -[(SR) 1-hydroxy-2-naphthalen-2-yl-ethyl]-piperidine-1-carboxylate as an amorphous yellow foam; MS: 596 (M+H)$^+$.

(c) In an analogous manner to that described in Example 99(e), from a mixture of tert-butyl (3RS,4SR)-4-[4-(3-benzyloxy-propoxy)-phenyl]-3-[(RS)- and -[(SR) 1-hydroxy-2-naphthalen-2-yl-ethyl]-piperidine-1-carboxylate with oxalyl chloride and dimethyl sulphoxide there was obtained tert-butyl (3RS,4SR)-4-[4-(3-benzyloxy-propoxy)-phenyl]-3-(naphthalen-2-yl-acetyl)-piperidine-1-carboxylate as a colourless oil; MS: 594 (M+H)$^+$.

(d) In an analogous manner to that described in Example 22(l), from tert-butyl 3RS,4SR)-4-[4-(3-benzyloxy-propoxy)-phenyl]-3-(naphthalen-2-yl-acetyl)-piperidine-1-carboxylate by cleavage of the BOC protecting group with hydrogen chloride in methanol there was obtained [(3RS,4SR)-4-[4-(3-benzyloxy-propoxy)-phenyl]-piperidin-3-yl]-2-naphthalen-2-yl-ethanone hydrochloride (1:1) in in the form of colourless crystals; MS: 494 (M+H)$^+$.

EXAMPLE 101

(a) 10.66 g (50.2 mmol) of 4-benzyloxy-benzaldehyde and 8.54 ml (56.2 mmol) of diethyl malonate were stirred at reflux under argon for 18 hours in 100 ml of toluene with the addition of 10.15 g of molecular sieve (4 Å), 1.0 ml (10.0 mmol) of piperidine and 1.0 ml (17.6 mmol) of glacial acetic acid. After filtration of the reaction mixture the solvent was distilled off in a water-jet vacuum and the residue was chromatographed on silica gel with n-hexane and ethyl acetate. There were thus obtained 14.05 g (83% of theory) of diethyl 2-(4-benzyloxy-benzylidene)-malonate in the form of yellow crystals; MS: 354 (M)$^+$.

(b) 6.42 g (48.9 mmol) of malonic acid monoethyl ester monoamide in 115 ml of abs. ethanol were treated with 5.49 g (48.9 mmol) of potassium tert-butylate under argon, then 17.35 g (48.9 mmol) of diethyl 2-(4-benzyloxy-benzylidene)-malonate were added at room temperature while stirring and the mixture was stirred at reflux for 2 hours. After cooling to 10° C. 13.0 ml (227 mmol) of glacial acetic acid were added dropwise. The reaction mixture was poured on to ice-water, the product was extracted three times with methylene chloride, the organic phases were washed twice with distilled water, then dried over magnesium sulphate, filtered and concentrated in a water-jet vacuum. The thus-obtained crude product was recrystallized from methylene chloride and n-hexane. There were thus obtained 16.76 g (78% of theory) of diethyl (3R,4s,5S)-4-(4-benzyloxy-phenyl)-2,6-dioxo-piperidine-3,5-dicarboxylate as a colourless solid; MS: 439 (M)$^+$.

(c) 3.83 g (100.9 mmol) of lithium aluminium hydride were suspended in 200 ml of tetrahydrofuran under argon, then a solution of 18.37 g (41.8 mmol) of diethyl (3R,4s,5S)-4-(4-benzyloxy-phenyl)-2,6-dioxo-piperidine-3,5-dicarboxylate in 200 ml of tetrahydrofuran was added dropwise and the mixture was subsequently stirred at reflux for 1 hour. Subsequently, 25 ml of distilled water were cautiously added dropwise to the reaction mixture at 5–10° C. After filtration of the reaction mixture the solvent was distilled off in a water-jet vacuum. There were thus obtained 11.04 g (81% of theory) of (3R,4s,5S)-[4-(4-benzyloxy-phenyl)-5-hydroxymethyl-piperidin-3-yl]-methanol in the form of colourless crystals; MS: 328 (M+H)$^+$.

(d) 8.10 g (24.7 mmol) of (3R,4s,5S)-[4-(4-benzyloxy-phenyl)-5-hydroxymethyl-piperidin-3-yl]-methanol were dissolved in 100 ml of dioxan under argon, then a solution of 4.44 g (52.8 mmol) of sodium hydrogen carbonate in 34 ml of water was added dropwise at room temperature and subsequently 6.46 g (29.6 mmol) of di-tert-butyl dicarbonate were introduced portionwise. After stirring at room temperature for 66 hours the reaction mixture was extracted 3 times with ethyl acetate, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 8.10 g (77% of theory) of tert-butyl (3R,4s,5S)-4-(4-benzyloxy-phenyl)-3,5-bis-hydroxymethyl-piperidine-1-carboxylate as an amorphous, colourless foam; MS: 428 (M+H)$^+$.

(e) 7.46 g (17.5 mmol) of tert-butyl (3R,4s,5S)-4-(4-benzyloxy-phenyl)-3,5-bis-hydroxymethyl-piperidine-1-carboxylate were hydrogenated under normal conditions for 2 hours in 250 ml of methanol with the addition of 1.5 g of palladium-charcoal (10%). The catalyst was subsequently filtered off over a Dicalite pad and the solvent was distilled off in a water-jet vacuum. The thus-obtained crude product was chromatographed on silica gel with methylene chloride and methanol. There were thus obtained 6.07 g (99% of theory) of tert-butyl (3R,4s,5S)-3,5-bis-hydroxymethyl-4-(4-hydroxy-phenyl)-piperidine-1-carboxylate as an amorphous, colourless foam; MS: 338 (M+H)$^+$.

(f) 6.77 g (20 mmol) of tert-butyl (3R,4s,5S)-3,5-bis-hydroxymethyl-4-(4-hydroxy-phenyl)-piperidine-1-carboxylate were placed in 90 ml of methyl ethyl ketone at room temperature under argon. Thereupon, 11.05 g (80 mmol) of potassium carbonate (anhydrous) and 10.25 ml (58 mmol) of benzyl 3-bromo-propyl ether were added and thereafter the mixture was stirred at reflux for 18 hours. After cooling to room temperature the reaction mixture was poured on to ice-water and the product was extracted 3 times with ethyl acetate, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 7.95 g (82% of theory) of tert-butyl (3R,4s,5S)-4-[4-(3-benzyloxy-propoxy)-phenyl]-3,5-bis-hydroxymethyl-piperidine-1-carboxylate as an amorphous, colourless foam; MS: 486 (M+H)$^+$.

(g) 1.51 g (33.2 mmol) of sodium hydride dispersion (55% in mineral oil) and 2.94 g (15.9 mmol) of 4-(2-chloroethyl)-morpholine hydrochloride were dissolved in 25 ml of dimethylformamide under argon, a solution of 7.33 g (15.1 mmol) of tert-butyl (3R,4s,5S)-4-[4-(3-benzyloxy-propoxy)-phenyl]-3,5-bis-hydroxymethyl-piperidine-1-carboxylate in 50 ml of dimethylformamide was added dropwise while stirring and 0.1 g (0.6 mmol) of potassium iodide was added. The reaction mixture was stirred at 100° C. for 9 hours. After cooling to room temperature the reaction mixture was poured on to ice-water and the product was extracted 3 times with methylene chloride, the organic phases were washed twice with distilled water, then dried over magnesium sulphate, filtered and concentrated in a water-jet vacuum. The thus-obtained crude product was chromatographed on silica gel with methylene chloride and methanol. There were thus obtained 0.29 g (3% of theory) of tert-butyl (3R,4S,5S)-4-[4-(3-benzyloxy-propoxy)-phenyl]-3,5-bis-(2-morpholin-4-yl-ethoxymethyl)-piperidine-1-carboxylate as a pale brown oil [MS: 712 (M+H)$^+$] and 2.37 g (26% of theory) of tert-butyl (3RS,4RS,5SR)-4-[4-(3-benzyloxy-propoxy)-phenyl]-3-hydroxymethyl-5-(2-morpholin-4-yl-ethoxymethyl)-piperidine-1-carboxylate as a pale brown oil; MS: 599 (M+H)$^+$.

(h) In an analogous manner to that described in Example 74(f), from tert-butyl (3RS,4RS,5SR)-4-[4-(3-benzyloxy-propoxy)-phenyl]-3-hydroxymethyl-5-(2-morpholin4-yl-ethoxymethyl)-piperidine-1-carboxylate by oxidation with dimethyl sulphoxide/oxalyl chloride in methylene chloride there was obtained tert-butyl (3RS,4SR,5SR)-4-[4-(3-benzyloxy-propoxy)-phenyl]-3-formyl-5-(2-morpholin-4-yl-ethoxymethyl)-piperidine-1-carboxylate as a yellow oil; MS: 597 (M+H)$^+$.

(i) 1.20 g (0.05 g atom) of magnesium shavings were placed in 15 ml of abs. ether at room temperature under argon, 1 crystal of iodine and 5 drops of 1,2-dibromomethane were added and the mixture was heated to reflux. After commencement of the reaction (decoloration) a solution of 1.77 g (10 mmol) of 2-(chloromethyl)-naphthalene in 10 ml of abs. ether was added dropwise during 30 minutes. After the addition the mixture was left to cool to room temperature and after one hour a solution of 0.70 g (1.17 mmol) of tert-butyl (3RS,4SR, 5SR)-4-[4-(3-benzyloxy-propoxy)-phenyl]-3-formyl-5-(2-morpholin-4-yl-ethoxymethyl)-piperidine-1-carboxylate in 15 ml of abs. ether was added dropwise. Then, the mixture was stirred at room temperature for 18 hours. After the dropwise addition of 3 ml of water while cooling with ice the reaction mixture was poured on to ice-water, the product was extracted 3 times with ether, the organic phases were washed twice with distilled water, then dried over magnesium sulphate, filtered and concentrated in a water-jet vacuum. The thus-obtained crude product was chromatographed on silica gel with methylene chloride and methanol. There was thus obtained 0.77 g (89% of theory) of a mixture of tert-butyl (3RS,4SR,5SR)-4-[4-(3-benzyloxy-propoxy)-phenyl]-3-[(RS)- and -[(SR)-1-hydroxy-2-naphthalen-2-yl-ethyl]-5-(2-morpholin-4-yl-ethoxymethyl)-piperidine-1-carboxylate; MS: 739 (M+H)$^+$.

(k) In an analogous manner to that described in Example 74(f), from 0.74 g (1 mmol) of a mixture of tert-butyl (3RS,4SR,5SR)-4-[4-(3-benzyloxy-propoxy)-phenyl]-3-[(RS)- and -[(SR)-1-hydroxy-2-naphthalen-2-yl-ethyl]-5-(2-morpholin-4-yl-ethoxymethyl)-piperidine-1-carboxylate by oxidation with dimethyl sulphoxide/oxalyl chloride in methylene chloride there was obtained 0.15 g (20% of theory) of tert-butyl (3RS,4SR,5SR)-4-[4-(3-benzyloxy-propoxy)-phenyl]-5-(2-morpholin-4-yl-ethoxymethyl)-3-(naphthalen-2-yl-acetyl)-piperidine-1-carboxylate as a pale yellow oil; MS: 737 (M+H)$^+$.

(l) In an analogous manner to that described in Example 73(d), from tert-butyl (3RS,4SR, 5SR)-4-[4-(3-benzyloxy-propoxy)-phenyl]-5-(2-morpholin-4-yl-ethoxymethyl)-3-(naphthalen-2-yl-acetyl)-piperidine-1-carboxylate by cleavage of BOC protecting group by means of anhydrous zinc bromide in methylene chloride there was obtained 1-[(3RS,4SR,5SR)-4-[4-(3-benzyloxy-propoxy)-phenyl]-5-(2-morpholin-4-yl-ethoxymethyl)-piperidin-3-yl]-2-naphthalen-2-yl-ethanone as a yellow oil MS: 637 (M+H)$^+$.

EXAMPLE 102

(a) 0.30 g (0.5 mmol) of tert-butyl (3RS,4SR)-4-[4-(3-benzyloxy-propoxy)-phenyl]-3-(naphthalen-2-yl-acetyl)-piperidine-1-carboxylate [Example 100(c)] and 0.071 g (0.5 mmol) of 3-(aminooxy)propionic acid hydrochloride [J. Am. Chem. Soc. 77, 2345 (1955)] in 3 ml of pyridine were stirred at 60° C. under argon for 18 hours. The reaction mixture was thereupon poured on to ice-water, adjusted to pH 3 with dilute hydrochloric acid, then the product was extracted 3 times with ethyl acetate, the organic phases were washed twice with distilled water, dried over magnesium sulphate, filtered and concentrated in a water-jet vacuum. The thus-obtained crude product was chromatographed on silica gel with methylene chloride and methanol. There was thus obtained 0.018 g (5% of theory) of a mixture of tert-butyl (E)- and (Z)-(3RS,4SR)-4-[4-(3-benzyloxy-propoxy)-phenyl]-3-[1-(2-carboxy-ethoxyimino)-2-naphthalen-2-yl-ethyl]-piperidine-1-carboxylate as a pale yellow oil [MS: 681 (M+H)⁺] and 0.21 g (69% of theory) of a mixture of tert-butyl (E)- and (Z)-(3RS,4SR)-4-[4-(3-benzyloxy-propoxy)-phenyl]-3-(1-hydroxyimino-2-naphthalen-2-yl-ethyl)-piperidine-1-carboxylate as a colourless oil; MS: 609 (M+H)⁺.

(b) In an analogous manner to that described in Example 22(l) from a mixture of tert-butyl (E)- and (Z)-(3RS,4SR)-4-[4-(3-benzyloxy-propoxy)-phenyl]-3-[1-(2-carboxy-ethoxyimino)-2-naphthalen-2-yl-ethyl]-piperidine-1-carboxylate by cleavage of the BOC protecting group with hydrogen chloride in dioxan there was obtained a mixture of (E)- and (Z)-3-(1-[(3RS,4SR)-4-[4-(3-benzyloxy-propoxy)-phenyl]-piperidin-3-yl]-2-naphthalen-2-yl-ethylidenaminooxy)-propionic acid as an amorphous, beige foam (MS: 581 (M+H)⁺] and from a mixture of tert-butyl (E)- and (Z)-(3RS,4SR)-4-[4-(3-benzyloxy-propoxy)-phenyl]-3-(1-hydroxy-imino-2-naphthalen-2-yl-ethyl)-piperidine-1-carboxylate by cleavage of the BOC protecting group with hydrogen chloride in methanol there was a obtained a mixture of (E)- and (Z)-1-[(3RS,4SR)-4-[4-(3-benzyloxy-propoxy)-phenyl]-piperidin-3-yl]-2-naphthalen-2-yl-ethanone oxime as a colourless solid; MS: 509 (M+H)⁺.

EXAMPLE 103

(a) 0.15 g (0.22 mmol) of a mixture of tert-butyl (E)- and (Z)-(3RS,4SR)-4-[4-(3-benzyloxy-propoxy)-phenyl]-3-(1-methoxycarbonyl-methoxyimino-2-naphthalen-2-yl-ethyl)-piperidine-1-carboxylate {Example 90(p)] was dissolved in 10 ml of methanol, treated with 1.3 ml of 3.1 molar hydrochloric acid in methanol (4 mmol) and the reaction mixture was stirred at room temperature for 7 hours. After the addition of 1 ml (9 mmol) of sodium hydroxide solution (28%) at 5° C. the reaction mixture was stirred at room temperature for 18 hours. The pH value of the reaction solution was adjusted to 1 by the dropwise addition of 0.7 ml (8.75 mmol) of hydrochloric acid (37%), the mixture was filtered and the solvent was distilled off in a high vacuum. The residue was suspended in 5 ml of abs. ethanol, filtered and the filtrate was concentrated. The thus-obtained crude product was chromatographed on silica gel with methylene chloride, methanol and ammonia solution (25%). There was thus obtained 0.059 g (47% of theory) of a mixture of (E)- and (Z)-(1-[(3RS,4SR)-4-[4-(3-benzyloxy-propoxy)-phenyl]-piperidin-3-yl]-2-naphthalen-2-yl-ethylidene-aminooxy)-acetic acid as an amorphous, beige foam; MS: 567 (M+H)⁺.

EXAMPLE 104

The following compounds were obtained analogously to Example 1(g) by synthesizing the corresponding BOC derivatives by alkylating of tert-butyl (3RS,4RS)-4-[4-(3-benzyloxy-propoxy)-phenyl]-3-hydroxy-piperidine-1-carboxylate [Example 86(n)] and using these derivatives without further purification and characterization in the cleavage reaction of the BOC group by means of hydrogen chloride in methanol analogously to Example 22(l) or by means of zinc bromide in methylene chloride analgously to Example 10(b):

1) By alkylation with 4-trifluoromethyl-benzyl bromide and cleavage of the BOC group by means of hydrogen chloride in methanol, (3RS,4RS)-4-[4-(3-benzyloxy-propoxy)-phenyl]-3-(4-trifluoromethyl-benzyloxy)-piperidine hydrochloride as a colourless oil; MS: 500 (M+H)⁺;

2) by alkylation with 4-fluoro-benzyl bromide and cleavage of the BOC group by means of hydrogen chloride in methanol, (3RS,4RS)-4-[4-(3-benzyloxy-propoxy)-phenyl]-3-(4-fluoro-benzyloxy)-piperidine hydrochloride as a colourless oil; MS: 450 (M+H)⁺;

3) by alkylation with 2-chloro-benzyl bromide and cleavage of the BOC group by means of hydrogen chloride in methanol, (3RS,4RS)-4-[4-(3-benzyloxy-propoxy)-phenyl]-3-(2-chloro-benzyloxy)-piperidine hydrochloride as a colourless oil; MS: 466 (M)⁺;

4) by alkylation with 4-bromo-benzyl bromide and cleavage of the BOC group by means of hydrogen chloride in methanol, (3RS,4RS)-4-[4-(3-benzyloxy-propoxy)-phenyl]-3-(4-bromo-benzyloxy)-piperidine hydrochloride as a colourless oil; MS: 510 (M)⁺;

5) by alkylation with 3-bromo-benzyl bromide and cleavage of the BOC group by means of hydrogen chloride in methanol, (3RS,4RS)-4-[4-(3-benzyloxy-propoxy)-phenyl]-3-(3-bromo-benzyloxy)-piperidine hydrochloride as a colourless oil; MS: 511 (M+H)⁺;

6) by alkylation with 4-iodo-benzyl bromide and cleavage of the BOC group by means of hydrogen chloride in methanol, (3RS,4RS)-4-[4-(3-benzyloxy-propoxy)-phenyl]-3-(4-iodo-benzyloxy)-piperidine hydrochloride as a colourless oil; MS: 558 (M+H)⁺;

7) by alkylation with 2-trifluoromethyl-benzyl bromide and cleavage of the BOC group by means of hydrogen chloride in methanol, (3RS,4RS)-4-[4-(3-benzyloxy-propoxy)-phenyl]-3-(2-trifluoromethyl-benzyloxy)-piperidine hydrochloride as a colourless oil; MS: 500 (M+H)⁺;

8) by alkylation with 3,5-dimethyl-benzyl bromide and cleavage of the BOC group by means of hydrogen chloride in methanol, (3RS,4RS)-4-[4-(3-benzyloxy-propoxy)-phenyl]-3-(3,5-dimethyl-benzyloxy)-piperidine hydrochloride as a colourless oil; MS: 460 (M+H)⁺;

9) by alkylation with 2,4-dimethyl-benzyl chloride and cleavage of the BOC group by means of hydrogen chloride in methanol, (3RS,4RS)-4-[4-(3-benzyloxy-propoxy)-phenyl]-3-(2,4-dimethyl-benzyloxy)-piperidine hydrochloride as a colourless oil; MS: 460 (M+H)⁺;

10) by alkylation with 4-methyl-benzyl bromide and cleavage of the BOC group by means of hydrogen chloride in methanol, (3RS,4RS)-4-[4-(3-benzyloxy-propoxy)-phenyl]-3-(4-methyl-benzyloxy)-piperidine hydrochloride as a colourless oil; MS: 446 (M+H)⁺;

11) by alkylation with 4-isopropyl-benzyl chloride and cleavage of the BOC group by means of hydrogen chloride in methanol, (3RS,4RS)-4-[4-(3-benzyloxy-propoxy)-phenyl]-3-(4-isopropyl-benzyloxy)-piperidine hydrochloride as a colourless oil; MS: 474 (M+H)⁺;

12) by alkylation with 4-tert-butyl-benzyl bromide and cleavage of the BOC group by means of hydrogen chloride in methanol, (3RS,4RS)-4-[4-(3-benzyloxy-propoxy)-phenyl]-3-(4-tert-butyl-benzyloxy)-piperidine hydrochloride as a colourless oil; MS: 488 (M+H)⁺;

13) by alkylation with 2-methoxy-benzyl chloride and cleavage of the BOC group by means of hydrogen chloride in methanol, (3RS,4RS)-4-[4-(3-benzyloxy-propoxy)-phenyl]-3-(2-methoxy-benzyloxy)-piperidine hydrochloride as a colourless oil; MS: 462 (M+H)⁺;

14) by alkylation with 2-fluoro-benzyl bromide and cleavage of the BOC group by means of hydrogen chloride in methanol, (3RS,4RS)-4-[4-(3-benzyloxy-propoxy)-phenyl]-3-(2-fluoro-benzyloxy)-piperidine hydrochloride as a colourless oil; MS: 450 (M+H)⁺;

15) by alkylation with 2-fluoro-6-trifluoromethyl-benzyl bromide and cleavage of the BOC group by means of hydrogen chloride in methanol, (3RS,4RS)-4-[4-(3-benzyloxy-propoxy)-phenyl]-3-(2-fluoro-6-trifluoromethyl-benzyloxy)-piperidine hydrochloride as a colourless oil; MS: 518 (M+H)$^+$;

16) by alkylation with 2-bromo-5-fluoro-benzyl bromide and cleavage of the BOC group by means of hydrogen chloride in methanol, (3RS,4RS)-4-[4-(3-benzyloxy-propoxy)-phenyl]-3-(2-bromo-5-fluoro-benzyloxy)-piperidine hydrochloride as a colourless oil; MS: 528 (M)$^+$;

17) by alkylation with 4-fluoro-3-trifluoromethyl-benzyl bromide and cleavage of the BOC group by means of hydrogen chloride in methanol, (3RS,4RS)- 4-[4-(3-benzyloxy-propoxy)-phenyl]-3-(4-fluoro-3-trifluoromethyl-benzyloxy)-piperidine hydrochloride as a colourless oil; MS: 518 (M+H)$^+$;

18) by alkylation with 3,5-di-trifluoromethyl-benzyl bromide and cleavage of the BOC group by means of hydrogen chloride in methanol, (3RS,4RS)-4-[4-(3-benzyloxy-propoxy)-phenyl]-3-(3,5-bis-trifluoromethyl-benzyloxy)-piperidine hydrochloride as a colourless oil; MS: 568 (M+H)$^+$;

19) by alkylation with 2-fluoro-3-methyl-benzyl bromide and cleavage of the BOC group by means of hydrogen chloride in methanol, (3RS,4RS)-4-[4-(3-benzyloxy-propoxy)-phenyl]-3-(2-fluoro-3-methyl-benzyloxy)-piperidine hydrochloride as a colourless oil; MS: 464 (M+H)$^+$;

20) by alkylation with 2-fluoro-4-trifluoromethyl-benzyl bromide and cleavage of the BOC group by means of hydrogen chloride in methanol, (3RS,4RS)-4-[4-(3-benzyloxy-propoxy)-phenyl]-3-(2-fluoro-4-trifluoromethyl-benzyloxy)-piperidine hydrochloride as a yellowish oil; MS: 518 (M+H)$^+$;

21) by alkylation with 2-fluoro-5-trifluoromethyl-benzyl bromide and cleavage of the BOC group by means of hydrogen chloride in methanol, (3RS,4RS)-4-[4-(3-benzyloxy-propoxy)-phenyl]-3-(2-fluoro-5-trifluoromethyl-benzyloxy)-piperidine hydrochloride as a yellowish oil; MS: 518 (M+H)$^+$;

22) by alkylation with 4-fluoro-2-trifluoromethyl-benzyl bromide and cleavage of the BOC group by means of hydrogen chloride in methanol, (3RS,4RS)-4-[4-(3-benzyloxy-propoxy)-phenyl]-3-(4-fluoro-2-trifluoromethyl-benzyloxy)-piperidine hydrochloride as a colourless oil; MS: 518 (M+H)$^+$;

23) by alkylation with 3,5-dichloro-benzyl chloride and cleavage of the BOC group by means of hydrogen chloride in methanol, (3RS,4RS)-4-[4-(3-benzyloxy-propoxy)-phenyl]-3-(3,5-dichloro-benzyloxy)-piperidine hydrochloride as a colourless oil; MS: 500 (M)$^+$;

24) by alkylation with 2,4-dichloro-benzyl chloride and cleavage of the BOC group by means of hydrogen chloride in methanol, (3RS,4RS)- 4-[4-(3-benzyloxy-propoxy)-phenyl]-3-(2,4-dichloro-benzyloxy)-piperidine hydrochloride as a colourless oil; MS: 500 (M)$^+$;

25) by alkylation with 2-bromo-benzyl chloride and cleavage of the BOC group by means of hydrogen chloride in methanol, (3RS,4RS)-4-[4-(3-benzyloxy-propoxy)-phenyl]-3-(2-bromo-benzyloxy)-piperidine hydrochloride as a colourless oil; MS: 510 (M)$^+$;

26) by alkylation with 2,6-dichloro-benzyl chloride and cleavage of the BOC group by means of hydrogen chloride in methanol, (3RS,4RS)-4-[4-(3-benzyloxy-propoxy)-phenyl]-3-(2,6-dichloro-benzyloxy)-piperidine hydrochloride as a colourless oil; MS: 500 (M+H)$^+$;

27) by alkylation with 3-fluoro-benzyl chloride and cleavage of the BOC group by means of hydrogen chloride in methanol, (3RS,4RS)-4-[4-(3-benzyloxy-propoxy)-phenyl]-3-(3-fluoro-benzyloxy)-piperidine hydrochloride as a colourless oil; MS: 450 (M+H)$^+$;

28) by alkylation with 6-chloro-2-fluoro-benzyl chloride and cleavage of the BOC group by means of hydrogen chloride in methanol, (3RS,4RS)-4-[4-(3-benzyloxy-propoxy)-phenyl]-3-(2-chlor-6-fluoro-benzyloxy)-piperidine hydrochloride as a colourless oil; MS: 484 (M)$^+$;

29) by alkylation with 2-iodo-benzyl chloride and cleavage of the BOC group by means of hydrogen chloride in methanol, (3RS,4RS)-4-[4-(3-benzyloxy-propoxy)-phenyl]-3-(2-iodo-benzyloxy)-piperidine hydrochloride as a colourless oil; MS: 558 (M+H)$^+$;

30) by alkylation with 3,4-difluoro-benzyl bromide and cleavage of the BOC group by means of hydrogen chloride in methanol, (3RS,4RS)-4-[4-(3-benzyloxy-propoxy)-phenyl]-3-(3,4-difluoro-benzyloxy)-piperidine hydrochloride as a colourless oil; MS: 468 (M+H)$^+$;

31) by alkylation with 2,3-difluoro-benzyl bromide and cleavage of the BOC group by means of hydrogen chloride in methanol, (3RS,4RS)- 4-[4-(3-benzyloxy-propoxy)-phenyl]-3-(2,3-difluoro-benzyloxy)-piperidine hydrochloride as a colourless oil; MS: 468 (M+H)$^+$;

32) by alkylation with 2,5-difluoro-benzyl bromide and cleavage of the BOC group by means of hydrogen chloride in methanol, (3RS,4RS)-4-[4-(3-benzyloxy-propoxy)-phenyl]-3-(2,5-difluoro-benzyloxy)-piperidine hydrochloride as a colourless oil; MS: 468 (M+H)$^+$;

33) by alkylation with 2,6-difluoro-benzyl chloride and cleavage of the BOC group by means of hydrogen chloride in methanol, (3RS,4RS)-4-[4-(3-benzyloxy-propoxy)-phenyl]-3-(2,6-difluoro-benzyloxy)-piperidine hydrochloride as a colourless oil; MS: 468 (M+H)$^+$;

34) by alkylation with 2,4-difluoro-benzyl bromide and cleavage of the BOC group by means of hydrogen chloride in methanol, (3RS,4RS)-4-[4-(3-benzyloxy-propoxy)-phenyl]-3-(2,4-difluoro-benzyloxy)-piperidine hydrochloride as a colourless oil; MS: 468 (M+H)$^+$;

35) by alkylation with 3,5-difluoro-benzyl bromide and cleavage of the BOC group by means of hydrogen chloride in methanol, (3RS,4RS)-4-[4-(3-benzyloxy-propoxy)-phenyl]-3-(3,5-difluoro-benzyloxy)-piperidine hydrochloride as a colourless oil; MS: 468 (M+H)$^+$;

36) by alkylation with methyl 4-bromomethyl-benzoate, saponification of the methyl ester during the aqueous working-up and subsequent cleavage of the BOC group by means of hydrogen chloride in methanol, 4-{(3RS,4RS)-4-[4-(3-benzyloxy-propoxy)-phenyl]-piperidin-3-yloxymethyl}-benzoic acid hydrochloride as a colourless oil; MS: 476 (M+H)$^+$;

37) by alkylation with 1-bromomethyl-4-trifluoromethoxy-benzene and cleavage of the BOC group by means of hydrogen chloride in methanol, 3RS,4RS)-4-[4-(3-benzyloxy-propoxy)-phenyl]-3-(4-trifluoromethoxy-benzyloxy)-piperidine hydrochloride as a colourless oil; MS: 516 (M+H)$^+$;

38) by alkylation with 3-bromomethyl-benzonitrile and cleavage of the BOC group by means of hydrogen chloride in methanol, 3-{(3RS,4RS)-4-[4-(3-benzyloxy-propoxy)-phenyl]-piperidin-3-yloxymethyl}-benzonitrile hydrochloride as a colourless oil; MS: 457 (M+H)$^+$;

39) by alkylation with 4-bromo-2-fluoro-benzyl bromide and cleavage of the BOC group by means of hydrogen chloride in methanol, (3RS,4RS)-4-[4-(3-benzyloxy-propoxy)-phenyl]-3-(4-bromo-2-fluoro-benzyloxy)-piperidine hydrochloride as a colourless oil; MS: 529 (M+H)$^+$;

40) by alkylation with 3-chloro-benzyl bromide and cleavage of the BOC group by means of hydrogen chloride in methanol, (3RS,4RS)-4-[4-(3-benzyloxy-propoxy)-phenyl]-3-(3-chloro-benzyloxy)-piperidine hydrochloride as a colourless oil; MS: 466 (M+H)$^+$;

41) by alkylation with 3-chloro-2-fluoro-benzyl bromide and cleavage of the BOC group by means of hydrogen chloride in methanol, (3RS,4RS)-4-[4-(3-benzyloxy-propoxy)-phenyl]-3-(3-chloro-2-fluoro-benzyloxy)-piperidine hydrochloride as a colourless oil; MS: 484 (M+H)$^+$;

42) by alkylation with 3,5-dibromo-benzyl bromide and cleavage of the BOC group by means of hydrogen chloride in methanol, (3RS,4RS)-4-[4-(3-benzyloxy-propoxy)-phenyl]-3-(3,5-dibromo-benzyloxy)-piperidine hydrochloride as a colourless oil; MS: 590 (M+H)$^+$;

43) by alkylation with 2,5-dimethoxy-benzyl chloride and cleavage of the BOC group by means of hydrogen chloride in methanol, (3RS,4RS)-4-[4-(3-benzyloxy-propoxy)-phenyl]-3-(2,5-dimethoxy-benzyloxy)-piperidine hydrochloride as a colourless oil; MS: 492 (M+H)$^+$;

44) by alkylation with 2-methy-benzyl chloride and cleavage of the BOC group by means of hydrogen chloride in methanol, (3RS,4RS)-4-[4-(3-benzyloxy-propoxy)-phenyl]-3-(2-methyl-benzyloxy)-piperidine as a colourless oil; MS: 446 (M+H)$^+$;

45) by alkylation with 3-bromomethyl-pyridine and cleavage of the BOC group by means of zinc bromide in methylene chloride, 3-[(3RS,4RS)-4-[4-(3-benzyloxy-propoxy)-phenyl]-piperidin-3-yloxymethyl]-pyridine as a colourless oil; R$_f$: 0.08 (SiO$_2$, methylene chloride:methanol=98:2, extracted against 5 vol. % saturated ammonia);

46) by alkylation with 4-methylthio-benzyl chloride [J.Org.Chem. (1988), 53(3), 561–569] and cleavage of the BOC group by means of zinc bromide in methylene chloride, (3RS,4RS)-4-[4-(3-benzyloxy-propoxy)-phenyl]-3-(4-methylsulphanyl-benzyloxy)-piperidine hydrochloride as a colourless oil; MS: 478 (M+H)$^+$;

47) by alkylation with 5-chloromethyl-benzo[1.3]dioxol and cleavage of the BOC group by means of zinc bromide in methylene chloride, (3RS,4RS)-3-(benzo[1,3]dioxol-5-ylmethoxy)-4-[4-(3-benzyloxy-propoxy)-phenyl]-piperidine hydrobromide as a colourless oil; MS: 476 (M+H)$^+$;

48) by alkylation with 4-methoxy-benzyl chloride and cleavage of the BOC group by means of zinc bromide in methylene chloride, (3RS,4RS)-4-[4-(3-benzyloxy-propoxy)-phenyl]-3-(4-methoxy-benzyloxy)-piperidine as a colourless oil; MS: 462 (M+H)$^+$;

49) by alkylation with 3,4,5-trimethoxy-benzyl chloride and cleavage of the BOC group by means of zinc bromide in methylene chloride, (3RS,4RS)-4-[4-(3-benzyloxy-propoxy)-phenyl]-3-(3,4,5-trimethoxy-benzyloxy)-piperidine as a colourless oil; MS: 522 (M+H)$^+$;

50) by alkylation with 4-methoxy-3-methyl-benzyl chloride and cleavage of the BOC group by means of zinc bromide in methylene chloride, (3RS,4RS)-4-[4-(3-benzyloxy-propoxy)-phenyl]-3-(4-methoxy-3-methyl-benzyloxy)-piperidine as a colourless oil; MS: 476 (M+H)$^+$;

51) by alkylation with 3,5-dimethoxy-benzyl chloride and cleavage of the BOC group by means of zinc bromide in methylene chloride, (3RS, 4RS)-4-[4-(3-benzyloxy-propoxy)-phenyl]-3-(3,5-dimethoxy-benzyloxy)-piperidine as a colourless oil; MS: 492 (M+H)$^+$;

52) by alkylation with 2,3,5,6-tetramethyl-benzyl chloride and cleavage of the BOC group by means of hydrogen chloride in methanol, (3RS,4RS)-4-[4-(3-benzyloxy-propoxy)-phenyl]-3-(2,3,5,6-tetramethyl-benzyloxy)-piperidine hydrochloride as a colourless oil; MS: 488 (M+H)$^+$;

53) by alkylation with 3-methyl-benzyl bromide and cleavage of the BOC group by means of hydrogen chloride in methanol, (3RS,4RS)-4-[4-(3-benzyloxy-propoxy)-phenyl]-3-(3-methyl-benzyloxy)-piperidine hydrochloride as a colourless oil; MS: 446 (M+H)$^+$;

54) by alkylation with 4-chloro-benzyl chloride and cleavage of the BOC group by means of hydrogen chloride in methanol, (3RS,4RS)-4-[4-(3-benzyloxy-propoxy)-phenyl]-3-(4-chloro-benzyloxy)-piperidine hydrochloride as a colourless oil; MS: 466 (M+H)$^+$.

EXAMPLE 105

The following compounds were obtained analogously to Example 12(b) by synthesizing the corresponding BOC derivatives by reacting the corresponding benzyl bromides with 3 equivalents of the respective alcoholates and using these derivatives without further purification and characterization in the cleavage of the BOC group by means of hydrogen chloride in methanol analogously to Example 22(l) or by means of zinc bromide in methylene chloride analogously to Example 10(b):

1) By reaction of tert-butyl (3RS,4RS)-4-[4-(3-benzyloxy-propoxy)-phenyl]-3-(3-bromomethyl-benzyloxy)-piperidine-1-carboxylate with ethanol and cleavage of the BOC group by means of zinc bromide in methylene chloride, (3RS,4RS)-4-[4-(3-benzyloxy-propoxy)-phenyl]-3-(3-ethoxymethyl-benzyloxy)-piperidine, MS: 490 (M+H)$^+$, and [3-[(3RS,4RS)-4-[4-(3-benzyloxy-propoxy)-phenyl]-piperidin-3-yloxymethyl]-phenyl]-methanol, MS: 479 (M+NH$_4$)$^+$, each as a colourless oil;

2) by reaction of tert-butyl (3RS,4RS)-4-[4-(3-benzyloxy-propoxy)-phenyl]-3-(3-bromomethyl-benzyloxy)-piperidine-1-carboxylate with cyclobutyl-methanol and cleavage of the BOC group by means of hydrogen chloride in methanol, (3RS,4RS)-4-[4-(3-benzyloxy-propoxy)-phenyl]-3-(3-cyclobutylmethoxymethyl-benzyloxy)-piperidine as a colourless oil; MS: 530 (M+H)$^+$;

3) by reaction of tert-butyl (3RS,4RS)-4-[4-(3-benzyloxy-propoxy)-phenyl]-3-(3-bromomethyl-benzyloxy)-piperidine-1-carboxylate with 3-phenyl-propan-1-ol and cleavage of the BOC group by means of hydrogen chloride in methanol, (3RS,4RS)-4-[4-(3-benzyloxy-propoxy)-phenyl]-3-[3-(3-phenyl-propoxymethyl)-benzyloxy]-piperidine as a colourless oil; MS: 580 (M+H)$^+$;

4) by reaction of tert-butyl (3RS,4RS)-4-[4-(3-benzyloxy-propoxy)-phenyl]-3-(3-bromomethyl-benzyloxy)-piperidine-1-carboxylate with 3,3-dimethyl-butan-1-ol and cleavage of the BOC group by means of hydrogen chloride in methanol, (3RS,4RS)-4-[4-(3-benzyloxy-propoxy)-phenyl]-3-[3-(3,3-dimethyl-butoxymethyl)-benzyloxy]-piperidine as a colourless oil; MS: 546 (M+H)$^+$;

5) by reaction of tert-butyl (3RS,4RS)-4-[4-(3-benzyloxy-propoxy)-phenyl]-3-(3-bromomethyl-benzyloxy)-piperidine-1-carboxylate with yyridin-3-yl-methanol and cleavage of the BOC group by means of hydrogen chloride in methanol, 3-[3-[(3RS,4RS)-4-[4-(3-benzyloxy-propoxy)-phenyl]-piperidin-3-yloxymethyl]-benzyloxymethyl]-pyridine as a colourless oil; MS: 553 (M+H)$^+$;

6) by reaction of tert-butyl (3RS,4RS)-4-[4-(3-benzyloxy-propoxy)-phenyl]-3-(3-bromomethyl-benzyloxy)- piperidine-1-carboxylate with pyridin-4-yl-methanol and cleavage of the BOC group by means of hydrogen chloride in methanol, 4-[3-[(3RS,4RS)-4-[4-(3-benzyloxy-propoxy)-phenyl]-piperidin-3-yloxymethyl]-benzyloxymethyl]-pyridine as a colourless oil; MS: 553 (M+H)$^+$;

7) by reaction of tert-butyl (3RS,4RS)-4-[4-(3-benzyloxy-propoxy)-phenyl]-3-(3-bromomethyl-benzyloxy)-piperidine-1-carboxylate with 2-pyridin-2-yl-ethanol and cleavage of the BOC group by means of hydrogen chloride in methanol, 2-[2-[3-[(3RS,4RS)-4-[4-(3-benzyloxy-propoxy)-phenyl]-piperidin-3-yloxymethyl]-benzyloxy]-ethyl]-pyridine as a colourless oil; MS: 567 (M+H)$^+$;

8) by reaction of tert-butyl (3RS,4RS)-4-[4-(3-benzyloxy-propoxy)-phenyl]-3-(4-bromomethyl-benzyloxy)-piperidine-1-carboxylate with cyclobutyl-methanol and cleavage of the BOC group by means of hydrogen chloride in methanol, (3RS,4RS)-4-[4-(3-benzyloxy-propoxy)-phenyl]-3-(4-cyclobutylmethoxymethyl-benzyloxy)-piperidine as a colourless oil; MS: 530 (M+H)$^+$;

9) by reaction of tert-butyl (3RS,4RS)-4-[4-(3-benzyloxy-propoxy)-phenyl]-3-(4-bromomethyl-benzyloxy)-piperidine-1-carboxylate with 3-phenyl-propan-1-ol and cleavage of the BOC group by means of hydrogen chloride in methanol, (3RS,4RS)-4-[4-(3-benzyloxy-propoxy)-phenyl]-3-[4-(3-phenyl-propoxymethyl)-benzyloxy]-piperidine as a colourless oil; MS: 580 (M+H)$^+$;

10) by reaction of tert-butyl (3RS,4RS)-4-[4-(3-benzyloxy-propoxy)-phenyl]-3-(4-bromomethyl-benzyloxy)-piperidine-1-carboxylate with 3,3-dimethyl-butan-1-ol and cleavage of the BOC group by means of hydrogen chloride in methanol, (3RS,4RS)-4-[4-(3-benzyloxy-propoxy)-phenyl]-3-[4-(3,3-dimethyl-butoxymethyl)-benzyloxy]-piperidine as a colourless oil; MS: 546 (M+H)$^+$;

11) by reaction of tert-butyl (3RS,4RS)-4-[4-(3-benzyloxy-propoxy)-phenyl]-3-(4-bromomethyl-benzyloxy)-piperidine-1-carboxylate with pyridin-3-yl-methanol and cleavage of the BOC group by means of hydrogen chloride in methanol, 3-[4-[(3RS,4RS)-4-[4-(3-benzyloxy-propoxy)-phenyl]-piperidin-3-yloxymethyl]-benzyloxymethyl]-pyridine as a colourless oil; MS: 553 (M+H)$^+$;

12) by reaction of tert-butyl (3RS,4RS)-4-[4-(3-benzyloxy-propoxy)-phenyl]-3-(4-bromomethyl-benzyloxy)-piperidine-1-carboxylate with pyridin-4-yl-methanol and cleavage of the BOC group by means of hydrogen chloride in methanol, 4-[4-[(3RS,4RS)-4-[4-(3-benzyloxy-propoxy)-phenyl]-piperidin-3-yloxymethyl]-benzyloxymethyl]-pyridine as a colourless oil; MS: 553 (M+H)$^+$;

13) by reaction of tert-butyl (3RS,4RS)-4-[4-(3-benzyloxy-propoxy)-phenyl]-3-(4-bromomethyl-benzyloxy)-piperidine-1-carboxylate with 2-pyridin-2-yl-ethanol and cleavage of the BOC group by means of hydrogen chloride in methanol, 2-[2-[4-[(3RS,4RS)-4-[4-(3-benzyloxy-propoxy)-phenyl]-piperidin-3-yloxymethyl]-benzyloxy]-ethyl]-pyridine as a colourless oil; MS: 567 (M+H)$^+$;

14) by reaction of tert-butyl (3RS,4RS)-4-[4-(3-benzyloxy-propoxy)-phenyl]-3-(2-bromomethyl-benzyloxy)-piperidine-1-carboxylate with 3-phenyl-propan-1-ol and cleavage of the BOC group by means of hydrogen chloride in methanol, (3RS,4RS)-4-[4-(3-benzyloxy-propoxy)-phenyl]-3-[2-(3-phenyl-propoxymethyl)-benzyloxy]-piperidine as a colourless oil; MS: 580 (M+H)$^+$;

15) by reaction of tert-butyl (3RS,4RS)-4-[4-(3-benzyloxy-propoxy)-phenyl]-3-(2-bromomethyl-benzyloxy)-piperidine-1-carboxylate with 3,3-dimethyl-butan-1-ol and cleavage of the BOC group by means of hydrogen chloride in methanol, (3RS,4RS)-4-[4-(3-benzyloxy-propoxy)-phenyl]-3-[2-(3,3-dimethyl-butoxymethyl)-benzyloxy]-piperidine as a colourless oil; MS: 546 (M+H)$^+$;

16) by reaction of tert-butyl (3RS,4RS)-4-[4-(3-benzyloxy-propoxy)-phenyl]-3-(2-bromomethyl-benzyloxy)-piperidine-1-carboxylate with pyridin-3-yl-methanol and cleavage of the BOC group by means of hydrogen chloride in methanol, 3-[2-[(3RS,4RS)-4-[4-(3-benzyloxy-propoxy)-phenyl]-piperidin-3-yloxymethyl]-benzyloxymethyl]-pyridine as a colourless oil; MS: 553 (M+H)$^+$;

17) by reaction of tert-butyl (3RS,4RS)-4-[4-(3-benzyloxy-propoxy)-phenyl]-3-(2-bromomethyl-benzyloxy)-piperidine-1-carboxylate with pyridin-4-yl-methanol and cleavage of the BOC group by means of hydrogen chloride in methanol, 4-[2-[(3RS,4RS)-4-[4-(3-benzyloxy-propoxy)-phenyl]-piperidin-3-yloxymethyl]-benzyloxymethyl]-pyridine as a colourless oil; MS: 553 (M+H)$^+$;

18) by reaction of tert-butyl (3RS,4RS)-4-[4-(3-benzyloxy-propoxy)-phenyl]-3-(2-bromomethyl-benzyloxy)-piperidine-1-carboxylate with 2-pyridin-2-yl-ethanol and cleavage of the BOC group by means of hydrogen chloride in methanol, 2-[2-[2-[(3RS,4RS)-4-[4-(3-benzyloxy-propoxy)-phenyl]-piperidin-3-yloxymethyl]-benzyloxy]-ethyl]-pyridine as a colourless oil; MS: 567 (M+H)$^+$.

19) by reaction of tert-butyl (3RS,4RS)-4-[4-(3-benzyloxy-propoxy)-phenyl]-3-(2-bromomethyl-benzyloxy)-piperidine-1-carboxylate with cyclobutyl-methanol and cleavage of the BOC group by means of hydrogen chloride in methanol, (3RS,4RS)-4-[4-(3-benzyloxy-propoxy)-phenyl]-3-(2-cyclobutylmethoxymethyl-benzyloxy)-piperidine as a colourless oil; MS: 530 (M+H)$^+$.

The benzyl bromides used as starting materials were prepared by alkylating tert-butyl (3RS,4RS)-4-[4-(3-benzyloxy-propoxy)-phenyl]-3-hydroxy-piperidine-1-carboxylate [Example 86(n)] with the corresponding bis-bromomethyl-benzene in an analogous manner to that described in Example 1(g), but using 4 equivalents of dibromide and by cautious hydrolysis of the reaction solution with ice-cold sodium bicarbonate solution:

(a) with 1,3-bis-bromomethyl-benzene, tert-butyl (3RS,4RS)-4-[4-(3-benzyloxy-propoxy)-phenyl]-3-(3-bromomethyl-benzyloxy)-piperidine-1-carboxylate as a colourless resin; MS: 624, 626 (M+H)$^+$;

(b) with 1,4-bis-bromomethyl-benzene, tert-butyl (3RS,4RS)-4-[4-(3-benzyloxy-propoxy)-phenyl]-3-(4-bromomethyl-benzyloxy)-piperidine-1-carboxylate as a yellowish oil; MS: 643, 645 (M+NH$_4$)$^+$;

(c) with 1,2-bis-bromomethyl-benzene, tert-butyl (3RS,4RS)-4-[4-(3-benzyloxy-propoxy)-phenyl]-3-(2-bromomethyl-benzyloxy)-piperidine-1-carboxylate as a colourless oil; MS: 624, 626 (M+H)$^+$.

EXAMPLE 106

The following compounds were obtained analogously to Example 1(g) by synthesizing the corresponding BOC derivatives by reacting the corresponding benzyl bromides with 3 equivalents of the respective alkoholates and using these derivatives, unless indicated otherwise, without further purification and characterization in the cleavage of the BOC group by means of hydrogen chloride in methanol analogously to Example 22(l):
1) by reaction of tert-butyl (3RS,4RS)-4-[4-(3-benzyloxy-propoxy)-phenyl]-3-(6-bromomethyl-naphthalen-2-ylmethoxy)-piperidine-1-carboxylate with (RS)-(2,2-dimethyl-[1,3]dioxolan-4-yl)-methanol and subsequent simultaneous cleavage of the BOC and dioxolan groups, a mixture of (3RS,4RS)- and (3SR,4SR)-4-[4-(3-benzyloxy-propoxy)-phenyl]-3-[6-[(RS)-2,3-dihydroxy-propoxymethyl]-naphthalen-2-ylmethoxy]-piperidine as a colourless oil; MS: 586 (M+H)$^+$.
2) by reaction of tert-butyl (3RS,4RS)-4-[4-(3-benzyloxy-propoxy)-phenyl]-3-(7-bromomethyl-naphthalen-2-ylmethoxy)-piperidine-1-carboxylate with (RS)-(2,2-dimethyl-[1,3]dioxolan-4-yl)-methanol and subsequent simultaneous cleavage of the BOC and dioxolan groups, a mixture of (3RS,4RS)- and (3SR,4SR)-4-[4-(3-benzyloxy-propoxy)-phenyl]-3-[7-[(RS)-2,3-dihydroxy-propoxymethyl]-naphthalen-2-ylmethoxy]-piperidine as a colourless oil; MS: 586 (M+H)$^+$.
3) by reaction of tert-butyl (3RS,4RS)-4-[4-(3-benzyloxy-propoxy)-phenyl]-3-(7-bromomethyl-naphthalen-2-ylmethoxy)-piperidine-1-carboxylate with rac-2-[(tetrahydro-2H-pyran-2-yl)oxy]-1-ethanol, a mixture of (3RS,4RS)- and (3SR,4SR)-4-[4-(3-benzyloxy-propoxy)-phenyl]-3-{7-[2-[(RS)-tetrahydro-pyran-2-yloxy]-ethoxymethyl]-naphthalen-2-ylmethoxy}-piperidine-1-carboxylate [colourless oil, MS: 740 (M+H)$^+$] and tert-butyl (3RS,4RS)-4-[4-(3-benzyloxy-propoxy)-phenyl]-3-(7-dimethylaminomethyl-naphthalen-2-ylmethoxy)-piperidine-1-carboxylate [byproduct, colourless oil, MS: 639 (M)$^+$]. Simultaneous cleavage of the BOC and tetrahydropyranyl groups from the main product gave 2-(7-{(3RS,4RS)-4-[4-(3-benzyloxy-propoxy)-phenyl]-piperidin-3-yloxymethyl}-naphthalen-2-ylmethoxy)-ethanol as a colourless oil; MS: 556 (M+H)$^+$. Cleavage of the BOC group from the byproduct gave (7-{(3RS,4RS)-4-[4-(3-benzyloxy-propoxy)-phenyl]-piperidin-3-yloxymethyl}-naphthalen-2-ylmethyl)-dimethyl-amine as a colourless oil; MS: 539 (M+H)$^+$.
4) by reaction of a mixture of tert-butyl (3RS,4RS)-4-[4-(3-benzyloxy-propoxy)-phenyl]-3-(8-bromomethyl-naphthalen-2-ylmethoxy)-piperidine-1-carboxylate and tert-butyl (3RS,4RS)-4-[4-(3-benzyloxy-propoxy)-phenyl]-3-(7-bromomethyl-naphthalen-1-ylmethoxy)-piperidine-1-carboxylate with (RS)-(2,2-dimethyl-[1,3]dioxolan-4-yl)-methanol and subsequent simultaneous cleavage of the BOC and dioxolan groups, a mixture of (3RS,4RS)- and (3SR,4SR)-4-[4-(3-benzyloxy-propoxy)-phenyl]-3-[8-[(RS)- 2,3-dihydroxy-propoxymethyl]-naphthalen-2-ylmethoxy]-piperidine and (3RS,4RS)- and (3SR,4SR)-4-[4-(3-benzyloxy-propoxy)-phenyl]-3-[7-[(RS)-2,3-dihydroxy-propoxymethyl]-naphthalen-1-ylmethoxy]-piperidine as a colourless oil; MS: 586 (M+H)$^+$.

The naphthylmethyl bromides used as starting materials were prepared by alkylating tert-butyl (3RS,4RS)-4-[4-(3-benzyloxy-propoxy)-phenyl]-3-hydroxy-piperidine-1-carboxylate [Example 86(n)] with the corresponding bis-bromomethyl-naphthalene in an analogous manner to that described in Example 1(g), but using 4 equivalents of dibromide and by cautious hydrolysis of the reaction solution with ice-cold sodium bicarbonate solution:

(a) with 2,6-bis-bromomethyl-naphthalene [J.Chem.Soc. (1961), 3741–3748], tert-butyl (3RS,4RS)-4-[4-(3-benzyloxy-propoxy)-phenyl]-3-(6-bromomethyl-naphthalen-2-ylmethoxy)-piperidine-1-carboxylate as a colourless oil; MS: 675 (M+H)$^+$;

(b) with 2,7-bis-bromomethyl-naphthalene [J.Am.Chem.Soc. (1979), 101 (15), 4259–4267], tert-butyl (3RS,4RS)-4-[4-(3-benzyloxy-propoxy)-phenyl]-3-(7-bromomethyl-naphthalen-2-ylmethoxy)-piperidine-1-carboxylate as a colourless oil; MS: 675 (M+H)$^+$;

(c) with 1,7-bis-bromomethyl-naphthalene [Chem. Ber. 91, 1981 (1958)], a mixture of tert-butyl (3RS,4RS)-4-[4-(3-benzyloxy-propoxy)-phenyl]-3-(8-bromo-methyl-naphthalen-2-ylmethoxy)-piperidine-1-carboxylate and tert-butyl (3RS,4RS)-4-[4-(3-benzyloxy-propoxy)-phenyl]-3-(7-bromomethyl-naphthalen-1-ylmethoxy)-piperidine-1-carboxylate as a colourless oil; MS: 675 (M+H)$^+$.

EXAMPLE 107

The following compounds were obtained analogously to Example 1(g) by synthesizing the corresponding BOC derivatives by alkylating of tert-butyl (3RS,4RS)-4-[4-(3-hydroxy-propoxy)-phenyl]-3-(naphthalen-2-ylmethoxy)-piperidine-1-carboxylate Example 57(c)] and using these derivatives without further purification and characterization in the cleavage of the BOC group by means of hydrogen chloride in methanol analogously to Example 22(l):

1 By alkylation with 4-fluoro-benzyl bromide and cleavage of the BOC group, (3RS,4RS)-4-{4-[3-(4-fluoro-benzyloxy)-propoxy]-phenyl}-3-(naphthalen-2-ylmethoxy)-piperidine hydrochloride as a colourless oil; MS: 500 (M+H)$^+$;
2) by alkylation with 2-chloro-benzyl bromide and cleavage of the BOC group, (3RS,4RS)-4-{4-[3-(2-chloro-benzyloxy)-propoxy]-phenyl}-3-(naphthalen-2-ylmethoxy)-piperidine as a colourless oil; MS: 516 (M)$^+$;
3) by alkylation with 2,3,4,5,6-pentafluoro-benzyl bromide and cleavage of the BOC group, (3RS,4RS)-3-(naphthalen-2-ylmethoxy)-4-{4-[3-(2,3,4,5,6-pentafluoro-benzyloxy)-propoxy]-phenyl}-piperidine as a colourless oil; MS: 572 (M+H)$^+$;
4) by alkylation with 4-bromo-benzyl bromide and cleavage of the BOC group, (3RS,4RS)-4-{4-[3-(4-bromo-benzyloxy)-propoxy]-phenyl}-3-(naphthalen-2-ylmethoxy)-piperidine hydrochloride as a colourless oil; MS: 560 (M)$^+$;
5) by alkylation with 3-bromo-benzyl bromide and cleavage of the BOC group, (3RS,4RS)-4-{4-[3-(3-bromo-benzyloxy)-propoxy]-phenyl}-3-(naphthalen-2-ylmethoxy)-piperidine hydrochloride as a colourless oil; MS: 560 (M)$^+$;
6) by alkylation with 4-iodo-benzyl bromide and cleavage of the BOC group, (3RS,4RS)-4-{4-[3-(4-iodo-benzyloxy)-propoxy]-phenyl}-3-(naphthalen-2-ylmethoxy)-piperidine hydrochloride as a colourless oil; MS: 608 (M+H)$^+$;
7) by alkylation with 2-trifluoromethyl-benzyl bromide and cleavage of the BOC group, (3RS,4RS)-3-(naphthalen-2-ylmethoxy)-4-{4-[3-(2-trifluoromethyl-benzyloxy)-propoxy]-phenyl}-piperidine hydrochloride as a colourless oil; MS: 550 (M+H)$^+$;
8) by alkylation with 3-trifluoromethyl-benzyl bromide and cleavage of the BOC group, (3RS,4RS)-3-(naphthalen-2-ylmethoxy)-4-{4-[3-(3-trifluoromethyl-benzyloxy)-propoxy]-phenyl}-piperidine hydrochloride as a colourless oil; MS: 550 (M+H)$^+$;
9) by alkylation with 4-trifluoromethyl-benzyl bromide and cleavage of the BOC group, (3RS,4RS)-3-(naphthalen-2-ylmethoxy)-4-{4-[3-(4-trifluoromethyl-benzyloxy)-propoxy]-phenyl}-piperidine hydrochloride as a colourless oil; MS: 550 (M+H)$^+$;
10) by alkylation with 2-fluoro-benzyl bromide-benzyl bromide and cleavage of the BOC group, (3RS,4RS)-4-{4-

[3-(2-fluoro-benzyloxy)-propoxy]-phenyl}-3-(naphthalen-2-ylmethoxy)-piperidine as a colourless oil; MS: 500 (M+H)+;

11) by alkylation with 2-methyl-benzyl chloride and cleavage of the BOC group, (3RS,4RS)-4-{4-[3-(2-methyl-benzyloxy)-propoxy]-phenyl}-3-(naphthalen-2-ylmethoxy)-piperidine hydrochloride as a colourless oil; MS: 496 (M+H)+;

12) by alkylation with 3,5-dimethyl-benzyl bromide and cleavage of the BOC group, (3RS,4RS)-4-{4-[3-(3,5-dimethyl-benzyloxy)-propoxy]-phenyl}-3-(naphthalen-2-ylmethoxy)-piperidine hydrochloride as a colourless oil; MS: 510 (M+H)+;

13) by alkylation with 3-methoxy-benzyl chloride and cleavage of the BOC group, (3RS,4RS)-4-{4-[3-(3-methoxy-benzyloxy)-propoxy]-phenyl}-3-(naphthalen-2-ylmethoxy)-piperidine hydrochloride as a colourless oil; MS: 512 (M+H)+;

14) by alkylation with 4-isopropyl-benzyl chloride and cleavage of the BOC group, (3RS,4RS)-4-{4-[3-(4-isopropyl-benzyloxy)-propoxy]-phenyl}-3-(naphthalen-2-ylmethoxy)-piperidine hydrochloride as a colourless oil; MS: 524 (M+H)+;

15) by alkylation with 2,4-dimethyl-benzyl chloride and cleavage of the BOC group, (3RS,4RS)-4-{4-[3-(2,4-dimethyl-benzyloxy)-propoxy]-phenyl}-3-(naphthalen-2-ylmethoxy)-piperidine hydrochloride as a colourless oil; MS: 510 (M+H)+;

16) by alkylation with 4-methyl-benzyl bromide and cleavage of the BOC group, (3RS,4RS)-4-{4-[3-(4-methyl-benzyloxy)-propoxy]-phenyl}-3-(naphthalen-2-ylmethoxy)-piperidine hydrochloride as a colourless oil; MS: 496 (M+H)+;

17) by alkylation with 4-tert-butyl-benzyl bromide and cleavage of the BOC group, (3RS,4RS)-4-{4-[3-(4-tert-butyl-benzyloxy)-propoxy]-phenyl}-3-(naphthalen-2-ylmethoxy)-piperidine hydrochloride as a colourless oil; MS: 538 (M+H)+;

18) by alkylation with 2,3,5,6-tetramethyl-benzyl chloride and cleavage of the BOC group, (3RS,4RS)-3-(naphthalen-2-ylmethoxy)-4-{4-[3-(2,3,5,6-tetramethyl-benzyloxy)-propoxy]-phenyl}-piperidine hydrochloride as a colourless oil; MS: 538 (M+H)+;

19) by alkylation with 3,5-dichloro-benzyl chloride and cleavage of the BOC group, (3RS,4RS)-4-{4-[3-(3,5-dichloro-benzyloxy)-propoxy]-phenyl}-3-(naphthalen-2-ylmethoxy)-piperidine hydrochloride as a colourless oil; MS: 550 (M+H)+;

20) by alkylation with 2,4-dichloro-benzyl chloride and cleavage of the BOC group, (3RS,4RS)-4-{4-[3-(2,4-dichloro-benzyloxy)-propoxy]-phenyl}-3-(naphthalen-2-ylmethoxy)-piperidine hydrochloride as a colourless oil; MS: 550 (M+H)+;

21) by alkylation with 2,6-dichloro-benzyl chloride and cleavage of the BOC group, (3RS,4RS)-4-{4-[3-(2,6-dichloro-benzyloxy)-propoxy]-phenyl}-3-(naphthalen-2-ylmethoxy)-piperidine hydrochloride as a colourless oil; MS: 550 (M+H)+;

22) by alkylation with 2,5-dichloro-benzyl chloride and cleavage of the BOC group, (3RS,4RS)-4-{4-[3-(2,5-dichloro-benzyloxy)-propoxy]-phenyl}-3-(naphthalen-2-ylmethoxy)-piperidine hydrochloride as a colourless oil; MS: 550 (M+H)+;

23) by alkylation with 2-chloro-6-fluoro-benzyl chloride and cleavage of the BOC group, (3RS,4RS)-4-{4-[3-(2-chloro-6-fluoro-benzyloxy)-propoxy]-phenyl}-3-(naphthalen-2-ylmethoxy)-piperidine hydrochloride as a colourless oil; MS: 534 (M+H)+;

24) by alkylation with 2-iodo-benzyl chloride and cleavage of the BOC group, (3RS,4RS)-4-{4-[3-(2-iodoo-benzyloxy)-propoxy]-phenyl}-3-(naphthalen-2-ylmethoxy)-piperidine hydrochloride as a colourless oil; MS: 608 (M+H)+;

25) by alkylation with 2-bromo-benzyl chloride and cleavage of the BOC group, (3RS,4RS)-4-{4-[3-(2-bromo-benzyloxy)-propoxy]-phenyl}-3-(naphthalen-2-ylmethoxy)-piperidine hydrochloride as a colourless oil; MS: 560 (M+H)+;

26) by alkylation with 4-chloro-benzyl chloride and cleavage of the BOC group, (3RS,4RS)-4-{4-[3-(4-chloro-benzyloxy)-propoxy]-phenyl}-3-(naphthalen-2-ylmethoxy)-piperidine hydrochloride as a colourless oil; MS: 517 (M+H)+;

27) by alkylation with 4-methylthio-benzyl chloride [J.Org.Chem. (1988), 53(3), 561–569] and cleavage of the BOC group, (3RS,4RS)-4-{4-[3-(4-methylsulphanyl-benzyloxy)-propoxy]-phenyl}-3-(naphthalen-2-ylmethoxy)-piperidine hydrochloride as a colourless oil; MS: 528 (M+H)+;

28) by alkylation with a mixture of 3- and 4-vinyl-benzyl chloride and cleavage of the BOC group, a mixture of (3RS,4RS)-3-(naphthalen-2-ylmethoxy)-4-{4-[3-(3- and 4-vinyl-benzyloxy)-propoxy]-phenyl}-piperidine hydrochloride as a colourless oil; MS: 508 (M+H)+;

29) by alkylation with 4-methoxy-benzyl chloride and cleavage of the BOC group, (3RS,4RS)-4-{4-[3-(4-methoxy-benzyloxy)-propoxy]-phenyl}-3-(naphthalen-2-ylmethoxy)-piperidine hydrochloride as a colourless oil; MS: 512 (M+H)+;

30) by alkylation with 2,4-dimethoxy-benzyl chloride and cleavage of the BOC group, (3RS,4RS)-4-{4-[3-(2,4-dimethoxy-benzyloxy)-propoxy]-phenyl}-3-(naphthalen-2-ylmethoxy)-piperidine hydrochloride as a colourless oil; MS: 542 (M+H)+;

31) by alkylation with 3,4,5-trimethoxy-benzyl chloride and cleavage of the BOC group, (3RS,4RS)-3-(naphthalen-2-ylmethoxy)-4-{4-[3-(3,4,5-trimethoxy-benzyloxy)-propoxy]-phenyl}-piperidine hydrochloride as a colourless oil; MS: 572 (M+H)+;

32) by alkylation with 5-chloromethyl-benzo[1.3]dioxol and cleavage of the BOC group, (3RS,4RS)-4-{4-[3-(Benzo[1,3]dioxol-5-ylmethoxy)-propoxy]-phenyl}-3-(naphthalen-2-ylmethoxy)-piperidine hydrochloride as a colourless oil; MS: 526 (M+H)+;

33) by alkylation with 3-chloro-4-methoxy-benzyl chloride and cleavage of the BOC group, (3RS,4RS)-4-{4-[3-(3-chloro-4-methoxy-benzyloxy)-propoxy]-phenyl}-3-(naphthalen-2-ylmethoxy)-piperidine hydrochloride as a colourless oil; MS: 546 (M+H)+;

34) by alkylation with 3-methyl-benzyl bromide and cleavage of the BOC group, (3RS,4RS)-4-{4-[3-(3-methyl-benzyloxy)-propoxy]-phenyl}-3-(naphthalen-2-ylmethoxy)-piperidine hydrochloride as a colourless oil; MS: 496 (M+H)+;

35) by alkylation with 3-fluoro-benzyl chloride and cleavage of the BOC group, (3RS,4RS)-4-{4-[3-(3-fluoro-benzyloxy)-propoxy]-phenyl}-3-(naphthalen-2-ylmethoxy)-piperidine hydrochloride as a colourless oil; MS: 500 (M+H)+;

36) by alkylation with 2-methoxy-benzyl chloride and cleavage of the BOC group, (3RS,4RS)-4-{4-[3-(2-methoxy-benzyloxy)-propoxy]-phenyl}-3-(naphthalen-2-ylmethoxy)-piperidine as a colourless oil; MS: 512 (M+H)+;

37) by alkylation with 2,5-dimethyl-benzyl chloride and cleavage of the BOC group, (3RS,4RS)-4-{4-[3-(2,5- dimethyl-benzyloxy)-propoxy]-phenyl}-3-(naphthalen-2-ylmethoxy)-piperidine hydrochloride as a colourless oil; MS: 510 (M+H)⁺;
38) by alkylation with 4-ethyl-benzyl chloride and cleavage of the BOC group, (3RS,4RS)-4-{4-[3-(4-ethyl-benzyloxy)-propoxy]-phenyl}-3-(naphthalen-2-ylmethoxy)-piperidine hydrochloride as a colourless oil; MS: 510 (M+H)⁺;

EXAMPLE 108

The following compounds were obtained analogously to Example 44(e) by synthesizing the corresponding BOC derivatives by alkylating tert-butyl (3RS,4RS)-4-{4-[3-(2-hydroxy-benzyloxy)-propoxy]-phenyl}-3-(naphthalen-2-ylmethoxy)-piperidine-1-carboxylate and using these derivatives without further purification and characterization in the cleavage of the BOC group by means of zinc bromide in methylene chloride analogously to Example 10(b):
1) by alkylation with 1-bromo-propane and cleavage of the BOC group, (3RS,4RS)-3-(naphthalen-2-ylmethoxy)-4-{4-[3-(2-propoxy-benzyloxy)-propoxy]-phenyl}-piperidine hydrobromide as a colourless oil; MS: 540 (M+H)⁺;
2) by alkylation with 1-bromo-butane and cleavage of the BOC group, (3RS,4RS)-4-{4-[3-(2-butoxy-benzyloxy)-propoxy]-phenyl}-3-(naphthalen-2-ylmethoxy)-piperidine hydrobromide as a colourless oil; MS: 554 (M+H)⁺;
3) by alkylation with bromomethyl-cyclopropane and cleavage of the BOC group, (3RS,4RS)4-{4-[3-(2-cyclopropylmethoxy-benzyloxy)-propoxy]-phenyl}-3-(naphthalen-2-ylmethoxy)-piperidine hydrobromide as a colourless oil; MS: 552 (M+H)⁺;
4) by alkylation with ethyl iodoide and cleavage of the BOC group, (3RS,4RS)-4-{4-[3-(2-ethoxy-benzyloxy)-propoxy]-phenyl}-3-(naphthalen-2-ylmethoxy)-piperidine hydrobromide as a colourless oil; MS: 526 (M+H)⁺;
5) by alkylation with bromomethyl-cyclobutane and cleavage of the BOC group, (3RS,4RS)-4-{4-[3-(2-cyclobutylmethoxy-benzyloxy)-propoxy]-phenyl}-3-(naphthalen-2-ylmethoxy)-piperidine hydrobromide as a colourless oil; MS: 566 (M+H)⁺;
6) by alkylation with isobutyl bromide and cleavage of the BOC group, (3RS,4RS)-4-{4-[3-(2-isobutoxy-benzyloxy)-propoxy]-phenyl}-3-(naphthalen-2-ylmethoxy)-piperidine hydrobromide as a colourless oil; MS: 554 (M+H)⁺;
7) by alkylation with benzyl bromide and cleavage of the BOC group, (3RS,4RS)-4-{4-[3-(2-benzyloxy-benzyloxy)-propoxy]-phenyl}-3-(naphthalen-2-ylmethoxy)-piperidine hydrobromide as a colourless oil; MS: 588 (M+H)⁺;
8) by alkylation with 4-bromo-1-butene and cleavage of the BOC group, (3RS,4RS)-4-{4-[3-(2-but-3-enyloxy-benzyloxy)-propoxy]-phenyl}-3-(naphthalen-2-ylmethoxy)-piperidine hydrobromide as a colourless oil; MS: 552 (M+H)⁺;
9) by alkylation with allyl bromide and cleavage of the BOC group, (3RS,4RS)-4-{4-[3-(2-allyloxy-benzyloxy)-propoxy]-phenyl}-3-(naphthalen-2-ylmethoxy)-piperidine hydrobromide as a colourless oil; MS: 538 (M+H)⁺;
10) by alkylation with bromo-cyclopropane and cleavage of the BOC group, (3RS,4RS)-4-{4-[3-(2-cyclopropyloxy-benzyloxy)-propoxy]-phenyl}-3-(naphthalen-2-ylmethoxy)-piperidine hydrobromide as a colourless oil; MS: 538 (M+H)⁺.

The tert-butyl (3RS,4RS)-4-{4-[3-(2-hydroxy-benzyloxy)-propoxy]-phenyl}-3-(naphthalen-2-ylmethoxy)-piperidine-1-carboxylate used as the starting material was obtained as follows:
(a) In an analogous manner to that described in Example 1(g), by alkylating tert-butyl (3RS,4RS)-4-[4-(3-hydroxy-propoxy)-phenyl]-3-(naphthalen-2-ylmethoxy)-piperidine-1-carboxylate [Example 57(c)] with 1-chloromethyl-(2-trimethylsilyl-ethoxymethoxy)-benzene [Example 17(c)] there was obtained tert-butyl (3RS,4RS)-3-(naphthalen-2-ylmethoxy)-4-(4-{3-[2-(2-trimethylsilanyl-ethoxymethoxy)-benzyloxy]-propoxy}-phenyl)-piperidine-1-carboxylate as a colourless oil; MS: 746 (M+NH₄)⁺.
(b) A solution of 50 mg (0.069 mmol) of 3-(naphthalen-2-ylmethoxy)-4-(4-{3-[2-(2-trimethylsilanyl-ethoxymethoxy)-benzyloxy]-propoxy}-phenyl)-piperidine- 1-carboxylate in 0.5 ml of methanol was cooled to 0° C. under argon and treated with 69 μl (0.138 mmol) of a 2N solution of hydrogen chloride in methanol. Subsequently, the mixture was left to warm to room temperature and was stirred for a further one hour. For the working-up, the reaction solution was treated with a 95:5 mixture of methylene chloride and methanol (extracted against 5 vol. % saturated ammonia) and evaporated to dryness under reduced pressure. For purification, the residue was chromatographed on silica gel using a 3:1 mixture of hexane and ethyl acetate as the eluent. There were obtained 33.1 mg (81% of theory) of tert-butyl (3RS,4RS)-4-{4-[3-(2-hydroxy-benzyloxy)-propoxy]-phenyl}-3-(naphthalen-2-ylmethoxy)-piperidine-1-carboxylate as a colourless oil; MS: 598 (M+H)⁺.

EXAMPLE 109

The following compounds were obtained by cleavage of the BOC group by means of hydrogen chloride in methanol analogously to Example 22(l) or by means of zinc bromide in methylene chloride analogously to Example 10(b):
1) From tert-butyl (3R,4s,5S)-4-[4-(3-benzyloxy-propoxy)-phenyl]-3,5-bis-(naphthalen-2-ylmethoxy)-piperidine-1-carboxylate by means of hydrogen chloride in methanol, (3R,4s,5S)-4-[4-(3-benzyloxy-propoxy)-phenyl]-3,5-bis-(naphthalen-2-ylmethoxy)-piperidine hydrochloride as a colourless solid; MS: 638 (M+H)⁺;
2) from tert-butyl (3RS,4SR,5SR)-4-[4-(3-benzyloxy-propoxy)-phenyl]-5-hydroxy-3-(naphthalen-2-ylmethoxy)-piperidine-1-carboxylate by means of hydrogen chloride in methanol, (3RS,4SR,5SR)-4-[4-(3-benzyloxy-propoxy)-phenyl]-3-(naphthalen-2-ylmethoxy)-piperidin-5-ol as a colourless oil; MS: 498 (M+H)⁺;
3) from tert-butyl (3R,4s,5S)-4-[4-(3-benzyloxy-propoxy)-phenyl]-3,5-bis-(1,4-dimethoxy-naphthalen-2-ylmethoxy)-piperidine-1-carboxylate by means of zinc bromide in methylene chloride, (3R,4s,5S)-4-[4-(3-benzyloxy-propoxy)-phenyl]-3,5-bis-(1,4-dimethoxy-naphthalen-2-ylmethoxy)-piperidine as a colourless wax; MS: 758 (M+H)⁺;
4) from tert-butyl (3RS,4SR,5SR)-4-[4-(3-benzyloxy-propoxy)-phenyl]-3-(1,4-dimethoxy-naphthalen-2-ylmethoxy)-5-hydroxy-piperidine-1-carboxylate by means of zinc bromide in methylene chloride, (3RS,4SR,5SR)-4-[4-(3-benzyloxy-propoxy)-phenyl]-3-(1,4-dimethoxy-naphthalen-2-ylmethoxy)-piperidin-5-ol as a colourless oil; MS: 558 (M+H)⁺;
5) from tert-butyl (3R,4s,5S)-4-[4-(3-benzyloxy-propoxy)-phenyl]-3,5-bis-(2,4-dichloro-benzyloxy)-piperidine-1-carboxylate by means of hydrogen chloride in methanol, (3R,4s,5S)-4-[4-(3-benzyloxy-propoxy)-phenyl]-3,5-bis-(2,4-dichloro-benzyloxy)-piperidine hydrochloride as a colourless solid; MS: 676 (M+H)+;

6) from tert-butyl (3RS,4SR,5SR)-4-[4-(3-benzyloxy-propoxy)-phenyl]-3-(2,4-dichloro-benzyloxy)-5-hydroxy-piperidine-1-carboxylate by means of hydrogen chloride in methanol, (3RS,4SR,5SR)-4-[4-(3-benzyloxy-propoxy)-phenyl]-3-(2,4-dichloro-benzyloxy)-piperidin-5-ol hydrochloride as a colourless oil; MS: 516 (M+H)+;

7) from tert-butyl (3R,4s,5S)-4-[4-(3-benzyloxy-propoxy)-phenyl]-3,5-bis-(2,5-difluoro-benzyloxy)-piperidine-1-carboxylate by means of hydrogen chloride in methanol, (3R,4s,5S)-4-[4-(3-benzyloxy-propoxy)-phenyl]-3,5-bis-(2,5-difluoro-benzyloxy)-piperidine hydrochloride as a colourless oil; MS: 610 (M+H)+;

8) from tert-butyl (3RS,4SR,5SR)-4-[4-(3-benzyloxy-propoxy)-phenyl]-3-(2,5-difluoro-benzyloxy)-5-hydroxy-piperidine-1-carboxylate by means of hydrogen chloride in methanol, (3RS,4SR,5SR)-4-[4-(3-benzyloxy-propoxy)-phenyl]-3-(2,5-difluoro-benzyloxy)-piperidin-5-ol hydrochloride as a colourless oil; MS: 484 (M+H)+;

9) from tert-butyl (3R,4s,5S)-4-[4-(3-benzyloxy-propoxy)-phenyl]-3,5-bis-(4-carboxy-benzyloxy)-piperidine-1-carboxylate by means of hydrogen chloride in methanol, (3R,4s,5S)-4-[4-(3-benzyloxy-propoxy)-phenyl]-3,5-bis-(4-carboxy-benzyloxy)-piperidine hydrochloride as a colourless oil; $R_f$: 0.63 ($SiO_2$, methylene chloride:methanol=95:5, extracted against 5 vol. % saturated aqueous ammonia solution);

10) from tert-butyl (3RS,4SR,5SR)-4-[4-(3-benzyloxy-propoxy)-phenyl]-3-(4-carboxy-benzyloxy)-5-hydroxy-piperidine-1-carboxylate by means of hydrogen chloride in methanol, 4-{4-(3RS,4SR,5SR)-[4-(3-benzyloxy-propoxy)-phenyl]-5-hydroxy-piperidin-3-yloxymethyl}-benzoic acid hydrochloride a colourless oil; $R_f$: 0.30 ($SiO_2$, methylene chloride:methanol=9:1, extracted against 5 vol. % saturated aqueous ammonia solution);

11) from tert-butyl (3R,4s,5S)-4-[4-(3-benzyloxy-propoxy)-phenyl]-3,5-bis-(2,4-difluoro-benzyloxy)-piperidine-1-carboxylate by means of hydrogen chloride in methanol, (3R,4s,5S)-4-[4-(3-benzyloxy-propoxy)-phenyl]-3,5-bis-(2,4-difluoro-benzyloxy)-piperidine hydrochloride as a colourless oil; MS: 610 (M+H)+;

12) from tert-butyl (3RS,4SR,5SR)-4-[4-(3-benzyloxy-propoxy)-phenyl]-3-(2,4-difluoro-benzyloxy)-5-hydroxy-piperidine-1-carboxylate by means of hydrogen chloride in methanol, (3RS,4SR,5SR)-4-[4-(3-benzyloxy-propoxy)-phenyl]-3-(2,4-difluoro-benzyloxy)-piperidin-5-ol hydrochloride as a colourless oil; $R_f$: 0.28 ($SiO_2$, methylene chloride:methanol=9:1, extracted against 5 vol. % saturated aqueous ammonia solution);

13) from tert-butyl (3R,4s,5S)-4-[4-(3-benzyloxy-propoxy)-phenyl]-3,5-bis-(4-chloro-benzyloxy)-piperidine-1-carboxylate by means of hydrogen chloride in methanol, (3R,4s,5S)-4-[4-(3-benzyloxy-propoxy)-phenyl]-3,5-bis-(4-chloro-benzyloxy)-piperidine hydrochloride as a colourless oil; MS: 606 (M+H)+;

14) from tert-butyl (3RS,4SR,5SR)-4-[4-(3-benzyloxy-propoxy)-phenyl]-3-(4-chloro-benzyloxy)-5-hydroxy-piperidine-1-carboxylate by means of hydrogen chloride in methanol, (3RS,4SR,5SR)-4-[4-(3-benzyloxy-propoxy)-phenyl]-3-(4-chloro-benzyloxy)-piperidin-5-ol hydrochloride as a colourless solid; MS: 482 (M+H)+;

15) from tert-butyl (3R,4s,5S)-4-[4-(3-benzyloxy-propoxy)-phenyl]-3,5-bis-(3,4-dichlorooo-benzyloxy)-piperidine-1-carboxylate by means of hydrogen chloride in methanol, (3R,4s,5S)-4-[4-(3-benzyloxy-propoxy)-phenyl]-3,5-bis-(3,4-dichloro-benzyloxy)-piperidine hydrochloride as a colourless solid; MS: 676 (M+H)+;

16) from tert-butyl (3RS,4SR,5SR)-4-[4-(3-benzyloxy-propoxy)-phenyl]-3-(3,4-dichloro-benzyloxy)-5-hydroxy-piperidine-1-carboxylate by means of hydrogen chloride in methanol, (3RS,4SR,5SR)-[4-(3-benzyloxy-propoxy)-phenyl]-3-(3,4-dichloro-benzyloxy)-piperidin-5-ol hydrochloride as a colourless solid; MS: 516 (M+H)+;

17) from tert-butyl (3R,4s,5S)-4-[4-(3-benzyloxy-propoxy)-phenyl]-3,5-bis-(3,5-dichloro-benzyloxy)-piperidine-1-carboxylate by means of hydrogen chloride in methanol, (3R,4s,5S)-4-[4-(3-benzyloxy-propoxy)-phenyl]-3,5-bis-(3,5-dichloro-benzyloxy)-piperidine hydrochloride as a colourless oil; MS: 676 (M+H)+;

18) from tert-butyl (3RS,4SR,5SR)-4-[4-(3-benzyloxy-propoxy)-phenyl]-3-(3,5-dichloro-benzyloxy)-5-hydroxy-piperidine-1-carboxylate by means of hydrogen chloride in methanol, (3RS,4SR,5SR)-4-[4-(3-benzyloxy-propoxy)-phenyl]-3-(3,5-dichloro-benzyloxy)-piperidin-5-ol hydrochloride as a colourless oil; MS: 516 (M+H)+;

19) from tert-butyl (3R,4s,5S)-4-[4-(3-benzyloxy-propoxy)-phenyl]-3,5-bis-(3-chloro-2-fluoro-benzyloxy)-piperidine-1-carboxylate by means of hydrogen chloride in methanol, (3R,4s,5S)-4-[4-(3-benzyloxy-propoxy)-phenyl]-3,5-bis-(3-chloro-2-fluoro-benzyloxy)-piperidine as a colourless oil; MS: 642 (M+H)+;

20) from tert-butyl (3RS,4SR,5SR)-4-[4-(3-benzyloxy-propoxy)-phenyl]-3-(3-chloro-2-fluoro-benzyloxy)-5-hydroxy-piperidine-1-carboxylate by means of hydrogen chloride in methanol, (3RS,4SR,5SR)-4-[4-(3-benzyloxy-propoxy)-phenyl]-3-(3-chloro-2-fluoro-benzyloxy)-piperidin-5-ol hydrochloride as a colourless oil; MS: 500 (M+H)+;

21) from tert-butyl (3R,4s,5S)-4-[4-(3-benzyloxy-propoxy)-phenyl]-3,5-bis-(quinolin-7-ylmethoxy)-piperidine-1-carboxylate by means of hydrogen chloride in methanol, (3R,4s,5S)-4-[4-(3-benzyloxy-propoxy)-phenyl]-3,5-bis-(quinolin-7-ylmethoxy)-piperidine hydrochloride as a colourless oil; MS: 640 (M+H)+;

22) from tert-butyl (3RS,4SR,5SR)-4-[4-(3-benzyloxy-propoxy)-phenyl]-5-hydroxy-3-(quinolin-7-ylmethoxy)-piperidine-1-carboxylate by means of hydrogen chloride in methanol, (3RS,4SR,5SR)-4-[4-(3-benzyloxy-propoxy)-phenyl]-3-(quinolin-7-ylmethoxy)-piperidin-5-ol hydrochloride as a colourless oil; MS: 499 (M+H)+;

23) from tert-butyl (3R,4s,5S)-4-[4-(3-benzyloxy-propoxy)-phenyl]-3,5-bis-(4-ethyl-benzyloxy)-piperidine-1-carboxylate by means of zinc bromide in methylene chloride, (3R,4s,5S)-4-[4-(3-benzyloxy-propoxy)-phenyl]-3,5-bis-(4-ethyl-benzyloxy)-piperidine as a colourless oil; MS: 594 (M+H)+;

24) from tert-butyl (3RS,4SR,5SR)-4-[4-(3-benzyloxy-propoxy)-phenyl]-3-(4-ethyl-benzyloxy)-5-hydroxy-piperidine-1-carboxylate by means of zinc bromide in methylene chloride, (3RS,4SR,5SR)-4-[4-(3-benzyloxy-propoxy)-phenyl]-3-(4-ethyl-benzyloxy)-piperidin-5-ol as a colourless oil; MS: 476 (M+H)+;

25) from tert-butyl (3R,4s,5S)-4-[4-(3-benzyloxy-propoxy)-phenyl]-3,5-bis-(4-vinyl-benzyloxy)-piperidine-1-carboxylate by means of zinc bromide in methylene chloride, (3R,4s,5S)-4-[4-(3-benzyloxy-propoxy)-phenyl]-3,5-bis-(4-vinyl-benzyloxy)-piperidine as a colourless oil; MS: 590 (M+H)+;

26) from tert-butyl (3RS,4SR,5SR)-4-[4-(3-benzyloxy-propoxy)-phenyl]-5-hydroxy-3-(4-vinyl-benzyloxy)-piperidine-1-carboxylate by means of zinc bromide in methylene chloride, (3RS,4SR,5SR)-4-[4-(3-benzyloxy-propoxy)-phenyl]-3-(4-vinyl-benzyloxy)-piperidin-5-ol as a colourless oil; MS: 474 (M+H)⁺;

27) from tert-butyl (3R,4s,5S)-4-[4-(3-benzyloxy-propoxy)-phenyl]-3,5-bis-(4-methoxy-benzyloxy)-piperidine-1-carboxylate by means of zinc bromide in methylene chloride, (3R,4s,5S)-4-[4-(3-benzyloxy-propoxy)-phenyl]-3,5-bis-(4-methoxy-benzyloxy)-piperidine as a colourless oil; MS: 598 (M+H)⁺;

28) from tert-butyl (3RS,4SR,5SR)-4-[4-(3-benzyloxy-propoxy)-phenyl]-5-hydroxy-3-(4-methoxy-benzyloxy)-piperidine-1-carboxylate by means of zinc bromide in methylene chloride, (3RS,4SR,5SR)-4-[4-(3-benzyloxy-propoxy)-phenyl]-3-(4-methoxy-benzyloxy)-piperidin-5-ol as a colourless oil; MS: 478 (M+H)⁺;

29) from tert-butyl (3R,4s,5S)-4-[4-(3-benzyloxy-propoxy)-phenyl]-3,5-bis-(3,4,5-trimethoxy-benzyloxy)-piperidine-1-carboxylate by means of zinc bromide in methylene chloride, (3R,4s,5S)-4-[4-(3-benzyloxy-propoxy)-phenyl]-3,5-bis-(3,4,5-trimethoxy-benzyloxy)-piperidine as a colourless oil; MS: 718 (M+H)⁺;

30) from tert-butyl (3RS,4SR,5SR)-4-[4-(3-benzyloxy-propoxy)-phenyl]-5-hydroxy-3-(3,4,5-trimethoxy-benzyloxy)-piperidine-1-carboxylate by means of zinc bromide in methylene chloride, (3RS,4SR,5SR)-4-[4-(3-benzyloxy-propoxy)-phenyl]-3-(3,4,5-trimethoxy-benzyloxy)-piperidin-5-ol as a colourless oil; MS: 538 (M+H)⁺;

31) from tert-butyl (3R,4s,5S)-4-[4-(3-benzyloxy-propoxy)-phenyl]-3,5-bis-(3,5-dimethoxy-benzyloxy)-piperidine-1-carboxylate by means of zinc bromide in methylene chloride, (3R,4s,5S)-4-[4-(3-benzyloxy-propoxy)-phenyl]-3,5-bis-(3,5-dimethoxy-benzyloxy)-piperidine as a colourless oil; MS: 658 (M+H)⁺;

32) from tert-butyl (3RS,4SR,5SR)-4-[4-(3-benzyloxy-propoxy)-phenyl]-3-(3,5-dimethoxy-benzyloxy)-5-hydroxy-piperidine-1-carboxylate by means of zinc bromide in methylene chloride, (3RS,4SR,5SR)-4-[4-(3-benzyloxy-propoxy)-phenyl]-3-(3,5-dimethoxy-benzyloxy)-piperidin-5-ol as a colourless oil; MS: 508 (M+H)⁺;

33) from tert-butyl (3R,4s,5S)-4-[4-(3-benzyloxy-propoxy)-phenyl]-3,5-bis-(4-trifluoromethoxy-benzyloxy)-piperidine-1-carboxylate by means of zinc bromide in methylene chloride, (3R,4s,5S)-4-[4-(3-benzyloxy-propoxy)-phenyl]-3,5-bis-(4-trifluoromethoxy-benzyloxy)-piperidine as a colourless oil; MS: 706 (M+H)⁺;

34) from tert-butyl (3RS,4SR,5SR)-4-[4-(3-benzyloxy-propoxy)-phenyl]-5-hydroxy-3-(4-trifluoromethoxy-benzyloxy)-piperidine-1-carboxylate by means of zinc bromide in methylene chloride, (3RS,4SR,5SR)-4-[4-(3-benzyloxy-propoxy)-phenyl]-3-(4-trifluoromethoxy-benzyloxy)-piperidin-5-ol as a colourless oil; MS: 532 (M+H)⁺;

35) from tert-butyl (3R,4s,5S)-4-[4-(3-benzyloxy-propoxy)-phenyl]-3,5-bis-(4-methylsulphanyl-benzyloxy)-piperidine-1-carboxylate by means of zinc bromide in methylene chloride, (3R,4s,5S)-4-[4-(3-benzyloxy-propoxy)-phenyl]-3,5-bis-(4-methylsulphanyl-benzyloxy)-piperidine as a colourless oil; MS: 630 (M+H)⁺;

36) from tert-butyl (3RS,4SR,5SR)-4-[4-(3-benzyloxy-propoxy)-phenyl]-5-hydroxy-3-(4-methylsulphanyl-benzyloxy)-piperidine-1-carboxylate by means of zinc bromide in methylene chloride, (3RS,4SR,5SR)-4-[4-(3-benzyloxy-propoxy)-phenyl]-3-(4-methylsulphanyl-benzyloxy)-piperidin-5-ol as a colourless oil; MS: 494 (M+H)⁺;

37) from tert-butyl (3R,4s,5S)-4-[4-(3-benzyloxy-propoxy)-phenyl]-3,5-bis-(4-isopropyl-benzyloxy)-piperidine-1-carboxylate by means of zinc bromide in methylene chloride, (3R,4s,5S)-4-[4-(3-benzyloxy-propoxy)-phenyl]-3,5-bis-(4-isopropyl-benzyloxy)-piperidine as a colourless oil; MS: 622 (M+H)⁺;

38) from tert-butyl (3RS,4SR,5SR)-4-[4-(3-benzyloxy-propoxy)-phenyl]-5-hydroxy-3-(4-isopropyl-benzyloxy)-piperidine-1-carboxylate by means of zinc bromide in methylene chloride, (3RS,4SR,5SR)-4-[4-(3-benzyloxy-propoxy)-phenyl]-3-(4-isopropyl-benzyloxy)-piperidin-5-ol as a colourless oil; MS: 490 (M+H)⁺;

39) from tert-butyl (3R,4s,5S)-4-[4-(3-benzyloxy-propoxy)-phenyl]-3,5-bis-(3-chloro-4-methoxy-benzyloxy)-piperidine-1-carboxylate by means of zinc bromide in methylene chloride, (3R,4s,5S)-4-[4-(3-benzyloxy-propoxy)-phenyl]-3,5-bis-(3-chloro-4-methoxy-benzyloxy)-piperidine as a colourless oil; MS: 666 (M+H)⁺;

40) from tert-butyl (3RS,4SR, 5SR)-4-[4-(3-benzyloxy-propoxy)-phenyl]-3-(3-chloro-4-methoxy-benzyloxy)-5-hydroxy-piperidine-1-carboxylate by means of zinc bromide in methylene chloride, (3RS,4SR,5SR)-4-[4-(3-benzyloxy-propoxy)-phenyl]-3-(3-chloro-4-methoxy-benzyloxy)-piperidin-5-ol as a colourless oil; MS: 512 (M+H)⁺;

41) from tert-butyl (3R,4s,5S)-4-[4-(3-benzyloxy-propoxy)-phenyl]-3,5-bis-(4-methoxy-3-methyl-benzyloxy)-piperidine-1-carboxylate by means of zinc bromide in methylene chloride, (3R,4s,5S)-4-[4-(3-benzyloxy-propoxy)-phenyl]-3,5-bis-(4-methoxy-3-methyl-benzyloxy)-piperidine as a colourless oil; MS: 626 (M+H)⁺;

42) from tert-butyl (3RS,4SR,5SR)-4-[4-(3-benzyloxy-propoxy)-phenyl]-5-hydroxy-3-(4-methoxy-3-methyl-benzyloxy)-piperidine-1-carboxylate by means of zinc bromide in methylene chloride, (3RS,4SR,5SR)-4-[4-(3-benzyloxy-propoxy)-phenyl]-3-(4-methoxy-3-methyl-benzyloxy)-piperidin-5-ol as a colourless oil; MS: 492 (M+H)⁺.

The BOC derivatives used as the starting materials were obtained as follows:

In an analogous manner to that described in Example 1(g), by alkylating tert-butyl (3R,4S,5S)-4-[4-(3-benzyloxy-propoxy)-phenyl]-3,5-dihydroxy-piperidine-1-carboxylate using one equivalent of a benzylic halide there were obtained in about the same proportions unreacted starting material and the corresponding mono- und dialkylated BOC derivatives. This mixture was subsequently separated by chromatography:

(a) By alkylation with 2-bromomethyl-naphthalene, tert-butyl (3R,4S,5S)-4-[4-(3-benzyloxy-propoxy)-phenyl]-3,5-bis-(naphthalen-2-ylmethoxy)-piperidine-1-carboxylate, MS: 739 (M+H)⁺, and tert-butyl (3RS,4SR,5SR)-4-[4-(3-benzyloxy-propoxy)-phenyl]-5-hydroxy-3-(naphthalen-2-ylmethoxy)-piperidine-1-carboxylate, MS: 598 (M+H)⁺, each as a colourless solid;

(b) by alkylation with 2-chloromethyl-1,4-dimethoxy-naphthalene [J.Org.Chem. (1983), 48(19),3265–3268], tert-butyl (3R,4s,5S)-4-[4-(3-benzyloxy-propoxy)-phenyl]-3,5-bis-(1,4-dimethoxy-naphthalen-2-ylmethoxy)-piperidine-1-carboxylate, MS: 876 (M+H)⁺, as a colourless foam and tert-butyl (3RS,4SR,5SR)-4-[4-(3-benzyloxy-propoxy)-phenyl]-3-(1,4-dimethoxy-naphthalen-2-ylmethoxy)-5-hydroxy-piperidine-1-carboxylate, MS: 659 (M+H)⁺, as a colourless oil;

(c) by alkylation with 2,4-dichloro-benzyl chloride, tert-butyl (3R,4s,5S)-4-[4-(3-benzyloxy-propoxy)-phenyl]-3, 5-bis-(2,4-dichloro-benzyloxy)-piperidine-1-carboxylate, $R_f$: 0.83 (SiO$_2$, methylene chloride:ethyl acetate=8:2), and tert-butyl (3RS,4SR,5SR)-4-[4-(3-benzyloxy-propoxy)-phenyl]-3-(2,4-dichloro-benzyloxy)-5-hydroxy-piperidine-1-carboxylate, $R_f$: 0.30 (SiO$_2$, methylene chloride:ethyl acetate=8:2), each as a colourless oil;

(d) by alkylation with 2,5-difluoro-benzyl bromide, tert-butyl (3R,4s,5S)-4-[4-(3-benzyloxy-propoxy)-phenyl]-3,5-bis-(2,5-difluoro-benzyloxy)-piperidine-1-carboxylate, MS: 727 (M+NH$_4$)$^+$, and tert-butyl (3RS,4SR,5SR)-4-[4-(3-benzyloxy-propoxy)-phenyl]-3-(2,5-difluoro-benzyloxy)-5-hydroxy-piperidine-1-carboxylate, $R_f$: 0.26 (SiO$_2$, methylene chloride:ethyl acetate=8:2), each as a colourless oil;

(e) by alkylation with methyl 4-bromomethyl-benzoate and saponification of the methyl ester during the aqueous working-up, tert-butyl (3R,4s,5S)-4-[4-(3-benzyloxy-propoxy)-phenyl]-3,5-bis-(4-carboxy-benzyloxy)-piperidine-1-carboxylate, $R_f$: 0.18 (SiO$_2$, methylene chloride:methanol=9:1), and tert-butyl (3RS,4SR,5SR)-4-[4-(3-benzyloxy-propoxy)-phenyl]-3-(4-carboxy-benzyloxy)-5-hydroxy-piperidine-1-carboxylate, $R_f$: 0.42 (SiO$_2$, methylene chloride:methanol=9:1), each as a colourless oil;

(f) by alkylation with 2,4-difluoro-benzyl bromide, tert-butyl (3R,4s,5S)-4-[4-(3-benzyloxy-propoxy)-phenyl]-3,5-bis-(2,4-difluoro-benzyloxy)-piperidine-1-carboxylate, MS: 727 (M+NH$_4$)$^+$, and tert-butyl (3RS,4SR,5SR)-4-[4-(3-benzyloxy-propoxy)-phenyl]-3-(2,4-difluoro-benzyloxy)-5-hydroxy-piperidine-1-carboxylate, $R_f$: 0.24 (SiO$_2$, methylene chloride:ethyl acetate=8:2), each as a colourless oil;

(g) by alkylation with 4-chloro-benzyl chloride, tert-butyl (3R,4s,5S)-4-[4-(3-benzyloxy-propoxy)-phenyl]-3,5-bis-(4-chloro-benzyloxy)-piperidine-1-carboxylate, MS: 724 (M+NH$_4$)$^+$, and tert-butyl (3RS,4SR,5SR)-4-[4-(3-benzyloxy-propoxy)-phenyl]-3-(4-chloro-benzyloxy)-5-hydroxy-piperidine-1-carboxylate, MS: 582 (M+H)$^+$, each as a colourless oil;

(h) by alkylation with 3,4-dichloro-benzyl choride, tert-butyl (3R,4s,5S)-4-[4-(3-benzyloxy-propoxy)-phenyl]-3,5-bis-(3,4-dichloro-benzyloxy)-piperidine-1-carboxylate, MS: 793 (M+NH$_4$)$^+$, and tert-butyl (3RS,4SR,5SR)-4-[4-(3-benzyloxy-propoxy)-phenyl]-3-(3,4-dichloro-benzyloxy)-5-hydroxy-piperidine-1-carboxylate, $R_f$: 0.55 (SiO$_2$, methylene chloride:ethyl acetate=8:2), each as a colourless oil;

(i) by alkylation with 3,5-dichloro-benzyl choride, tert-butyl (3R,4s,5S)-4-[4-(3-benzyloxy-propoxy)-phenyl]-3,5-bis-(3,5-dichloro-benzyloxy)-piperidine-1-carboxylate, MS: 793 (M+NH$_4$)$^+$, and tert-butyl (3RS,4SR,5SR)-4-[4-(3-benzyloxy-propoxy)-phenyl]-3-(3,5-dichloro-benzyloxy)-5-hydroxy-piperidine-1-carboxylate, MS: 634 (M+NH$_4$)$^+$, each as a colourless oil;

(j) by alkylation with 3-chloro-2-fluoro-benzyl bromide, tert-butyl (3R,4s,5S)-4-[4-(3-benzyloxy-propoxy)-phenyl]-3,5-bis-(3-chloro-2-fluoro-benzyloxy)-piperidine-1-carboxylate, MS: 760 (M+NH$_4$)$^+$, and tert-butyl (3RS,4SR,5SR)-4-[4-(3-benzyloxy-propoxy)-phenyl]-3-(3-chloro-2-fluoro-benzyloxy)-5-hydroxy-piperidine-1-carboxylate, $R_f$: 0.54 (SiO$_2$, methylene chloride:ethyl acetate=8:2), each as a colourless oil;

(k) by alkylation with 7-bromomethyl-quinoline hydrobromide [J.Am.Chem.Soc. 77, 1054 (1955)] using appropriately more sodium hydride, tert-butyl (3R,4s,5S)-4-[4-(3-benzyloxy-propoxy)-phenyl]-3,5-bis-(quinolin-7-ylmethoxy)-piperidine-1-carboxylate, MS: 740 (M+H)$^+$, and tert-butyl (3RS,4SR,5SR)-4-[4-(3-benzyloxy-propoxy)-phenyl]-5-hydroxy-3-(quinolin-7-ylmethoxy)-piperidine-1-carboxylate, MS: 599 (M+H)$^+$, $R_f$: 0.35 (SiO$_2$, methylene chloride:ethyl acetate=2:3), each as a colourless oil;

(l) by alkylation with 4-ethyl-benzyl chloride, tert-butyl (3R,4s,5S)-4-[4-(3-benzyloxy-propoxy)-phenyl]-3,5-bis-(4-ethyl-benzyloxy)-piperidine-1-carboxylate, MS: 711 (M+NH$_4$)$^+$, and tert-butyl (3RS,4SR,5SR)-4-[4-(3-benzyloxy-propoxy)-phenyl]-3-(4-ethyl-benzyloxy)-5-hydroxy-piperidine-1-carboxylate, $R_f$: 0.30 (SiO$_2$, methylene chloride:ethyl acetate=8:2), each as a colourless oil;

(m) by alkylation with 4-vinyl-benzyl chloride, tert-butyl (3R,4s,5S)-4-[4-(3-benzyloxy-propoxy)-phenyl]-3,5-bis-(4-vinyl-benzyloxy)-piperidine-1-carboxylate, MS: 707 (M+NH$_4$)$^+$, and tert-butyl (3RS,4SR,5SR)-4-[4-(3-benzyloxy-propoxy)-phenyl]-5-hydroxy-3-(4-vinyl-benzyloxy)-piperidine-1-carboxylate, $R_f$: 0.30 (SiO$_2$, methylene chloride:ethyl acetate=8:2), each as a colourless oil;

(n) by alkylation with 4-methoxy-benzyl chloride, tert-butyl (3R,4s,5S)-4-[4-(3-benzyloxy-propoxy)-phenyl]-3,5-bis-(4-methoxy-benzyloxy)-piperidine-1-carboxylate, MS: 715 (M+NH$_4$)$^+$, and tert-butyl (3RS,4SR,5SR)-4-[4-(3-benzyloxy-propoxy)-phenyl]-5-hydroxy-3-(4-methoxy-benzyloxy)-piperidine-1-carboxylate, MS: 595 (M+NH$_4$)$^+$, each as a colourless oil;

(o) by alkylation with 3,4,5-trimethoxy-benzyl chloride, tert-butyl (3R,4s,5S)-4-[4-(3-benzyloxy-propoxy)-phenyl]-3,5-bis-(3,4,5-trimethoxy-benzyloxy)-piperidine-1-carboxylate, MS: 835 (M+NH$_4$)$^+$, and tert-butyl (3RS,4SR,5SR)-4-[4-(3-benzyloxy-propoxy)-phenyl]-5-hydroxy-3-(3,4,5-trimethoxy-benzyloxy)-piperidine-1-carboxylate, MS: 655 (M+NH$_4$)$^+$, each as a colourless oil;

(p) by alkylation with 3,5-dimethoxy-benzyl chloride, tert-butyl (3R,4s,5S)-4-[4-(3-benzyloxy-propoxy)-phenyl]-3,5-bis-(3,5-dimethoxy-benzyloxy)-piperidine-1-carboxylate, MS: 775 (M+NH$_4$)$^+$, and tert-butyl (3RS,4SR,5SR)-4-[4-(3-benzyloxy-propoxy)-phenyl]-3-(3,5-dimethoxy-benzyloxy)-5-hydroxy-piperidine-1-carboxylate, MS: 625 (M+NH$_4$)$^+$, each as a colourless oil;

(q) by alkylation with 4-trifluoromethoxy-benzyl bromide, tert-butyl (3R,4s,5S)-4-[4-(3-benzyloxy-propoxy)-phenyl]-3,5-bis-(4-trifluoromethoxy-benzyloxy)-piperidine-1-carboxylate, MS: 823 (M+NH$_4$)$^+$, and tert-butyl (3RS,4SR,5SR)-4-[4-(3-benzyloxy-propoxy)-phenyl]-5-hydroxy-3-(4-trifluoromethoxy-benzyloxy)-piperidine-1-carboxylate, $R_f$: 0.32 (SiO$_2$, methylene chloride:ethyl acetate=8:2), each as a colourless oil;

(r) by alkylation with 4-methylthio-benzyl chloride [J.Org.Chem. (1988), 53(3), 561–569], tert-butyl (3R,4s,5S)-4-[4-(3-benzyloxy-propoxy)-phenyl]-3,5-bis-(4-methylsulphanyl-benzyloxy)-piperidine-1-carboxylate, MS: 747 (M+NH$_4$)$^+$, and tert-butyl (3RS,4SR,5SR)-4-[4-(3-benzyloxy-propoxy)-phenyl]-5-hydroxy-3-(4-methylsulphanyl-benzyloxy)-piperidine-1-carboxylate, MS: 611 (M+NH$_4$)$^+$, each as a colourless oil;

(s) by alkylation with 4-isopropyl-benzyl chloride, tert-butyl (3R,4s,5S)-4-[4-(3-benzyloxy-propoxy)-phenyl]-3,5-bis-(4-isopropyl-benzyloxy)-piperidine-1-carboxylate, MS: 739 (M+NH$_4$)$^+$, and tert-butyl (3RS,4SR,5SR)-4-[4-(3-benzyloxy-propoxy)-phenyl]-5-hydroxy-3-(4-isopropyl-benzyloxy)-piperidine-1-carboxylate, MS: 607 (M+NH$_4$)$^+$, each as a colourless oil;

(t) by alkylation with 3-chloro-4-methoxy-benzyl chloride, tert-butyl (3R,4s,5S)-4-[4-(3-benzyloxy-propoxy)- phenyl]-3,5-bis-(3-chloro-4-methoxy-benzyloxy)-piperidine-1-carboxylate, MS: 784 (M+NH$_4$)$^+$, and tert-butyl (3RS,4SR,5SR)-4-[4-(3-benzyloxy-propoxy)-phenyl]-3-(3-chloro-4-methoxy-benzyloxy)-5-hydroxy-piperidine-1-carboxylate, MS: 630 (M+NH$_4$)$^+$, each as a colourless oil;

(u) by alkylation with 4-methoxy-3-methyl-benzyl chloride, tert-butyl (3R,4s,5S)-4-[4-(3-benzyloxy-propoxy)-phenyl]-3,5-bis-(4-methoxy-3-methyl-benzyloxy)-piperidine-1-carboxylate, MS: 743 (M+NH$_4$)$^+$, and tert-butyl (3RS,4SR,5SR)-4-[4-(3-benzyloxy-propoxy)-phenyl]-5-hydroxy-3-(4-methoxy-3-methyl-benzyloxy)-piperidine-1-carboxylate, MS: 609 (M+NH$_4$)$^+$, each as a colourless oil.

The tert-butyl (3R,4s,5S)-4-[4-(3-benzyloxy-propoxy)-phenyl]-3,5-dihydroxy-piperidine-1-carboxylate used as the starting material was obtained as follows:

(α) 50.0 g (179 mmol) of 1-benzyl-4-(4-methoxy-phenyl)-1,2,3,6-tetrahydro-pyridine [Example 44 (b)] were dissolved in 500 ml of tetrahydrofuran, treated at room temperature with 36.3 ml (322 mmol) of 48 percent aqueous hydrobromic acid and the reaction mixture was subsequently concentrated on a rotary evaporator. The thus-formed residue was suspended twice with 500 ml of toluene and again concentrated, then dissolved in 1500 ml of dioxan and 1200 ml of water, treated with 51.6 g (501 mmol) of sodium bromide and 9.3 ml (181 mmol) of bromine and stirred at room temperature for 2 hours. The thus-obtained orange coloured solution was subsequently cooled to 0° C. and treated at 5° to 10° C. with 1240 ml of 2N sodium hydroxide solution and stirred at room temperature for a further 2 hours. Thereupon, the reaction mixture was extracted three times with 2 liters of ethyl acetate, the combined organic phases were washed with water, dried over magnesium sulphate and evaporated on a rotary evaporator at a maximum 40° C. There were thus obtained 53.64 g (about 100% of theory) of (1RS,6RS)-3-benzyl-6-(4-methoxy-phenyl)-7-oxa-3-aza-bicyclo[4.1.0]heptane in the form of a brown solid; MS: 295 (M)$^+$.

(β) 53.44 g (179 mmol) of (1RS,6RS)-3-benzyl-6-(4-methoxy-phenyl)-7-oxa-3-aza-bicyclo[4.1.0]heptane were suspended in 980 ml of ether and this suspension was added dropwise under argon and with the exclusion of moisture to 226 ml of 1.6M methyllithium solution in diethyl ether (362 mmol) at room temperature. Subsequently, the reaction mixture was heated under reflux for one hour. After cooling to room temperature it was poured into 1.5 liters of saturated sodium hydrogen carbonate solution and extracted twice with 1.5 liters of ethyl acetate, the combined ethyl acetate phases were washed with water, dried over sodium sulphate and evaporated on a rotary evaporator at a maximum 40° C. There were thus obtained 52.8 g (about 100% of theory) of RS)-1-benzyl-4-(4-methoxy-phenyl)-1,2,3,6-tetrahydro-pyridin-3-ol in the form of a brown oil; MS: 296 (M+H)$^+$.

(γ) 52.6 g (178 mmol) of RS)-1-benzyl-4-(4-methoxy-phenyl)-1,2,3,6-tetrahydro-pyridin-3-ol were dissolved in 300 ml of N,N-dimethylformamide, treated portionwise with 25 g (about 600 mmol) of sodium hydride dispersion in refined oil (55–65%) and the reaction mixture was heated to 50° C. under argon for 1 hour. After cooling to 5° C. the mixture was treated slowly with 23 ml (285 mmol) of ethyl iodide and stirred without cooling for one hour. Thereupon, the reaction mixture was poured into 2 liters of ice-water and extracted three times with 1 liter of ethyl acetate. The combined ethyl acetate phases were subsequently washed with water, dried over magnesium sulphate and evaporated on a rotary evaporator at a maximum 40° C. The residue which was thereby obtained was chromatographed on silica gel with hexane/ethyl acetate (5:1). There were thus obtained 42.51 g (74% of theory) of (RS)-1-benzyl-3-ethoxy-4-(4-methoxy-phenyl)-1,2,3,6-tetrahydro-pyridine in the form of an orange coloured oil; MS: 324 (M)$^+$.

(δ) 42.3 g (131 mmol) of (RS)-1-benzyl-3-ethoxy-4-(4-methoxy-phenyl)-1,2,3,6-tetrahydro-pyridine were dissolved in 500 ml of 1,2-dimethoxyethane, treated with 7.45 g (196 mmol) of sodium borohydride and treated while cooling at a maximum 28° C. with a solution of 44.3 ml (353 mmol) of boron trifluoride etherate in 44.3 ml of 1,2-dimethoxyethane and the reaction mixture was stirred at room temperature for 2 hours. Subsequently, while cooling at a maximum of 35° C., 169 ml of 4.1N potassium hydroxide solution followed by 33.9 ml of 30% hydrogen peroxide solution were added dropwise and the reaction mixture was heated under reflux for 3 hours. After cooling to room temperature the reaction solution was poured into 2 liters of water and extracted twice with 1 liter of methylene chloride each time. The combined methylene chloride phases were washed with water, dried over magnesium sulphate and evaporated on a rotary evaporator at a maximum 40° C. The residue which was thereby obtained was chromatographed on silica gel with hexane/ethyl acetate (initially 4:1, then ethyl acetate content increased stepwise to 1:1). There were thus obtained 22.1 g (49% of theory) of (3RS,4RS,5SR)-5-ethoxy-1-benzyl-3-hydroxy-4-(4-methoxy-phenyl)-piperidine in the form of a yellowish oil; MS: 342 (M+H)$^+$.

(ε) 52.39 g (153.4 mmol) of (3RS,4RS,5SR)-5-ethoxy-1-benzyl-3-hydroxy-4-(4-methoxy-phenyl)-piperidine were dissolved in 525 ml of methylene chloride and treated at a maximum of 40° C. with 306 ml of 1M borontribromide solution in methylene chloride and the reaction mixture was stirred at room temperature for 4 hours. Thereupon, the reaction mixture was cooled to 5° C. and the crystals formed were filtered off. These were subsequently dissolved in methylene chloride/methanol (8:2, extracted against 5 vol. % conc. aqueous ammonia) and chromatographed on silica gel with the same eluent. There were thus obtained 34.18 g (74% of theory) of (3R,4s,5S)-1-benzyl-4-(4-hydroxy-phenyl)-piperidin-3,5-diol in form of an amorphous, colourless solid; MS: 300 (M+H)$^+$.

(ζ) 33.98 g (113.5 mmol) of (3R,4s,5S)-1-benzyl-4-(4-hydroxy-phenyl)-piperidin-3,5-diol were dissolved in 1.7 liters of methanol, treated with 5.1 g of palladium-on-charcoal (10%) and exhaustively hydrogenated at room temperature under normal pressure. Subsequently, the reaction mixture was filtered over silica gel and concentrated in a water-jet vacuum. There were thus obtained 22.56 g (95% of theory) of (3R,4s,5S)-4-(4-hydroxy-phenyl)-piperidine-3,5-diol in the form of an amorphous, colourless solid; MS: 209 (M)$^+$.

(η) 22.36 g (106 mmol) of (3R,4s,5S)-4-(4-hydroxy-phenyl)-piperidine-3,5-diol were dissolved in 559 ml of dioxan and 186 ml of water, treated with 18.85 g (224 mmol) of sodium hydrogen carbonate and 25.65 g (117.5 mmol) of di-tert-butyl dicarbonate and stirred at room temperature for 2 hours. Thereupon, the reaction mixture was poured on to 1.5 liters of ice-water and extracted twice with 1.5 liters of ethyl acetate. The combined ethyl acetate phases were dried over magnesium sulphate and evaporated on a rotary evaporator at a maximum of 50° C. The residue thus obtained was chromatographed on silica gel with methylene chloride/methanol (95:5). There were thus obtained 15.79 g (48% of theory) of tert-butyl (3R,4s,5S)-3,5-dihydroxy-4-(4-hydroxy-phenyl)-piperidine-1-carboxylate in the form of colourless crystals, MS: 310 (M+H)$^+$.

(θ) 15.59 g (50.4 mmol) of tert-butyl (3R,4s,5S)-3,5-dihydroxy-4-(4-hydroxy-phenyl)-piperidine-1-carboxylate were dissolved in 510 ml of methyl ethyl ketone, treated with 28 g (201 mmol) of potassium carbonate followed by 34.7 g (151 mmol) of benzyl 3-bromopropyl ether and the reaction mixture was heated under reflux for 24 hours. After cooling to room temperature the mixture was poured on to 800 ml of ice-water and extracted twice with 500 ml of ethyl acetate, the combined ethyl acetate phases were washed with water, dried over magnesium sulphate and evaporated on a rotary evaporator at a maximum of 40° C. The thus-obtained residue was chromatographed on silica gel with methylene chloride/ethyl acetate (7:3). There were thus obtained 20.5 g (89% of theory) of tert-butyl (3R,4s,5S)-4-[4-(3-benzyloxy-propoxy)-phenyl]-3,5-dihydroxy-piperidine-1-carboxylate in the form of an amorphous, colourless solid; MS: 458 (M+H)$^+$.

EXAMPLE 110

The following compounds were obtained by cleavage of the BOC group by means of hydrogen chloride in methanol analogously to Example 22(l) or by means of zinc bromide in methylene chloride analogously to Example 10(b):

1) From tert-butyl (3RS,4SR,5SR)-4-[4-(3-benzyloxy-propoxy)-phenyl]-5-ethoxy-3-(naphthalen-2-ylmethoxy)-piperidine-1-carboxylate by means of zinc bromide in methylene chloride, (3RS,4SR,5SR)-4-[4-(3-benzyloxy-propoxy)-phenyl]-5-ethoxy-3-(naphthalen-2-ylmethoxy)-piperidine as a colourless oil; MS: 526 (M+H)$^+$;
2) from tert-butyl (3RS,4RS,5SR)-4-[4-(3-benzyloxy-propoxy)-phenyl]-5-[2-(4-methyl-piperazin-1-yl)-ethoxy]-3-(naphthalen-2-ylmethoxy)-piperidine-1-carboxylate by means of hydrogen chloride in methanol, 1-{2-[(3RS,4RS,5SR)-4-[4-(3-benzyloxy-propoxy)-phenyl]-3-(naphthalen-2-ylmethoxy)-piperidin-5-yloxy]-ethyl}-4-methyl-piperazine as a colourless oil; MS: 624 (M+H)$^+$;
3) from tert-butyl (3RS,4SR,5SR)-4-[4-(3-benzyloxy-propoxy)-phenyl]-3-(naphthalen-2-ylmethoxy)-5-propoxy-piperidine-1-carboxylate by means of hydrogen chloride in methanol, (3RS,4SR,5SR)-4-[4-(3-benzyloxy-propoxy)-phenyl]-3-(naphthalen-2-ylmethoxy)-5-propoxy-piperidine as a colourless oil; MS: 540 (M+H)$^+$;
4) from tert-butyl (3RS,4SR,5SR)-4-[4-(3-benzyloxy-propoxy)-phenyl]-5-butoxy-3-(naphthalen-2-ylmethoxy)-piperidine-1-carboxylate by means of hydrogen chloride in methanol, (3RS,4SR,5SR)-4-[4-(3-benzyloxy-propoxy)-phenyl]-5-butoxy-3-(naphthalen-2-ylmethoxy)-piperidine as a colourless oil; MS: 554 (M+H)$^+$;
5) from tert-butyl (3RS,4SR,5SR)-4-[4-(3-benzyloxy-propoxy)-phenyl]-5-methoxy-3-(naphthalen-2-ylmethoxy)-piperidine-1-carboxylate by means of hydrogen chloride in methanol, (3RS,4SR,5SR)-4-[4-(3-benzyloxy-propoxy)-phenyl]-5-methoxy-3-(naphthalen-2-ylmethoxy)-piperidine as a colourless oil; MS: 512 (M+H)$^+$;
6) from a mixture of tert-butyl (3RS,4RS,5SR)- and (3SR,4SR,5RS)-4-[4-(3-benzyloxy-propoxy)-phenyl]-3-(naphthalen-2-ylmethoxy)-5-[2-[(RS)-tetrahydro-pyran-2-yloxy]-äthoxy]-piperidine-1-carboxylate by means of hydrogen chloride in methanol with simultaneous cleavage of the tetrahydropyranyl group, 2-[(3RS,4RS,5SR)-4-[4-(3-benzyloxy-propoxy)-phenyl]-3-(naphthalen-2-ylmethoxy)-piperidin-5-yloxy]-ethanol as a colourless oil; MS: 542 (M+H)$^+$;
7) from a mixture of tert-butyl (3RS,4SR,5SR)- and (3SR,4RS,5RS)-4-[4-(3-benzyloxy-propoxy)-phenyl]-3-(naphthalen-2-ylmethoxy)-5-[3-[(RS)-tetrahydro-pyran-2-yloxy]-propoxy]-piperidine-1-carboxylate by means of hydrogen chloride in methanol with simultaneous cleavage of the tetrahydropyranyl group, 3-[(3RS,4SR,5SR)-4-[4-(3-benzyloxy-propoxy)-phenyl]-3-(naphthalen-2-ylmethoxy)-piperidin-5-yloxy]-propan-1-ol as a colourless oil; MS: 556 (M+H)$^+$;
8) from a mixture of tert-butyl (3RS,4SR,5SR)- and (3SR,4RS,5RS)-4-[4-(3-benzyloxy-propoxy)-phenyl]-3-(naphthalen-2-ylmethoxy)-5-[4-[(RS)-tetrahydro-pyran-2-yloxy]-butoxy]-piperidine-1-carboxylate by means of hydrogen chloride in methanol with simultaneous cleavage of the tetrahydropyranyl group, 4-[(3RS,4SR,5SR)-4-[4-(3-benzyloxy-propoxy)-phenyl]-3-(naphthalen-2-ylmethoxy)-piperidin-5-yloxy]-butan-1-ol as a colourless oil; MS: 570 (M+H)$^+$.
9) from tert-butyl (3RS,4RS,5SR)-4-[4-(3-benzyloxy-propoxy)-phenyl]-5-(2-morpholin-4-yl-ethoxy)-3-(naphthalen-2-ylmethoxy)-piperidine-1-carboxylate by means of hydrogen chloride in methanol, 4-{2-[(3RS,4RS,5SR)-4-[4-(3-benzyloxy-propoxy)-phenyl]-3-(naphthalen-2-ylmethoxy)-piperidin-5-yloxy]-ethyl}-morpholine as a colourless oil; MS: 611 (M+H)$^+$;
10) from tert-butyl (3RS,4RS)-3-(naphthalen-2-ylmethoxy)-4-(4-{3-[2-(2-trimethylsilanyl-ethoxymethoxy)-benzyloxy]-propoxy}-phenyl)-piperidine-1-carboxylate [Example 108(b)] by means of hydrogen chloride in methanol with simultaneous cleavage of the 2-trimethylsilanyl-ethoxymethoxy group, 2-(3-{4-[(3RS,4RS)-3-(naphthalen-2-ylmethoxy)-piperidin-4-yl]-phenoxy}-propoxymethyl)-phenol as a colourless oil; MS: 579 (M+H)$^+$.

The BOC derivatives used as starting materials were obtained from tert-butyl (3RS,4SR,5SR)-4-[4-(3-benzyloxy-propoxy)-phenyl]-5-hydroxy-3-(naphthalen-2-ylmethoxy)-piperidine-1-carboxylate [Example 109(a)] as follows in an analogous manner to that described in Example 1(g), but at a reaction temperature of 50° C. and using a large excess of sodium hydride and alkylating agent:

(a) By alkylation with ethyl bromide, tert-butyl (3RS,4SR,5SR)-4-[4-(3-benzyloxy-propoxy)-phenyl]-5-ethoxy-3-(naphthalen-2-ylmethoxy)-piperidine-1-carboxylate as a colourless oil; MS: 626 (M+H)$^+$;
(b) by alkylation with 1-(2-chloroethyl)-4-methyl-piperazine [Austr. J. Chem. 9 (1956), 89], tert-butyl (3RS,4RS,5SR)-4-[4-(3-benzyloxy-propoxy)-phenyl]-5-[2-(4-methyl-piperazin-1-yl)-ethoxy]-3-(naphthalen-2-ylmethoxy)-piperidine-1-carboxylate as a colourless oil; MS: 724 (M+H)$^+$;
(c) by alkylation with n-propyl bromide, tert-butyl (3RS,4SR,5SR)-4-[4-(3-benzyloxy-propoxy)-phenyl]-3-(naphthalen-2-ylmethoxy)-5-propoxy-piperidine-1-carboxylate as a yellowish oil; MS: 640 (M+H)$^+$;
(d) by alkylation with n-butyl bromide, tert-butyl (3RS,4SR,5SR)-4-[4-(3-benzyloxy-propoxy)-phenyl]-5-butoxy-3-(naphthalen-2-ylmethoxy)-piperidine-1-carboxylate as a yellowish oil; MS: 654 (M+H)$^+$;
(e) by alkylation with methyl iodide, tert-butyl (3RS,4SR,5SR)-4-[4-(3-benzyloxy-propoxy)-phenyl]-5-methoxy-3-(naphthalen-2-ylmethoxy)-piperidine-1-carboxylate as a yellowish oil; MS: 612 (M+H)$^+$;
(f) by alkylation with rac-2-(2-bromoethoxy)-tetrahydropyran [J. Amer. Chem. Soc. 70, 4187 (1948)], a mixture of tert-butyl (3RS,4RS,5SR)- and (3SR,4SR,5RS)-4-[4-(3-benzyloxy-propoxy)-phenyl]-3-(naphthalen-2-ylmethoxy)-5-[2-[(RS)-tetrahydro-pyran-2-yloxy]-ethoxy]-piperidine-1-carboxylate as a colourless oil; MS: 743 (M+NH$_4$)$^+$.

(g) by alkylation with rac-2-(3-bromo-propoxy)-tetrahydropyran [J. Chem. Soc. 1955, 1770], a mixture of tert-butyl (3RS,4SR,5SR)- and (3SR,4RS,5RS)-4-[4-(3-benzyloxy-propoxy)-phenyl]-3-(naphthalen-2-ylmethoxy)-5-[3-[(RS)-tetrahydro-pyran-2-yloxy]-propoxy]-piperidine-1-carboxylate as a colourless oil; MS: 740 (M+H)⁺.

(h) by alkylation with rac-2-(4-bromo-butoxy)-tetrahydropyran [S. W.Baldwin et al., J.Org.Chem. 1985, 50, 4432–4439], a mixture of tert-butyl (3RS,4SR,5SR)- and (3SR,4RS,5RS)-4-[4-(3-benzyloxy-propoxy)-phenyl]-3-(naphthalen-2-ylmethoxy)-5-[4-[(RS)-tetrahydro-pyran-2-yloxy]-butoxy]-piperidine-1-carboxylate as a colourless oil; MS: 771 (M+NH$_4$)⁺.

(i) by alkylation with 4-(2-chloroethyl)-morpholine, tert-butyl (3RS,4RS,5SR)-4-[4-(3-benzyloxy-propoxy)-phenyl]-5-(2-morpholin-4-yl-ethoxy)-3-(naphthalen-2-ylmethoxy)-piperidine-1-carboxylate as a colourless oil; MS: 711 (M+H)⁺.

EXAMPLE 111

The following compounds were obtained by cleavage of the BOC group and simultaneously of the tetrahydropyranyl protecting group (where present) by means of hydrogen chloride in methanol analogously to Example 22(l) or of the BOC group by means of zinc bromide in methylene chloride analogously to Example 10(b):

1) From tert-butyl (3RS,4SR,5RS)-4-[4-(3-benzyloxy-propoxy)-phenyl]-5-hydroxy-3-(naphthalen-2-ylmethoxy)-piperidine-1-carboxylate by means of zinc bromide in methylene chloride, (3RS,4SR,5RS)-4-[4-(3-benzyloxy-propoxy)-phenyl]-3-(naphthalen-2-ylmethoxy)-piperidin-5-ol as a colourless solid; MS: 499 (M+H)⁺;

2) from tert-butyl (RS)-4-[4-(3-benzyloxy-propoxy)-phenyl]-3-(naphthalen-2-ylmethoxy)-3,6-dihydro-2H-pyridine-1-carboxylate by means of hydrogen chloride in methanol, (RS)-4-[4-(3-benzyloxy-propoxy)-phenyl]-3-(naphthalen-2-ylmethoxy)-1,2,3,6-tetrahydro-pyridine in the form of a colourless oil; MS: 480 (M+H)⁺;

3) from tert-butyl (3RS,4SR,5SR)-5-amino-4-[4-(3-benzyloxy-propoxy)-phenyl]-3-(naphthalen-2-ylmethoxy)-piperidine-1-carboxylate by means of zinc bromide in methylene chloride, (3RS,4SR,5SR)-4-[4-(3-benzyloxy-propoxy)-phenyl]-3-(naphthalen-2-ylmethoxy)-piperidin-5-ylamine in the form of a colourless solid; MS: 497 (M+H)⁺.

4) from a mixture of tert-butyl (3RS,4RS,5SR)- and (3SR,4SR,5RS)-4-[4-(3-benzyloxy-propoxy)-phenyl]-3-(quinolin-7-ylmethoxy)-5-[2-[(RS)-tetrahydro-pyran-2-yloxy]-ethoxy]-piperidine-1-carboxylate, 2-[4-(3RS,4RS,5SR)-[4-(3-benzyloxy-propoxy)-phenyl]-3-(quinolin-7-ylmethoxy)-piperidin-5-yloxy]-ethanol in the form of a colourless oil; MS: 543 (M+H)⁺;

5) from a mixture of tert-butyl (3RS,4SR,5SR)- and (3SR,4RS,5RS)-4-[4-(3-benzyloxy-propoxy)-phenyl]-3-(quinolin-7-ylmethoxy)-5-[3-[(RS)-tetrahydro-pyran-2-yloxy]-propoxy]-piperidine-1-carboxylate, 3-[4-(3RS,4SR,5SR)-[4-(3-benzyloxy-propoxy)-phenyl]-3-(quinolin-7-ylmethoxy)-piperidin-5-yloxy]-propan-1-ol in the form of a colourless oil; MS: 557 (M+H)⁺;

6) from a mixture of tert-butyl (3RS,4SR,5SR)- and (3SR,4RS,5RS)-4-[4-(3-benzyloxy-propoxy)-phenyl]-3-(quinolin-7-ylmethoxy)-5-[4-[(RS)-tetrahydro-pyran-2-yloxy]-butoxy]-piperidine-1-carboxylate, 4-[4-(3RS,4SR,5SR)-[4-(3-benzyloxy-propoxy)-phenyl]-3-(quinolin-7-ylmethoxy)-piperidin-5-yloxy]-butan-1-ol in the form of a colourless oil; MS: 571 (M+H)⁺.

The BOC derivatives used as starting materials were prepared as follows:

(a) A solution of 850 mg (1.422 mmol) of tert-butyl(3RS,4SR,5SR)-4-[4-(3-benzyloxy-propoxy)-phenyl]-5-hydroxy-3-(naphthalen-2-ylmethoxy)-piperidine-1-carboxylate [Example 109(a)] and 1.884 g (7.11 mmol) of triphenylphosphine in 170 ml of dry tetrahydrofuran was treated while stirring with 274 µl (7.11 mmol) of dry formic acid and a solution of 1.238 g (7.11 mmol) of diethyl azodicarboxylate in 42.5 ml of tetrahydrofuran. The reaction mixture was subsequently stirred at room temperature for 90 hours. Thereupon, it was evaporated under reduced pressure at 40° C. and the residue was treated with a solution of 42.5 ml of methanol and 464 mg (7.11 mmol) of potassium hydroxide and stirred at room temperature for 3 hours. Subsequently, the solution was treated with 500 ml of deionized water and the mixture was extracted four times with 200 ml of methylene chloride each time. The combined organic phases were dried over sodium sulphate, evaporated under reduced pressure at 40° C. and the residue was dried in a high vacuum. The white crystalline residue (4.2 g) was chromatographed on silica gel using a 4:1 mixture of methylene chloride and ethyl acetate as the eluent. There were obtained 560 mg (66% of theory) of tert-butyl (3RS,4SR,5RS)-4-[4-(3-benzyloxy-propoxy)-phenyl]-5-hydroxy-3-(naphthalen-2-ylmethoxy)-piperidine-1-carboxylate in the form of a colourless solid; MS: 598 (M+H)⁺.

(b) A solution of 560 mg (0.937 mmol) of tert-butyl (3RS,4SR,5RS)-4-[4-(3-benzyloxy-propoxy)-phenyl]-5-hydroxy-3-(naphthalen-2-ylmethoxy)-piperidine-1-carboxylate and 273 mg (1.031 mmol) of triphenylphosphine in 20 ml of dry tetrahydrofuran was treated while stirring with 160.2 µl (1.031 mmol) of diethyl azodicarboxylate and ten minutes later with a solution of 319.8 µl (1.405 mmol) of diphenylphosphoryl azide in 2 ml of tetrahydrofuran. This mixture was stirred at room temperature for 72 hours, then evaporated under reduced pressure at 40° C. and the residue was dried in a high vacuum. The yellow oily residue was chromatographed on silica gel using a 4:1 mixture of n-hexane and ethyl aceatate and the eluent. There were obtained 210 mg (36% of theory) of tert-butyl (3RS,4SR,5SR)-5-azido-4-[4-(3-benzyloxy-propoxy)-phenyl]-3-(naphthalen-2-ylmethoxy)-piperidine-1-carboxylate in the form of a colourless oil [MS: 623 (M+H⁺)]. As a further product there were obtained 180 mg (33.1% of theory) of tert-butyl (RS)-4-[4-(3-benzyloxy-propoxy)-phenyl]-3-(naphthalen-2-ylmethoxy)-3,6-dihydro-2H-pyridine-1-carboxylate, likewise as a colourless oil; MS: 580 (M+H)⁺.

(c) A solution of 50 mg (0.0803 mmol) of tert-butyl (RS)-4-[4-(3-benzyloxy-propoxy)-phenyl]-3-(naphthalen-2-ylmethoxy)-3,6-dihydro-2H-pyridine-1-carboxylate in 0.36 ml of dry tetrahydrofuran was treated while stirring with 21 mg (0.0793 mmol) of triphenylphosphine dissolved in 0.36 ml of dry tetrahydrofuran. Thereupon, the mixture was stirred at room temperature for four hours (about 50% conversion) and subsequently again treated with 10.6 mg (0.040 mmol) of triphenylphosphine and finally stirred at room temperature for a further 24 h. Then, the mixture was treated with 2 µl (0.111 mmol) of deionized water and stirred at room temperature for one hour. Subsequently, the mixture was evaporated under reduced pressure at 40° C. and the residue was taken up in ether and extracted against water. The organic phase was dried over sodium sulphate and the filtrate was evaporated. The colourless oily residue (110 mg) was chromatographed on silica gel using a 4:1 mixture of n-hexane and ethyl acetate as the eluent. There were obtained 30 mg (63% of theory) of tert-butyl (3RS,4SR, 5SR)-5-amino-4-[4-(3-benzyloxy-propoxy)-phenyl]-3-(naphthalen-2-ylmethoxy)-piperidine-1-carboxylate in the form of a colourless solid; MS: 597 (M+H)⁺.

The following BOC derivatives were obtained from tert-butyl (3RS,4SR,5SR)-4-[4-(3-benzyloxy-propoxy)-phenyl]-5-hydroxy-3-(quinolin-7-ylmethoxy)-piperidine-1-carboxylate as follows in an analogous manner to that described in Example 1(g), but at a reaction temperature of 50° C.;

(d) By alkylation with rac-2-(2-bromoethoxy)-tetrahydropyran [J. Amer. Chem. Soc. 70, 4187 (1948)], a mixture of tert-butyl (3RS,4RS,5SR)- and (3SR,4SR,5RS)-4-[4-(3-benzyloxy-propoxy)-phenyl]-3-(quinolin-7-ylmethoxy)-5-[2-[(RS)-tetrahydro-pyran-2-yloxy]-ethoxy]-piperidine-1-carboxylate as a colourless oil; MS: 727 (M+H)⁺;

(e) by alkylation with rac-2-(3-bromo-propoxy)-tetrahydropyran [J. Chem. Soc. 1955, 1770], a mixture of tert-butyl (3RS,4SR,5SR)- and (3SR,4RS,5RS)-4-[4-(3-benzyloxy-propoxy)-phenyl]-3-(quinolin-7-ylmethoxy)-5-[3-[(RS)-tetrahydro-pyran-2-yloxy]-propoxy]-piperidine-1-carboxylate as a colourless oil; MS: 741 (M+H)⁺;

(f) by alkylation with rac-2-(4-bromo-butoxy)-tetrahydropyran [S. W.Baldwin et al., J.Org.Chem. 1985, 50, 4432–4439], a mixture of tert-butyl (3RS,4SR,5SR)- and (3SR,4RS,5RS)-4-[4-(3-benzyloxy-propoxy)-phenyl]-3-(quinolin-7-ylmethoxy)-5-[4-[(RS)-tetrahydro-pyran-2-yloxy]-butoxy]-piperidine-1-carboxylate as a colourless oil; MS: 755 (M+H)⁺.

EXAMPLE 112

The following compounds were obtained by cleavage of the BOC group by means of zinc bromide in methylene chloride analogously to Example 10(b):

1) From tert-butyl (3R,4s,5S)-3,5-bis-(4-methoxy-benzyloxy)-4-{4-[3-(2-methoxy-benzyloxy)-propoxy]-phenyl}-piperidine-1-carboxylate, (3R,4s,5S)-4-[4-[3-(2-methoxy-benzyloxy)-propoxy]-phenyl]-3,5-bis-(naphthalen-2-ylmethoxy)-piperidine as a colourless oil; MS: 628 (M+H)⁺;

2) from tert-butyl (3RS,4SR,5SR)-5-hydroxy-3-(4-methoxy-benzyloxy)-4-{4-[3-(2-methoxy-benzyloxy)-propoxy]-phenyl}-piperidine-1-carboxylate, (3RS,4SR,5S R)-3-(4-methoxy-benzyloxy)-4-{4-[3-(2-methoxy-benzyloxy)-propoxy]-phenyl}-piperidin-5-ol as a colourless oil; MS: 508 (M+H)⁺;

3) from tert-butyl (3R,4s,5S)-4-[4-[3-(2-methoxy-benzyloxy)-propoxy]-phenyl]-3,5-bis-(pyridin-2-ylmethoxy)-piperidine-1-carboxylate, (3R,4s,5S)-2-[5-(pyridin-2-ylmethoxy-4-[4-[3-(2-methoxy-benzyloxy)-propoxy]-phenyl]-piperidin-3-yloxymethyl]-pyridine as a colourless oil; MS: 570 (M+H)⁺;

4) from tert-butyl (3RS,4SR,5SR)-5-hydroxy-4-{4-[3-(2-methoxy-benzyloxy)-propoxy]-phenyl}-3-(pyridin-2-ylmethoxy)-piperidine-1-carboxylate, (3RS,4SR,5SR)-4-[4-[3-(2-methoxy-benzyloxy)-propoxy]-phenyl]-3-(pyridin-2-ylmethoxy)-piperidin-5-ol as a colourless oil; MS: 479 (M+H)⁺;

5) from tert-butyl (3R,4s,5S)-4-[4-[3-(2-methoxy-benzyloxy)-propoxy]-phenyl]-3,5-bis-(pyridin-3-ylmethoxy)-piperidine-1-carboxylate, (3R,4s,5S)-3-[5-(pyridin-3-ylmethoxy-4-[4-[3-(2-methoxy-benzyloxy)-propoxy]-phenyl]-piperidin-3-yloxymethyl]-pyridine as a colourless oil; MS: 570 (M+H)⁺;

6) from tert-butyl (3RS,4SR,5SR)-5-hydroxy-4-{4-[3-(2-methoxy-benzyloxy)-propoxy]-phenyl}-3-(pyridin-3-ylmethoxy)-piperidine-1-carboxylate, (3RS,4SR,5SR)-4-[4-[3-(2-methoxy-benzyloxy)-propoxy]-phenyl]-3-(pyridin-3-ylmethoxy)-piperidin-5-ol as a colourless oil; MS: 479 (M+H)⁺;

7) from tert-butyl (3R,4s,5S)-4-[4-[3-(2-methoxy-benzyloxy)-propoxy]-phenyl]-3,5-bis-(pyridin-4-ylmethoxy)-piperidine-1-carboxylate, (3R ,4s,5S)-4-[5-(pyridin-4-ylmethoxy-4-[4-[3-(2-methoxy-benzyloxy)-propoxy]-phenyl]-piperidin-3-yloxymethyl]-pyridine as a colourless oil; MS: 570 (M+H)⁺;

8) from tert-butyl (3RS,4SR,5SR)-5-hydroxy-4-{4-[3-(2-methoxy-benzyloxy)-propoxy]-phenyl}-3-(pyridin-4-ylmethoxy)-piperidine-1-carboxylate, (3RS,4SR,5SR)-4-[4-[3-(2-methoxy-benzyloxy)-propoxy]-phenyl]-3-(pyridin-4-ylmethoxy)-piperidin-5-ol as a colourless oil; MS: 479 (M+H)⁺;

9) from (3RS,4SR,5SR)-5-hydroxy-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidin-1-carboxylic acid tert-butylester. 1-[2-[7-[(3RS,4SR,5SR)-5-hydroxy-4-[4-[3-(2-methoxy-benzyloxy)-propoxy]-piperidin-3-yloxymethyl]-naphthalen-2-yloxy]-ethyl]-4-methyl-piperazine as an amorphous colourless solid, MS: 670 (M+H)⁺;

10) from (3R,4s,5S)-3,5-bis-(1,4-dimethoxy-naphthalen-2-ylmethoxy)-4-[4-[3-(2-methoxy-benzyloxy)-propoxy]-phenyl]-piperidin-1-carboxylic acid tert-butylester by means of zinc bromide in methylene chloride, (3R,4s,5S)-3,5-bis-(1,4-dimethoxy-naphthalen-2-ylmethoxy)-4-[4-[3-(2-methoxy-benzyloxy)-propoxy]-phenyl]-piperidine as a colourless wax; MS: 788 (M+H)⁺;

11) from (3RS,4SR,5SR)-3-(1,4-dimethoxy-naphthalen-2-ylmethoxy)-5-hydroxy-4-[4-[3-(2-methoxy-benzyloxy)-propoxy]-phenyl]-piperidin-1-carboxylic acid tert-butylester by means of zinc bromide in methylene chloride, (3RS,4SR,5SR)-3-(1,4-dimethoxy-naphthalen-2-ylmethoxy)-4-[4-[3-(2-methoxy-benzyloxy)-propoxy]-phenyl]-piperidin-5-ol as a colourless oil; MS: 588 (M+H)⁺.

The BOC derivatives used as starting materials were obtained as follows:

(α) In an analogous manner to that described in Example 44(e), by alkylating tert-butyl (3R,4s,5S)-3,5-dihydroxy-4-(4-hydroxy-phenyl)-piperidine-1-carboxylate [Example 109 (h)] with 2-methoxybenzyl 3-chloropropyl ether [Example 120(g)] there was obtained tert-butyl (3R,4s,5S)-3,5-dihydroxy-4-{4-[3-(2-methoxy-benzyloxy)-propoxy]-phenyl}-piperidine-1-carboxylate in the form of an amorphous, colourless solid; MS: 505 (M+NH₄)⁺.

(β) In an analogous manner to that described in Example 1(g), by alkylating tert-butyl (3R,4s,5S)-3,5-dihydroxy-4-{4-[3-(2-methoxy-benzyloxy)-propoxy]-phenyl}-piperidine-1-carboxylate using one equivalent of a benzylic halide there were obtained about equal proportions of unreacted starting material and of the corresponding mono- und dialkylated BOC derivatives. These mixtures were subsequently separated by chromatography:

(a) By alkylation with 4-methoxy-benzyl chloride, tert-butyl (3R,4s,5S)-3,5-bis-(4-methoxy-benzyloxy)-4-{4-[3-(2-methoxy-benzyloxy)-propoxy]-phenyl}-piperidine-1-carboxylate, MS: 746 (M+NH₄)⁺, and tert-butyl (3RS,4SR,5SR)-5-hydroxy-3-(4-methoxy-benzyloxy)-4-{4-[3-(2-methoxy-benzyloxy)-propoxy]-phenyl}-piperidine-1-carboxylate, MS: 626 (M+NH₄)⁺, each as an amorphous, colourless solid;

(b) by alkylation with 2-chloromethyl-pyridine hydrochloride and corresponding excess of base, tert-butyl (3R,4s, 5S)-4-[4-[3-(2-methoxy-benzyloxy)-propoxy]-phenyl]-3,5-bis-(pyridin-2-ylmethoxy)-piperidine-1-carboxylate, MS: 670 (M+H)$^+$, and tert-butyl (3RS,4SR,5SR)-5-hydroxy-4-{4-[3-(2-methoxy-benzyloxy)-propoxy]-phenyl}-3-(pyridin-2-ylmethoxy)-piperidine-1-carboxylate, MS: 579 (M+H)$^+$, each as an amorphous, colourless solid;

(c) by alkylation with 3-chloromethyl-pyridine hydrochloride and corresponding excess of base, tert-butyl (3R,4s,5S)-4-[4-[3-(2-methoxy-benzyloxy)-propoxy]-phenyl]-3,5-bis-(pyridin-3-ylmethoxy)-piperidine-1-carboxylate, MS: 670 (M+H)$^+$, and tert-butyl (3RS,4SR,5SR)-5-hydroxy-4-{4-[3-(2-methoxy-benzyloxy)-propoxy]-phenyl}-3-(pyridin-3-ylmethoxy)-piperidine-1-carboxylate, MS: 579 (M+H)$^+$, each as an amorphous, colourless solid;

(d) by alkylation with 4-chloromethyl-pyridine hydrochloride and corresponding excess of base, tert-butyl (3R,4s,5S)-4-[4-[3-(2-methoxy-benzyloxy)-propoxy]-phenyl]-3,5-bis-(pyridin-4-ylmethoxy)-piperidine-1-carboxylate, MS: 670 (M+H)$^+$, and tert-butyl (3RS,4SR,5SR)-5-hydroxy-4-{4-[3-(2-methoxy-benzyloxy)-propoxy]-phenyl}-3-(pyridin-4-ylmethoxy)-piperidine-1-carboxylate, MS: 579 (M+H)$^+$, each as an amorphous, colourless solid.

(e) by alkylating (3R,4s,5S)-3,5-dihydroxy-4-{4-[3-(2-methoxy-benzyloxy)-propoxy]-phenyl}-piperidin-1-carboxylic acid tert-butylester [Example 112(α)] with 2-chloromethyl-7-(2-trimethylsilanyl-ethoxymethoxy)-naphthalen [Example 6(u)] there was obtained (3RS,4SR,5SR)-5-hydroxy-4-[4-[3-(2-methoxy-benzyloxy)-propoxy]-phenyl]-3-[7-(2-trimethylsilanyl-ethoxymethoxy)-naphthalen-2-ylmethoxy]-piperidin-1-carboxylic acid tert-butylester as a püale yellow oil; MS: 774 (M+H)$^+$. This was then reacted in analogy to Example 95(b) by spliting off the SEM-protecting group to afford (3RS,4SR,5SR)-5-hydroxy-4-[4-[3-(2-methoxy-benzyloxy)-propoxy]-phenyl]-3-(7-hydroxy-naphthalen-2-ylmethoxy)-piperidin-1-carboxylic acid tert-butylester [yellow oil; MS: 644 (M+H)$^+$] which on alkylation with 1-(2-chloro-ethyl)-4-methyl-piperazine hydrochloride(1:2) [Chim. Ther. 4, 283 (1969)] in analogy to Example 90(n) gave (3RS,4SR,5SR)-5-hydroxy-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidin-1-carboxylic acid tert-butylester as a light brown oil; MS: 770 (M+H)$^+$;

(f) by alkylating (3R,4s,5S)-3,5-dihydroxy-4-{4-[3-(2-methoxy-benzyloxy)-propoxy]-phenyl}-piperidin-1-carboxylic acid tert-butylester [Example 112(α)] with 2-chloromethyl-1,4-dimethoxy-naphthalene [J.Org.Chem. (1983), 48(19),3265–3268] there was obtained (3R,4s,5S)-3,5-bis-(1,4-dimethoxy-naphthalen-2-ylmethoxy)-4-[4-[3-(2-methoxy-benzyloxy)-propoxy]-phenyl]-piperidin-1-carboxylic acid tert-butylester, MS: 906 (M+H)$^+$, as a colourless foam and (3RS,4SR,5SR)-3-(1,4-dimethoxy-naphthalen-2-ylmethoxy)-5-hydroxy-4-[4-[3-(2-methoxy-benzyloxy)-propoxy]-phenyl]-piperidin-1-carboxylic acid tert-butylester, MS:705 (M+NH$_4$)$^+$, as a colourless oil.

EXAMPLE 113

The following compounds were obtained by cleavage of the BOC group by means of zinc bromide in methylene chloride analogously to Example 10(b):

1) From tert-butyl (3RS,4SR,5SR)-4-[4-(3-benzyloxy-propoxy)-phenyl]-5-hydroxy-3-(4-hydroxy-benzyloxy)-piperidine-1-carboxylate, (3RS,4SR,5SR)-4-[4-(3-benzyloxy-propoxy)-phenyl]-3-(4-hydroxy-benzyloxy)-piperidin-5-ol as a colourless oil; MS: 464 (M+H)$^+$;

2) from tert-butyl (3R,4s,5S)-4-[4-(3-benzyloxy-propoxy)-phenyl]-3,5-bis-(4-hydroxy-benzyloxy)-piperidine-1-carboxylate,4-[(3R,4s,5S)-5-(4-hydroxybenzyloxy)-4-[4-(3-benzyloxy-propoxy)-phenyl]-piperidin-3-yloxymethyl}-phenol as a colourless oil; MS: 570 (M+H)$^+$.

The BOC derivatives used as starting materials were obtained as follows:

(a) (α) In an analogous manner to that described in Example 1(g), by alkylating tert-butyl (3R,4s,5S)-4-[4-(3-benzyloxy-propoxy)-phenyl]-3,5-dihydroxy-piperidine-1-carboxylate [Example 109(q)] with 1-chloromethyl-4-(2-trimethylsilanyl-ethoxymethoxy)-benzene there were obtained tert-butyl (3RS,4SR,5SR)-4-[4-(3-benzyloxy-propoxy)-phenyl]-5-hydroxy-3-[4-(2-trimethylsilanyl-ethoxymethoxy)-benzyloxy]-piperidine-1-carboxylate, R$_f$: 0.33 (SiO$_2$, n-hexane:ethyl acetate=2:1), and tert-butyl (3R,4s,5S)-4-[4-(3-benzyloxy-propoxy)-phenyl]-3,5-bis-[4-(2-trimethylsilanyl-ethoxymethoxy)-benzyloxy]-piperidine-1-carboxylate, R$_f$: 0.64 (SiO$_2$, n-hexane:ethyl acetate=2:1), each as an amorphous, colourless solid.

(a) (β) A solution of 2.16 g (3.113 mmol) of tert-butyl (3RS,4SR,5SR)-4-[4-(3-benzyloxy-propoxy)-phenyl]-5-hydroxy-3-[4-(2-trimethylsilanyl-ethoxymethoxy)-benzyloxy]-piperidine-1-carboxylate in 50 ml of methanol was treated with 2.02 ml (4.046 mmol) of an anhydrous 2M hydrogen chloride solution in methanol and stirred at room temperature for 2 hours. Subsequently, the mixture was treated with 100 ml of a 95:5 mixture of methylene chloride and methanol (extracted against 5 volume % of a saturated aqueous ammonia solution) and the solution was evaporated on a rotary evaporator at 30° C. The white solid (2.17 g) was thereupon chromatographed on silica gel using a 4:1 mixture of methylene chloride and ethyl acetate as the eluent. There were obtained 780 mg (45% of theory) of tert-butyl (3RS,4SR,5SR)-4-[4-(3-benzyloxy-propoxy)-phenyl]-5-hydroxy-3-(4-hydroxy-benzyloxy)-piperidine-1-carboxylate in the form of a colourless oil; MS: 581 (M+NH$_4$)$^+$.

(b) A solution of 1.1 g (1.18 mmol) of tert-butyl(3R,4s,5S)-4-[4-(3-benzyloxy-propoxy)-phenyl]-3,5-bis-[4-(2-trimethylsilanyl-ethoxymethoxy)-benzyloxy]-piperidine-1-carboxylate in 20 ml of methanol was treated with 1.30 ml (2.60 mmol) of an anhydrous 2M hydrogen chloride solution in methanol and stirred at room temperature for 70 minutes. Subsequently, the mixture was treated with 50 ml of a 95:5 mixture of methylene chloride and methanol (extracted against 5 volume % of a saturated aqueous ammonia solution) and the solution was evaporated on a rotary evaporator at 30° C. The white solid (920 mg) was thereupon chromatographed on silica gel using a 4:1 mixture of methylene chloride and ethyl acetate as the eluent. There were obtained 300 mg (38% of theory) of tert-butyl (3R,4s,5S)-4-[4-(3-benzyloxy-propoxy)-phenyl]-3,5-bis-(4-hydroxy-benzyloxy)-piperidine-1-carboxylate in the form of a colourless oil; R$_f$: 0.26 (SiO$_2$, n-hexane:ethyl acetate=1:1).

The 1-chloromethyl-4-(2-trimethylsilanyl-ethoxymethoxy)-benzene used at the alkylating agent was prepared in analogy to Example 5(a)–(c) from methyl 4-hydroxybenzoate by introducing the SEM group to give methyl 4-(2-trimethylsilanylethoxymethyl)-benzoate. Subsequent reduction with lithium aluminium hydride gave [4-(2-trimethylsilanylethoxy-methoxy)-phenyl]-methanol and chlorination of this gave 1-chlormethyl-4-(2-trimethylsilanyl-ethoxymethoxy)-benzene as a colourless oil; MS: 272 (M)$^+$.

EXAMPLE 114

The following compounds were obtained in analogy to the procedure described in Example 1(e) by cleavage of the SEM group by means of tetrabutylammonium fluoride in tetrahydrofuran:

1) From 2-trimethylsilylethyl (3RS,4RS)-4-(4-fluoro-phenyl)-3-[4-(2-morpholin-4-yl-ethoxy)-naphthalen-2-ylmethoxy]-piperidine-1-carboxylate, (3RS,4RS)-4-(4-fluoro-phenyl)-3-[4-(2-morpholin-4-yl-ethoxy)-naphthalen-2-ylmethoxy]-piperidine as a colourless solid; MS: 465 (M)$^+$;
2) from 2-trimethylsilylethyl (3RS,4RS)-4-(4-fluoro-phenyl)-3-[8-(3-methoxy-propoxy)-naphthalen-2-ylmethoxy]-piperidine-1-carboxylate, (3RS,4RS)-4-(4-fluoro-phenyl)-3-[8-(3-methoxy-propoxy)-naphthalen-2-ylmethoxy]-piperidine as a colourless solid; MS: 424 (M)$^+$;
3) from 2-trimethylsilylethyl (3RS,4RS)-4-(4-fluoro-phenyl)-3-[5-(3-methoxy-propoxy)-naphthalen-2-ylmethoxy]-piperidine-1-carboxylate, (3RS,4RS)-4-(4-fluoro-phenyl)-3-[5-(3-methoxy-propoxy)-naphthalen-2-ylmethoxy]-piperidine as a colourless solid; MS: 424 (M)$^+$;
4) from 2-trimethylsilylethyl (3RS,4RS)-4-(4-fluoro-phenyl)-3-[7-(3-methoxy-propoxy)-naphthalen-2-ylmethoxy]-piperidine-1-carboxylate, (3RS,4RS)-4-(4-fluoro-phenyl)-3-[7-(3-methoxy-propoxy)-naphthalen-2-ylmethoxy]-piperidine as a colourless solid; MS: 424 (M)$^+$.

The SEM derivatives used as starting materials were prepared as follows:

(a) From 2-trimethylsilylethyl (3RS,4RS)-4-(4-fluorophenyl)-3-(4-hydroxy-naphthalen-2-ylmethoxy)-piperidine-1-carboxylate [Example 5(g)] and 4-(2-chloroethyl)-morpholine hydrochloride,2-trimethylsilylethyl (3RS,4RS)-4-(4-fluoro-phenyl)-3-[4-(2-morpholin-4-yl-ethoxy)-naphthalen-2-ylmethoxy]-piperidine-1-carboxylate as a yellow oil; MS: 609 (M)$^+$;
(b) from 2-trimethylsilylethyl (3RS,4RS)-4-(4-fluorophenyl)-3-(8-hydroxy-naphthalen-2-ylmethoxy)-piperidine-1-carboxylate [Example 6(dd)] and 1-chloro-3-methoxypropane,2-trimethylsilylethyl (3RS,4RS)-4-(4-fluoro-phenyl)-3-[8-(3-methoxy-propoxy)-naphthalen-2-ylmethoxy]-piperidine-1-carboxylate as a light yellow oil; MS: 568 (M)$^+$;
(c) from 2-trimethylsilylethyl (3RS,4RS)-4-(4-fluorophenyl)-3-(5-hydroxy-naphthalen-2-ylmethoxy)-piperidine-1-carboxylate [Example 6(l)] and 1-chloro-3-methoxypropane, 2-trimethylsilylethyl (3RS,4RS)-4-(4-fluoro-phenyl)-3-[5-(3-methoxy-propoxy)-naphthalen-2-ylmethoxy]-piperidine-1-carboxylate as a colourless resin, which was used in the next step without further purification and characterization;
(d) from 2-trimethylsilylethyl (3RS,4RS)-4-(4-fluorophenyl)-3-(7-hydroxy-naphthalen-2-ylmethoxy)-piperidine-1-carboxylate [Example 6(x)] and 1-chloro-3-methoxypropane, 2-trimethylsilylethyl (3RS,4RS)-4-(4-fluoro-phenyl)-3-[7-(3-methoxy-propoxy)-naphthalen-2-ylmethoxy]-piperidine-1-carboxylate as a colourless resin, which was used in the next step without further purification and characterization.

EXAMPLE 115

(3RS,4RS)-4-(4-Fluorophenyl)-3-[4-[3-hydroxy-benzyloxy]-naphthalen-2-ylmethoxy]-piperidine was obtained as follows in an analogous manner to that described in Example 5:

(a) In an analogous manner to that described in Example 5(a)–(d), firstly from ethyl 3-hydroxybenzoate by introduction of the SEM group there was obtained ethyl 3-(2-trimethylsilylethoxymethoxy)-benzoate as a colourless oil; MS 238 [M-($C_2H_4$+$CH_2O$)]$^+$. Subsequent reduction gave [3-(2-trimethylsilylethoxy-methoxy)-phenyl]-methanol, MS: 196 [M-($C_2H_4$+$CH_2O$)]$^+$, as a colourless oil, chlorination of which yielded 1-chloromethyl-3-(2-trimethylsilyl-ethoxymethoxy)-benzene as a colourless oil; MS: 214, 216 [M-($C_2H_4$+$CH_2O$)]$^+$. Subsequent alkylation of 2-trimethylsilylethyl (3RS,4RS)-4-(4-fluorophenyl)-3-(4-hydroxy-naphthalen-2-ylmethoxy)-piperidine-1-carboxylate [Example 5(g)] with 1-chloromethyl-3-(2-trimethylsilyl-ethoxymethoxy)-benzene yielded 2-trimethylsilylethyl (3RS,4RS)-4-(4-fluorophenyl)-3-[4-[3-(2-trimethylsilyl-ethoxymethoxy)-benzyloxy]-naphthalen-2-ylmethoxy]-piperidine-1-carboxylate as a light yellow oil; MS: 749 (M+$NH_4$)$^+$.
(b) From 2-trimethylsilylethyl (3RS,4RS)-4-(4-fluorophenyl)-3-[4-[3-(2-trimethylsilyl-ethoxymethoxy)-benzyloxy]-naphthalen-2-ylmethoxy]-piperidine-1-carboxylate there was obtained in analogy to the procedure described in Example 1(e) by cleavage of the 2-trimethylsilylethyl carbamate with tetrabutyl-ammonium fluoride in tetrahydrofuran (3RS,4RS)-4-(4-fluorophenyl)-3-[4-[3-(2-trimethylsilyl-ethoxymethoxy)-benzyloxy]-naphthalen-2-ylmethoxy]-piperidine, MS: 588 (M+H)$^+$, as a light yellow oil, from which by cleavage of the SEM group by means of a 2N solution of hydrogen chloride in methanol analogously to the procedure described in Example 5(g) there was obtained (3RS,4RS)-4-(4-fluorophenyl)-3-[4-[3-hydroxy-benzyloxy]-naphthalen-2-ylmethoxy]-piperidine as a colourless solid; MS: 458 (M+H)$^+$.

EXAMPLE 116

The following compound was obtained in an analogous manner to that described in Example 10(b) by cleavage of the BOC group by means of zinc bromide in methylene chloride:

From tert-butyl (3RS,4RS)-3-(naphthalen-2-ylmethoxy)-4-[4-[2-(5-phenyl-[1,3,4]oxadiazol-2-yl)-ethyl]-phenyl]-piperidine-1-carboxylate by means of zinc bromide in methylene chloride, (3RS,4RS)-3-(naphthalen-2-ylmethoxy)-4-[4-[2-(5-phenyl-[1,3,4]oxadiazol-2-yl)-ethyl]-phenyl]-piperidine as a colourless solid; MS: 490 (M+H).

The BOC derivative used as the starting material was prepared as follows:

(a) From tert-butyl (3RS,4RS)-4-[4-(2-carboxy-ethyl)-phenyl]-3-(naphthalen-2-ylmethoxy)piperidine-1-carboxylate [Example 86(II)] by condensation with benzoic acid hydrazide in the presence of EDC in an analogous manner to that described in Example 38, tert-butyl (3RS,4RS)-4-[4-[3-(N'-benzoyl-hydrazino)-3-oxo-propyl]-phenyl]-3-(naphthalen-2-ylmethoxy)-piperidine-1-carboxylate as a colourless resin; MS: 608 (M+H)$^+$.
(b) A solution of 106 mg (0.174 mmol) of tert-butyl (3RS,4RS)-4-[4-[3-(N'-benzoyl-hydrazino)-3-oxo-propyl]-phenyl]-3-(naphthalen-2-ylmethoxy)-piperidine-1-carboxylate in 1.5 ml of hexamethyldisilazane was treated with 39 μl (0.039 mmol) of a 1M solution of tetrabutylammonium fluoride in tetrahydrofuran and heated to reflux for 20 hours. For the working-up, the reaction mixture was treated with 50 ml of a 1:1 mixture of methylene chloride and water, the organic phase was subsequently separated and the aqueous phase was back-extracted twice with 25 ml of methylene chloride each time. The combined organic phases were dried over sodium sulphate and evaporated under reduced pressure. The crude product was purified by flash chromatography on silica gel with a 7:3 mixture of hexane and ethyl acetate as the eluent. There were obtained 70 mg (68% of theory) of tert-butyl (3RS,4RS)-3-(naphthalen-2-ylmethoxy)-4-[4-[2-(5-phenyl-[1,3,4]oxadiazol-2-yl)-ethyl]-phenyl]-piperidine-1-carboxylate as a colourless solid; MS: 590 (M+H)$^+$.

EXAMPLE 117

The following compound was obtained in an analogous manner to that described in Example 22(l) by cleavage of the BOC group by means of hydrogen chloride in methanol:

From tert-butyl (3RS,4RS)-4-[4-(3-benzyloxy-propyl)-phenyl]-3-(naphthalen-2-ylmethoxy)-piperidine-1-carboxylate, (3RS,4RS)-4-[4-(3-benzyloxy-propyl)-phenyl]-3-(naphthalen-2-ylmethoxy)-piperidine as a colourless, amorphous solid; MS: 467 (M+H)$^+$.

The BOC derivative used as the starting material was prepared as follows:

In an analogous manner to that described in Example 1(g), by alkylating tert-butyl (3RS,4RS)-4-[4-(3-hydroxy-propyl)-phenyl]-3-(naphthalen-2-ylmethoxy)-piperidine-1-carboxylate [Example 24(t)] with benzyl bromide therer was obtained tert-butyl (3RS,4RS)-4-[4-(3-benzyloxy-propyl)-phenyl]-3-(naphthalen-2-ylmethoxy)-piperidine-1-carboxylate as a colourless, amorphous solid, which was used in the next step without characterization.

EXAMPLE 118

The following compounds were prepared by cleavage of the BOC group by means of hydrogen chloride in methanol analogously to Example 22(l):

1) From tert-butyl (3RS,4RS)-3-(naphthalen-2-ylmethoxy)-4-[4-(2-phenoxy-ethoxymethyl)-phenyl]-piperidine-1-carboxylate, (3RS,4RS)-3-(naphthalen-2-ylmethoxy)-4-[4-(2-phenoxy-ethoxymethyl)-phenyl]-piperidine as a light yellow oil; MS: 468 (M+H)$^+$;
2) from tert-butyl (3RS,4RS)-3-(naphthalen-2-ylmethoxy)-4-[4-(3-phenoxy-propoxymethyl)-phenyl]-piperidine-1-carboxylate, (3RS,4RS)-3-(naphthalen-2-ylmethoxy)-4-[4-(3-phenoxy-propoxymethyl)-phenyl]-piperidine as a colourless foam; MS: 482 (M+H)$^+$;
3) from tert-butyl (3RS,4RS)-4-[4-(3-benzyloxy-propoxymethyl)-phenyl]-3-(naphthalen-2-ylmethoxy)-piperidine-1-carboxylate, (3RS,4RS)-4-[4-(3-benzyloxy-propoxymethyl)-phenyl]-3-(naphthalen-2-ylmethoxy)-piperidine as a light yellow oil; MS: 496 (M+H)$^+$;
4) from tert-butyl (3RS,4RS)-4-[4-[3-(4-fluoro-phenoxy)-propoxymethyl]-phenyl]-3-(naphthalen-2-ylmethoxy)-piperidine-1-carboxylate, (3RS,4RS)-4-[4-[3-(4-fluoro-phenoxy)-propoxymethyl]-phenyl]-3-(naphthalen-2-ylmethoxy)-piperidine as a light yellow oil; MS: 500 (M+H)$^+$.

The BOC derivatives used as starting materials were prepared as follows by alkylating tert-butyl (3RS,4RS)-4-(4-hydroxymethyl-phenyl)-3-(naphthalen-2-ylmethoxy)-piperidine-1-carboxylate [Example 22(i)] in an analogous manner to that described in Example 1(g):

(a) By alkylation with b-bromophenetol, tert-butyl (3RS, 4RS)-3-(naphthalen-2-ylmethoxy)-4-[4-(2-phenoxy-ethoxymethyl)-phenyl]-piperidine-1-carboxylate, as a colourless resin, which was used in the next step without further characterization;
(b) by alkylation with 3-phenoxypropyl bromide, tert-butyl (3RS,4RS)-3-(naphthalen-2-ylmethoxy)-4-[4-(3-phenoxy-propoxymethyl)-phenyl]-piperidine-1-carboxylate as a colourless oil; MS: 582 (M+H)$^+$;
(c) by alkylation with benzyl 3-bromopropyl ether, tert-butyl (3RS,4RS)-4-[4-(3-benzyloxy-propoxymethyl)-phenyl]-3-(naphthalen-2-ylmethoxy)-piperidin-1-carboxylate as a colourless resin; MS: 596 (M+H)$^+$;
(d) by alkylation with 1-(3-chloropropoxy)-4-fluorobenzene, tert-butyl (3RS,4RS)-4-[4-[3-(4-fluoro-phenoxy)-propoxymethyl]-phenyl]-3-(naphthalen-2-ylmethoxy)-piperidine-1-carboxylate as a colourless resin; MS: 600 (M+H)$^+$.

EXAMPLE 119

The following compounds were obtained by cleavage of the BOC group by means of hydrogen chloride in methanol analogously to Example 22(l) or by means of zinc bromide in methylene chloride analogously to Example 10(b):

1) From tert-butyl (3RS,4RS)-4-[4-(3-benzyloxy-propoxy)-phenyl]-3-(8-hydroxy-naphthalen-2-ylmethoxy)-piperidine-1-carboxylate by means of hydrogen chloride in methanol, (3RS,4RS)-4-[4-(3-benzyloxy-propoxy)-phenyl]-3-(8-hydroxy-naphthalen-2-ylmethoxy)-piperidine as a colourless solid; MS: 498 (M+H)$^+$;
2) from tert-butyl (3RS,4RS)-4-[4-(3-benzyloxy-propoxy)-phenyl]-3-[8-(3-methoxy-ethoxy)-naphthalen-2-ylmethoxy]-piperidine-1-carboxylate by means of hydrogen chloride in methanol, (3RS,4RS)-4-[4-(3-benzyloxy-propoxy)-phenyl]-3-[8-(3-methoxy-ethoxy)-naphthalen-2-ylmethoxy]-piperidine as a light yellow oil; MS: 556 (M+H)$^+$;
3) from tert-butyl (3RS,4RS)-4-[4-(3-benzyloxy-propoxy)-phenyl]-3-[8-(3-methoxy-propoxy)-naphthalen-2-ylmethoxy]-piperidine-1-carboxylate by means of hydrogen chloride in methanol, (3RS,4RS)-4-[4-(3-benzyloxy-propoxy)-phenyl]-3-[8-(3-methoxy-propoxy)-naphthalen-2-ylmethoxy]-piperidine as a light yellow oil; MS: 570 (M+H)$^+$;
4) from tert-butyl (3RS,4RS)-4-[4-(3-benzyloxy-propoxy)-phenyl]-3-(8-methoxycarbonylmethoxy-naphthalen-2-ylmethoxy)-piperidine-1-carboxylate by means of hydrogen chloride in methanol, (3RS,4RS)-4-[4-(3-benzyloxy-propoxy)-phenyl]-3-(8-methoxycarbonylmethoxy-naphthalen-2-ylmethoxy)-piperidine as a colourless solid; MS: 570 (M+H)$^+$;
5) from tert-butyl (3RS,4RS)-4-[4-(3-benzyloxy-propoxy)-phenyl]-3-(8-carbamoylmethoxy-naphthalen-2-ylmethoxy)-piperidine-1-carboxylate by means of zinc bromide in methylene chloride, (3RS,4RS)-4-[4-(3-benzyloxy-propoxy)-phenyl]-3-(8-carbamoylmethoxy-naphthalen-2-ylmethoxy)-piperidine as a colourless foam; MS: 555 (M+H)$^+$;

The BOC derivatives used as starting materials were prepared as follows by alkylating tert-butyl (3RS,4RS)-4-[4-(3-benzyloxy-propoxy)-phenyl]-3-(8-hydroxy-naphthalen-2-ylmethoxy)-piperidine-1-carboxylate in an analogous manner to that described in Examples 1 and 5:

(a) By alkylation with 2-methoxyethyl bromide, tert-butyl (3RS,4RS)-4-[4-(3-benzyloxy-propoxy)-phenyl]-3-[8-(3-methoxy-ethoxy)-naphthalen-2-ylmethoxy]-piperidine-1-carboxylate as a colourless resin, which was used in the next step without characterization;
(b) by alkylation with 1-chloro-3-methoxypropane, tert-butyl (3RS,4RS)-4-[4-(3-benzyloxy-propoxy)-phenyl]-3-[8-(3-methoxy-propoxy)-naphthalen-2-ylmethoxy]-piperidine-1-carboxylate as a light yellow resin, which was used in the next step without characterization;
(c) by alkylation with methyl bromoacetate, tert-butyl (3RS, 4RS)-4-[4-(3-benzyloxy-propoxy)-phenyl]-3-(8- methoxycarbonylmethoxy-naphthalen-2-ylmethoxy)-piperidine-1-carboxylate as a colourless solid; MS: 670 (M+H)⁺;

(d) by alkylation with iodoacetamide, tert-butyl (3RS,4RS)-4-[4-(3-benzyloxy-propoxy)-phenyl]-3-(8-carbamoylmethoxy-naphthalen-2-ylmethoxy)-piperidine-1-carboxylate as a light yellow resin, which was used in the next step without characterization;

The tert-butyl (3RS,4RS)-4-[4-(3-benzyloxy-propoxy)-phenyl]-3-(8-hydroxy-naphthalen-2-ylmethoxy)-piperidine-1-carboxylate used as the starting material was prepared as follows as described in Examples 1, 5 and 6:

(a) By alkylating tert-butyl (3RS,4RS)-4-[4-(3-benzyloxy-propoxy)-phenyl]-3-hydroxy-piperidine-1-carboxylate [Example 86(n)] with 2-chloromethyl-8-(2-trimethylsilylethoxy-methoxy)-naphthalene [Example 6(aa)] there was obtained tert-butyl (3RS,4RS)-4-[4-(3-benzyloxy-propoxy)-phenyl]-3-[8-(2-trimethylsilanyl-ethoxymethoxy)-naphthalen-2-ylmethoxyperidine-1-carboxylate as a light yellow oil; MS: 728 (M+H)⁺.

(b) A solution of 552 mg of tert-butyl (3RS,4RS)-4-[4-(3-benzyloxy-propoxy)-phenyl]-3-[8-(2-trimethylsilanyl-ethoxymethoxy)-naphthalen-2-ylmethoxypiperidine-1-carboxylate in 4 ml of methanol was treated with 4 ml of a 2N solution of hydrogen chloride in methanol and stirred at room temperature for 45 minutes. For the working-up, the mixture was partitioned between 50 ml of ethyl acetate and 50 ml of aqueous 5% sodium hydrogen carbonate solution and then the organic phase was separated. The aqueous phase was extracted three times with 25 ml of ethyl acetate each time. The combined ethyl acetate phases were dried over magnesium sulphate and finally the solvent was distilled off under reduced pressure. The crude product (538 mg) was purified by chromatography on silica gel with a 1:2 mixture of ethyl acetate and hexane as the eluent. There were obtained 348 mg (77% of theory) of tert-butyl (3RS,4RS)-4-[4-(3-benzyloxy-propoxy)-phenyl]-3-(8-hydroxy-naphthalen-2-ylmethoxy)-piperidine-1-carboxylate as a colourless foam; MS: 598 (M+H)⁺.

EXAMPLE 120

The following compounds were prepared by cleavage of the BOC group by means of hydrogen chloride in methanol analogously to Example 22(l):

1) From tert-butyl (3RS,4RS)-4-[4-(3-benzyloxy-propoxy)-phenyl]-3-(quinolin-7-ylmethoxy)-piperidine-1-carboxylate, (3RS,4RS)-4-[4-(3-benzyloxy-propoxy)-phenyl]-3-(quinolin-7-ylmethoxy)-piperidine as a colourless oil; MS: 483 (M+H)⁺;

2) from tert-butyl (3RS,4RS)-4-[4-(3-benzyloxy-propoxy)-phenyl]-3-(1,2,3,4-tetrahydro-quinolin-7-ylmethoxy)-piperidine-1-carboxylate, (3RS,4RS)-4-[4-(3-benzyloxy-propoxy)-phenyl]-3-(1,2,3,4-tetrahydro-quinolin-7-ylmethoxy)-piperidine as a light yellow resin; MS: 487 (M+H)⁺;

3) from (3RS,4RS)-7-[4-[4-(3-benzyloxy-propoxy)-phenyl]-1-tert-butoxycarbonyl-piperidin-3-yloxymethyl]-1-methyl-quinolinium iodide, (3RS,4RS)-7-[4-[4-(3-benzyloxy-propoxy)-phenyl]-piperidin-3-yloxymethyl]-1-methyl-quinolinium chloride as a colourless solid; MS: 497 (M)⁺;

4) from tert-butyl (3RS,4RS)-4-[4-(3-benzyloxy-propoxy)-phenyl]-3-(1-methyl-1,2,3,4-tetrahydro-quinolin-7-ylmethoxy)-piperidine-1-carboxylate, (3RS,4RS)-4-[4-(3-benzyloxy-propoxy)-phenyl]-3-(1-methyl-1,2,3,4-tetrahydro-quinolin-7-ylmethoxy)-piperidine as a light yellow oil; MS: 501 (M+H)⁺;

5) from tert-butyl (3RS,4RS)-4-[4-(3-benzyloxy-propoxy)-phenyl]-3-(isoquinolin-6-ylmethoxy)-piperidine-1-carboxylate, (3RS,4RS)-4-[4-(3-benzyloxy-propoxy)-phenyl]-3-(isoquinolin-6-ylmethoxy)-piperidine as a light yellow resin; MS: 483 (M+H)⁺;

6) from tert-butyl (3RS,4RS)-4-[4-(3-benzyloxy-propoxy)-phenyl]-3-(2-methyl-1,2,3,4-tetrahydro-isoquinolin-6-ylmethoxy)-piperidine-1-carboxylate, (3RS,4RS)-4-[4-(3-benzyloxy-propoxy)-phenyl]-3-(2-methyl-1,2,3,4-tetrahydro-isoquinolin-6-ylmethoxy)-piperidine as a light yellow oil; MS: 501 (M+H)⁺;

7) from tert-butyl (3RS,4RS)-4-[4-[3-(2-methoxy-benzyloxy)-propoxy]-phenyl]-3-(quinolin-7-ylmethoxy)-piperidine-1-carboxylate, (3RS,4RS)-4-[4-[3-(2-methoxy-benzyloxy)-propoxy]-phenyl]-3-(quinolin-7-ylmethoxy)-piperidine as a light yellow resin; MS: 513 (M+H)⁺;

8) from tert-butyl (3RS,4RS)-3-(1H-benzimidazol-5-ylmethoxy)-4-[4-(3-benzyloxy-propoxy)-phenyl]-piperidine-1-carboxylate with hydrogen chloride in methanol, (3RS,4RS)-3-(1H-benzimidazol-5-ylmethoxy)-4-[4-(3-benzyloxy-propoxy)-phenyl]-piperidine as a colourless resin; MS: 472 (M+H)⁺;

9) from tert-butyl (3RS,4RS)-4-[4-[3-(2-methoxy-benzyloxy)-propoxy]-phenyl]-3-(1-oxy-quinolin-7-ylmethoxy)-piperidine-1-carboxylate with hydrogen chloride in methanol, (3RS,4RS)-4-[4-[3-(2-methoxy-benzyloxy)-propoxy]-phenyl]-3-(1-oxy-quinolin-7-ylmethoxy)-piperidine as a colourless solid; MS: 529 (M+H)⁺;

10) from tert-butyl (3RS,4RS)-4-[4-[3-(2-methoxy-benzyloxy)-propoxy]-phenyl]-3-(2-oxo-1,2-dihydro-quinolin-7-ylmethoxy)-piperidine-1-carboxylate with zinc bromide in methylene chloride, (3RS,4RS)-4-[4-[3-(2-methoxy-benzyloxy)-propoxy]-phenyl]-3-(2-oxo-1,2-dihydro-quinolin-7-ylmethoxy)-piperidine as a colourless solid; MS: 529 (M+H)⁺;

11) from tert-butyl (3RS,4RS)-3-(isoquinolin-7-ylmethoxy)-4-[4-[3-(2-methoxy-benzyloxy)-propoxy]-phenyl]-piperidine-1-carboxylate with hydrogen chloride in methanol, (3RS,4RS)-3-(isoquinolin-7-ylmethoxy)-4-[4-[3-(2-methoxy-benzyloxy)-propoxy]-phenyl]-piperidine as a light yellow oil; MS: 513 (M+H)⁺;

12) from tert-butyl (3RS,4RS)-4-[4-[3-(2-methoxy-benzyloxy)-propoxy]-phenyl]-3-(1,2,3,4-tetrahydro-quinolin-7-ylmethoxy)-piperidine-1-carboxylate with hydrogen chloride in methanol, (3RS,4RS)-4-[4-[3-(2-methoxy-benzyloxy)-propoxy]-phenyl]-3-(1,2,3,4-tetrahydro-quinolin-7-ylmethoxy)-piperidine as a pale yellow syrup; MS: 517 (M+H)⁺.

13) from (3RS,4RS)-4-[4-[3-(2-methoxy-benzyloxy)-propoxy]-phenyl]-3-(quinoxalin-6-ylmethoxy)-piperidin-1-carboxylic acid tert-butyl ester with zinc bromide in methylene chloride, (3RS,4RS)-4-[4-[3-(2-methoxy-benzyloxy)-propoxy]-phenyl]-3-(quinoxalin-6-ylmethoxy)-piperidine as a yellow oil; MS: 514 (M+H)⁺.

The BOC derivatives used as starting materials were prepared in an analogous manner to that described in Examples 1 and 5:

(a) By alkylating tert-butyl (3RS,4RS)-4-[4-(3-benzyloxy-propoxy)-phenyl]-3-hydroxy-piperidine-1-carboxylate [Example 86(n)] with 7-bromomethyl-quinoline hydrobromide [J.Am.Chem.Soc. 77,1054(1955)] analogously to Example 1(g) there was obtained tert-butyl (3RS,4RS)-4-[4-(3-benzyloxy-propoxy)-phenyl]-3-(quinolin-7-ylmethoxy)-piperidine-1-carboxylate as a colourless oil; MS: 583 (M+H)⁺.

(b) A solution of 116 mg (0.20 mmol) of tert-butyl (3RS,4RS)-4-[4-(3-benzyloxy-propoxy)-phenyl]-3-(quinolin-7-ylmethoxy)-piperidine-1-carboxylate in 1.5 ml of methanol was treated with 24 mg (0.1 mmol) of nickel(II) chloride hexahydrate and 30 mg (0.8 mmol) of sodium borohydride. The dark suspension was stirred at 0° C. for 1 hour and at room temperature for a further hour. For the working-up, the mixture was partitioned between 20 ml of ether and 5 ml of aqueous saturated ammonium chloride solution and then the organic phase was separated. The aqueous phase was extracted three times with 20 ml of ether each time. The combined ether phases were dried over magnesium sulphate and finally the solvent was distilled off under reduced pressure. The crude product (150 mg) was purified by chromatography on silica gel with a 1:1 mixture of ethyl acetate and hexane as the eluent. There were obtained 70 mg (60% of theory) of tert-butyl (3RS,4RS)-4-[4-(3-benzyloxy-propoxy)-phenyl]-3-(1,2,3,4-tetrahydro-quinolin-7-ylmethoxy)-piperidine-1-carboxylate as a light yellow resin; MS: 587 $(M+H)^+$.

(c) A solution of 146 mg (0.25 mmol) of tert-butyl (3RS,4RS)-4-[4-(3-benzyloxy-propoxy)-phenyl]-3-(quinolin-7-ylmethoxy)-piperidine-1-carboxylate in 0.5 ml of absolute chloroform was treated with 40 μl (0.6 mmol) of methyl iodide and heated to reflux for 3 hours. Subsequently, a further 40 μl of methyl iodide were added and the mixture was heated at reflux temperature overnight. The solvent was distilled off under reduced pressure and there was obtained crude (3RS,4RS)-7-[4-[4-(3-benzyloxy-propoxy)-phenyl]-1-tert-butoxycarbonyl-piperidin-3-yloxymethyl]-1-methyl-quinolinium iodide, which was used in the next step without characterization.

(d) A solution of 91 mg (0.125 mmol) of crude (3RS,4RS)-7-[4-[4-(3-benzyloxy-propoxy)-phenyl]-1-tert-butoxycarbonyl-piperidin-3-yloxymethyl]-1-methyl-quinolinium iodide in 1 ml of methanol was treated at 0° C. with 47 mg (0.125 mmol) of sodium borohydride, then warmed to room temperature and stirred at room temperature for 2 hours. For the working-up, the mixture was partitioned between 50 ml of ethyl acetate and 50 ml of aqueous 5% sodium hydrogen carbonate solution and thereafter the organic phase was separated. The aqueous phase was extracted three times with 25 ml of ethyl acetate each time. The combined ethyl acetate phases were dried over magnesium sulphate and finally the solvent was distilled off under reduced pressure. The crude tert-butyl (3RS,4RS)-4-[4-(3-benzyloxy-propoxy)-phenyl]-3-(1-methyl-1,2,3,4-tetrahydro-quinolin-7-ylmethoxy)-piperidine-1-carboxylate was used in the next step without characterization.

(e) By alkylating tert-butyl (3RS,4RS)-4-[4-(3-benzyloxy-propoxy)-phenyl]-3-hydroxy-piperidine-1-carboxylate [Example 86(n)] with 6-bromomethyl-isoquinoline hydrobromide (Example 4) analogously to Example 1(g) there was obtained tert-butyl (3RS,4RS)-4-[4-(3-benzyloxy-propoxy)-phenyl]-3-(isoquinolin-6-ylmethoxy)-piperidine-1-carboxylate as a colourless oil; MS: 583 $(M+H)^+$.

(f) In an analogous manner to that previously described, by alkylating tert-butyl (3RS,4RS)-4-[4-(3-benzyloxy-propoxy)-phenyl]-3-(isoquinolin-6-ylmethoxy)-piperidine-1-carboxylate with methyl iodide in chloroform and subsequently reducing with sodium borohydride in methanol there was obtained tert-butyl (3RS,4RS)-4-[4-(3-benzyloxy-propoxy)-phenyl]-3-(2-methyl-1,2,3,4-tetrahydro-isoquinolin-6-ylmethoxy)-piperidine-1-carboxylate, which was used in the next step as the crude product without further characterization.

(g) (α) A solution of 5.2 g (17.7 mmol) of tert-butyl (3RS,4RS)-3-hydroxy-4-(4-hydroxy-phenyl)-piperidine-1-carboxylate [Example 46(b)] and 3.37 ml (3.8 g,17.7 mmol) of 2-methoxybenzyl 3-chloropropyl ether in 18 ml of absolute DMF was treated with 3.7 g (26.9 mmol) of anhydrous potassium carbonate and stirred at 120° C. for 60 h. For the working-up, the reaction mixture was partitioned between 250 ml of water and 250 ml of ethyl acetate. The organic phase was separated and the aqueous phase was extracted three times with 100 ml of ethyl acetate each time. The combined organic phases were washed twice with 100 ml of water each time and finally the solvent was distilled off under reduced pressure. The crude product was crystallized by treatment with ether. There were obtained 7.3 g (88% of theory) of tert-butyl (3RS,4RS)-3-hydroxy-4-[4-[3-(2-methoxy-benzyloxy)-propoxy]-phenyl]-piperidine-1-carboxylate as a colourless solid; MS: 472 $(M+H)^+$.

(β) Subsequent alkylation of tert-butyl (3RS,4RS)-3-hydroxy-4-[4-[3-(2-methoxy-benzyloxy)-propoxy]-phenyl]-piperidine-1-carboxylate with 7-bromomethyl-quinoline hydrobromide ([J.Am.Chem.Soc. 77, 1054(1955)] analogously to Example 1(g) gave tert-butyl (3RS,4RS)-4-[4-[3-(2-methoxy-benzyloxy)-propoxy]-phenyl]-3-(quinolin-7-ylmethoxy)-piperidine-1-carboxylate as a light yellow resin; MS: 613 $(M+H)^+$.

The 2-methoxybenzyl 3-chloropropyl ether used as the alkylating agent was prepared as follows:

A solution of 24.6 g (0.157 mmol) of 2-methoxybenzyl chloride and 26 ml (29.4 g,0.311 mmol) of 3-chloro-1-propanol in 150 ml of absolute DMF was treated portionwise at 10° C. within 2.5 hours with 8.4 g (0.196 mmol) of sodium hydride dispersion (55% in refined oil) and stirred at room temperature for 1 hour. Subsequently, a further 1.0 g (0.023 mmol) of sodium hydride dispersion was added at room temperature and the mixture was stirred for a further 3 hours. For the working-up, the reaction mixture was partitioned between 500 ml of water and 500 ml of ethyl acetate. The organic phase was separated. The aqueous phase was extracted four times with 250 ml of ethyl acetate each time. The combined organic phases were washed twice with 250 ml of water each time and finally the solvent was distilled off under reduced pressure. The crude product (44 g) was purified by chromatography on silica gel with a 1:2 mixture of methylene chloride and hexane as the eluent. There were obtained 25.0 g (74% of theory) of 2-methoxybenzyl 3-chloropropyl ether as a colourless oil; MS: 214. 216 $(M)^+$.

(h) (α) A solution of 2.15 g (14.50 mmol) of (1H-benzimidazol-5-yl)-methanol (DE 2,813,523] in 55 ml of absolute DMF was treated with 4.01 g of anhydrous potassium carbonate and dropwise with 3.15 ml (2.96 g,16.02 mmol) of SEM chloride. After 3 hours at room temperature the reaction mixture was filtered and the majority of the DMF was distilled off under a high vacuum. For the working-up, the residue was partitioned between 60 ml of ethyl acetate and 60 ml of water and thereafter the organic phase was separated. The aqueous phase was extracted twice with 60 ml of ethyl acetate each time. The combined organic phases were dried over magnesium sulphate and finally the solvent was distilled off under reduced pressure. The crude product (4.57 g) was purified by chromatography on silica gel with a 14:1:0.1 mixture of methylene chloride, methanol and 28% ammonia solution as the eluent. There were obtained 1.26 g (31% of theory) of a 1:2 or 2:1 mixture of [3-(2-trimethylsilyl-ethoxymethyl)-3H-benzimidazol-5-yl]-methanol and [1-(2-trimethylsilyl-ethoxy-methyl)-1H-benzimidazol-5-yl]-methanol as an orange coloured oil; MS: 278 $(M)^+$.

(β) Chlorination of a 1:2 or 2:1 mixture of [3-(2-trimethylsilyl-ethoxymethyl)-3H-benzimidazol-5-yl]-methanol and [1-(2-trimethylsilyl-ethoxymethyl)-1H-benzimidazol-5-yl]-methanol was effected in an analogous manner to that described in Example 5(c) and yielded a 1:2 or 2:1 mixture of 6-chloromethyl-1-(2-trimethylsilyl-ethoxymethyl)-1H-benzimidazole and 5-chloromethyl-1-(2-trimethylsilyl-ethoxymethyl)-1H-benzimidazole as a light yellow oil; MS: 296, 298 (M)$^+$.

(γ) Alkylation of tert-butyl (3RS,4RS)-4-[4-(3-benzyloxy-propoxy)-phenyl]-3-hydroxy-piperidine-1-carboxylate [Example 86(n)] with a 1:2 or 2:1 mixture of 6-chloromethyl-1-(2-trimethylsilyl-ethoxymethyl)-1H-benzimidazole and 5-chloromethyl-1-(2-trimethylsilyl-ethoxymethyl)-1H-benzimidazole yielded a 2:1 or 1:2 mixture of tert-butyl (3RS,4RS)-4-[4-(3-benzyloxy-propoxy)-phenyl]-3-[1-(2-trimethylsilyl-ethoxymethyl)-1H-benzimidazol-5-ylmethoxy]-piperidine-1-carboxylate and tert-butyl (3RS,4RS)-4-[4-(3-benzyloxy-propoxy)-phenyl]-3-[3-(2-trimethylsilanyl-ethoxymethyl)-3H-benzimidazol-5-ylmethoxy]-piperidine-1-carboxylate as a yellow oil; MS: 702 (M+H)$^+$.

(δ) A solution of 328 mg (0.467 mmol) of a 2:1 or 1:2 mixture of (3RS,4RS)-4-[4-(3-benzyloxy-propoxy)-phenyl]-3-[1-(2-trimethylsilyl-ethoxymethyl)-1H-benzimidazol-5-ylmethoxy]-piperidine-1-carboxylate and tert-butyl (3RS,4RS)-4-[4-(3-benzyloxy-propoxy)-phenyl]-3-[3-(2-trimethylsilanyl-ethoxymethyl)-3H-benzimidazol-5-ylmethoxy]-piperidine-1-carboxylate in 14 ml of absolute tetrahydrofuran was treated with 3.5 ml of a 1.1M tetrabutylammonium fluoride solution in tetrahydrofuran and heated at reflux temperature for 2 hours. For the working-up, the reaction mixture was partitioned between 50 ml of ethyl acetate and 50 ml of sodium hydrogen carbonate solution (5%) and subsequently the organic phase was separated. The aqueous phase was extracted twice with 50 ml of ethyl acetate each time. The combined organic phases were washed with 25 ml of water each time, dried over magnesium sulphate and finally the solvent was distilled off under reduced pressure. The crude product (280 mg) was purified by chromatography on silica gel with a 14:1:0.1 mixture of methylene chloride, methanol and 28% ammonia solution as the eluent. There were obtained 176 mg (66% of theory) of tert-butyl 3RS,4RS)-3-(1H-benzimidazol-5-yimethoxy)-4-[4-(3-benzyloxy-propoxy)-phenyl]-piperidine-1-carboxylate as a yellow oil; MS: 572 (M+H)$^+$.

(i) A solution of 240 mg (about 0.82 mmol) of 60–70% 3-chloroperbenzic acid in 15 ml of chloroform was added dropwise at 0° C. to a solution of 459 mg (0.75 mmol) of tert-butyl (3RS,4RS)-4-[4-[3-(2-methoxy-benzyloxy)-propoxy]-phenyl]-3-(quinolin-7-ylmethoxy)-piperidine-1-carboxylate in 30 ml of chloroform. The reaction mixture was stirred at room temperature for 2.5 hours and then, for the working-up, partitioned between 50 ml of chloroform and 50 ml of 10% potassium carbonate solution. The organic phase was separated and the aqueous phase was extracted three times with 25 ml of chloroform each time. The combined organic phases were washed twice with 25 ml of water each time, dried over magnesium sulphate and finally the solvent was distilled off under reduced pressure. The crude product was purified by chromatography on silica gel with a 19:1 mixture of methylene chloride and methanol as the eluent. There were obtained 450 mg (96% of theory) of tert-butyl (3RS,4RS)-4-[4-[3-(2-methoxy-benzyloxy)-propoxy]-phenyl]-3-(1-oxy-quinolin-7-ylmethoxy)-piperidine-1-carboxylate as a light yellow resin; MS: 629 (M+H)$^+$.

(j) A solution of 50 mg (0.080 mmol) of tert-butyl (3RS,4RS)-4-[4-[3-(2-methoxy-benzyloxy)-propoxy]-phenyl]-3-(1-oxy-quinolin-7-ylmethoxy)-piperidine-1-carboxylate in 0.5 ml of chloroform was treated with 17 mg (0.088 mmol) of tosyl chloride and 0.5 ml of 10% potassium carbonate solution and stirred intensively at room temperature for 3 hours. For the working-up, the reaction mixture was partitioned between 20 ml of ethyl acetate and 20 ml of water, the organic phase was then separated and the aqueous phase was extracted three times with 20 ml of ethyl acetate each time. The combined organic phases were washed twice with 25 ml of water each time, dried over magnesium sulphate and finally the solvent was distilled off under reduced pressure. The crude product (60 mg) was purified by chromatography on silica gel with a 2:1 mixture of ethyl acetate and hexane as the eluent. There were obtained 37 mg (74% of theory) of tert-butyl (3RS,4RS)-4-[4-[3-( 2-methoxy-benzyloxy)-propoxy]-phenyl]-3-(2-oxo-1,2-dihydro-quinolin-7-ylmethoxy)-piperidine-1-carboxylate as a colourless solid, which was used directly in the next step without characterization.

(k) In an analogous manner to that described in Example 1(g), by alkylating tert-butyl (3RS,4RS)-3-hydroxy-4-[4-[3-(2-methoxy-benzyloxy)-propoxy]-phenyl]-piperidine-1-carboxylate [Example 120(g) (a)] with 7-bromomethyl-isoquinoline (WO 9,319,059) there was obtained tert-butyl (3RS,4RS)-3-(isoquinolin-7-ylmethoxy)-4-[4-[3-(2-methoxy-benzyloxy)-propoxy]-phenyl]-piperidine-1-carboxylate as a light yellow resin; MS: 613 (M+H)$^+$.

(l) In an analogous manner to that described in Example 120(b), by reducing tert-butyl (3RS,4RS)-4-[4-3-(2-methoxy-benzyloxy)-propoxy]-phenyl]-3-(quinolin-7-ylmethoxy)-piperidine-1-carboxylate [Example 120(g) (β)] by means of nickel(II) chloride hexahydrate and sodium borohydride there was obtained tert-butyl (3RS,4RS)-4-[4-[3-(2-methoxy-benzyloxy)-propoxy]-phenyl]-3-(1,2,3,4-tetrahydro-quinolin-7-ylmethoxy)-piperidine-1-carboxylate as a pale yellow syrup, which was used in the following step without further purification and characterization.

(m) In analogy to Example 1(g) by alkylating (3RS,4RS)-3-hydroxy-4-[4-[3-(2-methoxy-benzyloxy)-propoxy]-phenyl]-piperidin-1-carboxylic acid tert-butyl esters [Example 120(g) (α)] with 6-bromomethyl-quinoxalin [J. Heterocycl. Chem. 11, 595 (1974)] there was obtained (3RS,4RS)-4-[4-[3-(2-methoxy-benzyloxy)-propoxy]-phenyl]-3-(quinoxalin-6-ylmethoxy)-piperidin-1-carboylic acid tert-butyl ester as a pale yellow oil; MS: 614 (M+H)$^+$.

EXAMPLE 121

The following compounds were obtained by cleavage of the BOC group:

1) From a mixture of tert-butyl (3RS,4RS)- and (3SR,4SR)-4-[4-[(RS)-3-benzyloxy-2-methoxy-propoxy]-phenyl]-3-(1-methoxy-naphthalen-2-ylmethoxy)-piperidine-1-carboxylate by means of zinc bromide in methylene chloride, a mixture of (3RS,4RS)-4-[4-[(RS)- and [(SR)-3-benzyloxy- 2-methoxy-propoxy]-phenyl]-3-(1-methoxy-naphthalen-2-ylmethoxy)-piperidine as a yellow oil; MS: 542 (M+H)$^+$;

2) from a mixture of tert-butyl (3RS,4RS)- and (3SR,4SR)-4-[4-[(RS)-2-benzyloxy-3-phenoxy-propoxy]-phenyl]-3-(naphthalen-2-ylmethoxy)-piperidine-1-carboxylate by means of trifluoroacetic acid in methylene chloride, a mixture of (3RS,4RS)-4-[4-[(RS)- and -[(SR)-2-benzyloxy-3-phenoxy-propoxy]-phenyl]-3-(naphthalen-2-ylmethoxy)-piperidine trifluoroacetate as a white solid; MS: 574 (M+H)$^+$;

3) from a mixture of tert-butyl (3RS,4RS)- and (3SR,4SR)-4-[4-[(RS)-2-hydroxy-3-(4-methyl-phenylsulphonylamino)-propoxy]-phenyl]-3-(naphthalen-2-ylmethoxy)-piperidine-1-carboxylate by means of trifluoroacetic acid in methylene chloride, a mixture of N-[(RS)- and -(SR)-2-hydroxy-3-[(3RS,4RS)-4-[3-(naphthalen-2-ylmethoxy-piperidin-4-yl]-phenoxy]-propyl]-4-methyl-benzenesulphonamide trifluoroacetate as a white solid; MS: 561 (M+H)$^+$;

4) from a mixture of tert-butyl (3RS,4RS)- and (3SR,4SR)-4-[4-[(RS)-2-allyloxy-4-phenyl-butoxy]-phenyl]-3-(naphthalen-2-ylmethoxy)-piperidine-1-carboxylate by means of trifluoroacetic acid in methylene chloride, a mixture of (3RS,4RS)-4-[4-[(RS)- and -[(SR)-2-allyloxy-4-phenyl-butoxy]-phenyl]-3-(naphthalen-2-ylmethoxy)-piperidine trifluoroacetate as a white solid; MS: 522 (M+H)$^+$;

The BOC derivatives used as starting materials were prepared as follows:

(a) In an analogous manner to that described in Example 1(g), by alkylating a mixture of tert-butyl (3RS,4RS)- and (3SR,4SR)-3-hydroxy-4-[(RS)-4-oxiranylmethoxy-phenyl]-piperidine-1-carboxylate [Example 86(d)] with 1-methoxy-2-bromomethyl-naphthalene [Example 7(f)] there was obtained a mixture of tert-butyl (3RS,4RS)- and (3SR,4SR)-3-(1-methoxy-naphthalen-2-ylmethoxy)-4-[(RS)-4-oxiranylmethoxy-phenyl]-piperidine-1-carboxylate. Subsequent epoxide opening with sodium benzylate in N,N-dimethylformamide yielded a mixture of tert-butyl (3RS, 4RS)- and (3SR,4SR)-4-[4-[(RS)-3-benzyloxy-2-hydroxy-propoxy]-phenyl]-3-(1-methoxy-naphthalen- 2-ylmethoxy)-piperidine-1-carboxylate, alkylation of which with methyl iodide analogously to Example 1(g) gave a mixture of tert-butyl (3RS,4RS)- and (3SR,4SR)-4-[4-[(RS)-3-benzyloxy-2-methoxy-propoxy]-phenyl]-3-(1-methoxy-naphthalen-2-ylmethoxy)-piperidine-1-carboxylate as a colourless oil; MS: 628 (M+H)$^+$;

(b) In an analogous manner to that described in Example 1(g), by alkylating a mixture of tert-butyl (3RS,4RS)- and (3SR,4SR)-4-[4-[(RS)-2-hydroxy-3-phenoxy-propoxy]-phenyl]-3-(naphthalen-2-ylmethoxy)-piperidine-1-carboxylate [Example 86(d)] with benzyl bromide there was obtained a mixture of tert-butyl (3RS,4RS)- and (3SR,4SR)-4-[4-[(RS)-2-benzyloxy-3-phenoxy-propoxy]-phenyl]-3-(naphthalen-2-ylmethoxy)-piperidine-1-carboxylate as a solid; MS: 674 (M+H)$^+$;

(c) Epoxide opening of a mixture of tert-butyl (3RS,4RS)- and (3SR,4SR)-3-(naphthalen-2-ylmethoxy)-4-[(RS)-4-oxiranylmethoxy-phenyl]-piperidine-1-carboxylate [Example 86(d)] with potassium toluene-4-sulphonamide in analogy to Example 71(a) yielded a mixture of tert-butyl (3RS,4RS)- and (3SR,4SR)-4-[4-[(RS)-2-hydroxy-3-(4-methyl-phenylsulphonylamino)-propoxy]-phenyl]-3-(naphthalen-2-ylmethoxy)-piperidine-1-carboxylate as a white solid; MS: 661 (M+H)$^+$;

(d) Epoxide opening of a mixture of tert-butyl (3RS,4RS)- and (3SR,4SR)-3-(naphthalen-2-ylmethoxy)-4-[(RS)-4-oxiranylmethoxy-phenyl]-piperidine-1-carboxylate [Example 86(d)] with benzylmagnesium chloride in tetrahydrofuran yielded a mixture of tert-butyl (3RS,4RS)- and (3SR,4SR)-4-[4-[(RS)-2-hydroxy-4-phenyl-butoxy]-phenyl]-3-(naphthalen-2-ylmethoxy)-piperidine-1-carboxylate, alkylation of which with allyl bromide analogously to Example 1(g) gave a mixture of tert-butyl (3RS, 4RS)- and (3SR,4SR)-4-[4-[(RS)-2-allyloxy-4-phenyl-butoxy]-phenyl]-3-(naphthalen-2-ylmethoxy)-piperidine-1-carboxylate as a colourless oil; MS: 621 (M)$^+$.

EXAMPLE 122

The following compounds were obtained by cleavage of the BOC group:

1) From tert-butyl (3RS,4RS)-3-(naphthalen-2-ylmethoxy)-4-[4-(3-phenyl-propoxy)-phenyl]-piperidine-1-carboxylate by means of trifluoroacetic acid in methylene chloride, (3RS,4RS)-3-(naphthalen-2-ylmethoxy)-4-[4-(3-phenyl-propoxy)-phenyl]-piperidine trifluoroacetate as a colourless solid; MS: 452 (M+H)$^+$;

2) from tert-butyl (3RS,4RS)-3-(naphthalen-2-ylmethoxy)-4-[4-(4-phenyl-butoxy)-phenyl]-piperidine-1-carboxylate by means of trifluoroacetic acid in methylene chloride, (3RS,4RS)-3-(naphthalen-2-ylmethoxy)-4-[4-(4-phenyl-butoxy)-phenyl]-piperidine trifluoroacetate as a colourless solid; MS: 466 (M+H)$^+$;

3) from tert-butyl (3RS,4RS)-3-(naphthalen-2-ylmethoxy)-4-[4-(5-phenyl-pentyloxy)-phenyl]-piperidine-1-carboxylate by means of trifluoroacetic acid in methylene chloride, (3RS,4RS)-3-(naphthalen-2-ylmethoxy)-4-[4-(5-phenyl-pentyloxy)-phenyl]-piperidine trifluoroacetate as a colourless solid; MS: 480 (M+H)$^+$;

4) from tert-butyl (E)-(3RS,4RS)-3-(naphthalen-2-ylmethoxy)-4-[4-(3-phenyl-allyloxy)-phenyl]-piperidine-1-carboxylate by means of zinc bromide in methylene chloride, (E)-(3RS,4RS)-3-(naphthalen-2-ylmethoxy)-4-[4-(3-phenyl-allyloxy)-phenyl]-piperidine as a colourless solid; MS: 450 (M+H)$^+$;

5) from tert-butyl (E)-(3RS,4RS)-3-(1,4-dimethoxy-naphthalen-2-ylmethoxy)-4-[4-(3-phenyl-allyloxy)-phenyl]-piperidine-1-carboxylate by means of zinc bromide in methylene chloride, (E)-(3RS,4RS)-3-(1,4-dimethoxy-naphthalen-2-ylmethoxy)-4-[4-(3-phenyl-allyloxy)-phenyl]-piperidine as a beige solid; MS: 510 (M+H)$^+$;

6) from tert-butyl (E)-(3RS,4RS)-3-(4-methylsulphanyl-benzyloxy)-4-[4-(3-phenyl-allyloxy)-phenyl]-piperidine-1-carboxylate by means of zinc bromide in methylene chloride, (E)-(3RS,4RS)-3-(4-methylsulphanyl-benzyloxy)-4-[4-(3-phenyl-allyloxy)-phenyl]-piperidine as a yellowish oil; MS: 446 (M+H)$^+$;

7) from tert-butyl (E)-(3RS,4RS)-3-(1,4-dimethoxy-naphthalen-2-ylmethoxy)-4-[4-(4-phenyl-but-3-enyloxy)-phenyl]-piperidine-1-carboxylate by means of zinc bromide in methylene chloride, (E)-(3RS,4RS)-3-(1, 4-dimethoxy-naphthalen-2-ylmethoxy)-4-[4-(4-phenyl-but-3-enyloxy)-phenyl]-piperidine as a beige solid; MS: 524 (M+H)$^+$;

8) from tert-butyl (3RS,4RS)-4-[4-(3-cyano-benzyloxy)-phenyl]-3-[1-(2-methoxy-ethoxy)-naphthalen-2-ylmethoxy]-piperidine-1-carboxylate by means of zinc bromide in methylene chloride, (3RS,4RS)-3-[4-[3-[1-(2-methoxy-ethoxy)-naphthalen-2-ylmethoxy]-piperidin-4-yl]-phenoxymethyl]-benzonitrile as a viscous, pale yellow oil; MS: 523 (M+H)$^+$;

9) from tert-butyl (3RS,4RS)-3-(1,4-dimethoxy-naphthalen-2-ylmethoxy)-4-[4-(4-phenyl-butoxy)-phenyl]-piperidine-1-carboxylate by means of zinc bromide, (3RS,4RS)-3-(1,4-dimethoxy-naphthalen-2-ylmethoxy)-4-[4-(4-phenyl-butoxy)-phenyl]-piperidine as a beige solid; MS: 526 (M+H)$^+$.

The BOC derivatives used as starting materials were prepared as follows:

(a) In an analogous manner to that described in Example 44(e), by alkylating tert-butyl (3RS,4RS)-3-hydroxy-4-(4-hydroxy-phenyl)-piperidine-1-carboxylate [Example 46(b)] with 1-bromo-3-phenyl-propane in the presence of potassium carbonate, tert-butyl (3RS,4RS)-3-hydroxy-4-[4-(3- phenyl-propoxy)-phenyl]-piperidine-1-carboxylate, alkylation of which analogously to Example 1(g) with 2-bromomethyl-naphthalene yielded tert-butyl (3RS,4RS)-3-(naphthalen-2-ylmethoxy)-4-[4-(3-phenyl-propoxy)-phenyl]-piperidine-1-carboxylate as a colourless solid; MS: 551 (M)$^+$.

(b) In an analogous manner to that described in Example 44(e), by alkylating tert-butyl (3RS,4RS)-3-hydroxy-4-(4-hydroxy-phenyl)-piperidine-1-carboxylate [Example 46(b)] with 4-phenyl-butanol mesylate, prepared according to a generally known procedure, in the presence of potassium carbonate there was obtained tert-butyl (3RS,4RS)-3-hydroxy-4-[4-(4-phenyl-butoxy)-phenyl]-piperidine-1-carboxylate, alkylation of which analogously to Example 1(g) with 2-bromomethyl-naphthalene yielded tert-butyl (3RS,4RS)-3-(naphthalen- 2-ylmethoxy)-4-[4-(4-phenyl-butoxy)-phenyl]-piperidine-1-carboxylate as a colourless oil; MS: 566 (M+H)$^+$.

(c) In an analogous manner to that described in Example 44(e), by alkylating tert-butyl (3RS,4RS)-3-hydroxy-4-(4-hydroxy-phenyl)-piperidine-1-carboxylate [Example 46(b)] with 5-phenyl-pentanol mesylate, prepared according to a generally known procedure, in the presence of potassium carbonate in DMF there was obtained tert-butyl (3RS,4RS)-3-hydroxy-4-[4-(3-phenyl-propoxy)-phenyl]-piperidine-1-carboxylate, alkylation of which analogously to Example 1(g) with 2-bromomethyl-naphthalene yielded tert-butyl (3RS,4RS)-3-(naphthalen-2-ylmethoxy)-4-[4-(5-phenyl-pentyloxy)-phenyl]-piperidine-1-carboxylate as a colourless solid; MS: 580 (M+H)$^+$.

(d) In an analogous manner to that described in Example 44(e), by alkylating tert-butyl (3RS,4RS)-3-hydroxy-4-(4-hydroxy-phenyl)-piperidine-1-carboxylate [Example 46(b)] with cinnamyl bromide in the presence of potassium carbonate in acetone there was obtained tert-butyl (E)-(3RS,4RS)-3-hydroxy-4-[4-(3-phenyl-allyloxy)-phenyl]-piperidine-1-carboxylate, alkylation of which analogously to Example 1(g) with 2-bromomethyl-naphthalene yielded tert-butyl (E)-(3RS,4RS)-3-(naphthalen-2-ylmethoxy)-4-[4-(3-phenyl-allyloxy)-phenyl]-piperidine-1-carboxylate as a colourless solid; MS: 550 (M+H)$^+$.

(e) Alkylation of tert-butyl (E)-(3RS,4RS)-3-hydroxy-4-[4-(3-phenyl-allyloxy)-phenyl]-piperidine-1-carboxylate analogously to Example 1(g) with 2-chloromethyl-1,4-dimethoxy-naphthalene [J.Org.Chem. (1983),48(19), 3265–3268] gave tert-butyl (E)-(3RS,4RS)-3-(1,4-dimethoxy-naphthalen-2-ylmethoxy)-4-[4-(3-phenyl-allyloxy)-phenyl]-piperidine-1-carboxylate as a yellowish solid; MS: 610 (M+H)$^+$.

(f) Alkylation of tert-butyl (E)-(3RS,4RS)-3-hydroxy-4-[4-(3-phenyl-allyloxy)-phenyl]-piperidine-1-carboxylate analogously to Example 1(g) with 4-methylthio-benzyl chloride [J.Org.Chem. (1988),53(3),561–569] gave tert-butyl (E)-(3RS,4RS)-3-(4-methylsulphanyl-benzyloxy)-4-[4-(3-phenyl-allyloxy)-phenyl]-piperidine-1-carboxylate as a yellowish solid; MS: 546 (M+H)$^+$.

(g) In an analogous manner to that described in Example 44(e), by alkylating tert-butyl (3RS,4RS)-3-hydroxy-4-(4-hydroxy-phenyl)-piperidine-1-carboxylate [Example 46(b)] with (E)-4-phenyl-3-buten-1-ol mesylate there was obtained tert-butyl (E)-(3RS,4RS)-3-hydroxy-4-[4-(4-phenyl-but-3-enyloxy)-phenyl]-piperidine-1-carboxylate, alkylation of which analogously to Example 1(g) with 2-chloromethyl-1, 4-dimethoxy-naphthalene yielded (E)-(3RS,4RS)-3-(1,4-dimethoxy-naphthalen-2-ylmethoxy)-4-[4-(4-phenyl-but-3-enyloxy)-phenyl]-piperidine-1-carboxylate as a viscous, pale yellow oil; MS: 624 (M+H)$^+$.

The (E)-4-phenyl-but-3-enyl methanesulphonate used as the starting material was prepared as follows:

(α) A solution of 3.24 mg (20 mmol) of (E)-styrylacetic acid in 20 ml of methanol,2 ml of trimethyl orthoformate and 192 mg (2 mmol) of methanesulphonic acid was stirred at 50° C. under argon for one hour. For the working-up, the mixture was neutralized with 2 mmol of sodium methylate and subsequently the solvent mixture was distilled off under reduced pressure. There was obtained methyl (E)-4-phenyl-but-3-enoate as a colourless liquid in quantitative yield; MS: 176 (M)$^+$.

(β) In an analogous manner to that described in Example 5(b), by reducing methyl (E)-4-phenyl-but-3-enoate by means of lithium aluminium hydride in tetrahydrofuran there was obtained (E)-4-phenyl-but-3-en-1-ol, which was converted into (E)-4-phenyl-but-3-enyl methanesulphonate in analogy to the procedure described in J.Chem.Soc. Perk-.Trans. 1 (1988), (6),1517–1519 for the preparation of the (Z) isomer.

(h) In an analogous manner to that described in Example 1(g), by alkylating tert-butyl (3RS,4RS)-4-(4-allyloxy-phenyl)-3-hydroxy-piperidine-1-carboxylate [Example 86(b)] with 2-chloromethyl-1-(2-methoxy-ethoxy)-naphthalene there was obtained (3RS,4RS)-4-(4-allyloxy-phenyl)-3-[1-(2-methoxy-ethoxy)-naphthalen-2-ylmethoxy]-piperidine-1-carboxylate, from which after cleavage of the allyl group by means of bis-(triphenylphosphine)-palladium(II) diacetate analogously to Example 152(e) there resulted tert-butyl (3RS,4RS)-4-(4-hydroxy-phenyl)-3-[1-(2-methoxy-ethoxy)-naphthalen-2-ylmethoxy]-piperidine- 1-carboxylate, alkylation of which analogously to Example 44(e) with 3-bromomethyl-benzonitrile gave tert-butyl (3RS,4RS)-4-[4-(3-cyano-benzyloxy)-phenyl]-3-[1-(2-methoxy-ethoxy)-naphthalen-2-ylmethoxy]-piperidine-1-carboxylate as a colourless oil; MS: 623 (M+H)$^+$.

The 2-chloromethyl-1-(2-methoxy-ethoxy)-naphthalene used as the alkylating agent was obtained as follows:

By alkylating methyl 1-hydroxy-naphthalene-2-carboxylate analogously to Example 1(g) with 2-bromoethyl methyl ether there was obtained methyl 1-(2-methoxy-ethoxy)-naphthalene-2-carboxylate, which was subsequently converted analogously to Example 5(b)–(c) firstly into [1-(2-methoxy-ethoxy)-naphthalen-2-yl]-methanol and then into 2-chloromethyl-1-(2-methoxy-ethoxy)-naphthalene, which was finally obtained as a beige solid; MS: 250 (M)$^+$.

(i) In an analogous manner to that described in Example 1(g), by alkylating tert-butyl (3RS,4RS)-3-hydroxy-4-[4-(4-phenyl-butoxy)-phenyl]-piperidine-1-carboxylate [Example 122(b)] with 2-chloromethyl-1,4-dimethoxy-naphthalene [J.Org.Chem. (1983),48(19),3265–3268] there was obtained tert-butyl (3RS,4RS)-3-(1,4-dimethoxy-naphthalen-2-ylmethoxy)-4-[4-(4-phenyl-butoxy)-phenyl]-piperidine-1-carboxylate as a colourless, viscous oil; MS: 626 (M+H)$^+$.

EXAMPLE 123

The following compounds were obtained by cleavage of the BOC group:

1) From tert-butyl (3RS,4RS)-4-[4-(3-benzyloxy-propoxy)-phenyl]-3-(1,4-dimethoxy-naphthalen-2-ylmethoxy)-piperidine-1-carboxylate by means of zinc bromide in methylene chloride, (3RS,4RS)-4-[4-(3-benzyloxy-propoxy)-phenyl]-3-(1,4-dimethoxy-naphthalen-2-ylmethoxy)-piperidine hydrobromide as a beige solid; MS: 542 (M+H)$^+$;

2) from tert-butyl (3RS,4RS)-3-(1,4-dimethoxy-naphthalen-2-ylmethoxy)-4-{4-[3-(thiophen-2-ylmethoxy)- propoxy]-phenyl}-piperidine-1-carboxylate by means of zinc bromide in methylene chloride, {3RS,4RS}-3-{1,4-dimethoxy-naphthalen-2-ylmethoxy}-4-[4-[3-(thiophen-2-ylmethoxy)-propoxy]-phenyl]-piperidine as a beige solid; MS: 548 (M+H)$^+$;

3) from tert-butyl (3RS,4RS)-3-(4-methylsulphanyl-benzyloxy)-4-[4-[3-(thiophen-2-ylmethoxy)-propoxy]-phenyl]-piperidine-1-carboxylate by means of zinc bromide in methylene chloride, (3RS,4RS)-3-(4-methylsulphanyl-benzyloxy)-4-[4-[3-(thiophen-2-ylmethoxy)-propoxy]-phenyl]-piperidine as a yellowish resin; MS: 484 (M+H)$^+$;

4) from tert-butyl (3RS,4RS)-4-[4-(3-benzylsulphanyl-propoxy)-phenyl]-3-(1,4-dimethoxy-naphthalen-2-ylmethoxy)-piperidine-1-carboxylate by means of zinc bromide in methylene chloride, (3RS,4RS)-4-[4-(3-benzylsulphanyl-propoxy)-phenyl]-3-(1,4-dimethoxy-naphthalen-2-ylmethoxy)-piperidine as a yellow solid; MS: 558 (M+H)$^+$;

5) from tert-butyl (3RS,4RS)-4-[4-(3-benzylsulphanyl-propoxy)-phenyl]-3-(naphthalen-2-ylmethoxy)-piperidine-1-carboxylate by means of trifluoroacetic acid in methylene chloride, (3RS,4RS)-4-[4-(3-benzylsulphanyl-propoxy)-phenyl]-3-(naphthalen-2-ylmethoxy)-piperidine trifluoroacetate as a colourless solid; MS: 498 (M+H)$^+$;

6) from tert-butyl (3RS,4RS)-3-(naphthalen-2-ylmethoxy)-4-[4-(2-phenethyloxy-ethoxy)-phenyl]-piperidine-1-carboxylate by means of trifluoroacetic acid in methylene chloride, (3RS,4RS)-3-(naphthalen-2-ylmethoxy)-4-[4-(2-phenethyloxy-ethoxy)-phenyl]-piperidine trifluoroacetate as a colourless solid; MS: 482 (M+H)$^+$;

7) from tert-butyl (3RS,4RS)-3-(4-methylsulphanyl-benzyloxy)-4-[4-(2-phenethyloxy-ethoxy)-phenyl]-piperidine-1-carboxylate by means of zinc bromide in methylene chloride, (3RS,4RS)-3-(4-methylsulphanyl-benzyloxy)-4-[4-(2-phenethyloxy-ethoxy)-phenyl]-piperidine hydrobromide as a pale yellow solid; MS: 478 (M+H)$^+$;

8) from tert-butyl (3RS,4RS)-3-(1,4-dimethoxy-naphthalen-2-ylmethoxy)-4-[4-(2-phenethyloxy-ethoxy)-phenyl]-piperidine-1-carboxylate by means of zinc bromide in methylene chloride, (3RS,4RS)-3-(1,4-dimethoxy-naphthalen-2-ylmethoxy)-4-[4-(2-phenethyloxy-ethoxy)-phenyl]-piperidine as a colourless solid; MS: 542 (M+H)$^+$;

9) from tert-butyl (3RS,4RS)-3-(naphthalen-2-ylmethoxy)-4-[4-[2-(pyrimidin-2-yloxy)-ethoxy]-phenyl]-piperidine-1-carboxylate by means of trifluoroacetic acid in methylene chloride, (3RS,4RS)-2-(2-[4-[3-(naphthalen-2-ylmethoxy)-piperidin-4-yl]-phenoxy]-ethoxy)-piperidine trifluoroacetate as a colourless solid; MS: 456 (M+H)$^+$;

10) from tert-butyl (3RS,4RS)-3-(naphthalen-2-ylmethoxy)-4-[4-(3-phenoxy-propoxy)-phenyl]-piperidine-1-carboxylate by means of trifluoroacetic acid in methylene chloride, (3RS,4RS)-3-(naphthalen-2-ylmethoxy)-4-[4-(3-phenoxy-propoxy)-phenyl]-piperidine trifluoroacetate as a colourless solid; MS: 468 (M+H)$^+$;

11) from tert-butyl (3RS,4RS)-3-(naphthalen-2-ylmethoxy)-4-[4-(4-phenoxy-butoxy)-phenyl]-piperidine-1-carboxylate by means of trifluoroacetic acid in methylene chloride, (3RS,4RS)-3-(naphthalen-2-ylmethoxy)-4-[4-(4-phenoxy-butoxy)-phenyl]-piperidine trifluoroacetate as a colourless solid; MS: 482 (M+H)$^+$;

12) from tert-butyl (3RS,4RS)-3-(1,4-dimethoxy-naphthalen-2-ylmethoxy)-4-[4-(4-phenoxy-butoxy)-phenyl]-piperidine-1-carboxylate by means of zinc bromide in methylene chloride, (3RS,4RS)-3-(1,4-dimethoxy-naphthalen-2-ylmethoxy)-4-[4-(4-phenoxy-butoxy)-phenyl]-piperidine as a colourless solid; MS: 542 (M+H)$^+$;

13) from tert-butyl (3RS,4RS)-3-(1,4-dimethoxy-naphthalen-2-ylmethoxy)-4-[4-(3-phenylsulphanyl-propoxy)-phenyl]-piperidine-1-carboxylate by means of zinc bromide in methylene chloride, (3RS,4RS)-3-(1,4-dimethoxy-naphthalen-2-ylmethoxy)-4-[4-(3-phenylsulphanyl-propoxy)-phenyl]-piperidine as a brown solid; MS: 544 (M+H)$^+$;

14) from tert-butyl (3RS,4RS)-3-(naphthalen-2-ylmethoxy)-4-[4-(4-phenoxy-but-2-ynyloxy)-phenyl]-piperidine-1-carboxylate by means of zinc bromide in methylene chloride, (3RS,4RS)-3-(naphthalen-2-ylmethoxy)-4-[4-(4-phenoxy-but-2-ynyloxy)-phenyl]-piperidine as a yellow, viscous oil; MS: 478 (M+H)$^+$;

15) from tert-butyl (3RS,4RS)-3-(1,4-dimethoxy-naphthalen-2-ylmethoxy)-4-[4-(4-phenoxy-but-2-ynyloxy)-phenyl]-piperidine-1-carboxylate by means of zinc bromide in methylene chloride, (3RS,4RS)-3-(1,4-dimethoxy-naphthalen-2-ylmethoxy)-4-[4-(4-phenoxy-but-2-ynyloxy)-phenyl]-piperidine as a brown solid; MS: 538 (M+H)$^+$;

16) from tert-butyl (E)-(3RS,4RS)-3-(naphthalen-2-ylmethoxy)-4-[4-(4-phenoxy-but-2-enyloxy)-phenyl]-piperidine-1-carboxylate by means of zinc bromide in methylene chloride, (E)-(3RS,4RS)-3-(naphthalen-2-ylmethoxy)-4-[4-(4-phenoxy-but-2-enyloxy)-phenyl]-piperidine as a colourless solid; MS: 480 (M+H)$^+$;

17) from tert-butyl (Z)-(3RS,4RS)-3-(naphthalen-2-ylmethoxy)-4-[4-(4-phenoxy-but-2-enyloxy)-phenyl]-piperidine-1-carboxylate by means of zinc bromide in methylene chloride, (Z)-(3RS,4RS)-3-(naphthalen-2-ylmethoxy)-4-[4-(4-phenoxy-but-2-enyloxy)-phenyl]-piperidine as a pale yellow solid; MS: 480 (M+H)$^+$;

18) from tert-butyl (3RS,4RS)-3-(4,8-dimethoxy-naphthalen-2-ylmethoxy)-4-{4-[3-(thiophen-2-ylmethoxy)-propoxy]-phenyl}-piperidine-1-carboxylate by means of zinc bromide in methylene chloride, (3RS,4RS)-3-(4,8-dimethoxy-naphthalen-2-ylmethoxy)-4-[4-[3-(thiophen-2-ylmethoxy)-propoxy]-phenyl]-piperidine as a beige solid; MS: 548 (M+H)$^+$;

19) from tert-butyl (3RS,4RS)-3-(7-hydroxy-naphthalen-2-ylmethoxy)-4-{4-[3-(thiophen-2-ylmethoxy)-propoxy]-phenyl}-piperidine-1-carboxylate by means of hydrogen chloride in methanol, (3RS,4RS)-7-[4-[4-[3-(thiophen-2-ylmethoxy)-propoxy]-phenyl]-piperidin-3-yloxymethyl]-naphthalen-2-ol as a colourless solid; MS: 504 (M+H)$^+$;

20) from tert-butyl (3RS,4RS)-3-[8-methoxy-4-(3-methoxy-propoxy)-naphthalen-2-ylmethoxy]-4-{4-[3-(thiophen-2-ylmethoxy)-propoxy]-phenyl}-piperidine-1-carboxylate by means of zinc bromide in methylene chloride, (3RS,4RS)-3-[8-methoxy-4-(3-methoxy-propoxy)-naphthalen-2-ylmethoxy]-4-[4-[3-(thiophen-2-ylmethoxy)-propoxy]-phenyl]-piperidine as a beige solid; MS: 606 (M+H)$^+$;

21) from a mixture of tert-butyl (3RS,4RS)- and (3SR,4SR)-3-[7-[(RS)-2,3-dimethoxy-propoxy]-naphthalen-2-ylmethoxy]-4-{4-[3-(thiophen-2-ylmethoxy)-propoxy]-phenyl}-piperidine-1-carboxylate by means of zinc bromide in methylene chloride, a mixture of (3RS,4RS)- and (3SR,4SR)-3-[7-[(RS)-2,3-dimethoxy-propoxy]-naphthalen-2-ylmethoxy]-4-[4-[3-(thiophen-2-ylmethoxy)-propoxy]-phenyl]-piperidine as a yellow, viscous oil; MS: 606 (M+H)+;

22) from a mixture of tert-butyl (3RS,4RS)- and (3SR,4SR)-3-[1-[(RS)-2,3-dimethoxy-propoxy]-naphthalen-2- ylmethoxy]-4-{4-[3-(thiophen-2-ylmethoxy)-propoxy]-phenyl}-piperidine-1-carboxylate by means of zinc bromide in methylene chloride, a mixture of (3RS,4RS)- and (3SR,4SR)-3-[1-[(RS)-2,3-dimethoxy-propoxy]-naphthalen-2-ylmethoxy]-4-[4-[3-(thiophen-2-ylmethoxy)-propoxy]-phenyl]-piperidine as a yellow, viscous oil; MS: 606 (M+H)+;

23) from tert-butyl (3RS,4RS)-3-(1,4-dimethoxy-naphthalen-2-ylmethoxy)-4-{4-[3-(thiophen-3-ylmethoxy)-propoxy]-phenyl}-piperidine-1-carboxylate by means of zinc bromide in methylene chloride, (3RS, 4RS)-3-(1,4-dimethoxy-naphthalen-2-ylmethoxy)-4-[4-[3-(thiophen-3-ylmethoxy)-propoxy]-phenyl]-piperidine as a brown solid; MS: 548 (M+H)$^+$;

24) from tert-butyl (3RS,4RS)-3-(7-hydroxy-naphthalen-2-ylmethoxy)-4-{4-[3-(thiophen-3-ylmethoxy)-propoxy]-phenyl}-piperidine-1-carboxylate by means of zinc bromide in methylene chloride, (3RS,4RS)-7-[4-[4-[3-(thiophen-3-ylmethoxy)-propoxy]-phenyl]-piperidin-3-yloxymethyl]-naphthalen-2-ol as a brown solid; MS: 504 (M+H)$^+$;

25) from tert-butyl (3RS,4RS)-3-[8-methoxy-4-(3-methoxy-propoxy)-naphthalen-2-ylmethoxy]-4-{4-[3-(thiophen-3-ylmethoxy)-propoxy]-phenyl}-piperidine-1-carboxylate by means of zinc bromide in methylene chloride, (3RS, 4RS)-3-[8-methoxy-4-(3-methoxy-propoxy)-naphthalen-2-ylmethoxy]-4-[4-[3-(thiophen-3-ymethoxy)-propoxy]-phenyl]-piperidine as a yellowish, viscous oil; MS: 606 (M+H)$^+$;

26) from tert-butyl (3RS,4RS)-3-(1,4-dimethoxy-naphthalen-2-ylmethoxy)-4-[4-(3-phenoxy-propoxy)-phenyl]-piperidine-1-carboxylate by means of zinc bromide in methylene chloride, (3RS,4RS)-3-(1,4-dimethoxy-naphthalen-2-ylmethoxy)-4-[4-(3-phenoxy-propoxy)-phenyl]-piperidine as a yellow, viscous oil; MS: 528 (M+H)$^+$;

27) from tert-butyl (3RS,4RS)-3-(1,4-dimethoxy-naphthalen-2-ylmethoxy)-4-{4-[3-(2-methoxy-phenoxy)-propoxy]-phenyl}-piperidine-1-carboxylate by means of zinc bromide in methylene chloride, (3RS,4RS)-3-(1,4-dimethoxy-naphthalen-2-ylmethoxy)-4-[4-[3-(2-methoxy-phenoxy)-propoxy]-phenyl]-piperidine as a pale brown solid; MS: 558 (M+H)$^+$;

28) from tert-butyl (3RS,4RS)-3-(1,4-dimethoxy-naphthalen-2-ylmethoxy)-4-{4-[3-(3-methoxy-phenoxy)-propoxy]-phenyl}-piperidine-1-carboxylate by means of zinc bromide in methylene chloride, (3RS,4RS)-3-(1,4-dimethoxy-naphthalen-2-ylmethoxy)-4-[4-[3-(3-methoxy-phenoxy)-propoxy]-phenyl]-piperidine as a yellow, viscous oil; MS: 558 (M+H)$^+$;

29) from tert-butyl (3RS,4RS)-4-{4-[3-(2-chloro-phenoxy)-propoxy]-phenyl}-3-(1,4-dimethoxy-naphthalen-2-ylmethoxy)-piperidine-1-carboxylate by means of zinc bromide in methylene chloride, (3RS,4RS)-4-[4-[3-(2-chloro-phenoxy)-propoxy]-phenyl]-3-(1,4-dimethoxy-naphthalen-2-ylmethoxy)-piperidine as a yellow, semi-solid product; MS: 562 (M+H)$^+$;

30) from tert-butyl (3RS,4RS)-3-(1,4-dimethoxy-naphthalen-2-ylmethoxy)-4-{4-[3-(2-methoxy-phenylsulphanyl)-propoxy]-phenyl}-piperidine-1-carboxylate by means of zinc bromide in methylene chloride, (3RS,4RS)-3-(1,4-dimethoxy-naphthalen-2-ylmethoxy)-4-[4-[3-(2-methoxy-phenylsulphanyl)-propoxy]-phenyl]-piperidine as a yellow, viscous oil; MS: 574 (M+H)$^+$;

31) from tert-butyl (3RS,4RS)-4-[4-(3-benzylsulphanyl-propoxy)-phenyl]-3-(4,8-dimethoxy-naphthalen-2-ylmethoxy)-piperidine-1-carboxylate by means of zinc bromide in methylene chloride, (3RS,4RS)-4-[4-(3-benzylsulphanyl-propoxy)-phenyl]-3-(4,8-dimethoxy-naphthalen-2-ylmethoxy)-piperidine as a colourless solid; MS: 558 (M+H)$^+$;

32) from tert-butyl (3RS,4RS)-3-(1,4-dimethoxy-naphthalen-2-ylmethoxy)-4-[4-[3-(2-methoxy-benzyloxy)-propoxy]-phenyl}-piperidine-1-carboxylate by means of zinc bromide in methylene chloride, (3RS, 4RS)-3-(1,4-dimethoxy-naphthalen-2-ylmethoxy)-4-[4-[3-(2-methoxy-benzyloxy)-propoxy]-phenyl]-piperidine as a yellow syrup; MS: 572 (M+H)$^+$;

33) from a 1:1 mixture of tert-butyl (3R,4R)- and (3S,4S)-3-[7-[(R)-2-hydroxy-3-morpholin-4-yl-propoxy]-naphthalen-2-ylmethoxy]-4-{4-[3-(thiophen-2-ylmethoxy)-propoxy]-phenyl}-piperidine-1-carboxylate by means of hydrogen chloride in methanol, a 1:1 mixture of (R)-1-morpholin-4-yl-3-[(3R,4R)- and -[(3S,4S)-7-[4-[4-[3-(thiophen-2-ylmethoxy)-propoxy]-phenyl]-piperidin-3-yloxymethyl]-naphthalen-2-yloxy]-propan-2-ol dihydrochloride as a beige solid; MS: 647 (M+H)$^+$;

34) from tert-butyl (3RS,4RS)-3-(1,4-dimethoxy-naphthalen-2-ylmethoxy)-4-[4-(2-phenethyloxy-ethoxy)-phenyl]-piperidine-1-carboxylate by means of zinc bromide in methylene chloride, (3RS,4RS)-3-(1,4-dimethoxy-naphthalen-2-ylmethoxy)-4-[4-(2-phenethyloxy-ethoxy)-phenyl]-piperidine, which was oxidized as follows:

A solution of 240 mg of Cer(IV) ammonium nitrate in 1 ml of water was added dropwise at room temperature to a solution of 118 mg of (3RS,4RS)-3-(1,4-dimethoxy-naphthalen-2-ylmethoxy)-4-[4-(2-phenethyloxy-ethoxy)-phenyl]-piperidine in 10 ml of acetonitrile. The reaction solution was stirred at room temperature for 15 minutes and subsequently evaporated under reduced pressure. The residue was partitioned between methylene chloride and water, the organic phase was dried and evaporated under reduced pressure. For purification, the crude product was chromatographed on silica gel using a 9:1 mixture of methylene chloride and methanol as the eluent. There were obtained 95 mg (85% of theory) of (3RS,4RS)-2-[4-[4-(2-phenethyloxy-ethoxy)-phenyl]-piperidin-3-yloxymethyl]-[1,4] naphthoquinone as a red solid; MS: 512 (M+H)$^+$.

The BOC derivatives used as starting materials were prepared as follows:

(a) In an analogous manner to that described in Example 1(g), by alkylating tert-butyl (3RS,4RS)-4-[4-(3-benzyloxy-propoxy)-phenyl]-3-hydroxy-piperidine-1-carboxylate [Example 86(n)] with 2-chloromethyl-1,4-dimethoxy-naphthalene [J.Org.Chem. (1983),48(19),3265–3268] there was obtained (3RS,4RS)-4-[4-(3-benzyloxy-propoxy)-phenyl]-3-(1,4-dimethoxy-naphthalen-2-ylmethoxy)-piperidine-1-carboxylate as a colourless solid; MS: 642 (M+H)$^+$.

(b) In an analogous manner to that described in Example 1(g), by alkylating tert-butyl (RS)-2-(3-bromo-propoxy)-tetrahydro-pyran with 2-hydroxymethyl-thiophene in DMF there was obtained (RS)-2-[3-(thiophen-2-ylmethoxy)-propoxy]-tetrahydro-pyran, which after cleavage of the THP group analogously to Example 53(c), yielded 3-(thiophen-2-ylmethoxy)-propan-1-ol. Subsequent conversion into the mesylate according to a procedure known from the literature and alkylation effected with the latter analogously to Example 44(e) of tert-butyl (3RS,4RS)-3-hydroxy-4-(4-hydroxy-phenyl)-piperidine-1-carboxylate gave tert-butyl (3RS,4RS)-3-hydroxy-4-[4-[3-(thiophen-2-ylmethoxy)-propoxy]-phenyl]-piperidine-1-carboxylate. By alkylation with 2-chloromethyl-1,4-dimethoxy-naphthalene analogously to Example 1(g) there was obtained (3RS,4RS)-3-(1,4-dimethoxy-naphthalen-2-ylmethoxy)-4-{4-[3-(thiophen-2-ylmethoxy)-propoxy]-phenyl}-piperidine-1-carboxylate as a pale yellow resin; MS: 648 (M+H)+.

(c) In an analogous manner to that described in Example 1(g), by alkylating tert-butyl (3RS,4RS)-3-hydroxy-4-[4-[3-(thiophen-2-ylmethoxy)-propoxy]-phenyl]-piperidine-1-carboxylate with 4-methylthio-benzyl chloride [J.Org.Chem. (1988), 53(3),561–569] there was obtained tert-butyl (3RS,4RS)-3-(4-methylsulphanyl-benzyloxy)-4-[4-[3-(thiophen-2-ylmethoxy)-propoxy]-phenyl]-piperidine-1-carboxylate as a yellowish oil; MS: 584 (M+H)+.

(d) In an analogous manner to that described in Example 44(e), by alkylating tert-butyl (3RS,4RS)-3-hydroxy-4-(4-hydroxy-phenyl)-piperidine-1-carboxylate [Example 46(b)] with (3-bromo-propylsulphanylmethyl)-benzene [J.Org.Chem. (1986),51, 846–850] in the presence of potassium carbonate there was obtained tert-butyl (3RS,4RS)-4-[4-(3-benzylsulphanyl-propoxy)-phenyl]- 3-hydroxy-piperidine-1-carboxylate, alkylation of which with 2-chloromethyl-1,4-dimethoxy-naphthalene analogously to Example 1(g) gave tert-butyl (3RS,4RS)-4-[4-(3-benzylsulphanyl-propoxy)-phenyl]-3-(1,4-dimethoxy-naphthalen-2-ylmethoxy)-piperidine-1-carboxylate as a pale yellow oil; MS: 584 (M+H)+.

(e) In an analogous manner to that described in Example 1(g), by alkylating tert-butyl (3RS,4RS)-4-[4-(3-benzylsulphanyl-propoxy)-phenyl]-3-hydroxy-piperidine-1-carboxylate with 2-bromomethyl-naphthalene there was obtained tert-butyl (3RS,4RS)-4-[4-(3-benzylsulphanyl-propoxy)-phenyl]-3-(naphthalen-2-ylmethoxy)-piperidine-1-carboxylate as a colourless resin; MS: 598 (M+H)+.

(f) In an analogous manner to that described in Example 44(e), by alkylating tert-butyl (3RS,4RS)-3-hydroxy-4-(4-hydroxy-phenyl)-piperidine-1-carboxylate [Example 46(b)] with 2-phenethyloxy-ethanol mesylate [J.Med.Chem. (1983),26 (11),1570–1576], prepared according to a procedure known from the literature, in the presence of potassium carbonate there was obtained tert-butyl (3RS,4RS)-3-hydroxy-4-[4-(2-phenethyloxy-ethoxy)-phenyl]-piperidine-1-carboxylate, alkylation of which analogously to Example 1(g) yielded tert-butyl (3RS,4RS)-3-(naphthalen-2-ylmethoxy)-4-[4-(2-phenethyloxy-ethoxy)-phenyl]-piperidine-1-carboxylate as a colourless oil; MS: 582 (M+H)+.

(g) In an analogous manner to that described in Example 1(g), by alkylating tert-butyl (3RS,4RS)-3-hydroxy-4-[4-(2-phenethyloxy-ethoxy)-phenyl]-piperidine-1-carboxylate with 4-methylthio-benzyl chloride [J.Org.Chem. (1988),53 (3),561–569] there was obtained tert-butyl (3RS,4RS)-3-(4-methylsulphanyl-benzyloxy)-4-[4-(2-phenethyloxy-ethoxy)-phenyl]-piperidine-1-carboxylate as a colourless oil; MS: 578 (M+H)+.

(h) In an analogous manner to that described in Example 1(g), by alkylating tert-butyl (3RS,4RS)-3-hydroxy-4-[4-(2-phenethyloxy-ethoxy)-phenyl]-piperidine-1-carboxylate with 2-chloromethyl-1,4-dimethoxy-naphthalene there was obtained tert-butyl (3RS,4RS)-3-(1,4-dimethoxy-naphthalen-2-ylmethoxy)-4-[4-(2-phenethyloxy-ethoxy)-phenyl]-piperidine-1-carboxylate as a yellow solid; MS: 642 (M+H)+.

(i) In an analogous manner to that described in Example 1(g), by alkylating tert-butyl (3RS,4RS)-4-[4-(2-hydroxy-ethoxy)-phenyl]-3-(naphthalen-2-ylmethoxy)-piperidine-1-carboxylate [Example 53(c)] with 2-chloro-pyrimidine there was obtained tert-butyl (3RS,4RS)-3-(naphthalen-2-ylmethoxy)-4-[4-[2-(pyrimidin-2-yloxy)-ethoxy]-phenyl]-piperidine-1-carboxylate as a colourless solid; MS: 556 (M+H)+.

(j) In an analogous manner to that described in Example 44(e), by alkylating tert-butyl (3RS,4RS)-3-hydroxy-4-(4-hydroxy-phenyl)-piperidine-1-carboxylate [Example 46(b)] with 3-phenoxy-propanol mesylate, prepared according to a procedure known from the literature, there was obtained tert-butyl (3RS,4RS)-3-hydroxy-4-[4-(3-phenoxy-propoxy)-phenyl]-piperidine-1-carboxylate, alkylation of which with 2-bromomethyl-naphthalene analogously to Example 1(g) yielded tert-butyl (3RS,4RS)-3-(naphthalen-2-ylmethoxy)-4-[4-(3-phenoxy-propoxy)-phenyl]-piperidine-1-carboxylate as a colourless solid; MS: 568 (M+H)+.

(k) In an analogous manner to that described in Example 44(e), by alkylating tert-butyl (3RS,4RS)-3-hydroxy-4-(4-hydroxy-phenyl)-piperidine-1-carboxylate [Example 46(b)] with (E)-(4-bromo-but-2-enyloxy)-benzene there was obtained tert-butyl (E)-(3RS,4RS)-3-hydroxy-4-[4-(4-phenoxy-but-2-enyloxy)-phenyl]-piperidine-1-carboxylate. Subsequent hydrogenation with palladium/charcoal analogously to Example 73(c) yielded tert-butyl (3RS,4RS)-3-hydroxy-4-[4-(4-phenoxy-butoxy)-phenyl]-piperidine-1-carboxylate, alkylation of which with 2-bromomethyl-naphthalene analogously to Example 1(g) gave tert-butyl (3RS,4RS)-3-(naphthalen-2-ylmethoxy)-4-[4-(4-phenoxy-butoxy)-phenyl]-piperidine-1-carboxylate as a colourless solid; MS: 582 (M+H)+.

The (E)-(4-bromo-but-2-enyloxy)-benzene used as the alkylating agent was obtained by alkylating phenol with 1,4-dibromo-2-butene in an analogous manner to that described in Example 44(e).

(l) In an analogous manner to that described in Example 1(g), by alkylating tert-butyl (3RS,4RS)-3-hydroxy-4-[4-(4-phenoxy-butoxy)-phenyl]-piperidine-1-carboxylate with 2-chloromethyl-1,4-dimethoxy-naphthalene there was obtained tert-butyl (3RS,4RS)-3-(1,4-dimethoxy-naphthalen-2-ylmethoxy)-4-[4-(4-phenoxy-butoxy)-phenyl]-piperidine-1-carboxylate as a pale yellow solid; MS: 642 (M+H)+.

(m) In an analogous manner to that described in Example 44(e), by alkylating tert-butyl (3RS,4RS)-3-hydroxy-4-(4-hydroxy-phenyl)-piperidine-1-carboxylate [Example 46(b)] with 3-phenylthio-propanol mesylate, prepared according to a procedure known from the literature, there was obtained tert-butyl (3RS,4RS)-3-hydroxy-4-[4-(3-phenylsulphanyl-propoxy)-phenyl]-piperidine-1-carboxylate, alkylation of which analogously to Example 1(g) with 2-chloromethyl-1,4-dimethoxy-naphthalene yielded tert-butyl (3RS,4RS)-3-(1,4-dimethoxy-naphthalen-2-ylmethoxy)-4-[4-(3-phenylsulphanyl-propoxy)-phenyl]-piperidine-1-carboxylate as a yellow, viscous oil; MS: 644 (M+H)+.

(n) In an analogous manner to that described in Example 44(e), by alkylating tert-butyl (3RS,4RS)-3-hydroxy-4-(4-hydroxy-phenyl)-piperidine-1-carboxylate [Example 46(b)] with 4-phenoxy-but-2-ynyl methanesulphonate there was obtained tert-butyl (3RS,4RS)-3-hydroxy-4-[4-(4-phenoxy-but-2-ynyloxy)-phenyl]-piperidine-1-carboxylate, alkylation of which with 2-bromomethyl-naphthalene gave tert-butyl (3RS,4RS)-3-(naphthalen-2-ylmethoxy)-4-[4-(4-phenoxy-but-2-ynyloxy)-phenyl]-piperidine-1-carboxylate as a pale yellow, viscous oil; MS: 578 (M+H)+.

The 4-phenoxy-but-2-ynyl methanesulphonate used as the alkylating agent was obtained in an analogous manner to that described in Example 44(e) by alkylating phenol with 2-butyne-1,4-diol dimesylate, prepared according to a procedure known from the literature.

(o) In an analogous manner to that described in Example 1(g), by alkylating tert-butyl (3RS,4RS)-3-hydroxy-4-[4-(4-phenoxy-but-2-ynyloxy)-phenyl]-piperidine-1-carboxylate with 2-chloromethyl-1,4-dimethoxy-naphthalene there was obtained tert-butyl (3RS,4RS)-3-(1,4-dimethoxy-naphthalen-2-ylmethoxy)-4-[4-(4-phenoxy-but-2-ynyloxy)-phenyl]-piperidine-1-carboxylate as a pale yellow solid; MS: 638 (M+H)$^+$.

(p) In an analogous manner to that described in Example 1(g), by alkylating tert-butyl (E)-(3RS,4RS)-3-hydroxy-4-[4-(4-phenoxy-but-2-enyloxy)-phenyl]-piperidine-1-carboxylate [Example 123(k)] with 2-bromomethyl-naphthalene there was obtained tert-butyl (E)-(3RS,4RS)-3-(naphthalen-2-ylmethoxy)-4-[4-(4-phenoxy-but-2-enyloxy)-phenyl]-piperidine-1-carboxylate as a colourless solid; MS: 580 (M+H)$^+$.

(q) In an analogous manner to that described in Example 44(e), by alkylating tert-butyl (3RS,4RS)-3-hydroxy-4-(4-hydroxy-phenyl)-piperidine-1-carboxylate [Example 46(b)] with (Z)-4-phenoxy-but-2-enyl methanesulphonate there was obtained tert-butyl (Z)-(3RS,4RS)-3-hydroxy-4-[4-(4-phenoxy-but-2-enyloxy)-phenyl]-piperidine-1-carboxylate, alkylation of which with 2-bromomethyl-naphthalene gave tert-butyl (Z)-(3RS,4RS)-3-(naphthalen-2-ylmethoxy)-4-[4-(4-phenoxy-but-2-enyloxy)-phenyl]-piperidine-1-carboxylate as a colourless solid; MS: 580 (M+H)$^+$.

The (Z)-4-phenoxy-but-2-enyl methanesulphonate used as the alkylating agent was obtained in an analogous manner to that described in Example 44(e) by alkylating phenol with (Z)-4-methylsulphonyloxy-but-2-enyl methanesulphonate, prepared from (Z)-2-butene-1,4-diol according to a procedure known from the literature.

(r) In an analogous manner to that described in Example 1g), by alkylating tert-butyl (3RS,4RS)-3-hydroxy-4-[4-[3-(thiophen-2-ylmethoxy)-propoxy]-phenyl]-piperidine-1-carboxylate [Example 123 b)] with 2-chloromethyl-4,8-dimethoxy-naphthalene there was obtained tert-butyl (3RS, 4RS)-3-(4,8-dimethoxy-naphthalen-2-ylmethoxy)-4-{4-[3-(thiophen-2-ylmethoxy)-propoxy]-phenyl}-piperidine-1-carboxylate as a beige solid; MS: 648 (M+H)$^+$.

The 2-chloromethyl-4,8-dimethoxy-naphthalene used as the alkylating agent was prepared as follows:

(α) In an analogous manner to that described in Example 5b), by reducing methyl 4,8-dimethoxy-naphthalene-2-carboxylate (J.Chem.Soc. 1959, 1024) by means of lithium aluminium hydride there was obtained (4,8-dimethoxy-naphthalen-2-yl)-methanol, MS: 218 (M)$^+$, as a colourless solid.

(β) A solution of 3.92 g of methanesulphonyl chloride in 20 ml of methylene chloride was added dropwise to a solution, cooled to −10° C., of 7.7 g (35.3 mmol) of (4,8-dimethoxy-naphthalen-2-yl)-methanol and 4.4 g (38.8 mmol) of triethylamine in 50 ml of methylene chloride. The reaction mixture was stirred at room temperature for 18 hours. For the working-up, the mixture was extracted with 50 ml of ice-cold sodium hydrogen carbonate solution and the aqueous phase was separated and back-extracted with 25 ml of methylene chloride. The combined organic phases were dried over sodium sulphate and subsequently evaporated under reduced pressure. For purification, the residue was filtered over a layer of silica gel using methylene chloride as the eluent. There were obtained 7.2 g of 2-chloromethyl-4,8-dimethoxy-naphthalene as a beige solid; MS: 296 (M)$^+$.

(s) In an analogous manner to that described in Example 1g), by alkylating tert-butyl (3RS,4RS)-3-hydroxy-4-[4-[3-(thiophen-2-ylmethoxy)-propoxy]-phenyl]-piperidine-1-carboxylate [Example 123b)] with 2-chloromethyl-7-(2-trimethyl-silylethoxymethoxy)-naphthalene [Example 6u)] there was obtained tert-butyl (3RS,4RS)-4-{4-[3-(thiophen-2-ylmethoxy)-propoxy]-phenyl}-3-[7-(2-trimethylsilanyl-ethoxymethoxy)-naphthalen-2-ylmethoxy]-piperidine-1-carboxylate as a colourless, viscous oil, MS: 734 (M+H)$^+$, from which by cleavage of the SEM group by means of hydrogen chloride in methanol there was obtained tert-butyl (3RS,4RS)-3-(7-hydroxy-naphthalen-2-ylmethoxy)-4-{4-[3-(thiophen-2-ylmethoxy)-propoxy]-phenyl}-piperidine-1-carboxylate as a colourless solid; MS: 604 (M+H)$^+$.

(t) In an analogous manner to that described in Example 1g), by alkylating tert-butyl (3RS,4RS)-3-hydroxy-4-[4-[3-(thiophen-2-ylmethoxy)-propoxy]-phenyl]-piperidine-1-carboxylate [Example 123b)] with 3-chloromethyl-5-methoxy-1-(3-methoxy-propoxy)-naphthalene there was obtained tert-butyl (3RS,4RS)-3-[8-methoxy-4-(3-methoxy-propoxy)-naphthalen-2-ylmethoxy]-4-{4-[3-(thiophen-2-ylmethoxy)-propoxy]-phenyl}-piperidine-1-carboxylate as a pale yellow, viscous oil; MS: 706 (M+H)$^+$.

The 3-chloromethyl-5-methoxy-1-(3-methoxy-propoxy)-naphthalene used as the alkylating agent was prepared as follows:

In an analogous manner to that described in Example 44e), by alkylating methyl 4-hydroxy-8-methoxy-naphthalene-2-carboxylate [Justus Liebigs Ann.Chem. (1967),702, 94–100] with 3-methoxy-butan-1-ol mesylate, prepared according to a procedure known from the literature, there was obtained ethyl 8-methoxy-4-(3-methoxy-propoxy)-naphthalene-2-carboxylate, reduction of which with lithium aluminium hydride analogously to Example 5(b) gave [8-methoxy-4-(3-methoxy-propoxy)-naphthalen-2-yl]-methanol. Subsequent chlorination analogously to Example 123(r) (b) yielded 3-chloromethyl-5-methoxy-1-(3-methoxy-propoxy)-naphthalene as a pale yellow liquid; MS: 276 (M)$^+$.

(u) In an analogous manner to that described in Example 1(g), by alkylating tert-butyl (3RS,4RS)-3-hydroxy-4-[4-[3-(thiophen-2-ylmethoxy)-propoxy]-phenyl]-piperidine-1-carboxylate [Example 123b)] with (RS)-2-chloromethyl-7-(2,3-dimethoxy-propoxy)-naphthalene there was obtained a mixture of tert-butyl (3RS,4RS)- and (3SR,4SR)-3-[7-[(RS)-2,3-dimethoxy-propoxy]-naphthalen-2-ylmethoxy]-4-{4-[3-(thiophen-2-ylmethoxy)-propoxy]-phenyl}-piperidine-1-carboxylate as a colourless, viscous oil; MS: 706 (M+H)$^+$.

The (RS)-2-chloromethyl-7-(2,3-dimethoxy-propoxy)-naphthalene used as the alkylating agent was prepared as follows:

In an analogous manner to that described in Example 44(e), by alkylating ethyl 7-hydroxy-naphthalene-2-carboxylate (EPA 61800) with (RS)-2,3-dimethoxy-propan-1-ol mesylate (J.Chem.Soc. C,1966, 415–419), prepared in a manner known from the literature, there was obtained methyl (RS)-7-(2,3-dimethoxy-propoxy)-naphthalene-2-carboxylate, reduction of which with lithium aluminium hydride analogously to Example 5(b) gave (RS)-[7-(2,3-dimethoxy-propoxy)-naphthalen-2-yl]-methanol. Subsequent chlorination analogously to Example 123(r) (b) yielded (RS)-2-chloromethyl-7-(2,3-dimethoxy-propoxy)-naphthalene as a colourless solid; MS: 294 (M)$^+$.

(v) In an analogous manner to that described in Example 1(g), by alkylating tert-butyl (3RS,4RS)-3-hydroxy-4-[4-[3-(thiophen-2-ylmethoxy)-propoxy]-phenyl]-piperidine-1-carboxylate [Example 123(b)] with (RS)-2-chloromethyl-1-(2,3-dimethoxy-propoxy)-naphthalene there was obtained a mixture of tert-butyl (3RS,4RS)- and (3SR,4SR)-3-[1-[(RS)-2,3-dimethoxy-propoxy]-naphthalen-2-ylmethoxy]-4-{4-[3-(thiophen-2-ylmethoxy)-propoxy]-phenyl}-piperidine-1-carboxylate as a colourless oil; MS: 706 (M+H)$^+$.

The (RS)-2-chloromethyl-1-(2,3-dimethoxy-propoxy)-naphthalene used as the alkylating agent was prepared as follows:

In an analogous manner to that described in Example 44(e), with (RS)-2,3-dimethoxy-propan-1-ol mesylate (J.Chem.Soc. C,1966, 415–419), prepared according to a method known from the literature, there was obtained methyl (RS)-1-(2,3-dimethoxy-propoxy)-naphthalene-2-carboxylate, reduction of which with lithium aluminium hydride analogously to Example 5(b) gave (RS)-[1-(2,3-dimethoxy-propoxy)-naphthalen-2-yl]-methanol. Subsequent chlorination analogously to Example 123(r) (b) yielded (RS)-2-chloromethyl-1-(2,3-dimethoxy-propoxy)-naphthalene as a colourless, viscous oil; MS: 294 (M)$^+$.

(w) In an analogous manner to that described in Example 1(g), by alkylating tert-butyl (RS)-2-(3-bromo-propoxy)-tetrahydro-pyran with 3-hydroxymethyl-thiophene in DMF there was obtained (RS)-2-[3-(thiophen-3-ylmethoxy)-propoxy]-tetrahydro-pyran, which after cleavage of the THP group analogously to Example 53(c) yielded 3-(thiophen-3-ylmethoxy)-propan-1-ol. Subsequent conversion into the mesylate according to a procedure known from the literature and alkylation therewith effected analogously to Example 44(e) of tert-butyl (3RS,4RS)-3-hydroxy-4-(4-hydroxy-phenyl)-piperidine-1-carboxylate [Example 46(b)] gave tert-butyl (3RS,4RS)-3-hydroxy-4-[4-[3-(thiophen-3-ylmethoxy)-propoxy]-phenyl]-piperidine-1-carboxylate. By alkylation with 2-chloromethyl-1,4-dimethoxy-naphthalene analogously to Example 1(g) there was obtained tert-butyl (3RS,4RS)-3-(1,4-dimethoxy-naphthalen-2-ylmethoxy)-4-{4-[3-(thiophen-3-ylmethoxy)-propoxy]-phenyl}-piperidine-1-carboxylate as a pale yellow solid; MS: 648 (M+H)$^+$.

(x) In an analogous manner to that described in Example 1(g), by alkylating tert-butyl (3RS,4RS)-3-hydroxy-4-[4-[3-(thiophen-3-ylmethoxy)-propoxy]-phenyl]-piperidine-1-carboxylate with 2-allyloxy-7-chloromethyl-naphthalene there was obtained tert-butyl (3RS,4RS)-3-(7-allyloxy-naphthalen-2-ylmethoxy)-4-{4-[3-(thiophen-3-ylmethoxy)-propoxy]-phenyl}-piperidine-1-carboxylate, from which after cleavage of the allyl group by means of bis-(triphenylphosphine)-palladium(II) diacetate analogously to Example 152(e) there was obtained tert-butyl (3RS,4RS)-3-(7-hydroxy-naphthalen-2-ylmethoxy)-4-{4-[3-(thiophen-3-yl-methoxy)-propoxy]-phenyl}-piperidine-1-carboxylate as a yellowish, viscous oil; MS: 604 (M+H)$^+$.

The 2-allyloxy-7-chloromethyl-naphthalene used as the alkylating agent was prepared as follows:

In an analogous manner to that described in Example 44(e), by alkylating ethyl tert-butyl 7-hydroxy-naphthalene-2-carboxylate (EPA 61800) with allyl bromide there was obtained methyl 7-allyloxy-naphthalene-2-carboxylate, reduction of which with lithium aluminium hydride analogously to Example 5(b) gave (7-allyloxy-naphthalen-2-yl)-methanol. Subsequent chlorination analogously to Example 123(r) (b) yielded 2-allyloxy-7-chloromethyl-naphthalene as a colourless solid; MS: 232 (M)$^+$.

(y) In an analogous manner to that described in Example 1(g), by alkylating tert-butyl (3RS,4RS)-3-hydroxy-4-[4-[3-(thiophen-3-ylmethoxy)-propoxy]-phenyl]-piperidine-1-carboxylate with 3-chloromethyl-5-methoxy-1-(3-methoxy-propoxy)-naphthalene [Example 123(t)] there was obtained tert-butyl (3RS,4RS)-3-[8-methoxy-4-(3-methoxy-propoxy)-naphthalen-2-ylmethoxy]-4-{4-[3-(thiophen-3-ylmethoxy)-propoxy]-phenyl}-piperidine-1-carboxylate as a pale yellow, viscous oil; MS: 723 (M+NH$_4$)$^+$.

(z) In an analogous manner to that described in Example 1(g), by alkylating tert-butyl (3RS,4RS)-3-hydroxy-4-[4-(3-phenoxy-propoxy)-phenyl]-piperidine-1-carboxylate [Example 123(j)] with 2-chloromethyl-1,4-dimethoxy-naphthalene there was obtained tert-butyl (3RS,4RS)-3-(1,4-dimethoxy-naphthalen- 2-ylmethoxy)-4-[4-(3-phenoxy-propoxy)-phenyl]-piperidine-1-carboxylate as a viscous, yellow oil; MS: 628 (M+H)$^+$.

(aa) In an analogous manner to that described in Example 44(e), by alkylating tert-butyl (3RS,4RS)-3-hydroxy-4-(4-hydroxy-phenyl)-piperidine-1-carboxylate [Example 46(b)] with 1-(3-bromo-propoxy)-2-methoxy-benzene there was obtained tert-butyl (3RS,4RS)-3-hydroxy-4-{4-[3-(2-methoxy-phenoxy)-propoxy]-phenyl}-piperidine-1-carboxylate, further alkylation of which with 2-chloromethyl-1,4-dimethoxy-naphthalene gave tert-butyl (3RS,4RS)-3-(1,4-dimethoxy-naphthalen-2-ylmethoxy)-4-{4-[3-(2-methoxy-phenoxy)-propoxy]-phenyl}-piperidine-1-carboxylate as a pale yellow solid; MS: 657 (M)$^+$.

The 1-(3-bromo-propoxy)-2-methoxy-benzene used as the alkylating agent was obtained as a colourless liquid, MS: 244, 246 (M)$^+$, by alkylating 2-methoxyphenol with 1,3-dibromo-propane analogously to Example 44(e).

(bb) In an analogous manner to that described in Example 44(e), by alkylating tert-butyl (3RS,4RS)-3-hydroxy-4-(4-hydroxy-phenyl)-piperidine-1-carboxylate [Example 46(b)] with 1-(3-bromo-propoxy)-3-methoxy-benzene there was obtained tert-butyl (3RS,4RS)-3-hydroxy-4-{4-[3-(3-methoxy-phenoxy)-propoxy]-phenyl}-piperidine-1-carboxylate, further alkylation of which with 2-chloromethyl-1,4-dimethoxy-naphthalene gave tert-butyl (3RS,4RS)-3-(1,4-dimethoxy-naphthalen-2-ylmethoxy)-4-{4-[3-(3-methoxy-phenoxy)-propoxy]-phenyl}-piperidine-1-carboxylate as a pale yellow solid; MS: 658 (M+H)$^+$.

The 1-(3-bromo-propoxy)-3-methoxy-benzene used as the alkylating agent was obtained as a colourless liquid, MS: 244, 246 (M)$^+$, by alkylating 3-methoxyphenol with 1,3-dibromo-propane analogously to Example 44(e).

(cc) In an analogous manner to that described in Example 44(e), by alkylating tert-butyl (3RS,4RS)-3-hydroxy-4-(4-hydroxy-phenyl)-piperidine-1-carboxylate [Example 46(b)] with 1-(3-bromo-propoxy)-2-chloro-benzene there was obtained tert-butyl (3RS,4RS)-4-{4-[3-(2-chloro-phenoxy)-propoxy]-phenyl}-3-hydroxy-piperidine-1-carboxylate, further alkylation of which with 2-chloromethyl-1,4-dimethoxy-naphthalene gave (3RS,4RS)-4-{4-[3-( 2-chloro-phenoxy)-propoxy]-phenyl}-3-(1,4-dimethoxy-naphthalen-2-ylmethoxy)-piperidine-1-carboxylate as a colourless, viscous oil; MS: 662 (M+H)$^+$.

The 1-(3-bromo-propoxy)-2-chloro-benzene used as the alkylating agent was obtained as a colourless liquid, MS: 248 (M)$^+$, by alkylating 2-chlorophenol with 1,3-dibromo-propane analogously to Example 44(e).

(dd) In an analogous manner to that described in Example 44(e), by alkylating tert-butyl (3RS,4RS)-3-hydroxy-4-(4-hydroxy-phenyl)-piperidine-1-carboxylate [Example 46(b)] with 3-(2-methoxy-phenylsulphanyl)-propyl methane-sulphonate there was obtained tert-butyl (3RS,4RS)-3-hydroxy-4-{4-[3-(2-methoxy-phenylsulphanyl)-propoxy]-phenyl}-piperidine-1-carboxylate, further alkylation of which with 2-chloromethyl-1,4-dimethoxy-naphthalene gave tert-butyl (3RS,4RS)-3-(1,4-dimethoxy-naphthalen-2-ylmethoxy)-4-{4-[3-(2-methoxy-phenylsulphanyl)- propoxy]-phenyl}-piperidine-1-carboxylate as a pale yellow, viscous oil; MS: 674 (M+H)⁺.

The 3-(2-methoxy-phenylsulphanyl)-propyl methanesulphonate used as the alkylating agent was prepared as follows:

(α) In an analogous manner to that described in Example 44 e), by alkylating tert-butyl 2-methoxy-thiophenol with (RS)-2-(3-bromo-propoxy)-tetrahydro-pyran there was obtained (RS)-2-[3-(2-methoxy-phenylsulphanyl)-propoxy]-tetrahydro-pyran.

(β) A solution of 9.5 g (33.6 mmol) of (RS)-2-[3-(2-methoxy-phenylsulphanyl)-propoxy]-tetrahydro-pyran and 1.0 g (4 mmol) of pyridinium toluene-4-sulphonate in 100 ml of methanol was heated to reflux for 2 hours. For the working-up, the solvent was distilled off under reduced pressure and then the residue was partitioned between ethyl acetate and saturated sodium hydrogen carbonate solution. The organic phase was subsequently dried over sodium sulphate and evaporated under reduced pressure. The 3-(2-methoxy-phenylsulphanyl)-propane-1-ol was obtained as a yellowish liquid in quantitative yield; MS: 198 (M)⁺. Reaction with mesyl chloride, effected according to a generally known procedure, yielded 3-(2-methoxy-phenylsulphanyl)-propyl methanesulphonate as a pale yellow liquid; MS: 276 (M)⁺.

(ee) In an analogous manner to that described in Example 1(g), by alkylating tert-butyl (3RS,4RS)-4-[4-(3-benzylsulphanyl-propoxy)-phenyl]-3-hydroxy-piperidine-1-carboxylate [Example 123d)] with 3-chloromethyl-1,5-dimethoxy-naphthalene [Example 123r)] there was obtained tert-butyl (3RS,4RS)-4-[4-(3-benzylsulphanyl-propoxy)-phenyl]-3-(4,8-dimethoxy-naphthalen-2-ylmethoxy)-piperidine-1-carboxylate as a yellow, viscous oil; MS: 658 (M+H)⁺.

(ff) In an analogous manner to that described in Example 1(g), by alkylating tert-butyl (3RS,4RS)-3-hydroxy-4-[4-[3-(2-methoxy-benzyloxy)-propoxy]-phenyl]-piperidine-1-carboxylate with 2-chloromethyl-1,4-dimethoxy-naphthalene there was obtained tert-butyl (3RS,4RS)-3-(1,4-dimethoxy-naphthalen-2-ylmethoxy)-4-{4-[3-(2-methoxy-benzyloxy)-propoxy]-phenyl}-piperidine-1-carboxylate as a pale yellow syrup; MS: 689 (M+NH₄)⁺.

(gg) In an analogous manner to that described in Example 1(g), by alkylating tert-butyl (3RS,4RS)-3-(7-hydroxy-naphthalen-2-ylmethoxy)-4-{4-[3-(thiophen-2-ylmethoxy)-propoxy]-phenyl}-piperidine-1-carboxylate [Example 123 (s)] with (R)-oxiranylmethyl toluene-4-sulphonate there was obtained a 1:1 mixture of tert-butyl (3R,4R)- and (3S,4S)-3-[(R)-7-oxiranylmethoxy-naphthalen-2-ylmethoxy]-4-{4-[3-(thiophen-2-ylmethoxy)-propoxy]-phenyl}-piperidine-1-carboxylate, MS: 660 (M+H)⁺, as a yellowish, viscous oil. Subsequent epoxide opening analogously to Example 71(a) with morpholine yielded a 1:1 mixture of tert-butyl (3R,4R)- and (3S,4S)-3-[7-[(R)-2-hydroxy-3-morpholin-4-yl-propoxy]-naphthalen-2-ylmethoxy]-4-{4-[3-(thiophen-2-ylmethoxy)-propoxy]-phenyl}-piperidine-1-carboxylate as a colourless solid; MS: 747 (M+H)⁺.

EXAMPLE 124

The following compounds were obtained by cleavage of the BOC group:

1) From tert-butyl (3RS,4RS)-4-{4-[3-(2-methoxy-phenyl)-[1,2,4]oxadiazol-5-ylmethoxy]-phenyl}-3-(4-methylsulphanyl-benzyloxy)-piperidine-1-carboxylate by means of zinc bromide in methylene chloride, (3RS,4RS)-4-[4-[3-(2-methoxy-phenyl)-[1,2,4]oxadiazol-5-ylmethoxy]-phenyl]-3-(4-methylsulphanyl-benzyloxy)-piperidine as a colourless oil; MS: 518 (M+H)⁺;

2) from tert-butyl 3-(4-methanesulphonyl-benzyloxy)-4-{4-[3-(2-methoxy-phenyl)-[1,2,4]oxadiazol-5-ylmethoxy]-phenyl}-piperidine-1-carboxylate by means of zinc bromide in methylene chloride, (3RS,4RS)-4-[4-[3-(2-methoxy-phenyl)-[1,2,4]oxadiazol-5-ylmethoxy]-phenyl]-3-(4-methylsulphonyl-benzyloxy)-piperidine as a beige solid; MS: 550 (M+H)⁺;

3) from a mixture of tert-butyl (3RS,4RS)-3-[4-[(RS)- and -[(SR)-2,3-dimethoxy-propoxy]-8-methoxy-naphthalen-2-ylmethoxy]-4-{4-[3-(2-methoxy-phenyl)-[1,2,4]oxadiazol-5-ylmethoxy]-phenyl}-piperidine-1-carboxylate by means of zinc bromide in methylene chloride a mixture of (3RS,4RS)-3-[4-[(RS)- and -[(SR)-2,3-dimethoxy-propoxy]-8-methoxy-naphthalen-2-ylmethoxy]-4-[4-[3-(2-methoxy-phenyl)-[1,2,4]oxadiazol-5-ylmethoxy]-phenyl]-piperidine as a beige solid; MS: 670 (M+H)⁺;

4) from tert-butyl (3RS,4RS)-3-(1,4-dimethoxy-naphthalen-2-ylmethoxy)-4-[4-[3-(2-methoxy-phenyl)-[1,2,4]oxadiazol-5-ylmethoxy]-phenyl]-piperidine-1-carboxylate by means of zinc bromide in methylene chloride, (3RS,4RS)-3-(1,4-dimethoxy-naphthalen-2-ylmethoxy)-4-[4-[3-(2-methoxy-phenyl)-[1,2,4]oxadiazol-5-ylmethoxy]-phenyl]-piperidine as a beige solid; MS: 582 (M+H)⁺;

5) from tert-butyl (3RS,4RS)-3-(1,4-dimethoxy-naphthalen-2-ylmethoxy)-4-{4-[3-(3,4,5-trimethoxy-phenyl)-[1,2,4]oxadiazol-5-ylmethoxy]-phenyl}-piperidine-1-carboxylate by means of zinc bromide in methylene chloride, (3RS,4RS)-3-(1,4-dimethoxy-naphthalen-2-ylmethoxy)-4-[4-[3-(3,4,5-trimethoxy-phenyl)-[1,2,4]oxadiazol-5-ylmethoxy]-phenyl]-piperidine as a beige solid; MS: 642 (M+H)⁺;

6) from tert-butyl (3RS,4RS)-3-(4-methylsulphanyl-benzyloxy)-4-[4-(3-thiophen-2-yl-[1,2,4]oxadiazol-5-ylmethoxy)-phenyl]-piperidine-1-carboxylate by means of zinc bromide in methylene chloride, (3RS,4RS)-3-(4-methylsulphanyl-benzyloxy)-4-[4-(3-thiophen-2-yl-[1,2,4]oxadiazol-5-ylmethoxy)-phenyl]-piperidine as a pale yellow, viscous oil; MS: 494 (M+H)⁺;

7) from tert-butyl (3RS,4RS)-3-(1,4-dimethoxy-naphthalen-2-ylmethoxy)-4-[4-(3-thiophen-2-yl-[1,2,4]oxadiazol-5-ylmethoxy)-phenyl]-piperidine-1-carboxylate by means of zinc bromide in methylene chloride, (3RS,4RS)-3-(1,4-dimethoxy-naphthalen-2-ylmethoxy)-4-[4-(3-thiophen-2-yl-[1,2,4]oxadiazol-5-ylmethoxy)-phenyl]-piperidine as a beige solid; MS: 558 (M+H)⁺;

8) from tert-butyl 3-[1-(2-methoxy-ethoxymethoxy)-naphthalen-2-ylmethoxy]-4-[4-(3-thiophen-2-yl-[1,2,4]oxadiazol-5-ylmethoxy)-phenyl]-piperidine-1-carboxylate by means of zinc bromide in methylene chloride with simultaneous cleavage of the MEM group, (3RS,4RS)-2-[4-[4-(3-thiophen-2-yl-[1,2,4]oxadiazol-5-ylmethoxy)-phenyl]-piperidin-3-yloxymethyl]-naphthalen-1-ol as a brown solid; MS: 514 (M+H)⁺;

9) from tert-butyl (3RS,4RS)-3-[1-(2-methoxy-ethoxy)-naphthalen-2-ylmethoxy]-4-[4-(3-thiophen-2-yl-[1,2,4]oxadiazol-5-ylmethoxy)-phenyl]-piperidine-1-carboxylate by means of zinc bromide in methylene chloride, (3RS,4RS)-3-[1-(2-methoxy-ethoxy)-naphthalen-2-ylmethoxy]-4-[4-(3-thiophen-2-yl-[1,2,4]oxadiazol-5-ylmethoxy)-phenyl]-piperidine hydrobromide as a colourless solid; MS: 572 (M+H)⁺;

10) from tert-butyl (3RS,4RS)-3-(naphthalen-2-ylmethoxy)-4-[4-(3-thiophen-2-yl-[1,2,4]oxadiazol-5-ylmethoxy)-phenyl]-piperidine-1-carboxylate by means of trifluoroacetic acid in methylene chloride, (3RS,4RS)-3-

(naphthalen-2-ylmethoxy)-4-[4-(3-thiophen-2-yl-[1,2,4]oxadiazol-5-ylmethoxy)-phenyl]-piperidine trifluoroacetate as a colourless solid; MS: 498 (M+H)$^+$;

11) from tert-butyl (3RS,4RS)-4-[4-(3-furan-2-yl-[1,2,4]oxadiazol-5-ylmethoxy)-phenyl]-3-(naphthalen-2-ylmethoxy)-piperidine-1-carboxylate by means of trifluoroacetic acid in methylene chloride, (3RS,4RS)-4-[4-(3-furan-2-yl-[1,2,4]oxadiazol-5-ylmethoxy)-phenyl]-3-(naphthalen-2-ylmethoxy)-piperidine trifluoroacetate as a colourless solid; MS: 482 (M+H)$^+$;

12) from tert-butyl (3RS,4RS)-4-[4-[3-(2-chloro-phenyl)-[1,2,4]oxadiazol-5-ylmethoxy]-phenyl]-3-(naphthalen-2-ylmethoxy)-piperidine-1-carboxylate by means of trifluoroacetic acid in methylene chloride, (3RS,4RS)-4-[4-[3-(2-chloro-phenyl)-[1,2,4]oxadiazol-5-ylmethoxy]-phenyl]-3-(naphthalen-2-ylmethoxy)-piperidine trifluoroacetate as a colourless solid; MS: 526 (M+H)$^+$;

13) from tert-butyl (3RS,4RS)-3-(1,4-dimethoxy-naphthalen-2-ylmethoxy)-4-[4-(2-phenyl-oxazol-5-ylmethoxy)-phenyl]-piperidine-1-carboxylate by means of zinc bromide in methylene chloride, (3RS,4RS)-3-(1,4-dimethoxy-naphthalen-2-ylmethoxy)-4-[4-(2-phenyl-oxazol-5-ylmethoxy)-phenyl]-piperidine as a colourless solid; MS: 551 (M+H)$^+$;

14) from tert-butyl (3RS,4RS)-3-(1,4-dimethoxy-naphthalen-2-ylmethoxy)-4-[4-(2-phenyl-thiazol-5-ylmethoxy)-phenyl]-piperidine-1-carboxylate by means of zinc bromide in methylene chloride, {3RS,4RS}-3-(1,4-dimethoxy-naphthalen-2-ylmethoxy)-4-[4-(2-phenyl-thiazol-5-ylmethoxy)-phenyl]-piperidine as a beige solid; MS: 567 (M+H)$^+$;

15) from tert-butyl (3RS,4RS)-3-[1-(2-methoxy-ethoxy)-naphthalen-2-ylmethoxy]-4-[4-(3-phenyl-isoxazol-5-ylmethoxy)-phenyl]-piperidine-1-carboxylate by means of zinc bromide in methylene chloride, (3RS,4RS)-3-[1-(2-methoxy-ethoxy)-naphthalen-2-ylmethoxy]-4-[4-(3-phenyl-isoxazol-5-ylmethoxy)-phenyl-piperidine as a colourless solid; MS: 565 (M+H)$^+$;

16) from tert-butyl (3RS,4RS)-3-(1,4-dimethoxy-naphthalen-2-ylmethoxy)-4-[4-(3-phenyl-isoxazol-5-ylmethoxy)-phenyl]-piperidine-1-carboxylate by means of zinc bromide in methylene chloride, (3RS,4RS)-3-(1,4-dimethoxy-naphthalen-2-ylmethoxy)-4-[4-(3-phenyl-isoxazol-5-ylmethoxy)-phenyl]-piperidine as a colourless solid; MS: 551 (M+H)$^+$;

17) from tert-butyl (3RS,4RS)-3-(1-methoxy-naphthalen-2-ylmethoxy)-4-[4-(3-phenyl-isoxazol-5-ylmethoxy)-phenyl]-piperidine-1-carboxylate by means of trifluoroacetic acid in methylene chloride, (3RS,4RS)-3-(1-methoxy-naphthalen-2-ylmethoxy)-4-[4-(3-phenyl-isoxazol-5-ylmethoxy)-phenyl]-piperidine trifluoroacetate as a colourless solid; MS: 521 (M+H)$^+$.

The BOC derivatives used as starting materials were prepared as follows:

(a) In an analogous manner to that described in Example 1(g), by alkylating tert-butyl (3RS,4RS)-4-(4-allyloxy-phenyl)-3-hydroxy-piperidine-1-carboxylate [Example 86(b)] with 4-methylthio-benzyl chloride [J.Org.Chem. (1988),53(3), 561–569] there was obtained tert-butyl (3RS,4RS)-4-(4-allyloxy-phenyl)-3-(4-methylsulphanyl-benzyloxy)-piperidine-1-carboxylate, from which by cleavage of the allyl group by means of bis-(triphenylphosphine)-palladium(II) diacetate analogously to Example 152(e) there was obtained tert-butyl (3RS,4RS)-4-(4-hydroxy-phenyl)-3-(4-methylsulphanyl-benzyloxy)-piperidine-1-carboxylate. Subsequent alkylation with 5-bromomethyl-3-(2-methoxy-phenyl)-[1,2,4]oxadiazole analogously to Example 44(e) gave tert-butyl (3RS,4RS)-4-{4-[3-(2-methoxy-phenyl)-[1,2,4]oxadiazol-5-ylmethoxy]-phenyl}-3-(4-methylsulphanyl-benzyloxy)-piperidine-1-carboxylate as a pale yellow, viscous oil; MS: 618 (M+H)$^+$.

(b) In an analogous manner to that described in Example 152(c), by oxidizing tert-butyl (3RS,4RS)-4-{4-[3-(2-methoxy-phenyl)-[1,2,4]oxadiazol-5-ylmethoxy]-phenyl}-3-(4-methylsulphanyl-benzyloxy)-piperidine-1-carboxylate with m-chloroperbenzoic acid there was obtained tert-butyl (3RS,4RS)-3-(4-methane-sulphonyl-benzyloxy)-4-{4-[3-(2-methoxy-phenyl)-[1,2,4]oxadiazol-5-ylmethoxy]-phenyl}-piperidine-1-carboxylate as a beige solid; MS: 650 (M+H)$^+$.

(c) In an analogous manner to that described in Example 1(g), by alkylating tert-butyl (3RS,4RS)-4-(4-allyloxy-phenyl)-3-hydroxy-piperidine-1-carboxylate [Example 86(b)] with (RS)-3-chloromethyl-1-(2,3-dimethoxy-propoxy)-5-methoxy-naphthalene there was obtained a mixture of (3RS,4RS)-4-(4-allyloxy-phenyl)-3-[4-[(RS)- and [(SR)-2,3-dimethoxy-propoxy]-8-methoxy-naphthalen-2-ylmethoxy]-piperidine-1-carboxylate, from which by cleavage of the allyl group by means of bis-(triphenylphosphine)-palladium(II) diacetate analogously to Example 152(e) there was obtained a mixture of tert-butyl (3RS,4RS)-3-[4-[(RS)- and [(SR)-2,3-dimethoxy-propoxy]-8-methoxy-naphthalen-2-ylmethoxy]-4-(4-hydroxy-phenyl)-piperidine-1-carboxylate. Subsequent alkylation with 5-bromo-methyl-3-(2-methoxy-phenyl)-[1,2,4]oxadiazole analogously to Example 44(e) gave a mixture of tert-butyl (3RS,4RS)-3-[4-[(RS)- and [(SR)-2,3-dimethoxy-propoxy]-8-methoxy-naphthalen-2-ylmethoxy]-4-{4-[3-( 2-methoxy-phenyl)-[1,2,4]oxadiazol-5-ylmethoxy]-phenyl}-piperidine-1-carboxylate as a beige solid; MS: 770 (M+H)$^+$.

The (RS)-3-chloromethyl-1-(2,3-dimethoxy-propoxy)-5-methoxy-naphthalene used as the alkylating agent was prepared as follows:

Ethyl 4-acetoxy-8-methoxy-naphthalene-2-carboxylate [Chem.Pharm.Bull.19 (6),1245–1256 (1971)] was saponified by means of aqueous potassium carbonate in ethanol to ethyl 4-hydroxy-8-methoxy-naphthalene-2-carboxylate, which in analogy to Example 44(e) was alkylated in the presence of potassium carbonate with (RS)-2,3-dimethoxy-propyl methanesulphonate, obtained from (RS)-2,3-dimethoxy-propan-1-ol [J.Chem.Soc. (1931),450] according to a procedure known from the literature, to give ethyl (RS)-4-(2,3-dimethoxy-propoxy)-8-methoxy-naphthalen-2-carboxylate. Subsequent reduction by means of lithium aluminium hydride analogously to Example 5(b) gave (RS)-[4-(2,3-dimethoxy-propoxy)-8-methoxy-naphthalen-2-yl]-methanol, which was converted in analogy to Example 5(c) into (RS)-3-chloromethyl-1-(2,3-dimethoxy-propoxy)-5-methoxy-naphthalene; MS: 324 (M)$^+$.

(d) Alkylation of tert-butyl (3RS,4RS)-3-(1,4-dimethoxy-naphthalen-2-ylmethoxy)-4-(4-hydroxy-phenyl)-piperidine-1-carboxylate [Example 152(e)] with 5-bromomethyl-3-(2-methoxy-phenyl)-[1,2,4]oxadiazole analogously to Example 44(e) gave tert-butyl (3RS,4RS)-3-(1,4-dimethoxy-naphthalen-2-ylmethoxy)-4-[4-[3-(2-methoxy-phenyl)-[1,2,4]oxadiazol-5-ylmethoxy]-phenyl]-piperidine-1-carboxylate as a colourless solid; MS: 682 (M+H)$^+$.

(e) Alkylation of tert-butyl (3RS,4RS)-3-(1,4-dimethoxy-naphthalen-2-ylmethoxy)-4-(4-hydroxy-phenyl)-piperidine-1-carboxylate [Example 152(e)] with 5-bromomethyl-3-(3,4,5-trimethoxy-phenyl)-[1,2,4]oxadiazole analogously to Example 44(e) gave tert-butyl (3RS,4RS)-3-(1,4-dimethoxy-naphthalen-2-ylmethoxy)-4-{4-[3-(3,4,5-trimethoxy-phenyl)-[1,2,4]oxadiazol-5-ylmethoxy]-phenyl}-piperidine-1-carboxylate as a colourless solid; MS: 742 (M+H)$^+$.

(f) Alkylation of tert-butyl (3RS,4RS)-4-(4-hydroxy-phenyl)-3-(naphthalen-2-ylmethoxy)-piperidine-1-carboxylate [Example 61(c)] with 5-bromomethyl-3-(2-chloro-phenyl)-[1,2,4]oxadiazole analogously to Example 44(e) gave tert-butyl (3RS,4RS)-4-[4-[3-(2-chloro-phenyl)-[1,2,4]oxadiazol-5-ylmethoxy]-phenyl]-3-(naphthalen-2-ylmethoxy)-piperidine-1-carboxylate as a yellow solid; MS: 626 (M+H)$^+$.

(g) Alkylation of tert-butyl (3RS,4RS)-4-(4-hydroxy-phenyl)-3-(4-methylsulphanyl-benzyloxy)-piperidine-1-carboxylate with 5-bromomethyl-3-thiophen-2-yl-[1,2,4]oxadiazole analogously to Example 44(e) gave tert-butyl (3RS,4RS)-3-(4-methylsulphanyl-benzyloxy)-4-[4-(3-thiophen-2-yl-[1,2,4]oxadiazol-5-ylmethoxy)-phenyl]-piperidine-1-carboxylate as a colourless solid; MS: 594 (M+H)$^+$.

(h) Alkylation of tert-butyl (3RS,4RS)-3-(1,4-dimethoxy-naphthalen-2-ylmethoxy)-4-(4-hydroxy-phenyl)-piperidine-1-carboxylate [Example 152(e)] with 5-bromomethyl-3-thiophen-2-yl-[1,2,4]oxadiazole analogously to Example 44(e) gave tert-butyl (3RS,4RS)-3-(1,4-dimethoxy-naphthalen-2-ylmethoxy)-4-[4-(3-thiophen-2-yl-[1,2,4]oxadiazol-5-ylmethoxy)-phenyl]-piperidine-1-carboxylate as a colourless, viscous oil; MS: 658 (M+H)$^+$.

(i) In an analogous manner to that described in Example 1(g), by alkylating tert-butyl (3RS,4RS)-4-(4-allyloxy-phenyl)-3-hydroxy-piperidine-1-carboxylate [Example 86(b)] with 2-chloromethyl-1-(2-methoxy-ethoxymethoxy)-naphthalene there was obtained tert-butyl (3RS,4RS)-4-(4-allyloxy-phenyl)-3-[1-(2-methoxy-ethoxymethoxy)-naphthalen-2-ylmethoxy]-piperidine-1-carboxylate, from which by cleavage of the allyl group by means of bis-(triphenylphosphine)-palladium(II) diacetate analogously to Example 152(e) there was obtained tert-butyl (3RS,4RS)-4-(4-hydroxy-phenyl)-3-[1-(2-methoxy-ethoxymethoxy)-naphthalen-2-ylmethoxy]-piperidine-1-carboxylate. Subsequent alkylation with 5-bromomethyl-3-thiophen-2-yl-[1,2,4]oxadiazole analogously to Example 44(e) gave tert-butyl (3RS,4RS)-3-[1-(2-methoxy-ethoxymethoxy)-naphthalen-2-ylmethoxy]-4-[4-(3-thiophen-2-yl-[1,2,4]oxadiazol-5-ylmethoxy)-phenyl]-piperidine-1-carboxylate as a colourless, viscous oil; MS: 702 (M+H)$^+$.

The 2-chloromethyl-1-(2-methoxy-ethoxymethoxy)-naphthalene used as the alkylating agent was prepared as follows:

(α) A solution of 2.3 g (11.4 mmol) of methyl 1-hydroxy-naphthalene-2-carboxylate in 15 ml of dry tetrahydrofuran was treated with 0.51 g (17 mmol) of sodium hydride (80%) and subsequently 2.13 g of 2-methoxyethoxymethyl chloride were added dropwise while cooling with ice. After 3 hours at room temperature the solution was extracted with aqueous sodium hydrogen carbonate solution and the organic phase was separated, dried over sodium sulphate and evaporated under reduced pressure. For purification, the crude product was chromatographed on silica gel using a 9:1 mixture of methylene chloride and ether as the eluent. In addition to 1.55 g of starting material there were obtained 1.2 g of methyl 1-(2-methoxy-ethoxymethyl)-naphthalene-2-carboxylate; MS: 290 (M)$^+$.

(β) In an analogous manner to that described in Example 5(b)–(c), from methyl 1-(2-methoxy-ethoxymethoxy)-naphthalene-2-carboxylate by reduction by means of lithium aluminium hydride there was obtained [1-(2-methoxy-ethoxymethoxy)-naphthalen-2-yl]-methanol, which was then converted into 2-chloromethyl-1-(2-methoxy-ethoxymethoxy)-naphthalene; MS: 280 (M)$^+$.

(j) Alkylation of tert-butyl (3RS,4RS)-4-(4-hydroxy-phenyl)-3-[1-(2-methoxy-ethoxy)-naphthalen-2-ylmethoxy]-piperidine-1-carboxylate [Example 122(h)] with 5-bromomethyl-3-thiophen-2-yl-[1,2,4]oxadiazole analogously to Example 44(e) gave tert-butyl (3RS,4RS)-3-[1-(2-methoxy-ethoxy)-naphthalen-2-ylmethoxy]-4-[4-(3-thiophen-2-yl-[1,2,4]oxadiazol-5-ylmethoxy)-phenyl]-piperidine-1-carboxylate as a colourless, viscous oil; MS: 672 (M+H)$^+$.

(k) Alkylation of tert-butyl (3RS,4RS)-4-(4-hydroxy-phenyl)-3-(naphthalen-2-ylmethoxy)-piperidine-1-carboxylate [Example 61(c)] with 5-bromomethyl-3-thiophen-2-yl-[1,2,4]oxadiazole analogously to Example 44(e), gave tert-butyl (3RS,4RS)-3-(naphthalen-2-ylmethoxy)-4-[4-(3-thiophen-2-yl-[1,2,4]oxadiazol-5-ylmethoxy)-phenyl]-piperidine-1-carboxylate as a colourless, viscous oil; MS: 597 (M+H)$^+$.

(l) Alkylation of tert-butyl (3RS,4RS)-4-(4-hydroxy-phenyl)-3-(naphthalen-2-ylmethoxy)-piperidine-1-carboxylate [Example 61(c)] with 5-bromomethyl-3-furan-2-yl-[1,2,4]oxadiazole analogously to Example 44(e) gave tert-butyl (3RS,4RS)-4-[4-(3-furan-2-yl-[1,2,4]oxadiazol-5-ylmethoxy)-phenyl]-3-(naphthalen-2-ylmethoxy)-piperidine-1-carboxylate as a colourless solid; MS: 582 (M+H)$^+$.

(m) Alkylation of tert-butyl (3RS,4RS)-3-(1,4-dimethoxy-naphthalen-2-ylmethoxy)-4-(4-hydroxy-phenyl)-piperidine-1-carboxylate [Example 152(e)] with 4-chloromethyl-2-phenyl-oxazole [Arch.Pharmazie (1971),425] analogously to Example 44(e) gave tert-butyl (3RS,4RS)-3-(1,4-dimethoxy-naphthalen-2-ylmethoxy)-4-[4-(2-phenyl-oxazol-5-ylmethoxy)-phenyl]-piperidine-1-carboxylate as a colourless solid; MS: 651 (M+H)$^+$.

(n) Alkylation of tert-butyl (3RS,4RS)-3-(1,4-dimethoxy-naphthalen-2-ylmethoxy)-4-(4-hydroxy-phenyl)-piperidine-1-carboxylate [Example 152(e)] with 4-chloromethyl-2-phenyl-thiazole [Chem.Ber. (1961),2887] analogously to Example 44(e) gave tert-butyl (3RS,4RS)-3-(1,4-dimethoxy-naphthalen-2-ylmethoxy)-4-[4-(2-phenyl-thiazol-5-ylmethoxy)-phenyl]-piperidine-1-carboxylate as a pale yellow solid; MS: 667 (M+H)$^+$.

(o) In an analogous manner to that described in Example 1(g), by alkylating tert-butyl (3RS,4RS)-4-(4-allyloxy-phenyl)-3-hydroxy-piperidine-1-carboxylate [Example 86(b)] with 2-chloromethyl-1-(2-methoxy-ethoxy)-naphthalene [Example 122(h)] there was obtained tert-butyl (3RS,4RS)-4-(4-allyloxy-phenyl)-3-[1-(2-methoxy-ethoxy)-naphthalen-2-ylmethoxy]-piperidine-1-carboxylate, from which by cleavage of the allyl group by means of bis-(triphenylphosphine)-palladium(II) diacetate analogously to Example 152(e) there was obtained tert-butyl (3RS,4RS)-4-(4-hydroxy-phenyl)-3-[1-(2-methoxy-ethoxy)-naphthalen-2-ylmethoxy]-piperidine-1-carboxylate. Subsequent alkylation with 3-phenyl-isoxazol-5-ylmethyl methanesulphonate analogously to Example 44(e) gave tert-butyl (3RS,4RS)-3-[1-(2-methoxy-ethoxy)-naphthalen-2-ylmethoxy]-4-[4-(3-phenyl-isoxazol-5-ylmethoxy)-phenyl]-piperidine-1-carboxylate as a colourless solid; MS: 665 (M+H)$^+$.

(p) In an analogous manner to that described in Example 44(e), by alkylating tert-butyl (3RS,4RS)-3-hydroxy-4-(4-hydroxy-phenyl)-piperidine-1-carboxylate [Example 46(b)] with 3-phenyl-isoxazol-5-ylmethyl methanesulphonate there was obtained tert-butyl (3RS,4RS)-3-hydroxy-4-[4-(3-phenyl-isoxazol-5-yl-methoxy)-phenyl]-piperidine-1-carboxylate, further alkylation of which with 2-chloromethyl-1,4-dimethoxy-naphthalene [J.Org.Chem. (1983),48(19),3265–3268)] analogously to Example 1(g) yielded tert-butyl (3RS,4RS)-3-(1,4-dimethoxy-naphthalen- 2-ylmethoxy)-4-[4-(3-phenyl-isoxazol-5-ylmethoxy)-phenyl]-piperidine-1-carboxylate as a colourless solid; MS: 651 (M+H)⁺.

(q) Alkylation of tert-butyl (3RS,4RS)-3-hydroxy-4-[4-(3-phenyl-isoxazol-5-ylmethoxy)-phenyl]-piperidine-1-carboxylate with 1-methoxy-2-bromomethyl-naphthalene [Example 7(f)] analogously to Example 1(g) yielded tert-butyl (3RS,4RS)-3-(1-methoxy-naphthalen-2-ylmethoxy)-4-[4-(3-phenyl-isoxazol-5-yl-methoxy)-phenyl]-piperidine-1-carboxylate as a colourless solid; MS: 621 (M+H)⁺.

The preparation of the substituted 5-bromomethyl-[1,2,4]oxadiazoles used as alkylating agents:

5-bromomethyl-3-(2-methoxy-phenyl)-[1,2,4]oxadiazole, 5-bromomethyl-3-(3,4,5-trimethoxy-phenyl)-[1,2,4]oxadiazole, 5-bromomethyl-3-(2-chloro-phenyl)-[1,2,4]oxadiazole, 5-bromomethyl-3-thiophen-2-yl-[1,2,4]oxadiazole and 5-bromomethyl-3-furan-2-yl-[1,2,4]oxadiazole was effected analogously to the procedure described in J.Med.Chem. 1986, 26, 2174–2183.

The 3-phenyl-isoxazol-5-ylmethyl methanesulphonate used as the alkylating agent was synthesized as follows:

(α) 1.47 g (11 mmol) of N-chlorosuccinimide were added at −30° C. to a solution of 1.21 g of benzaldoxime in 10 ml of methylene chloride. After 2 hours a solution of 1.0 g of triethylamine and 1.4 g of (RS)-tetrahydro-2-(2-propynyloxy)-2H-pyran in 5 ml of methylene chloride was added dropwise. The reaction mixture was stirred at room temperature for 5 hours, the solvent was thereafter distilled off and, for purification, the crude product was chromatographed on silica gel using methylene chloride as the eluent. There were obtained 1.8 g of (RS)-3-phenyl-5-(tetrahydro-pyran-2-yloxymethyl)-isoxazole as a colourless liquid; MS: 259 (M)⁺.

(β) Subsequent cleavage of the THP group was effected analogously to Example 53(c). The thus-obtained (3-phenyl-isoxazole-5-yl)-methanol was converted according to a procedure known in the literature into 3-phenyl-izoxazol-5-ylmethyl methanesulphonate and was thereby obtained as a colourless solid; MS: 253 (M)⁺.

EXAMPLE 125

(a) A suspension of 13.32 g (0.1 mmol) of (E)-3-(4-pyridyl)-2-propenal [Tetrahedron Letters 26, 6447 (1985)] and 19.92 g (0.1 mol) of 2-(phenylsulphonyl)-acetamide [Synthesis 1987, 56] in 300 ml of ethanol was treated dropwise at room temperature while stirring during 45 minutes with 20 ml of Triton B solution (40% in methanol) and subsequently stirred at room temperature for 16 hours and under reflux for 90 minutes. After cooling the mixture was treated with 100 ml of glacial acetic acid and subsequently heated under reflux for 2.5 hours. Then, it was concentrated in a water-jet vacuum, treated with 200 ml of water followed by 16.4 g (0.2 mol) of sodium acetate and again concentrated. The residue was taken up in methylene chloride, filtered, the filtrate was concentrated and the thus-obtained residue was recrystallized from isopropanol. There were thus obtained 3.9 g (23% of theory) of 1H-[4,4']bipyridin-2-one in the the of slightly yellow crystals; m.p. 263–265° C.

(b) 15 ml of methyl iodide were added to a suspension of 9.0 g (52.3 mmol) of 1H-[4,4']bipyridin-2-one in 150 ml of N,N-dimethylformamide and the reaction mixture was stirred at room temperature for 20 hours. Subsequently,300 ml of ether were added dropwise and the precipitate which thereby formed was filtered off, washed with ether and dried in a high vacuum. There were thus obtained 15.8 g (96% of theory) of 1-methyl-4-(2-oxo-1,2-dihydro-pyridin-4-yl)-pyridinium iodide in the form of slightly yellow crystals; m.p.: 264–266° C.

(c) 5.3 g (16.9 mmol) of 1-methyl-4-(2-oxo-1,2-dihydro-pyridin-4-yl)-pyridinium iodide were suspended in 100 ml of methanol and treated portionwise under argon at room temperature with 1.1 g (29 mmol) of sodium borohydride. Thereupon, the reaction mixture was heated under reflux for 5 hours and subsequently concentrated in a water-jet vacuum. The thus-obtained residue was partitioned between saturated sodium chloride solution and methylene chloride/methanol (9:1) and the combined methylene chloride phases were dried over magnesium sulphate and concentrated. Recrystallization of the residue from methanol/ethyl acetate finally yielded 2.7 g (84% of theory) of 1'-methyl-1',2',3',6'-tetrahydro-1H-[4,4']bipyridin-2-one in the form of slightly yellow crystals: m.p.: 250–252° C.

(d) 0.88 g (4.6 mmol) of 1'-methyl-1',2',3',6'-tetrahydro-1H-[4,4']bipyridin-2-one, 180 mg (2.4 mmol) of lithium carbonate and 2 g of molecular seive (4 Å) were suspended in 20 ml of 1,2-dichloroethane, treated with 1.1 ml (10 mmol) of 1-chloroethyl chloroformate and heated under reflux for 18 hours. Thereupon, the reaction mixture was concentrated in a water-jet vacuum and stirred at room temperature for 18 hours with 2.2 g (10 mmol) of di-tert-butyl dicarbonate and 2 g (24 mmol) of sodium hydrogen carbonate in 60 ml of dioxan/water (2:1). Subsequently, the mixture was again concentrated in a water-jet vacuum and the residue thus obtained was partitioned between methylene chloride and 0.1N hydrochloric acid. The combined methylene chloride phases were dried over magnesium sulphate and recrystallized from ether. There was thus obtained 0.24 g (19% of theory) of tert-butyl 2'-oxo-1',2',3,6-tetrahydro-2H-[4,4']bipyridine-1-carboxylate in the form of a yellowish solid; MS: 277 (M+H)⁺.

(e) 0.50 g (1.8 mmol) of tert-butyl 2'-oxo-1',2',3,6-tetrahydro-2H-[4,4']bipyridine-1-carboxylate,0.50 g (2.5 mmol) of (2-bromoethoxy)-benzene and 0.35 g (2.5 mmol) of potassium carbonate were heated at 75° C. for 20 hours in 6 ml of acetonitrile. Thereupon, the reaction mixture was concentrated in a water-jet vacuum and partitioned between water and methylene chloride, the combined methylene chloride phases were dried over magnesium sulphate, concentrated and the thus-obtained residue was chromatographed on silica gel with methylene chloride/ethyl acetate (1:1). There was thus obtained 0.41 g (58% of theory) of tert-butyl 2'-oxo-1'-(2-phenoxy-ethyl)-1',2',3,6-tetrahydro-2H-[4,4']bipyridine-1-carboxylate in the form of an amorphous yellowish solid; MS: 397 (M+H)⁺.

(f) 0.20 g (0.5 mmol) of tert-butyl 2'-oxo-1'-(2-phenoxy-ethyl)-1',2',3,6-tetrahydro-2H-[4,4']bipyridine-1-carboxylate was dissolved in 5 ml of 1,2-dimethoxyethane, treated with 1.5 mg of 1 molar borane-tetrahydrofuran solution and stirred at room temperature for 48 hours. Thereupon, a further 1.0 ml of 1 molar borane-tetrahydrofuran solution was added and the mixture was stirred at room temperature for a further 60 hours. Subsequently,2.5 ml of 50% KOH in water followed by 2.5 ml of 30% hydrogen peroxide solution in water were added while cooling with ice and the reaction mixture was heated under reflux for 2 hour. Now, the reaction solution was partitioned between water and methylene chloride, the combined methylene chloride phases were dried over magnesium sulphate, concentrated and the residue thus obtained was chromatographed on silica gel with methylene chloride/methanol (95:5). There were thus obtained 23 mg (11% of theory) of tert-butyl (3RS,4RS)-3-hydroxy-2'oxo-1'-(2- phenoxy-ethyl)-3,4,5,6,1',2'-hexahydro-2H-[4,4']-bipyridine-1-carboxylate in the form of an amorphous, yellowish solid; MS: 414 (M)⁺.

(g) A solution of 21 mg (0.051 mmol) of tert-butyl (3RS,4RS)-3-hydroxy-2'oxo-1'-(2-phenoxy-ethyl)-3,4,5,6,1',2'-hexahydro-2H-[4,4']-bipyridine-1-carboxylate and 15 mg (0.068 mmol) of 2-bromomethylnaphthalene in 0.5 ml of dimethylformamide was treated with 4.0 mg (0.083 mmol) of sodium hydride (50% dispersion in refined oil) and the mixture was stirred at room temperature for 0.5 hour. Subsequently, the reaction mixture was partitioned between ether and water and the combined ether phases were dried over magnesium sulphate and concentrated in a water-jet vacuum. The crude product was chromatographed on silica gel with methylene chloride/methanol (95:5). There were thus obtained 20 mg (71% of theory) of tert-butyl (3'RS,4'RS)-3'-(naphthalen-2-ylmethoxy)-1-(2-phenoxy-ethyl)-1',2',3',4',5',6'-hexahydro-1H-[4,4']bipyridin-2-one-1'-carboxylate in the form of an amorphous, yellowish solid; MS: 555 (M+H)⁺.

(h) 20 mg (0.036 mmol) of tert-butyl (3'RS,4'RS)-3'-(naphthalen-2-ylmethoxy)-1-(2-phenoxy-ethyl)-1',2',3',4',5',6'-hexahydro-1H-[4,4']bipyridin-2-one-1'-carboxylate were dissolved in 3 ml of methylene chloride, treated with 40 mg (0.18 mmol) of anhydrous zinc bromide and stirred at room temperature for 3 hours. Thereupon, the reaction mixture was poured into aqueous sodium carbonate solution this was extracted with methylene chloride. The combined methylene chloride phases were dried over magnesium sulphate and concentrated, and the thus obtained residue was chromatographed on silica gel with a 9:1 mixture of methylene chloride and methanol as the eluent. Therefrom there were obtained 5.8 mg (35% of theory) of (3'RS,4'RS)-3'-(naphthalen-2-ylmethoxy)-1-(2-phenoxy-ethyl)-1',2',3',4',5',6'-hexahydro-1H-[4,4']bipyridin-2-one in the form of and amorphous, colourless solid; MS: 455 (M+H)⁺.

EXAMPLE 126

(a) 41 g (0.173 mol) of 2,5-dibromopyridine and 20.1 g (0.173 mol) of 3-phenyl-1-propyne were dissolved in 450 ml of triethylamine under argon and with the exclusion of moisture, treated while cooling with ice with 740 mg (3.88 mmol) of copper(I) iodide and 2.7 g (3.88 mmol) of bis-(triphenylphosphine)-palladium dichloride and stirred at 0–5° C. for 1 hour and at room temperature for 1 hour. Now, the reaction solution was poured on to ice-water and extracted with methylene chloride, the combined methylene chloride phases were dried over magnesium sulphate, concentrated and the thus obtained residue was chromatographed on silica gel once with methylene chloride and once with hexane/ethyl acetate (9:1). There were thus obtained 27 g (57% of theory) of 5-bromo-2-(3-phenyl-prop-1-ynyl)-pyridine as a colourless solid; MS: 271, 273 (M)⁺.

(b) 17 g (0.062 mol) of 5-bromo-2-(3-phenyl-prop-1-ynyl)-pyridine were dissolved in 300 ml of ethanol, treated with 150 mg of platinum oxide and hydrogenated in a hydrogen atmosphere for 1 hour. Subsequently, the reaction mixture was filtered over a 0.8μ cellulose filter and concentrated in a water-jet vacuum. The thus obtained residue was chromatographed on silica gel with methylene chloride. There were thus obtained 5.2 g (30% of theory) of 5-bromo-2-(3-phenyl-propyl)-pyridine in the form of a yellowish oil; MS: 171, 173 (M-vinylbenzole)⁺.

(c) 100 ml of a 1.6 molar n-butyllithium solution in hexane (about 0.16 mol) were added dropwise to 21.5 ml (0.152 mol) of diisopropylamine dissolved in 145 ml of tetrahydrofuran under argon and with the exclusion of moisture in such a manner that the temperature did not rise above −70° C. Thereupon, 29 g (0.145 mol) of tert-butyl 4-piperidone-1-carboxylate dissolved in 145 ml of tetrahydrofuran were added dropwise during 45 minutes, with the temperature being held below −70° C. After stirring for 10 minutes at the same temperature a solution of 56 g (0.157 mol) of N-phenyl-bis-(trifluoromethanesulphonamide) in 145 ml of tetrahydrofuran was added dropwise within 30 minutes in such a manner that the temperature did not rise above −70° C. Thereupon, the reaction mixture was left to warm to 0° C. and was stirred at this temperature for a further 3 hours. Subsequently, the reaction solution was concentrated at 40° C. in a water-jet vacuum and the thus obtained residue was chromatographed on basic Alox with hexane/ethyl acetate (9:1). There were thus obtained 41 g (85% of theory) of tert-butyl 4-trifluoromethylsulphonyloxy-3,6-dihydro-2H-pyridine-1-carboxylate in the form of a colourless oil; MS: 332 (M+H)⁺.

(d) 1.05 g (3.8 mmol) of 5-bromo-2-(3-phenyl-propyl)-pyridine,1.12 ml (5.4 mmol) of hexamethyldistannate,100 mg (0.086 mmol) of tetrakis-(triphenylphosphine)-palladium,3 g of molecular seive (4 Å) and a few crystals of 2,6-di-tert-butyl-p-cresol were suspended in 15 ml of dioxan and the reaction mixture was stirred at 100° C. under argon for 3 hours. Thereupon, the reaction mixture was filtered, concentrated in a water-jet vacuum and the residue was chromatographed on silica gel with hexane/ethyl acetate (3:1). There was thus obtained 0.93 g (68% of theory) of 2-(3-phenyl-propyl)-5-trimethylstannyl-pyridine in the form of a yellowish oil; MS: 362 (M+H)⁺.

(e) 0.93 g (2.6 mmol) of 2-(3-phenyl-propyl)-5-trimethylstannyl-pyridine,0.9 g (2.7 mmol) of tert-butyl 4-trifluoromethylsulphonyloxy-3,6-dihydro-2H-pyridine-1-carboxylate,0.345 g (8.0 mmol) of lithium chloride,100 mg (0.086 mmol) of tetrakis-(triphenylphosphine)-palladium,3 g of molecular seive (4 Å) and a few crystals of 2,6-di-tert-butyl-p-cresol were suspended in 40 ml of 1,2-dimethoxyethane and the reaction mixture was stirred under reflux for 8 hours under argon. Thereupon, the mixture was filtered, concentrated in a water-jet vacuum and the residue was chromatographed on silica gel with methylene chloride/ether (3:2). There was thus obtained 0.411 g (42% of theory) of tert-butyl 6-(3-phenyl-propyl)-3',6'-dihydro-2'H-[3,4'] bipyridine-1'-carboxylate in the form of a yellowish oil; MS: 379 (M+H)⁺.

(f) 0.587 g (1.55 mmol) of tert-butyl 6-(3-phenyl-propyl)-3',6'-dihydro-2'H-[3,4']bipyridine-1'-carboxylate were dissolved in 8 ml of 1,2-dimethoxyethane, treated with 6 ml of 1 molar borane-tetrahydrofuran solution and stirred at 60° to 65° C. for 4 hours in a flask closed with a Teflon stopper. Thereafter, a further 3 ml of 1 molar borane-tetrahydrofuran solution were added and after 24 hours a further 2.2 ml of 1 molar borane-tetrahydrofuran solution were added and the mixture was stirred at 60 to 65° C. for a total of 48 hours. Subsequently, while cooling with ice,7.0 ml of 50% KOH solution in water followed by 6.0 ml of 30% hydrogen peroxide solution in water were added and the reaction mixture was heated under reflux for 2 hours. Now, the reaction solution was partitioned between water and methylene chloride, the combined methylene chloride phases were dried over magnesium sulphate, concentrated and the thus obtained residue was chromatographed on silica gel with ether/methanol (99:1). There were thus obtained 211 mg (34% of theory) of tert-butyl (3'RS,4'RS)-3'-hydroxy-6-(3-phenyl-propyl)-3',4',5',6'-tetra-hydro-2'H-[3,4'] bipyridine-1'-carboxylate in the form of an amorphous, colourless solid; MS: 397 (M+H)⁺.

(g) In an analogous manner to that described in Example 125(g), from tert-butyl (3'RS,4'RS)-3'-hydroxy-6-(3-phenylpropyl)-3',4',5',6'-tetrahydro-2'H-[3,4']bipyridine-1'-carboxylate and 2-bromomethylnaphthalene there was obtained tert-butyl (3'RS,4'RS)-3'-(naphthalen-2-ylmethoxy)-6-(3-phenyl-propyl)-3',4',5',6'-tetrahydro-2'H-[3,4']bipyridine-1'-carboxylate in the form of an amorphous, colourless solid; MS: 537 (M+H)⁺.

(h) In an analogous manner to that described in Example 125(h), from tert-butyl (3'RS,4'RS)-3'-(naphthalen-2-ylmethoxy)-6-(3-phenyl-propyl)-3',4',5',6'-tetrahydro-2'H-[3,4']bipyridine-1'-carboxylate by cleavage of the BOC group by means of anhydrous zinc bromide there was obtained (3'RS,4'RS)-3'-(naphthalen-2-ylmethoxy)-6-(3-phenyl-propyl)-1',2',3',4',5',6'-hexahydro-[3,4']bipyridine in the form of an amorphous, colourless foam; MS: 437 (M+H)⁺.

EXAMPLE 127

(a) 1.24 g (5.7 mmol) of 5-bromo-2-(3-hydroxy-propyl)-pyridine [J. Org. Chem. 53, 386 (1988)] were dissolved in 4 ml of N,N-dimethylformamide, treated with 0.7 ml (5.9 mmol) of benzyl bromide followed by 285 mg (about 5.9 mmol) of sodium hydride dispersion (about 50% in mineral oil) and stirred at room temperature under argon for 90 minutes. Now, the reaction solution was partitioned between water and methylene chloride, the combined methylene chloride phases were dried over magnesium sulphate, filtered and concentrated in a water-jet vacuum. The thus obtained residue was chromatographed on silica gel with ether/methylene chloride (5:95). There were thus obtained 1.57 g (90% of theory) of 2-(3-benzyloxy-propyl)-5-bromo-pyridine in the form of a yellowish oil.

(b) 1.57 g (5.10 mmol) of 2-(3-benzyloxy-propyl)-5-bromo-pyridine,1.6 ml (7.5 mmol) of hexamethyldistannate,150 mg (0.129 mmol) of tetrakis-(triphenylphosphine)-palladium,3 g of molecular seive (4 Å) and a few crystals of 2,6-di-tert-butyl-p-cresol were suspended in 18 ml of dioxan and the reaction mixture was stirred at 100° C. under argon for 2.5 hours. Thereupon, the reaction mixture was filtered, concentrated in a water-jet vacuum and the residue was chromatographed on silica gel with hexane/ethyl acetate (3:1). There were thus obtained 1.43 g (72% of theory) of 2-(3-benzyloxy-propyl)-5-trimethylstannanyl-pyridine in the form of a yellowish oil; MS: 392 (M+H)⁺.

(c) 1.43 g (3.66 mmol) of 2-(3-benzyloxy-propyl)-5-trimethylstannanyl-pyridine, 1.32 g (4.00 mmol) of tert-butyl 4-trifluoromethylsulphonyloxy-3,6-dihydro-2H-pyridine-1-carboxylate (Example 126(c)),0.477 g (11.3 mmol) of lithium chloride, 150 mg (0.129 mmol) of tetrakis-(triphenylphosphine)-palladium,3 g of molecular seive (4 Å) and a few crystals of 2,6-di-tert-butyl-p-cresol were suspended in 40 ml of 1,2-dimethoxyethane and the reaction mixture was stirred under reflux for 8 hours under argon. Thereupon, the mixture was filtered, concentrated in a water-jet vacuum and the residue was chromatographed on silica gel with methylene chloride/ether (1:1). There was thus obtained 0.903 g (60% of theory) of tert-butyl 6-(3-benzyloxy-propyl)-3',6'-dihydro-2'H-[3,4']bipyridinyl-1'-carboxylate in the form of a yellowish oil; MS: 409 (M+H)⁺.

(d) 0.115 g (0.28 mmol) of tert-butyl 6-(3-benzyloxy-propyl)-3',6'-dihydro-2'H-[3,4']bipyridinyl-1'-carboxylate were dissolved in 1 ml of 1,2-dimethoxyethane, treated with 1 ml of 1 molar borane-tetrahydrofuran solution and stirred at room temperature for 96 hours. Subsequently, while cooling with ice,1.0 ml of 50% KOH solution in water followed by 1.0 ml of 30% hydrogen peroxide solution in water were added and the reaction mixture was heated under reflux for 2 hours. Now, the reaction solution was partitioned between water and methylene chloride and the combined methylene chloride phases were dried over magnesium sulpahte and concentrated. There were thus obtained 105 mg (88% of theory) of tert-butyl (3'RS,4'RS)-6-(3-benzyloxy-propyl)-3'-hydroxy-3',4',5',6'-tetrahydro-2'H-[3,4'] bipyridine-1'-carboxylate in the form of a yellowish oil, which was used directly in the next step.

(e) In an analogous manner to that described in Example 125(g), from tert-butyl (3'RS,4'RS)-6-(3-benzyloxy-propyl)-3'-hydroxy-3',4',5',6'-tetrahydro-2'H-[3,4'] bipyridine-1'-carboxylate and 2-bromomethyinaphthalene there was obtained tert-butyl (3'RS,4'RS)-6-(3-benzyloxy-propyl)-3'-(naphthalen-2-ylmethoxy)-3',4',5',6'-tetrahydro-2'H-[3,4']bipyridine-1'-carboxylate in the form of a colourless oil; MS: 568 (M+H)⁺.

(f) In an analogous manner to that described in Example 125(h), from tert-butyl (3'RS,4'RS)-6-(3-benzyloxy-propyl)-3'-(naphthalen-2-ylmethoxy)-3',4',5',6'-tetrahydro-2'H-[3,4']bipyridine-1'-carboxylate by cleavage of the BOC group by means of anhydrous zinc bromide there was obtained (3'RS,4'RS)-6-(3-benzyloxy-propyl)-3'-(naphthalen-2-ylmethoxy)-1',2',3',4',5',6'-hexahydro-[3,4'] bipyridine in the form of a colourless oil; MS: 467 (M+H)⁺.

EXAMPLE 128

(a) 19 g of sodium hydride dispersion (50% in oil,0.38 mol) were introduced portionwise at at maximum of 30° C. into 104 ml (1.0 mol) of benzyl alcohol dissolved in 175 ml of N,N-dimethylformamide and the mixture was stirred at room temperature for 2 hours. Thereupon,46.4 g (0.183 mol) of 5-bromo-2-(2-trimethylsilyl)ethynyl-pyridine [J. Org. Chem. 53, 386 (1988)] in 50 ml of N,N-dimethylformamide were added dropwise within 10 minutes and the mixture was stirred at room temperature for 2 hours. Subsequently, the reaction mixture was poured into 1000 ml of saturated sodium hydrogen carbonate solution and extracted with ether. The combined ether phases were washed with saturated sodium chloride solution, dried over magnesium sulpahte, filtered and concentrated in a water-jet vacuum. The residue thus obtained was chromatographed on silica gel with methylene chloride/ether (99:1). There were thus obtained 19.5 g (37% of theory) of (E)-2-(2-benzyloxy-vinyl)-5-bromo-pyridine in the form of a yellowish solid.

(b) 17.5 g (0.0603 mol) of (E)-2-(2-benzyloxy-vinyl)-5-bromo-pyridine were dissolved in 650 ml of toluene, treated with about 3 g of Raney-nickel (moist, washed with methanol and toluene) and stirred at room temperature in a hydrogen atmosphere for 72 hours. Within this period a further three similar amount of Raney-nickel were added. Thereupon, the mixture was filtered over a Dicalite pad, concentrated in a water-jet vacuum and the residue was chromatographed on silica gel with methylene chloride/ether (95:5). There were thus obtained 13.2 g (75.4% of theory) of 2-(2-benzyloxy-ethyl)-5-bromo-pyridine in the form of a reddish foam; MS: 292,294 (M+H)⁺.

(c) In analogy to Example 127(b)–(d), from 2-(2-benzyloxy-ethyl)-5-bromo-pyridine via 2-(2-benzyloxy-ethyl)-5-trimethylstannanyl-pyridine [yellowish oil, MS: 362 (M-CH₃)⁺] as well as tert-butyl 4-trifluoromethylsulphonyloxy-3,6-dihydro-2H-pyridine-1-carboxylate, and tert-butyl 6-(2-benzyloxy-ethyl)-3',6'-dihydro-2'H-[3,4']bipyridine-1'-carboxylate [colourless oil, MS: 395 (M+H)⁺], there was obtained tert-butyl (3'RS, 4'RS)-6-(2-benzyloxy-ethyl)-3'-hydroxy-3',4',5',6'-tetrahydro-2'H-[3,4']-bipyridine-1'-carboxylate in the form of a colourless solid; MS: 413 (M+H)⁺.

(d) In an analogous manner to that described in Example 125(g), from tert-butyl (3'RS,4'RS)-6-(2-benzyloxy-ethyl)-3'-hydroxy-3',4',5',6'-tetrahydro-2'H-[3,4']-bipyridine-1'- carboxylate and 2-bromomethyinaphthalene there was obtained tert-butyl (3'RS,4'RS)-6-(2-benzyloxy-ethyl)-3'-(naphthalen-2-ylmethoxy)-3',4',5',6'-tetrahydro-2'H-[3,4']bipyridine-1'-carboxylate in the form of an amorphous, colourless solid; MS: 553 (M+H)$^+$.

(e) In an analogous manner to that described in Example 125(h), from tert-butyl (3'RS,4'RS)-6-(2-benzyloxy-ethyl)-3'-(naphthalen-2-ylmethoxy)-3',4',5',6'-tetrahydro-2'H-[3,4']bipyridine-1'-carboxylate by cleavage of the BOC group by means of anhydrous zinc bromide there was obtained (3'RS, 4'RS)-6-(2-benzyloxy-ethyl)-3'-(naphthalen-2-ylmethoxy)-1',2',3',4',5',6'-hexahydro-[3,4']bipyridine in the form of a beige gum; MS: 453 (M+H)$^+$.

EXAMPLE 129

(a) In analogy to Example 127(b)–(d), from 5-bromo-2-methylsulphanyl-pyrimidine [J. Chem. Soc. 1953, 3129] via 2-methylsulphanyl-5-trimethylstannanyl-pyrimidine (yellowish oil) as well as tert-butyl 4-trifluoromethylsulphonyloxy-3,6-dihydro-2H-pyridine-1-carboxylate, and tert-butyl 4-(2-methylsulphanyl-pyrimidin-5-yl)-3,6-dihydro-2H-pyridine-1-carboxylate (yellowish solid, MS: 308 (M+H)$^+$), there was obtained tert-butyl (3RS,4RS)-3-hydroxy-4-(2-methylsulphanyl-pyrimidin-5-yl)-piperidine-1-carboxylate in the form of a yellowish, amorphous solid; MS: 326 (M+H)$^+$.

(b) In an analogous manner to that described in Example 125(g), from tert-butyl (3RS,4RS)-3-hydroxy-4-(2-methylsulphanyl-pyrimidin-5-yl)-piperidine-1-carboxylate and 2-bromomethyinaphthalene there was obtained tert-butyl (3RS,4RS)-4-(2-methylsulphanyl-pyrimidin-5-yl)-3-(naphthalen-2-ylmethoxy)-piperidine-1-carboxylate in the form of an amorphous, yellowish solid; MS: 466 (M+H)$^+$.

(c) 0.138 g (0.296 mmol) of tert-butyl (3RS,4RS)-4-(2-methylsulphanyl-pyrimidin-5-yl)-3-(naphthalen-2-ylmethoxy)-piperidine-1-carboxylate was dissolved in 5 ml of methylene chloride, treated with 0.113 g (about 0.46 mmol) of m-chloroperbenzoic acid (about 70%), stirred at room temperature for 3 hours, treated with a further 0.050 g (about 0.20 mmol) of m-chloroperbenzoic acid and stirred at room temperature for a further 16 hours. Thereupon, the reaction mixture was partitioned between methylene chloride and saturated soda solution and the combined methylene chloride phases were dried over magnesium sulphate, filtered and concentrated in a water-jet vacuum. The thus obtained residue was crystallized from ether. There was thus obtained 0.102 g (69% of theory) of tert-butyl (3RS,4RS)-4-(2-methylsulphonyl-pyrimidin-5-yl)-3-(naphthalen-2-ylmethoxy)-piperidine-1-carboxylate in the form of a colourless solid; MS: 498 (M+H)$^+$.

(d) 0.027 g (0.24 mmol) of potassium tert-butylate was placed in 1 ml of tetrahydrofuran and 0.038 g (0.22 mmol) of 3-benzyloxy-propanol dissolved in 0.5 ml of tetrahydrofuran was added dropwise at 0° C. After stirring at 0° C. for 15 minutes 0.098 g (0.20 mmol) of tert-butyl (3RS,4RS)-4-(2-methylsulphonyl-pyrimidin-5-yl)-3-(naphthalen-2-ylmethoxy)-piperidine-1-carboxylate dissolved in 1 ml of tetrahydrofuran was added dropwise at the same temperature and the reaction mixture was stirred at room temperature for 18 hours. Thereupon, the mixture was poured on to ice-water and extracted with ether. The combined ether phases were washed with saturated sodium chloride solution, dried over magnesium sulphate, filtered and concentrated in a water-jet vacuum. The residue thus obtained was chromatographed on silica gel with methylene chloride/methanol (95:5). There was thus obtained 0.076 g (66% of theory) of tert-butyl (3RS,4RS)-4-[2-(3-benzyloxy-propoxy)-pyrimidin-5-yl]-3-(naphthalen-2-ylmethoxy)-piperidine-1-carboxylate in the form of a colourless solid; MS: 585 (M+H)$^+$.

(e) In an analogous manner to that described in Example 125(h), from tert-butyl (3RS,4RS)-4-[2-(3-benzyloxy-propoxy)-pyrimidin-5-yl]-3-(naphthalen-2-ylmethoxy)-piperidine-1-carboxylate by cleavage of the BOC group by means of anhydrous zinc bromide there was obtained 2-(3-benzyloxy-propoxy)-5-[(3RS,4RS)-3-(naphthalen-2-ylmethoxy)-piperidin-4-yl]-pyrimidine in the form of a yellowish gum; MS: 485 (M+H)$^+$.

EXAMPLE 130

(a) 0.90 g (2.18 mmol) of tert-butyl (3'RS,4'RS)-6-(2-benzyloxy-ethyl)-3'-hydroxy-3',4',5',6'-tetrahydro-2'H-[3,4']-bipyridine-1'-carboxylate [Example 128(c)] dissolved in 15 ml of tetrahydrofuran was treated with 0.3 ml of acetic acid and 250 mg of palladium-on-charcoal (10%) and the reaction mixture was stirred in a hydrogen atmosphere for 14 days. Subsequently, the mixture was filtered over a 0.8$\mu$ cellulose filter and concentrated in a water-jet vacuum. The residue thus obtained was partitioned between methylene chloride and saturated soda solution, the combined methylene chloride phases were dried over magnesium sulphate, filtered and concentrated in a water-jet vacuum. The crude product was subsquently chromatographed on silica gel with methylene chloride/methanol (95:5). There was thus obtained 0.555 g (80% of theory) of tert-butyl (3'RS,4'RS)-3'-hydroxy-6-(2-hydroxy-ethyl)-3',4',5',6'-tetrahydro-2'H-[3,4']bipyridine-1'-carboxylate in the form of a colourless gum; MS: 323 (M+H)$^+$.

(b) 0.46 g (1.43 mmol) of tert-butyl (3'RS,4'RS)-3'-hydroxy-6-(2-hydroxy-ethyl)-3',4',5',6'-tetrahydro-2'H-[3,4']bipyridine-1'-carboxylate, 0.18 g (1.5 mmol) of 4-dimethylamino-pyridine and 0.32 ml (2.2 mmol) of triethylamine were placed in 5 ml of methylene chloride and treated with 0.55 g (1.7 mmol) of bromotriphenylmethane. After stirring at room temperature for 16 hours a further 0.32 ml (2.2 mmol) of triethylamine and 0.50 g (1.5 mmol) of bromotriphenylmethane were added and the mixture was stirred at room temperature for a futher hour. Thereupon, the reaction mixture was partitioned between methylene chloride and saturated soda solution and the combined methylene chloride phases were dried over magnesium sulphate, filtered and concentrated in a water-jet vacuum. The thus obtained residue was chromatographed on silica gel with methylene chloride/methanol (95:5). There was thus obtained 0.67 g (83% of theory) of tert-butyl (3'RS,4'RS)-3'-hydroxy-6-(2-trityloxy-ethyl)-3',4',5',6'-tetrahydro-2'H-[3,4']bipyridine-1'-carboxylate in the form of a colourless foam; MS: 566 (M+H)$^+$.

(c) In an analogous manner to that described in Example 125(g), from tert-butyl (3'RS,4'RS)-3'-hydroxy-6-(2-trityloxy-ethyl)-3',4',5',6'-tetrahydro-2'H-[3,4']bipyridine-1'-carboxylate and 2-bromomethyinaphthalene there was obtained tert-butyl (3'RS,4'RS)-3'-(naphthalen-2-ylmethoxy)-6-(2-trityloxy-ethyl)-3',4',5',6'-tetrahydro-2'H-[3,4']bipyridine-1'-carboxylate in the form of an amorphous, colourless solid; MS: 706 (M+H)$^+$.

(d) 0.35 g (0.50 mmol) of tert-butyl (3'RS,4'RS)-3'-(naphthalen-2-ylmethoxy)-6-(2-trityloxy-ethyl)-3',4',5',6'-tetrahydro-2'H-[3,4']bipyridine-1'-carboxylate was dissolved in 8 ml of methylene chloride and treated rapidly at room temperature with a solution of 240 mg of trifluoroacetic acid and 440 mg of trifluoroacetic anhydride in 2 ml of methylene chloride and the reaction mixture was stirred for 50 seconds. Thereupon, while cooling with ice, 2.2 ml of triethylamine followed by 3 ml of methanol were added and the mixture was stirred without cooling for 10 minutes. Thereupon, the reaction mixture was partitioned between methylene chloride and saturated soda solution, the combined methylene chloride phases were dried over magnesium sulphate, filtered and concentrated in a water-jet vacuum. The residue thus obtained was chromatographed on silica gel with methylene chloride/methanol (95:5). There was thus obtained 0.189 g (82% of theory) of tert-butyl (3'RS,4'RS)-6-(2-hydroxy-ethyl)-3'-(naphthalen-2-ylmethoxy)-3',4',5',6'-tetrahydro-2'H-[3,4']bipyridine-1'-carboxylate in the form of an amorphous, orange solid; MS: 463 (M+H)⁺.

(e) 0.060 g (0.129 mmol) of tert-butyl (3'RS,4'RS)-6-(2-hydroxy-ethyl)-3'-(naphthalen-2-ylmethoxy)-3',4',5',6'-tetrahydro-2'H-[3,4']bipyridine-1'-carboxylate and 0.022 g (0.129 mmol) of 2-chloro-benzothiazole were dissolved in 0.5 ml of N,N-dimethylformamide and treated with 0.008 g (about 50% in mineral oil, about 0.17 mmol) of sodium hydride and the reaction mixture was stirred at room temperature for 4.5 hours. Thereupon, the mixture was treated with ice-water and extracted with ether. The combined ether phases were dried over magnesium sulphate, filtered and concentrated in a water-jet vacuum. The thus obtained residue was chromatographed on silica gel with methylene chloride/ether (1:1). There was thus obtained 0.053 g (70% of theory) of tert-butyl (3'RS,4'RS)-3'-(naphthalen-2-ylmethoxy)-6-vinyl-3',4',5',6'-tetrahydro-2'H-[3,4']bipyridine-1'-carboxylate in the form of an amorphous, colourless solid; MS: 446 (M+H)⁺.

(f) 0.041 g (0.091 mmol) of tert-butyl (3'RS,4'RS)-3'-(naphthalen-2-ylmethoxy)-6-vinyl-3',4',5',6'-tetrahydro-2'H-[3,4']bipyridine-1'-carboxylate and 0.054 g (0.32 mmol) of 2-mercaptobenzothiazole were dissolved in 0.5 ml of acetonitrile, treated with 0.2 ml (0.12 mmol) of 0.6M sodium methylate solution in methanol and stirred at 80° C. for 3.5 hours. Thereupon, the reaction mixture was concentrated and the residue was chromatographed on silica gel with ethyl acetate/hexane (3:2). There was thus obtained 0.040 g (72% of theory) of tert-butyl (3'RS,4'RS)-3'-(naphthalen-2-ylmethoxy)-6-[2-(2-thioxo-benzothiazol-3-yl)-ethyl]-3',4',5',6'-tetrahydro-2'H-[3,4']bipyridine-1'-carboxylate in the form of an amorphous, yellowish solid; MS: 612 (M+H)⁺.

(g) In an analogous manner to that described in Example 125(h), from tert-butyl (3'RS,4'RS)-3'-(naphthalen-2-ylmethoxy)-6-[2-(2-thioxo-benzothiazol-3-yl)-ethyl]-3',4',5',6'-tetrahydro-2'H-[3,4']bipyridine-1'-carboxylate by cleavage of the BOC group by means of anhydrous zinc bromide there was obtained 3-[2-[(3'RS,4'RS)-3'-(naphthalen-2-ylmethoxy)-1',2',3',4',5',6'-hexahydro-[3,4']bipyridin-6-yl]-ethyl]-3H-benzothiazole-2-thione in the form of an amorphous, colourless solid; MS: 512 (M+H)⁺.

EXAMPLE 131

(a) 0.15 g (0.56 mmol) of 5-bromomethyl-3-(2-chlorophenyl)-[1,2,4]oxadiazole [Example 124], 0.21 g of potassium carbonate and 0.15 g of sodium hydrogen carbonate were stirred at 65° C. for 42 hours in a mixture of 4.5 ml of tetrahydrofuran and 1.0 ml of water. Thereupon, the reaction mixture was cooled, diluted with water and extracted with ether. The combined ether phases were dried over magnesium sulphate, filtered and concentrated in a water-jet vacuum. The thus obtained residue was chromatographed on silica gel with methylene chloride/ether (9:1). There was thus obtained 0.041 g (35% of theory) of [3-(2-chlorophenyl)-[1,2,4]oxadiazol-5-yl]-methanol in the form of a colourless solid; MS: 210 (M)⁺.

(b) 0.040 g (0.19 mmol) of [3-(2-chloro-phenyl)-[1,2,4]oxadiazol-5-yl]-methanol and 0.094 g (0.19 mmol) of tert-butyl (3RS,4RS)-4-(2-methylsulphonyl-pyrimidin-5-yl)-3-(naphthalen-2-ylmethoxy)-piperidine-1-carboxylate [Example 129(c)] were dissolved in 0.5 ml of N,N-dimethylformamide, treated while cooling with ice with 0.0095 g (about 50% in mineral oil, about 0.20 mmol) of sodium hydride and the reaction mixture was stirred at room temperature for 1 hour. Thereupon, the mixture was treated with ice-water and extracted with ether. The combined ether phases were dried over magnesium sulphate, filtered and concentrated in a water-jet vacuum. The residue thus obtained was chromatographed on silica gel with ether. There was thus obtained 0.112 g (94% of theory) of tert-butyl (3RS,4RS)-4-[2-[3-(2-chlorophenyl)-[1,2,4]oxadiazol-5-ylmethoxy]-pyrimidin- 5-yl]-3-(naphthalen-2-ylmethoxy)-piperidine-1-carboxylate in the form of an amorphous, reddish gum; MS: 628 (M+H)⁺.

(c) In an analogous manner to that described in Example 125(h), from tert-butyl (3RS,4RS)-4-[2-[3-(2-chlorophenyl)-[1,2,4]oxadiazol-5-ylmethoxy]-pyrimidin-5-yl]-3-(naphthalen-2-ylmethoxy)-piperidine-1-carboxylate by cleavage of the BOC group by means of anhydrous zinc bromide there was obtained 2-[3-(2-chloro-phenyl)-[1,2,4]oxadiazol-5-ylmethoxy]-5-[(3RS,4RS)-3-(naphthalen-2-ylmethoxy)-piperidin-4-yl]-pyrimidine in the form of an amorphous yellowish solid; MS: 528 (M+H)⁺.

EXAMPLE 132

(a) 2.3 g (10 mmol) of 3-benzyloxy-1-bromo-propane and 0.76 g (10 mmol) of thiourea were heated under reflux in 5.0 ml of ethanol for 3.5 hours. Thereupon, the mixture was cooled to room temperature, treated with 0.6 g (15 mmol) of sodium hydroxide in 6.0 ml of water and stirred under argon for a further 3 hours. Thereupon, the mixture was acidified with dilute hydrochloric acid and extracted with ether. The combined ether phases were dried over magnesium sulphate, filtered and concentrated in a water-jet vacuum. The thus obtained residue was chromatographed on silica gel with hexane/methylene chloride (1:1). There were thus obtained 1.5 g (83% of theory) of 3-benzyloxy-propane-1-thiol as a colourless liquid.

(b) In an analogous manner to that described in Example 131(b), from 3-benzyloxy-propane-1-thiol and tert-butyl (3RS,4RS)-4-(2-methylsulphonyl-pyrimidin-5-yl)-3-(naphthalen-2-ylmethoxy)-piperidine-1-carboxylate [Example 129(c)] there was obtained tert-butyl (3RS,4RS)-4-[2-(3-benzyloxy-propylsulphanyl)-pyrimidin-5-yl]-3-(naphthalen-2-ylmethoxy)-piperidine-1-carboxylate in the form of an amorphous, pink solid; MS: 600 (M+H)⁺.

(c) In an analogous manner to that described in Example 125(h), from tert-butyl (3RS,4RS)-4-[2-(3-benzyloxy-propylsulphanyl)-pyrimidin-5-yl]-3-(naphthalen-2-ylmethoxy)-piperidine-1-carboxylate by cleavage of the BOC group by means of anhydrous zinc bromide there was obtained 2-( 3-benzyloxy-propylsulphanyl)-5-[(3RS,4RS)-3-(naphthalen-2-ylmethoxy)-piperidin-4-yl]-pyrimidine in in the form of an amorphous, colourless solid; MS: 500 (M+H)⁺.

EXAMPLE 133

(a) 0.50 g (2.2 mmol) of 3-benzyloxy-1-bromo-propane was treated with 2.5 ml of 30 percent methylamine solution in ethanol and stirred at 60° C. in a sealed vessel for 10 hours. Thereupon, the mixture was treated with ice-water and extracted with ether. The combined ether phases were dried over magnesium sulphate, filtered and concentrated in a water-jet vacuum. The thus obtained residue was chromatographed on silica gel with methylene chloride/methanol (9:1). There was thus obtained 0.16 g (41% of theory) of (3-benzyloxy-propyl)-methyl-amine as a colourless oil.

(b) 0.15 g (0.84 mmol) of (3-benzyloxy-propyl)-methyl-amine and 0.060 g (0.12 mmol) of tert-butyl (3RS,4RS)-4-

(2-methylsulphonyl-pyrimidin-5-yl)-3-(naphthalen-2-ylmethoxy)-piperidine-1-carboxylate [Example 129(c)] were stirred at 80° C. in 1.5 ml of triethylamine for 18 hours under argon. Thereupon, the mixture was treated with ice-water and extracted with ether. The combined ether phases were dried over magnesium sulphate, filtered and concentrated in a water-jet vacuum. The thus obtained residue was chromatographed on silica gel with methylene chloride/ethyl acetate (1:1). There was thus obtained 0.070 g (97% of theory) of tert-butyl (3RS,4RS)-4-[2-[(3-benzyloxy-propyl)-methyl-amino]-pyrimidin-5-yl]-3-(naphthalen-2-ylmethoxy)-piperidine-1-carboxylate in the form of a brownish gum; MS: 598 (M+H)$^+$.

(c) In an analogous manner to that described in Example 125(h), from tert-butyl (3RS,4RS)-4-[2-[(3-benzyloxy-propyl)-methyl-amino]-pyrimidin-5-yl]-3-(naphthalen-2-ylmethoxy)-piperidine-1-carboxylate by cleavage of BOC group by means of anhydrous zinc bromide there was obtained (3-benzyloxy-propyl)-methyl-[5-[(3RS,4RS)-3-(naphthalen-2-ylmethoxy)-piperidin-4-yl]-pyrimidin-2-yl]-amine in the form of an amorphous colourless solid; MS: 498 (M+H)$^+$.

EXAMPLE 134

(a) 1.15 g (5.0 mmol) of 3-benzyloxy-1-bromo-propane and 1.02 g (5.5 mmol) of potassium phthalimide were stirred at 70–80° C. in 10 ml of N,N-dimethylformamide for 2 hours. Thereupon, the mixture was treated with ice-water and the precipitate which thereupon formed was filtered off, washed with water and dried over phosphorus pentoxide in a water-jet vacuum. There were thus obtained 1.4 g (95% of theory) of 2-(3-benzyloxy-propyl)-isoindole-1,3-dione as a colourless solid.

(b) 1.4 g (4.7 mmol) of 2-(3-benzyloxy-propyl)-isoindole-1,3-dione and 0.9 ml of hydrazine monohydrate were stirred at 100° C. in 10 ml of absolute ethanol under argon for 2 hours. After cooling the mixture was treated with ether, filtered and the filtrate was concentrated. There was thus obtained 0.75 g (96% of theory) of 3-benzyloxy-propylamine as a light yellowish oil.

(c) In an analogous manner to that described in Example 133(b), from 3-benzyloxy-propylamine and tert-butyl (3RS,4RS)-4-(2-methylsulphonyl-pyrimidin-5-yl)-3-(naphthalen-2-ylmethoxy)-piperidine-1-carboxylate [Example 129(c)] there was obtained tert-butyl (3RS,4RS)-4-[2-(3-benzyloxy-propylamino)-pyrimidin-5-yl]-3-(naphthalen-2-ylmethoxy)-piperidine-1-carboxylate in the form of a brownish gum; MS: 583 (M+H)$^+$.

(d) In an analogous manner to that described in Example 125(h), from tert-butyl (3RS,4RS)-4-[2-(3-benzyloxy-propylamino)-pyrimidin-5-yl]-3-(naphthalen-2-ylmethoxy)-piperidine-1-carboxylate by cleavage of the BOC group by means of anhydrous zinc bromide there was obtained (3-benzyloxy-propyl)-{5-[(3RS,4RS)-3-(naphthalen-2-ylmethoxy)-piperidin-4-yl]-pyrimidin-2-yl}-amine in the form of a brownish gum; MS: 483 (M+H)$^+$.

EXAMPLE 135

The following compounds were obtained in an analogous manner to that described in Example 125(h) by cleavage of the BOC group by means of anhydrous zinc bromide:

1) From tert-butyl (3RS,4RS)-4-(2-methylsulphanyl-pyrimidin-5-yl)-3-(naphthalen-2-ylmethoxy)-piperidine-1-carboxylate [Example 129(b)], 2-methylsulphanyl-5-[(3RS,4RS)-3-(naphthalen-2-ylmethoxy)-piperidin-4-yl]-pyrimidine in the form of an amorphous, yellowish solid; MS: 366 (M+H)$^+$;

2) from tert-butyl (3'RS,4'RS)-6-(3-benzyloxy-propyl)-3'-(naphthalen-2-ylmethoxy)-1-oxy-3',4',5',6'-tetrahydro-2'H-[3,4']bipyridine-1'-carboxylate, (3'RS,4'RS)-6-(3-benzyloxy-propyl)-3'-(naphthalen-2-ylmethoxy)-1',2',3',4',5',6'-hexahydro-[3,4']bipyridine-1-oxide in the form of a colourless oil; MS: 483 (M+H)$^+$;

3) from tert-butyl (3'RS,4'RS)-3'-(naphthalen-2-ylmethoxy)-6-(3-phenyl-propyl)-1-oxy-3',4',5',6'-tetrahydro-2'H-[3,4']bipyridine-1'-carboxylate, (3'RS,4'RS)-3'-(naphthalen-2-ylmethoxy)-6-(3-phenyl-propyl)-1',2',3',4',5',6'-hexahydro-[3,4']bipyridine-1-oxide in the form of an amorphous, yellowish solid; MS: 453 (M+H)$^+$;

4) from tert-butyl (3RS,4RS)-3-(naphthalen-2-ylmethoxy)-4-[2-(4-phenyl-butylamino)-pyrimidin-5-yl]-piperidine-1-carboxylate, [5-[(3RS,4RS)-3-(naphthalen-2-ylmethoxy)-piperidin-4-yl]pyrimidin-2-yl]-(4-phenyl-butyl)-amine in the form of an amorphous, reddish solid; MS: 467 (M+H)$^+$;

5) from tert-butyl (3RS,4RS)-4-{2-[methyl-(4-phenyl-butyl)-amino]-pyrimidin-5-yl}-3-(naphthalen-2-ylmethoxy)-piperidine-1-carboxylate, methyl-{5-[(3RS,4RS)-3-(naphthalen-2-ylmethoxy)-piperidin-4-yl]-pyrimidin-2-yl}-(4-phenyl-butyl)-amine in the form of an amorphous, colourless solid; MS: 481 (M+H)$^+$.

The BOC derivatives used as starting materials were prepared as follows:

(b) 0.074 g (0.13 mmol) of tert-butyl(3'RS,4'RS)-6-(3-benzyloxy-propyl)-3'-(naphthalen-2-ylmethoxy)-3',4',5',6'-tetrahydro-2'H-[3,4']bipyridine-1'-carboxylate [Example 127(e)] was dissolved in 1.5 ml of methylene chloride, treated with 0.046 g (about 0.19 mmol) of m-chloroperbenzoic acid (about 70%) and stirred at room temperature for 30 minutes. Thereupon, the reaction mixture was partitioned between methylene chloride and saturated soda solution and the combined methylene chloride phases are dried over magnesium sulphate, filtered and concentrated in a water-jet vacuum. The thus obtained residue was chromatographed on silica gel with methylene chloride/methanol (95:5). There was thus obtained 0.032 g (42% of theory) of tert-butyl (3'RS,4'RS)-6-(3-benzyloxy-propyl)-3'-(naphthalen-2-ylmethoxy)-1-oxy-3',4',5',6'-tetrahydro-2'H-[3,4']bipyridine-1'-carboxylate in the form of an amorphous, colourless solid; MS: 584 (M+H)$^+$.

(c) In an analogous manner to that described in Example 135(b), from tert-butyl (3'RS,4'RS)-3'-(naphthalen-2-ylmethoxy)-6-(3-phenyl-propyl)-3',4',5',6'-tetrahydro-2'H-[3,4']bipyridine-1'-carboxylate [Example 126(g)] there was obtained tert-butyl (3'RS,4'RS)-3'-(naphthalen-2-ylmethoxy)-6-(3-phenyl-propyl)-1-oxy-3',4',5',6'-tetrahydro-2'H-[3,4']bipyridine-1'-carboxylate in the form of a colourless oil; MS: 553 (M+H)$^+$.

(d) In an analogous manner to that described in Example 133(b), from tert-butyl (3RS,4RS)-4-(2-methylsulphonyl-pyrimidin-5-yl)-3-(naphthalen-2-ylmethoxy)-piperidine-1-carboxylate and 4-phenylbutylamine there was obtained tert-butyl (3RS,4RS)-3-(naphthalen-2-ylmethoxy)-4-[2-(4-phenyl-butylamino)-pyrimidin-5-yl]-piperidine-1-carboxylate in the form of an amorphous, colourless solid; MS: 568 (M+H)$^+$.

(e) 0.058 g (0.10 mmol) of tert-butyl (3RS,4RS)-3-(naphthalen-2-ylmethoxy)-4-[2-(4-phenyl-butylamino)-pyrimidin-5-yl]-piperidine-1-carboxylate was dissolved in 1.0 ml of N,N-dimethylformamide and treated at 0° C. with 0.08 ml (1.3 mmol) of methyl iodide followed by 0.010 g (about 0.2 mmol) of sodium hydride dispersion (about 50% in mineral oil) and stirred at room temperature under argon for 90 minutes. Now, the reaction solution was partitioned between water and ether and the combined ether phases were dried over magnesium sulphate, filtered and concentrated in a water-jet vacuum. The residue thus obtained was chromatographed on silica gel with hexane/ethyl acetate (1:1). There was thus obtained 0.021 g (35% of theory) of tert-butyl (3RS,4RS)-4-{2-[methyl-(4-phenyl-butyl)-amino]-pyrimidin-5-yl}-3-(naphthalen-2-ylmethoxy)-piperidine-1-carboxylate in the form of an amorphous, colourless solid; MS: 582 (M+H)$^+$.

EXAMPLE 136

(a) A solution of 40 mg (0.080 mmol) of tert-butyl (3RS, 4RS)-4-(2-methylsulphonyl-pyrimidin-5-yl)-3-(naphthalen-2-ylmethoxy)-piperidine-1-carboxylate [Example 129(c)] in 1.1 ml 2M hydrogen chloride in methanol was stirred at room temperature for 5 hours. Subsequently, the reaction solution was partitioned between saturated sodium carbonate solution and methylene chloride and the combined methylene phases were dried over magnesium sulphate and concentrated. There were thus obtained 33 mg (95% of theory) of 2-methylsulphonyl-5-[(3RS,4RS)-3-(naphthalen-2-ylmethoxy)-piperidin-4-yl]-pyrimidine hydrochloride in the form of a colourless solid; MS: 398 (M+H)$^+$.

(b) The following compounds were obtained by reacting 2-methylsulphonyl-5-[(3RS,4RS)-3-(naphthalen-2-ylmethoxy)-piperidin-4-yl]-pyrimidine hydrochloride with alcohols in an analogous manner to that described in Example 131(b), but using 2 equivalents of sodium hydride:

1) With (E)-3-phenyl-2-propen-1-ol, (E)-5-[(3RS,4RS)-3-(naphthalen-2-ylmethoxy)-piperidin-4-yl]-2-(3-phenyl-allyloxy)-pyrimidine in the form of an amorphous, yellowish solid; MS: 452 (M+H)$^+$;
2) with (E)-2-methyl-3-phenyl-2-propen-1-ol, (E)-2-(2-methyl-3-phenyl-allyloxy)-5-[(3RS,4RS)-3-(naphthalen-2-ylmethoxy)-piperidin-4-yl]-pyrimidine in the form of an amorphous, yellowish solid; MS: 466 (M+H)$^+$.

EXAMPLE 137

The following compounds were obtained by reacting tert-butyl (3RS,4RS)-4-(2-methylsulphonyl-pyrimidin-5-yl)-3-(naphthalen-2-ylmethoxy)-piperidine-1-carboxylate [Example 129(c)] with alcohols and phenols in an analogous manner to that described in Example 131(b) and subsequently cleaving off the BOC group by means of 2M hydrogen chloride in methanol as described in Example 136(a):

1) With 3-hydroxy-biphenyl,2-(biphenyl-3-yloxy)-5-[(3RS,4RS)-3-(naphthalen-2-ylmethoxy)-piperidin-4-yl]-pyrimidine in the form of an amorphous, colourless solid; MS: 488 (M+H)$^+$;
2) with 3-phenoxy-benzyl alcohol,5-[(3RS,4RS)-3-(naphthalen-2-ylmethoxy)-piperidin-4-yl]-2-(3-phenoxy-benzyloxy)-pyrimidine in the form of an amorphous, brownish solid; MS: 519 (M+H)$^+$;
3) with 4-phenoxy-phenol,5-[(3RS,4RS)-3-(naphthalen-2-ylmethoxy)-piperidin-4-yl]-2-(4-phenoxy-phenoxy)-pyrimidine in the form of an amorphous, brownish solid; MS: 504 (M+H)$^+$, as well as 2-methoxy-5-[(3RS,4RS)-3-(naphthalen-2-ylmethoxy)-piperidin-4-yl]-pyrimidine in the form of an amorphous, brownish gum; MS: 349 (M+H)$^+$;
4) with 4-hydroxy-biphenyl,2-(biphenyl-4-yloxy)-5-[(3RS,4RS)-3-(naphthalen-2-ylmethoxy)-piperidin-4-yl]-pyrimidine in the form of an amorphous, colourless solid; MS: 488 (M+H)$^+$.
5) with 3-phenyl-2-propyn-1-ol,5-[(3RS,4RS)-3-(naphthalen-2-ylmethoxy)-piperidin-4-yl]-2-(3-phenyl-prop-2-ynyloxy)-pyrimidine in the form of an amorphous, brownish solid; MS: 451 (M+H)$^+$;
6) with 2-hydroxymethyl-2,3-dihydro-benzo[1,4]dioxin,2-(2RS and 2SR)-(2,3-dihydro-benzo[1,4]dioxin-2-ylmethoxy)-5-[(3RS,4RS)-3-(naphthalen-2-ylmethoxy)-piperidin-4-yl]-pyrimidine in the form of a colourless solid; MS: 484 (M+H)$^+$;
7) with 4-biphenyl-ethanol [Chemische Berichte 85, 897 (1952)],2-(2-biphenyl-4-yl-ethoxy)-5-[(3RS,4RS)-3-(naphthalen-2-ylmethoxy)-piperidin-4-yl]-pyrimidine in the form of an amorphous, yellowish gum; MS: 517 (M+H)$^+$;
8) with 4-phenoxy-benzyl alcohol,5-[(3RS,4RS)-3-(naphthalen-2-ylmethoxy)-piperidin-4-yl]-1-(4-phenoxy-benzyl)-1H-pyrimidin-2-one in the form of an amorphous, colourless solid; MS: 518 (M+H)$^+$;
9) with 4-biphenyl-methanol,2-(biphenyl-4-ylmethoxy)-5-[(3RS,4RS)-3-(naphthalen-2-ylmethoxy)-piperidin-4-yl]-pyrimidine in the form of a yellowish gum; MS: 503 (M+H)$^+$;
10) with [1-(4-chloro-phenyl)-cyclopentyl]-methanol,2-[[1-(4-chloro-phenyl)-cyclopentyl]-methoxy]-5-[(3RS,4RS)-3-(naphthalen-2-ylmethoxy)-piperidin-4-yl]-pyrimidine in the form of a colourless solid; MS: 528 (M+H)$^+$;
11) with 2-naphthalene-methanol,2-(naphthalen-2-ylmethoxy)-5-[(3RS,4RS)-3-(naphthalen-2-ylmethoxy)-piperidin-4-yl]-pyrimidine in the form of an amorphous, yellowish solid; MS: 476 (M+H)$^+$;
12) with 2-naphthalene-ethanol,2-(2-naphthalen-2-yl-ethoxy)-5-[(3RS,4RS)-3-(naphthalen-2-ylmethoxy)-piperidin-4-yl]-pyrimidine in the form of an amorphous, brownish solid; MS: 490 (M+H)$^+$;
13) with 2-(4-bromophenyl)-ethanol,2-[2-(4-bromo-phenyl)-ethoxy]-5-[(3RS,4RS)-3-(naphthalen-2-ylmethoxy)-piperidin-4-yl]-pyrimidine in the form of an amorphous, brownish solid; MS: 518, 520 (M+H)$^+$;
14) with 2-(2-chloro-phenoxy)-ethanol,2-[2-(2-chloro-phenoxy)-ethoxy]-5-[(3RS,4RS)-3-(naphthalen-2-ylmethoxy)-piperidin-4-yl]-pyrimidine in the form of an amorphous, brownish solid; MS: 490 (M+H)$^+$;
15) with 2-benzyloxy-ethanol,2-(2-benzyloxy-ethoxy)-5-[(3RS,4RS)-3-(naphthalen-2-ylmethoxy)-piperidin-4-yl]-pyrimidine in the form of an amorphous, yellowish solid; MS: 470 (M+H)$^+$;
16) with 3-cyclohexyl-propanol,2-(3-cyclohexyl-propoxy)-5-[(3RS,4RS)-3-(naphthalen-2-ylmethoxy)-piperidin-4-yl]-pyrimidine in the form of an amorphous, brownish solid; MS: 461 (M+H)$^+$;
17) with 3-(6-methyl-pyridin-2-yl)-propanol,2-[3-(6-methyl-pyridin-2-yl)-propoxy]-5-[(3RS,4RS)-3-(naphthalen-2-ylmethoxy)-piperidin-4-yl]-pyrimidine in the form of an amorphous, brownish solid; MS: 469 (M+H)$^+$;
18) with 2-cyclohexyloxy-ethanol,2-(2-cyclohexyloxy-ethoxy)-5-[(3RS,4RS)-3-(naphthalen-2-ylmethoxy)-piperidin-4-yl]-pyrimidine in the form of an amorphous, yellowish solid; MS: 462 (M+H)$^+$;
19) with 2-(phenylthio)-ethanol,5-[(3RS,4RS)-3-(naphthalen-2-ylmethoxy)-piperidin-4-yl]-2-(2-phenylsulphanyl-ethoxy)-pyrimidine in the form of an amorphous, yellowish solid; MS: 472 (M+H)$^+$;
20) with 2-(5-methyl-2-phenyloxazol-4-yl)-ethanol (acquired from Maybridge Chemical Company),2-[2-(5-methyl-2-phenyl-oxazol-4-yl)-ethoxy]-5-[(3RS,4RS)-3-(naphthalen-2-ylmethoxy)-piperidin-4-yl]-pyrimidine in the form of an amorphous, brownish solid; MS: 522 (M+H)$^+$;

21) with 2-cyclohexyl-ethanol,2-(2-cyclohexyl-ethoxy)-5-[(3RS,4RS)-3-(naphthalen-2-ylmethoxy)-piperidin-4-yl]-pyrimidine in the form of an amorphous, colourless solid; MS: 447 (M+H)$^+$;

22) with (RS)-4-(2-hydroxy-ethyl)-5-methyl-2-phenyl-2,4-dihydro-pyrazol-3-one (acquired from Maybridge Chemical Company), a mixture of (RS)- and (SR)-5-methyl-4-[2-[5-[(3RS,4RS)-3-(naphthalen-2-ylmethoxy)-piperidin-4-yl]-pyrimidin-2-yloxy]-ethyl]-2-phenyl-2,4-dihydro-pyrazol-3-one in the form of an amorphous, colourless solid; MS: 536 (M+H)$^+$.

EXAMPLE 138

0.045 g (0.082 mmol) of tert-butyl (3'RS,4'RS)-3'-(naphthalen-2-ylmethoxy)-6-(3-phenyl-propyl)-1-oxy-3',4',5',6'-tetrahydro-2'H-[3,4']bipyridine-1'-carboxylate [Example 135(c)] was dissolved in 1.5 ml of N,N-dimethylformamide, treated with 0.10 ml (0.8 mmol) of trifluoroacetic anhydride and stirred at room temperature for 2 hours. Thereupon, the reaction mixture was partitioned between methylene chloride and saturated bicarbonate solution and the combined methylene chloride phases were dried over magnesium sulphate, filtered and concentrated in a water-jet vacuum. The thus obtained residue was chromatographed on silica gel with methylene chloride/methanol (95:5). There was thus obtained 0.019 g (52% of theory) of (3'RS,4'RS)-3'-(naphthalen-2-ylmethoxy)-6-(3-phenyl-propyl)-1',2',3',4',5',6'-hexahydro-[3,4']bipyridin-4-ol in the form of an amorphous, colourless solid; MS: 453 (M+H)$^+$.

EXAMPLE 139

The following compounds were obtained by reacting tert-butyl (3RS,4RS)-3-(1,4-dimethoxy-naphthalen-2-ylmethoxy)-4-(2-methylsulphonyl-pyrimidin-5-yl)-piperidine-1-carboxylate with alcohols in an analogous manner to that described in Example 131(b) and subsequently cleaving off the BOC group by means of anhydrous zinc bromide in methylene chloride as described in Example 125(h):

1) With 3-phenyl-2-propyn-1-ol,5-[(3RS,4RS)-3-(1,4-dimethoxy-naphthalen-2-ylmethoxy)-piperidin-4-yl]-2-(3-phenyl-prop-2-ynyloxy)-pyrimidine in the form of an amorphous, yellowish solid; MS: 510 (M+H)$^+$;
2) with 3-cyclohexyl-propanol,2-(3-cyclohexyl-propoxy)-5-[(3RS,4RS)-3-(1,4-dimethoxy-naphthalen-2-ylmethoxy)-piperidin-4-yl]-pyrimidine in the form of an amorphous, brownish solid; MS: 521 (M+H)$^+$;
3) with 4-cyclohexyl-butanol,2-(4-cyclohexyl-butoxy)-5-[(3RS,4RS)-3-(1,4-dimethoxy-naphthalen-2-ylmethoxy)-piperidin-4-yl]-pyrimidine in the form of an amorphous, yellowish solid; MS: 535 (M+H)$^+$;
4) with 2-indan-2-yl-ethanol [J. Am. Chem. Soc. 87, 1297 (1965)], 5-[(3RS,4RS)-3-(1,4-dimethoxy-naphthalen-2-ylmethoxy)-piperidin-4-yl]-2-(2-indan-2-yl-ethoxy)-pyrimidine in the form of an amorphous, yellowish solid; MS: 540 (M+H)$^+$;
5) with 3-(2-methoxy-benzyloxy)-propan-1-ol (prepared by alkylating propylene glycol in a large excess with 2-methoxy-benzyl chloride using sodium hydride in N,N-dimethylformamide),5-[(3RS,4RS)-3-(1,4-dimethoxy-naphthalen-2-ylmethoxy)-piperidin-4-yl]-2-[3-(2-methoxy-benzyloxy)propoxy]-pyrimidine in the form of an amorphous, colourless solid; MS: 574 (M+H)$^+$;
6) with (E)-4-phenyl-but-3-en-1-ol [Example 122(b)],5-[(3RS,4RS)-3-(1,4-dimethoxy-naphthalen-2-ylmethoxy)-piperidin-4-yl]-2-[(E)-4-phenyl-but-3-enyloxy]-pyrimidine in the form of an amorphous, colourless solid; MS: 526 (M+H)$^+$;
7) with 2-(5-phenyl-pyridin-2-yl)-ethanol [Example 139 (b)],5-[(3RS,4RS)-3-(1,4-dimethoxy-naphthalen-2-ylmethoxy)-piperidin-4-yl]-2-[2-(5-phenyl-pyridin-2-yl)-ethoxy]-pyrimidine in the form of an amorphous, colourless solid; MS: 576 (M)$^+$;
8) with 5-phenyl-4-pentyn-1-ol,5-[(3RS,4RS)-3-(1,4-dimethoxy-naphthalen-2-ylmethoxy)-piperidin-4-yl]-2-(5-phenyl-pent-4-ynyloxy)-pyrimidine in the form of an amorphous, orange solid; MS: 537 (M)$^+$.

The following compounds were obtained by reacting tert-butyl (3RS,4RS)-3-(1,4-dimethoxy-naphthalen-2-ylmethoxy)-4-(2-methylsulphonyl-pyrimidin-5-yl)-piperidine-1-carboxylate with amines in an analogous manner to that described in Example 133(b) and subsequently cleaving off the BOC group by means of anhydrous zinc bromide in methylene chloride as described in Example 125(h):

9) With 4-phenylbutylamine, {5-[(3RS,4RS)-3-(1,4-dimethoxy-naphthalen-2-ylmethoxy)-piperidin-4-yl]-pyrimidin-2-yl}-(4-phenyl-butyl)-amine in the form of an amorphous, orange solid; MS: 527 (M+H)$^+$;
10) with 2-(5-phenyl-pyridin-2-yl)-ethylamine [Example 139(d)], {5-[(3RS,4RS)-3-(1,4-dimethoxy-naphthalen-2-ylmethoxy)-piperidin-4-yl]-pyrimidin-2-yl}-[2-(5-phenyl-pyridin-2-yl)-ethyl]-amine in the form of an amorphous, colourless solid; MS: 576 (M+H)$^+$;
11) with 3-methoxy-benzylamine, {5-[(3RS,4RS)-3-(1,4-dimethoxy-naphthalen-2-ylmethoxy)-piperidin-4-yl]-pyrimidin-2-yl}-(3-methoxy-benzyl)-amine in the form of an amorphous, colourless solid; MS: 514 (M)$^+$;
12) with 4-methoxy-benzylamine, {5-[(3RS,4RS)-3-(1,4-dimethoxy-naphthalen-2-ylmethoxy)-piperidin-4-yl]-pyrimidin-2-yl}-(4-methoxy-benzyl)-amine in the form of an amorphous, yellowish solid; MS: 514 (M)$^+$;
13) with 3-bromo-benzylamine, (3-bromo-benzyl)-{5-[(3RS,4RS)-3-(1,4-dimethoxy-naphthalen-2-ylmethoxy)-piperidin-4-yl]-pyrimidin-2-yl}-amine in the form of an amorphous, colourless solid; MS: 562, 564 (M)$^+$;
14) with 3-methyl-benzylamine, {5-[(3RS,4RS)-3-(1,4-dimethoxy-naphthalen-2-ylmethoxy)-piperidin-4-yl]-pyrimidin-2-yl}-(3-methyl-benzyl)-amine in the form of an amorphous, colourless solid; MS: 499 (M+H)$^+$;
15) with 4-bromo-benzylamine, (4-bromo-benzyl)-{5-[(3RS,4RS)-3-(1,4-dimethoxy-naphthalen-2-ylmethoxy)-piperidin-4-yl]-pyrimidin-2-yl}-amine in the form of an amorphous, colourless solid; MS: 563, 565 (M+H)$^+$.

The tert-butyl (3RS,4RS)-3-(1,4-dimethoxy-naphthalen-2-ylmethoxy)-4-(2-methylsulphonyl-pyrimidin-5-yl)-piperidine-1-carboxylate required as the starting material was prepared as follows:

(a) In an analogous manner to that described in Example 125(g), from tert-butyl (3RS,4RS)-3-hydroxy-4-(2-methylsulphanyl-pyrimidin-5-yl)-piperidine-1-carboxylate [Example 129(a)] and 2-chloromethyl-1,4-dimethoxy-naphthalene [J. Amer. Chem. Soc. 64, 2657 (1942)] there was obtained tert-butyl (3RS,4RS)-3-(1,4-dimethoxy-naphthalen-2-ylmethoxy)-4-(2-methylsulphanyl-pyrimidin-5-y5)-piperidine-1-carboxylate in the form of an amorphous, colourless solid; MS: 527 (M+H)$^+$.

(b) In an analogous manner to that described in Example 129(c), from tert-butyl (3RS,4RS)-3-(1,4-dimethoxy-naphthalen-2-ylmethoxy)-4-(2-methylsulphanyl-pyrimidin-5-yl)-piperidine-1-carboxylate by oxidation with m-chloroperbenzoic acid there was obtained tert-butyl (3RS,4RS)-3-(1,4-dimethoxy-naphthalen-2-ylmethoxy)-4-(2- methylsulphonyl-pyrimidin-5-yl)-piperidin-1-carboxylate in the form of a colourless solid; MS: 558 (M+H)$^+$.

The 2-(5-phenyl-pyridin-2-yl)-ethanol and 2-(5-phenyl-pyridin-2-yl)-ethylamine used as condensation reagents were prepared as follows:

(α) 1.16 g (4 mmol) of 2-(2-benzyloxy-ethyl)-5-bromo-pyridine [Example 128(b)],139 mg (1.13 mmol) of tetrakis-(triphenylphosphine)-palladium and 537 mg (8.2 mmol) of phenylboric acid were dissolved in a small amout of ethanol and added all at once to 80 ml of toluene. Subsequently,1.87 g (17.6 mmol) of sodium carbonate in 4.4 ml of water were added and the reaction mixture was heated under reflux for 7.5 hours under argon. After cooling the reaction solution was concentrated in a water-jet vacuum and partitioned between methylene chloride and water. The combined methylene chloride phases were dried over magnesium sulphate, filtered and concentrated in a water-jet vacuum. The thus obtained residue was thereupon chromatographed on silica gel with methylene chloride/ether (93:7). There were thus obtained 1.005 g (87% of theory) of 2-(2-benzyloxy-ethyl)-5-phenyl-pyridine as a colourless solid; $R_f$: 0.08 (SiO$_2$, methylene choride:ether=93:7).

(β) 1.0 g (3.5 mmol) of 2-(2-benzyloxy-ethyl)-5-phenyl-pyridine was dissolved in 1 ml of glacial acetic acid, treated with 1.8 ml (6.7 mmol) of hydrobromic acid in glacial acetic acid (30%) and the reaction mixture was stirred at room temperature for 18 hours. Thereupon, it was poured on to ice-water, extracted twice with hexane, the hexane phases were discarded and the aqueous phase was made alkaline with sodium carbonate solution and extracted three times with ether. The combined ether phases were dried over magnesium sulphate, filtered and concentrated in a water-jet vacuum. The thus obtained 2-(5-phenyl-pyridin-2-yl)-ethyl acetate was thereupon taken up in 12 ml of acetonitrile and treated with 5 ml of water and 4 ml of 2N sodium hydroxide solution and stirred at room temperature for 2.5 hours. Thereupon, aqueous ammonium chloride solution was added and the mixture was extracted with methylene chloride. The combined methylene chloride phases were dried over magnesium sulphate, filtered and concentrated in a water-jet vacuum. The thus obtained residue was thereupon chromatographed on silica gel with methylene chloride/ether (1:1). There was thus obtained 0.656 g (94% of theory) of 2-(5-phenyl-pyridin-2-yl)-ethanol as a colourless solid; $R_f$:0.09 (SiO$_2$, methylene chloride:ether=1:1).

(γ) 0.473 g (2.4 mmol) of 2-(5-phenyl-pyridin-2-yl)-ethanol, 0.420 g (2.85 mmol) of phthalimide and 0.747 g (2.85 mmol) of triphenylphosphine were dissolved in 10 ml of tetrahydrofuran and the reaction mixture was thereupon treated under argon at −5° C. with 0.47 ml (3.0 mmol) of diethyl azodicarboxylate and stirred at −5° C. for a further 20 minutes and at room temperature for a further 18 hours. Thereupon, the reaction mixture was concentrated in a water-jet vacuum and the residue was chromatographed on silica gel with methylene chloride/methanol (98:2). There was thus obtained 0.657 g (83% of theory) of 2-[2-(5-phenyl-pyridin-2-yl)-ethyl]-isoindole-1,3-dione as a colourless solid; $R_f$: 0.38 (SiO$_2$, hexane:ethyl acetate=1:1).

(δ) 0.657 g (2.0 mmol) of 2-[2-(5-phenyl-pyridin-2-yl)-ethyl]-isoindole-1,3-dione, 0.5 ml of hydrazine hydrate and 5 ml of ethanol were heated under reflux for 3.5 hours under argon. Thereupon, the mixture was diluted with 5 ml of ethanol and 20 ml of ether, filtered and the filtrate was concentrated in a water-jet vacuum. The thus obtained residue was subsequently chromatographed on silica gel with methylene chloride/methanol/conc. aq. ammonia (89:10:1). There was thus obtained 0.250 g (63% of theory) of 2-(5-phenyl-pyridin-2-yl)-ethylamine as a yellowish, amorphous solid; $R_f$: 0.17 (SiO$_2$, methylene chloride:methanol:conc. aq. ammonia=89:10:1).

EXAMPLE 140

The following compounds were obtained by reacting tert-butyl (3'RS,4'RS)-3'-(1,4-dimethoxy-naphthalen-2-ylmethoxy)-6-methylsulphonyl-3',4',5',6'-tetrahydro-2'H-[3, 4']bipyridine-1'-carboxylate with alcohols in an analogous manner to that described in Example 129(d) and subsequently cleaving off the BOC group by means of anhydrous zinc bromide in methylene chloride as described in Example 125(h):

1) With 3-cyclohexyl-propanol, (3'RS,4'RS)-6-(3-cyclohexyl-propoxy)-3'-(1,4-dimethoxy-naphthalen-2-ylmethoxy)-1',2',3',4',5',6'-hexahydro-[3,4']bipyridine in the form of a colourless solid; MS: 519 (M+H)$^+$.

2) With 3-(2-methoxy-benzyloxy)-propan-1-ol (prepared by alkylating propylene glycol in a large excess with 2-methoxy-benzyl chloride using sodium hydride in N,N-dimethylformamide), (3'RS,4'RS)-3'-(1,4-dimethoxy-naphthalen-2-ylmethoxy)-6-[3-(2-methoxybenzyloxy)-propoxy]-1',2',3',4',5',6'-hexahydro-[3,4-bipyridine in the form of an amorphous, colourless solid; MS: 573 (M+H)$^+$.

3) With 4-cyclohexyl-butanol, (3'RS,4'RS)-6-(4-cyclohexyl-butoxy)-3'-(1,4-dimethoxy-naphthalen-2-ylmethoxy)-1', 2',3',4',5',6'-hexahydro-[3,4']bipyridine in the form of an amorphous, colourless oil; MS: 533 (M+H)$^+$.

The tert-butyl (3'RS,4'RS)-3'-(1,4-dimethoxy-naphthalen-2-ylmethoxy)-6-methylsulphonyl-3',4',5',6'-tetrahydro-2'H-[3,4']bipyridine-1'-carboxylate used as the starting material was prepared as follows:

(a) In an analogous manner to that described in Example 127(b)–(c), from tert-butyl 2-methylsulphanyl-5-bromo-pyridine [Tetrahedron 41, 1373 (1985)] via 2-methylsulphanyl-5-trimethylstannanyl-pyridine [colourless oil, MS: 289 (M)$^+$], as well as 4-trifluormethylsulphonyloxy-3,6-dihydro-2H-pyridine-1-carboxylate there was obtained tert-butyl 6-methylsulphanyl-3',6'-dihydro-2'H-[3,4']bipyridine-1'-carboxylate in the form of a yellowish solid; MS: 307 (M+H)$^+$.

(b) 1.5 g (4.9 mmol) of tert-butyl 6-methylsulphanyl-3',6'-dihydro-2'H-[3,4']bipyridine-1'-carboxylate were dissolved in 15 ml of 1,2-dimethoxyethane, treated at 3–4° C. with 8.8 ml of 1 molar borane-tetrahydrofuran solution and subsequently stirred at room temperature for 4 hours. Thereupon, while cooling with ice,15 ml of water and subsequently portionwise 3.5 g (22.3 mmol) of solid sodium percarbonate were added and the reaction mixture was heated to 50° C. for 1 hour. Now, the reaction solution was partitioned between water and methylene chloride and the combined methylene chloride phases were washed with sodium pyrosulphite solution and water, dried over magnesium sulphate and concentrated. The thus obtained residue was subsequently chromatographed on silica gel with hexane/ethyl acetate (1:1). There were thus obtained 330 mg (21% of theory) of tert-butyl (3'RS,4'RS)-3'-hydroxy-6-methylsulphanyl-3',4', 5',6'-tetrahydro-2'H-[3,4']bipyridine-1'-carboxylate in the form of a colourless amorphous solid; MS: 324 (M)$^+$.

(c) In an analogous manner to that described in Example 125(g), from tert-butyl (3'RS,4'RS)-3'-hydroxy-6-methylsulphanyl-3',4',5',6'-tetrahydro-2'H-[3,4']bipyridine-1'-carboxylate by alkylation with 2-chloromethyl-1,4-dimethoxy-naphthalene [J. Amer. Chem. Soc. 64, 2657 (1942)] there was obtained tert-butyl (3'RS,4'RS)-3'-(1,4- dimethoxy-naphthalen-2-ylmethoxy)-6-methylsulphanyl-3',4',5',6'-tetrahydro-2'H-[3,4']bipyridine-1'-carboxylate in the form of a colourless solid; MS: 526 (M+H)⁺.

(d) In an analogous manner to that described in Example 129(c), from tert-butyl (3'RS,4'RS)-3'-(1,4-dimethoxy-naphthalen-2-ylmethoxy)-6-methylsulphanyl-3',4',5',6'-tetrahydro-2'H-[3,4']bipyridine-1'-carboxylate by oxidation with m-chloroperbenzoic acid there was obtained tert-butyl (3'RS,4'RS)-3'-(1,4-dimethoxy-naphthalen-2-ylmethoxy)-6-methylsulphonyl-3',4',5',6'-tetrahydro-2'H-[3,4']bipyridine-1'-carboxylate in the form of an amorphous, colourless solid; MS: 557 (M+H)⁺.

EXAMPLE 141

(a) 50.0 g (0.6 mol) of 1,2,5,6-tetrahydropyridine and 135.3 g (0.6 mol) of di-tert-butyl dicarbonate in 1250 ml of water (deionized)/dioxan (3:2) were stirred at room temperature for 3 hours with the addition of 166.0 g (1.2 mol) of potassium carbonate (anhydrous). The mixture was poured on to ice-water, the product was extracted 3 times with 300 ml of ethyl acetate each time, the organic phases were washed twice with 500 ml of distilled water each time, then dried over magnesium sulphate, filtered and concentrated in a water-jet vacuum. The thus obtained crude product was chromatographed on silica gel with hexane and ethyl acetate. After drying in a high vacuum for 3 hours at room temperature there were thus obtained 109.4 g (99% of theory) of tert-butyl 3,6-dihydro-2H-pyridine-1-carboxylate as a pale yellow oil; MS: 183 (M)⁺.

(b) 127.0 g (0.6 mol) of m-chloroperbenzoic acid were dissolved in 1.5 l of methylene chloride under argon, then a solution of 108 g (0.59 mol) of tert-butyl 3,6-dihydro-2H-pyridine-1-carboxylate in 500 ml of methylene chloride was added dropwise at 5° C. within 1 hour and the mixture was subsequently stirred at room temperature overnight. The mixture was poured on to ice-water, adjusted to pH>8 with potassium carbonate solution and, after phase separation, back-extracted twice with 500 ml of methylene chloride each time; the organic phases were washed neutral twice with water, then dried over magnesium sulphate, filtered and the solvent was distilled off in a water-jet vacuum. The crude product was chromatographed on silica gel with hexane and ethyl acetate. There were thus obtained 86.64 g (74% of theory) of tert-butyl (1RS,6SR)-7-oxa-3-aza-bicyclo[4.1.0]heptane-3-carboxylate as a pale yellow oil; MS: 199 (M)⁺.

(c) 19.9 g (100 mmol) of tert-butyl (1RS,6SR)-7-oxa-3-aza-bicyclo[4.1.0]heptane-3-carboxylate and 32.5 g (500 mmol) of sodium azide were stirred at reflux for 3 hours with the addition of 39.1 g (250 mmol) of magnesium sulphate dihydrate in 500 ml of abs. methanol. The mixture was thereupon cooled to 10° C., filtered and the solvent was distilled off in a water-jet vacuum. The residue was taken up in 300 ml of methylene chloride, again filtered and the solvent was distilled off in a water-jet vacuum. The thus obtained crude product was chromatographed on silica gel with n-hexane and ethyl acetate. There were thus obtained 15.86 g (66% of theory) of tert-butyl (3RS,4RS)-4-azido-3-hydroxy-piperidine-1-carboxylate in the form of colourless crystals; MS: 242 (M)⁺.

(d) 15.4 g (63.5 mmol) of tert-butyl (3RS,4RS)-4-azido-3-hydroxy-piperidine-1-carboxylate and 15.5 g (69.9 mmol) of 2-bromomethyl-naphthalene were placed in 200 ml of dimethylformamide under argon at 5° C. Thereupon,3.33 g (76.2 mmol) of sodium hydride dispersion (55% in mineral oil) were added in one portion with external cooling and then the mixture was stirred at room temperature overnight. The mixture was poured on to ice-water, the product was extracted 3 times with 200 ml of ethyl acetate each time, the organic phases were washed twice with 300 ml of water each time, then dried over magnesium sulphate, filtered and concentrated in a water-jet vacuum. The thus obtained crude product was chromatographed on silica gel with n-hexane and ethyl acetate. There were thus obtained 23.18 g (95% of theory) of tert-butyl (3RS,4RS)-4-azido-3-(naphthalen-2-ylmethoxy)-piperidine-1-carboxylate as a pale yellow oil; MS: 383 (M+H)⁺.

(e) 3.20 g (8.37 mmol) of tert-butyl (3RS,4RS)-4-azido-3-(naphthalen-2-ylmethoxy)-piperidine-1-carboxylate and 9.87 ml (176.3 mmol) of propargyl alcohol were stirred at reflux in 80 ml of toluene for 5 hours. After distilling off the solvent in a water-jet vacuum the crude product was chromatographed on silica gel with methylene chloride and methanol. There were thus obtained 1.47 g (40% of theory) of tert-butyl (3RS,4RS)-4-(4-hydroxymethyl-[1,2,3]triazol-1-yl)-3-(naphthalen-2-ylmethoxy)-4-piperidine-1-carboxylate in the form of colourless crystals [MS: 439 (M+H)⁺] and 0.81 g (22% of theory) of tert-butyl (3RS,4RS)-4-(5-hydroxymethyl-[1,2,3]triazol-1-yl)-3-(naphthalen-2-ylmethoxy)-4-piperidine-1-carboxylate in the form of colourless crystals; MS: 439 (M+H)⁺.

(f) 0.22 g (0.5 mmol) of tert-butyl (3RS,4RS)-4-(5-hydroxymethyl-[1,2,3]triazol-1-yl)-3-(naphthalen-2-ylmethoxy)-4-piperidine-1-carboxylate and 0.064 ml (0.5 mmol) of ortho-chloro-benzoyl chloride were placed in 10 ml of methylene chloride under argon at room temperature. Thereupon, there were added firstly while stirring 0.41 ml (3 mmol) of triethylamine and then 0.025 g (0.2 mmol) of 4-dimethylamino-pyridine and the mixture was stirred at room temperature for 18 hours. After distillation of the solvent in a water-jet vacuum the crude product was chromatographed on silica gel with methylene chloride and methanol. There were thus obtained 0.14 g (49% of theory) of tert-butyl (3RS,4RS)-4-[4-(2-chloro-benzoyloxymethyl)-[1,2,3]triazol-1-yl]-3-(naphthalen-2-ylmethoxy)-piperidine-1-carboxylate as a colourless resin; MS: 577 (M+H)⁺.

(g) In an analogous manner to that described in Example 136(a), from tert-butyl (3RS,4RS)-4-[4-(2-chloro-benzoyloxymethyl)-[1,2,3]triazol-1-yl]-3-(naphthalen-2ylmethoxy)-piperidine-1-carboxylate by cleavage of the BOC group with hydrogen chloride in methanol there was obtained 1-[(3RS,4RS)-3-(naphthalen-2-ylmethoxy)-piperidin-4-yl]-1H-[1,2,3]triazol-4-ylmethyl 2-chloro-benzoate hydrochloride (1:1) in the form of colourless crystals; MS: 477 (M+H)⁺.

EXAMPLE 142

The following compounds were obtained in an analogous manner to that described in Example 136(a) by cleavage of the BOC group by means of hydrogen chloride in methanol:

1) From tert-butyl (3RS,4RS)-4-(5-benzyloxymethyl-[1,2,3]triazol-1-yl)-3-(naphthalen-2-ylmethoxy)-piperidine-1-carboxylate, (3RS,4RS)-4-(5-benzyloxymethyl-[1,2,3]triazol-1-yl)-3-(naphthalen-2-ylmethoxy)-piperidine as a pale yellow oil; MS: 429 (M+H)⁺;

2) from tert-butyl (3RS,4RS)-4-(4-benzyloxymethyl-[1,2,3]triazol-1-yl)-3-(naphthalen-2-ylmethoxy)-piperidine-1-carboxylate, (3RS,4RS)-4-(4-benzyloxymethyl-[1,2,3]triazol-1-yl)-3-(naphthalen-2-ylmethoxy)-piperidine hydrochloride (1:1) in the form of colourless crystals; MS: 429 (M+H)⁺;

3) from tert-butyl (3RS,4RS)-4-[5-(3-benzyloxy-propoxymethyl)-[1,2,3]triazol-1-yl]-3-(naphthalen-2-ylmethoxy)-piperidine-1-carboxylate, (3RS,4RS)-4-[5-(3-benzyloxy-propoxymethyl)-[1,2,3]triazol-1-yl]-3-(naphthalen-2-ylmethoxy)-piperidine as a colourless oil; MS: 487 (M+H)⁺;

4) from tert-butyl (3RS,4RS)-4-[4-(3-benzyloxy-propoxymethyl)-[1,2,3]triazol-1-yl]-3-(naphthalen-2-ylmethoxy)-piperidine-1-carboxylate, (3RS,4RS)-4-[4-(3-benzyloxy-propoxymethyl)-[ 1,2,3]triazol-1-yl]-3-(naphthalen-2-ylmethoxy)-piperidine as a colourless oil; MS: 487 (M+H)$^+$.

The BOC derivatives used as starting materials were prepared as follows:

(a) 0.22 g (0.5 mmol) of tert-butyl (3RS,4RS)-4-(5-hydroxymethyl-[1,2,3]triazol-1-yl)-3-(naphthalen-2-ylmethoxy)-4-piperidine-1-carboxylate [Example 141(e)] and 0.09 ml (0.75 mmol) of benzyl bromide were placed in 5 ml of dimethylformamide under argon at 5° C., then 0.044 g (1 mmol) of sodium hydride dispersion (55% in mineral oil) was added in one portion and the mixture was stirred at room temperature for 18 hours. The mixture was thereupon poured on to ice-water, the product was extracted 3 times with 30 ml of ethyl acetate each time and the organic phases were washed twice with 25 ml of distilled water each time, dried over magnesium sulphate, filtered and concentrated in a water-jet vacuum. The thus obtained crude product was chromatographed on silica gel with methylene chloride and methanol. There was thus obtained 0.24 g (91% of theory) of tert-butyl (3RS,4RS)-4-(5-benzyloxymethyl-[1,2,3]triazol- 1-yl)-3-(naphthalen-2-ylmethoxy)-piperidine-1-carboxylate as a pale yellow oil; MS: 529 (M+H)$^+$.

(b) In an analogous manner to that described in Example 142(a), from tert-butyl (3RS,4RS)-4-(4-hydroxymethyl-[1,2,3] triazol-1-yl)-3-(naphthalen-2-ylmethoxy)-4-piperidine-1-carboxylate [Example 141(e)] there was obtained tert-butyl (3RS,4RS)-4-(4-benzyloxymethyl-[1,2,3]triazol-1-yl)-3-(naphthalen-2-ylmethoxy)-piperidine-1-carboxylate as a yellow oil; MS: 529 (M+H)$^+$.

(c) 0.22 g (0.5 mmol) of tert-butyl (3RS,4RS)-4-(5-hydroxymethyl-[1,2,3] triazol-1-yl)-3-(naphthalen-2-ylmethoxy)-4-piperidine-1-carboxylate [Example 141(e)] and 0.13 ml (0.75 mmol) of 3-benzyloxy-propyl bromide were placed in 5 ml of dimethylformamide under argon at 5° C., then 0.17 g (1 mmol) of potassium iodide followed by 0.044 g (1 mmol) of sodium hydride dispersion (55% in mineral oil) were added all at once and thereafter the mixture was stirred at room temperature for 72 hours. The mixture was thereupon poured on to ice-water, the product was extracted 3 times with 30 ml of ethyl acetate each time, the organic phases were washed twice with 25 ml of distilled water each time, dried over magnesium sulphate, filtered and concentrated in a water-jet vacuum. The thus obtained crude product was chromatographed on silica gel with methylene chloride and methanol. There was thus obtained 0.27 g (92% of theory) of tert-butyl (3RS,4RS)-4-[5-(3-benzyloxy-propoxymethyl)-[1,2,3]triazol-1-yl]-3-(naphthalen-2-ylmethoxy)-piperidine-1-carboxylate as a pale yellow oil; MS: 586 (M)$^+$.

(d) In an analogous manner to that described in Example 142(c), from tert-butyl (3RS,4RS)-4-(4-hydroxymethyl-[1,2,3] triazol-1-yl)-3-(naphthalen-2-ylmethoxy)-4-piperidine-1-carboxylate Example 141(e)] there was obtained tert-butyl (3RS,4RS)-4-[4-(3-benzyloxy-propoxymethyl)-[1,2,3]triazol-1-yl]-3-(naphthalen-2ylmethoxy)-piperidine-1-carboxylate as a pale yellow oil; MS: 586 (M)$^+$.

EXAMPLE 143

The following compounds were obtained in an analogous manner to that described in Example 136(a) by cleavage of the BOC group by means of hydrogen chloride in methanol:

1) From tert-butyl (3'RS,4'RS)-3'-(naphthalen-2-ylmethoxy)-3',4',5',6'-tetrahydro-2'H-[2,4']-bipyridine-1-carboxylate, (3'RS,4'RS)-3'-(naphthalen-2-ylmethoxy)-1',2',3',4',5',6'-hexahydro-[2,4']-bipyridine as a light yellow oil; MS: 319 (M+H)$^+$;

2) from tert-butyl (3'RS,4'RS)-3'-(naphthalen-2-ylmethoxy)-3',4',5',6'-tetrahydro-2'H-[3,4']-bipyridine-1-carboxylate, (3'RS,4'RS)-3'-(naphthalen-2-ylmethoxy)-1',2',3',4',5',6'-hexahydro-[3,4']bipyridine as a yellow oil; MS: 319 (M+H)$^+$.

The BOC derivatives used as starting materials were prepared as follows:

(a) (α) A solution of 662 mg (2.0 mmol) of tert-butyl 4-trifluoromethyl-sulphonyloxy-3,6-dihydro-2H-pyridine-1-carboxylate [Example 126(c)],884 mg (2.4 mmol) of 2-tributylstannylpyridine (obtained from Maybridge Chemical Company) and 254 mg (6.0 mmol) of anhydrous lithium chloride in 30 ml of absolute DMF was flushed with argon, thereafter treated with 115 mg (0.1 mmol) of tetrakis-(triphenylphosphine)-palladium(IV) and then heated to reflux under argon for 3 hours. For the working-up, the reaction mixture was poured into 25 ml of 10% ammonia solution and finally stirred intensively for 5 minutes. The light yellow solution was treated with 100 ml of methylene chloride and stirred for 5 minutes. The organic phase was separated and the aqueous phase was extracted 3 times with 25 ml of methylene chloride each time. The combined organic phases were washed twice with 25 ml of water each time, dried over magnesium sulphate, and finally the solvent was distilled off under reduced pressure. The crude product was purified by flash chromatography on silica gel with a 2:1 mixture of hexane and ethyl acetate as the eluent. There were obtained 354 mg (68% of theory) of tert-butyl 3',6'-dihydro-2'H-[2,4']bipyridine-1'-carboxylate as a yellow oil; MS: 261 (M+H)$^+$.

(β) A solution of 1.30 g (5.0 mmol) of tert-butyl 3',6'-dihydro-2'H-[2,4']bipyridine-1'-carboxylate in 15 ml of absolute tetrahydrofuran was treated dropwise at 0° C. under argon with 1.0 ml (801 mg ,10.0 mmol) of borane-dimethyl sulphide complex (95%) in dimethyl sulphide. The mixture was heated to boiling such that a slow distillation of the solvent took place (about 1 drop per minute). After 3 hours 3 ml of 2N sodium hydroxide solution and 2 ml of hydrogen peroxide solution (30%) were added dropwise at 0° C. The mixture was stirred at 50° C. for 6 hours, then cooled to room temperature and, for working-up, poured into a mixture of 200 ml of ether, 200 ml of water and 25 ml of sodium pyrosulphite solution (10%) while stirring vigorously. The organic phase was separated and the aqueous phase was extracted three times with 50 ml of ether each time. The combined organic phases were washed twice with 25 ml of water each time, dried over magnesium sulphate and finally the solvent was distilled off under reduced pressure. The crude product was purified by flash chromatography on silica gel with a 1:1 mixture of hexane and ethyl acetate as the eluent. There were obtained 354 mg (24% of theory) of tert-butyl (3'RS,4'RS)-3'-hydroxy-3',4',5',6'-tetrahydro-2'H-[2,4']bipyridine-1'-carboxylate as a yellow oil; MS: 279 (M+H)$^+$.

(γ) In an analogous manner to that described in Example 125(g), by alkylating tert-butyl (3'RS,4'RS)-3'-hydroxy-3',4',5',6'-tetrahydro-2'H-[2,4']-bipyridine-1'-carboxylate with 2-bromomethynaphthalene there was obtained tert-butyl (3'RS,4'RS)-3'-(naphthalen-2-ylmethoxy)-3',4',5',6'-tetrahydro-2'H-[2,4']-bipyridine-1-carboxylate as a colourless resin; MS: 419 (M+H)$^+$.

(b) (α) A solution of 16.7 g (106 mmol) of 3-bromo-pyridine in 200 ml of tert-butyl methyl ether was cooled to −75° C. Thereto there was added dropwise within 45 minutes a solution of 66 ml (106 mmol) of n-butyllithium (1.6M in hexane) and the mixture was stirred at −75° C. for one hour. Subsequently, a solution of 10.0 g (52.8 mmol) of 1-benzyl-4-piperidone in 50 ml of tert-butyl methyl ether was added dropwise at −70° C. to −75° C. and thereafter the mixture was stirred for 2 hours. Subsequently, the mixture was left to warm to room temperature. Thereafter, it was hydrolyzed with 50 ml of water and extracted with 100 ml of ethyl acetate. The organic phase was dried over magnesium sulphate and finally the solvent was evaporated under reduced pressure, with the product beginning to separate. From the evaporated mother liquor there were isolated by crystallization from a mixture of ethyl acetate and hexane a further 1.9 g, so that a total of 8.4 g (60% of theory) of 1'-benzyl-2',3',5',6'-tetrahydro-1'H-[3,4']bipyridinyl-4'-ol were obtained as a colourless solid; MS: 268 (M+H)$^+$.

(β) A dispersion of 4.52 g (16.8 mmol) of 1'-benzyl-2',3',5',6'-tetrahydro-1'H-[3,4']bipyridinyl-4'-ol and 18 g (71 mmol) of potassium disulphate in 35 ml of decalin was stirred at 190° C. for 30 minutes. After cooling to room temperature the reaction mixture was dissolved in water and extracted twice with 50 ml of toluene each time. Subsequently, the aqueous phase was made alkaline with sodium hydroxide solution and extracted with ethyl acetate. The ethyl acetate phase was thereafter dried over sodium sulphate and evaporated under reduced pressure. For purification, the crude product was chromatographed on silica gel using a 98:2:0.1 mixture of methylene chloride, methanol and ammonia as the eluent. There were obtained 4.03 g (61% of theory) of 1'-benzyl-1',2',3',6'-tetrahydro-3,4'-bipyridine as a yellowish oil; MS: 250 (M)$^+$.

(γ) In an analogous manner to that described in Example 126(f, by hydroboration of 1'-benzyl-1',2',3',6'-tetrahydro-3,4'-bipyridine there was obtained (3'RS,4'RS)-1'-benzyl-1',2',3',4',5',6'-hexahydro-[3,4']bipyridinyl-3'-ol as a yellowish oil; MS: 268 (M)$^+$. Subsequent cleavage of the benzyl group by means of catalytic hydrogenation in the presence of palladium-charcoal (10%) at room temperature under normal pressure in methanol for 18 hours yielded (3'RS,4'RS)-1',2',3',4',5',6'-hexahydro-[3,4']bipyridinyl-3'-ol, which after reaction with di-tert-butyl-dicarbonate analogously to Example 141(a) yielded tert-butyl (3'RS,4'RS)-3'-hydroxy-3',4',5',6'-tetrahydro-2'H-[3,4']bipyridine-1'-carboxylate as a yellowish oil; MS: 279 (M+H)$^+$. Subsequent alkylation with 2-bromomethyl-naphthalene analogously to Example 125 (g) yielded tert-butyl (3'RS,4'RS)-3'-(naphthalen-2-ylmethoxy)-3',4',5',6'-tetrahydro-2'H-[3,4']-bipyridine-1'-carboxylate, which was used as the crude product in the cleavage reaction of the BOC group by means of hydrogen chloride in methanol.

EXAMPLE 144

The following compounds were obtained by cleavage of the BOC group:

1) From tert-butyl (3'RS,4'RS)-6-(3-benzyloxy-propoxy)-3'-(naphthalen-2-ylmethoxy)-3',4',5',6'-tetrahydro-2'H-[3,4']bipyridine-1'-carboxylate by means of zinc bromide in methylene chloride analogously to Example 125(h), (3'RS,4'RS)-6-(3-benzyloxy-propoxy)-3'-(naphthalen-2-ylmethoxy)-1',2',3',4',5',6'-hexahydro-[3,4']bipyridine as a colourless solid; MS: 483 (M+H)$^+$;

2) from tert-butyl (3'RS,4'RS)-5-(2-benzyloxy-ethoxymethyl)-3'-(naphthalen-2-ylmethoxy)-3',4',5',6'-tetrahydro-2'H-[2,4']bipyridine-1'-carboxylate by means of hydrogen chloride in methanol analogously to Example 136(a), (3'RS,4'RS)-5-(2-benzyloxy-ethoxymethyl)-3'-(naphthalen-2-ylmethoxy)-1',2',3',4',5',6'-hexahydro-[2,4']bipyridine as a light yellow oil; MS:483 (M+H)$^+$.

The BOC derivatives used as starting materials were prepared as follows:

(a) (α) A solution of 10.62 g (40.2 mmol) of 2-benzyloxy-5-bromopyridine [J.Org.Chem. 60, 1408 (1995)] and 10.0 ml (15.8 g,48.2 mmol) of hexamethyldistannate in 100 ml of absolute dioxane was flushed with argon and treated with 2.32 g (2.0 mmol) of tetrakis-(triphenylphoshine)-palladium (IV). The mixture was boiled under reflux for 15 hours. For the working-up, the dark solution was filtered over Speedex and the solvent was distilled off under reduced pressure. The residue was dissolved in 300 ml of methylene chloride, washed twice with 100 ml of water each time, dried over magnesium sulphate and finally the solvent was distilled off under reduced pressure. The crude product was purified by flash chromatography on silica gel with a 3:1 mixture of hexane and methylene chloride as the eluent. There were obtained 10.4 g (74% of theory) of 2-benzyloxy-5-trimethylstannyl-pyridine as a colourless oil; MS: 349 (M+H$^+$).

(β) In an analogous manner to that described above, by a palladium catalyzed coupling of 2-benzyloxy-5-trimethylstannyl-pyridine with tert-butyl 4-trifluoromethylsulphonyloxy-3,6-dihydro-2H-pyridine-1-carboxylate [Example 126(c)] there was obtained tert-butyl 6-benzyloxy-3',6'-dihydro-2H-[3,4']bipyridine-1'-carboxylate as a colourless solid MS: 367 (M+H)$^+$.

(γ) A solution of 0.75 g (2.04 mmol) of tert-butyl 6-benzyloxy-3',6'-dihydro-2H-[3,4']bipyridine-1'-carboxylate in 3 ml of absolute tetrahydrofuran was treated dropwise at 0° C. under argon with 0.42 ml (4.20 mmol) of borane-dimethyl sulphide complex (95%) in dimethyl sulphide. The mixture was heated to 60° C. and simultaneously a weak stream of argon was conducted through. After 1.5 hours 3 ml of tetrahydrofuran and 2 ml of water were added dropwise at 0° C. Subsequently,740 mg (4.71 mmol) of sodium percarbonate were added portionwise, the mixture was warmed to room temperature and subsequently heated at 60° C. for 1 hour. Thereafter, the mixture was cooled to room temperature and, for working-up, was poured into a mixture of 100 ml of ether,100 ml of water and 10 ml of 10% sodium pyrosulphite solution while stirring vigorously. The organic phase was separated and the aqueous phase was extracted 3 times with 25 ml of ether each time. The combined organic phases were washed twice with 10 ml of water each time, dried over magnesium sulphate and finally the solvent was distilled off under reduced pressure. The crude product (0.9 g) was purified by flash chromatography on silica gel with a 4:1 mixture of methylene chloride and ethyl acetate as the eluent. There was obtained 0.630 g (80% of theory) of a 4:1 mixture of tert-butyl (3'RS,4'RS)-6-benzyloxy-3'-hydroxy-3',4',5',6'-tetrahydro-2'H-[3,4']bipyridine-1'-carboxylate and tert-butyl 6-benzyloxy-4'-hydroxy-3',4',5',6'-tetrahydro-2'H-[3,4']bipyridine-1'-carboxylate as a colourless solid; MS: 385 (M+H)$^+$.

(δ) A solution of 256 mg (0.67 mmol) of a 4:1 mixture of tert-butyl (3'RS,4'RS)-6-benzyloxy-3'-hydroxy-3',4',5',6'-tetrahydro-2'H-[3,4']bipyridine-1'-carboxylate and tert-butyl 6-benzyloxy-4'-hydroxy-3',4',5',6'-tetrahydro-2'H-[3,4']bipyridine-1'-carboxylate in 6 ml of absolute methanol was treated with 40 mg of palladium-charcoal (10%) and hydrogenated at normal pressure for 6 hours. After filtration of the catalyst and subsequent distillation of the solvent under reduced pressure there was obtained a 4:1 mixture of tert-butyl (3'RS,4'RS)-3'-hydroxy-6-oxo-1,6,3',4',5',6'-hexahydro-2'H-[3,4']bipyridine-1'-carboxylate and tert-butyl 4'-hydroxy-6-oxo-1,6,3',4',5',6'-hexahydro-2'H-[3,4']bipyridine-1'-carboxylate as a colourless solid; MS: 295 (M+H)$^+$.

(ε) A solution of 74 mg (0.25 mmol) of a 4:1 mixture of tert-butyl (3'RS,4'RS)-3'-hydroxy-6-oxo-1,6,3',4',5',6'-hexahydro-2'H-[3,4']bipyridine-1'-carboxylate and 4'-hydroxy-6-oxo-1,6,3',4',5',6'-hexahydro-2'H-[3,4']bipyridine-1'-carboxylate,99 mg (0.375 mmol) of triphenylphosphine and 52 mg (0.312 mmol) of 3-benzyloxy-1-propanol in 5 ml of absolute tetrahydrofuran was treated portionwise with 69 mg (0.30 mmol) of di-tert-butyl azodicarboxylate and stirred at room temperature for 6 hours. Subsequently, the reaction mixture was treate with 0.25 ml of methanol and, for working-up, was poured into 10 ml of methylene chloride and 10 ml of water while stirring vigorously. The organic phase was separated and the aqueous phase was extracted three times with 10 ml of methylene chloride each time. The combined organic phases were washed twice with 100 ml of water each time, dried over sodium sulphate and finally the solvent was distilled off under reduced pressure. The crude product (280 mg) was purified by flash chromatograpy on silica gel with a 4:1 mixture of methylene chloride and ethyl acetate as the eluent. There were obtained 37 mg (34% of theory) of a 4:1 mixture of tert-butyl (3'RS,4'RS)-6-(3-benzyloxy-propoxy)-3'-hydroxy-3',4',5',6'-tetrahydro-2'H-[3,4']bipyridine-1'-carboxylate and tert-butyl 6-(3-benzyloxy-propoxy)-4'-hydroxy-3',4',5',6'-tetrahydro-2'H-[3,4']bipyridine-1'-carboxylate as a colourless oil; MS: 443 (M+H)$^+$.

(ζ) In an analogous manner to that described in Example 125(g), by alkylating a 4:1 mixture of tert-butyl (3'RS,4'RS)-6-(3-benzyloxy-propoxy)-3'-hydroxy-3',4',5',6'-tetrahydro-2'H-[3,4']bipyridine-1'-carboxylate and tert-butyl 6-(3-benzyloxy-propoxy)-4'-hydroxy-3',4',5',6'-tetrahydro-2'H-[3,4']bipyridine-1'-carboxylate with 2-bromomethyinaphthalene and subsequent separation of the isomers there was obtained tert-butyl (3'RS,4'RS)-6-(3-benzyloxy-propoxy)-3'-(naphthalen-2-ylmethoxy)-3',4',5',6'-tetrahydro-2'H-[3,4']bipyridine-1'-carboxylate as a colourless oil; MS: 583 (M+H)$^+$.

(b) (α) Firstly, a solution of 53 ml (86 mmol) of methyllithium (1.6M in ether) was prepared at 0° C. in 100 ml of absolute tetrahydrofuran. Thereafter, a solution of 20 ml (96.8 mmol) of hexamethyldistannate in 100 ml of absolute tetrahydrofuran was added dropwise within 30 minutes at 0° C. and the mixture was stirred at 0° C. for 30 minutes. The pale yellow solution was cooled to −78° C. A solution of 14.2 g (71.3 mmol) of N-tert-butoxycarbonyl-4-piperidone in 80 ml of absolute tetrahydrofuran was added dropwise thereto at −78° C. within 45 minutes. After 4 hours at −78° C. 60 ml of saturated potassium sodium tartrate solution were added dropwise and the mixture was warmed to room temperature. The organic phase was separated and the aqueous phase was extracted three times with 200 ml of ether each time. The combined organic phases were washed twice with 100 ml of saturated ammonium chloride solution each time and twice with 100 ml of saturated sodium chloride solution each time, dried over magnesium sulphate and finally the solvent was distilled off under reduced pressure. The resulting yellow oil (23.1 g) was dissolved in 250 ml of methylene chloride, treated with 25.6 ml (183.9 mmol) of triethylamine and cooled to 0° C. A solution of 9.82 ml (18.4 mmol) of methanesulphonyl chloride in 90 ml of methylene chloride was added dropwise within 1 hour at 0° C. and the mixture was then stirred at 0° C. for 1 hour. Subsequently,28.3 ml (190.3 mmol) of 1,8-diazabicyclo [5.4.0]undec-7-ene (DBU) were added dropwise at 0° C. within 30 minutes. The red solution was stirred at room temperature for 15 hours. For the working-up, the mixture was treated with 200 ml of water while stirring vigorously. The organic phase was separated and the aqueous phase was extracted three times with 100 ml of methylene chloride each time. The combined organic phases were washed twice with 100 ml of saturated sodium chloride solution each time, dried over magnesium sulphate and finally the solvent was distilled off under reduced pressure. The crude product (21.4 g) was purified by flash chromatography on silica gel with methylene chloride at the eluent. There were obtained 12.9 g (37.2 mmol,52% of theory) of tert-butyl 4-trimethylstannyl-3,6-2H-pyridine-1-carboxylate as a yellow oil; MS: 348 (M+H)$^+$.

(β) In an analogous manner to that described above, by a palladium catalyzed coupling of tert-butyl 4-trimethylstannyl-3,6-2H-pyridine-1-carboxylate with (rac)-2-chloro-5-[(tetrahydro-2H-pyran-2-yloxy)methyl]-pyridine [EP 475 273] there was obtained tert-butyl (RS)-5-(tetrahydro-pyran-2-yloxymethyl)-3',6'-dihydro-2'H-[2,4']bipyridine-1'-carboxylate as a yellow oil; MS: 375 (M+H)$^+$.

(γ) A solution of 2.56 g (6.84 mmol) of tert-butyl (RS)-5-(Tetrahydro-pyran-2-yloxymethyl)-3',6'-dihydro-2'H-[2,4']bipyridine-1'-carboxylate in 10 ml of absolute tetrahydrofuran was treated dropwise at 0° C. under argon with 1.40 ml (1.12 g, 14.0 mmol) of borane-dimethyl sulphide complex (95%) in dimethyl sulphide. The mixture was heated to 50° C. and simultaneously a weak stream of argon was passed through. After 45 minutes 10 ml of tetrahydrofuran were added, the mixture was cooled to 0° C. and 1.58 g (21.0 mmol) of solid trimethylamine N-oxide were added portionwise, with the temperature being held at 5–10° C. The mixture was warmed to room temperature, heated under reflux for 1 hour, treated with 10 ml of methanol and subsequently heated under reflux for a further hour. The mixture was cooled to room temperature and, for working-up, poured into a mixture of 200 ml of methylene chloride, 200 ml of water and 10 ml of 2N sodium hydroxide solution while stirring vigorously. The organic phase was separated and the aqueous phase was extracted three times with 50 ml of methylene chloride each time. The combined organic phases were washed twice with 50 ml of sodium pyrosulphite solution (10%) (the pH being adjusted to about 9 by the addition of 2N sodium hydroxide solution) and twice with 25 ml of water, thereafter dried over magnesium sulphate and finally evaporated under reduced pressure. The crude product (2.59 g) was purified by flash chromatography on silica gel with a 1:1 mixture of methylene chloride and ethyl acetate as the eluent. There was obtained 0.280 g (10% of theory) of a 1:1 mixture of tert-butyl (3'RS,4'RS)-3'-hydroxy-5-[(RS)- and -[(S R)-tetrahydro-pyran-2-yloxymethyl]-3',4',5',6'-tetrahydro-2'H-[2,4']bipyridine-1'-carboxylate as a light yellow oil; MS: 393 (M+H)$^+$.

(δ) In an analogous manner to that described in Example 125(g), by alkylating a 1:1 mixture of tert-butyl (3'RS,4'RS)-3'-hydroxy-5-[(RS)- and -[(SR)-tetrahydro-pyran-2-yloxymethyl]-3',4',5',6'-tetrahydro-2'H-[2,4']bipyridine-1'-carboxylate with 2-bromomethylnaphthalene there was obtained a 1:1 mixture of tert-butyl (3'RS,4'RS)-3'-(naphthalen-2-ylmethoxy)-5-[(RS)- and -[(SR)-tetrahydro-pyran-2-yloxymethyl]-3',4',5',6'-tetrahydro-2'H-[2,4'] bipyridine-1-carboxylate as a yellow oil; MS: 533 (M+H)$^+$.

(ε) A solution of 102 mg (0.19 mmol) of a 1:1 mixture of tert-butyl (3'RS,4'RS)-3'-(naphthalen-2-ylmethoxy)-5-[(RS)- and -[(SR)-tetrahydro-pyran-2-yloxymethyl]-3',4',5', 6'-tetrahydro-2'H-[2,4']bipyridine-1-carboxylate was dissolved in 2 ml of methanol and cooled to −15° C. 2 ml of a 2N solution of hydrogen chloride in methanol were added dropwise within 2 minutes at −10 to −15° C. The mixture was warmed to room temperature and stirred for 30 minutes, and then, for working-up, partitioned between 25 ml of ethyl acetate and 25 ml of aqueous 5% sodium hydrogen carbonate solution. The organic phase was separated and the aqueous phase was extracted three times with 10 ml of ethyl acetate each time. The combined ethyl acetate phases were dried over magnesium sulphate and finally evaporated under reduced pressure. The crude product (96 mg) was purified by chromatography on silica gel with a 1:1 mixture of ethyl acetate and methylene chloride as the eluent. There were obtained 78 mg (92% of theory) of tert-butyl (3'RS,4'RS)-5-hydroxymethyl- 3'-(naphthalen-2-ylmethoxy)-3',4',5',6'-tetrahydro-2'H-[2,4']bipyridine-1'-carboxylate as a light yellow oil; MS: 449 (M+H)$^+$.

(ζ) A solution of 70 mg (0.156 mmol) of tert-butyl (3'RS,4'RS)-5-hydroxymethyl-3'-(naphthalen-2-ylmethoxy)-3',4',5',6'-tetrahydro-2'H-[2,4']bipyridine-1'-carboxylate in 2 ml of absolute DMF was cooled to −10° C. and treated with 26 μl (19 mg,0.187 mmol) of triethylamine. 13 μl (20 mg, 0.172 mmol) of methanesulphonyl chloride and 2 mg of N,N-dimethylaminopyridine (DMAP) were added at −10 to −15° C. and subsequently the mixture was stirred at 0° C. for 1 hour. For the working-up, the mixture was partitioned between 25 ml of ethyl acetate and 25 ml of aqueous 5% ammonium chloride solution and the organic phase was separated. The aqueous phase was extracted three times with 10 ml of ethyl acetate each time. The combined ethyl acetate phases were dried over magnesium sulphate and finally evaporated under reduced pressure. The crude product was purified by chromatography on silica gel with a 1:1 mixture of ethyl acetate and hexane as the eluent. There were obtained 22 mg (35% of theory) of tert-butyl (3'RS,4'RS)-5-chloromethyl-3'-(naphthalen-2-ylmethoxy)-3',4',5',6'-tetrahydro-2'H-[2,4']bipyridine-1'-carboxylate as a light yellow oil; MS: 467, 469 (M+H)$^+$.

(η) A solution of 22 mg (0.047 mmol) of tert-butyl (3'RS,4'RS)-5-chloromethyl-3'-(naphthalen-2-ylmethoxy)-3',4',5',6'-tetrahydro-2'H-[2,4']bipyridine-1'-carboxylate in 0.5 ml of DMF was treated with 67 μl (72 mg 0.47 mmol) of 2-benzyloxyethanol and 19 mg (0.47 mmol) of sodium hydride (60% dispersion in oil) and subsequently stirred at room temperature for 2 hours. For the working-up, the mixture was partitioned between 15 ml of ethyl acetate and 15 ml of aqueous 5% ammonium chloride solution and then the organic phase was separated. The aqueous phase was extracted three times with 5 ml of ethyl acetate each time. The combined ethyl acetate phases were dried over magnesium sulphate and finally the solvent was distilled off under reduced pressure. The crude tert-butyl (3'RS,4'RS)-5-(2-benzyloxy-ethoxymethyl)-3'-(naphthalen-2-ylmethoxy)-3',4',5',6'-tetrahydro-2'H-[2,4']bipyridine-1'-carboxylate was used in the next step without further purification and characterization.

EXAMPLE 145

(a) A solution of 10.8 g (54.3 mmol) of tert-butyl (1RS,6SR)-7-oxa-3-aza-bicyclo[4.1.0]heptane-3-carboxylate [Example 141(b)] in 250 ml of acetonitrile was treated with 7.98 g (162.9 mmol) of powdered sodium cyanide and 17.3 g (162.0 mmol) of lithium perchlorate and the reaction mixture was stirred at 95° C. under argon for 24 hours. For the working-up, the brownish solution was cooled, treated with 150 ml of ethyl acetate and filtered over Decalite. The filtrate was washed with 100 ml of water and the phases were separated. The aqueous phase was adjusted to pH 5 and extracted three times with 60 ml of ethyl acetate each time. The combined organic phases were dried over sodium sulphate and evaporated under reduced pressure. For purification, the residue was chromatographed on silica gel using a 4:1 mixture of hexane and ethyl acetate as the eluent. There were obtained 9.9 g (80.5% of theory) of a 4:1 mixture of tert-butyl (3RS,4RS)-4-cyano-3-hydroxy-piperidine-1-carboxylate and tert-butyl (3RS,4SR)-3-cyano-4-hydroxy-piperidine-1-carboxylate in the form of colourless crystals; MS: 227 (M+H)$^+$.

(b) A solution of 5.8 g (25.6 mmol) of a 4:1 mixture of tert-butyl (3RS,4RS)-4-cyano-3-hydroxy-piperidine-1-carboxylate and tert-butyl (3RS,4SR)-3-cyano-4-hydroxy-piperidine-1-carboxylate in 50 ml of N,N-dimethylformamide was stirred at room temperature under argon for 4 hours with 1.8 g (38.4 mmol) of sodium hydrogen sulphide monohydrate and 2.05 g (38.4 mmol) of ammonium chloride. For the working-up, the reaction mixture was evaporated under reduced pressure and the residue was taken up in 150 ml of methylene chloride. The solution obtained was washed twice with 10 ml of water each time and the organic phase was separated, dried over sodium sulphate and then evaporated under reduced pressure. For purification and separation of the isomer mixture, the residue was chromatographed on silica gel using a 95:5:0.1 mixture of methylene chloride, methanol and ammonia as the eluent. There were obtained 3.48 g (52% of theory) of tert-butyl (3RS,4SR)-3-hydroxy-4-thiocarbamoyl-piperidine-1-carboxylate, (R$_f$: 0.37, silica gel; methylene chloride:methanol:ammonia=90:10:0.1 v/v/v), MS: 260 (M)$^+$, as well as 1.2 g of a mixture of tert-butyl (3RS,4SR)-3-hydroxy-4-thiocarbamoyl-piperidine- 1-carboxylate and tert-butyl (3RS,4RS)-4-hydroxy-3-thiocarbamoyl-piperidine-1-carboxylate, each as a colourless oil.

(c) 4 ml of methyl iodide were added at room temperature to a solution of 1.88 g (7.22 mmol) of tert-butyl (3RS,4SR)-3-hydroxy-4-thiocarbamoyl-piperidine-1-carboxylate in 5 ml of acetone. After stirring at room temperature for 14 hours the product had separated. 10 ml of ether were added and the reaction mixture was stirred for 30 minutes. After filtration and drying there were obtained 2.76 g (98% of theory) of (3RS,4SR)-[amino-(1-tert-butoxycarbonyl-3-hydroxy-piperidine-4-yl)-methylene-methyl-sulphonium iodide as colourless crystals; R$_f$: 0.22 (silica gel; methylene chloride:methanol:ammonia=95:5:0.1 v/v/v).

(d) A solution of 2.76 g (7.09 mmol) of (3RS,4SR)-[amino-(1-tert-butoxycarbonyl-3-hydroxy-piperidine-4-yl)-methylene-methyl-sulphonium iodide in 15 ml of methanol was treated with 0.41 g (3.55 mmol) of ammonium carbonate and stirred at room temperature for 18 hours. For the working-up, the reaction mixture was evaporated under reduced pressure. 2.5 g (95% of theory) of tert-butyl (3RS,4RS)-4-carbamimidoyl-3-hydroxy-piperidine-1-carboxylate iodide were obtained as a colourless foam. A solution of 715 mg (1.92 mmol) of tert-butyl (3RS,4RS)-4-carbamimidoyl-3-hydroxy-piperidine-1-carboxylate iodide in 20 ml of methanol was stirred at room temperature for 1 hours with 321 mg (1.92 mmol) of silver acetate. The precipitated silver iodide was filtered off and washed with 20 ml of methanol. The light yellow filtrate obtained was evaporated under reduced pressure. There were obtained 538 mg (92% of theory) of tert-butyl (3RS,4RS)-4-carbamimidoyl-3-hydroxy-piperidine-1-carboxylate acetate as a colourless foam.

(e) A solution of 372 mg (1 mmol) of tert-butyl (3RS,4RS)-4-carbamimidoyl-3-hydroxy-piperidine-1-carboxylate acetate in 10 ml of methanol was treated with 1 ml of 1N sodium methylate solution and stirred at room temperature. Subsequently,205 mg (1 mmol) of 2-benzyloxy-3-dimethylamino-acrolein (EPA 0 477 901) were added thereto and the solution was heated to reflux for 18 hours.

For the working-up, the reaction mixture was evaporated under reduced pressure and the residue was taken up in 20 ml of methylene chloride and washed with 5 ml of water. The organic phase was separated, dried over sodium sulphate and finally evaporated under reduced pressure. For purification, the residue was chromatographed on silica gel using a 1:4 mixture of methylene chloride and ethyl acetate as the eluent. There were obtained 106 mg (27% of theory) of tert-butyl (3RS,4RS)-4-(5-benzyloxy-pyrimidin-2-yl)-3-hydroxy-piperidine-1-carboxylate as a colourless oil; MS: 386 (M+H)$^+$.

(f) A solution of 110 mg (0.29 mmol) of tert-butyl (3RS,4RS)-4-(5-benzyloxy-pyrimidin-2-yl)-3-hydroxy-piperidine-1-carboxylate in 5 ml of methanol was treated with 20 mg of 5% palladium-charcoal and hydrogenated at room temperature for 12 hours. For the working-up, the catalyst was filtered off and washed with 20 ml of methanol. The methanol solution was evaporated under reduced pressure and the resulting oil was crystallized by the addition of ether. There were obtained 80 mg (93% of theory) of tert-butyl (3RS,4RS)-3-hydroxy-4-(5-hydroxy-pyrimidin-2-yl)-piperidine-1-carboxylate in the form of colourless, slightly delequesent crystals; MS: 296 (M+H)$^+$.

(g) A mixture of 65 mg (0.22 mmol) of tert-butyl (3RS,4RS)-3-hydroxy-4-(5-hydroxy-pyrimidin-2-yl)-piperidine-1-carboxylate and 151.2 mg (0.66 mmol) of (3-bromo-propoxymethyl)-benzene in 10 ml of methyl ethyl ketone was stirred at 80° C. for 48 hours under argon. For the working-up, the reaction mixture was evaporated under reduced pressure, the residue was taken up in methylene chloride and the solution was chromatographed directly on silica gel using a 1:4 mixture of methylene chloride and ethyl acetate as the eluent. There were obtained 40 mg (41% of theory) of tert-butyl (3RS,4RS)-4-[5-(3-benzyloxy-propoxy)-pyrimidin-2-yl]-3-hydroxy-piperidine-1-carboxylate as a foam; R$_f$: 0.43 (silica gel; methylene chloride:ethyl acetate=1:4 v/v).

(h) A solution of 40 mg (0.09 mmol) of tert-butyl (3RS,4RS)-4-[5-(3-benzyloxy-propoxy)-pyrimidin-2-yl]-3-hydroxy-piperidine-1-carboxylate and 23 mg (0.1 mmol) of 2-bromomethyl-naphthalene in 5 ml of N,N-dimethylformamide was treated with 5 mg (0.1 mmol) of sodium hydride (50% dispersion in oil) and stirred at room temperature for 18 hours. For the working-up, the reaction mixture was evaporated under reduced pressure, the residue obtained was taken up in 3 ml of methylene chloride and the solution was chromatographed directly on silica gel using a 2:1 mixture of hexane and ethyl acetate as the eluent. There were obtained 40 mg (76% of theory) of tert-butyl (3RS,4RS)-4-[5-(3-benzyloxy-propoxy)-pyrimidin-2-yl]-3-(naphthalen-2-ylmethoxy)-piperidine-1-carboxylate as an oil; MS: 584 (M+H)$^+$.

(i) A solution of 40 mg (0.07 mmol) of tert-butyl (3RS,4RS)-4-[5-(3-benzyloxy-propoxy)-pyrimidin-2-yl]-3-(naphthalen-2-ylmethoxy)-piperidine-1-carboxylate and 0.1 ml of trifluoroacetic acid in 1 ml of methylene chloride was stirred at room temperature for 2 hours. Thereafter, the solution was evaporated and the residue was taken up in 1 ml of ethyl acetate and crystallized by the addition of hexane. There were obtained 25 mg (60% of theory) of (3RS,4RS)-5-(3-benzyloxy-propoxy)-2-[3-(naphthalen-2-ylmethoxy)-piperidin-4-yl]-pyrimidine trifluoroacetate in the form of colourless crystals; MS: 484 (M+H)$^+$.

EXAMPLE 146

(a) In an analogous manner to that described in Example 145(a), by epoxide opening by means of 4-benzyloxy-2(1H)-pyridone [Chem. Pharm. Bull. 22, 763–770 (1974)], from tert-butyl (1RS,6SR)-7-oxa-3-aza-bicyclo[4.1.0]heptane-3-carboxylate [Example 141(b)] there was obtained a 1:1 mixture of tert-butyl (3'RS,4'RS)-4-benzyloxy-4'-hydroxy-2-oxo-3',4',5',6'-tetrahydro-2H-2'H-[1,3']bipyridine-1'-carboxylate and tert-butyl (3'RS,4'RS)-4-benzyloxy-3'-hydroxy-2-oxo-3',4',5',6'-tetrahydro-2H-2'H-[1,4']bipyridine-1'-carboxylate as colourless crystals; MS: 401 (M+H)$^+$.

(b) In an analogous manner to that described in Example 145(f) from a 1:1 mixture of tert-butyl (3'RS,4'RS)-4-benzyloxy-4'-hydroxy-2-oxo-3',4',5',6'-tetrahydro-2H-2'H-[1,3']bipyridine-1'-carboxylate and tert-butyl (3'RS,4'RS)-4-benzyloxy-3'-hydroxy-2-oxo-3',4',5',6'-tetrahydro-2H-2'H-[1,4']bipyridine-1'-carboxylate by means of catalytic hydrogenation there was obtained a 1:1 mixture of tert-butyl (3'RS,4'RS)-4,3'-dihydroxy-2-oxo-3',4',5',6'-tetrahydro-2H,2'H-[1,4']bipyridine-1'-carboxylate and tert-butyl (3'RS,4'RS)-4,4'-dihydroxy-2-oxo-3',4',5',6'-tetrahydro-2H,2'H-[1,3']bipyridine-1'-carboxylate as a colourless foam; MS: 311 (M+H)$^+$.

(c) In an analogous manner to that described in Example 145(g), from a 1:1 mixture of tert-butyl (3'RS,4'RS)-4,3'-dihydroxy-2-oxo-3',4',5',6'-tetrahydro-2H,2'H-[1,4']bipyridine-1'-carboxylate and tert-butyl (3'RS,4'RS)-4,4'-dihydroxy-2-oxo-3',4',5',6'-tetrahydro-2H,2'H-[1,3']bipyridine-1'-carboxylate by reaction with (3-bromo-propoxymethyl)-benzene in the presence of potassium carbonate there was obtained a mixture of tert-butyl (3'RS,4'RS)-4-(3-benzyloxy-propoxy)-3'-hydroxy-2-oxo-3',4',5',6'-tetrahydro-2H,2'H-[1,4']bipyridine-1'-carboxylate and tert-butyl (3'RS,4'RS)-4-(3-benzyloxy-propoxy)-4'-hydroxy-2-oxo-3',4',5',6'-tetrahydro-2H,2'H-[1,3']bipyridine-1'-carboxylate as a colourless oil; MS: 459 (M+H)$^+$.

(d) In an analogous manner to that described in Example 145(h), from a mixture of tert-butyl (3'RS,4'RS)-4-(3-benzyloxy-propoxy)-3'-hydroxy-2-oxo-3',4',5',6'-tetrahydro-2H,2'H-[1,4']bipyridine-1'-carboxylate and tert-butyl (3'RS,4'RS)-4-(3-benzyloxy-propoxy)-4'-hydroxy-2-oxo-3',4',5',6'-tetrahydro-2H,2'H-[1,3'bipyridine-1'-carboxylate by means of alkylation with 2-bromomethyl-naphthalene and after chromatographic separation of the two isomers on silica gel using a 1:4 mixture of methylene chloride and ethyl acetate as the eluent there was obtained tert-butyl (3'RS,4'RS)-4-(3-benzyloxy-propoxy)-4'-(naphthalen-2-ylmethoxy)-2-oxo-3',4',5',6'-tetrahydro-2H,2'H-[1,3']bipyridine-1'-carboxylate, (R$_f$: 0.64, SiO$_2$; methylene chloride:ethyl acetate=1:4 v/v), and tert-butyl (3'RS,4'RS)-4-(3-benzyloxy-propoxy)-3'-(naphthalen-2-ylmethoxy)-2-oxo-3',4',5',6'-tetrahydro-2H,2'H-[1,4']bipyridine-1'-carboxylate, MS: 599 (M+H)$^+$, (R$_f$: 0.44, SiO$_2$; methylene chloride:ethyl acetate=1:4 v/v), each as a yellowish oil.

(e) In an analogous manner to that described in Example 145(i), from tert-butyl (3'RS,4'RS)-4-(3-benzyloxy-propoxy)-3'-(naphthalen-2-ylmethoxy)-2-oxo-3',4',5',6'-tetrahydro-2H,2'H-[1,4']bipyridine-1'-carboxylate by cleavage of the BOC group by means of trifluoroacetic acid there was obtained (3'RS,4'RS)-4-(3-benzyloxy-propoxy)-3'-(naphthalen-2-ylmethoxy)-1',2',3',4',5',6'-hexahydro-[1,4']bipyridin-2-one trifluoroacetate as a colourless solid; MS: 499 (M+H)$^+$.

EXAMPLE 147

The following compounds were obtained in an analogous manner to that described in Example 22(l) by cleavage of the BOC group by means of hydrogen chloride in methanol:

1) From tert-butyl (1RS,2RS,3RS,5SR)-3-[4-(2-benzyloxy-ethoxymethyl)-phenyl]-2-(naphthalen-2-ylmethoxy)-8-aza-bicyclo[3.2.1]octane-8-carboxylate, (1RS,2RS,3RS,5SR)-3-[4-(2-benzyloxy-ethoxymethyl)-phenyl]-2-(naphthalen-2-yl-methoxy)-8-aza-bicyclo[3.2.1]octane as a colourless oil; R$_f$: 0.15 (silica gel; methylene chloride:methanol:ammonia=95:5:0.1);
2) from tert-butyl (1RS,2RS,3RS,5SR)-2-(naphthalen-2-ylmethoxy)-3-[4-(2-phenoxy-ethoxymethyl)-phenyl]-8-aza-bicyclo[3.2.1 ]octane-8-carboxylate, (1RS,2RS,3RS,5SR)-2-(naphthalen-2-ylmethoxy)-3-[4-(2-phenoxy-ethoxymethyl)-phenyl]-8-aza-bicyclo[3.2.1]octane as a yellow oil; R$_f$: 0.21 (silica gel; methylene chloride:methanol:ammonia=95:5:0.1);
3) from tert-butyl (1RS,2RS,3RS,5SR)-3-(4-benzyloxymethyl-phenyl)-2-(naphthalen-2-ylmethoxy)-8-aza-bicyclo3.2.1]octane-8-carboxylate, (1RS,2RS,3RS,5SR)-3-(4-benzyloxymethyl-phenyl)-2-(naphthalen-2-ylmethoxy)-8-aza-bicyclo[3.2.1]octane hydrochloride as a colourless oil; MS: 464 (M+H)$^+$;
4) from tert-butyl (1RS,2RS,3RS,5SR)-2-(naphthalen-2-ylmethoxy)-3-(4-phenylsulphanylmethyl-phenyl)-8-aza-bicyclo[3.2.1]octane-8-carboxylate, (1RS,2RS,3RS,5SR)-2-(naphthalen-2-ylmethoxy)-3-(4-phenylsulphanylmethyl-phenyl)-8-aza-bicyclo[3.2.1]octane hydrochloride as a colourless oil; MS: 566 (M+H)$^+$;
5) from tert-butyl (1RS,2RS,3RS,5SR)-3-[4-(2-chloro-benzoyloxymethyl)-phenyl]-2-(naphthalen-2-ylmethoxy)-8-aza-bicyclo[3.2.1]octane-8-carboxylate, (1RS,2RS,3RS,5SR)-4-[2-(naphthalen-2-ylmethoxy)-8-aza-bicyclo[3.2.1]oct-3-yl]-benzyl 2-chloro-benzoate as a yellowish foam; MS: 512 (M+H)$^+$;

The BOC compounds used as starting materials were prepared as follows:
(a) In an analogous manner to that described in Example 1(g), by alkylating tert-butyl (1RS,2RS,3RS,5SR)-3-(4-hydroxymethyl-phenyl)-2-(naphthalen-2-ylmethoxy)-8-aza-bicyclo[3.2.1]octane-8-carboxylate [Example 86(eee)] with 2-(benzyloxy)-ethyl iodide [Helv.Chim.Acta Vol.71, (1988), 2039] there was obtained tert-butyl (1RS,2RS,3RS,5SR)-3-[4-(2-benzyloxy-ethoxymethyl)-phenyl]-2-(naphthalen-2-ylmethoxy)-8-aza-bicyclo[3.2.1]octane-8-carboxylate as a colourless oil; MS: 625 (M+NH$_4$)$^+$.
(b) In an analogous manner to that described in Example 1(g), by alkylating tert-butyl (1RS,2RS,3RS,5SR)-3-(4-hydroxymethyl-phenyl)-2-(naphthalen-2-ylmethoxy)-8-aza-bicyclo[3.2.1]octane-8-carboxylate [Example 86(eee)] with phenoxy-ethyl bromide there was obtained tert-butyl (1RS,2RS,3RS,5SR)-2-(naphthalen-2-ylmethoxy)-3-[4-(2-phenoxy-ethoxymethyl)-phenyl]-8-aza-bicyclo[3.2.1]octane-8-carboxylate as a colourless oil; MS: 611 (M+NH$_4$)$^+$.
(c) In an analogous manner to that described in Example 1(g), by alkylating tert-butyl (1RS,2RS,3RS,5SR)-3-(4-hydroxymethyl-phenyl)-2-(naphthalen-2-ylmethoxy)-8-aza-bicyclo[3.2.1]octane-8-carboxylate [Example 86(eee)] with benzyl bromide there was obtained tert-butyl (1RS,2RS,3RS,5SR)-3-(4-benzyloxymethyl-phenyl)-2-(naphthalen-2-ylmethoxy)-8-aza-bicyclo[3.2.1 ]octane-8-carboxylate, which was used as the crude product in the reaction for BOC cleavage.
(d) In an analogous manner to that described in Example 33(a), by reacting tert-butyl (1RS,2RS,3RS,5SR)-3-(4-hydroxymethyl-phenyl)-2-(naphthalen-2-ylmethoxy)-8-aza-bicyclo[3.2.1]octane-8-carboxylate [Example 86(eee)] with diphenyl disulphide in the presence of tributylphosphine there was obtained tert-butyl (1RS,2RS,3RS,5SR)-2-(naphthalen-2-ylmethoxy)-3-(4-phenyl-sulphanylmethyl-phenyl)-8-aza-bicyclo[3.2.1]octane-8-carboxylate as a colourless oil; MS: 566 (M+H)$^+$.
(e) In an analogous manner to that described in Example 22(k), by esterifying tert-butyl (1RS,2RS,3RS,5SR)-3-(4-hydroxymethyl-phenyl)-2-(naphthalen-2-ylmethoxy)-8-aza-bicyclo[3.2.1]octane-8-carboxylate [Example 86 (eee)] with 2-chloro-benzoyl chloride there was obtained tert-butyl (1RS,2RS,3RS,5SR)-4-[2-(naphthalen-2-ylmethoxy)-8-aza-bicyclo[3.2.1]oct-3-yl]-benzyl 2-chloro-benzoate as a colourless oil, which was used as the crude product in the reaction for BOC cleavage.

EXAMPLE 148

In an analogous manner to that described in Example 22(l), from tert-butyl (3SR,4RS,5RS)-4-[4-(3-benzyloxy-propoxy)-phenyl]-3-methoxymethyl-5-(naphthalen-2-ylmethoxy)-piperidine-1-carboxylate by cleavage of the BOC group by means of hydrogen chloride in methanol there was obtained (3SR,4RS,5RS)-4-[4-(3-benzyloxy-propoxy)-phenyl]-3-methoxymethyl-5-(naphthalen-2-ylmethoxy)-piperidine as an amorphous, colourless solid; MS: 526 (M+H)$^+$.

The tert-butyl (3SR,4RS,5RS)-4-[4-(3-benzyloxy-propoxy)-phenyl]-3-methoxymethyl-5-(naphthalen-2-ylmethoxy)-piperidine-1-carboxylate used as the starting material was synthesized as follows:
(a) In an analogous manner to that described in Example 68(a)–(b), firstly the primary hydroxy function of (3RS, 4RS)- and (3SR,4RS)-1-benzyl-3-hydroxymethyl-piperidin-4-ol [E.Jaeger and J. H.Biel, J.Org.Chem. 30 (3),740–744 (1965)] was protected by using triphenylchloromethane analogously to Example 22(h) in pyridine in place of tert-butyldiphenylchlorosilane and there was thus obtained (3RS,4RS)- and (3SR,4RS)-1-benzyl-3-trityloxymethyl-piperidin-4-ol. Subsequent oxidation with oxalyl chloride in dimethyl sulphoxide yielded (RS)-1-benzyl-3-trityloxymethyl-piperidin-4-one as a colourless foam; MS: 462 (M+H)$^+$. Subsequent reaction with 4-iodoanisole analogously to Example 62(b) yielded a mixture of (3RS,4RS)- and (3RS,4SR)-1-benzyl-4-(4-methoxy-phenyl)-3-trityloxymethyl-piperidin-4-ol as a colourless solid; MS: 570 (M+H)$^+$.
(b) A solution of 5.5 ml (58.7 mmol) of phosphorus oxychloride in 20 ml of dry pyridine was added dropwise within 20 minutes to a solution of 8.36 g (14.6 mmol) of a mixture of (3RS,4RS)- and (3RS,4SR)-1-benzyl-4-(4-methoxy-phenyl)-3-trityloxymethyl-piperidin-4-ol in 20 ml of dry pyridine. The reaction mixture was stirred at 60° C. for 20 hours. The dark red reaction mixture was cooled and evaporated under reduced pressure. The residue was taken up in methylene chloride and treated with saturated sodium carbonate solution. The organic phase was separated, dried over sodium sulphate and evaporated under reduced pressure. The residue was chromatographed on silica gel using a 20:1 mixture of toluene and ethyl acetate as the eluent. There were obtained 6.1 g (75% of theory) of (RS)-1-benzyl-4-(4-methoxy-phenyl)-3-trityloxymethyl-1,2,3,6-tetrahydro-pyridine as a colourless solid; MS: 552 (M+H)$^+$.
(c) In an analogous manner to that described in Example 62(d), by hydroboration of (RS)-1-benzyl-4-(4-methoxy-phenyl)-3-trityloxymethyl-1,2,3,6-tetrahydro-pyridine with borane-tetrahydrofuran and subsequent oxidation by means of sodium percarbonate there was obtained (3RS,4RS,5SR)-1-benzyl-4-(4-methoxy-phenyl)-5-trityloxymethyl-piperidin-3-ol as a colourless foam; MS: 570 (M+H)$^+$.

(d) In an analogous manner to that described in Example 44(d), by simultaneous cleavage of the methoxy and trityloxy groups by means of boron tribromide in methylene chloride from tert-butyl (3RS,4RS,5SR)-1-benzyl-4-(4-methoxy-phenyl)-5-trityloxy-methyl-piperidin-3-ol there was obtained (3RS,4RS,5SR)-1-benzyl-5-hydroxymethyl-4-(4-hydroxy-phenyl)-piperidin-3-ol hydrobromide as a white solid; MS: 314 (M+H)⁺.

(e) In an analogous manner to that described in Example 2(e), by catalytic hydrogenation at atmospheric pressure using a 10% palladium-charcoal catalyst in methanol from tert-butyl (3RS,4RS,5SR)-1-benzyl-5-hydroxymethyl-4-(4-hydroxy-phenyl)-piperidin-3-ol hydrobromide there was obtained (3RS,4RS,5SR)-5-hydroxymethyl-4-(4-hydroxy-phenyl)-piperidin-3-ol hydrobromide as a colourless foam; MS: 224 (M+H)⁺.

(f) In an analogous manner to that described in Example 1(f), by reacting (3RS,4RS,5SR)-5-hydroxymethyl-4-(4-hydroxy-phenyl)-piperidin-3-ol hydrobromide with di-tert-butyl dicarbonate there was obtained tert-butyl (3RS,4RS,5SR)-3-hydroxy-5-hydroxymethyl-4-(4-hydroxy-phenyl)-piperidine-1-carboxylate as a colourless foam.

(g) In an analogous manner to that described in Example 44(e), by alkylating tert-butyl (3RS,4RS,5SR)-3-hydroxy-5-hydroxymethyl-4-(4-hydroxy-phenyl)-piperidine-1-carboxylate with benzyl 3-bromopropyl ether in the presence of potassium carbonate in butan-2-one there was obtained tert-butyl (3RS,4RS,5SR)-4-[4-(3-benzyloxy-propoxy)-phenyl]-3-hydroxy-5-hydroxymethyl-piperidine-1-carboxylate as a colourless oil; MS: 472 (M+H)⁺.

(h) In an analogous manner to that described in Example 22(h), by reacting tert-butyl (3RS,4RS,5SR)-4-[4-(3-benzyloxy-propoxy)-phenyl]-3-hydroxy-5-hydroxymethyl-piperidine-1-carboxylate with triphenylchloromethane in pyridine there was obtained tert-butyl (3RS,4RS,5SR)-4-[4-(3-benzyloxy-propoxy)-phenyl]-3-hydroxy-5-trityloxymethyl-piperidine-1-carboxylate, [MS: 731 (M+NH₄)⁺], as a colourless foam, alkylation of which with 2-bromomethyl-naphthalene analogously to Example 62(h) gave tert-butyl (3RS,4RS,5SR)-4-[4-(3-benzyloxy-propoxy)-phenyl]-3-(naphthalen-2-ylmethoxy)-5-trityloxymethyl-piperidine-1-carboxylate, [MS: 871 (M+NH₄)⁺], as a colourless foam. Subsequent selective cleavage of the trityl group by means of a mixture of trifluoroacetic acid and trifluoroacetic anhydride in methylene chloride analogously to Example 86(u) yielded tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate as a colourless solid; MS: 612 (M+H)⁺. Subsequent alkylation with methyl iodide analogously to Example 62(h) gave tert-butyl (3SR,4RS,5RS)-4-[4-(3-benzyloxy-propoxy)-phenyl]-3-methoxymethyl-5-(naphthalen-2-ylmethoxy)-piperidine-1-carboxylate as a colourless solid; MS: 626 (M+H)⁺.

EXAMPLE 149

The following compounds were obtained in an analogous manner to that described in Example 22(l) by cleavage of the BOC group by means of hydrogen chloride in methanol:

1) From tert-butyl (3SR,4RS,5RS)-4-[4-(3-benzyloxy-propoxy)-phenyl)-3-hydroxymethyl-5-(naphthalen-2-ylmethoxy)-piperidine-1-carboxylate [Example 148(h)], (3SR,4RS,5RS)-[4-[4-(3-benzyloxy-propoxy)-phenyl]-5-(naphthalen- 2-ylmethoxy)-piperidin-3-yl]-methanol hydrochloride as a colourless solid; MS: 512 (M+H)⁺;

2) from tert-butyl (3RS,4RS,5SR)-4-[4-(3-benzyloxy-propoxy)-phenyl]-3-(naphthalen-2-ylmethoxy)-5-(pyridine-4-ylsulphanylmethyl)-piperidine-1-carboxylate, (3SR,4RS,5RS)-4-[4-[4-(3-benzyloxy-propoxy)-phenyl]-5-(naphthalen-2-ylmethoxy)-piperidin-3-ylmethylsulphanyl]-pyridine hydrochloride as a colourless solid; MS: 605 (M+H)⁺;

3) from tert-butyl (3RS,4RS,5SR)-4-[4-(3-benzyloxy-propoxy)-phenyl]-3-(naphthalen-2-ylmethoxy)-5-phenylsulphanylmethyl-piperidine-1-carboxylate, (3RS,4RS,5SR)-4-[4-(3-benzyloxy-propoxy)-phenyl]-3-(naphthalen-2-ylmethoxy)-5-phenylsulphanylmethyl-piperidine hydrochloride as a colourless oil; MS: 604 (M+H)⁺;

4) from tert-butyl (3SR,4RS,5RS)-4-[4-(3-benzyloxy-propoxy)-phenyl]-3-(2-morpholin-4-yl-ethoxymethyl)-5-(naphthalen-2-ylmethoxy)-piperidine-1-carboxylate, (3SR,4RS,5RS)-4-[2-[4-[4-(3-benzyloxy-propoxy)-phenyl]-5-(naphthalen-2-ylmethoxy)-piperidin-3-ylmethoxy]-ethyl]-morpholine as a colourless oil; MS: 625 (M+H)⁺;

5) from tert-butyl (3RS,4RS,5RS)-4-[4-(3-benzyloxy-propoxy)-phenyl]-3-diethylaminomethyl-5-(naphthalen-2-ylmethoxy)-piperidine-1-carboxylate, (3SR,4RS,5RS)-[4-[4-(3-benzyloxy-propoxy)-phenyl]-5-(naphthalen-2-ylmethoxy)-piperidin-3-ylmethyl]-diethyl-amine as a yellowish oil; MS: 567 (M+H)⁺;

6) from tert-butyl (3RS,4RS,5RS)-4-[4-(3-benzyloxy-propoxy)-phenyl]-3-[[(2-dimethylamino-ethyl)-methyl-amino]-methyl]-5-(naphthalen-2-ylmethoxy)-piperidine-1-carboxylate, (3SR,4RS,5RS)-N-[4-[4-(3-benzyloxy-propoxy)-phenyl]-5-(naphthalen-2-ylmethoxy)-piperidin-3-ylmethyl]-N,N',N'-trimethyl-ethane-1,2-diamine as a yellowish oil; MS: 596 (M+H)⁺;

7) from tert-butyl (3RS,4RS,5SR)-4-[4-(3-benzyloxy-propoxy)-phenyl]-3-(naphthalen-2-ylmethoxy)-5-[1,2,4]triazol-1-ylmethyl-piperidine-1-carboxylate, (3RS,4RS,5SR)-4-[4-(3-benzyloxy-propoxy)-phenyl]-3-(naphthalen-2-ylmethoxy)-5-[1,2,4]triazol-1-ylmethyl-piperidine hydrochloride as a colourless solid; MS: 563 (M+H)⁺;

8) from tert-butyl (3RS,4RS,5RS)-4-[4-(3-benzyloxy-propoxy)-phenyl]-3-(naphthalen-2-ylmethoxy)-5-(2-oxo-imidazolidin-1-ylmethyl)-piperidine-1-carboxylate, (3SR,4RS,5RS)-1-[4-[4-(3-benzyloxy-propoxy)-phenyl]-5-(naphthalen-2-ylmethoxy)-piperidin-3-ylmethyl]-imidazolidin-2-one s a colourless solid; MS: 580 (M+H)⁺;

9) from tert-butyl (3RS,4RS,5RS)-4-[4-(3-benzyloxy-propoxy)-phenyl]-3-(naphthalen-2-ylmethoxy)-5-sulphooxymethyl-piperidine-1-carboxylate trimethylammonium salt, mono-(3SR,4RS,5RS)-[4-[4-(3-benzyloxy-propoxy)-phenyl]-5-(naphthalen-2-ylmethoxy)-piperidin-3-ylmethyl] sulphate as a colourless solid; MS: 590 (M–H)⁻.

The BOC derivatives used as starting materials were prepared as follows:

(a) In an analogous manner to that described in Example 33(a), by reacting tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] with 4,4'-dithiopyridine in the presence of tributylphosphine there was obtained tert-butyl (3RS,4RS,5SR)-4-[4-(3-benzyloxy-propoxy)-phenyl]-3-(naphthalen-2-ylmethoxy)-5-(pyridine-4-ylsulphanylmethyl)-piperidine-1-carboxylate as a yellow, semi-solid substance; MS: 705 (M+H)⁺.

(b) In an analogous manner to that described in Example 33(a), by reacting tert-butyl (3SR,4RS,5RS)-4-[4-(3-benzyloxy-propoxy)-phenyl]-3-hydroxymethyl-5-

(naphthalen-2-ylmethoxy)-piperidine-1-carboxylate [Example 148(h)] with diphenyl disulphide in the presence of tributylphosphine there was obtained tert-butyl (3RS,4RS,5SR)-4-[4-(3-benzyloxy-propoxy)-phenyl]-3-(naphthalen-2-ylmethoxy)-5-phenylsulphanylmethyl-piperidine-1-carboxylate as a colourless oil; MS: 721 $(M+NH_4)^+$.

(c) In an analogous manner to that described in Example 1(g), by alkylating tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] with 4-(2-chloroethyl)-morpholine there was obtained tert-butyl (3SR,4RS,5RS)-4-[4-(3-benzyloxy-propoxy)-phenyl]-3-(2-morpholin-4-yl-ethoxymethyl)-5-(naphthalen-2-ylmethoxy)-piperidine-1-carboxylate as a colourless oil; MS: 725 $(M+H)^+$.

(d) By reacting tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] with mesyl chloride according to a method known from the literature there was obtained tert-butyl (3SR,4RS,5RS)-4-[4-(3-benzyloxy-propoxy)-phenyl]-3-methanesulphonyloxymethyl-5-(naphthalen-2-ylmethoxy)-piperidine-1-carboxylate [MS: 707 $(M+NH_4)^+$] as a colourless solid. Further reaction with diethylamine in acetonitrile at 50° C. analogously to Example 34 gave tert-butyl (3RS,4RS,5RS)-4-[4-(3-benzyloxy-propoxy)-phenyl]-3-diethylaminomethyl-5-(naphthalen-2-ylmethoxy)-piperidine-1-carboxylate as a brown foam; MS: 667 $(M+H)^+$.

(e) Reaction of tert-butyl (3SR,4RS,5RS)-4-[4-(3-benzyloxy-propoxy)-phenyl]-3-methanesulphonyloxymethyl-5-(naphthalen-2-ylmethoxy)-piperidine-1-carboxylate with N,N,N'-trimethyl-ethylenediamine in dimethylformamide at 100° C. analogously to Example 34 yielded tert-butyl (3RS,4RS,5RS)-4-[4-(3-benzyloxy-propoxy)-phenyl]-3-[[(2-dimethylamino-ethyl)-methyl-amino]-methyl]-5-(naphthalen-2-ylmethoxy)-piperidine-1-carboxylate as a colourless oil; MS: 696 $(M+H)^+$.

(f) A solution of 22 mg (0.32 mmol) of 1,2,4-triazole in 5 ml of DMF was cooled to 0° C. and treated with 15 mg (0.29 mmol) of sodium hydride (50% dispersion in refined oil). Subsequently, the mixture was left to warm to room temperature and was stirred for a further 1 hour. 70 mg (0.105 mmol) of tert-butyl (3SR,4RS,5RS)-4-[4-(3-benzyloxy-propoxy)-phenyl]-3-methane-sulphonyloxymethyl-5-(naphthalen-2-ylmethoxy)-piperidine-1-carboxylate were added to this solution. The reaction mixture was heated to 100° C. for 24 hours. For the working-up, the reaction mixture was evaporated under reduced pressure, the residue was partitioned between water and methylene chloride and the organic phase was separated, dried over sodium sulphate and evaporated. For purification, the crude product (70 mg) was chromatographed on silica gel using a 98:2 mixture of methylene chloride and methanol as the eluent. There were obtained 52 mg (77% of theory) of tert-butyl (3RS,4RS,5SR)-4-[4-(3-benzyloxy-propoxy)-phenyl]-3-(naphthalen-2-ylmethoxy)-5-[1,2,4]triazol-1-ylmethyl-piperidine-1-carboxylate as a colourless solid; MS: 663 $(M+H)^+$.

(g) In an analogous manner to that described in Example 149(f), by reacting tert-butyl (3SR,4RS,5RS)-4-[4-(3-benzyloxy-propoxy)-phenyl]-3-methanesulphonyloxymethyl-5-(naphthalen-2-ylmethoxy)-piperidine-1-carboxylate with imidazolidin-2-one there was obtained tert-butyl (3RS,4RS,5RS)-4-[4-(3-benzyloxy-propoxy)-phenyl]-3-(naphthalen-2-ylmethoxy)-5-(2-oxo-imidazolidin-1-ylmethyl)-piperidine-1-carboxylate as a yellowish oil.

(h) A solution of 100 mg (0.136 mmol) of tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] in 10 ml of dry pyridine was treated with 78 mg (0.43 mmol) of sulphur trioxide-trimethylamine complex and stirred at room temperature for 36 hours. For the working-up, the reaction mixture was evaporated under reduced pressure and the crude product was purified directly by flash chromatography using a 9:1 mixture of methylene chloride and methanol as the eluent. There were obtained 102 mg of tert-butyl (3SR,4RS,5RS)-4-[4-(3-benzyloxy-propoxy)-phenyl]-3-(naphthalen-2-ylmethoxy)-5-sulphooxymethyl-piperidine-1-carboxylate trimethylammonium salt as a colourless solid; MS: 690 $(M-H)^-$.

EXAMPLE 150

The following compounds were obtained In an analogous manner to that described in Example 10(b) by cleavage of the BOC group by means of zinc bromide in methylene chloride:

1) From tert-butyl (3SR,4RS,5RS)-4-[4-(3-benzyloxy-propoxy)-phenyl]-3-[3-(4-methyl-piperazin-1-yl)-propylcarbamoyloxymethyl]-5-(naphthalen-2-ylmethoxy)-piperidine-1-carboxylate, (3SR,4RS,5RS)-4-[4-( 3-benzyloxy-propoxy)-phenyl]-5-(naphthalen-2-ylmethoxy)-piperidin-3-ylmethyl [3-(4-methyl-piperazin-1-yl)-propyl]-carbamate as a colourless solid; MS: 695 $(M+H)^+$.

2) From tert-butyl (3SR,4RS,5RS)-4-[4-(3-benzyloxy-propoxy)-phenyl]-3-(2-morpholin-4-yl-ethylcarbamoyloxymethyl)-5-(naphthalen-2-ylmethoxy)-piperidine-1-carboxylate, (3SR,4RS,5RS)-4-[4-(3-benzyloxypropoxy)-phenyl]-5-(naphthalen-2-ylmethoxy)-piperidin-3-ylmethyl (2-morpholin-4-yl-ethyl)-carbamate as a colourless oil; MS: 668 $(M+H)^+$.

3) From tert-butyl (3SR,4RS,5RS)-4-[4-(3-benzyloxy-propoxy)-phenyl]-3-carbamoyloxymethyl-5-(naphthalen-2-ylmethoxy)-piperidine-1-carboxylate, (3SR,4RS,5RS)-4-[4-(3-benzyloxy-propoxy)-phenyl]-5-(naphthalen-2-ylmethoxy)-piperidin-3-ylmethyl carbamate as a colourless solid; MS: 555 $(M+H)^+$.

The BOC derivatives used as starting materials were prepared as follows:

(a) A mixture of 90 mg (0.15 mmol) of tert-butyl 3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] and 60 mg (0.75 mmol) of lithium carbonate in 10 ml of dry tetrahydrofuran was cooled to 0° C. A solution of 0.90 ml (1.6 mmol) of phosgene in toluene (1.93N) was added dropwise thereto while cooling with ice. The mixture was stirred at room temperature overnight in order complete the reaction. The reaction mixture was evaporated under reduced pressure in order to remove the excess phosgene and the crude chloroformate obtained was taken up in 10 ml of tetrahydrofuran. This mixture was treated with 58 mg (0.38 mmol) of 1-(3-aminopropyl)-4-methylpiperizine and stirred at room temperature for 3 hours. For the working-up, the reaction mixture was diluted with 40 ml of methylene chloride and then extracted with 20 ml of water. The organic phase was dried over sodium sulphate and subsequently evaporated under reduced pressure. For purification, the residue was chromatographed on silica gel using a 95:5:0.1 mixture of methylene chloride, methanol and ammonia as the eluent. There were obtained 85 mg (73% of theory) of tert-butyl (3SR,4RS,5RS)-4-[4-(3-benzyloxy-propoxy)-phenyl]-3-[3-

(4-methyl-piperazin-1-yl)-propylcarbamoyloxymethyl]-5-(naphthalen-2-ylmethoxy)-piperidine-1-carboxylate as a colourless solid; MS: 795 (M+H)⁺.

(b) In an analogous manner to that described in Example 150(a), from tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] there was synthesized the corresponding chloroformate, reaction of which with 4-(2-aminoethyl)-morpholine gave tert-butyl (3SR,4RS,5RS)-4-[4-(3-benzyloxy-propoxy)-phenyl]-3-(2-morpholin-4-yl-ethylcarbamoyloxymethyl)-5-(naphthalen-2-ylmethoxy)-piperidine-1-carboxylate as a colourless solid; MS: 768 (M+H)⁺.

(c) In an analogous manner to that described in Example 150(a), from tert-butyl (3SR,4RS,5RS)-4-[4-(3-benzyloxy-propoxy)-phenyl]-3-hydroxymethyl-5-(naphthalen-2-ylmethoxy)-piperidine-1-carboxylate [Example 148(h)] there was synthesized the corresponding chloroformate, reaction of which with a solution of ammonia in tetrahydrofuran gave tert-butyl (3SR,4RS,5RS)-4-[4-(3-benzyloxy-propoxy)-phenyl]-3-carbamoyloxymethyl-5-(naphthalen-2-ylmethoxy)-piperidine-1-carboxylate as a colourless solid; MS: 672 (M+NH₄)⁺.

EXAMPLE 151

The following compounds were obtained in an analogous manner to that described in Example 22(l) by cleavage of the BOC group by means of hydrogen chloride in methanol:
1) From tert-butyl (3RS,4RS)-4-[4-(2-benzyloxy-ethoxymethyl)-phenyl]-3-(naphthalen-2-ylmethoxy)-piperidine-1-carboxylate, (3RS,4RS)-4-[4-(2-benzyloxy-ethoxymethyl)-phenyl]-3-(naphthalen-2-ylmethoxy)-piperidine as a colourless foam; MS: 482 (M+H)⁺;
2) from tert-butyl (3SR,4RS,5RS)-4-[4-(2-benzyloxy-ethoxymethyl)-phenyl]-3-hydroxymethyl-5-(naphthalen-2-ylmethoxy)-piperidine-1-carboxylate, (3S R,4RS,5RS)-[4-[4-(2-benzyloxy-ethoxymethyl)-phenyl]-5-(naphthalen-2-ylmethoxy)-piperidin-3-yl]-methanol as a colourless oil; MS: 512 (M+H)⁺;
3) from tert-butyl (3SR,4RS,5RS)-4-[4-(2-benzyloxy-ethoxymethyl)-phenyl]-3-methoxymethyl-5-(naphthalen-2-ylmethoxy)-piperidine-1-carboxylate, (3SR,4RS,5RS)-4-[4-(2-benzyloxy-ethoxymethyl)-phenyl]-3-methoxymethyl-5-(naphthalen-2-ylmethoxy)-piperidine as a colourless oil; MS: 526 (M+H)⁺;
4) from tert-butyl (3RS,4RS,5SR)-4-[4-(2-benzyloxy-ethoxymethyl)-phenyl]-3-(naphthalen-2-ylmethoxy)-5-(pyridin-3-ylmethoxymethyl)-piperidine-1-carboxylate, (3SR,4RS,5RS)-3-[4-[4-(2-benzyloxy-ethoxymethyl)-phenyl]-5-(naphthalen-2-ylmethoxy)-piperidin-3-ylmethoxymethyl]-pyridine as a colourless oil; MS: 603 (M+H)⁺;
5) from tert-butyl (3SR,4RS,5RS)-4-[4-(2-benzyloxy-ethoxymethyl)-phenyl]-3-(2-methoxy-ethoxymethyl)-5-(naphthalen-2-ylmethoxy)-piperidine-1-carboxylate, (3SR,4RS,5RS)-4-[4-(2-benzyloxy-ethoxymethyl)-phenyl]-3-(2-methoxy-ethoxymethyl)-5-(naphthalen-2-ylmethoxy)-piperidine as a colourless oil; MS: 570 (M+H)⁺;
6) from a mixture of tert-butyl (3RS,4RS,5SR)- and (3SR,4SR,5RS)-4-[4-(2-benzyloxy-ethoxymethyl)-phenyl]-3-(naphthalen-2-ylmethoxy)-5-[3-[(RS)-tetrahydro-pyran-2-yloxy]-propoxymethyl]-piperidine-1-carboxylate with simultaneous cleavage of the THP group, (3SR,4RS,5RS)-3-[4-[4-(2-benzyloxy-ethoxymethyl)-phenyl]-5-(naphthalen-2-ylmethoxy)-piperidin-3-ylmethoxy]-propan-1-ol as a colourless oil; MS: 570 (M+H)⁺;
7) from tert-butyl (3SR,4RS,5RS)-3-methoxymethyl-4-{4-[(methyl-phenyl-carbamoyloxy)-methyl]-phenyl}-5-(naphthalen-2-ylmethoxy)-piperidine-1-carboxylate, (3SR,4RS,5RS)-4-[3-methoxymethyl-5-(naphthalen-2-ylmethoxy)-piperidin-4-yl]-benzyl methyl-phenyl-carbamate as a colourless oil; MS: 525 (M+H)⁺;
8) from tert-butyl (3S R,4RS,5RS)-4-[4-[(benzyl-methyl-carbamoyloxy)-methyl]-phenyl]-3-methoxymethyl-5-(naphthalen-2-ylmethoxy)-piperidine-1-carboxylate, (3SR,4RS,5RS)-4-[3-methoxymethyl-5-(naphthalen-2-ylmethoxy)-piperidin-4-yl]-benzyl benzyl-methyl-carbamate as a colourless oil; MS: 539 (M+H)⁺.

The BOC derivatives used as starting materials were obtained as follows:
(a) In an analogous manner to that described in Example 1(g), by alkylating tert-butyl (3RS,4RS)-4-(4-hydroxymethyl-phenyl)-3-(naphthalen-2-ylmethoxy)-piperidine-1-carboxylate [Example 22(j)] with 2-(benzyloxy)-ethyl iodide [Helv.Chim.Acta Vol.71, (1988), 2039] there was obtained tert-butyl (3RS,4RS)-4-[4-(2-benzyloxy-ethoxymethyl)-phenyl]-3-(naphthalen-2-ylmethoxy)-piperidine-1-carboxylate as a colourless foam; MS: 599 (M+NH₄)⁺.

(b) In an analogous manner to that described in Example 22(d), from tert-butyl (3RS,4RS,5SR)-1-benzyl-4-(4-bromo-phenyl)-5-hydroxymethyl-piperidin-3-ol [Example 68(e)] by a palladium catalyzed carbonylation with carbon monoxide in methanol there was obtained methyl (3RS,4RS,5SR)-4-(1-benzyl-3-hydroxy-5-hydroxymethyl-piperidin-4-yl)-benzoate, hydrogenolysis of which in the presence of 5% palladium-charcoal at atmospheric pressure in methanol analogously to Example 2(e) gave methyl 4-(3-hydroxy-5-hydroxymethyl-piperidin-4-yl)-benzoate. Subsequent introduction of the BOC group analogously to Example 1 (f) yielded tert-butyl (3RS,4RS,5SR)-3-hydroxy-5-hydroxymethyl-4-(4-methoxycarbonyl-phenyl)-piperidine-1-carboxylate, from which by reaction with triphenylchloromethane analogously to Example 68(i) there was obtained tert-butyl (3RS,4RS,5SR)-3-hydroxy-4-(4-methoxycarbonyl-phenyl)-5-trityloxymethyl-piperidine-1-carboxylate. Subsequent alkylation by means of 2-bromomethyl-naphthalene analogously to Example 1(g) yielded tert-butyl (3RS,4RS,5SR)-4-(4-methoxycarbonyl-phenyl)-3-(naphthalen-2-ylmethoxy)-5-trityloxymethyl-piperidine-1-carboxylate, reduction of which with lithium borohydride analogously to Example 22(e) yielded tert-butyl (3RS,4RS,5SR)-4-(4-hydroxymethyl-phenyl)-3-(naphthalen-2-ylmethoxy)-5-trityloxymethyl-piperidine-1-carboxylate as a colourless foam; MS: 737 (M+NH₄)⁺. Further alkylation with 2-(benzyloxy)-ethyl iodide [Helv.Chim. Acta Vol.71, (1988),2039] analogously to Example 1(g) gave tert-butyl (3RS,4RS,5SR)-4-[4-(2-benzyloxy-ethoxymethyl)-phenyl]-3-(naphthalen-2-ylmethoxy)-5-trityloxymethyl-piperidine-1-carboxylate, from which after cleavage of the trityl group by means of a mixture of trifluoroacetic acid and trifluoroacetic anhydride in methylene chloride analogously to Example 86(u) there was obtained tert-butyl (3SR,4RS,5RS)-4-[4-(2-benzyloxy-ethoxymethyl)-phenyl]- 3-hydroxymethyl-5-(naphthalen-2-ylmethoxy)-piperidine-1-carboxylate as a colourless oil; MS: 629 (M+NH₄)⁺.

(c) In an analogous manner to that described in Example 1(g), by alkylating tert-butyl (3SR,4RS,5RS)-4-[4-(2-benzyloxy-ethoxymethyl)-phenyl]-3-hydroxymethyl-5-(naphthalen-2-ylmethoxy)-piperidine-1-carboxylate with methyl iodide there was obtained tert-butyl (3SR,4RS,5RS)-4-[4-(2-benzyloxy-ethoxymethyl)-phenyl]-3- methoxymethyl-5-(naphthalen-2-ylmethoxy)-piperidine-1-carboxylate as a colourless oil; MS: 643 (M+NH$_4$)$^+$.

(d) In an analogous manner to that described in Example 1(g), by alkylating tert-butyl (3SR,4RS,5RS)-4-[4-(2-benzyloxy-ethoxymethyl)-phenyl]-3-hydroxymethyl-5-(naphthalen-2-ylmethoxy)-piperidine-1-carboxylate with 3-(chloromethyl)-pyridine there was obtained tert-butyl (3RS,4RS,5SR)-4-[4-(2-benzyloxy-ethoxymethyl)-phenyl]-3-(naphthalen-2-ylmethoxy)-5-(pyridine-3-ylmethoxymethyl)-piperidine-1-carboxylate as a colourless oil; MS: 703 (M+H)$^+$.

(e) In an analogous manner to that described in Example 1(g), by alkylating tert-butyl (3SR,4RS,5RS)-4-[4-(2-benzyloxy-ethoxymethyl)-phenyl]-3-hydroxymethyl-5-(naphthalen-2-ylmethoxy)-piperidine-1-carboxylate with 2-methoxy-ethyl bromide there was obtained tert-butyl (3SR,4RS,5RS)-4-[4-(2-benzyloxy-ethoxymethyl)-phenyl]-3-(2-methoxy-ethoxymethyl)-5-(naphthalen-2-ylmethoxy)-piperidine-1-carboxylate as a colourless oil; MS: 687 (M+NH$_4$)$^+$.

(f) In an analogous manner to that described in Example 1(g), by alkylating tert-butyl (3SR,4RS,5RS)-4-[4-(2-benzyloxy-ethoxymethyl)-phenyl]-3-hydroxymethyl-5-(naphthalen-2-ylmethoxy)-piperidine-1-carboxylate with rac-2-(3-bromo-propoxy)-tetrahydro-2H-pyran [J.Org.Chem. 53, (1988),25, 5903–5908] there was obtained a mixture of tert-butyl (3RS,4RS,5SR)- and (3SR,4SR,5RS)-4-[4-(2-benzyloxy-ethoxymethyl)-phenyl]-3-(naphthalen-2-ylmethoxy)-5-[3-[(RS)-tetrahydro-pyran-2-yloxy]-propoxymethyl]-piperidine-1-carboxylate as a colourless oil; MS: 771 (M+NH$_4$)$^+$.

(g) In an analogous manner to that described in Example 24(m), reaction of tert-butyl (3RS,4RS,5SR)-4-(4-hydroxymethyl-phenyl)-3-(naphthalen-2-ylmethoxy)-5-trityloxymethyl-piperidine-1-carboxylate with phenyl isocyanate gave (3RS,4RS,5SR)-3-(naphthalen-2-ylmethoxy)-4-(4-phenylcarbamoyloxymethyl-phenyl)-5-trityloxymethyl-piperidine-1-carboxylate, from which by cleavage of the trityl group by means of a mixture of trifluoroacetic acid and trifluoroacetic anhydride in methylene chloride analogously to Example 86(u) there was obtained tert-butyl (3SR,4RS,5RS)-3-hydroxymethyl-5-(naphthalen-2-ylmethoxy)-4-(4-phenylcarbamoyloxymethyl-phenyl)-piperidine-1-carboxylate. Subsequent alkylation with methyl iodide analogously to Example 1(g) yielded tert-butyl (3SR,4RS,5RS)-3-methoxymethyl-4-{4-[(methyl-phenyl-carbamoyloxy)-methyl]-phenyl}-5-(naphthalen-2-ylmethoxy)-piperidine-1-carboxylate as a colourless oil; MS: 642 (M+NH$_4$)$^+$.

(h) In an analogous manner to that described in Example 24(m), reaction of tert-butyl (3RS,4RS,5SR)-4-(4-hydroxymethyl-phenyl)-3-(naphthalen-2-ylmethoxy)-5-trityloxymethyl-piperidine-1-carboxylate with benzyl isocyanate gave tert-butyl (3RS,4RS,5SR)-4-(4-benzylcarbamoyloxymethyl-phenyl)-3-(naphthalen-2-ylmethoxy)-5-trityloxymethyl-piperidine-1-carboxylate, from which by cleavage of the trityl group by means of a mixture of trifluoroacetic acid and trifluoroacetic anhydride in methylene chloride analogously to Example 86(u) there was obtained tert-butyl (3SR,4RS,5RS)-4-(4-benzylcarbamoyloxymethyl-phenyl)-3-hydroxymethyl-5-(naphthalen-2-ylmethoxy)-piperidine-1-carboxylate. Subsequent alkylation with methyl iodide analogously to Example 1(g) yielded tert-butyl (3SR,4RS,5RS)-4-[4-[(benzyl-methyl-carbamoyloxy)-methyl]-phenyl]-3-methoxymethyl-5-(naphthalen-2-ylmethoxy)-piperidine-1-carboxylate as a colourless oil; MS: 656 (M+NH$_4$)$^+$.

EXAMPLE 152

The following compounds were obtained by cleavage of the BOC group by means of zinc bromide in methylene chloride:

1) From tert-butyl (3RS,4RS)-4-(4-fluoro-phenyl)-3-(4-methylsulphanyl-benzyloxy)-piperidine-1-carboxylate, (3RS,4RS)-4-(4-fluoro-phenyl)-3-(4-methylsulphanyl-benzyloxy)-piperidine as a yellowish oil; MS: 332 (M+H)$^+$;

2) from a mixture of tert-butyl (3RS,4RS)- and (3SR,4SR)-4-(4-fluoro-phenyl)-3-[(RS)-4-methansulphinyl-benzyloxy)-piperidine-1-carboxylate, a mixture of (3RS,4RS)- and (3SR,4SR)-4-(4-fluoro-phenyl)-3-[(RS)-4-methylsulphinyl-benzyloxy]-piperidine as a yellowish oil; MS: 348 (M+H)$^+$;

3) from tert-butyl (3RS,4RS)-4-(4-fluoro-phenyl)-3-(4-methylsulphonyl-benzyloxy)-piperidine-1-carboxylate, (3RS,4RS)-4-(4-fluoro-phenyl)-3-(4-methylsulphonyl-benzyloxy)-piperidine hydrobromide as a yellowish solid; MS: 364 (M+H)$^+$;

4) from tert-butyl (3RS,4RS)-3-(1,4-dimethoxy-naphthalen-2-ylmethoxy)-4-(4-hydroxy-phenyl)-piperidine-1-carboxylate, (3RS,4RS)-4-[3-(1,4-dimethoxy-naphthalen-2-ylmethoxy)-piperidin-4-yl]-phenol as a colourless solid; MS: 394 (M+H)$^+$;

5) from tert-butyl (3RS,4RS)-4-[4-(3-Cyano-benzyloxy)-phenyl]-3-(1,4-dimethoxy-naphthalen-2-ylmethoxy)-piperidine-1-carboxylate, by means of zinc bromide, (3RS,4RS)-3-[4-[3-(1,4-dimethoxy-naphthalen-2-ylmethoxy)-piperidin-4-yl]-phenoxymethyl]-benzonitrile as a colourless solid; MS: 509 (M+H)$^+$.

The BOC derivatives used as starting materials were prepared as follows:

(a) In an analogous manner to that described in Example 1(g), by alkylating tert-butyl (3RS,4RS)-4-(4-fluoro-phenyl)-3-hydroxy-piperidine-1-carboxylate [Example 3(b)] with 4-methylthio-benzyl chloride [J.Org.Chem. (1988),53(3), 561–569] there was obtained tert-butyl (3RS,4RS)-4-(4-fluoro-phenyl)-3-(4-methylsulphanyl-benzyloxy)-piperidine-1-carboxylate as a colourless oil; MS: 432 (M+H)$^+$.

(b) In an analogous manner to that described in Example 58(i), by oxidizing tert-butyl (3RS,4RS)-4-(4-fluoro-phenyl)-3-(4-methylsulphanyl-benzyloxy)-piperidine-1-carboxylate by means of sodium metaperiodate there was obtained a mixture of (3RS,4RS)- and (3SR,4SR)-4-(4-fluoro-phenyl)-3-[(RS)-4-methanesulphinyl-benzyloxy)-piperidine-1-carboxylate as a yellowish oil; MS: 448 (M+H)$^+$.

(c) 126 mg (0.586 mmol) of m-perbenzoic acid (80%) were added to a solution of 115 mg (0.27 mmol) of tert-butyl (3RS,4RS)-4-(4-fluoro-phenyl)-3-(4-methylsulphanyl-benzyloxy)-piperidine-1-carboxylate in 2 ml of methylene chloride. Ther reaction solution was stirred at room temperature for 2 hours and thereafter neutralized with potassium carbonate in methanol. Subsequently, the solution was diluted with methylene chloride. Thereafter, it was worked-up in the usual manner and the crude product obtained was purified by chromatography on silica gel using a 4:1 mixture of methylene chloride and ether as the eluent. There were obtained 1.05 mg (85% of theory) of tert-butyl (3RS,4RS)-4-(4-fluoro-phenyl)-3-(4-methylsulphonyl-benzyloxy)-piperidine-1-carboxylate as a colourless, viscous oil; MS: 464 (M+H)$^+$.

(d) (a) In an analogous manner to that described in Example 1(g), by alkylating tert-butyl (3RS,4RS)-4-(4-allyloxy-phenyl)-3-hydroxy-piperidine-1-carboxylate [Example 86(b)] with 2-chloromethyl-1,4-dimethoxy-naphthalene [J.Org.Chem. (1983),48(19),3265–3268) there was obtained tert-butyl (3RS,4RS)-4-(4-allyloxy-phenyl)-3-(1,4-dimethoxy-naphthalen-2-ylmethoxy)-piperidine-1-carboxylate as a pale yellow solid; MS: 534 (M+H)$^+$.

(β) A solution of 315 mg (0.59 mmol) of tert-butyl (3RS,4RS)-4-(4-allyloxy-phenyl)-3-(1,4-dimethoxy-naphthalen-2-ylmethoxy)-piperidine-1-carboxylate, 44 mg (0.059 mmol) of bis-(triphenylphosphine)-palladium(II) diacetate and 132 mg (1.18 mmol) of 1,4-diazabicyclo [2.2.2]octane in 10 ml of 95% ethanol was heated to reflux under argon for 2 hours. Subsequently, the reaction mixture was cooled to 0–50° C. and treated with 0.6 ml of 1N hydrochloric acid. Thereafter, the solvent was distilled off under reduced pressure and the residue was partitioned between ethyl acetate and water. After extraction and drying of the organic phase over sodium sulphate it was evaporated under reduced pressure.

The residue was purified on silica gel using a 9:1 mixture of methylene chloride and ether as the eluent. There were obtained 265 mg (91% of theory) of tert-butyl (3RS,4RS)-3-(1,4-dimethoxy-naphthalen-2-ylmethoxy)-4-(4-hydroxy-phenyl)-piperidine-1-carboxylate as a yellowish foam; MS: 494 (M+H)$^+$.

(e) In an analogous manner to that described in Example 44 e), by alkylating tert-butyl (3RS,4RS)-3-(1,4-dimethoxy-naphthalen-2-ylmethoxy)-4-( 4-hydroxy-phenyl)-piperidine-1-carboxylate with 3-bromomethyl-benzonitrile there was obtained tert-butyl (3RS,4RS)-4-[4-(3-cyano-benzyloxy)-phenyl]-3-(1,4-dimethoxy-naphthalen-2-ylmethoxy)-piperidine-1-carboxylate as a beige solid; MS: 609 (M+H)$^+$.

EXAMPLE 153

A solution of 736 mg (1.28 mmol) of (3R,4R)-4-(4-bromophenyl)-3-(naphthalen-2-ylmethoxy)-1-[(1S,4R)-4,7,7-trimethyl-3-oxo-2-oxabicyclo[2.2.1]heptane-1-carbonyl]-piperidine in 32 ml of absolute tetrahydrofuran was cooled to −70° C. Thereto there was added dropwise a solution of 1.86 ml (6.5 mmol) of sodium dihydrido-bis-(2-methoxyethoxy)-aluminate (70% in toluene, about 3.5M) in 32 ml of tetrahydrofuran. The mixture was warmed to −40° C., stirred at −40° C. for 8 hours, thereafter cooled to −78° C. and treated dropwise with a solution of 0.5 ml of glacial acetic acid in 10 ml of tetrahydrofuran. For the working-up, the reaction mixture was partitioned between 200 mg of ethyl acetate and 200 ml of aqueous 5% sodium hydrogen carbonate solution. The organic phase was separated and the aqueous phase was back-extracted three times with 50 ml of ethyl acetate each time. The combined organic phases were dried over magnesium sulphate and finally the solvent was distilled off under reduced pressure. The crude product (800 mg) was purified by chromatography on silica gel with a 9:1 mixture of methylene chloride and methanol as the eluent. There were obtained 344 mg (68% of theory) of (3R,4R)-4-(4-bromophenyl)-3-(naphthalen-2-ylmethoxy)-piperidine as a colourless solid; MS: 396, 398 (M+H)$^+$.

The camphanic acid derivative used as the starting material was prepared as follows:

A solution of 1.98 g (5.00 mmol) of (3RS,4RS)-4-(4-bromophenyl)-3-(naphthalen-2-ylmethoxy)-piperidine (Example 2.6) in 20 ml of methylene chloride was cooled to 0° C. and treated with 0.84 ml (0.61 g,6.0 mmol) of triethylamine. Thereto there was added dropwise under argon at 0° C. a solution of 1.19 g (5.5 mmol) of (−)-(1S,4R)-camphanoyl chloride in 20 ml of methylene chloride and the mixture was subsequently stirred at 0° C. for 30 minutes and at room temperature for a further 2 hours. For the working-up, the reaction mixture was partitioned between 200 ml of methylene chloride and 200 ml of ice-water. The organic phase was separated and the aqueous phase was extracted three times with 50 ml of ethyl acetate each time. The combined organic phases were dried over magnesium sulphate and finally the solvent was distilled off under reduced pressure. The crude isomer mixture (2.89 g) was separated by chromatography on silica gel with a 2:3 mixture of ethyl acetate and hexane as the eluent. There were obtained 1.14 g (40% of theory) of (3R,4R)-4-(4-bromophenyl)-3-(naphthalen-2-ylmethoxy)-1-[(1S,4R)-4,7,7-trimethyl-3-oxo-2-oxabicyclo[2.2.1]heptane-1-carbonyl]-piperidine, MS: 575, 577 (M)$^+$, and 1.01 g (35% of theory of (3S,4S)-4-(4-bromophenyl)-3-(naphthalen-2-ylmethoxy)-1-[(1S,4R)-4,7,7-trimethyl-3-oxo-2-oxabicyclo[2.2.1]heptane-1-carbonyl]-piperidine, MS: 575, 577 (M)$^+$, each as a colourless solid.

EXAMPLE 154

The following compounds were obtained in an analogous manner to that described in the foregoing Example by reductive cleavage of the camphanyl group:

1) From (3S,4S)-4-(4-bromophenyl)-3-(naphthalen-2-ylmethoxy)-1-[(1S,4R)-4,7,7-trimethyl-3-oxo-2-oxabicyclo[2.2.1]heptane-1-carbonyl]-piperidine, (3S,4S)-4-(4-bromophenyl)-3-(naphthalen-2-ylmethoxy)-piperidine as a colourless solid; MS: 396, 398 (M+H)$^+$;

2) from tert-butyl (3R,4R)-4-(4-chlorophenyl)-3-(4-methoxy-benzyloxy)-1-[(1S,4R)-4,7,7-trimethyl-3-oxo-2-oxabicyclo[2.2.1]heptane-1-carbonyl]-piperidine, (3R,4R)-4-(4-chlorophenyl)-3-(4-methoxy-benzyloxy)-piperidine as a colourless solid; MS: 332, 334 (M+H)$^+$;

3) from tert-butyl (3S,4S)-4-(4-chlorophenyl)-3-(4-methoxy-benzyloxy)-1-[(1S,4R)-4,7,7-trimethyl-3-oxo-2-oxabicyclo[2.2.1]heptane-1-carbonyl]-piperidine, (3S,4S)-4-(4-chlorophenyl)-3-(4-methoxy-benzyloxy)-piperidine as a colourless solid; MS: 332, 334 (M+H)$^+$;

4) from tert-butyl (3R,4R)-4-naphthalen-1-yl-3-(naphthalen-2-ylmethoxy)-1-[(1S,4R)-4,7,7-trimethyl-3-oxo-2-oxabicyclo[2.2.1]heptane-1-carbonyl]-piperidine, (3R,4R)-4-naphthalen-1-yl-3-(naphthalen-2-ylmethoxy)-piperidine as a colourless solid; MS: 368 (M+H)$^+$;

5) from tert-butyl (3S,4S)-4-naphthalen-1-yl-3-(naphthalen-2-ylmethoxy)-1-[(1S,4R)-4,7,7-trimethyl-3-oxo-2-oxabicyclo[2.2.1]heptane-1-carbonyl]-piperidine, (3S,4S)-4-naphthalen-1-yl-3-(naphthalen-2-ylmethoxy)-piperidine as a colourless solid; MS: 368 (M+H)$^+$;

6) from tert-butyl (3R,4R)-3-(4-benzyloxy-naphthalen-2-ylmethoxy)-4-(4-fluoro-phenyl)-1-[(1S,4R)-4,7,7-trimethyl-3-oxo-2-oxabicyclo[2.2.1]heptane-1-carbonyl]-piperidine, (3R,4R)-3-(4-benzyloxy-naphthalen-2-ylmethoxy)-4-(4-fluoro-phenyl)-piperidine as a colourless solid; MS: 441 (M)$^+$;

7) from tert-butyl (3S,4S)-3-(4-benzyloxy-naphthalen-2-ylmethoxy)-4-(4-fluoro-phenyl)-1-[(1S,4R)-4,7,7-trimethyl-3-oxo-2-oxabicyclo[2.2.1]heptane-1-carbonyl]-piperidine, (3S,4S)-3-(4-benzyloxy-naphthalen-2-ylmethoxy)-4-(4-fluoro-phenyl) piperidine as a colourless solid; MS: 441 (M)$^+$.

The following derivatives were prepared in an analogous manner to that described in the preceding Example by acylation with (−)-camphanoyl chloride:

(a) From (3RS,4RS)-4-(4-chlorophenyl)-3-(4-methoxy-benzyloxy)-piperidine [prepared as described in den Examples 1 and 2 for (3RS,4RS)-3-(4-methoxy-benzyloxy)-4-p-tolyl-piperidine (Example 2.4)], (3R,4R)-

4-(4-chlorophenyl)-3-(4-methoxy-benzyloxy)-1-[(1S, 4R)-4,7,7-trimethyl-3-oxo-2-oxabicyclo[2.2.1]heptane-1-carbonyl]-piperidine, MS: 511, 513 (M)$^+$, and (3S,4S)-4-(4-chlorophenyl)-3-(4-methoxy-benzyloxy)-1-[(1S,4R)-4,7,7-trimethyl-3-oxo-2-oxabicyclo[2.2.1]heptane-1-carbonyl]-piperidine, MS: 511, 513 (M)$^+$, each as a colourless solid;

(b) from tert-butyl (3RS,4RS)-4-naphthalen-1-yl-3-(naphthalen-2-ylmethoxy)-piperidine (Example 2.12), (3R,4R)-4-naphthalen-1-yl-3-(naphthalen-2-ylmethoxy)-1-[(1S,4R)-4,7,7-trimethyl-3-oxo- 2-oxabicyclo[2.2.1] heptane-1-carbonyl]-piperidine, MS: 547 (M)$^+$, and (3S, 4S)-4-naphthalen-1-yl-3-(naphthalen-2-ylmethoxy)-1-[(1S,4R)-4,7,7-trimethyl-3-oxo-2-oxabicyclo[2.2.1] heptane-1-carbonyl]-piperidine, MS: 547 (M)$^+$, each as a colourless foam;

(c) from tert-butyl (3RS,4RS)-3-(4-benzyloxy-naphthalen-2-ylmethoxy)-4-(4-fluoro-phenyl)-piperidine (Example 14.13), (3R,4R)-3-(4-benzyloxy-naphthalen-2-ylmethoxy)-4-(4-fluoro-phenyl)-1-[(1S,4R)-4,7,7-trimethyl-3-oxo-2-oxabicyclo[2.2.1]heptane-1-carbonyl]-piperidine, MS: 621 (M)$^+$, and (3S,4S)-3-(4-benzyloxy-naphthalen-2-ylmethoxy)-4-($^4$-fluoro-phenyl)-1-[(1S, 4R)-4,7,7-trimethyl-3-oxo-2-oxabicyclo[2.2.1]heptane-1-carbonyl]-piperidine, MS: 621 (M)$^+$, each as a colourless foam.

EXAMPLE A

Oral, Aqueous Suspension

Composition:

| | |
|---|---|
| Compound of formula I, e.g. (3RS,4RS)-4-[4-(3-benzyloxy-propoxy)-phenyl]-3-(naphthalen-2-ylmethoxy)-piperidine, micronized | 5.0 g |
| Polysorbate 80 | 0.3 g |
| Hydroxypropylmethylcellulose | 1.0 g |
| Flavour | q.s. |
| Methylparaben | 0.2 g |
| Propyleneparaben | 0.04 g |
| Water | ad 100.0 ml |

EXAMPLE B

Tablets

Composition:

| | |
|---|---|
| 1) Compound of formula I, e.g. (3RS,4RS)-4-[4-(3-benzyloxy-propoxy)-phenyl]-3-(naphthalen-2-yl-methoxy)-piperidine | 200 mg |
| 2) Anhydrous lactose | 160 mg |
| 3) Hydroxypropylmethylcellulose | 18 mg |
| 4) Sodium-carboxymethylcellulose | 20 mg |
| 5) Magnesium stearate | 2 mg |
| Tablet weight | 400 mg |

Production: 1) and 2) are mixed intensively. The mixture is thereafter moistened with an aqueous solution of 3) and kneaded, and the resulting mass is granulated, dried and sieved. The granulate is mixed with 4) and 5) and pressed to tablets of suitable size.

EXAMPLE C

Capsules

Composition

| | |
|---|---|
| 1) Compound of formula I, e.g. (3RS,4RS)-4-[4-(3-benzyl-oxy-propoxy)-phenyl]-3-(naphthalen-2-ylmethoxy)-piperidin | 200 mg |
| 2) Anhydrous lactose | 160 mg |
| 3) Hydroxypropylmethylcellulose | 18 mg |
| 4) Sodium-carboxymethylcellulose | 20 mg |
| 5) Magnesium stearate | 2 mg |
| Capsule fill weight | 400 mg |

Production: 1) and 2) are mixed intensively. The mixture is thereafter moistened with an aqueous solution of 3) and kneaded, and the resulting mass is granulated, dried and sieved. The granulate is mixed with 4) and 5), the mixture is filled into capsules of suitable size.

EXAMPLE D

Injection Solution

Composition

| | |
|---|---|
| 4-[2-[7-[(3RS,4RS)-4-[4-(3-benzyloxy-propoxy)-phenyl]-piperidin-3-yloxymethyl]-naphthalen-2-yloxy]-ethyl]-morpholine hydrochloride (1:2) | 1 ml |
| | 3 mg |
| Pyrogen-free D-mannitol | 10 mg |
| Water for injection purposes | ad 1.0 ml |

Production: The active ingredient and the mannitol are dissolved in nitrogen-gassed water and subsequently sterilized according to a conventional procedure.

EXAMPLE E

Injektion Solution in Form of a Mixed Micelle Solution

Composition

| | |
|---|---|
| Compound of formula I, e.g., (3RS,4RS)-4-[4-(3-benzyloxy-propoxy)-phenyl]-3-(naphthalen-2-ylmethoxy)-piperidine | 2.0 mg |
| Sodium glycocholate | 98.5 mg |
| Soya lecithin | 158.2 mg |
| Sodium dihydrogen phosphate | 1.8 mg |
| Disodium-hydrogen phosphate | 9.5 mg |
| Water for injection purposes | ad 1.0 ml |

Production: The compound of formula 1, sodium glycocholate and soya lecithin are dissolved in the required amount of ethanol (or an adequate volatile solvent). The solvent is evaporated under reduced pressure and slight heating. The residue is dissolved in the buffered aqueous phase. The solution is processed by conventional procedures.

What is claimed is:
1. A compound of the formula:

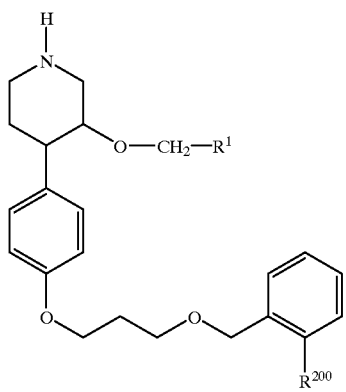

wherein:
R¹ is 6-quinolyl, 7-quinolyl, 6-isoquinolyl, 7-isoquinolyl, 6-tetrahydroquinolyl, 7-tetrahydroquinolyl, 6-tetrahydroisoquinolyl, 7-tetrahydroisoquinolyl, 6-tetrahydroquinolyl substituted by oxo, 7-tetrahydroquinolyl substituted by oxo, 6-tetrahydroisoquinolyl substituted by oxo, or 7-tetrahydroisoquinolyl substituted by oxo; and $R^{200}$ is hydrogen or lower alkoxy;

or a pharmaceutically usable salt thereof.

2. The compound of claim 1, wherein the compound is (3RS,4RS)-4-[4-[3-(2-methoxy-benzyloxy)-propoxy]-phenyl]-3-(quinolin-7-ylmethoxy)-piperidine.

3. The compound of claim 1, wherein the compound is (3RS,4RS)-3-(isoquinolin-7-ylmethoxy)-4-[4-[3-(2-methoxy-benzyloxy)-propoxy]-phenyl]-piperidine.

4. The compound of claim 1, wherein the compound is (3RS,4RS)-4-[4-[3-(2-methoxy-benzyloxy)-propoxy]-phenyl]-3-(1,2,3,4-tetrahydro-quinolin-7-ylmethoxy)-piperidine.

5. The compound of claim 1, wherein the compound is (3RS,4RS)-4-[4-[3-(2-methoxy-benzyloxy)-propoxy]-phenyl]-3-(2-oxo-1,2-dihydro-quinolin-7-ylmethoxy)-piperidine.

* * * * *